(12) United States Patent
Inoue et al.

(10) Patent No.: US 10,147,889 B2
(45) Date of Patent: Dec. 4, 2018

(54) BISCARBAZOLE DERIVATIVE AND ORGANIC ELECTROLUMINESCENT ELEMENT USING SAME

(71) Applicant: IDEMITSU KOSAN CO., LTD., Tokyo (JP)

(72) Inventors: Tetsuya Inoue, Chiba (JP); Mitsunori Ito, Chiba (JP); Kumiko Gorai, Chiba (JP); Kazuki Nishimura, Chiba (JP); Kiyoshi Ikeda, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 49 days.

(21) Appl. No.: 15/165,142

(22) Filed: May 26, 2016

(65) Prior Publication Data

US 2016/0268517 A1     Sep. 15, 2016

Related U.S. Application Data

(63) Continuation of application No. 13/983,687, filed as application No. PCT/JP2012/052639 on Feb. 6, 2012.

(30) Foreign Application Priority Data

| Feb. 7, 2011 | (JP) | ................................. | 2011-024452 |
| Feb. 7, 2011 | (JP) | ................................. | 2011-024453 |
| Oct. 18, 2011 | (JP) | ................................. | 2011-229117 |

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/60* (2013.01); *C07D 209/86* (2013.01);
(Continued)

(58) Field of Classification Search
CPC .. C07D 209/82; C07D 209/86; C07D 209/88; C07D 403/02; C07D 403/04;
(Continued)

(56) References Cited

U.S. PATENT DOCUMENTS 7,329,722 B2   2/2008  Vaitkeviciene et al.
8,040,047 B2   10/2011 Ushikubo et al.
(Continued)

FOREIGN PATENT DOCUMENTS

| CN | 101126020 A | 2/2008 |
| CN | 101270075 A | 9/2008 |

(Continued)

OTHER PUBLICATIONS

International Search Report dated Mar. 27, 2012 in PCT/JP2012/052639.
(Continued)

*Primary Examiner* — Jennifer A Chriss
*Assistant Examiner* — Dylan C Kershner
(74) *Attorney, Agent, or Firm* — Oblon, McClelland, Maier & Neustadt, L.L.P.

(57) ABSTRACT

A biscarbazole derivative having a specific group, which is represented by formula (1):
(Continued)

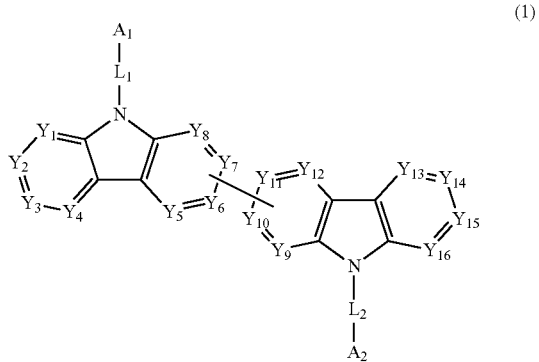

(1)

and an organic electroluminescence device in which a plurality of organic thin-film layers including a light emitting layer are disposed between a cathode and an anode, and at least one of the organic thin-film layers include the biscarbazole derivative. The organic electroluminescence device exhibits high emission efficiency and has a long lifetime. In formula (1), each of $A_1$ and $A_2$ independently represents a substituted or unsubstituted aromatic hydrocarbon group having 6 to 30 ring carbon atoms; each of $Y_1$ to $Y_{16}$ independently represents C(R) or a nitrogen atom; each of R groups independently represents a hydrogen atom, etc.; and each of $L_1$ and $L_2$ independently represents a single bond, etc.; provided that at least one of $A_1$, $A_2$ and R represents a substituted or unsubstituted fluoranthenyl group, etc.

29 Claims, 1 Drawing Sheet

(51) Int. Cl.
    *C07D 403/04* (2006.01)
    *C07D 403/14* (2006.01)
    *C09K 11/06* (2006.01)
    *H05B 33/14* (2006.01)
    *C07D 471/04* (2006.01)
    *C07D 209/60* (2006.01)
    *C07D 209/86* (2006.01)
    *C09K 11/02* (2006.01)
    *H01L 51/52* (2006.01)

(52) U.S. Cl.
    CPC .......... *C07D 403/04* (2013.01); *C07D 403/14* (2013.01); *C07D 471/04* (2013.01); *C09K 11/025* (2013.01); *C09K 11/06* (2013.01); *H01L 51/0052* (2013.01); *H01L 51/0054* (2013.01); *H01L 51/0055* (2013.01); *H01L 51/0058* (2013.01); *H01L 51/0067* (2013.01); *H01L 51/0085* (2013.01); *H05B 33/14* (2013.01); C09K 2211/1007 (2013.01); C09K 2211/1011 (2013.01); C09K 2211/1029 (2013.01); C09K 2211/1059 (2013.01); C09K 2211/185 (2013.01); H01L 51/5016 (2013.01); H01L 51/5056 (2013.01); H01L 51/5072 (2013.01); H01L 51/5092 (2013.01); H01L 51/5206 (2013.01); H01L 51/5221 (2013.01); H01L 51/5231 (2013.01); H01L 2251/301 (2013.01); H01L 2251/308 (2013.01); H01L 2251/5361 (2013.01)

(58) Field of Classification Search
    CPC .. C07D 403/14; C07D 209/80; C07D 209/60; C07D 471/04; C07D 471/14; H01L 51/0067; H01L 51/0072; H01L 51/50; H01L 51/5016; H01L 51/5056; H01L 51/0052; H01L 51/0054; H01L 51/0055; H01L 51/0058; H01L 51/0085; H01L 51/5012; H01L 51/5072; H01L 51/5092; H01L 2251/301; H01L 2251/308; H01L 2251/5361; C09K 11/06; C09K 11/025; C09K 2211/1007; C09K 2211/1011; C09K 2211/1029; C09K 2211/1044; C09K 2211/1059; C09K 2211/185; H05B 33/14

USPC .............. 428/690, 691, 917; 427/58, 66; 313/500–512; 257/40, 88–104, 257/E51.001–E51.052; 252/301.16–301.35; 548/439, 440, 442, 548/420, 444, 445

See application file for complete search history.

(56) References Cited

U.S. PATENT DOCUMENTS

| | | | |
|---|---|---|---|
| 8,227,801 B2 | 7/2012 | Xia et al. | |
| 8,251,765 B2 | 8/2012 | Ushikubo et al. | |
| 8,283,856 B2 | 10/2012 | Ushikubo | |
| 8,362,466 B2 | 1/2013 | Ushikubo et al. | |
| 9,082,986 B2 | 7/2015 | Kato et al. | |
| 2003/0118866 A1 | 6/2003 | Oh et al. | |
| 2005/0067955 A1 | 3/2005 | Cho et al. | |
| 2006/0046172 A1 | 3/2006 | Vaitkeviciene et al. | |
| 2006/0051611 A1 | 3/2006 | Brunner et al. | |
| 2006/0073357 A1 | 4/2006 | Brunner et al. | |
| 2006/0088728 A1* | 4/2006 | Kwong | C07D 209/82 428/690 |
| 2006/0180806 A1 | 8/2006 | Arakane et al. | |
| 2008/0131731 A1 | 6/2008 | Igawa et al. | |
| 2008/0242871 A1 | 10/2008 | Kawakami et al. | |
| 2009/0015144 A1* | 1/2009 | Takashima | C07C 13/62 313/504 |
| 2009/0066235 A1* | 3/2009 | Yabunouchi | C07D 209/86 313/504 |
| 2009/0072732 A1 | 3/2009 | Arakane et al. | |
| 2009/0085479 A1 | 4/2009 | Ushikubo | |
| 2009/0102366 A1 | 4/2009 | Ushikubo et al. | |
| 2009/0236980 A1 | 9/2009 | Ohsawa | |
| 2009/0284139 A1 | 11/2009 | Ushikubo et al. | |
| 2009/0302745 A1 | 12/2009 | Otsu et al. | |
| 2010/0051106 A1 | 3/2010 | Kim et al. | |
| 2010/0148165 A1 | 6/2010 | Ushikubo et al. | |
| 2010/0148166 A1 | 6/2010 | Ushikubo et al. | |
| 2010/0200847 A1 | 8/2010 | Kawakami et al. | |
| 2010/0237339 A1 | 9/2010 | Nomura et al. | |
| 2010/0237773 A1 | 9/2010 | Nomura et al. | |
| 2010/0253211 A1* | 10/2010 | Iwakuma | C07C 13/66 313/504 |
| 2011/0031482 A1 | 2/2011 | Furukawa et al. | |
| 2011/0063485 A1 | 3/2011 | Nomura et al. | |
| 2011/0260138 A1 | 10/2011 | Xia et al. | |
| 2011/0278552 A1 | 11/2011 | Numata et al. | |
| 2011/0278555 A1 | 11/2011 | Inoue et al. | |
| 2011/0279020 A1 | 11/2011 | Inoue et al. | |
| 2012/0040482 A1 | 2/2012 | Ushikubo et al. | |
| 2012/0104379 A1 | 5/2012 | Kawakami et al. | |
| 2012/0126205 A1 | 5/2012 | Kawamura et al. | |
| 2012/0126208 A1 | 5/2012 | Kawamura et al. | |
| 2012/0138911 A1 | 6/2012 | Inoue et al. | |
| 2012/0138912 A1 | 6/2012 | Inoue et al. | |
| 2012/0175599 A1 | 7/2012 | Yokoyama et al. | |
| 2012/0181524 A1 | 7/2012 | Kato et al. | |
| 2012/0205642 A1 | 8/2012 | Yokoyama et al. | |
| 2012/0211736 A1 | 8/2012 | Kim et al. | |
| 2012/0223295 A1 | 9/2012 | Inoue et al. | |
| 2012/0235123 A1 | 9/2012 | Lee et al. | |
| 2012/0273767 A1 | 11/2012 | Yokoyama et al. | |

(56) References Cited

U.S. PATENT DOCUMENTS

| | | | |
|---|---|---|---|
| 2012/0302751 | A1 | 11/2012 | Nomura et al. |
| 2012/0305900 | A1 | 12/2012 | Kim et al. |
| 2012/0309984 | A1 | 12/2012 | Kawakami et al. |
| 2013/0009140 | A1 | 1/2013 | Ushikubo |
| 2013/0020565 | A1 | 1/2013 | Numata et al. |
| 2013/0056720 | A1 | 3/2013 | Kim et al. |
| 2013/0075716 | A1 | 3/2013 | Nishimura et al. |
| 2013/0087776 | A1 | 4/2013 | Lee et al. |
| 2013/0092913 | A1 | 4/2013 | Nishimura et al. |
| 2013/0105787 | A1 | 5/2013 | Tanaka et al. |
| 2013/0112950 | A1 | 5/2013 | Yokoyama et al. |
| 2013/0134406 | A1 | 5/2013 | Ushikubo et al. |
| 2013/0214258 | A1 | 8/2013 | Mizuki et al. |
| 2013/0256644 | A1 | 10/2013 | Kim et al. |
| 2013/0270540 | A1 | 10/2013 | Numata |
| 2013/0323870 | A1 | 12/2013 | Kawakami et al. |
| 2014/0054564 | A1 | 2/2014 | Kim et al. |
| 2014/0084271 | A1 | 3/2014 | Lee et al. |
| 2015/0021574 | A1 | 1/2015 | Ito |
| 2015/0021585 | A1 | 1/2015 | Yu et al. |
| 2015/0053933 | A1 | 2/2015 | Lee et al. |
| 2015/0228915 | A1 | 8/2015 | Cho et al. |

FOREIGN PATENT DOCUMENTS

| | | | |
|---|---|---|---|
| CN | 102482216 A | 5/2010 | |
| CN | 101838262 A | 9/2010 | |
| CN | 102421772 A | 4/2012 | |
| CN | 102439004 A | 5/2012 | |
| CN | 102576813 A | 7/2012 | |
| CN | 102598343 A | 7/2012 | |
| CN | 102918677 A | 2/2013 | |
| CN | 102971395 A | 3/2013 | |
| EP | 1 972 619 A1 | 9/2008 | |
| EP | 2 051 310 A1 | 4/2009 | |
| EP | 2 120 275 A2 | 11/2009 | |
| EP | 2 141 214 A2 | 1/2010 | |
| EP | 2 182 039 A2 | 5/2010 | |
| EP | 2 423 209 A1 | 2/2012 | |
| EP | 2 471 771 A1 | 7/2012 | |
| EP | 2 492 985 A1 | 8/2012 | |
| EP | 2 492 986 A1 | 8/2012 | |
| EP | 2 497 811 A2 | 9/2012 | |
| EP | 2 555 272 A1 | 2/2013 | |
| EP | 2 568 030 A2 | 3/2013 | |
| EP | 2 595 208 A1 | 5/2013 | |
| EP | 2 617 712 A1 | 7/2013 | |
| EP | 2 660 890 A1 | 11/2013 | |
| JP | 01-174084 A | 7/1989 | |
| JP | 3-139321 | 6/1991 | |
| JP | 4-357781 | 12/1992 | |
| JP | 8-3547 | 1/1996 | |
| JP | 08003547 A | 1/1996 | |
| JP | 2-814435 | 8/1998 | |
| JP | 11-135260 A | 1/1999 | |
| JP | 11-74084 A | 3/1999 | |
| JP | 11-144873 A | 5/1999 | |
| JP | 11-149987 A | 6/1999 | |
| JP | 11149987 A | 6/1999 | |
| JP | 11-329737 A | 11/1999 | |
| JP | 2002-069044 | 3/2002 | |
| JP | 2002-540572 A | 11/2002 | |
| JP | 2003-081988 A | 3/2003 | |
| JP | 2003-133075 | 5/2003 | |
| JP | 2003-133075 A | 5/2003 | |
| JP | 2003-151774 A | 5/2003 | |
| JP | 2003-515897 A | 5/2003 | |
| JP | 2003133075 A | 5/2003 | |
| JP | 2003-238534 A | 8/2003 | |
| JP | 2003-526876 A | 9/2003 | |
| JP | 2004-71380 A | 3/2004 | |
| JP | 2004-342391 A | 12/2004 | |
| JP | 2005-289914 A | 10/2005 | |
| JP | 2006-143845 A | 6/2006 | |
| JP | 2007-194241 A | 8/2007 | |
| JP | 2007-201189 A | 8/2007 |
| JP | 2007-201193 A | 8/2007 |
| JP | 2007-201194 A | 8/2007 |
| JP | A-2007-288035 | 11/2007 |
| JP | 2008-135498 A | 6/2008 |
| JP | 2008-266309 A | 11/2008 |
| JP | 2008-294161 A | 12/2008 |
| JP | 2010-135467 A | 6/2010 |
| JP | 5562970 B2 | 6/2014 |
| JP | 2015-065248 A | 4/2015 |
| KR | 10-2009-0028943 A | 3/2009 |
| KR | 10-2010-099460 A | 9/2009 |
| KR | 10-2010-0079458 A | 7/2010 |
| KR | 10-2011-0041727 A | 4/2011 |
| KR | 10-2011-0043270 A | 4/2011 |
| KR | 10-2011-0088898 A | 8/2011 |
| KR | 10-2011-0138596 A | 12/2011 |
| KR | 2014-0141951 A | 12/2014 |
| KR | 2015-0001101 A | 1/2015 |
| KR | 2015-0006199 A | 1/2015 |
| KR | 2015-0006722 A | 1/2015 |
| KR | 2015-0007476 A | 1/2015 |
| KR | 2015-0030511 A | 3/2015 |
| TW | 201132739 A1 | 10/2011 |
| TW | 201136921 A1 | 11/2011 |
| TW | 201211003 A1 | 3/2012 |
| TW | 201211034 A1 | 3/2012 |
| TW | 201226407 A1 | 7/2012 |
| WO | WO 2004/055129 A1 | 7/2004 |
| WO | WO 2004/066685 A1 | 8/2004 |
| WO | WO 2004/072205 A2 | 8/2004 |
| WO | WO 2007/119816 A1 | 10/2007 |
| WO | WO 2009/008100 A1 | 1/2009 |
| WO | WO 2009/060779 A1 | 5/2009 |
| WO | WO 2009/116605 A1 | 9/2009 |
| WO | WO 2010/044342 A1 | 9/2009 |
| WO | WO 2009/130991 A1 | 10/2009 |
| WO | WO 2010/004877 A1 | 1/2010 |
| WO | WO 2010/044342 A1 | 4/2010 |
| WO | WO 2010/095621 A1 | 8/2010 |
| WO | WO 2010/114264 A2 | 10/2010 |
| WO | WO 2011/081423 A2 | 12/2010 |
| WO | WO 2011/024451 A1 | 3/2011 |
| WO | WO 2011/048821 A1 | 4/2011 |
| WO | WO 2011/048822 A1 | 4/2011 |
| WO | WO 2011/055934 A2 | 5/2011 |
| WO | WO 2011/149240 A2 | 5/2011 |
| WO | WO 2011/122132 A1 | 10/2011 |
| WO | WO 2011/125680 A1 | 10/2011 |
| WO | WO 2011/132683 A1 | 10/2011 |
| WO | WO 2011/132684 A1 | 10/2011 |
| WO | WO 2011/139055 A2 | 11/2011 |
| WO | WO 2011/155507 A1 | 12/2011 |
| WO | WO 2011/155508 A1 | 12/2011 |
| WO | WO 2012/001986 A1 | 1/2012 |
| WO | WO 2012/011756 A1 | 1/2012 |
| WO | WO 2012/023947 A1 | 2/2012 |
| WO | WO 2012/029253 A1 | 3/2012 |
| WO | WO 2012/036482 A1 | 3/2012 |
| WO | WO 2012/086170 A1 | 6/2012 |
| WO | WO 2012/087007 A1 | 6/2012 |
| WO | WO 2012/108389 A1 | 8/2012 |
| WO | WO 2015/029354 A1 | 3/2015 |
| WO | WO 2015/050173 A1 | 4/2015 |

OTHER PUBLICATIONS

M.A. Baldo, et al. "Very high-efficiency green organic light-emitting devices based on electrophospherescence" Applied Physics Letters, vol. 75 No. 4, 1999, 4 Pages.

Extended European Search Report dated Jun. 27, 2014 in Patent Application No. 12744512.0.

Extended European Search Report dated Jun. 30, 2014 in Patent Application No. 12744393.5.

Combined Chinese Office Action and Search Report dated Sep. 9, 2014 in Patent Application No. 201280008015.1 (with English translation of categories of cited documents).

(56) References Cited

OTHER PUBLICATIONS

Min-Ge Shin, et al., "A new N-fluorenyl carbazole host material: Synthesis, physical properties and applications for highly efficient phosphorescent organic light emitting diodes" Organic Electronics, vol. 12, No. 5, Feb. 2011, pp. 785-793.

Yu Tao, et al., "Research progress of carbazole derivatives as organic electroluminescent materials" New Chemical Materials, vol. 37, No. 5, May 2009, pp. 6-8.

Japanese Office Action dated Apr. 21, 2015 in corresponding Japanese patent application No. 2012-556880, 7 pp.

Combined Office Action and Search Report dated Oct. 14, 2015 in Taiwanese Patent Application No. 101103834 (with English translation of Category of Cited Documents).

Office Action dated Nov. 1, 2016 in Japanese Patent Application No. 2016-084843.

* cited by examiner

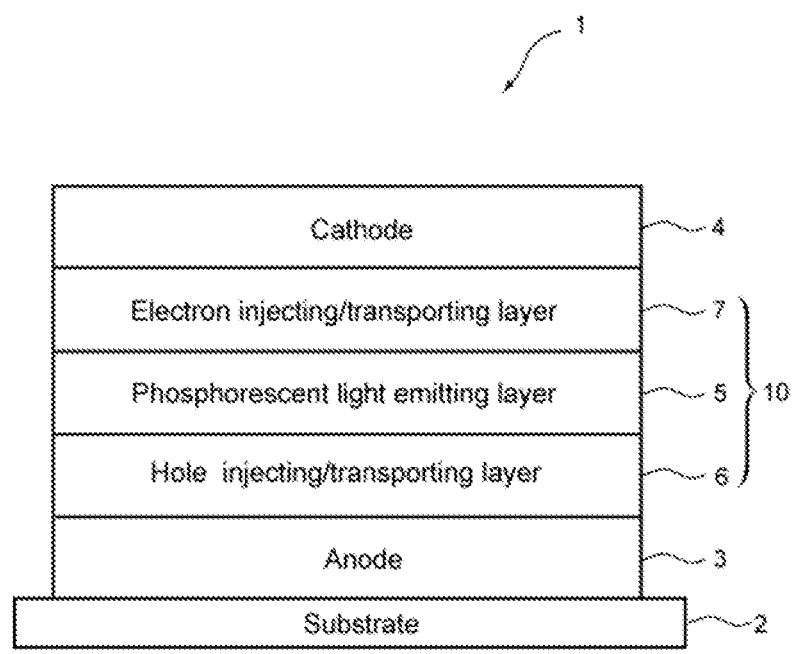

BISCARBAZOLE DERIVATIVE AND ORGANIC ELECTROLUMINESCENT ELEMENT USING SAME

CROSS-REFERENCE TO RELATED APPLICATIONS

The present application is a continuation of U.S. Ser. No. 13/983,687, filed Oct. 2, 2013, which is a National Stage (371) of PCT/JP12/052639, filed Feb. 6, 2012, and claims priority to JP 2011-229117, filed Oct. 18, 2011, JP 2011-024452, filed. Feb. 7, 2011, and JP 2011-024453, filed Feb. 7, 2011.

TECHNICAL FIELD

The present invention relates to a biscarbazole derivative and an organic electroluminescence device using the derivative, in particular, relates to an organic electroluminescence device having high emission efficiency and a long lifetime, and a biscarbazole derivative for realizing the device.

BACKGROUND ART

In recent years, many studies have been actively made on an organic thin-film light emitting device that emits light upon recombination of electrons injected from a cathode and holes injected from an anode in an organic light emitting body interposed between both the electrodes. The light emitting device has been attracting attention because the device is thin and emits light with high luminance under a low driving voltage, and multi-color emission can be obtained by selecting light emitting materials.

When a voltage is applied to an organic electroluminescence device (hereinafter referred to as "organic EL device"), holes and electrons are injected into a light emitting layer from an anode and a cathode, respectively. Then, the holes and the electrons thus injected recombine in the light emitting layer to form excitons. At this time, singlet excitons and triplet excitons are produced at a ratio of 25%:75% according to the statistics theorem of electron spins. When the organic EL devices are classified by their light emission principles, the internal quantum efficiency of a fluorescent organic EL device is said to be at most 25% because the device uses light emission based on a singlet exciton. On the other hand, it has been known that as a phosphorescent organic EL device uses light emission based on a triplet exciton, its internal quantum efficiency reaches 100% when the intersystem crossing from a singlet exciton is efficiently performed.

The device design of organic EL devices has been optimized according to the emission mechanisms of fluorescent devices and phosphorescent devices. In particular, it has been known that a high-performance phosphorescent EL device is not obtained by merely applying the fluorescent device technology because of the difference in their emission properties. The reason for this is generally considered to be as described below.

First, the phosphorescent emission is light emission from a triplet exciton and therefore a compound to be used in the light emitting layer must have a large energy gap. This is because that the energy gap of a certain compound (hereinafter also referred to as "singlet energy") is generally larger than the triplet energy of the compound (energy difference between the lowest excited triplet state and the ground state).

Therefore, to confine the triplet energy of a phosphorescent emitting dopant material efficiently in the device, first, a host material having a larger triplet energy than the triplet energy of the phosphorescent emitting dopant material must be used in the light emitting layer. Further, an electron transporting layer and a hole transporting layer must be provided adjacent to the light emitting layer, and a compound having a larger triplet energy than that of the phosphorescent emitting dopant material must be used in each of the electron transporting layer and the hole transporting layer. Therefore, according to the organic EL device design conventionally employed, a phosphorescent organic EL device using a compound having a larger energy gap than that of a compound used in fluorescent organic EL devices is resulted, this increasing the driving voltage of entire organic EL device.

In addition, a hydrocarbon compound having high oxidation resistance or high reduction resistance that has been useful in a fluorescent device has a small energy gap because of its wide distribution of $\pi$-electron cloud. Therefore, such a hydrocarbon compound is hardly selected in the phosphorescent organic EL device and an organic compound containing a heteroatom such as oxygen or nitrogen is selected instead. However, the organic compound containing a heteroatom shortens the lifetime of phosphorescent organic EL device as compared with that of fluorescent organic EL device.

Further, the device performance is largely affected by the fact that the exciton relaxation rate of a triplet exciton of the phosphorescent emitting dopant material is extremely longer than that of a singlet exciton. Since the relaxation of a singlet exciton which causes emission is fast, the diffusion of the exciton into layers adjacent to the light emitting layer (such as a hole transporting layer and an electron transporting layer) hardly occurs and the efficient light emission is expected. On the other hand, since the emission from a triplet exciton is a spin-forbidden process, and therefore, the relaxation causing the emission is slow, the exciton is apt to diffuse into the adjacent layers, thereby causing the thermal energy deactivation of the exciton, although some specific phosphorescent emitting compounds lead to different results. Therefore, the control of the recombination zone of electrons and holes is more important, as compared with fluorescent organic EL devices.

For the reasons described above, the development of a high-performance phosphorescent organic EL device needs the material selection and device design which are different from those for the fluorescent organic EL devices.

One of the most important problems to be solved in the organic thin-film light emitting device is the compatibility between high emission efficiency and a low driving voltage. To obtain a high-efficiency light emitting device, it has been known to form a light emitting layer by doping a host material with a several percent of a dopant material (Patent Document 1). The host material is required to have a high carrier mobility, a uniform film formability, etc. and the dopant material is required to have a high fluorescent quantum yield, a uniform dispersibility, etc.

A fluorescent (singlet light emission) material has been generally used as the dopant material. To improve the emission efficiency, the use of a phosphorescent (triplet light emission) material has been attempted, and a group of Princeton University has reported that the phosphorescent material provides much higher emission efficiency than obtained by the fluorescent material (Non-Patent Document 1). Many techniques for using a metal complex containing a central metal such as iridium, osmium, rhodium, palladium, and platinum as the phosphorescent dopant material have been disclosed (Patent Documents 2 to 4). As to the host material to be combinedly used with the phosphorescent dopant material, the techniques of using a carbazole derivative, an aromatic amine derivative, a quinolinol metal complex, etc. have been disclosed (Patent Documents 2 to 6). However, a sufficient emission efficiency and a low driving voltage has not been obtained by none of the proposed materials.

A technique of using a biscarbazole derivative as a hole transporting material of a fluorescent device has been disclosed (Patent Document 7). Some patent documents disclose a technique of using a biscarbazole derivative as a host material of phosphorescent device. For example, Patent Document 8 describes a biscarbazole derivative as a host material to be combinedly used with a specific metal complex dopant. However, a high light emission is not obtained by the disclosed biscarbazole derivatives. Patent Document 9 describes the use of a biscarbazole derivative as a host material, in which a substituent for improving the carrier transporting ability of the host material, such as an amino-substituted phenyl group, a naphthyl group, or a fluorenyl group, is introduced into the N-position of a carbazole structure. Although the driving voltage of a light emitting device is reduced by the proposed biscarbazole derivative, its effect on the lifetime is unclear.

PRIOR ART DOCUMENTS

Patent Documents

Patent Document 1: JP 2814435
Patent Document 2: JP 2003-526876A
Patent Document 3: JP 2003-515897A
Patent Document 4: JP 2003-81988A
Patent Document 5: JP 2003-133075A
Patent Document 6: JP 2002-540572A
Patent Document 7: JP 3139321
Patent Document 8: JP 4357781
Patent Document 9: JP 2008-135498A Non-Patent Document Non-Patent Document 1: Applied Physics Letters, 1999, vol. 75, No. 1, p. 4

SUMMARY OF INVENTION

Problem to be Solved

The present invention has been made under such circumstances, and an object of the present invention is to provide an organic electroluminescence device having high emission efficiency and a long lifetime, and a biscarbazole derivative for realizing the device.

Solution to Problem

As a result of extensive studies, the inventors have found that the object is achieved by a biscarbazole derivative having a specific substituent. The present invention is based on this finding.

Namely, the present invention provides the following biscarbazole derivatives, materials for organic electroluminescence devices, and organic electroluminescence devices. The definition of "hydrogen" referred herein includes a deuterium.

1. A biscarbazole derivative represented by formula (1):

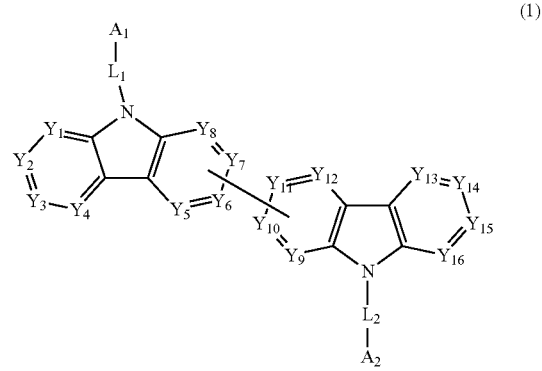

(1)

wherein:
each of $A_1$ and $A_2$ independently represents a substituted or unsubstituted aromatic hydrocarbon group having 6 to 30 ring carbon atoms;
each of $Y_1$ to $Y_{16}$ independently represents C(R) or a nitrogen atom, and each of R groups independently represents a hydrogen atom, a substituent, or a valence bonded to a carbazole skeleton; and
each of $L_1$ and $L_2$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms,
provided that:
at least one of $A_1$, $A_2$ and R represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, a substituted or unsubstituted benzofluorenyl group, or a naphthyl group;
when $Y_1$ to $Y_{16}$ all represent C(R) wherein R is a hydrogen atom, $Y_6$ and $Y_{11}$ are bonded to each other via a single bond, each of $L_1$ and $L_2$ represents a single bond, and $A_1$ represents a phenanthrenyl group, $A_2$ represents a phenyl group, a biphenylyl group, or a naphthyl group; and
when $Y_1$ to $Y_{16}$ all represent C(R) wherein R is a hydrogen atom, $Y_6$ and $Y_{11}$ are bonded to each other via a single bond, each of $L_1$ and $L_2$ represents a single bond, and $A_1$ represents a naphthyl group, $A_1$ and $A_2$ are different from each other;

2. The biscarbazole derivative according to item 1, wherein at least one of $A_1$ and $A_2$ of formula (1) represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, or a substituted or unsubstituted benzofluorenyl group;

3. The biscarbazole derivative according to item 1 or 2, which is represented by formula (2):

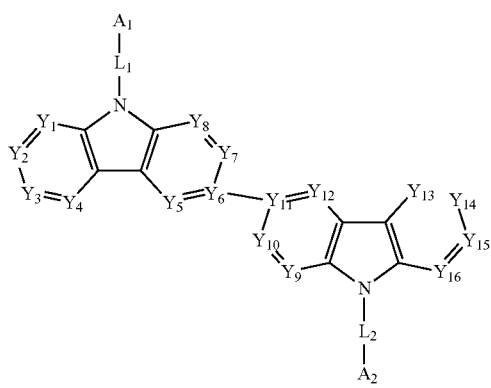

(2)

wherein each of $A_1$, $A_2$, $Y_1$ to $Y_{16}$, $L_1$, and $L_2$ is as defined in formula (1);

4. The biscarbazole derivative according to item 1 or 2, which is represented by formula (3) or (4):

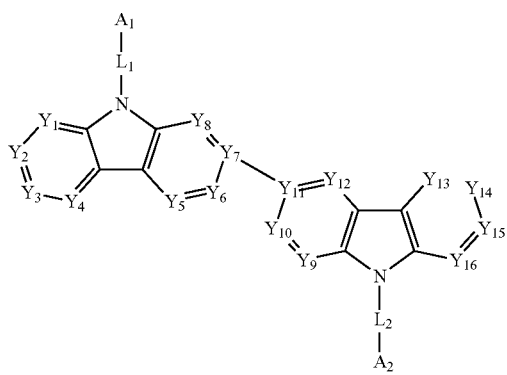

(3)

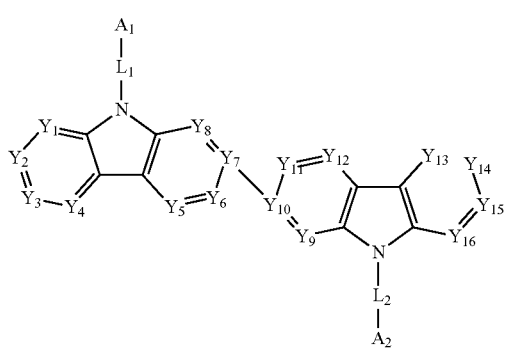

(4)

wherein each of $A_1$, $A_2$, $Y_1$ to $Y_{16}$, $L_1$, and $L_2$ is as defined in formula (1);

5. The biscarbazole derivative according to any one of items 1 to 4, wherein -$L_1$-$A_1$ and -$L_1$-$A_2$ are different from each other;

6. The biscarbazole derivative according to any one of items 1 to 5, wherein each of $L_1$ and $L_2$ represents a divalent linking group;

7. The biscarbazole derivative according to any one of items 1 to 6, wherein $A_1$ represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, or a substituted or unsubstituted benzofluorenyl group, and $A_2$ represents a substituted or unsubstituted aromatic hydrocarbon group having 6 to 30 ring carbon atoms;

8. A biscarbazole derivative represented by formula (1a):

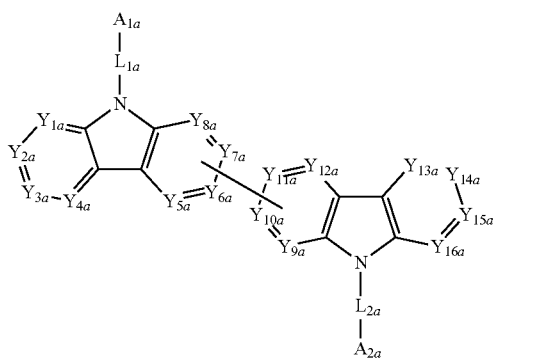

(1a)

wherein:

one of $A_{1a}$ and $A_{2a}$ represents a group represented by formula (a) and the other represents a substituted or unsubstituted fluoranthenyl group, a substituted or unsubstituted benzophenanthrenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, or a substituted or unsubstituted benzofluorenyl group;

each of $Y_{1a}$ to $Y_{16a}$ independently represents C(R) or a nitrogen atom, and each of R groups independently represents a hydrogen atom, a substituent, or a valence bonded to a carbazole skeleton;

each of $L_{1a}$ and $L_{2a}$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms;

(a)

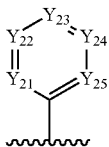

wherein each of $Y_{21}$ and $Y_{25}$ independently represents $C(R_a)$ or a nitrogen atom, and each of $R_a$ groups independently represents a hydrogen atom or a substituent;

9. A material for an organic electroluminescence device comprising the biscarbazole derivative according to any one of items 1 to 8;

10. An organic electroluminescence device comprising a plurality of organic thin-film layers between a cathode and an anode, wherein the organic thin-film layers comprises a light emitting layer and at least one layer of the organic thin-film layers comprises the biscarbazole derivative according to any one of items 1 to 9;

11. An organic electroluminescence device comprising a plurality of organic thin-film layers between a cathode and an anode, wherein the organic thin-film layers comprises a light emitting layer and at least one layer of the organic thin-film layers comprises a biscarbazole derivative represented by formula (10):

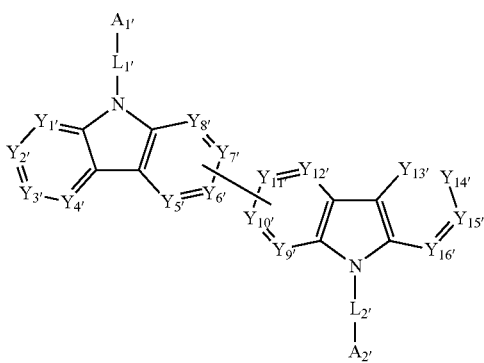

(10)

wherein:

one of $A_{1'}$ and $A_{2'}$ represents a substituted or unsubstituted fluorenyl group and the other represents a substituted or unsubstituted aromatic hydrocarbon group having 6 to 30 ring carbon atoms;

each of $Y_{1'}$ to $Y_{16'}$ independently represents C(R') or a nitrogen atom, and each of R' groups independently represents a hydrogen atom, a substituent, or a valence bonded to a carbazole skeleton; and each of $L_{1'}$ and $L_{2'}$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms;

12. The organic electroluminescence device according to item 10 or 11, wherein the light emitting layer comprises the biscarbazole derivative as a host material;

13. The organic electroluminescence device according to item 12, wherein the light emitting layer comprises a phosphorescent material;

14. The organic electroluminescence device according to item 13, wherein the light emitting layer comprises the host material and the phosphorescent material which is an ortho-metallated complex of a metal atom selected from iridium (Ir), osmium (Os), and platinum (Pt);

15. The organic electroluminescence device according to item 14, wherein the device further comprises an electron injecting layer between the cathode and the light emitting layer, and the electron injecting layer comprises a nitrogen-containing ring derivative;

16. The organic electroluminescence device according to item 15, wherein the device further comprises an electron transporting layer between the cathode and the light emitting layer, and the electron transporting layer comprises the biscarbazole derivative;

17. The organic electroluminescence device according to item 16, wherein the device further comprises a hole transporting layer between the anode and the light emitting layer, and the hole transporting layer comprises the biscarbazole derivative;

18. The organic electroluminescence device according to item 17, wherein the device further comprises a reducing dopant on an interface between the cathode and the organic thin-film layer;

19. A lighting device comprising the organic electroluminescence device according to any one of items 10 to 18; and 20. A display device comprising the organic electroluminescence device according to any one of items 10 to 19.

Effects of Invention

The present invention provides the organic electroluminescence device having high emission efficiency and a long lifetime, and the biscarbazole derivative for realizing the device.

BRIEF DESCRIPTION OF DRAWINGS

The FIGURE is a schematic view illustrating the construction of an example of the organic electroluminescence device (also referred to as "organic EL device") according to the present invention.

EMBODIMENTS FOR CARRYING OUT THE INVENTION

The present invention will be described below in detail.
Structure of Organic El Device The device structure of the organic EL device is first described.

Typical examples of the device structure of organic EL device include:

(1) anode/light emitting layer/cathode;
(2) anode/hole injecting layer/light emitting layer/cathode;
(3) anode/light emitting layer/electron injecting/transporting layer/cathode;
(4) anode/hole injecting layer/light emitting layer/electron injecting/transporting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting/transporting layer/light emitting layer/electron injecting/transporting layer/cathode;

(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting/transporting layer/light emitting layer/insulating layer/cathode; and
(13) anode/insulating layer/hole injecting/transporting layer/light emitting layer/electron injecting/transporting layer/cathode.

Of the above, the structure (8) is preferably used, although not limited thereto.

A space layer may be provided between the light emitting layers to prevent excitons generated in a phosphorescent light emitting layer from diffusing into a fluorescent light emitting layer.

An example of the device structure of the organic EL device of the invention is schematically shown in The FIGURE.

The organic EL device 1 includes a transparent an anode 3, a cathode 4, and an organic thin-film layer 10 disposed between the anode 3 and the cathode 4.

The organic thin-film layer 10 includes a phosphorescent light emitting layer 5 including a phosphorescent host as a host material and a phosphorescent dopant as a phosphorescent material. A layer, such as a hole injecting/transporting layer 6, may be provided between the phosphorescent light emitting layer 5 and the anode 3 while a layer, such as an electron injecting/transporting layer 7, may be provided between the phosphorescent light emitting layer 5 and the cathode 4.

An electron blocking layer may be provided on the anode 3 side of the phosphorescent light emitting layer 5 while a hole blocking layer may be provided on the cathode 4 side of the phosphorescent light emitting layer 5.

With these blocking layers, electrons and holes can be confined in the phosphorescent light emitting layer 5, thereby enhancing the exciton generation in the phosphorescent light emitting layer 5.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer. Representative layered structures of the emission unit are shown below.

(a) Hole transporting layer/light emitting layer(/electron transporting layer);
(b) Hole transporting layer/first phosphorescent light emitting layer/second phosphorescent light emitting layer(/electron transporting layer);
(c) Hole transporting layer/phosphorescent light emitting layer/space layer/fluorescent light emitting layer(/electron transporting layer);
(d) Hole transporting layer/first phosphorescent light emitting layer/second phosphorescent light emitting layer/space layer/fluorescent light emitting layer(/electron transporting layer);
(e) Hole transporting layer/first phosphorescent light emitting layer/space layer/second phosphorescent light emitting layer/space layer/fluorescent light emitting layer(/electron transporting layer); and
(f) Hole transporting layer/phosphorescent light emitting layer/space layer/first fluorescent light emitting layer/second fluorescent light emitting layer(/electron transporting layer).

Representative device structure of the tandem-type organic EL device is shown below:
anode/first emission unit/intermediate layer/second emission unit/cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

In the present invention, a host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures.

Namely, in the present invention, the term "fluorescent host" means a material for constituting a fluorescent emitting layer containing a fluorescent dopant and does not mean a material that can be utilized only as a host for a fluorescent material.

Similarly, the term "phosphorescent host" means a material for constituting a phosphorescent emitting layer containing a phosphorescent dopant and does not mean a material that can be utilized only as a host for a phosphorescent material.

The term "hole injecting/transporting layer" as used herein refers to at least one of a hole injecting layer and a hole transporting layer, and the term "electron injecting/transporting layer" as used herein refers to at least one of an electron injecting layer and an electron transporting layer.

Transparent Substrate

The organic EL device of the invention is formed on a light-transmissive substrate. The light-transmissive substrate serves as a support for the organic EL device and preferably a flat substrate having a transmittance of 50% or more to 400 to 700 nm visible light.

Examples of the substrate include a glass plate and a polymer plate.

The glass plate may include a plate made of soda-lime glass, barium-strontium-containing glass, lead glass, aluminosilicate glass, borosilicate glass, barium borosilicate glass, or quartz.

The polymer plate may include a plate made of polycarbonate, acryl, polyethylene terephthalate, polyether sulfide, or polysulfone.

Anode and Cathode

The anode of the organic EL device injects holes to the hole injecting layer, the hole transporting layer or the light emitting layer, and an anode having a work function of 4.5 eV or more is effective.

Examples of the material for anode include indium tin oxide alloy (ITO), tin oxide (NESA), indium zinc oxide alloy, gold, silver, platinum, and cupper.

The anode is formed by making the electrode material into a thin film by a method, such as a vapor deposition method or a sputtering method.

When getting the light emitted from the light emitting layer through the anode as in the embodiment of the invention, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm.

The cathode is formed preferably from a material having a small work function in view of injecting electrons to the electron injecting layer, the electron transporting layer or the light emitting layer.

Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

Like the anode, the cathode is formed by making the material into a thin film by a method, such as the vapor deposition method and the sputtering method. The emitted light may be taken through the cathode.

Light Emitting Layer

The light emitting layer of the organic EL device combines the following functions:
(i) The injecting function: the function of allowing the injection of holes from the anode or the hole injecting layer and allowing the injection of electrons from the cathode or the electron injecting layer when an electric field is applied;
(ii) The transporting function: the function of transporting injected charges (i.e., electrons and holes) by the force of the electric field; and
(iii) The light emitting function: the function of providing the area for recombination of electrons and holes and leading the recombination to the emission of light.

The light emitting layer may be different in its easiness of hole injection and its easiness of electron injection, and also in the hole transporting ability and the electron transporting ability each being expressed by mobility.

The light emitting layer is formed, for example, by a known method, such as a vapor deposition method, a spin coating method, and LB method.

The light emitting layer is preferably a molecular deposit film.

The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The light emitting layer can be formed also by making a solution of a binder, such as resin, and the material for the light emitting layer in a solvent into a thin film by a method such as spin coating.

The organic EL device of the invention comprises an organic thin film layer. The organic thin film layer comprises one or more layers at least one of which is a light emitting layer. At least one layer of the organic thin film layer comprises at least one kind of phosphorescent material and at least one kind of material for organic electroluminescence devices of the invention to be described later. Preferably, at least one light emitting layer comprises the material for organic electroluminescence devices of the invention and at least one kind of phosphorescent material.

Biscarbazole Derivative

The organic EL device of the present invention has a plurality of organic thin-film layers including a light emitting layer between the cathode and the anode, and at least one layer of the organic thin-film layers comprises the biscarbazole derivative. In the present invention, the definition of "hydrogen" includes a heavy hydrogen. In addition, the biscarbazole derivative of the present invention preferably has only two carbazole structures in a molecule thereof.

The biscarbazole derivative of the present invention has, at a specific position, a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted phenanthrenyl group, a substituted or unsubstituted fluorenyl group, a substituted or unsubstituted binaphthyl group, a substituted or unsubstituted benzonaphthofuranyl group, a substituted or unsubstituted benzonaphthothiophenyl group, a substituted or unsubstituted dibenzophenanthrenyl group, a substituted or unsubstituted naphthotriphenylenyl group, a substituted or unsubstituted benzofluoranthenyl group, a substituted or unsubstituted benzofluorenyl group, or a substituted or unsubstituted phenyl group. Examples thereof include compounds represented by any of formulae (1) to (4), (1'), (1a), and (10).

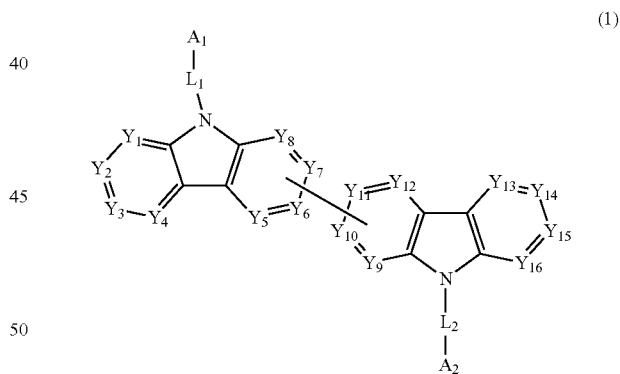

(1)

wherein:

each of $A_1$ and $A_2$ independently represents a substituted or unsubstituted aromatic hydrocarbon group having 6 to 30 ring carbon atoms;

each of $Y_1$ to $Y_{16}$ independently represents C(R) or a nitrogen atom, and each of R groups independently represents a hydrogen atom, a substituent, or a valence bonded to a carbazole skeleton; and each of $L_1$ and $L_2$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that:

at least one of $A_1$, $A_2$ and R represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, a substituted or unsubstituted benzofluorenyl group, or a naphthyl group;

when $Y_1$ to $Y_{16}$ all represent C(R) wherein R is a hydrogen atom, $Y_6$ and $Y_{11}$ are bonded to each other via a single bond, each of $L_1$ and $L_2$ represents a single bond, and $A_1$ represents a phenanthrenyl group, $A_2$ represents a phenyl group, a biphenylyl group, or a naphthyl group; and when $Y_1$ to $Y_{16}$ all represent C(R) wherein R is a hydrogen atom, $Y_6$ and $Y_{11}$ are bonded to each other via a single bond, each of $L_1$ and L represents a single bond, and $A_1$ represents a naphthyl group, $A_1$ and $A_2$ are different from each other In formulae (1) and (1'), at least one of $Y_1$ to $Y_4$ represents C(R), at least one of $Y_5$ to $Y_8$ represents C(R), at least one of $Y_9$ to $Y_{12}$ represents C(R), and at least one of $Y_{13}$ to $Y_{16}$ represent C(R).

In addition, at least one of $Y_5$ to $Y_8$ represents C(R) and at least one of $Y_9$ to $Y_{12}$ represents C(R), wherein two R groups represent valences which are bonded to each other.

The R groups in formulae (1) and (1') may be the same or different.

In formula (1a), at least one of $Y_{1a}$ to $Y_{4a}$ represents C(R), at least one of $Y_{5a}$ to $Y_{8a}$ represents C(R), at least one of $Y_{9a}$ to $Y_{12a}$ represents C(R), and at least one of $Y_{13a}$ to $Y_{16a}$ represents C(R).

In addition, at least one of $Y_{5a}$ to $Y_{8a}$ represents C(R) and at least one of $Y_{9a}$ to $Y_{12a}$ represents C(R), wherein two R groups represent valences which are bonded to each other.

The R groups in formula (1a) may be the same or different.

In formula (10), at least one of $Y_{1'}$ to $Y_{4'}$ represents C(R'), at least one of $Y_{5'}$ to $Y_{8'}$ represents C(R'), at least one of $Y_{9'}$ to $Y_{12'}$ represents C(R'), and at least one of $Y_{13'}$ to $Y_{16'}$ represents C(R').

In addition, at least one of $Y_{5'}$ to $Y_{8'}$ represents C(R') and at least one of $Y_{9'}$ to $Y_{12'}$ represents C(R'), wherein two R' groups represent valences which are bonded to each other.

The R' groups in formula (10) may be the same or different.

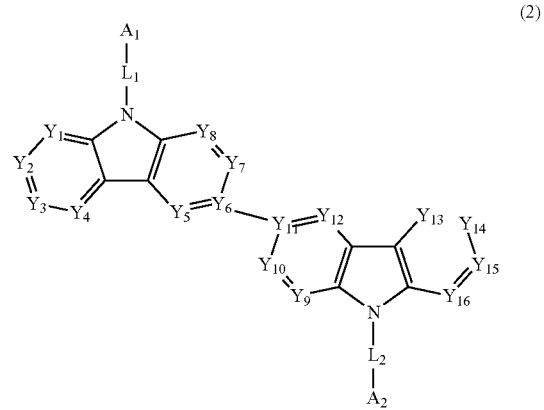

(2)

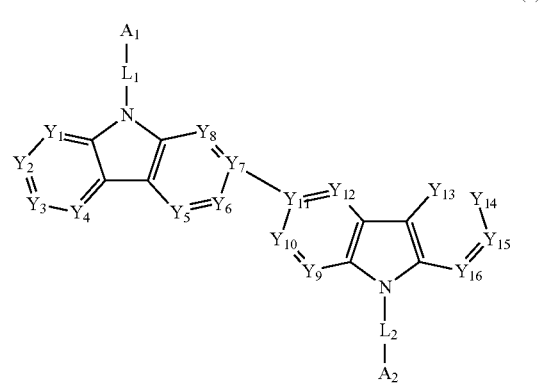

(3)

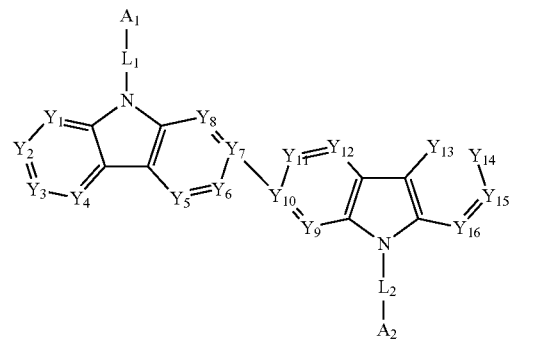

(4)

wherein each of $A_1$, $A_2$, $Y_1$ to $Y_{16}$, $L_1$, and $L_2$ in formulae (2) to (4) is as defined or formula (1).

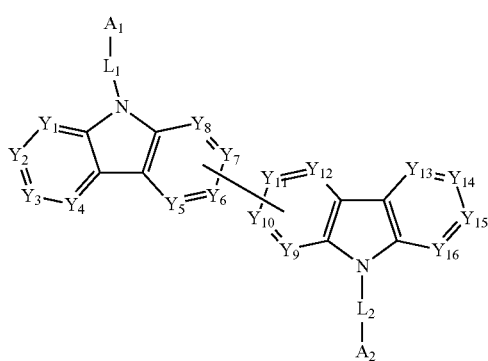

(1')

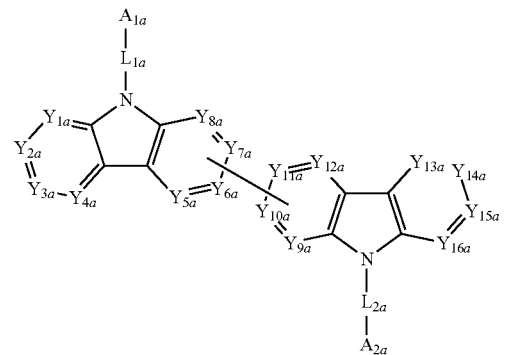

(1a)

wherein:

each of $A_1$ and $A_2$ independently represents a substituted or unsubstituted aromatic hydrocarbon group having 6 to 30 ring carbon atoms or a substituted or unsubstituted aromatic heterocyclic group having 2 to 30 ring carbon atoms;

each of $Y_1$ to $Y_{16}$ independently represents C(R) or a nitrogen atom, and each of R groups independently represents a hydrogen atom, a substituent, or a valence bonded to a carbazole skeleton; and each of $L_1$ and $L_2$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms, provided that:

at least one of $A_1$, $A_2$ and R represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted phenanthrenyl group, a substituted or unsubstituted fluorenyl group, a substituted or unsubstituted binaphthyl group, a substituted or unsubstituted benzonaphthofuranyl group, a substituted or unsubstituted benzonaphthothiophenyl group, a substituted or unsubstituted dibenzophenanthrenyl group, a substituted or unsubstituted naphthotriphenylenyl group, a substituted or unsubstituted benzofluorenyl group, or a substituted or unsubstituted phenyl group;

when $Y_1$ to $Y_{16}$ all represent C(R) wherein R is a hydrogen atom, $Y_6$ and $Y_{11}$ are bonded to each other via a single bond, each of $L_1$ and $L_2$ represents a single bond, and $A_1$ represents a phenanthrenyl group, $A_2$ does not represent a phenanthrenyl group;

when $Y_1$ to $Y_{16}$ all represent C(R), $Y_6$ and $Y_{11}$ are bonded to each other via a single bond, and each of $L_1$ and $L_2$ represents a single bond, each of R groups does not represent a fluorenyl group; and when $A_1$ represents a fluorenyl group, $A_2$ does not represent a phenyl group, a naphthyl group, or a fluorenyl group.

wherein:

one of $A_{1a}$ and $A_{2a}$ represents a group represented by formula (a) and the other represents a substituted or unsubstituted fluoranthenyl group, a substituted or unsubstituted benzophenanthrenyl group, a substituted or unsubstituted picenyl group, a substituted or unsubstituted benzo[b]fluoranthenyl group, a substituted or unsubstituted phenanthrenyl group, a substituted or unsubstituted binaphthyl group, a substituted or unsubstituted dibenzophenanthrenyl group, a substituted or unsubstituted naphthotriphenylenyl group, or a substituted or unsubstituted benzofluorenyl group;

each of $Y_{1a}$ to $Y_{16a}$ independently represents C(R) or a nitrogen atom, and each of R groups independently represents a hydrogen atom, a substituent, or a valence bonded to a carbazole skeleton;

each of $L_{1a}$ and $L_{2a}$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms:

(a)

wherein each of $Y_{21}$ and $Y_{25}$ independently represents $C(R_a)$ or a nitrogen atom, and each of $R_a$ groups independently represents a hydrogen atom or a substituent.

The details of $A_{1a}$, $A_{2a}$, $Y_{1a}$ to $Y_{16a}$, $L_{1a}$, and $R_a$ in formulae (1a) and (a) are the same as those of $A_1$, $A_2$, $Y_1$ to $Y_{16}$, $L_1$, $L_2$, and R in formula (1).

When one of $A_{1a}$ and $A_{2a}$ represents a group represented by formula (a) and the other represents a group including a large molecular weight fused ring, such as a triphenylenyl group and a chrysenyl group, the compound represented by formula (1a) has an excessively large molecular weight, increasing the vapor deposition temperature and therefore likely to increase the amount of thermally decomposed components. Therefore, when one of $A_{1a}$ and $A_{2a}$ represents a group represented by formula (a), the other preferably represents a substituted or unsubstituted fluoranthenyl group or a substituted or unsubstituted phenanthrenyl group.

(10)

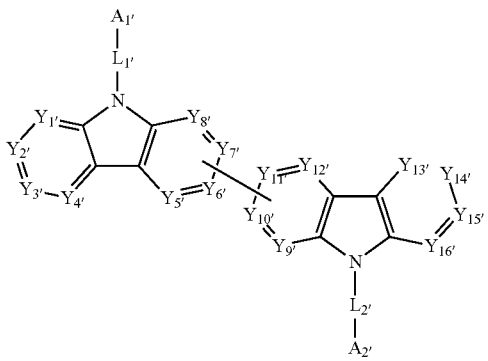

wherein:
one of $A_{1'}$ and $A_{2'}$ represents a substituted or unsubstituted naphthyl group or a substituted or unsubstituted fluorenyl group and the other represents a substituted or unsubstituted aromatic hydrocarbon group having 6 to 30 ring carbon atoms;
each of $Y_{1'}$ to $Y_{16'}$ independently represents C(R') or a nitrogen atom, and each of R' groups independently represents a hydrogen atom, a substituent, or a valence bonded to a carbazole skeleton; and
each of $L_{1'}$ and $L_{2'}$ independently represents a single bond, a substituted or unsubstituted, divalent aromatic hydrocarbon group having 6 to 30 ring carbon atoms, or a substituted or unsubstituted, divalent aromatic heterocyclic group having 2 to 30 ring carbon atoms.

The details of $A_{1'}$, $A_{2'}$, $L_{1'}$, $L_{2'}$, $Y_{1'}$ to $Y_{16'}$, and R' in formula (10) are the same as those of $A_1$, $A_2$, $L_1$, $L_2$, $Y_1$ to $Y_{16}$, and R in formula (1).

In formulae (1) to (4) and (1'), at least one of $A_1$, $A_2$ and R preferably represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted benzofuranyl group, a substituted or unsubstituted dibenzofuranyl group, a substituted or unsubstituted benzothiophenyl group, a substituted or unsubstituted dibenzothiophenyl group, a substituted or unsubstituted phenanthrenyl group, a substituted or unsubstituted fluorenyl group, or a substituted or unsubstituted binaphthyl group, because these groups are moderately bulky. More preferably, at least one of $A_1$ and $A_2$ represents a substituted or unsubstituted fluoranthenyl group, a substituted or unsubstituted triphenylenyl group, a substituted or unsubstituted benzophenanthrenyl group, a substituted or unsubstituted benzotriphenylenyl group, a substituted or unsubstituted dibenzotriphenylenyl group, a substituted or unsubstituted chrysenyl group, a substituted or unsubstituted benzochrysenyl group, a substituted or unsubstituted picenyl group, a substituted or unsubstituted benzo[b]fluoranthenyl group, a substituted or unsubstituted benzofuranyl group, a substituted or unsubstituted dibenzofuranyl group, a substituted or unsubstituted benzothiophenyl group, a substituted or unsubstituted dibenzothiophenyl group, or a substituted or unsubstituted binaphthyl group.

Also preferably, each of $A_1$ and $A_2$ in formulae (1) to (4) and (1') independently represents a substituted or unsubstituted fluoranthenyl group, a substituted or unsubstituted triphenylenyl group, a substituted or unsubstituted benzotriphenylenyl group, a substituted or unsubstituted benzophenanthrenyl group, a substituted or unsubstituted dibenzofuranyl group, or a substituted or unsubstituted dibenzothiophenyl group.

In addition, $-L_1-A_1$ and $-L_2-A_2$ in formulae (1) to (4) and (1') are preferably different from each other.

The substituted or unsubstituted phenyl group for any of $A_1$, $A_2$ and R is preferably a phenyl group substituted by an aromatic hydrocarbon group having 10 to 30 ring carbon atoms and particularly preferably a naphthylphenyl group.

When at least one of $A_1$ and $A_2$ in formulae (1) to (4) and (1') represents a group represented by formula (a), the biscarbazole derivative is particularly preferred as a host material to be used in combination with a green emitting dopant.

In formula (a), $Y_{21}$ and/or $Y_{25}$ preferably represents a nitrogen atom, and each of $Y_{22}$ and $Y_{24}$ more preferably represents $C(R_a)$.

Specific examples of the substituent which $A_1$ and $A_2$ in formulae (1) to (4) and (1') may have and the substituents represented by R and $R_a$ include a fluorine atom; a cyano group; a substituted or unsubstituted, linear, branched, or cyclic alkyl group having 1 to 20 carbon atoms; a linear, branched, or cyclic alkylene group having 1 to 20 carbon atoms; a linear, branched, or cyclic, divalent, unsaturated hydrocarbon group having 1 to 20 carbon atoms; a substituted or unsubstituted, linear, branched, or cyclic alkoxy group having 1 to 20 carbon atoms; a substituted or unsubstituted, linear, branched, or cyclic haloalkyl group having 1 to 20 carbon atoms; a substituted or unsubstituted, linear, branched, or cyclic haloalkoxy group having 1 to 20 carbon atoms; a substituted or unsubstituted, linear, branched, or cyclic alkylsilyl group having 1 to 10 carbon atoms; a substituted or unsubstituted arylsilyl group having 6 to 30 carbon atoms; a substituted or unsubstituted aromatic hydrocarbon group having 6 to 30 ring carbon atoms; and a substituted or unsubstituted aromatic heterocyclic group having 2 to 30 ring carbon atoms. In addition, a plurality of substituents of any such kind may exist, and when the plurality of substituents exist, the substituents may be the same or different from each other.

The R groups on adjacent ring carbon atoms may be bonded to each other to form a ring structure together with the ring carbon atoms.

Examples of the linear, branched, or cyclic alkyl group having 1 to 20 carbon atoms include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a cyclopentyl group, a cyclohexyl group, a cyclooctyl group, a 3,5-tetramethylcyclohexyl group, a trifluoromethyl group, a 2,2,2-trifluoroethyl group, and a 1,1,1,3,3,3-hexafluoro-2-propyl group.

Examples of the linear, branched, or cyclic alkylene group having 1 to 20 carbon atoms include an ethylene group, a propylene group, and a butylene group.

Examples of the linear, branched, or cyclic, divalent unsaturated hydrocarbon group having 1 to 20 carbon atoms include a 1,3-butadiene-1,4-diyl group.

Examples of the linear, branched, or cyclic alkylsilyl group having 1 to 10 carbon atoms include a trimethylsilyl group, a triethylsilyl group, a tributylsilyl group, a dimethylethylsilyl group, a dimethylisopropylsilyl group, a dimethylpropylsilyl group, a dimethylbutylsilyl group, a dimethyl-t-butylsilyl group, and a diethylisopropylsilyl group.

Examples of the arylsilyl group having 6 to 30 carbon atoms include a phenyldimethylsilyl group, a diphenylmethylsilyl group, a diphenyl-t-butylsilyl group, and a triphenylsilyl group.

Examples of the halogen atom include a fluorine atom.

Examples of the aromatic heterocyclic group having 2 to 30 ring carbon atoms include non-fused aromatic heterocyclic and fused aromatic heterocyclic groups, more specifically, a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a thienyl group, and residues of a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, and a benzo[c]dibenzofuran ring.

Examples of the aromatic hydrocarbon group having 6 to 30 ring carbon atoms include non-fused aromatic hydrocarbon groups and fused aromatic hydrocarbon groups, more specifically, a phenyl group, a naphthyl group, a phenanthryl group, a biphenyl group, a terphenyl group, a quaterphenyl group, a fluoranthenyl group, a triphenylenyl group, a phenanthrenyl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl group.

Examples of the divalent linking group represented by $L_1$ and $L_2$ in formulae (1) to (4) and (1') include a substituted or unsubstituted, divalent aromatic hydrocarbon group having 6 to 30 ring carbon atoms and a substituted or unsubstituted, divalent aromatic heterocyclic group having 2 to 30 ring carbon atoms.

Examples of the divalent aromatic hydrocarbon group having 6 to 30 ring carbon atoms include groups obtained by making the examples of the aromatic hydrocarbon group having 6 to 30 ring carbon atoms mentioned above into divalent groups.

In addition, specific examples of the divalent aromatic heterocyclic group having 2 to 30 ring carbon atoms include groups obtained by making the examples of the aromatic heterocyclic group having 2 to 30 ring carbon atoms mentioned above into divalent groups.

In each of formulae (1) to (4) and (1'), $Y_1$ to $Y_{16}$ all preferably represent C(R).

In each of formulae (1) to (4) and (1'), the number of substituents represented by R in $Y_1$ to $Y_8$ or in $Y_9$ to $Y_{16}$ is preferably 0 to 2, more preferably 0 or 1.

Specific examples of the biscarbazole derivative of the present invention represented by any one of formulae (1) to (4), (1'), and (10) include the following compounds. In the following structural formulae, D represents a heavy hydrogen (deuterium).

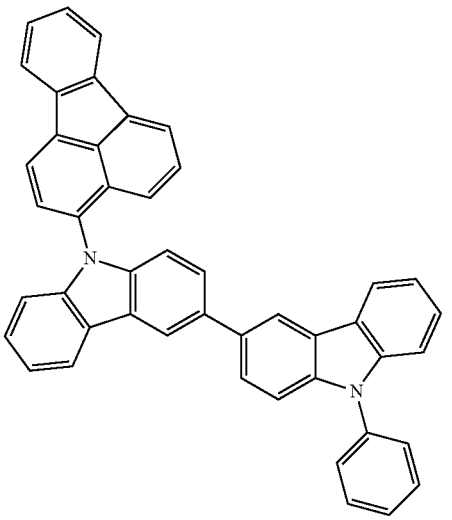

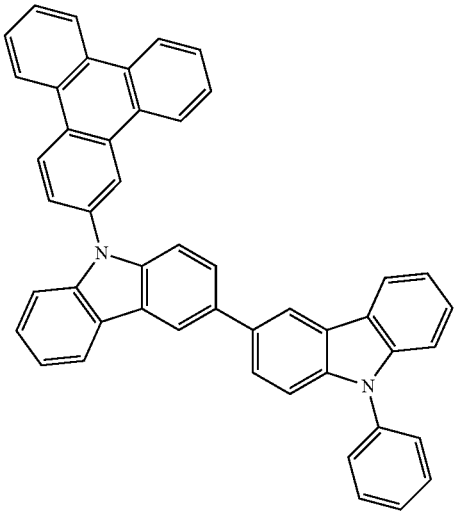

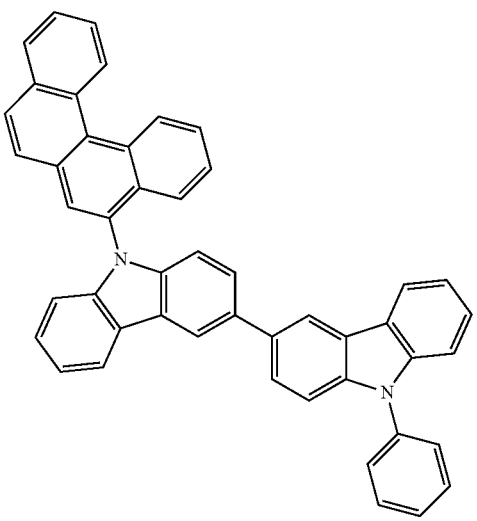

-continued
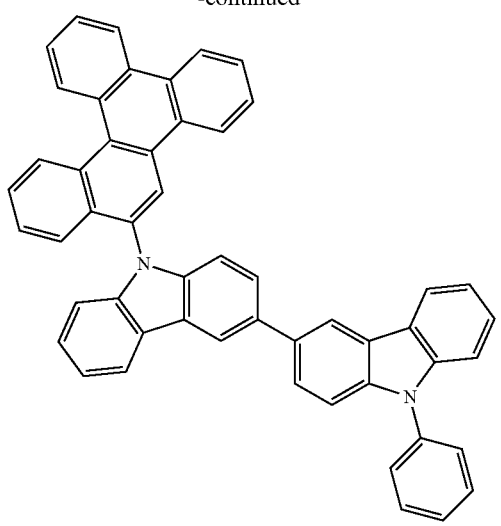
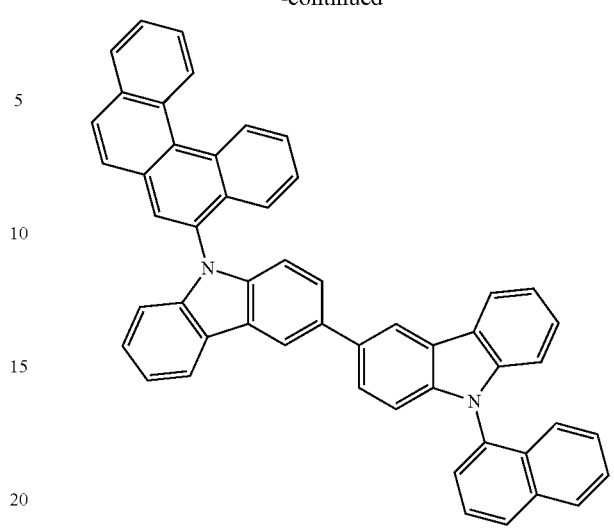
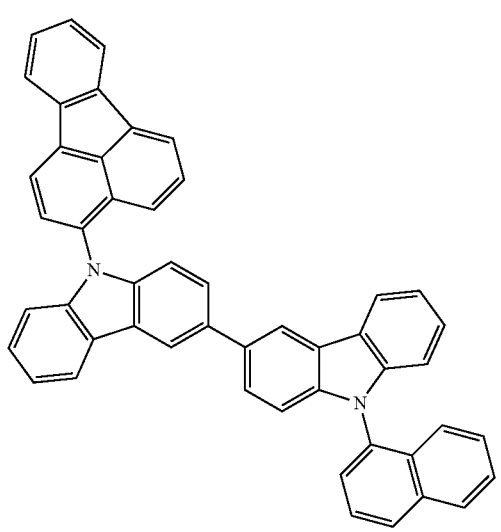
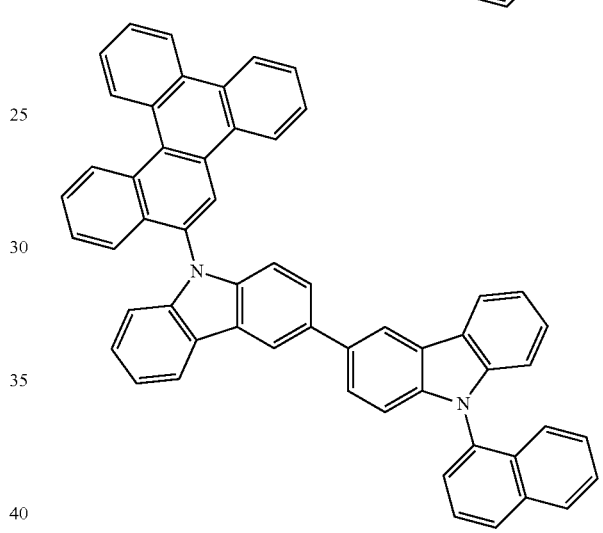
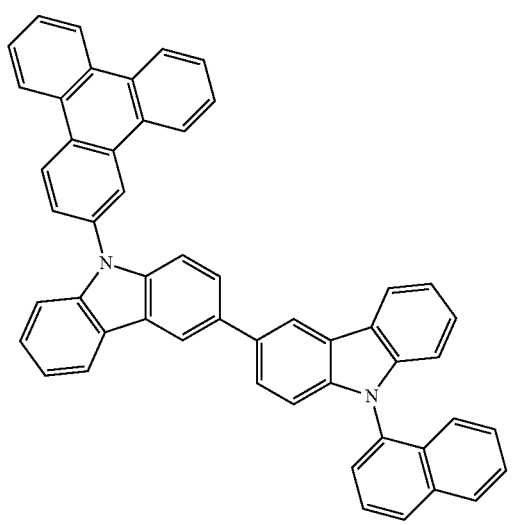
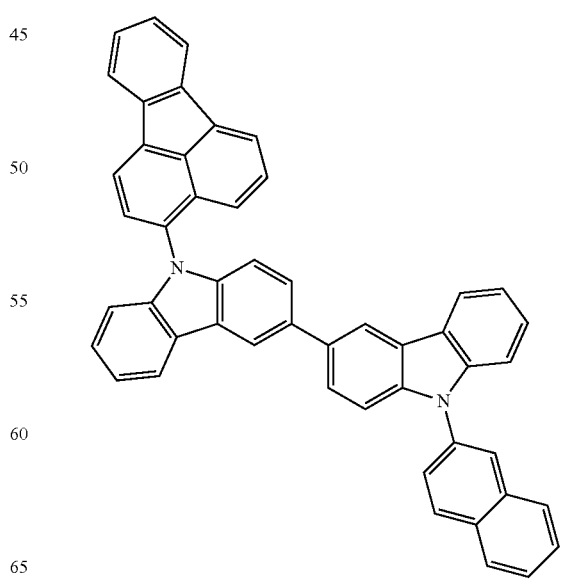

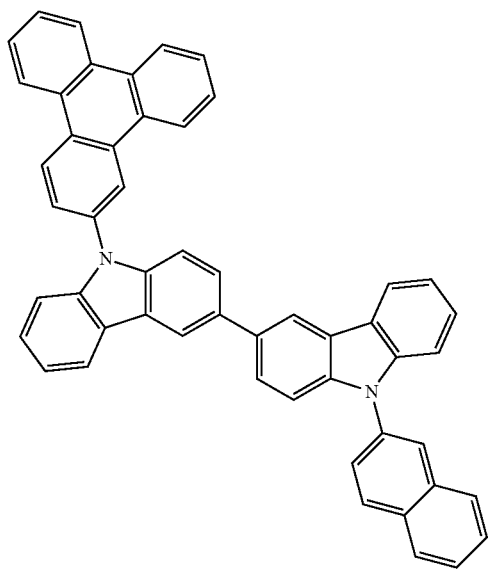
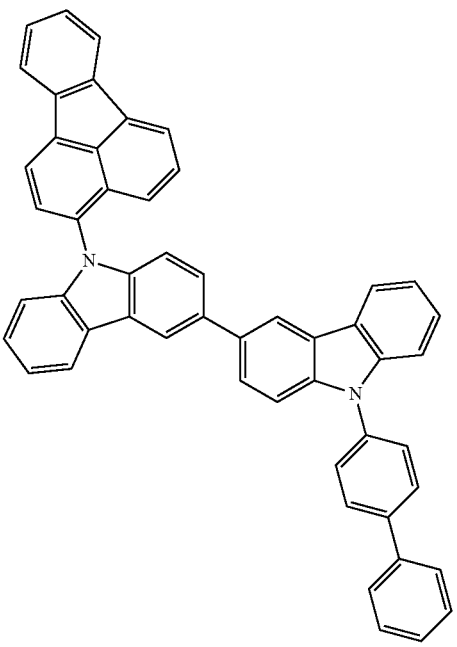

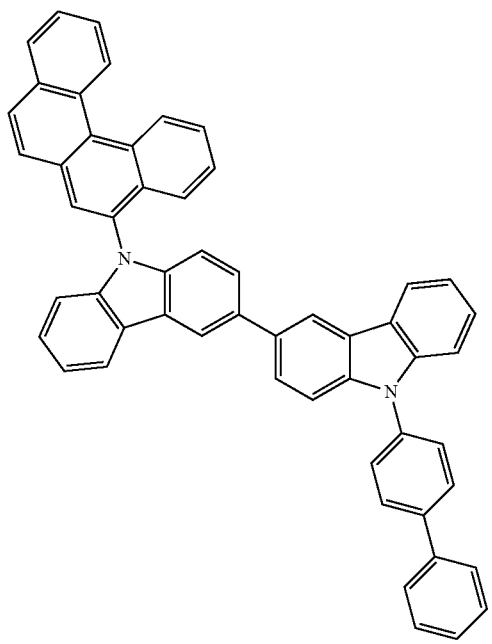
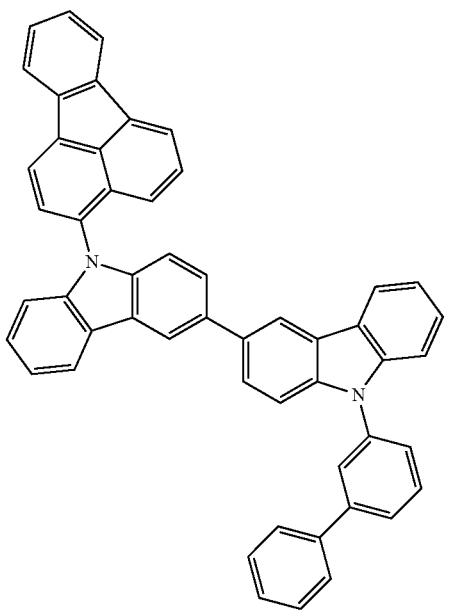
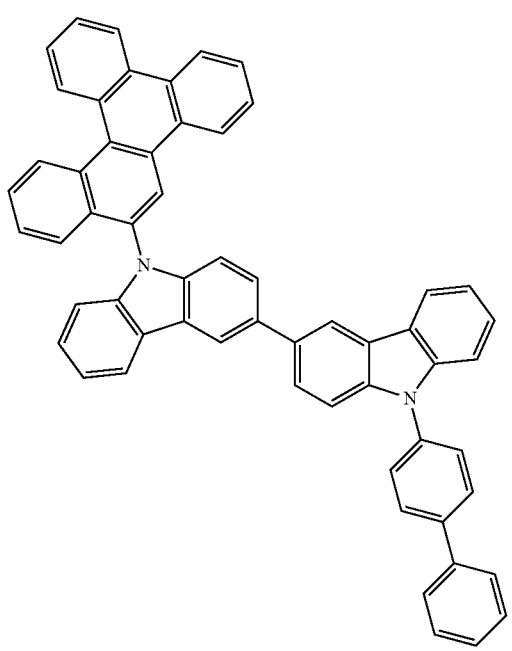
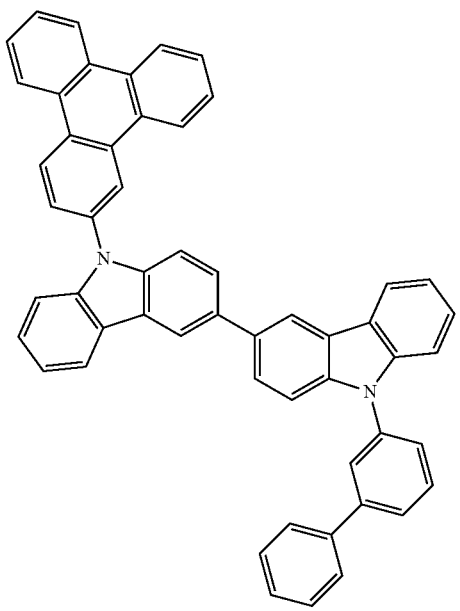

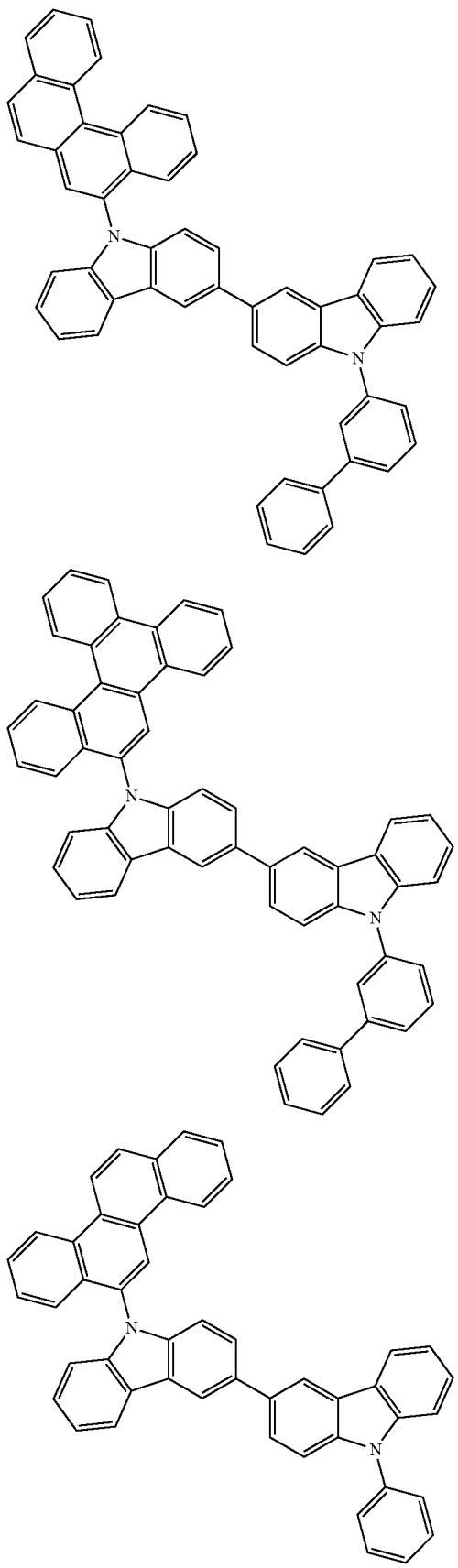
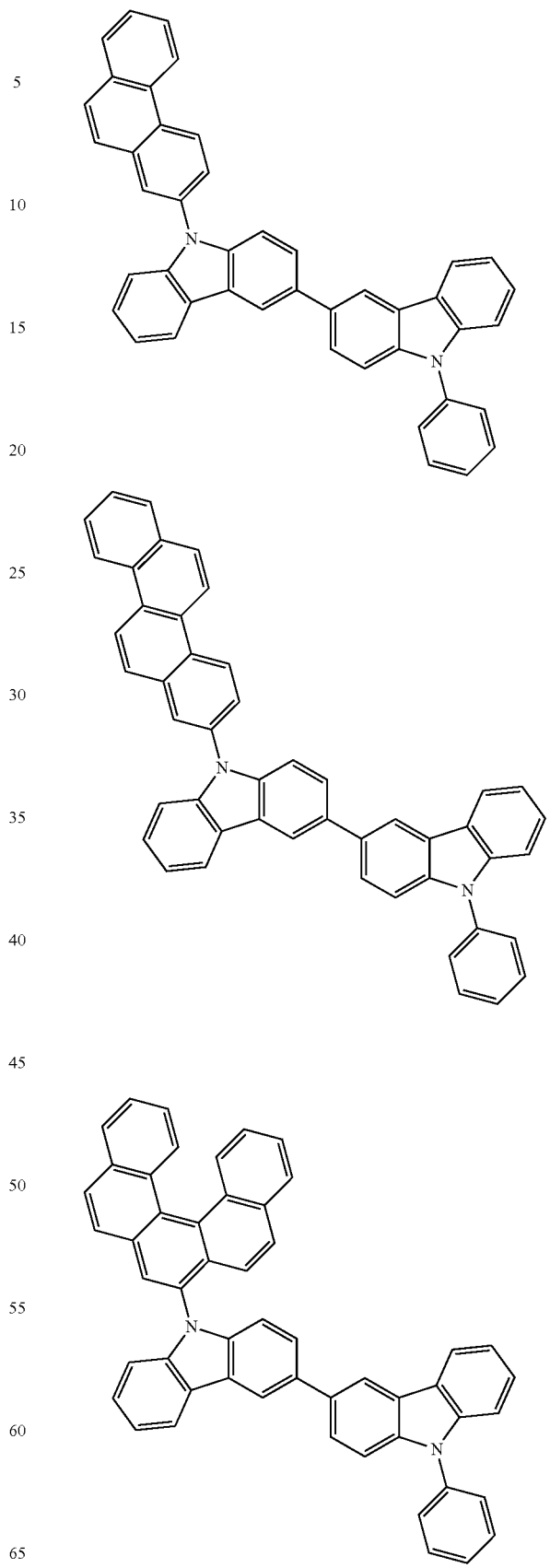

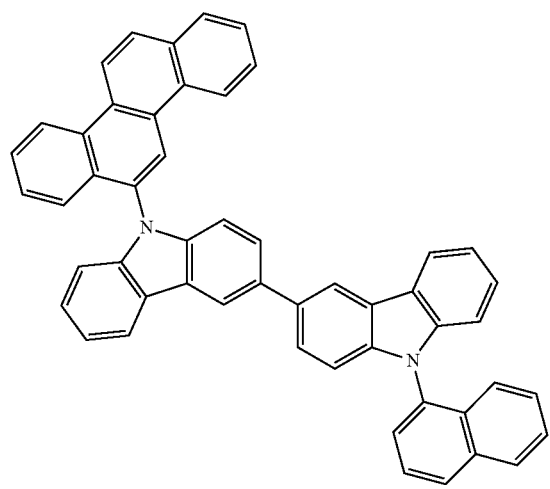
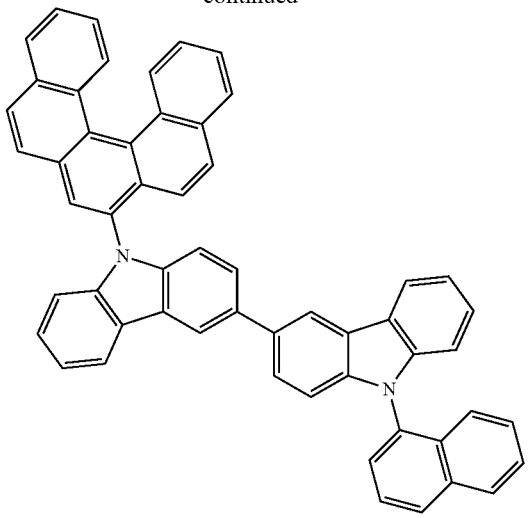
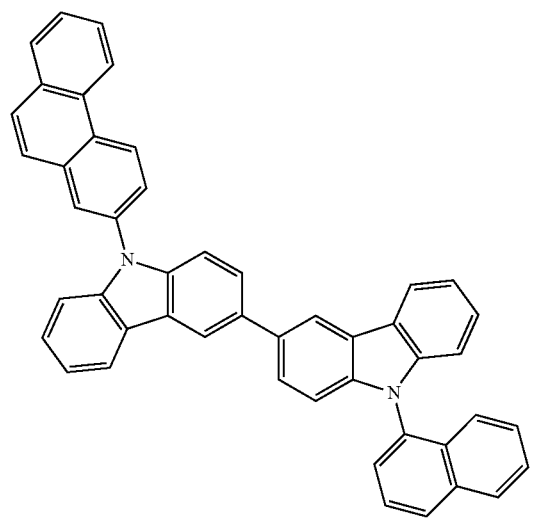
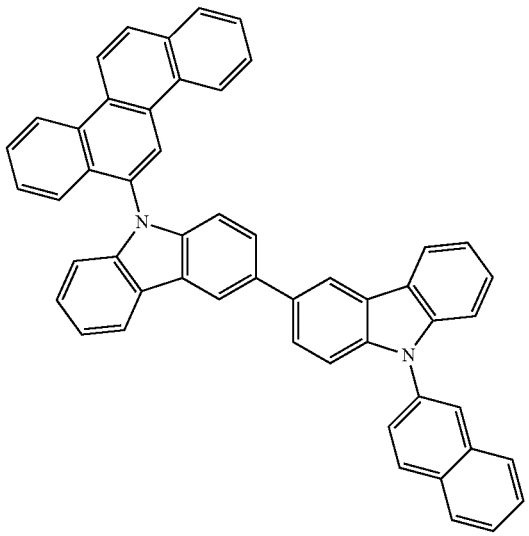
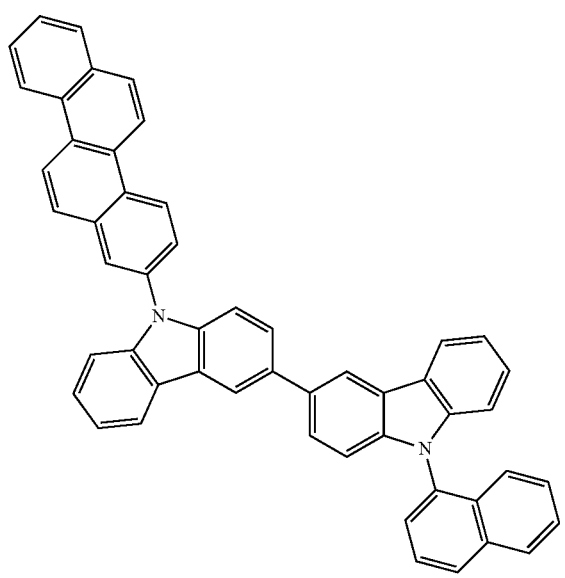
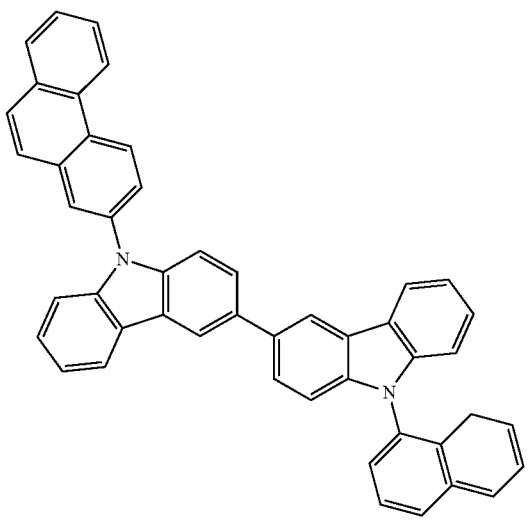

31
-continued
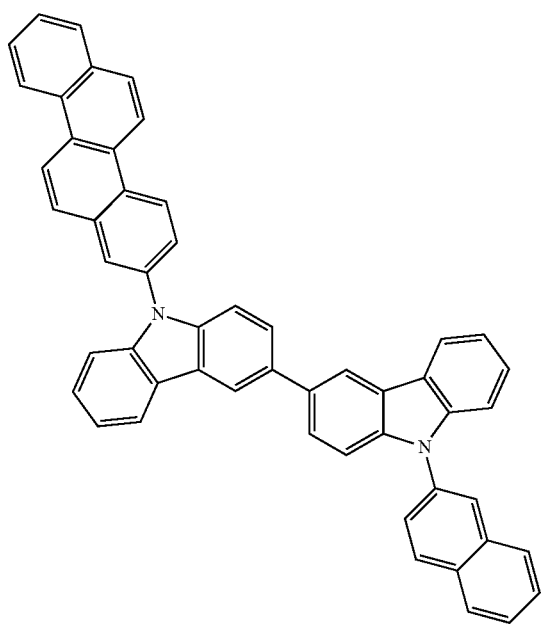
32
-continued
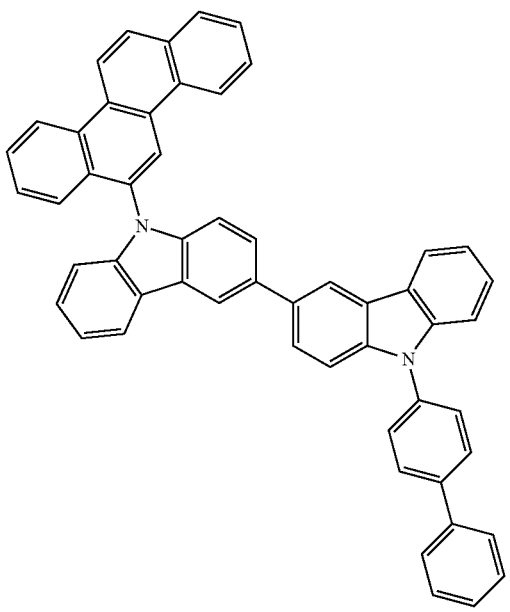
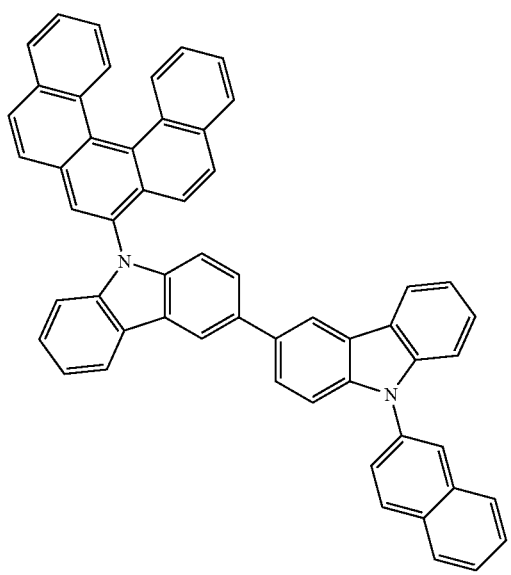
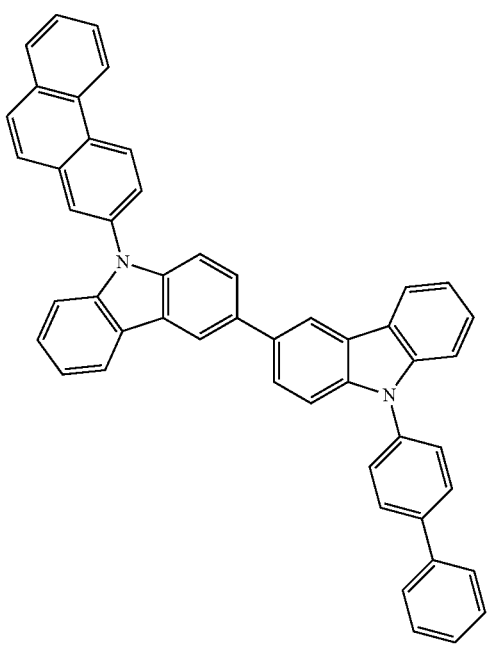

33
-continued
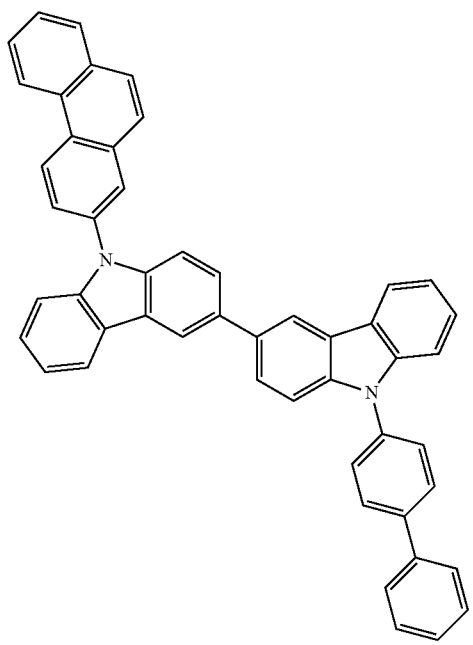
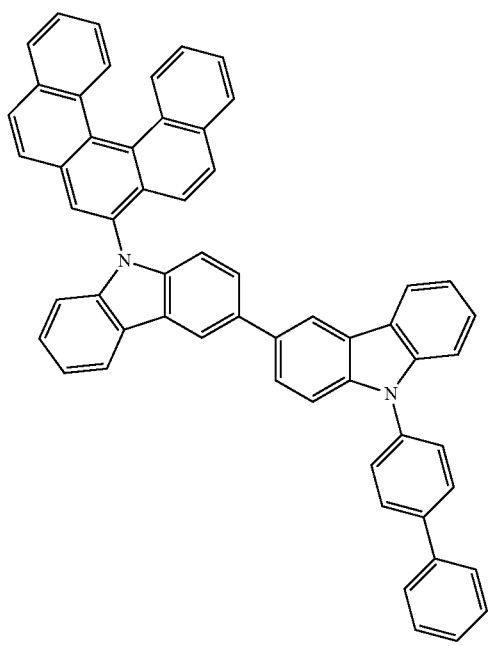
34
-continued
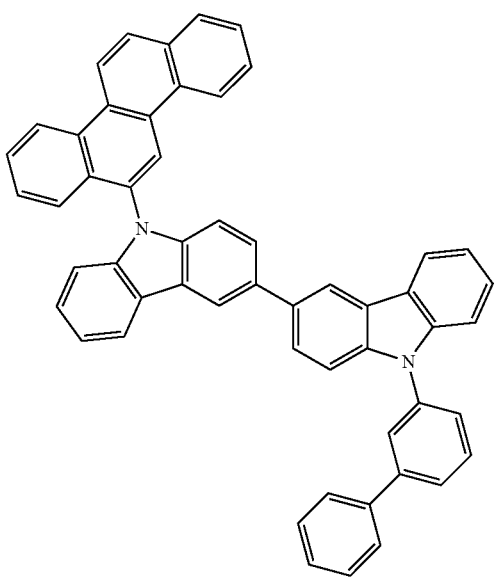
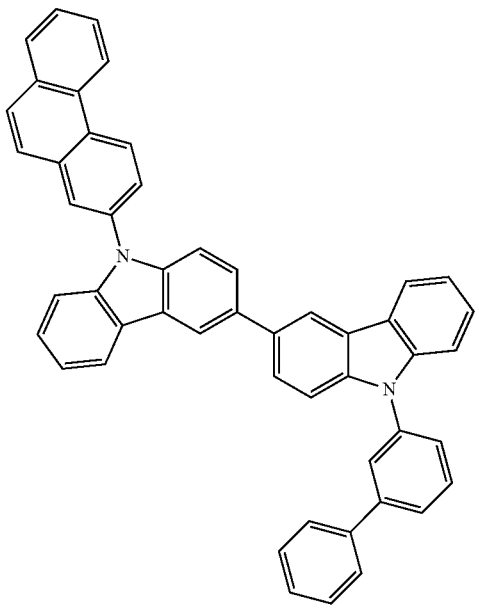

35
-continued
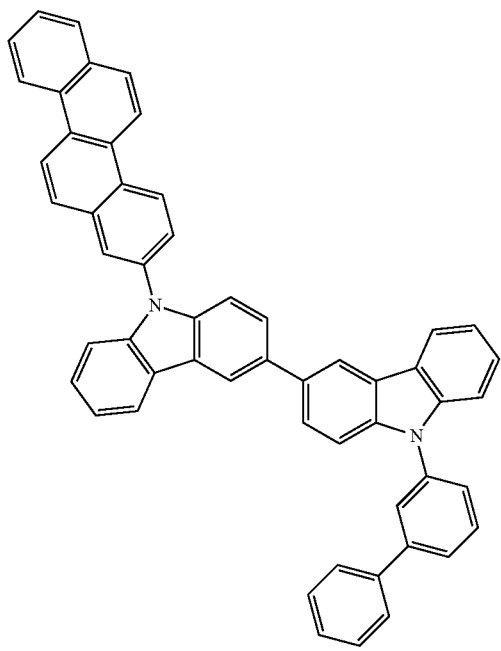
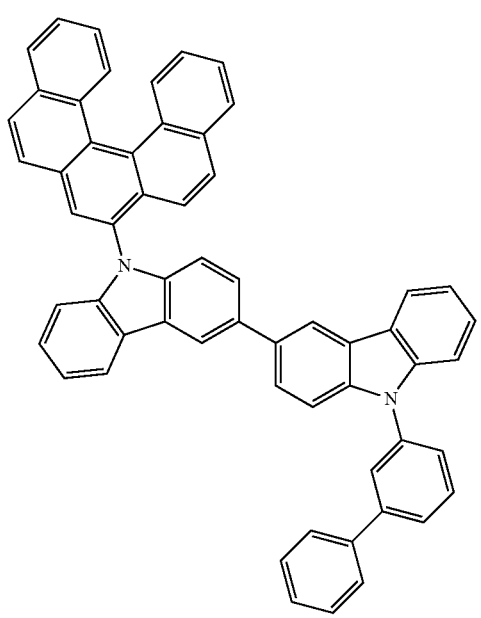
36
-continued
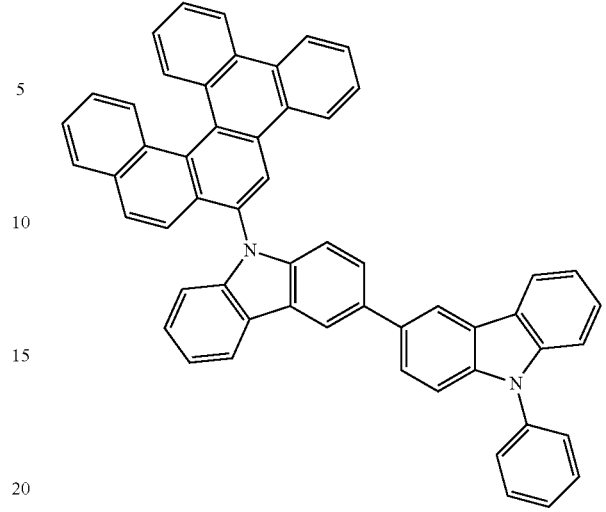
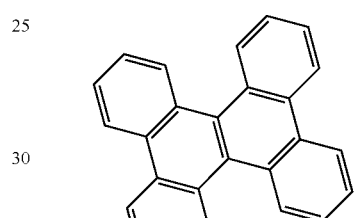
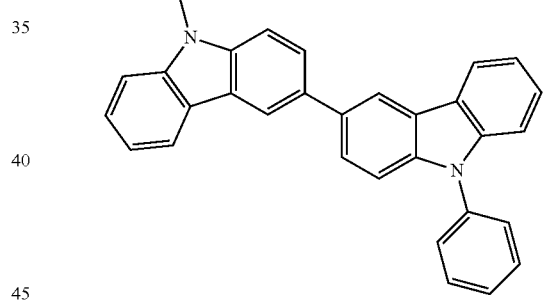
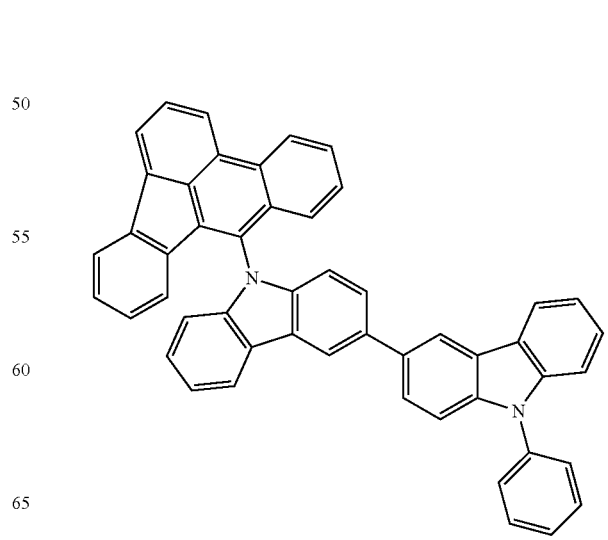

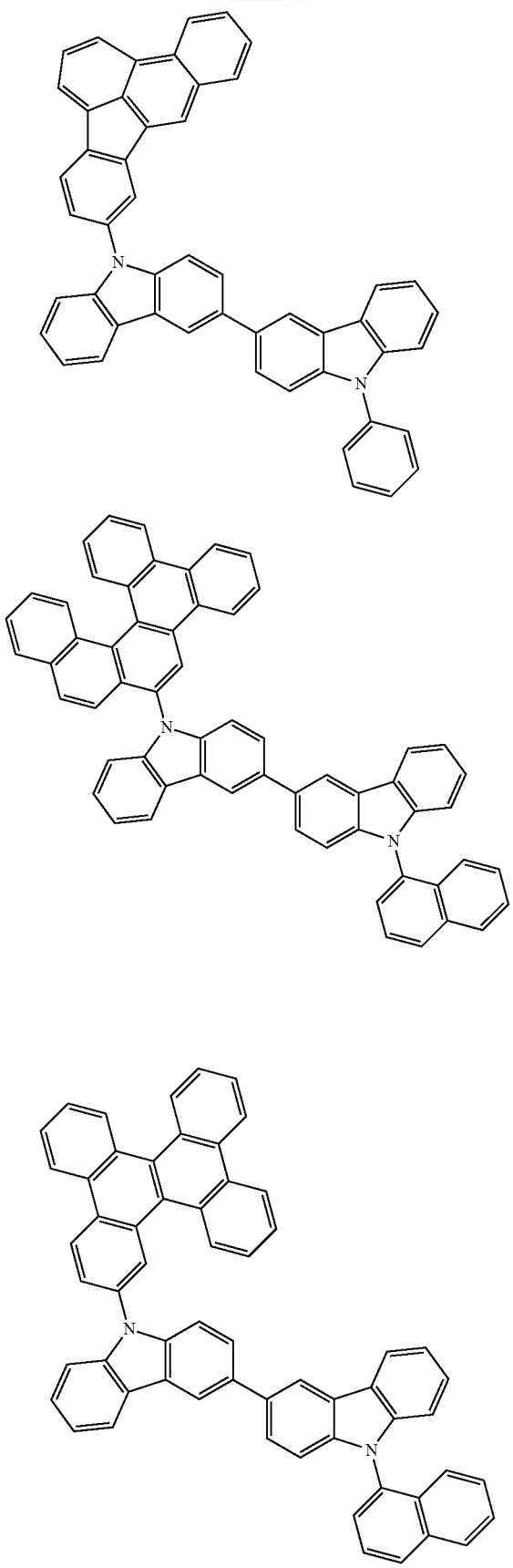
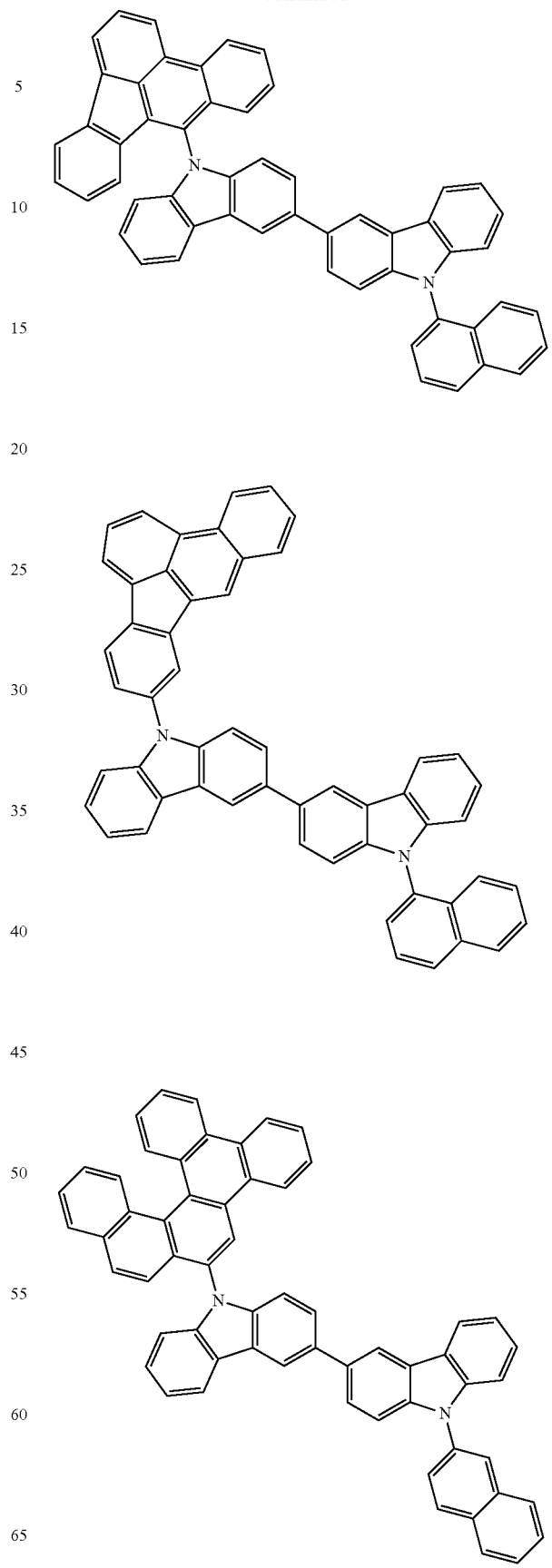

39
-continued
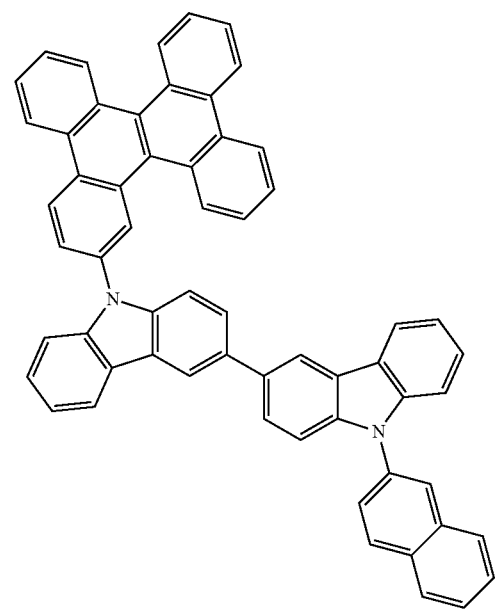
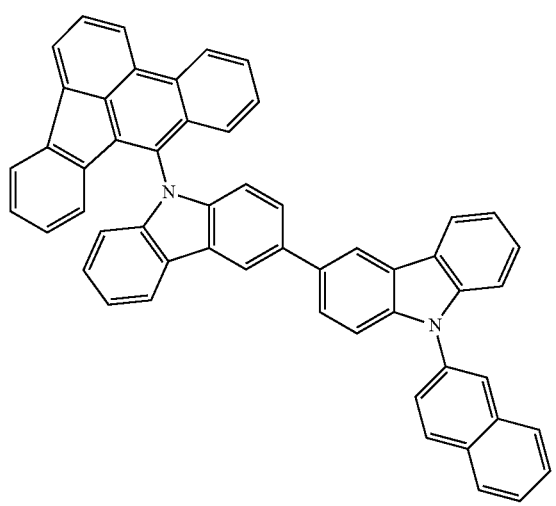
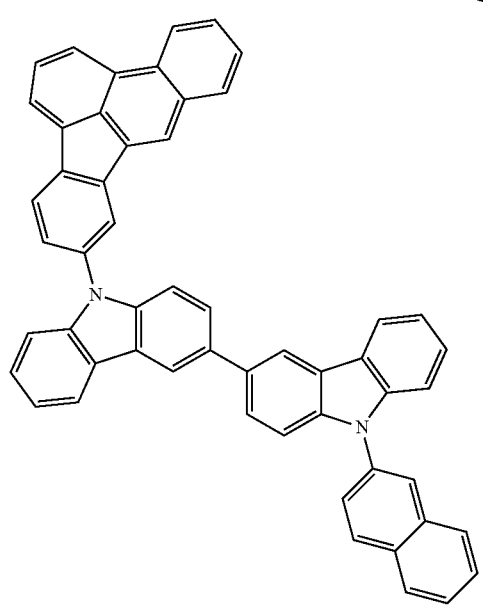
40
-continued
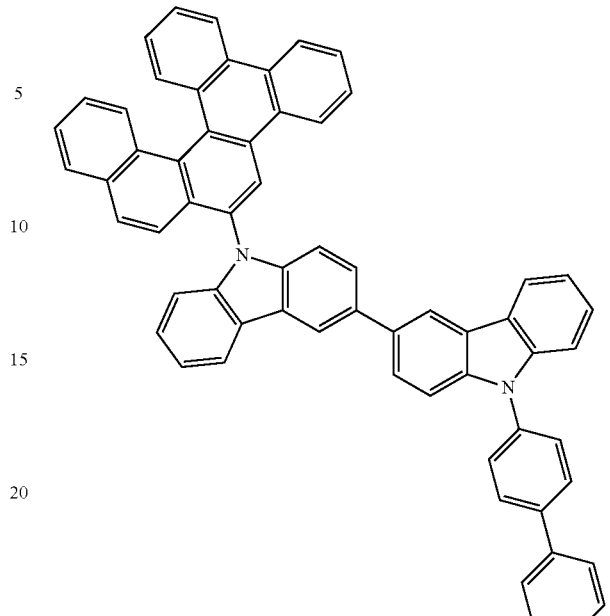
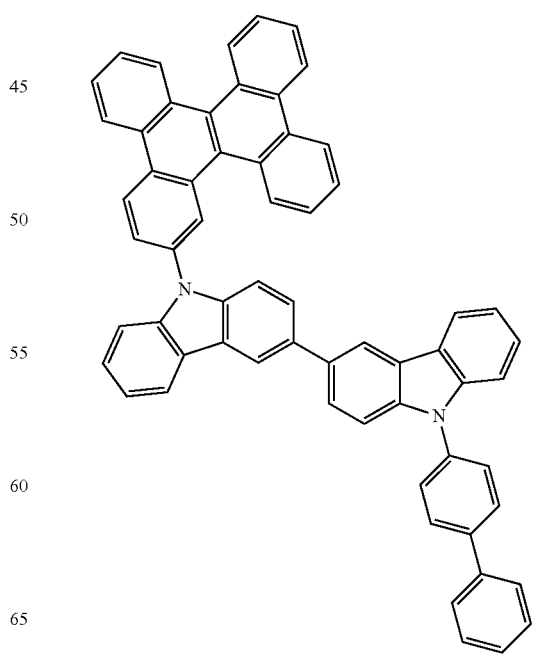

41
-continued
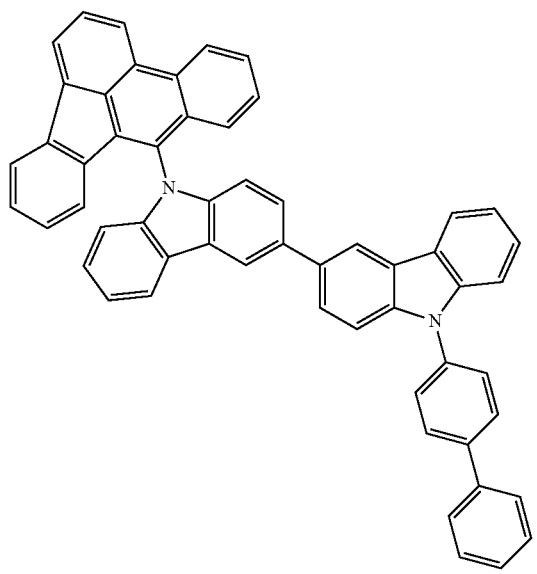
42
-continued
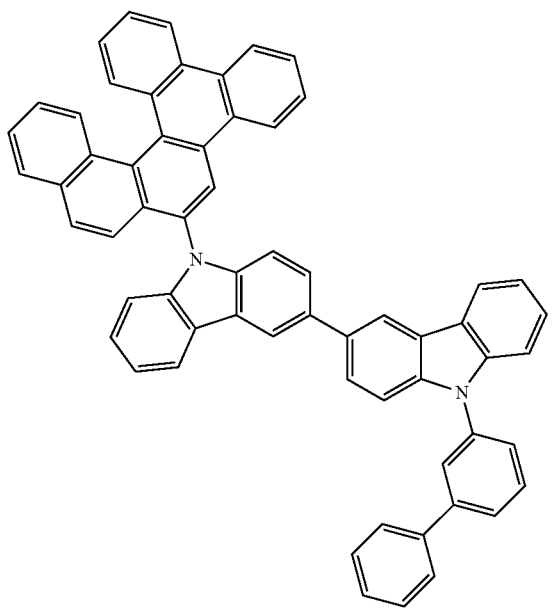
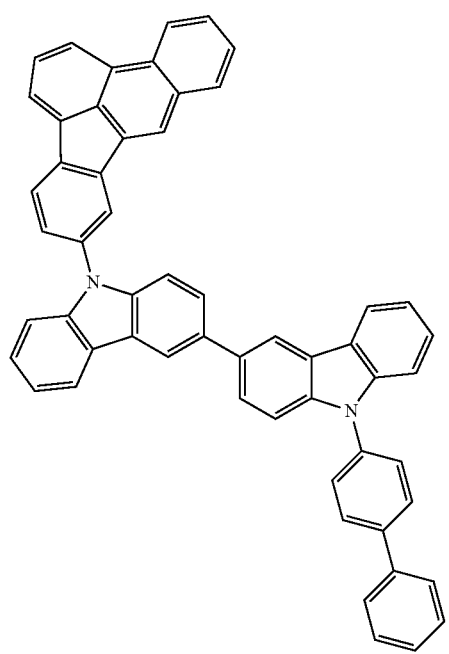
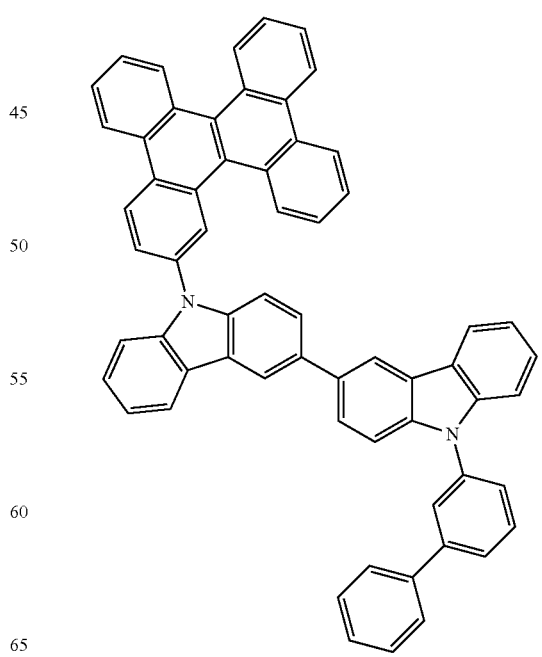

-continued
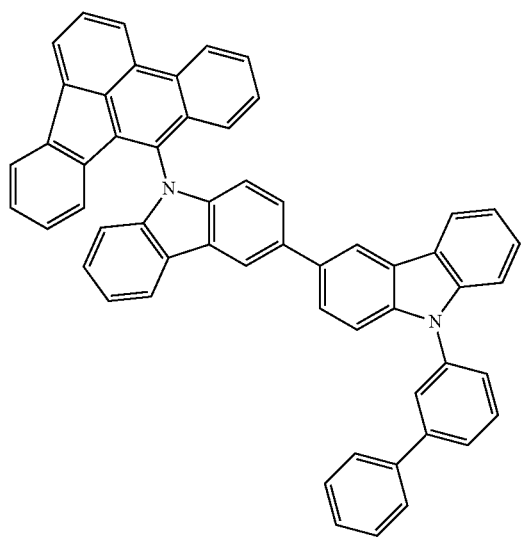
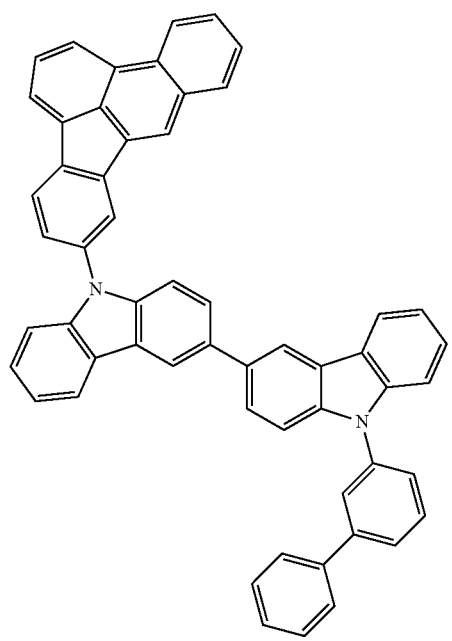
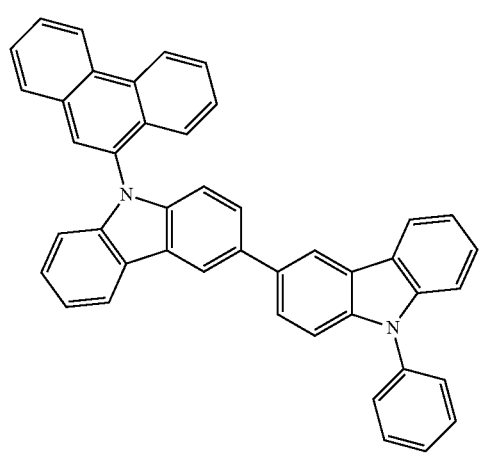
-continued
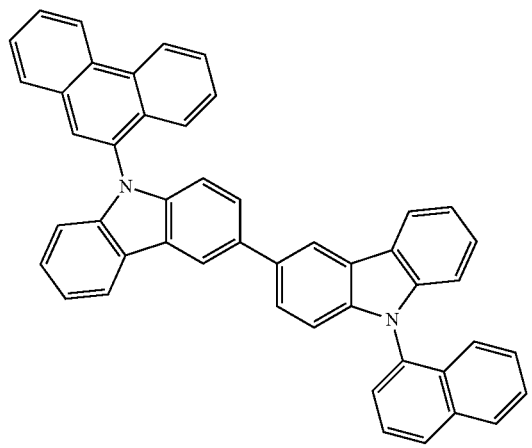
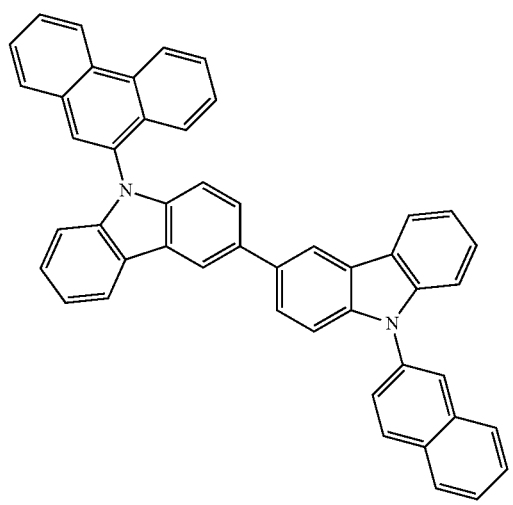
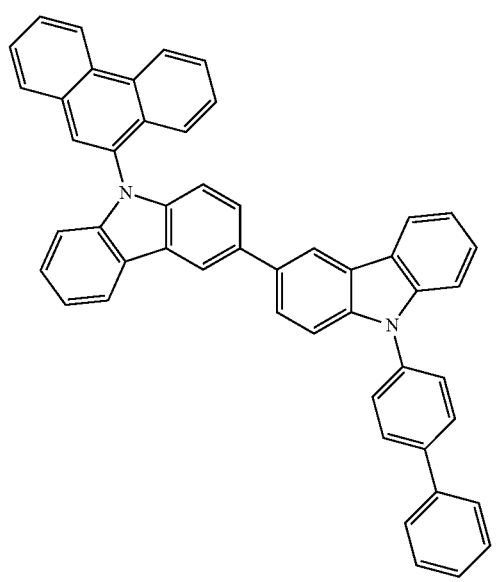

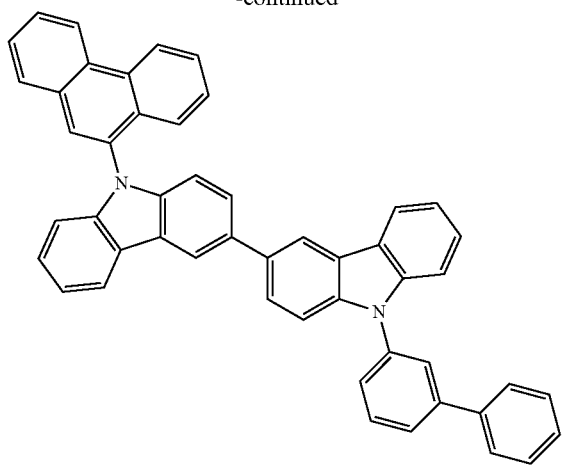
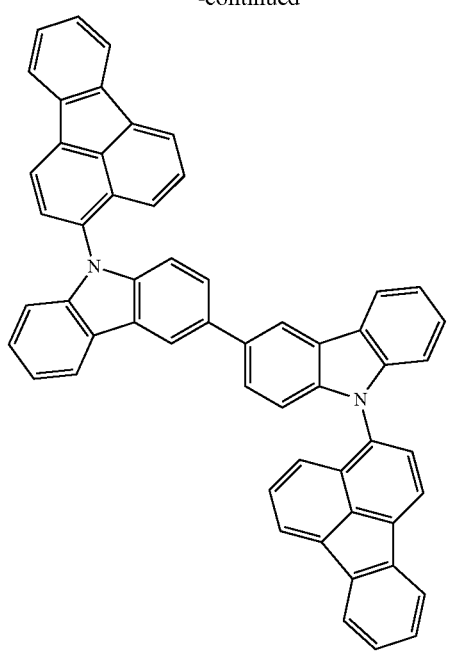
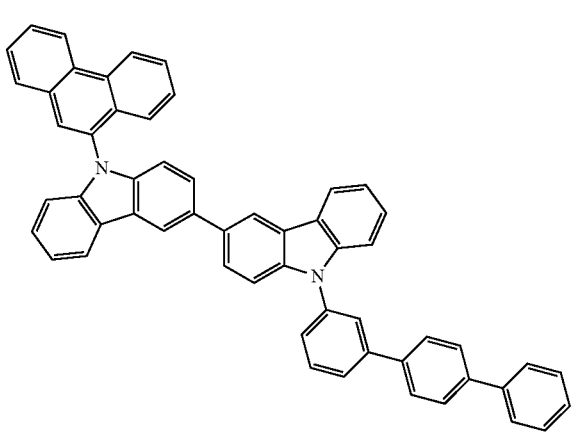
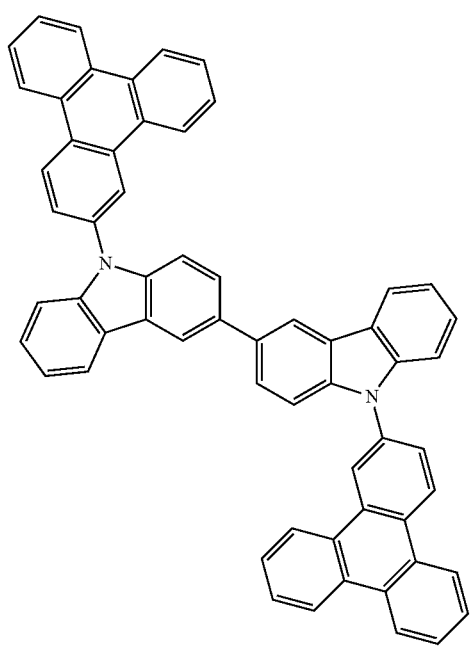

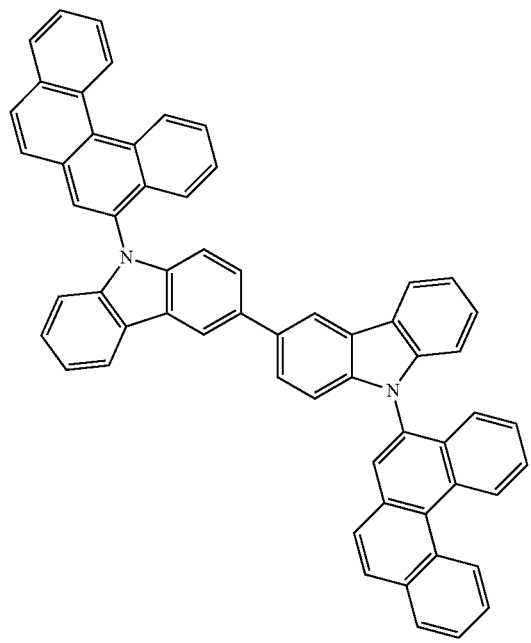
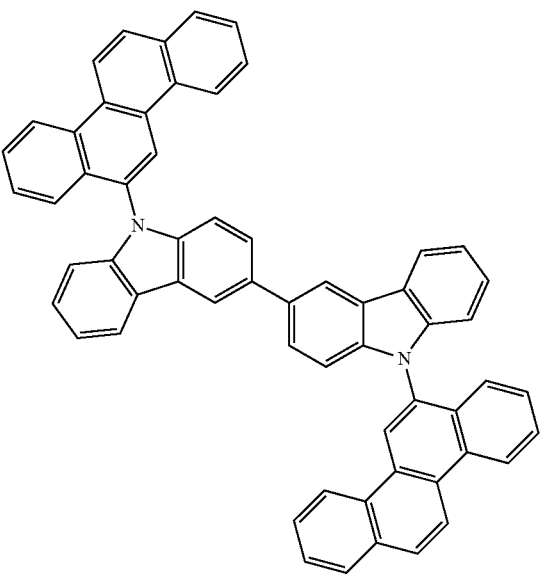
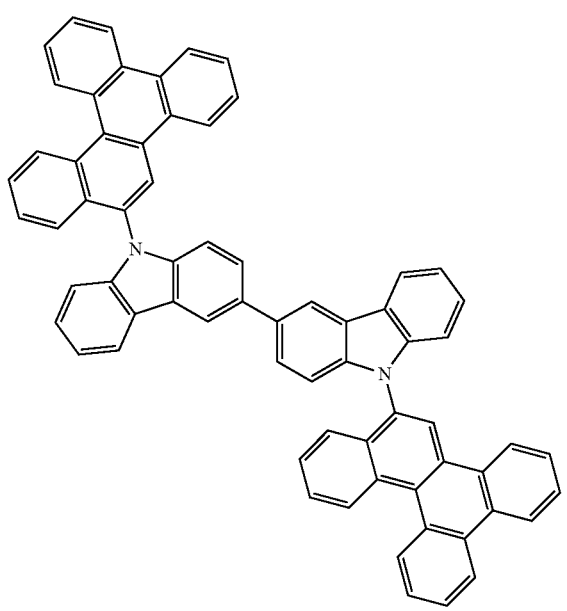
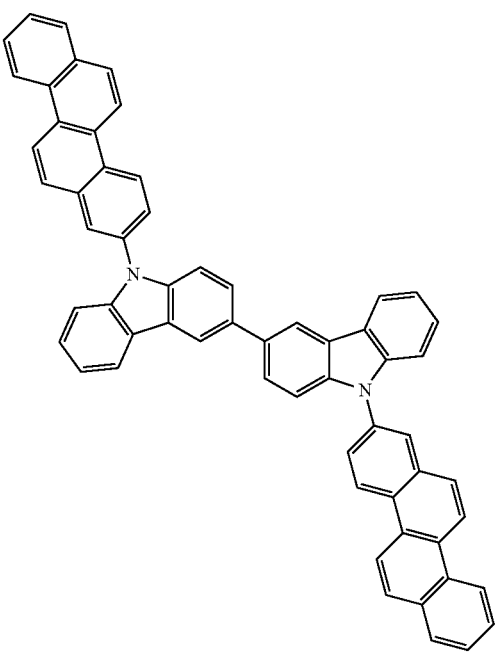

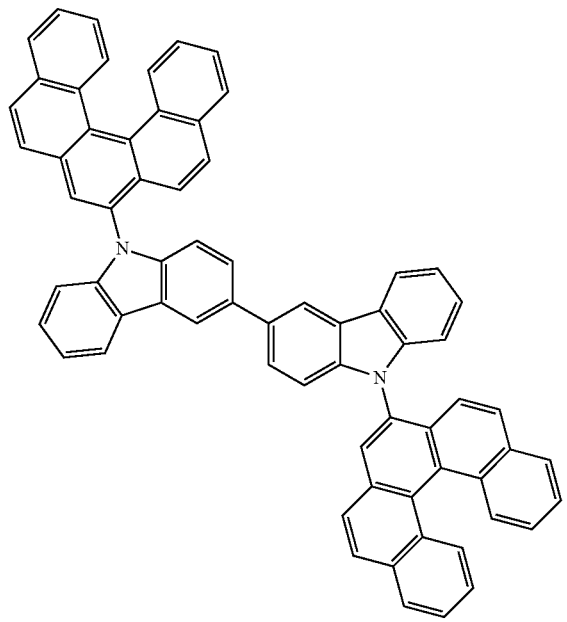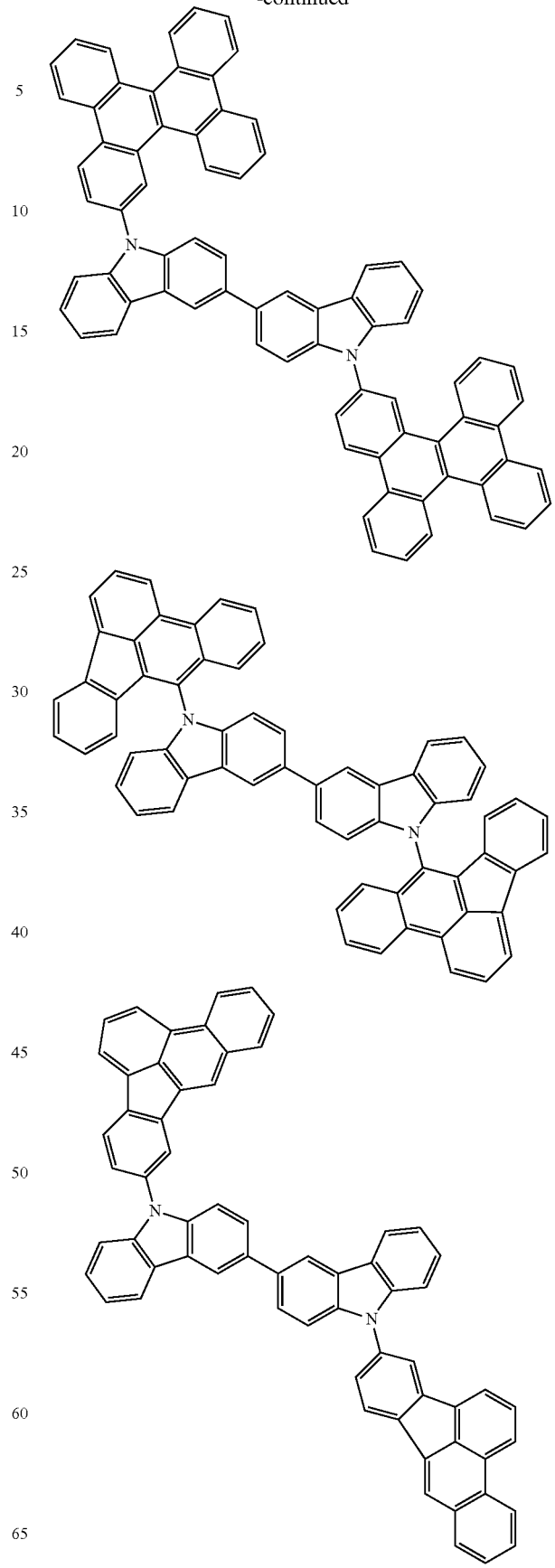

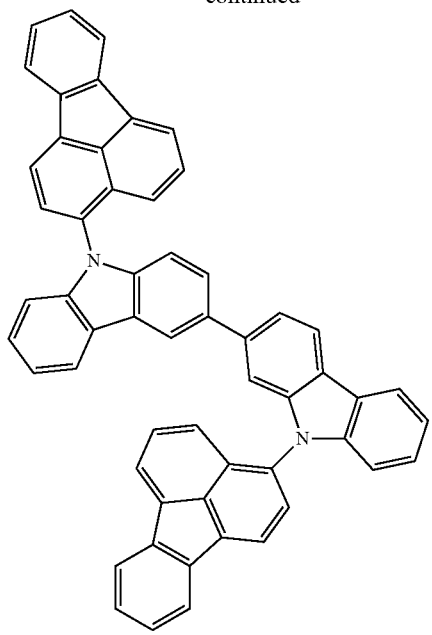
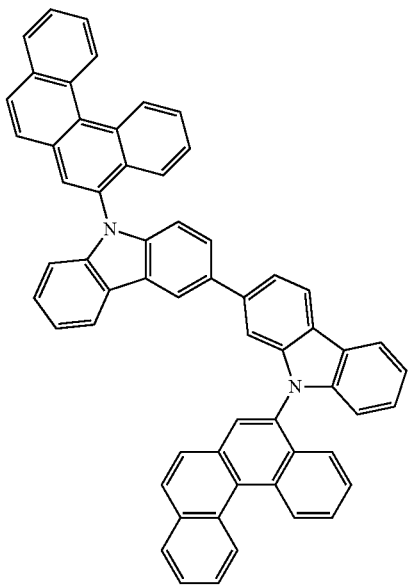
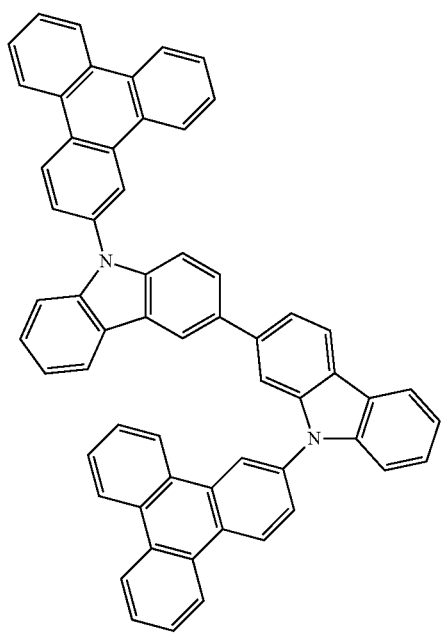
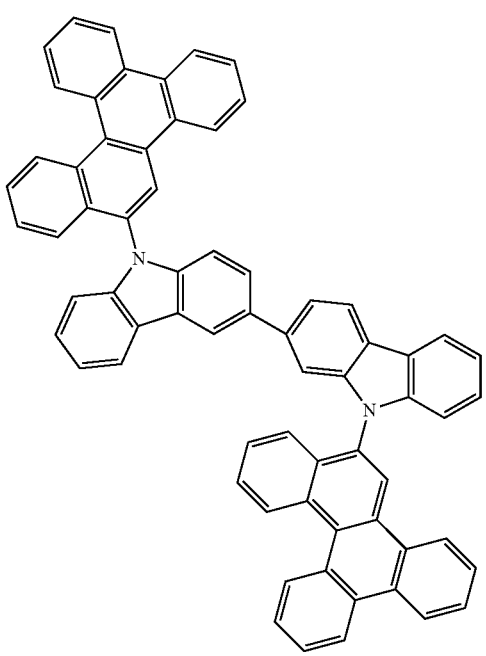

53
-continued
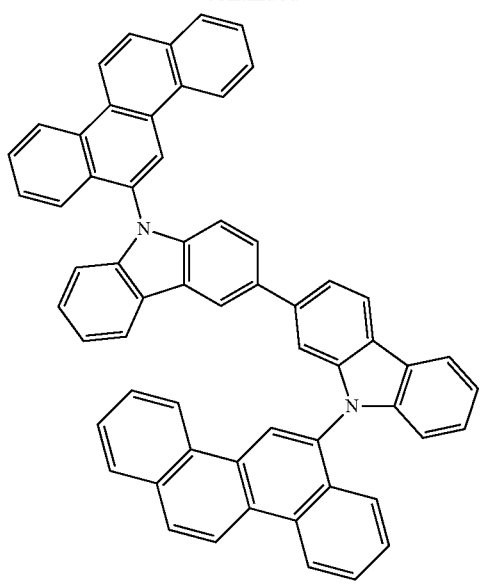
54
-continued
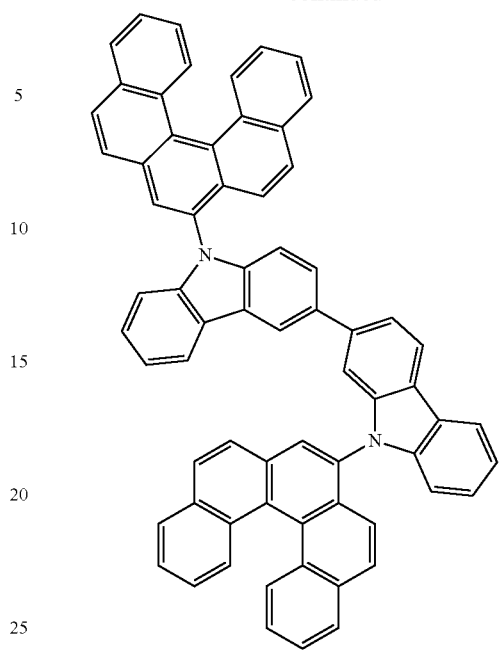
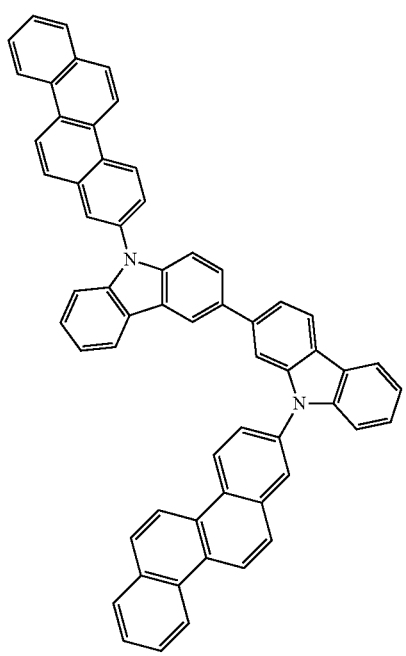
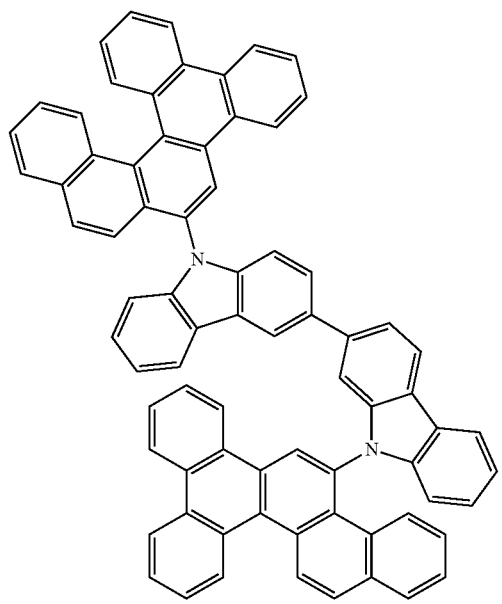

55
-continued
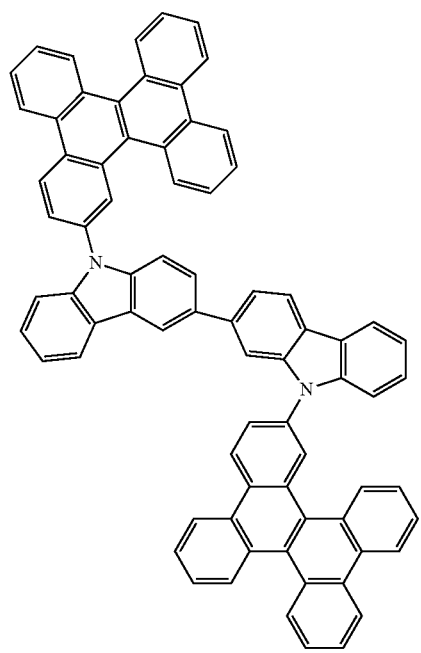
56
-continued
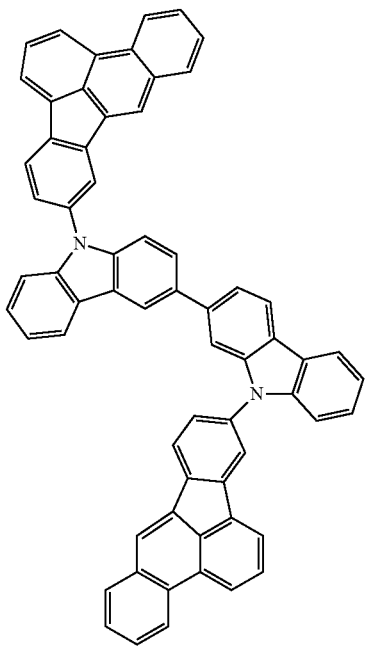
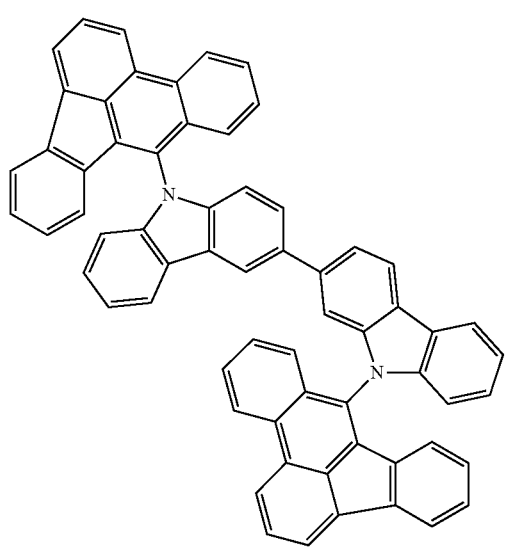
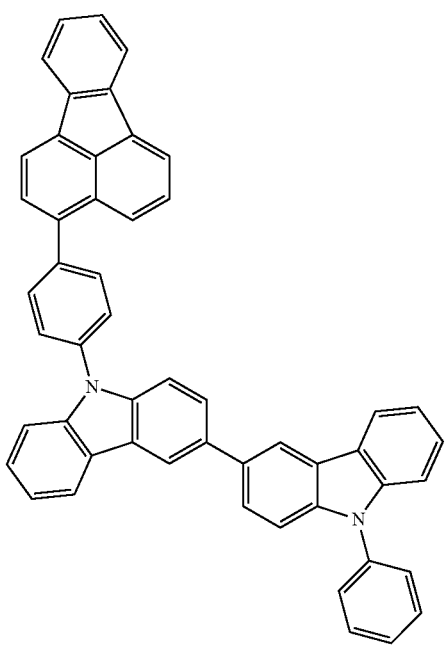

57
-continued
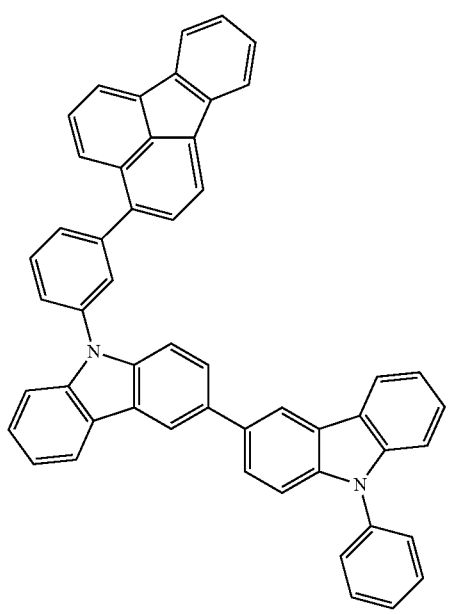
58
-continued
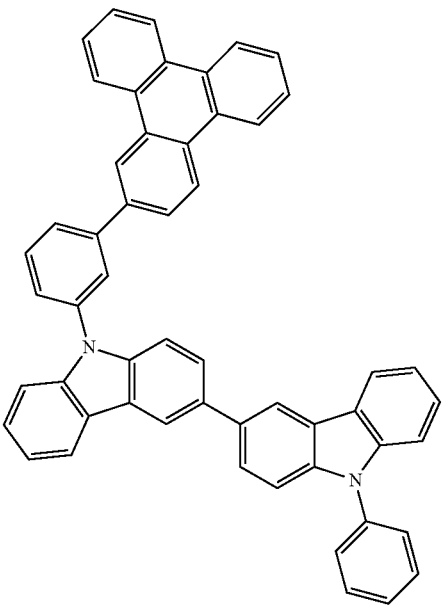
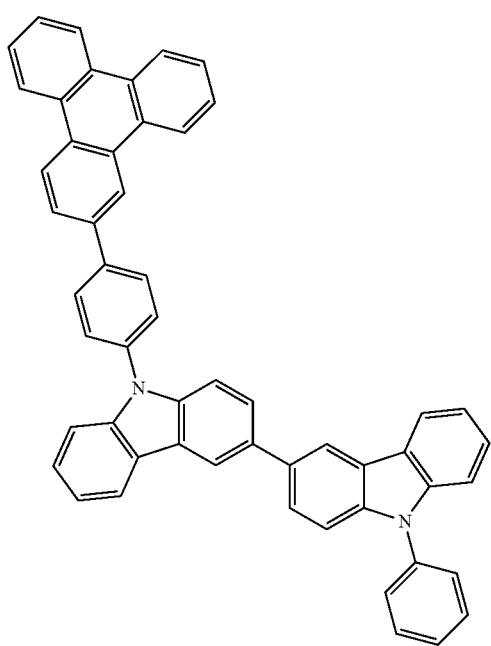
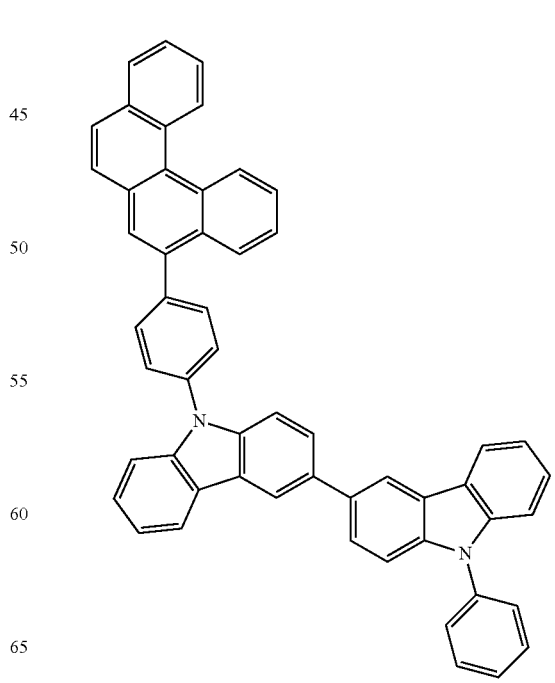

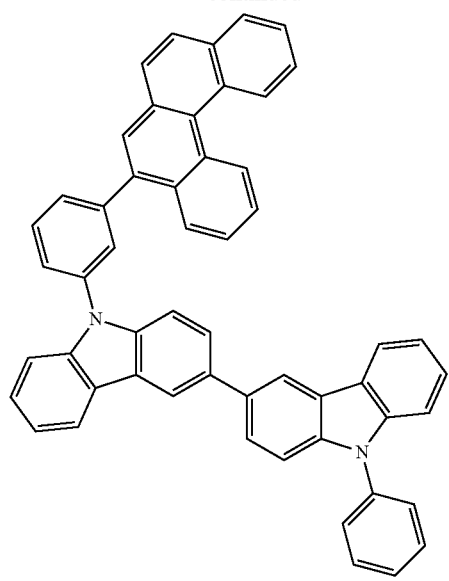
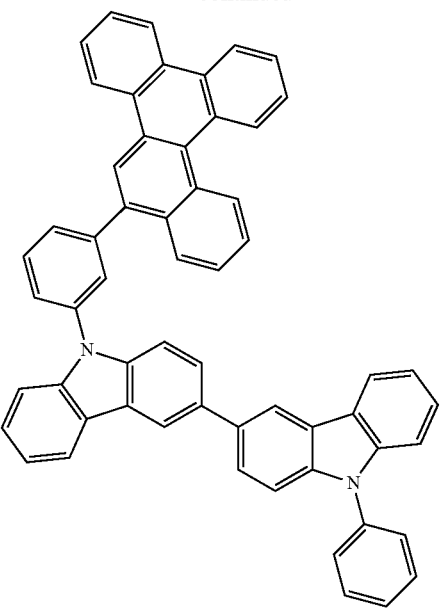
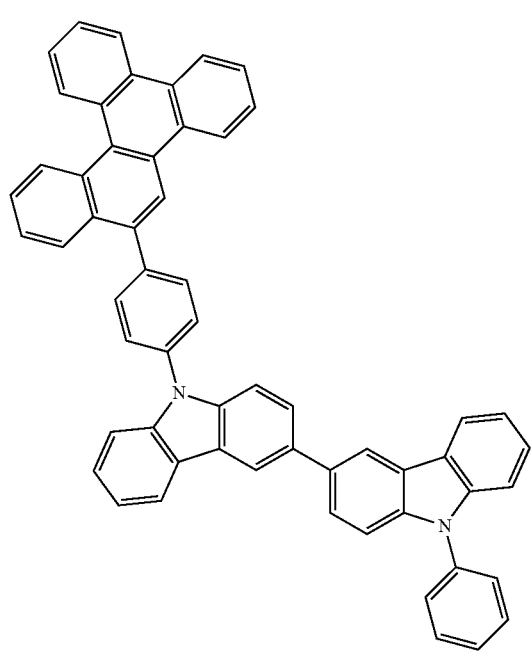
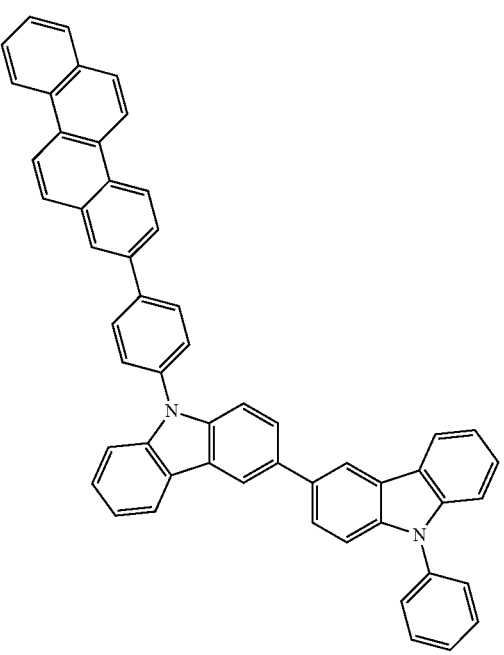

61
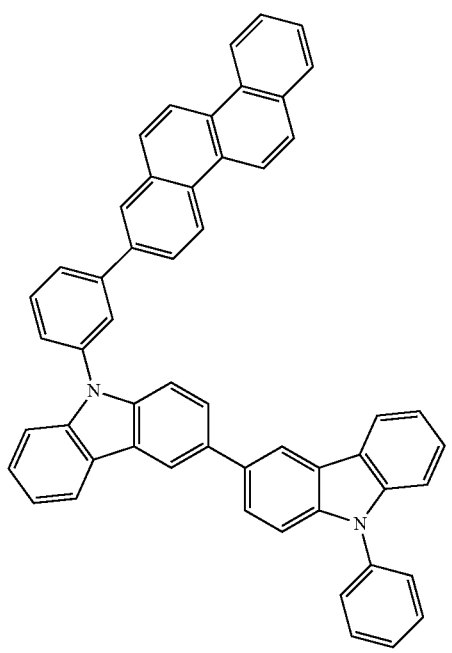
62
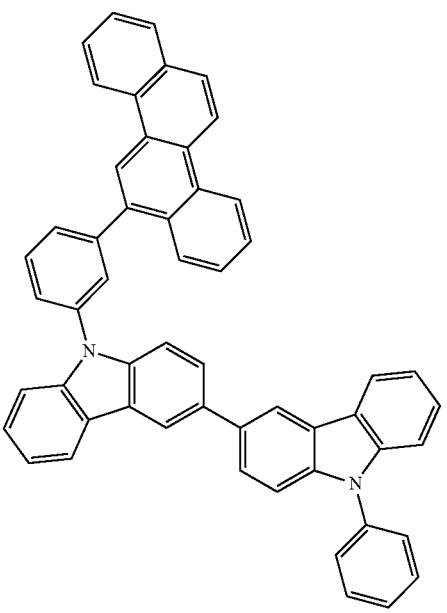
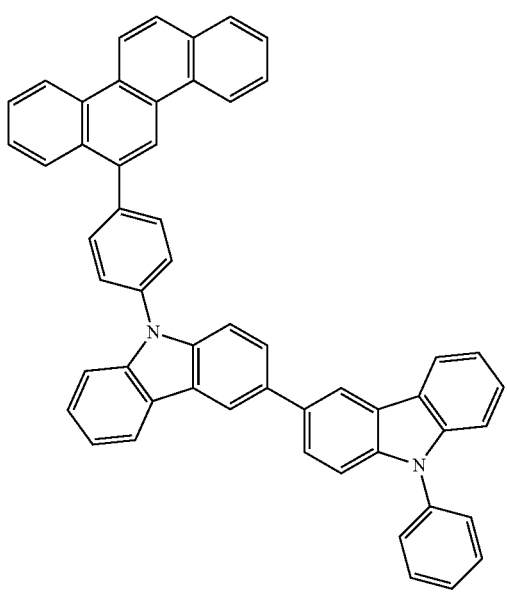
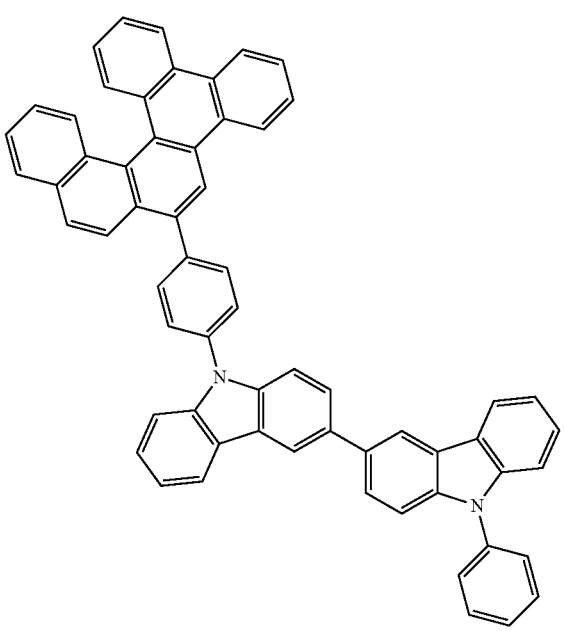

63
-continued
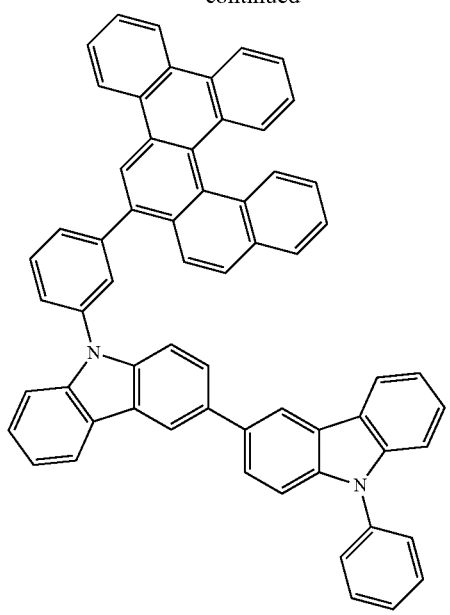
64
-continued
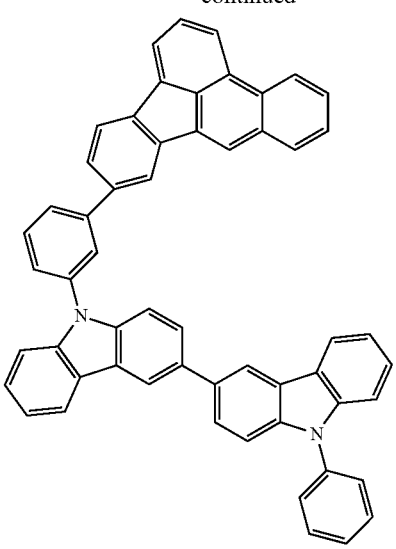
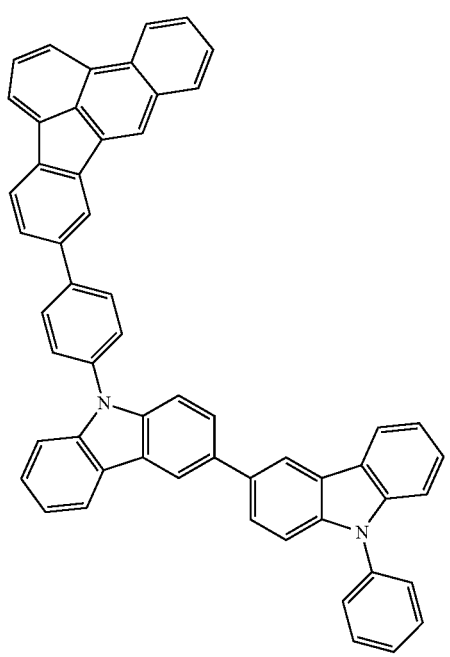
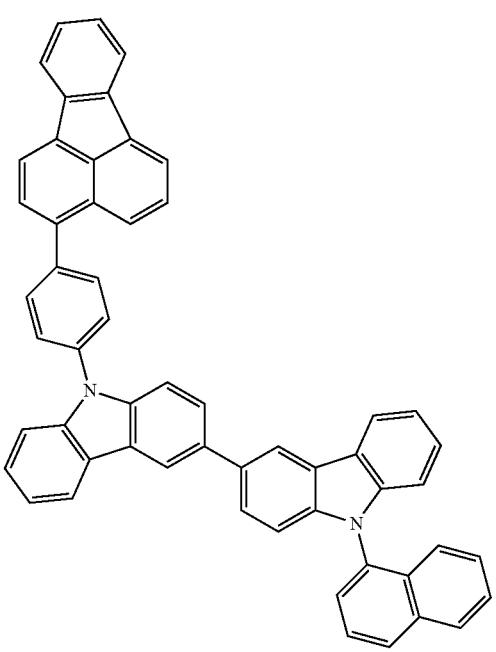

65
-continued
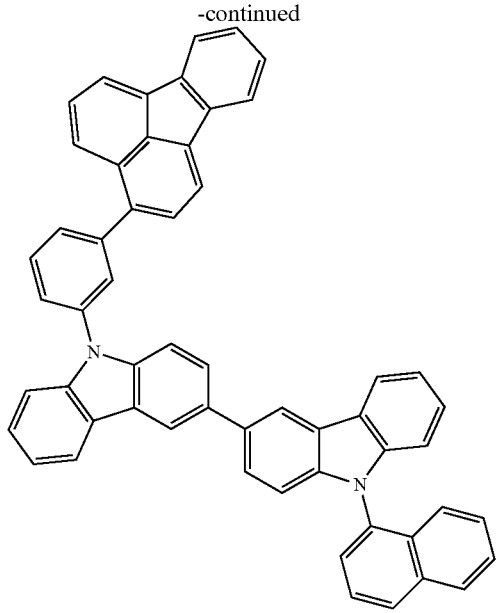
66
-continued
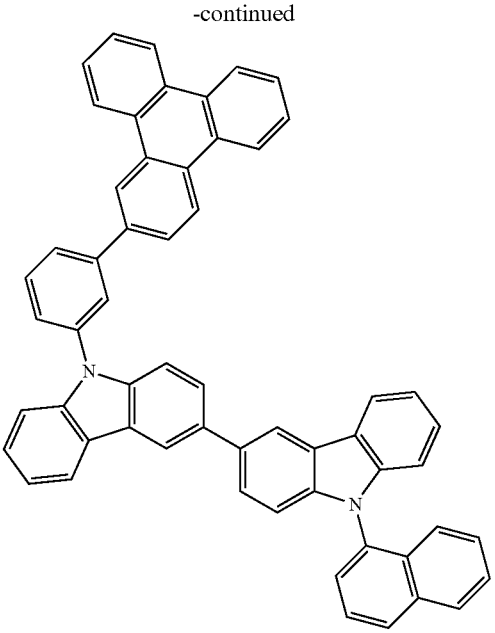
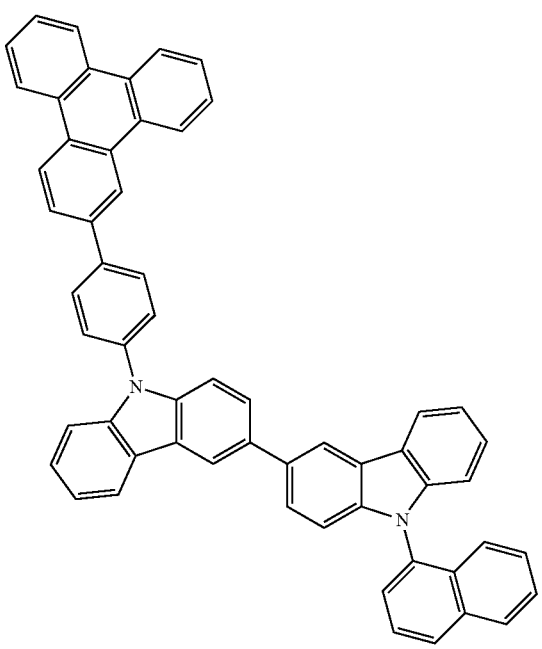
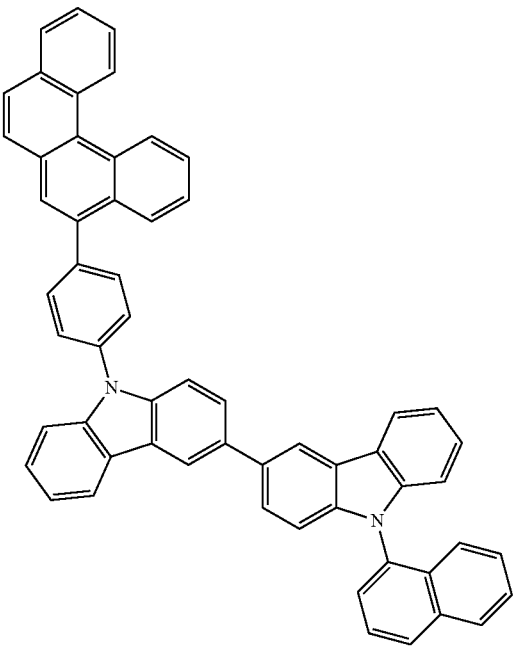

67
-continued
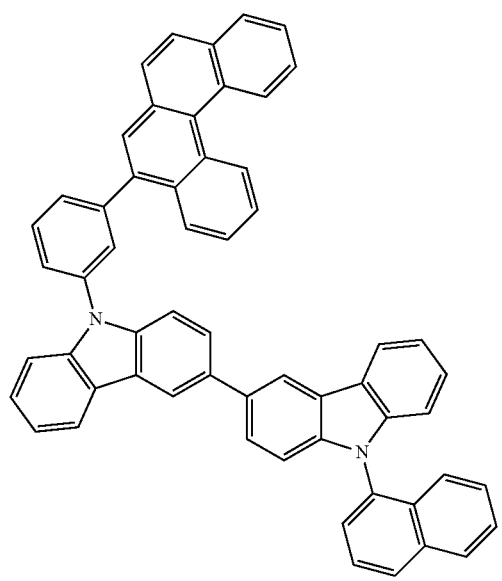
68
-continued
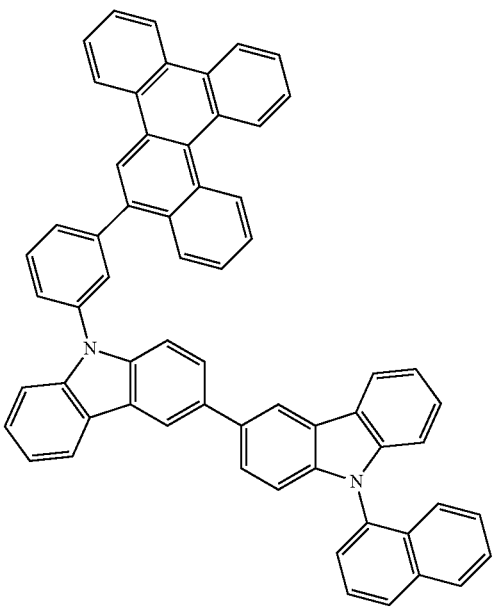
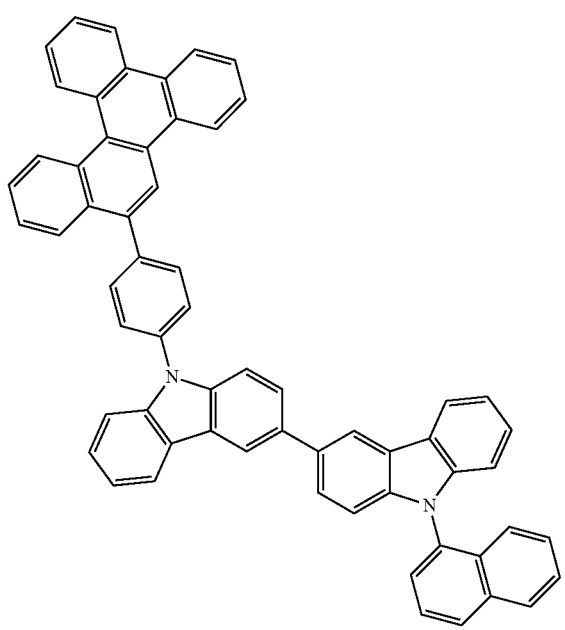
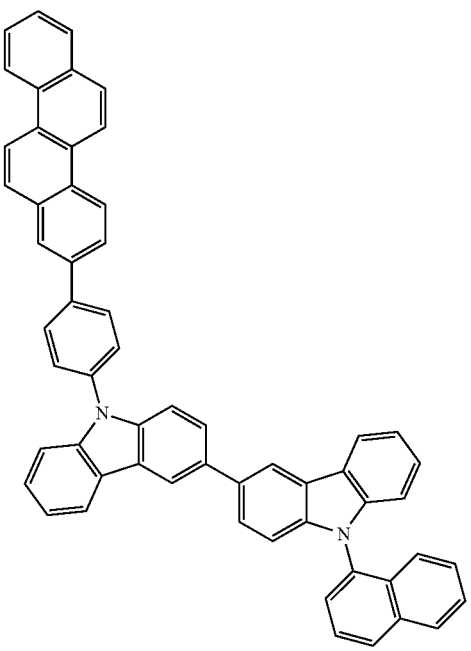

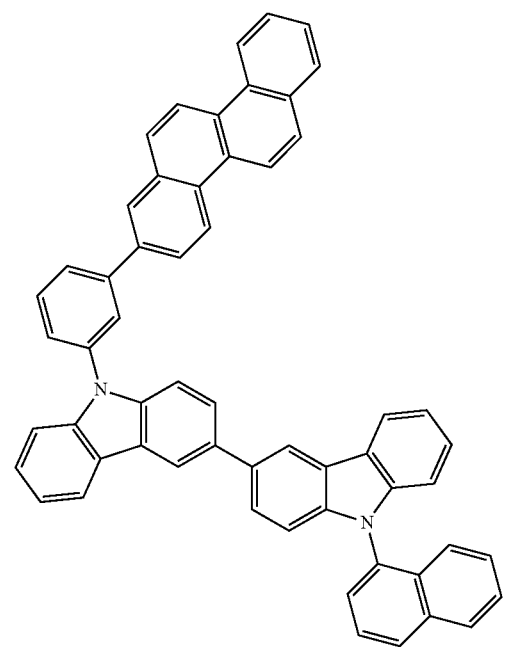
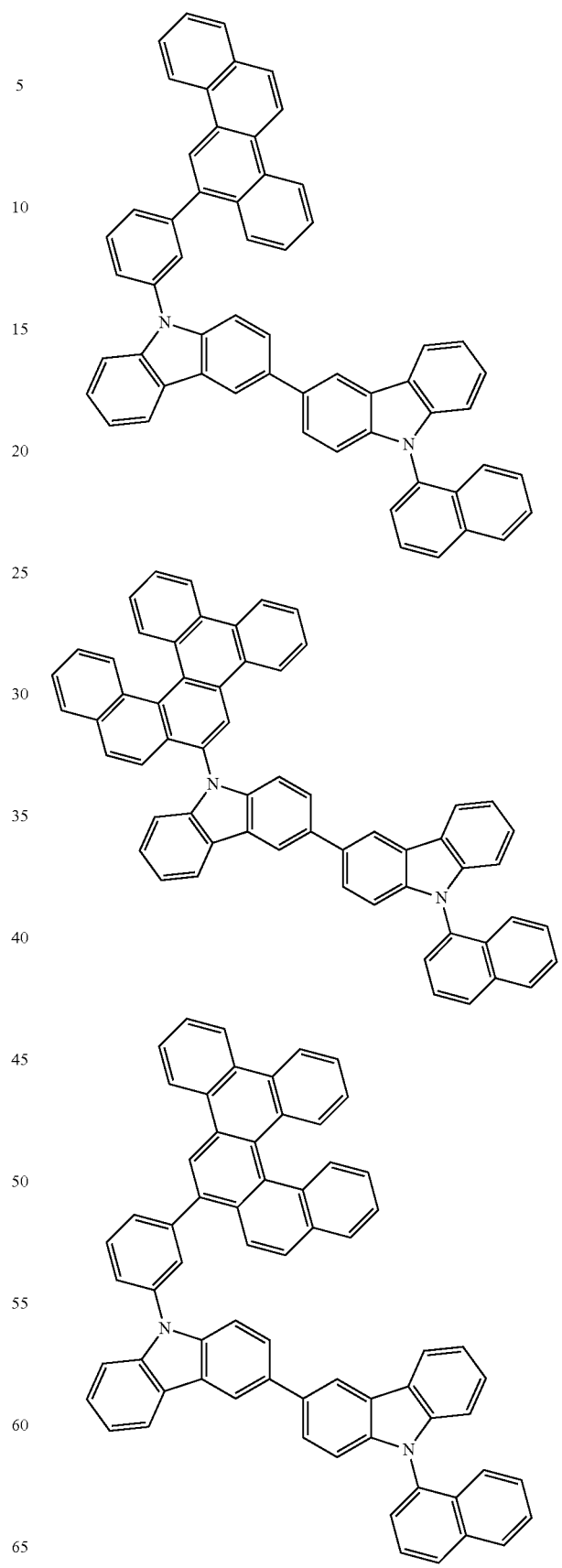

71
-continued
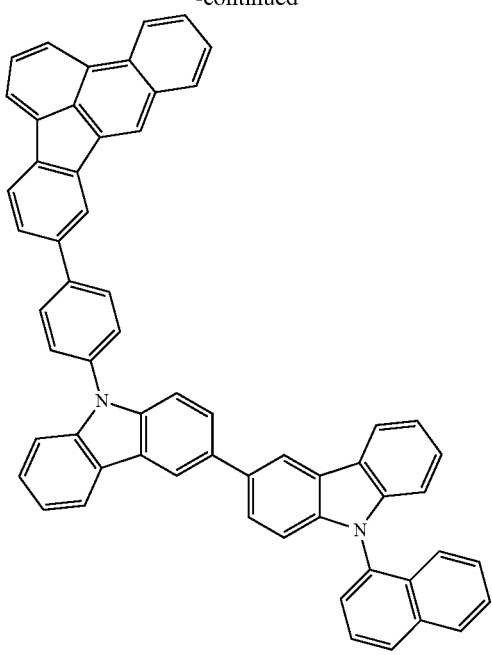
72
-continued
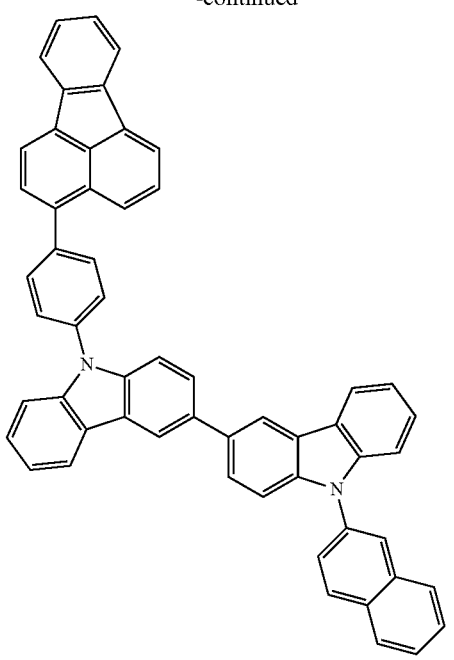
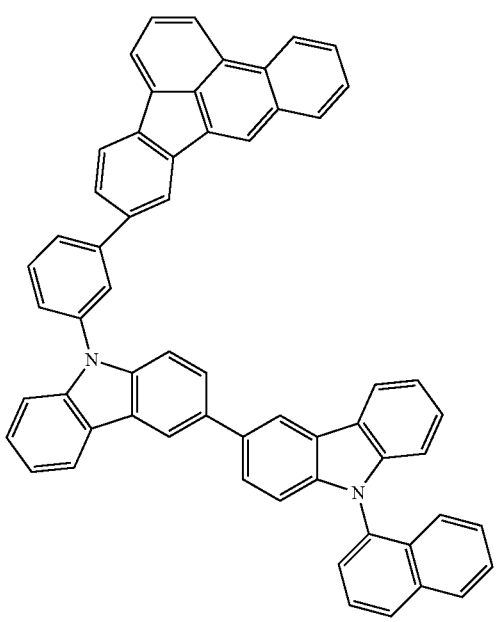
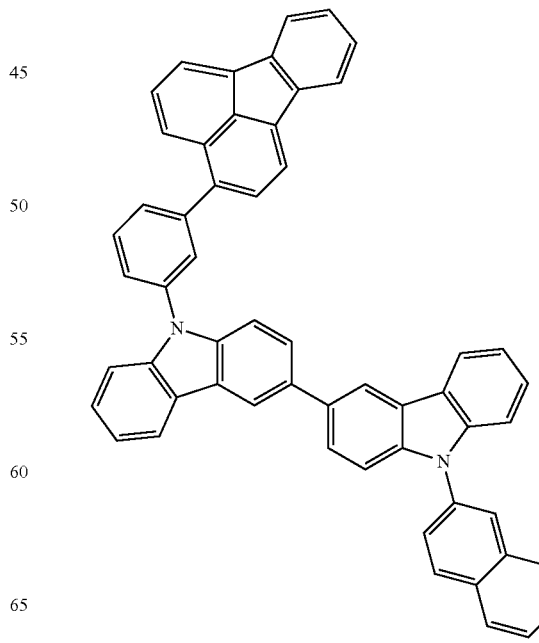

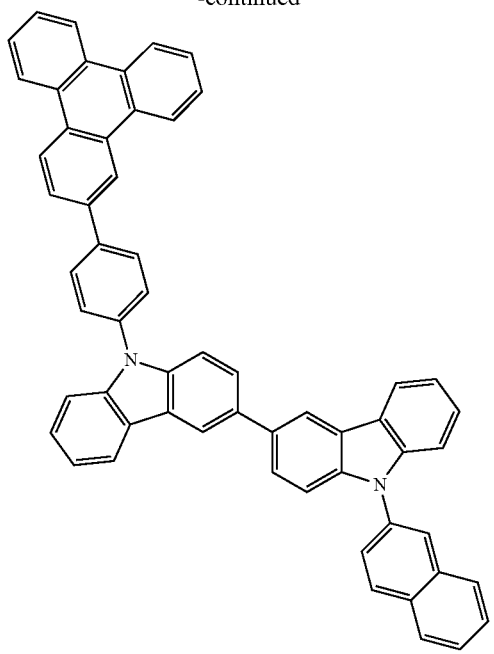
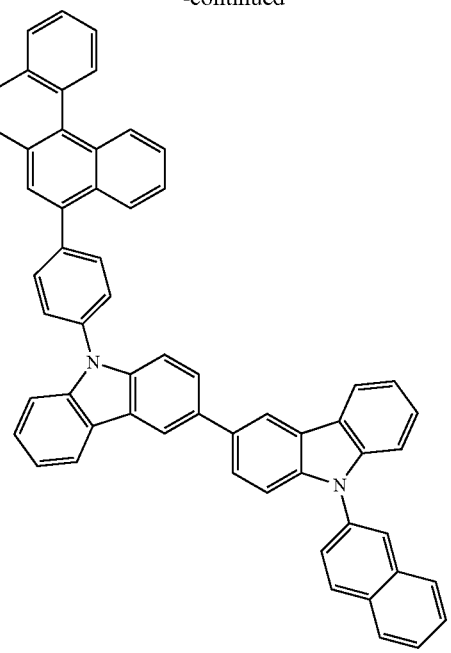
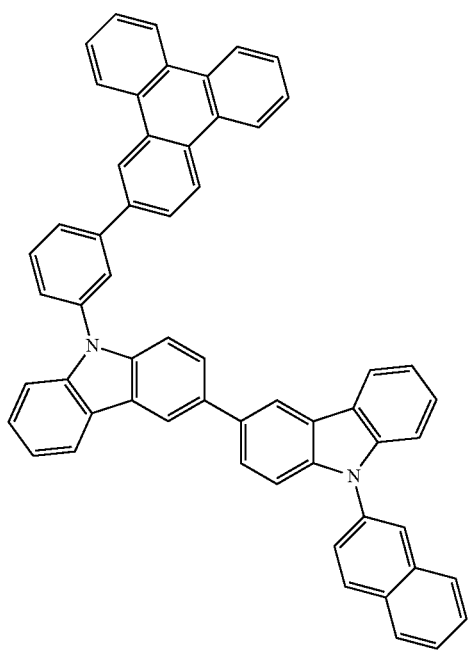
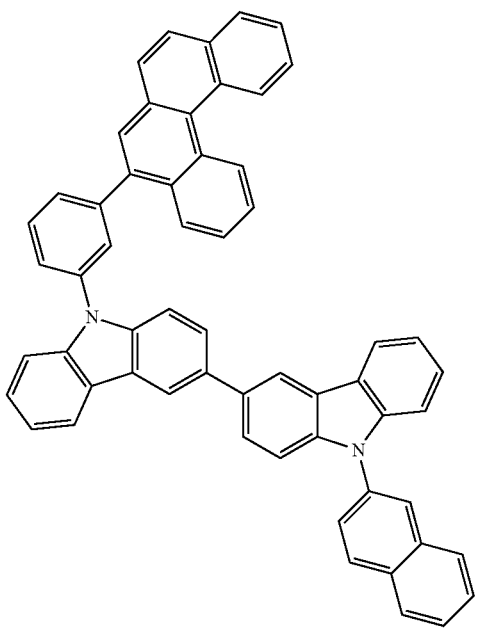

75
-continued
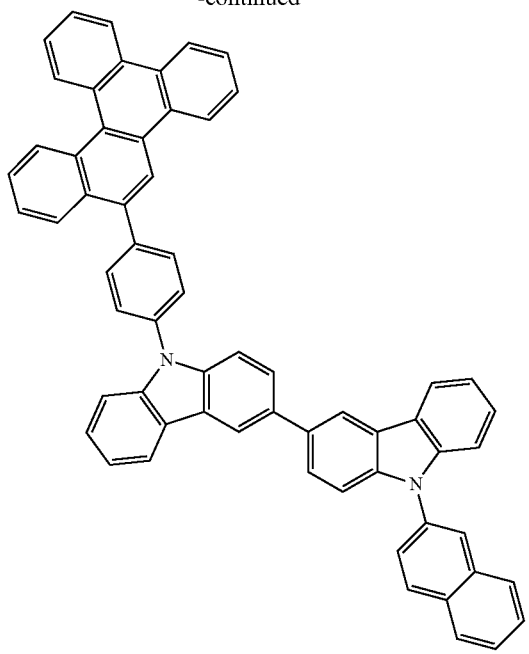
76
-continued
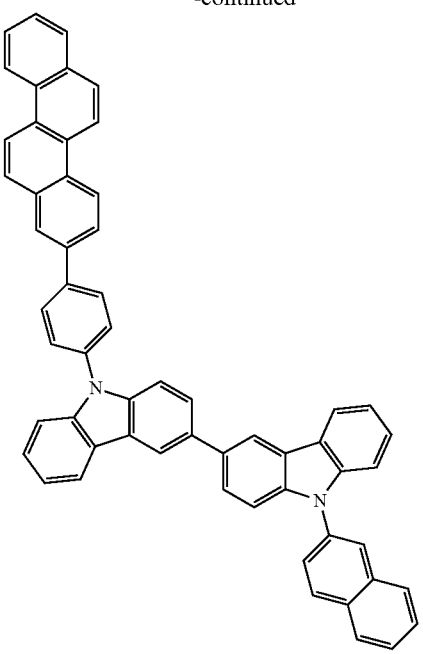
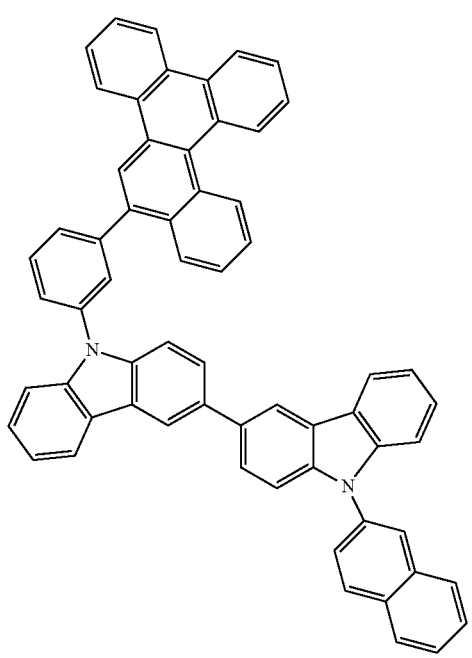
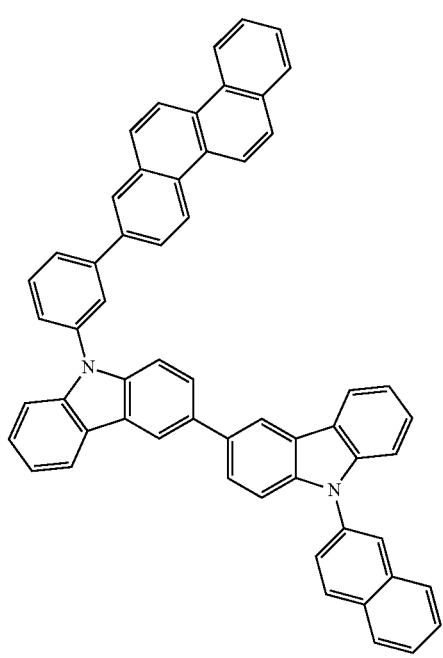

77
-continued
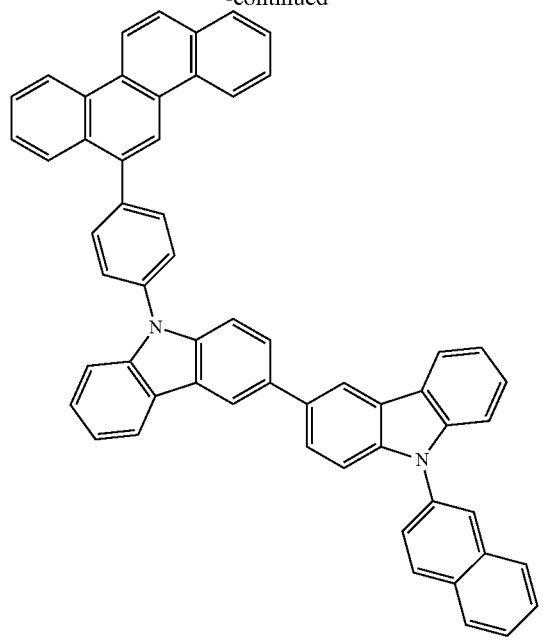
78
-continued
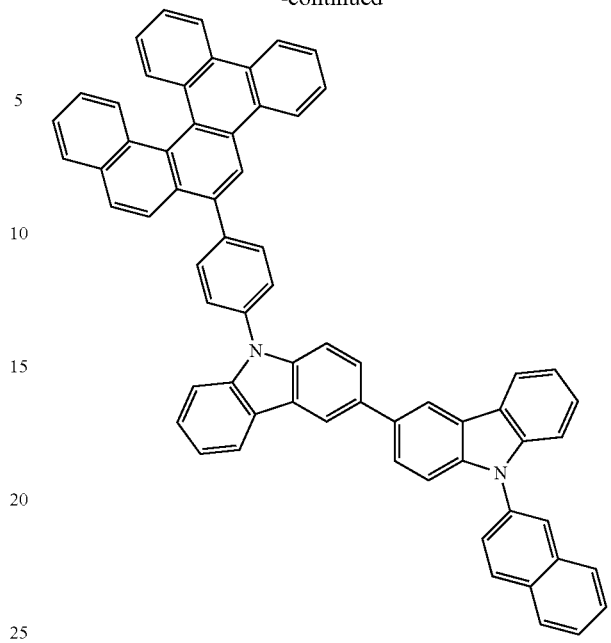
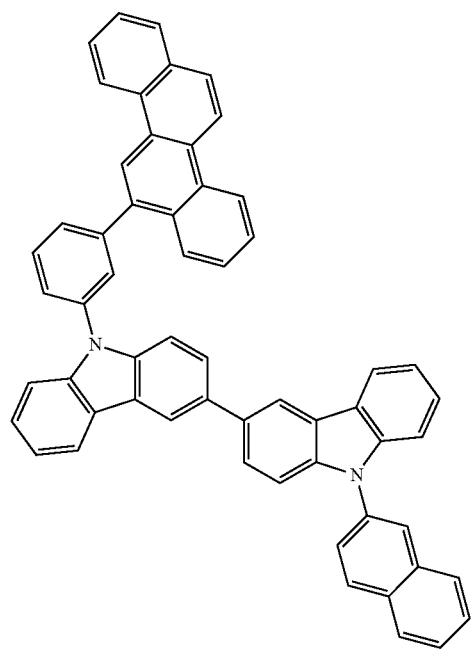
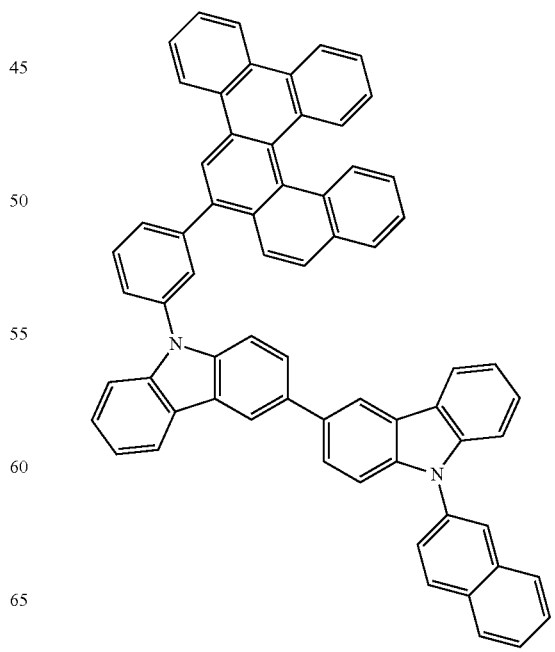

79
-continued
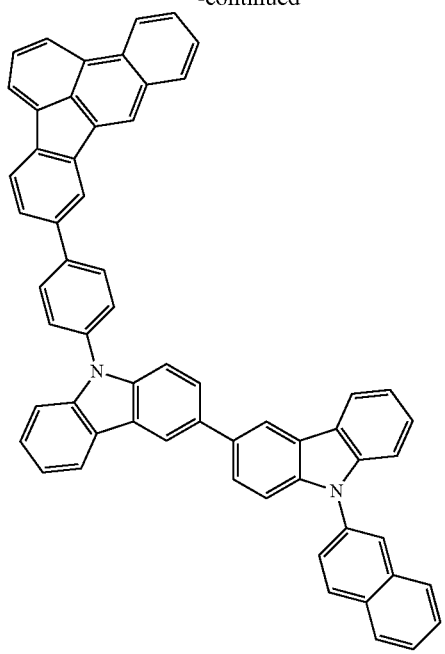
80
-continued
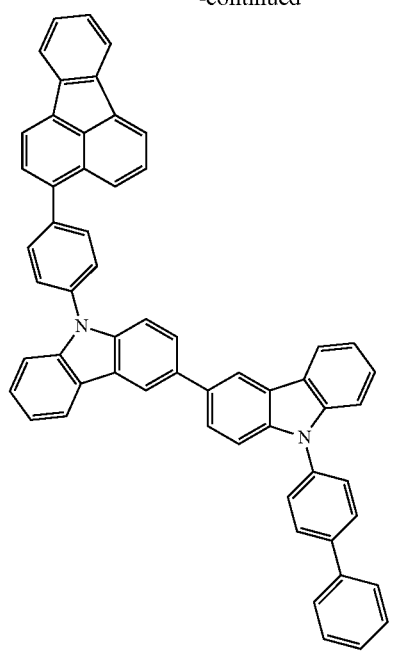
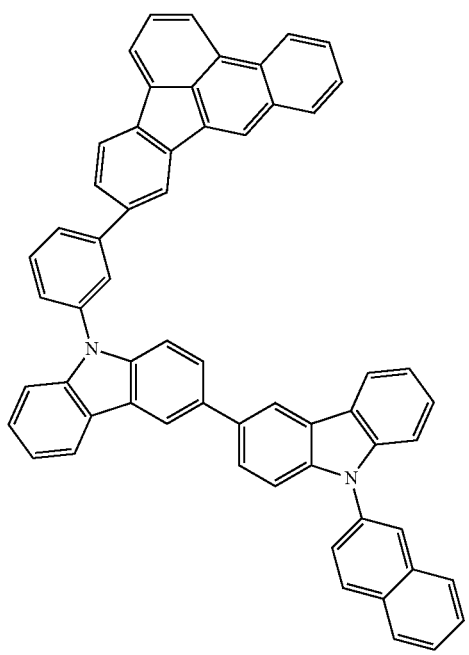
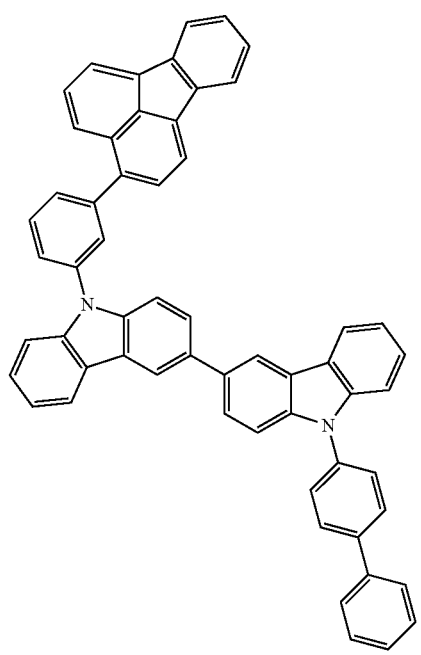

81
-continued
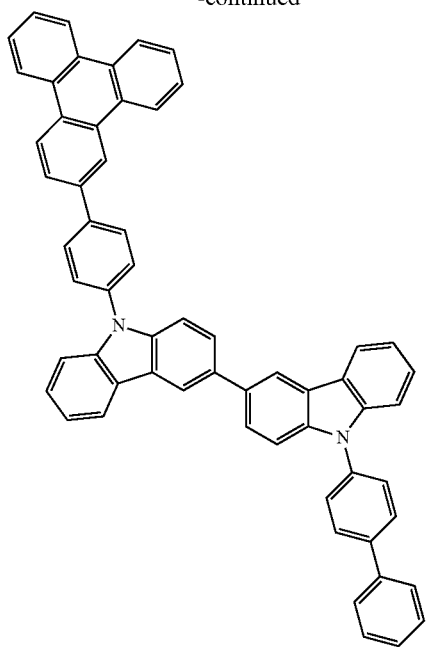
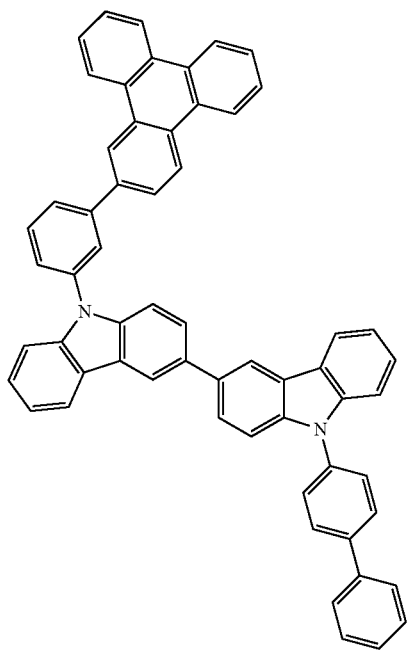
82
-continued
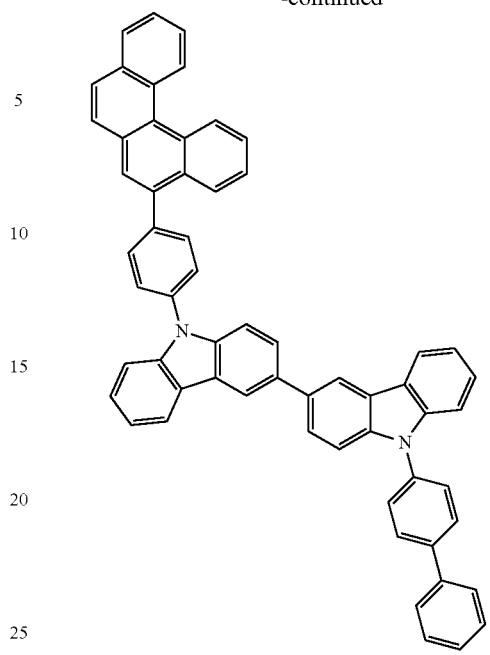
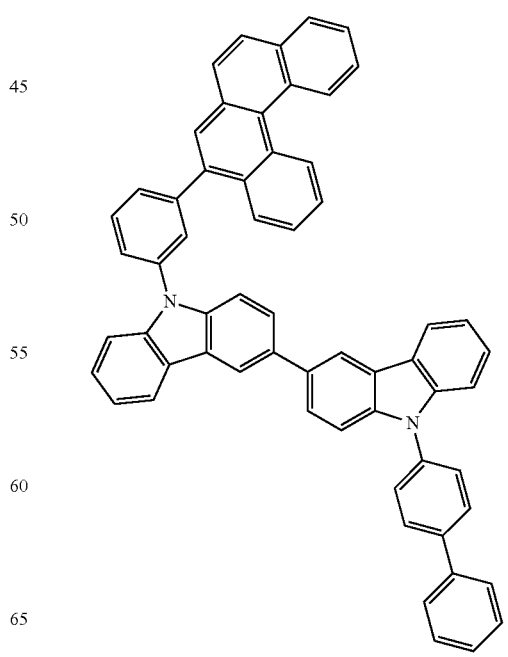

83
-continued
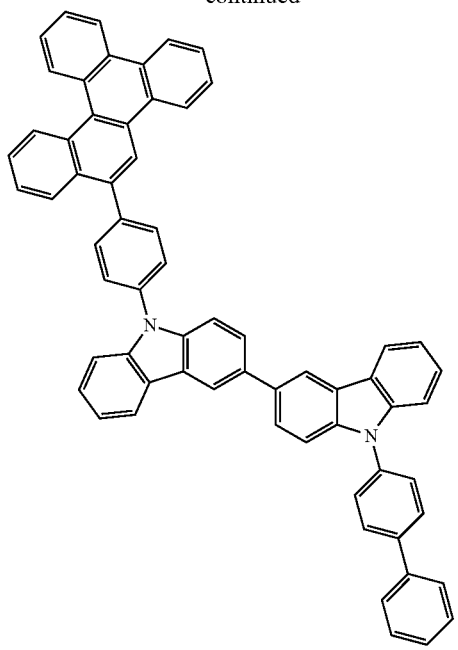
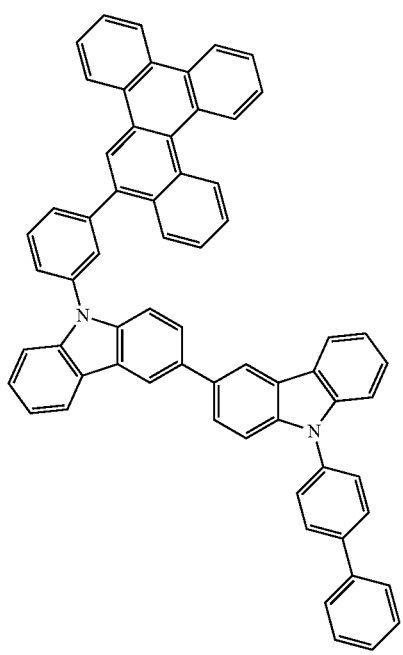
84
-continued
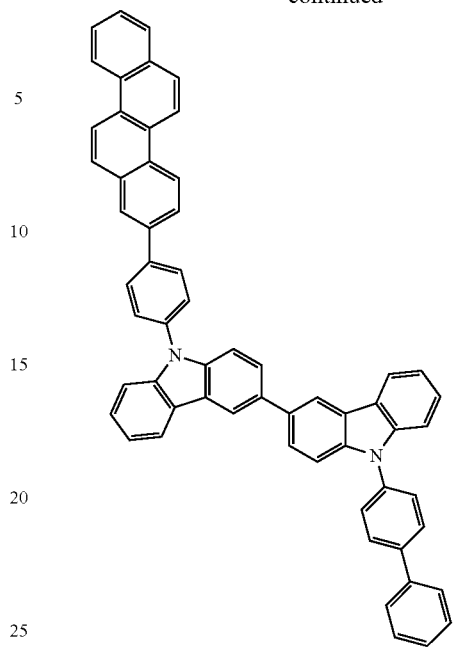
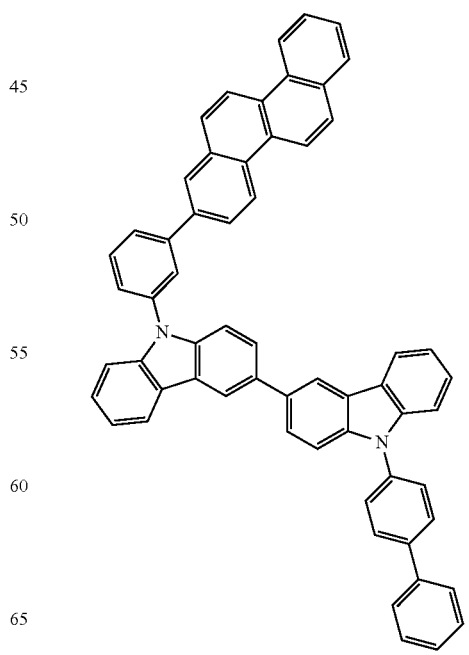

85
-continued
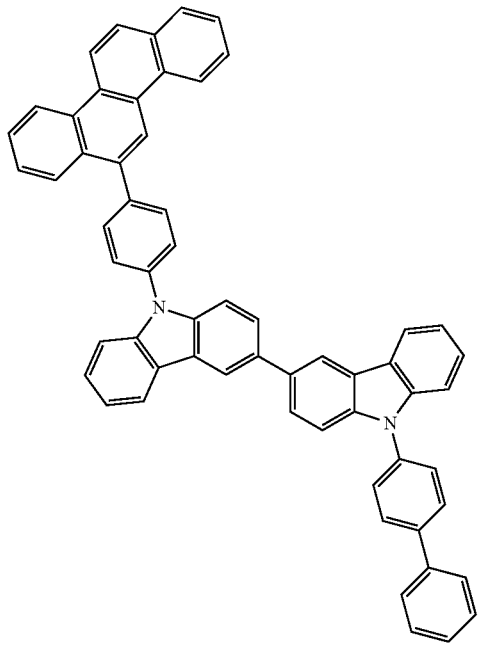
86
-continued
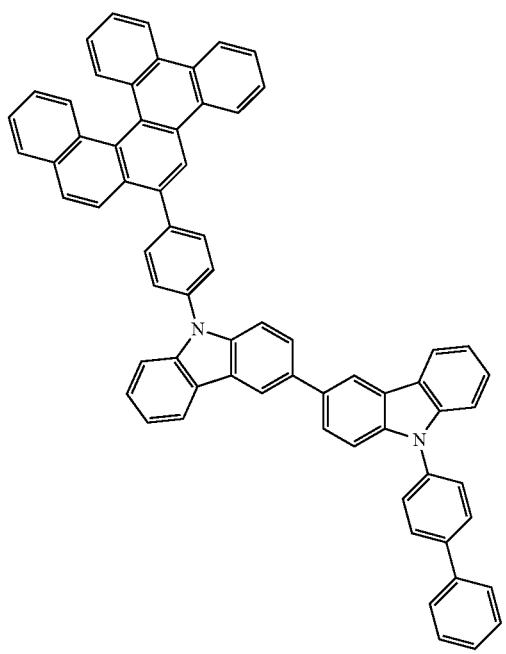
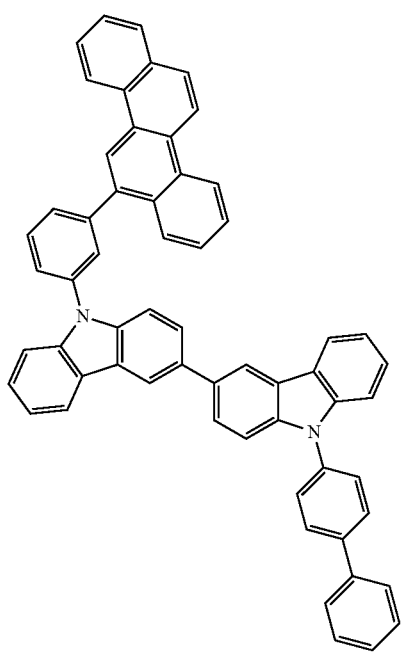
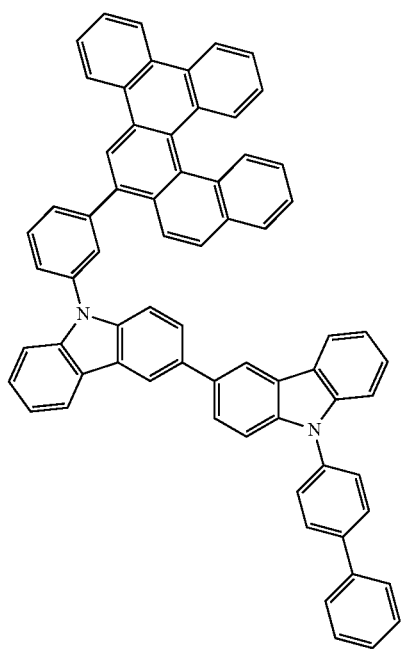

87
-continued
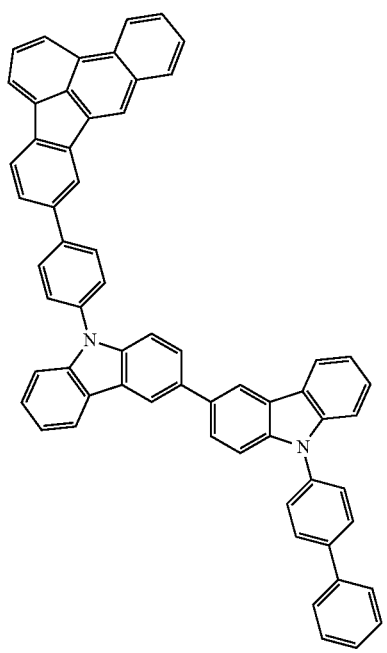
88
-continued
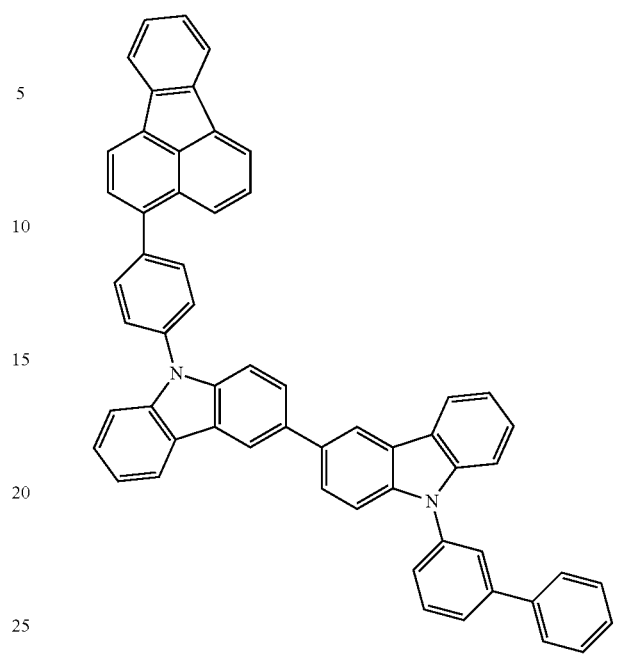
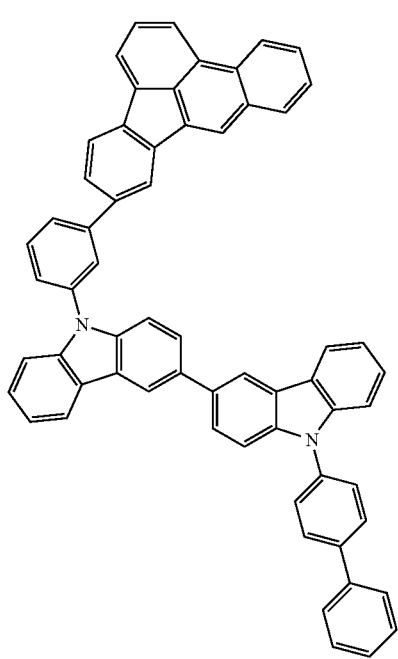
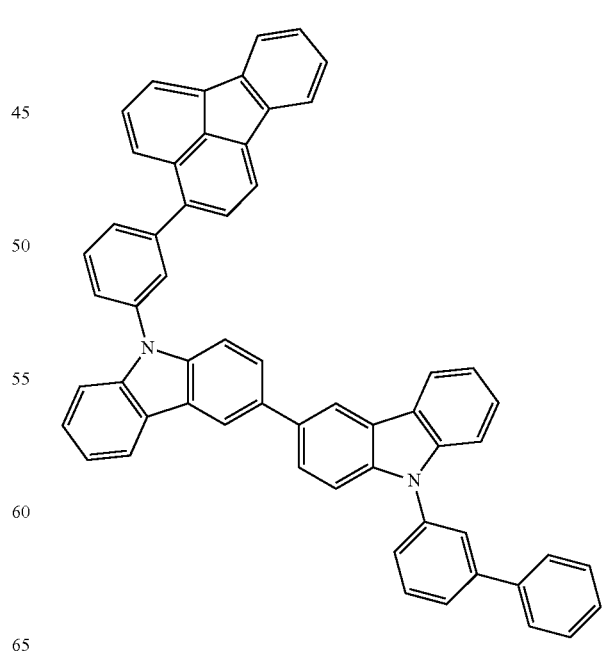

89
-continued
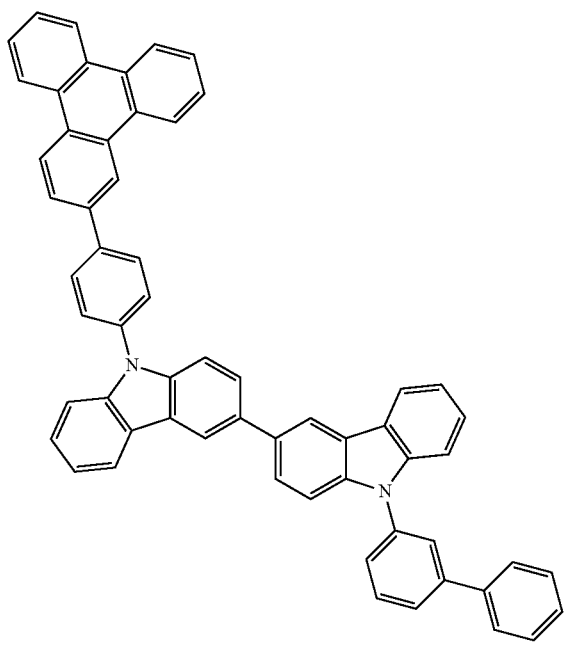
90
-continued
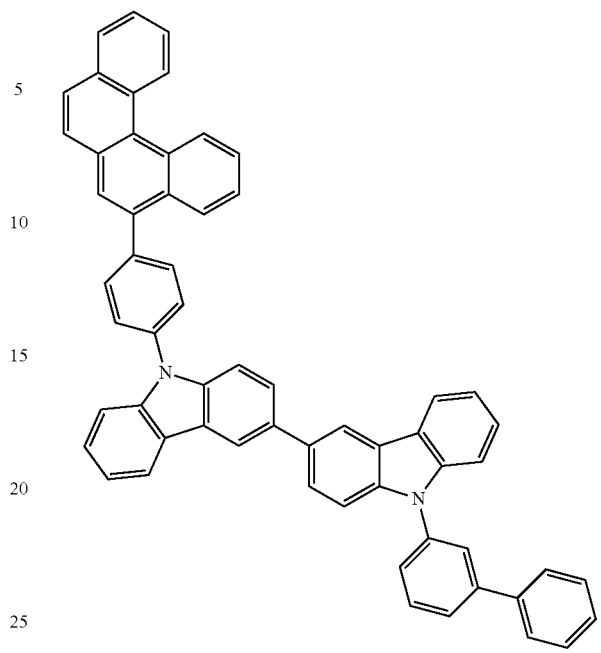
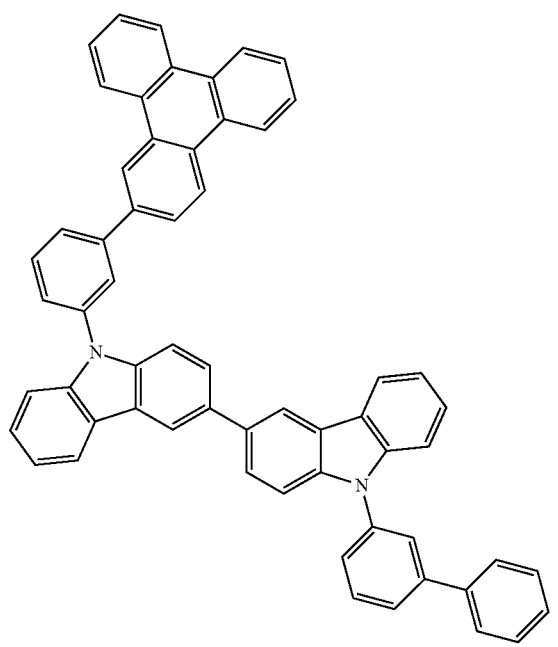

91
-continued
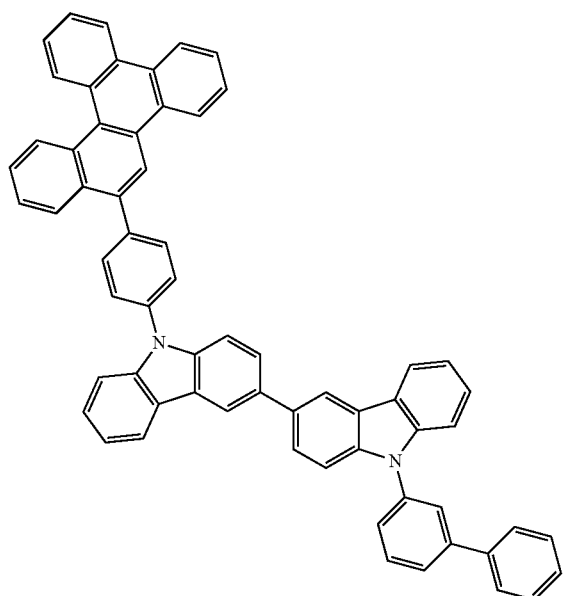
92
-continued
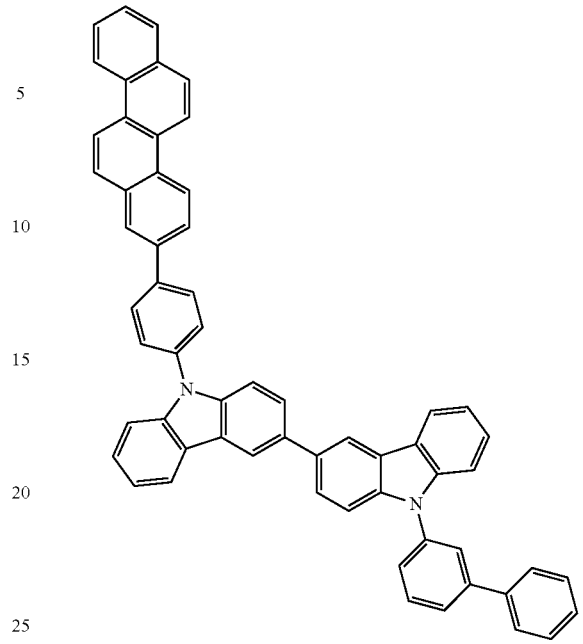
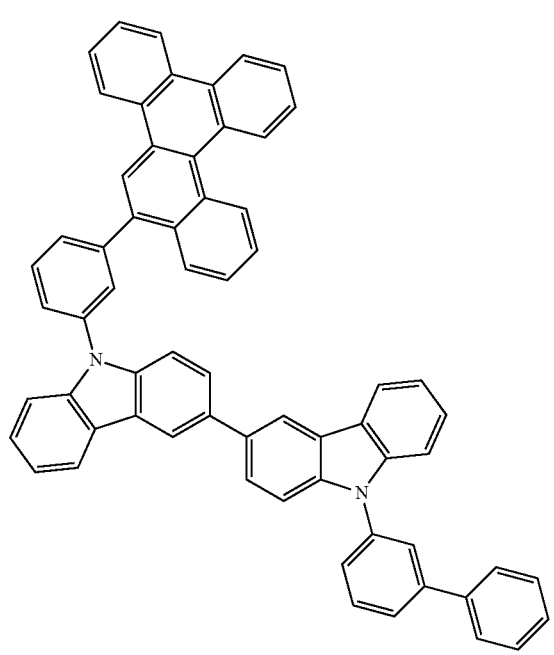
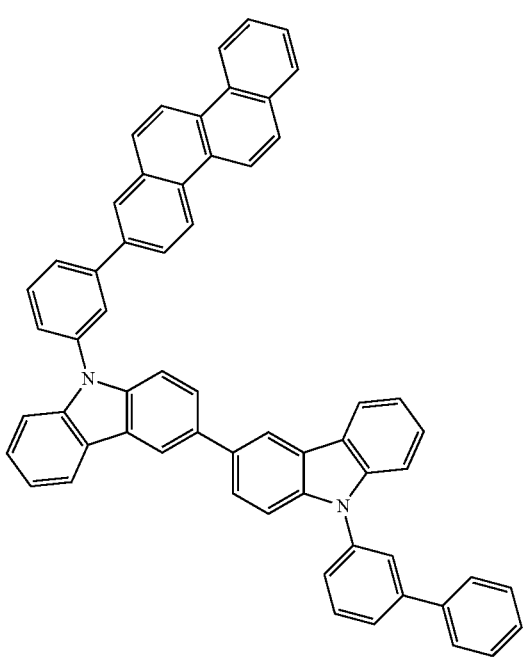

93
-continued
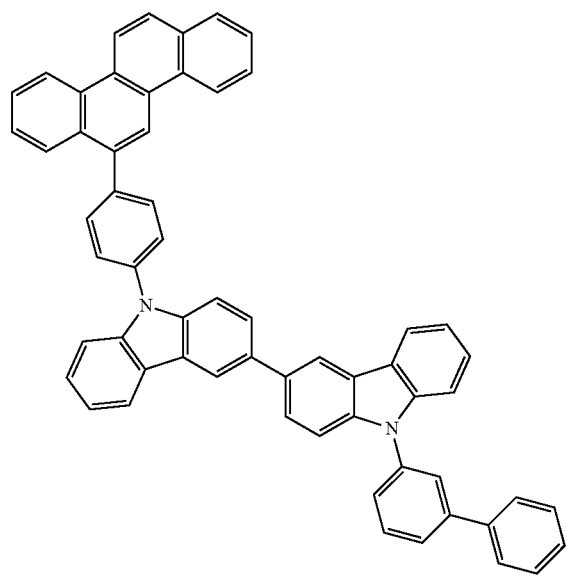
94
-continued
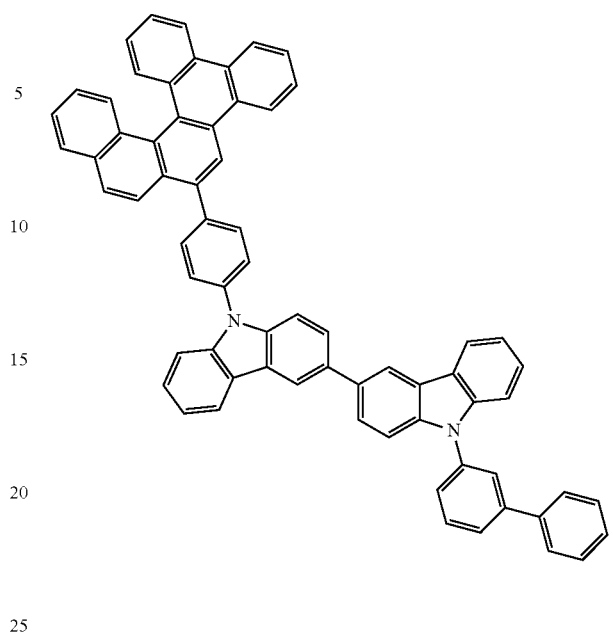
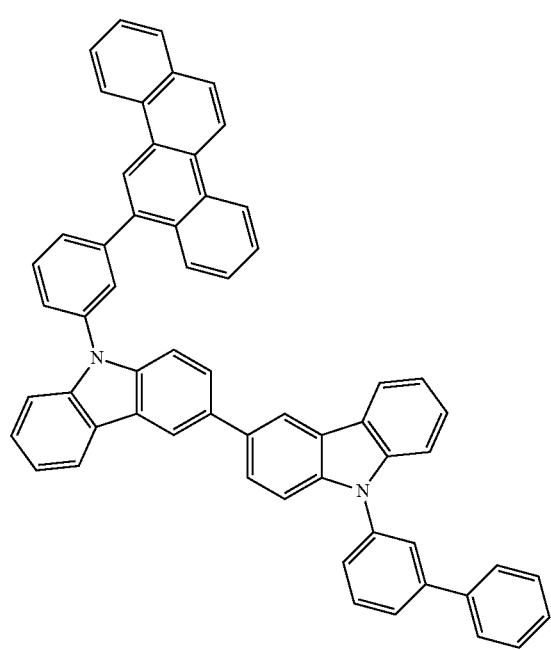
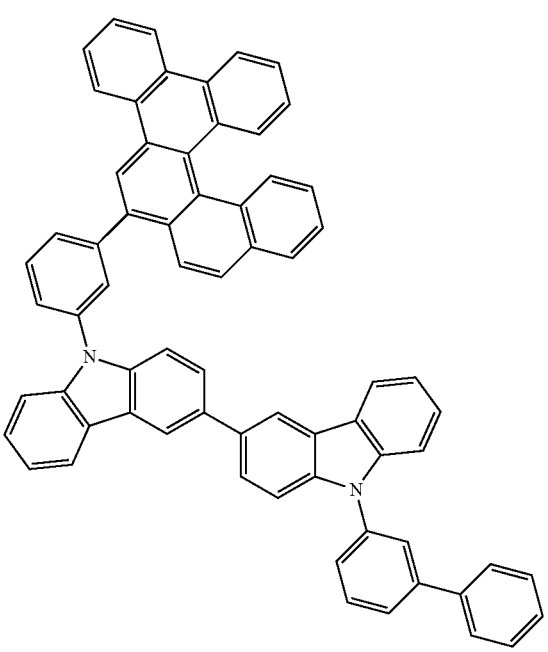

95
-continued
96
-continued
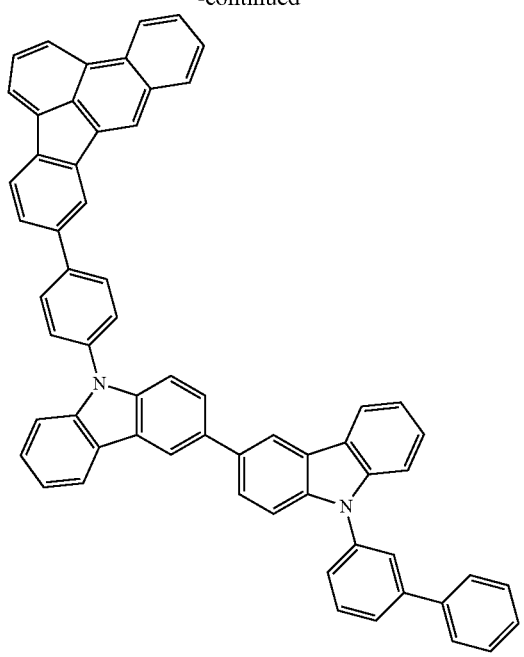
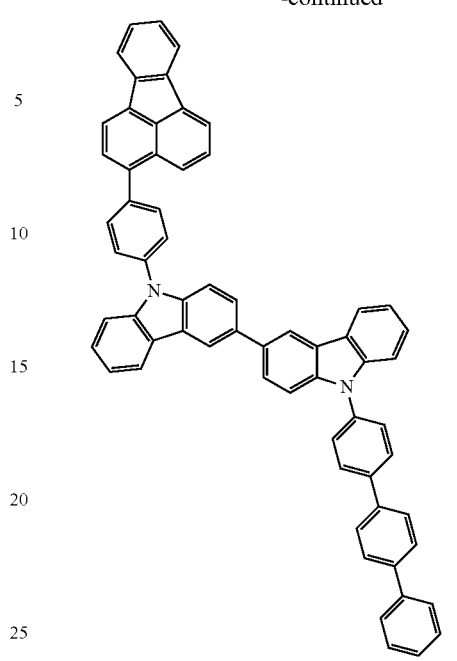
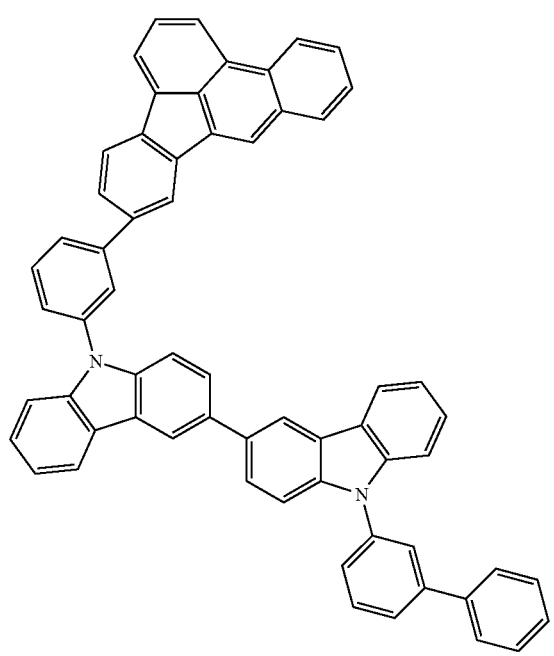

97
-continued
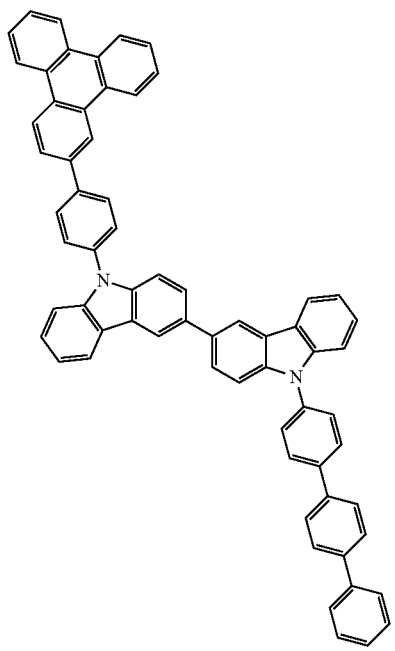
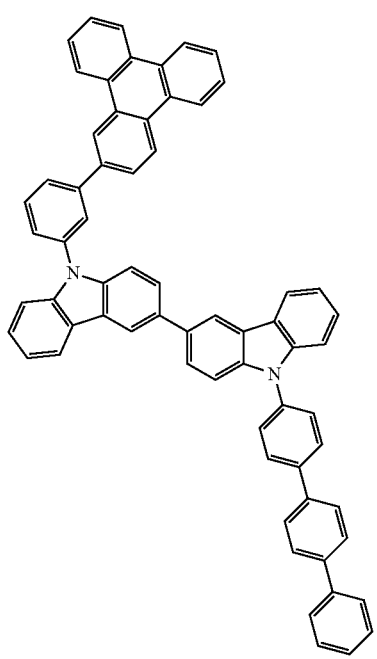
98
-continued
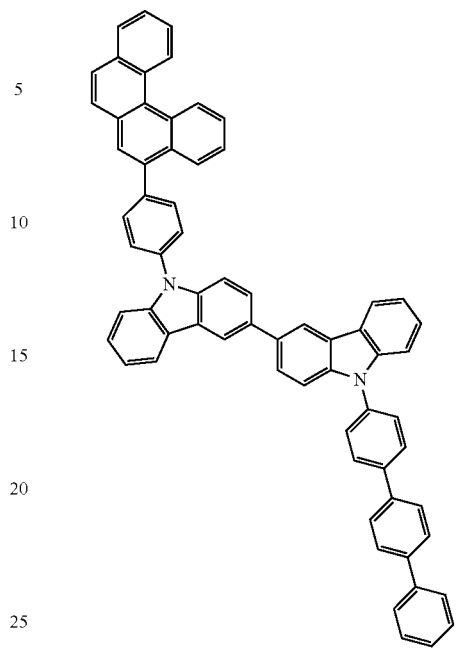
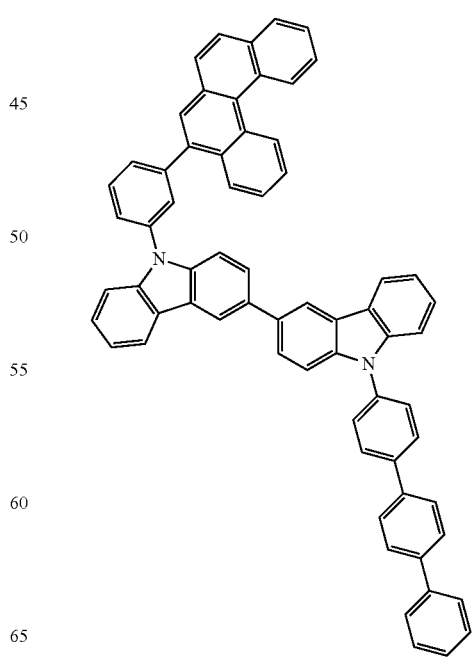

99
-continued
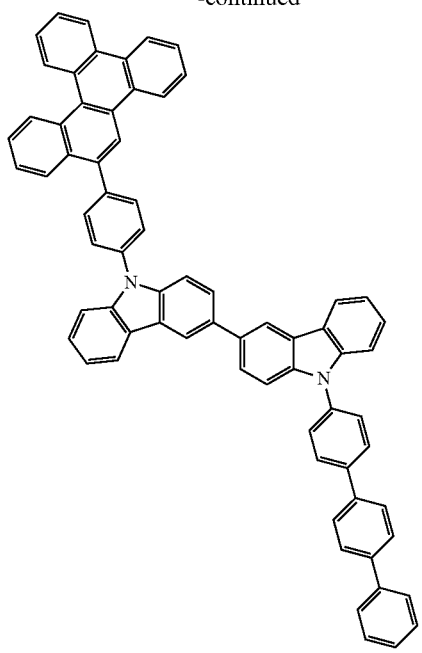
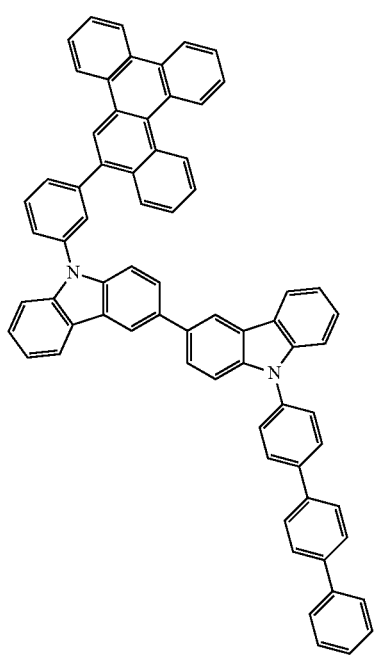
100
-continued
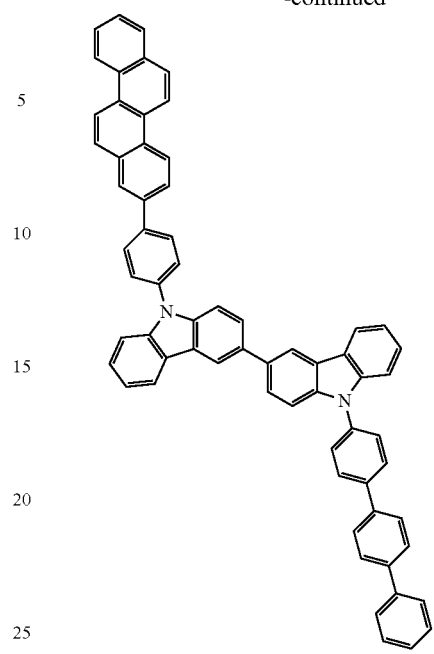
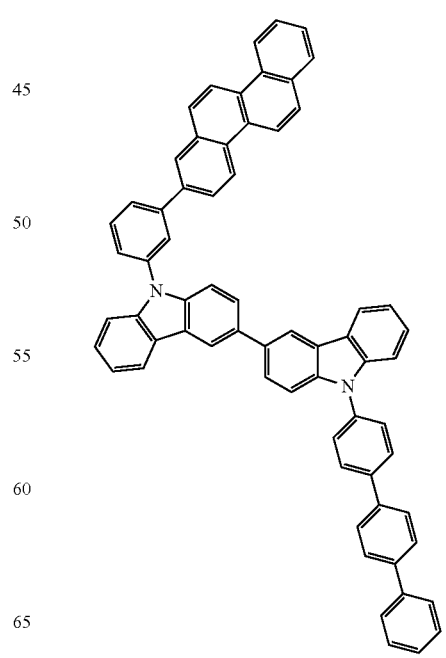

101
-continued
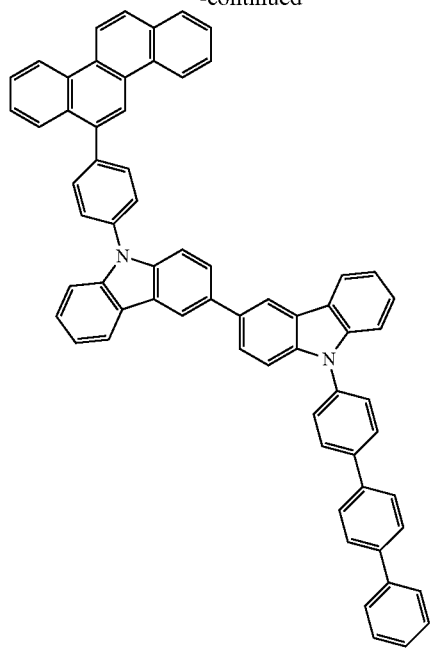
102
-continued
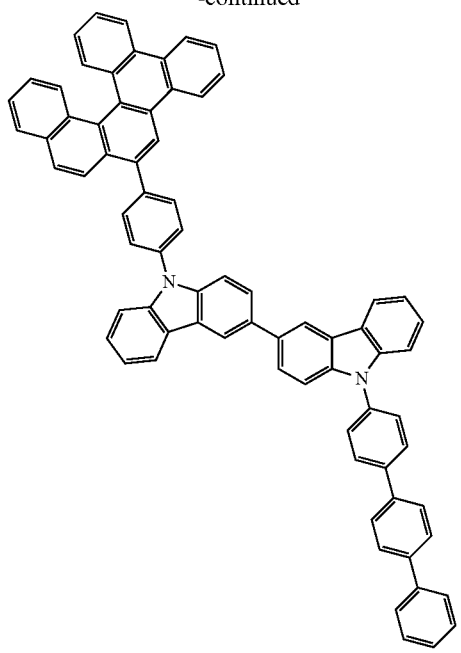
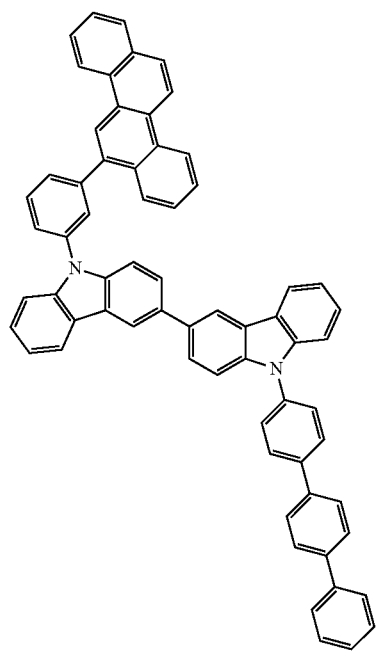
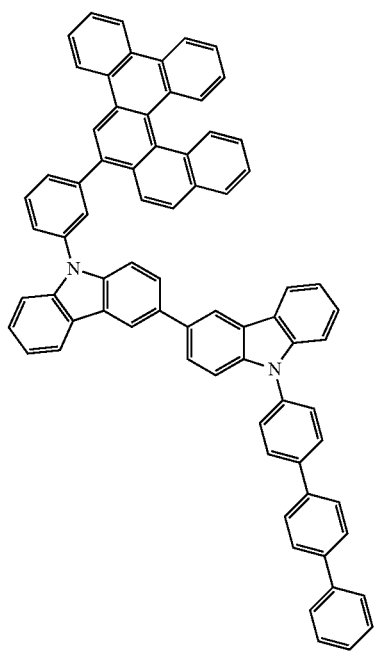

103
-continued
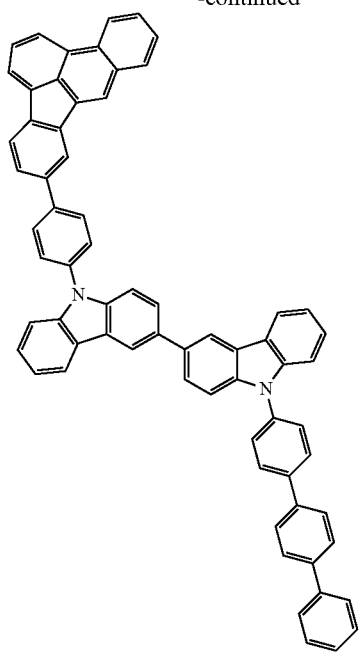
104
-continued
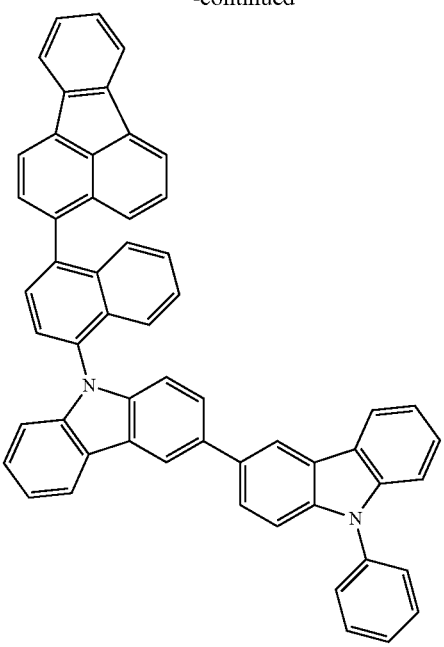
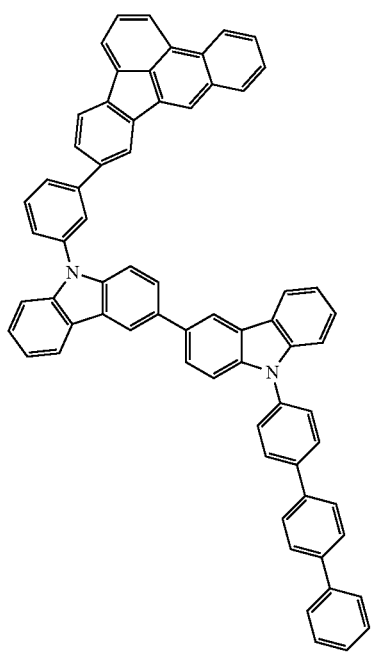
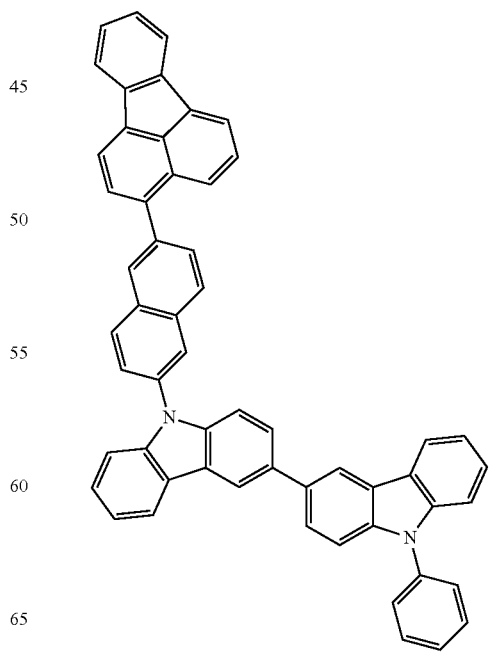

105
-continued
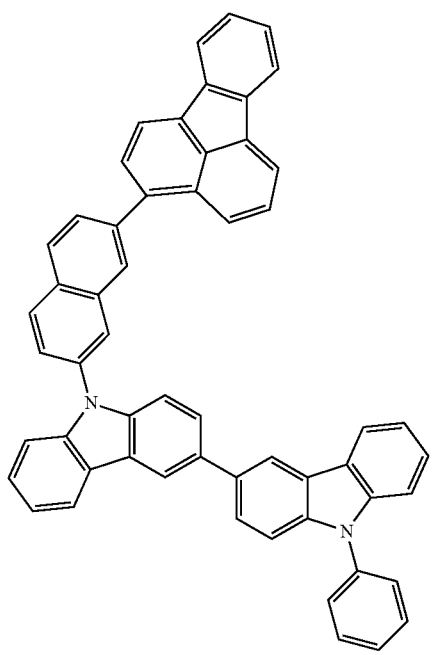
106
-continued
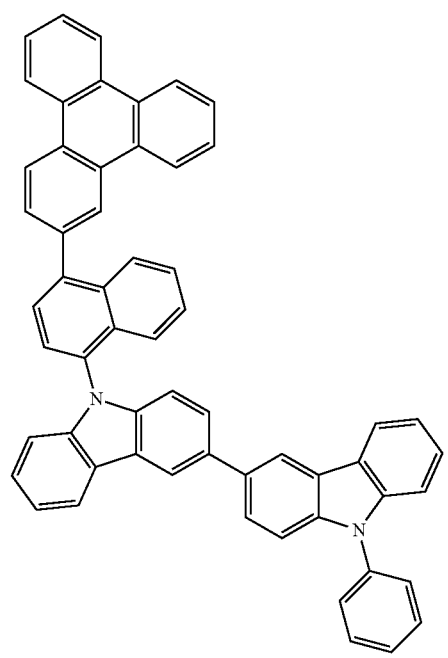
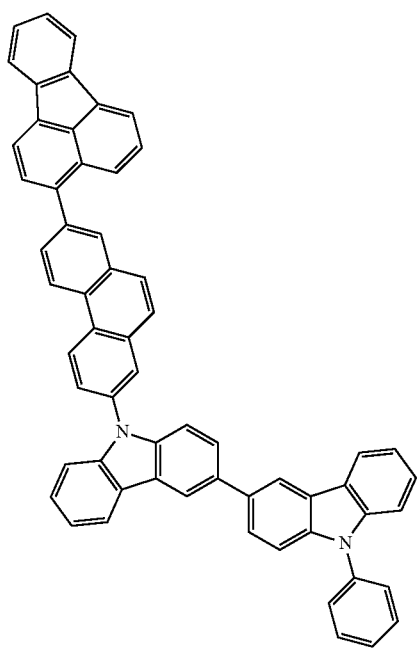
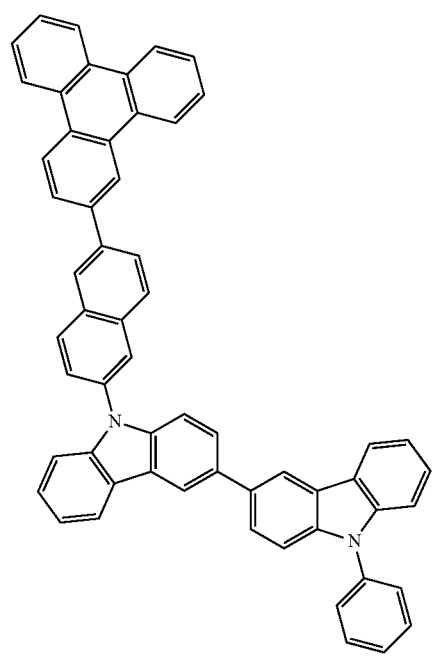

107
-continued
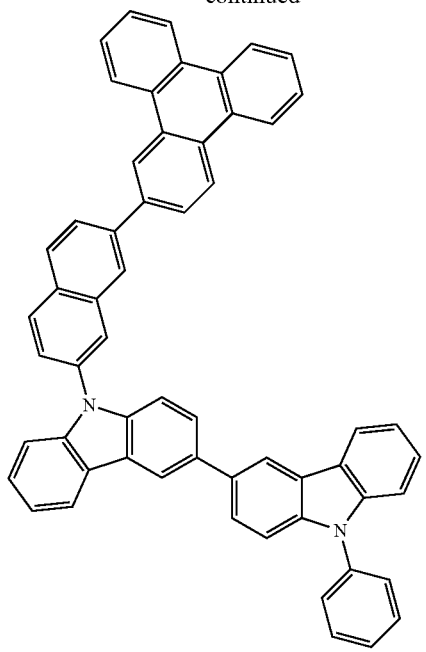
108
-continued
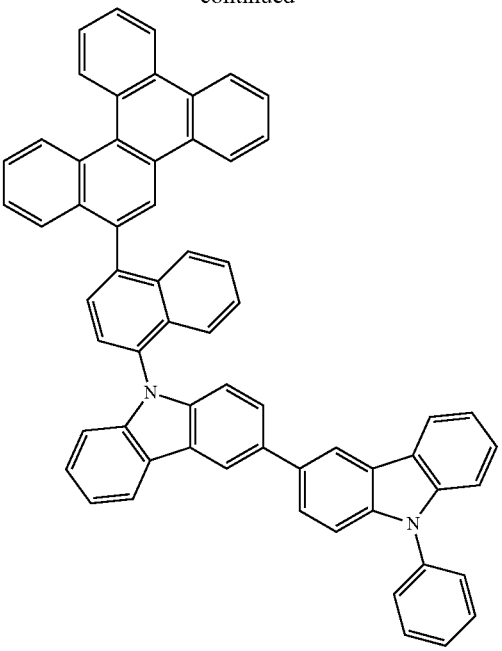
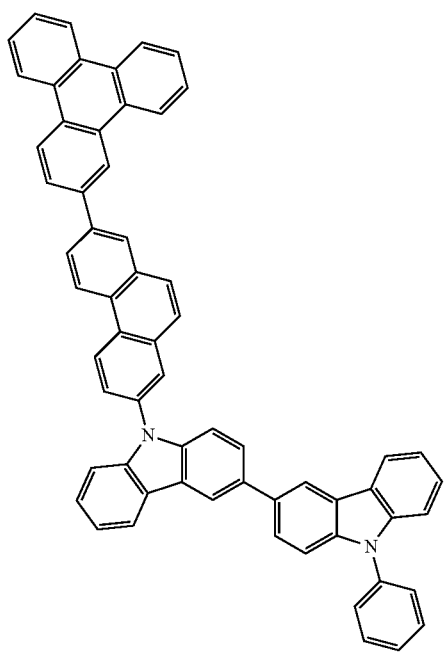
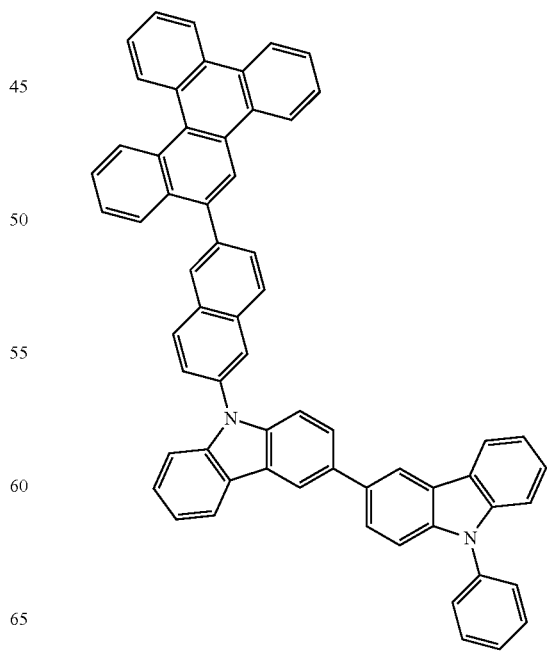

109
-continued
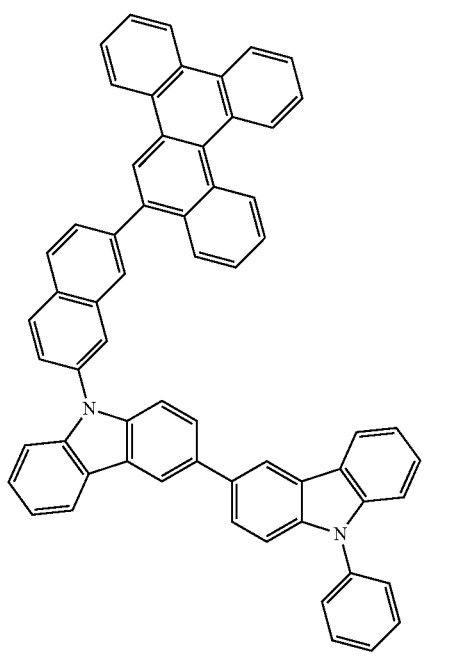
110
-continued
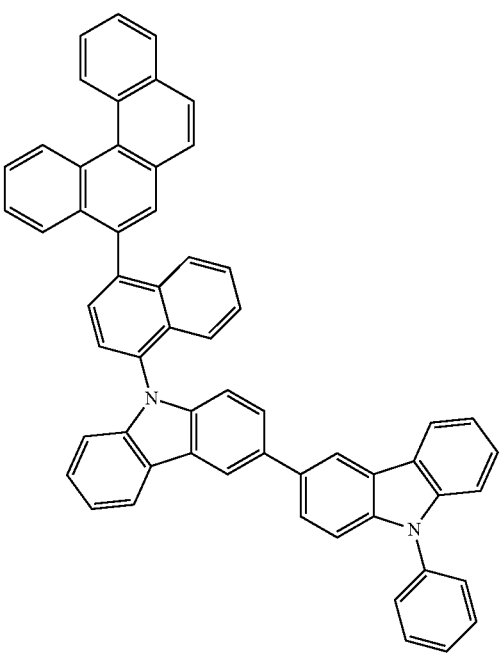
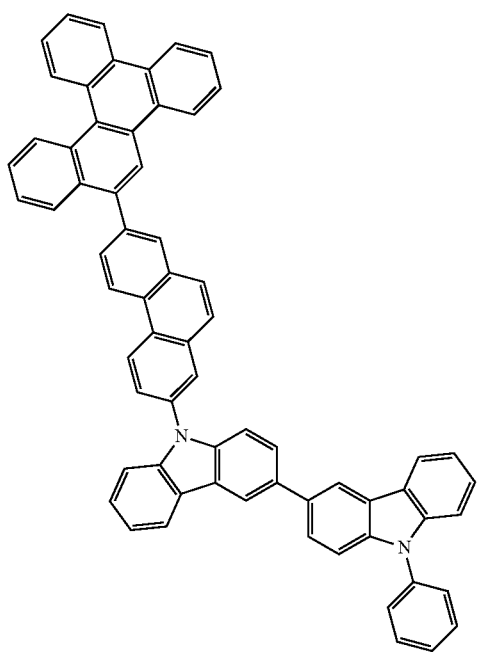
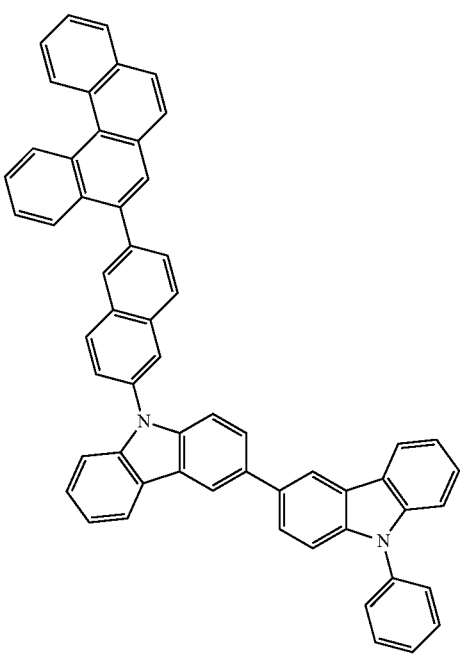

111
-continued
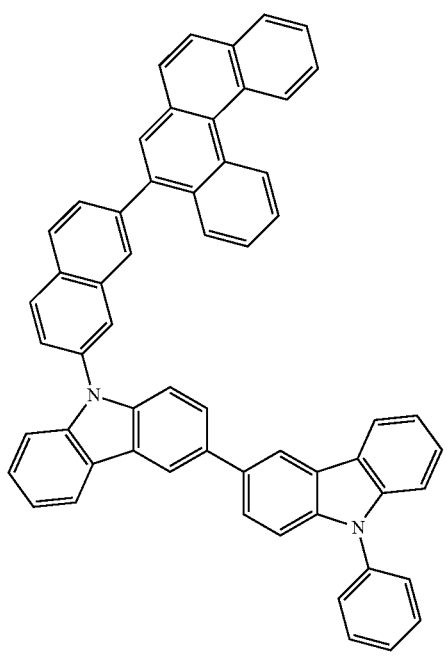
112
-continued
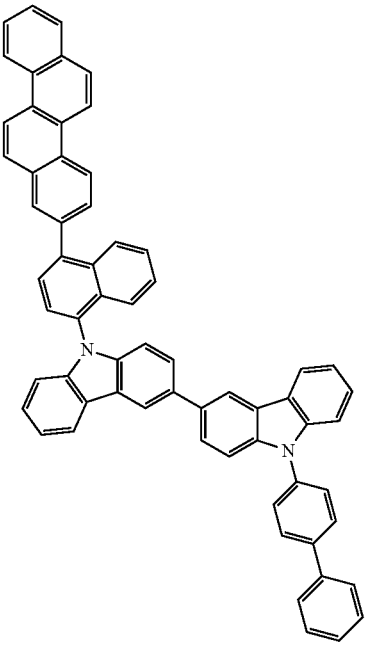
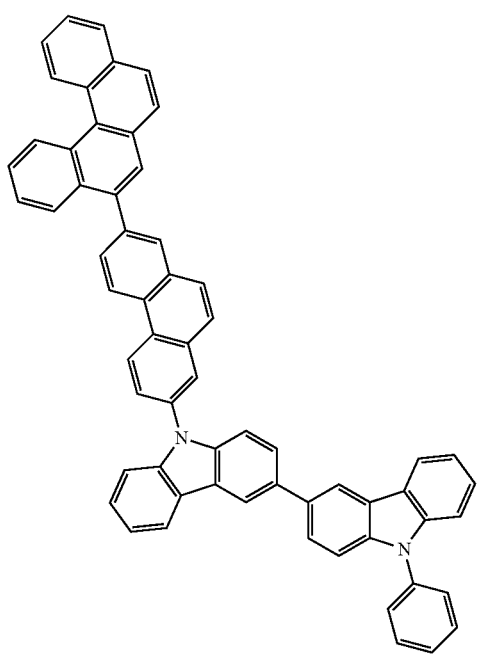
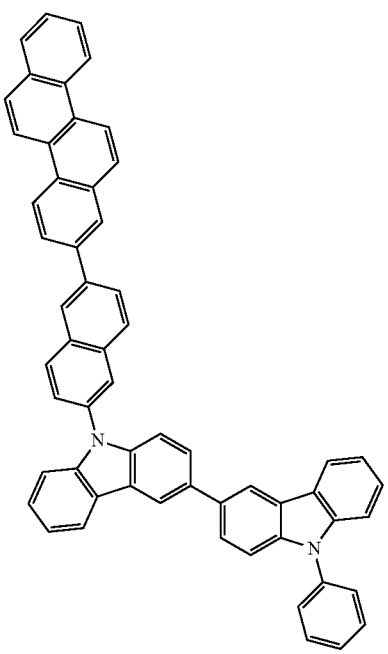

113
-continued
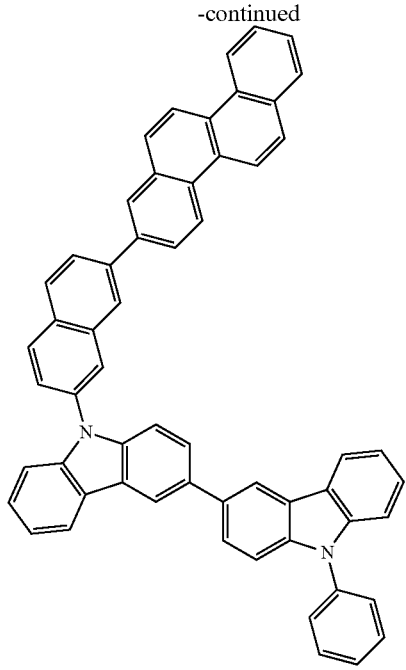
114
-continued
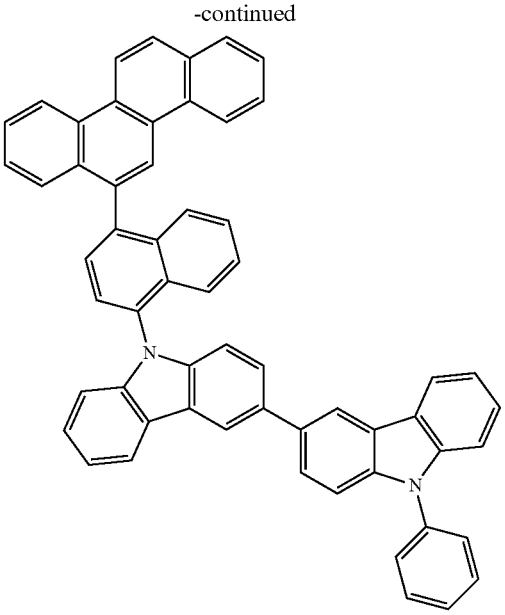
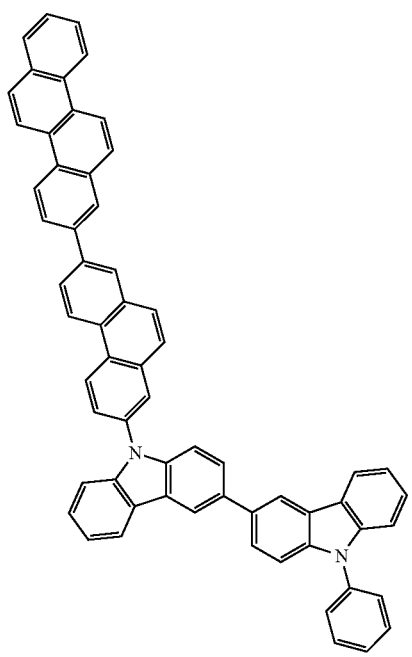
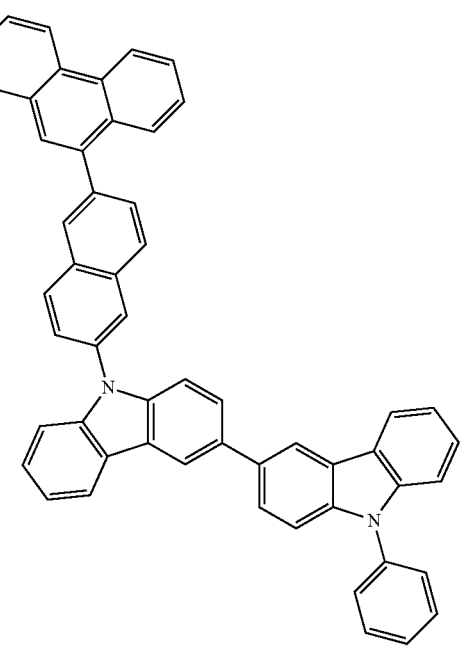

115
-continued
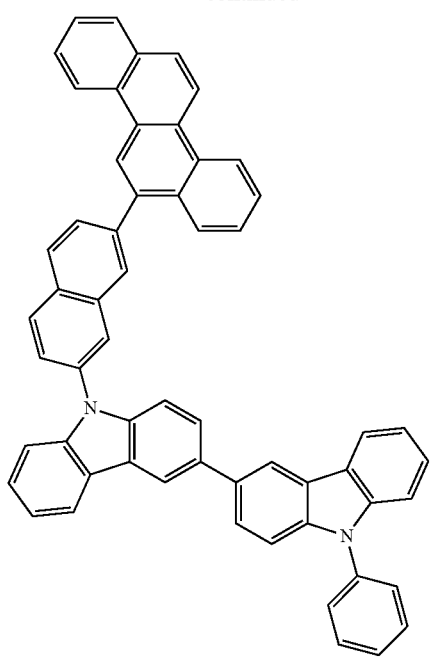
116
-continued
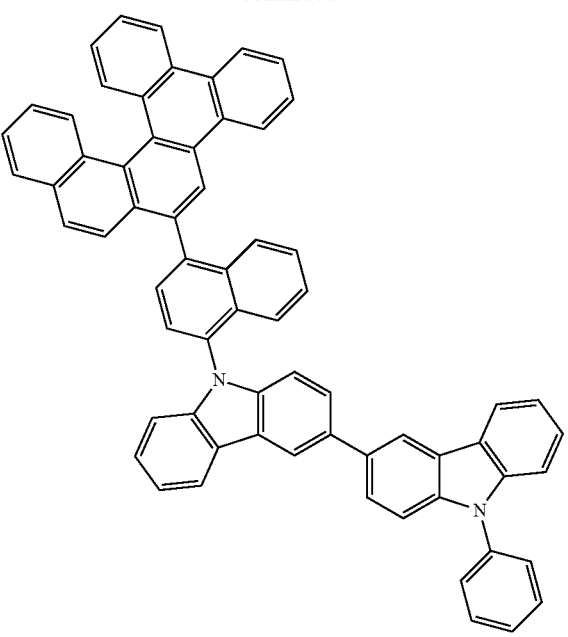
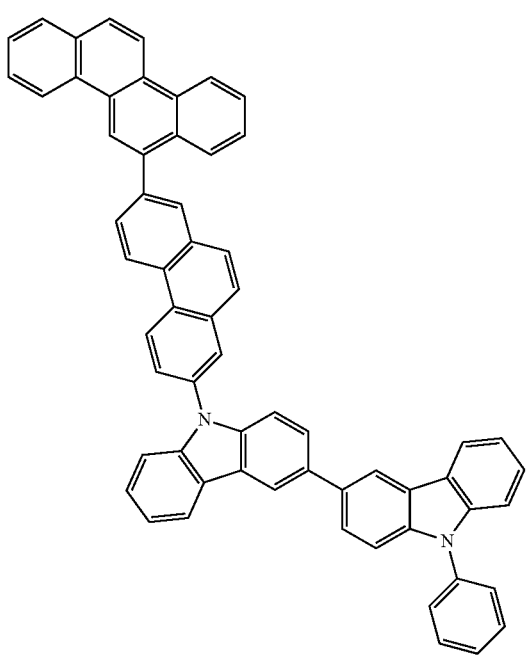
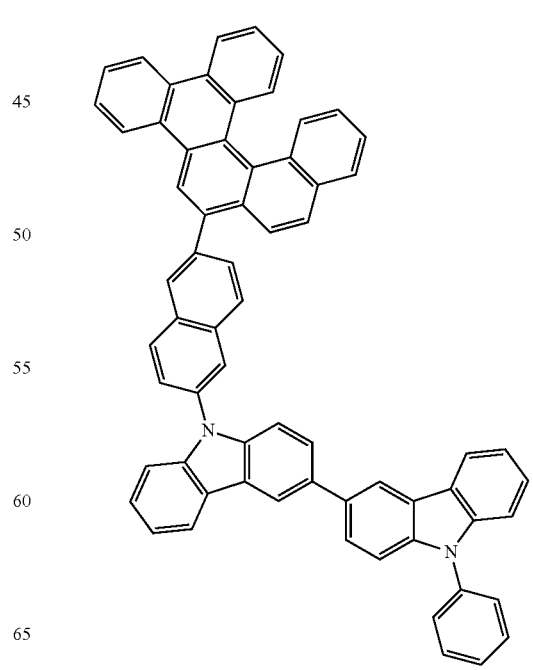

117
-continued
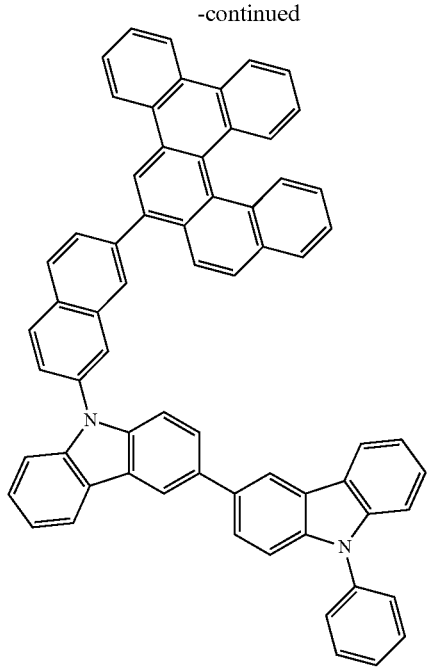
118
-continued
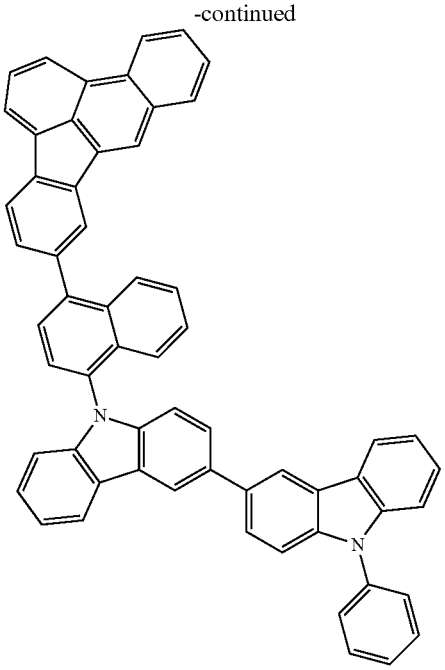
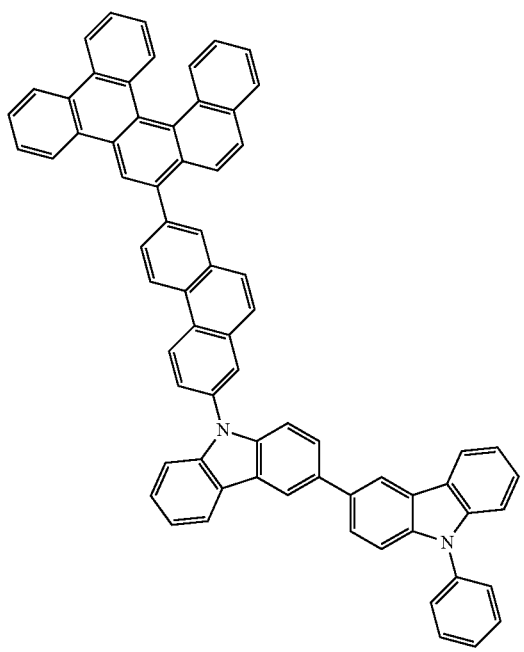
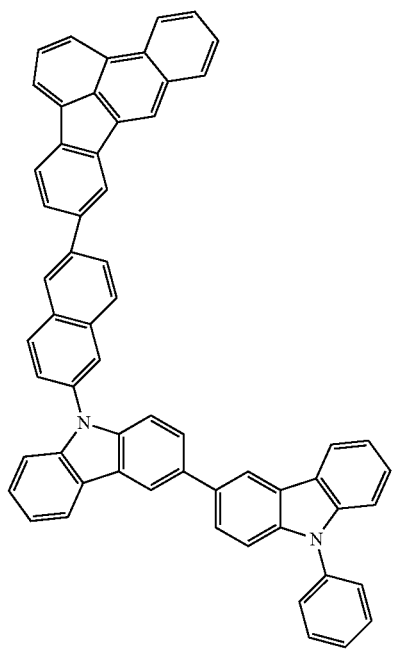

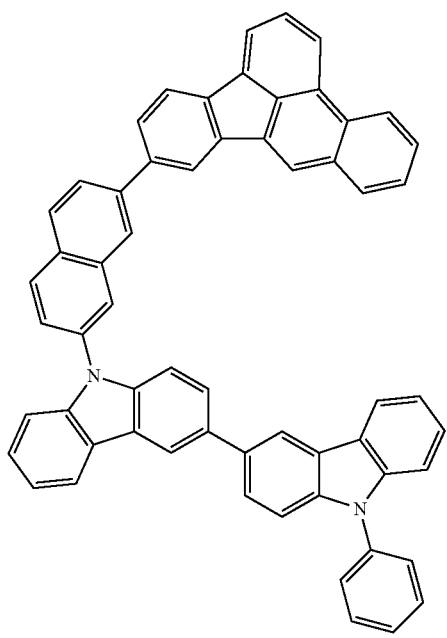
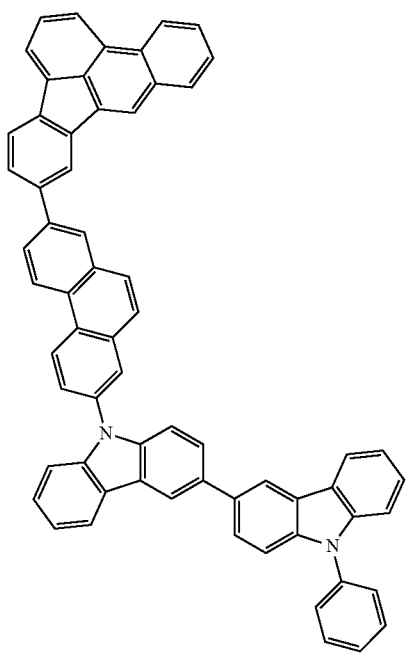
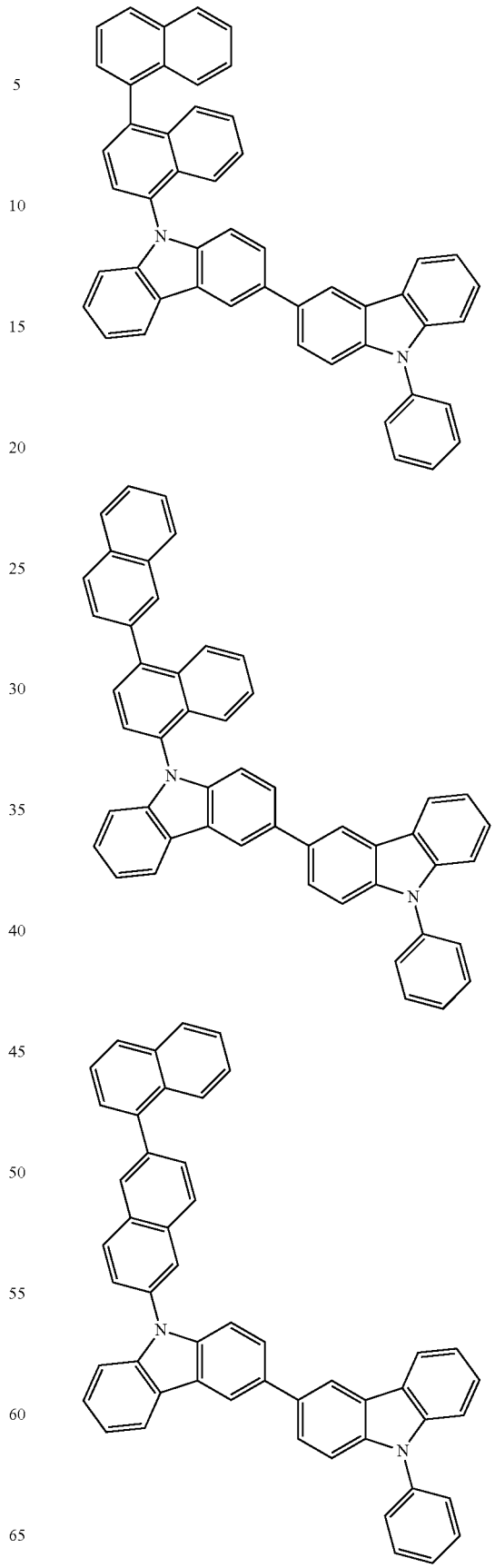

121
-continued
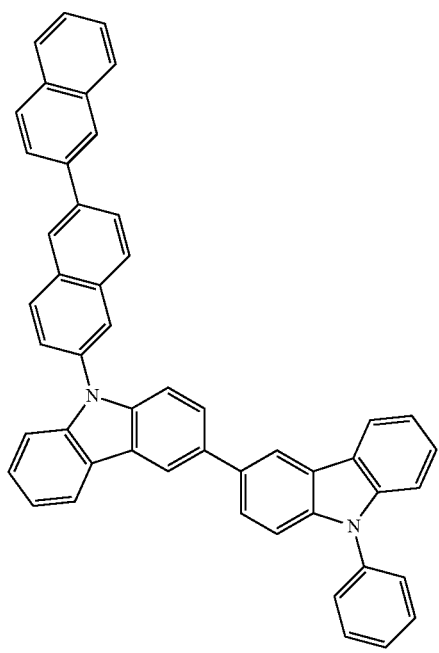
122
-continued
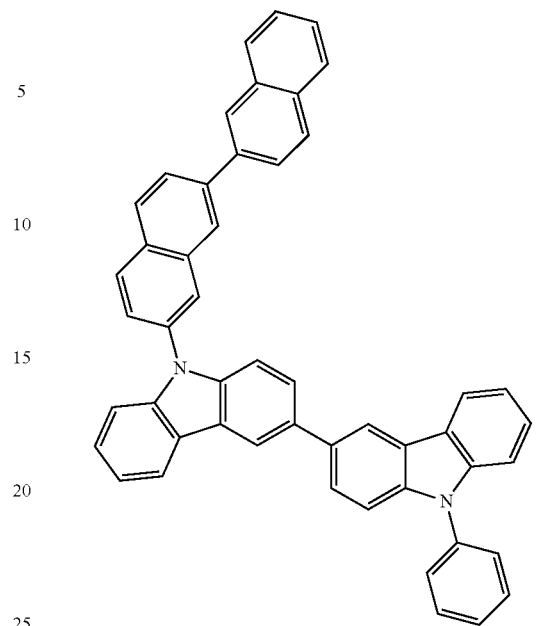
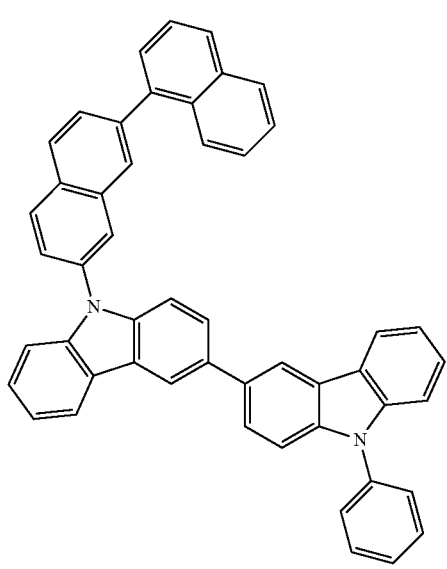
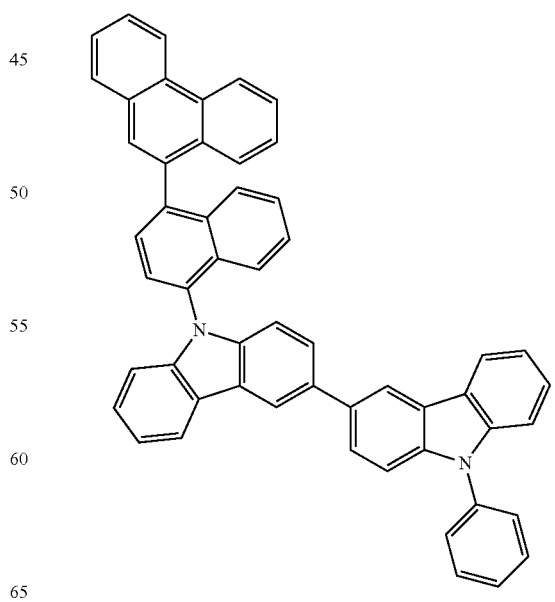

123
-continued
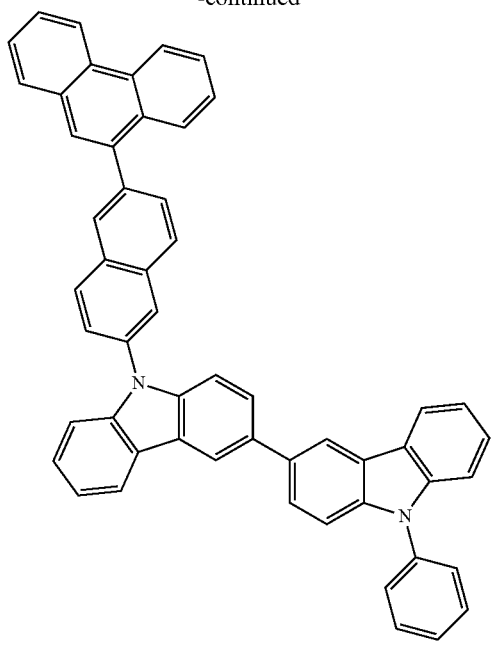
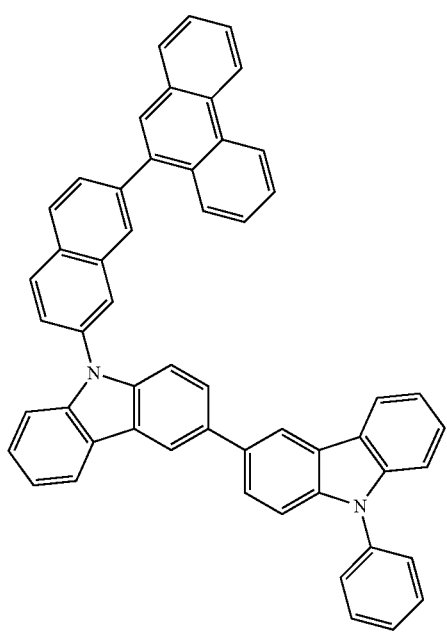
124
-continued
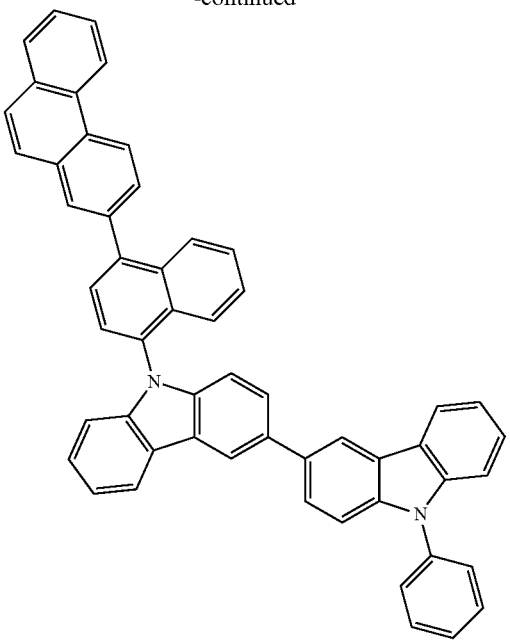
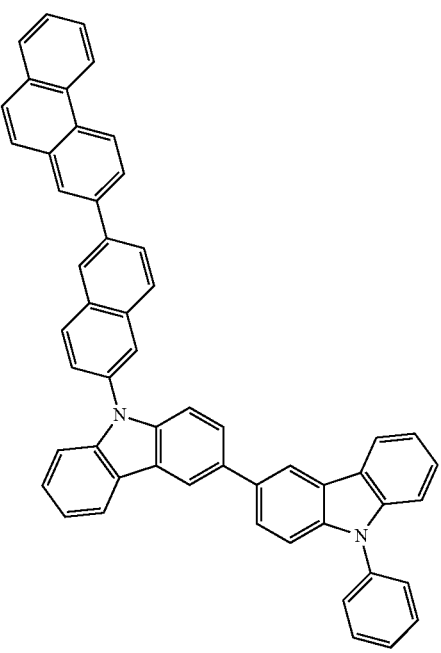

125
-continued
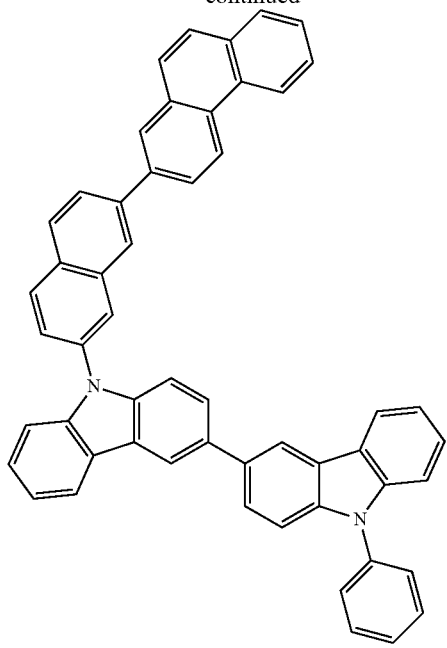
126
-continued
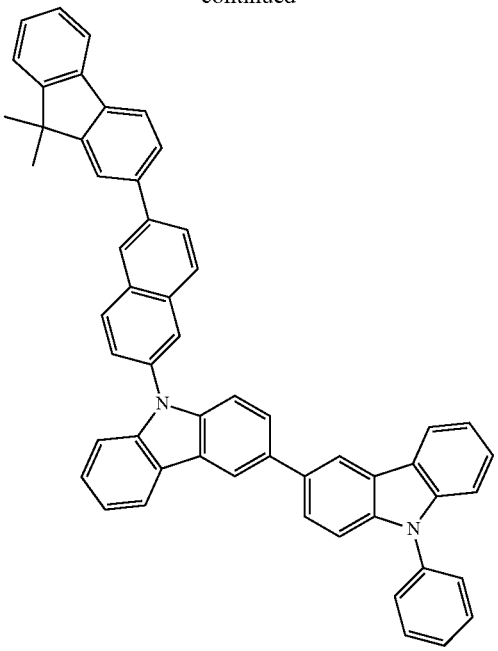
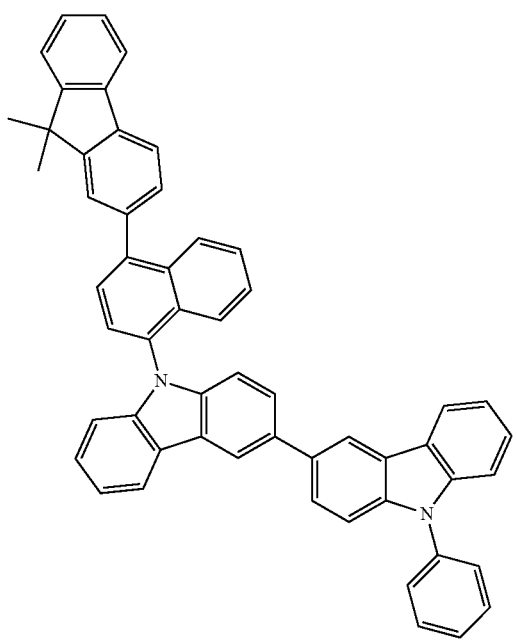
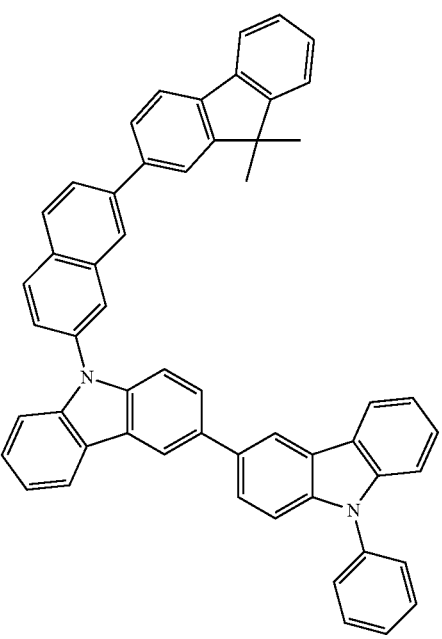

127
-continued
128
-continued
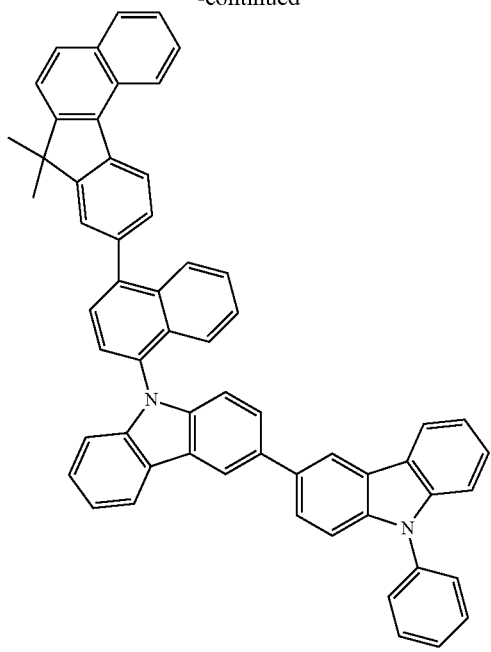
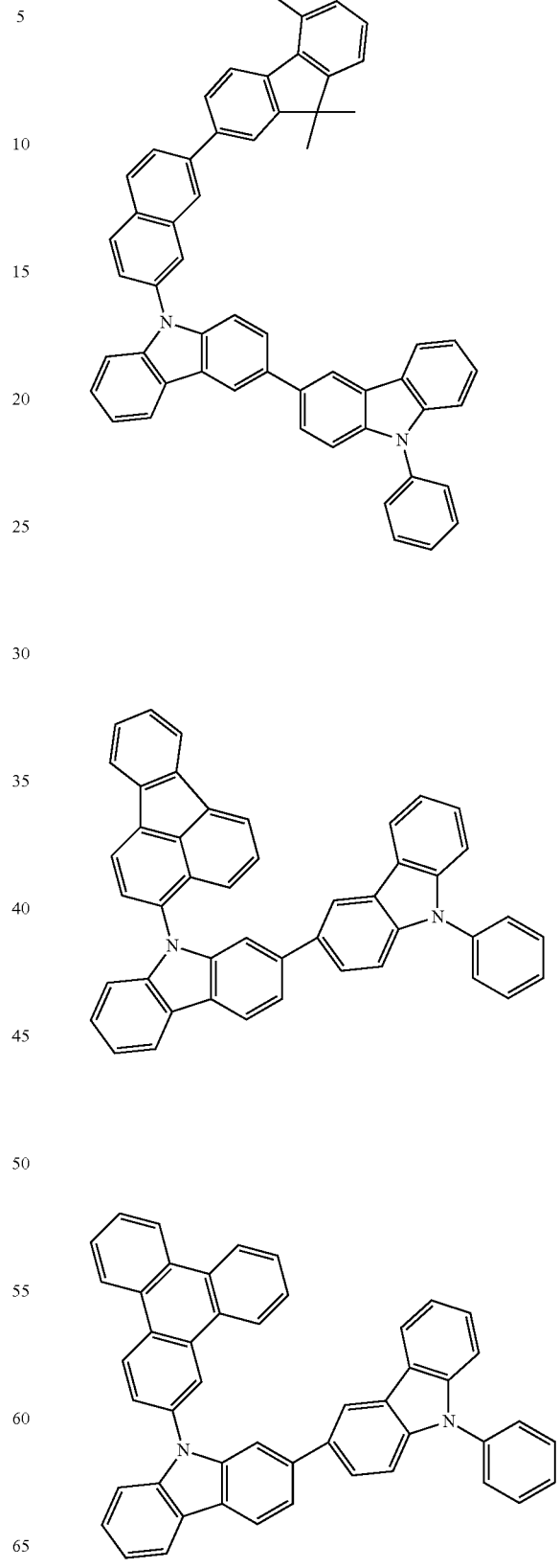

129
-continued
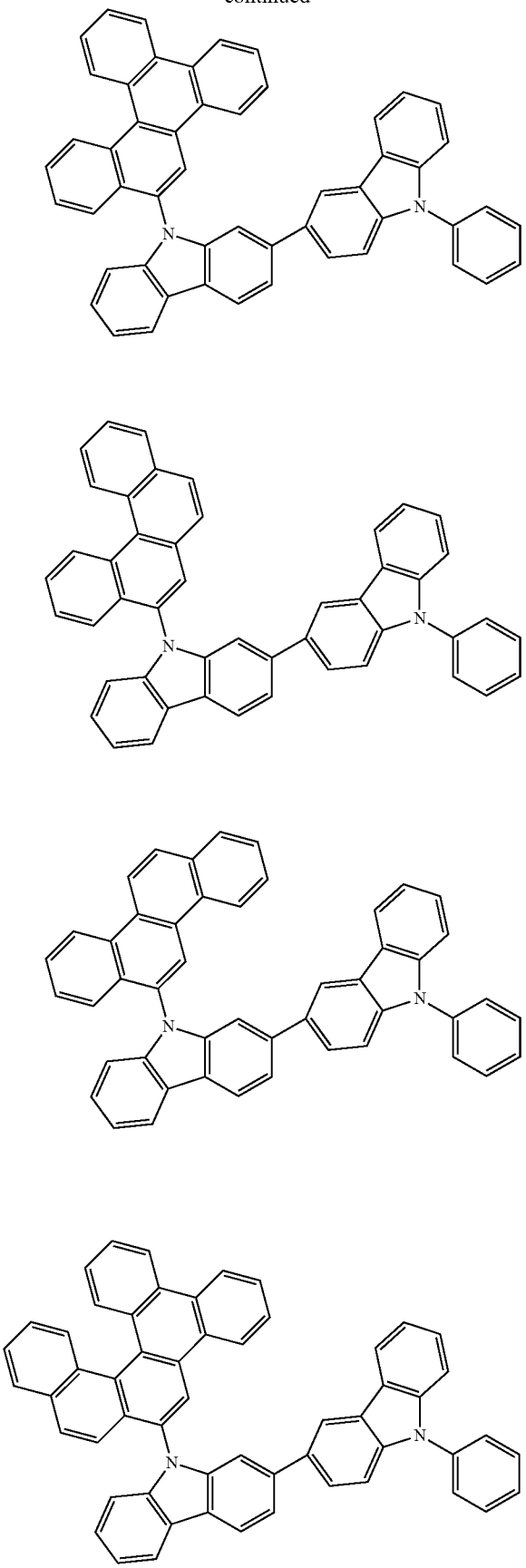
130
-continued
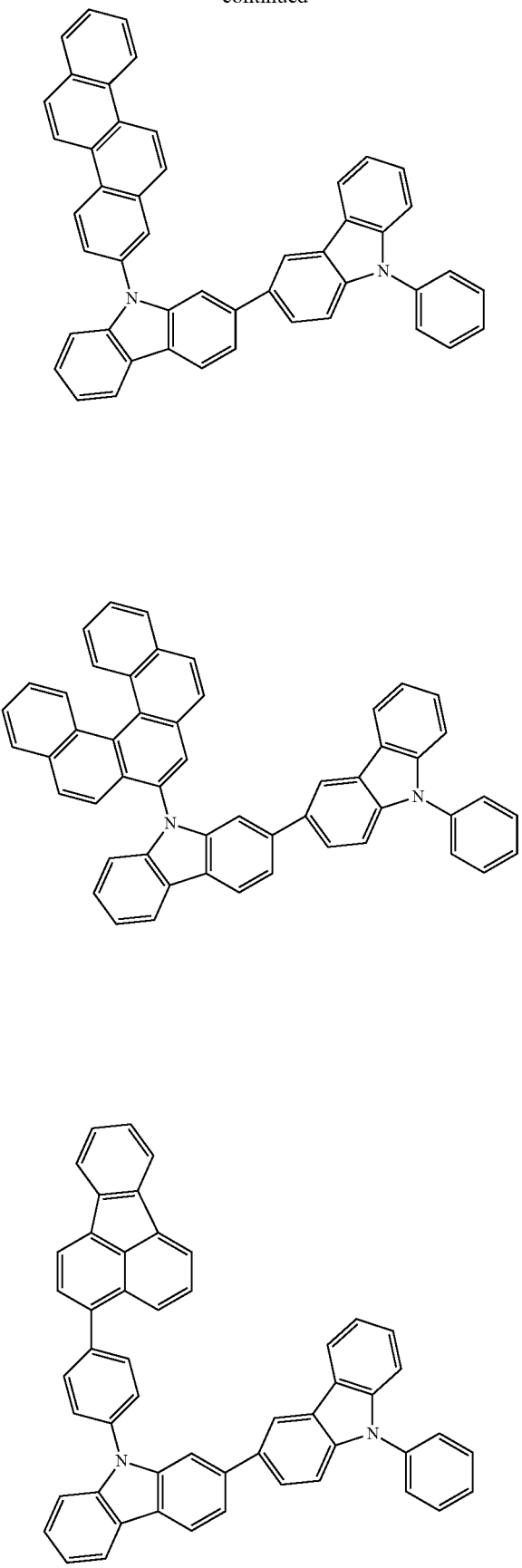

131
-continued
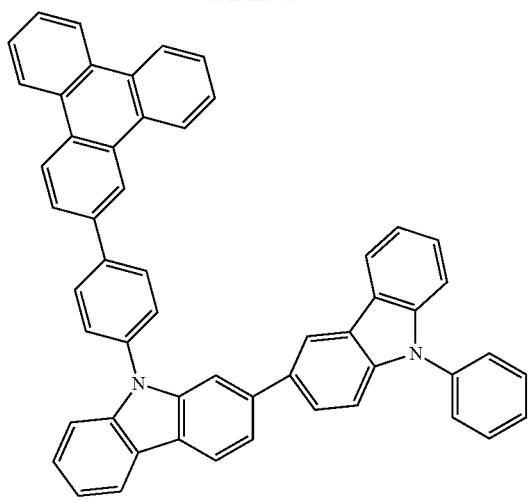
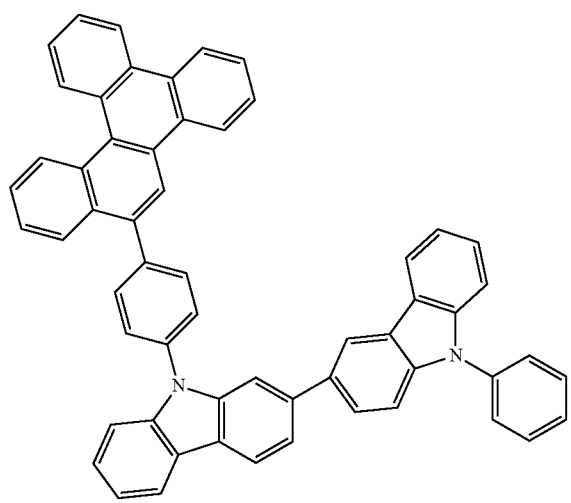
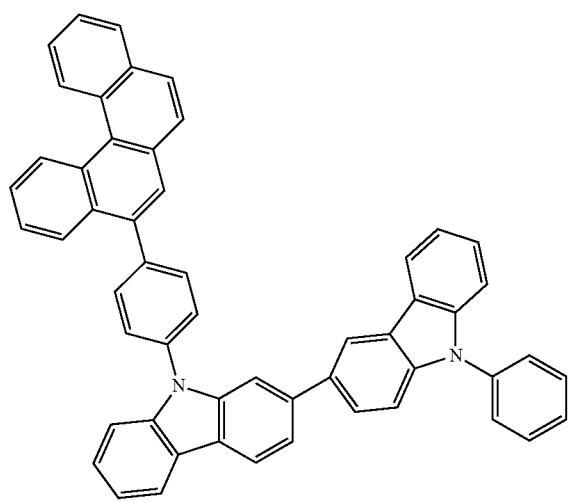
132
-continued
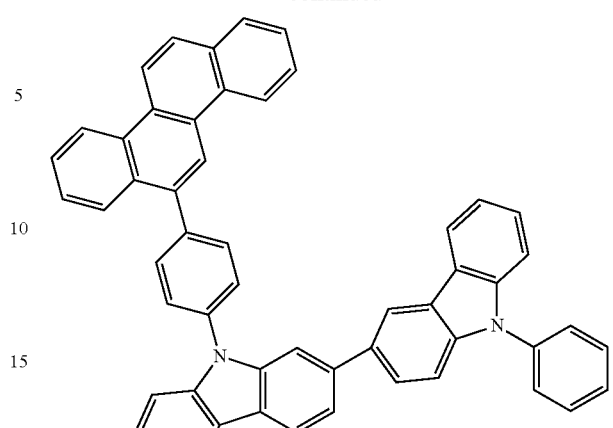
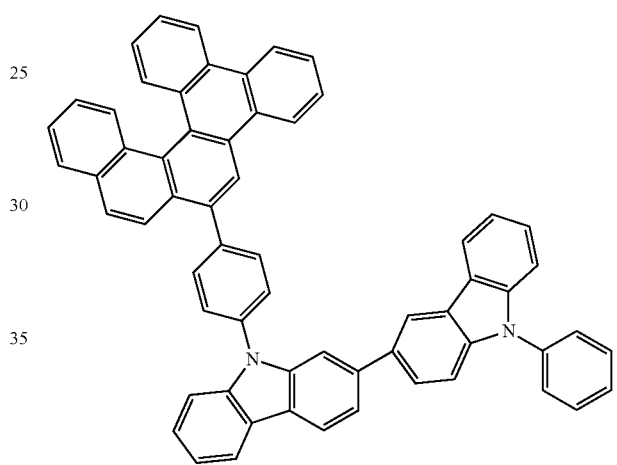
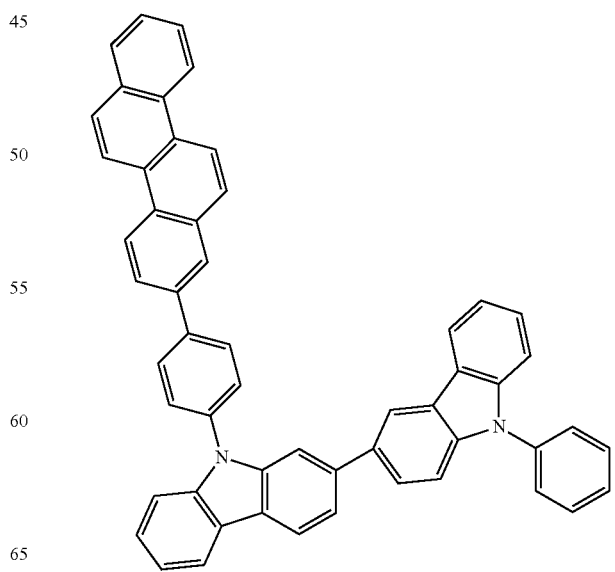

133
-continued
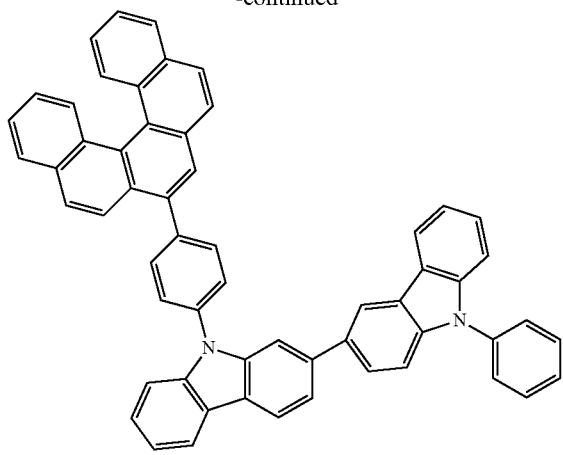
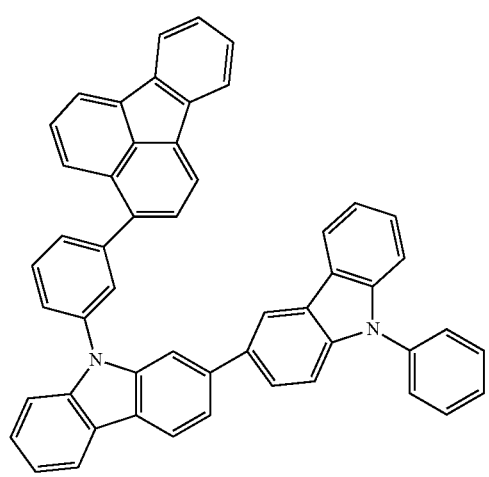
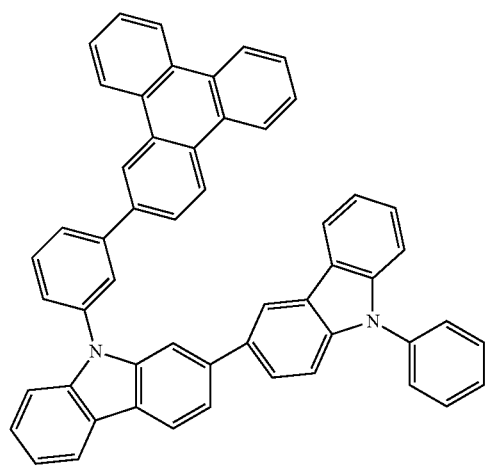
134
-continued
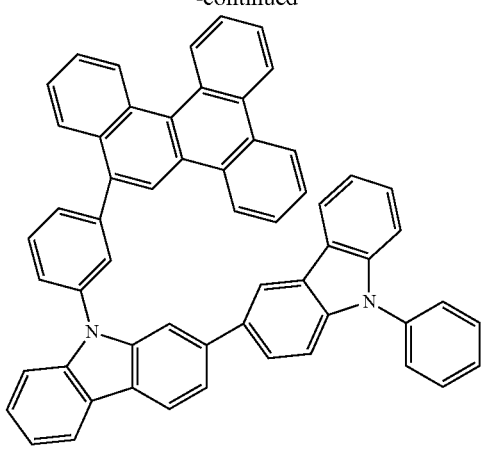
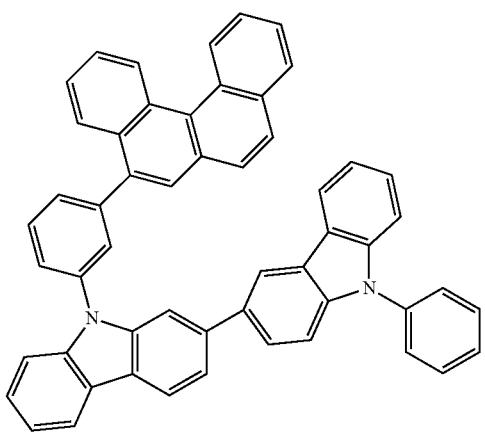
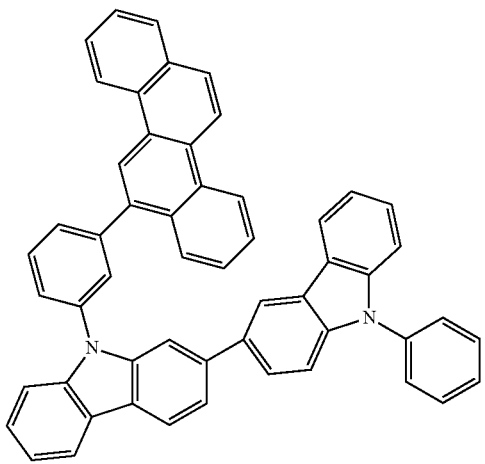

135
-continued
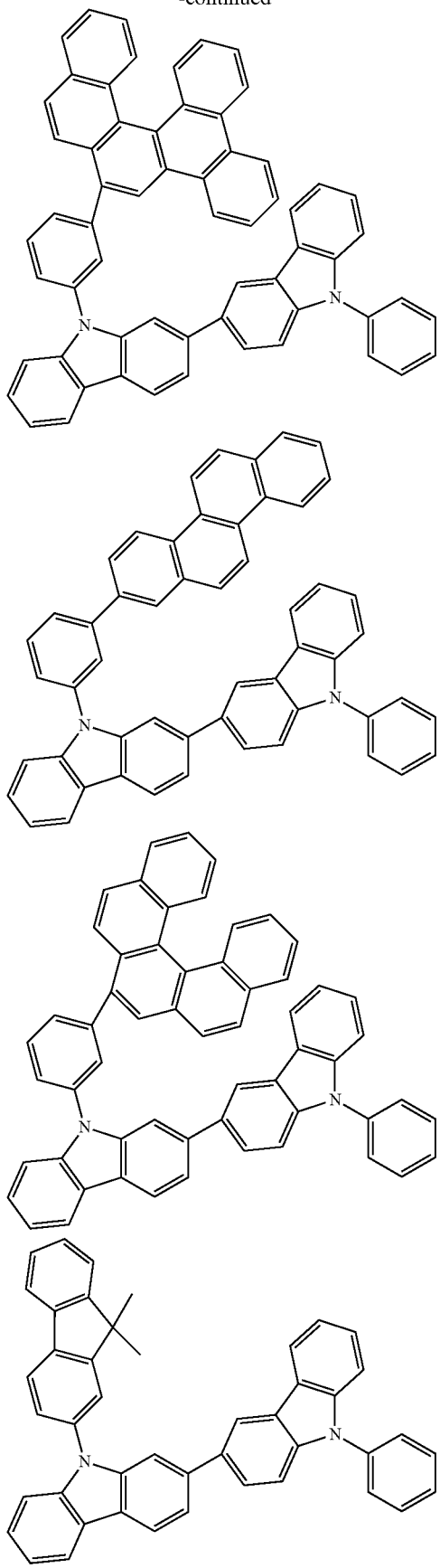
136
-continued
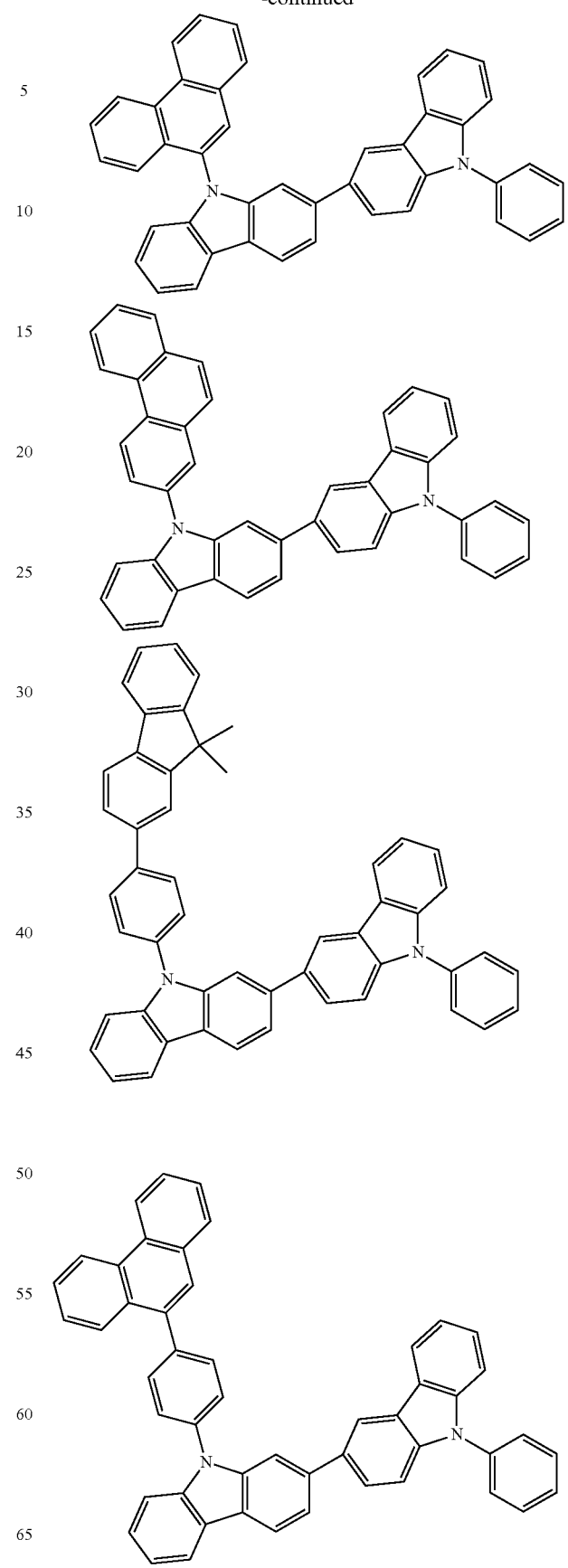

137
-continued
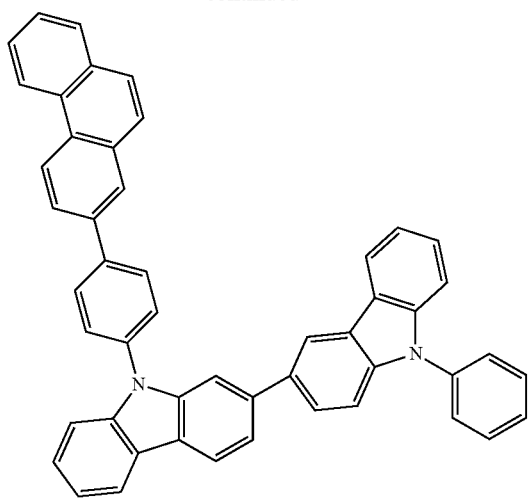
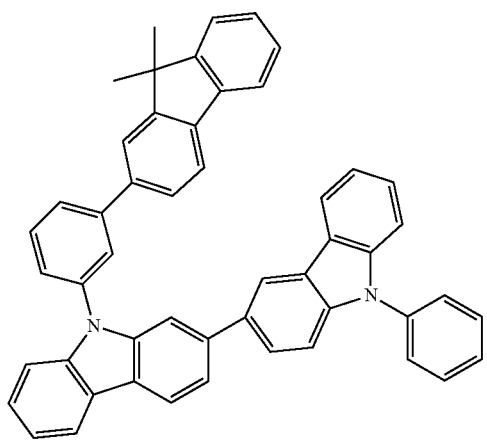
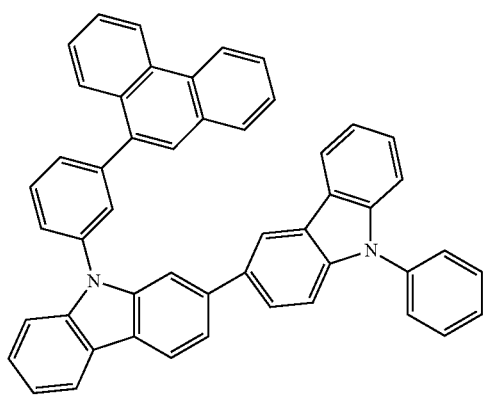
138
-continued
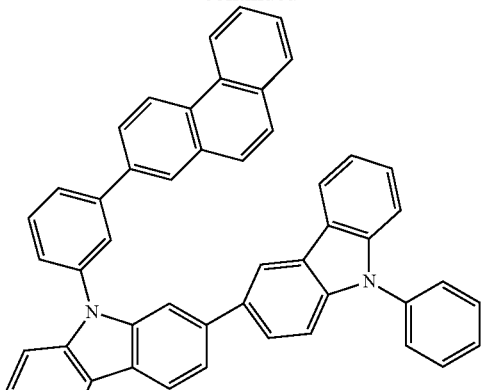
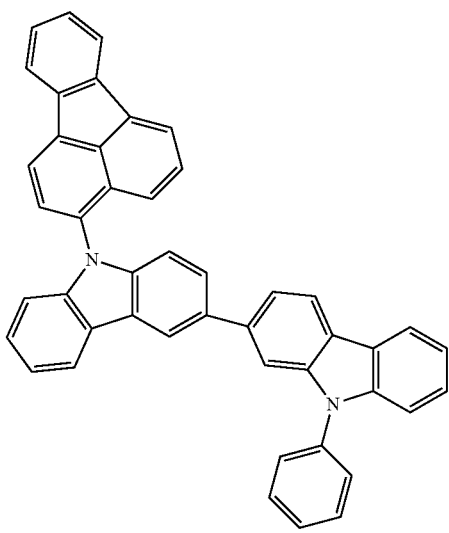
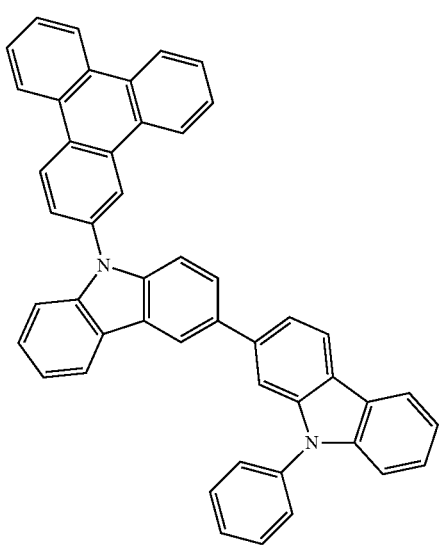

139
-continued
140
-continued
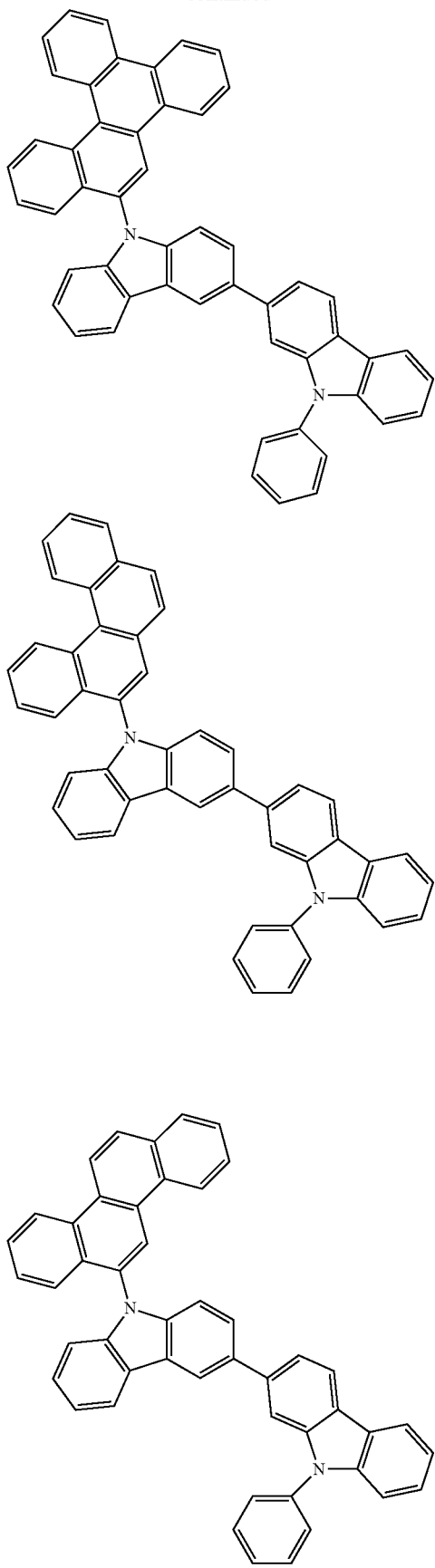
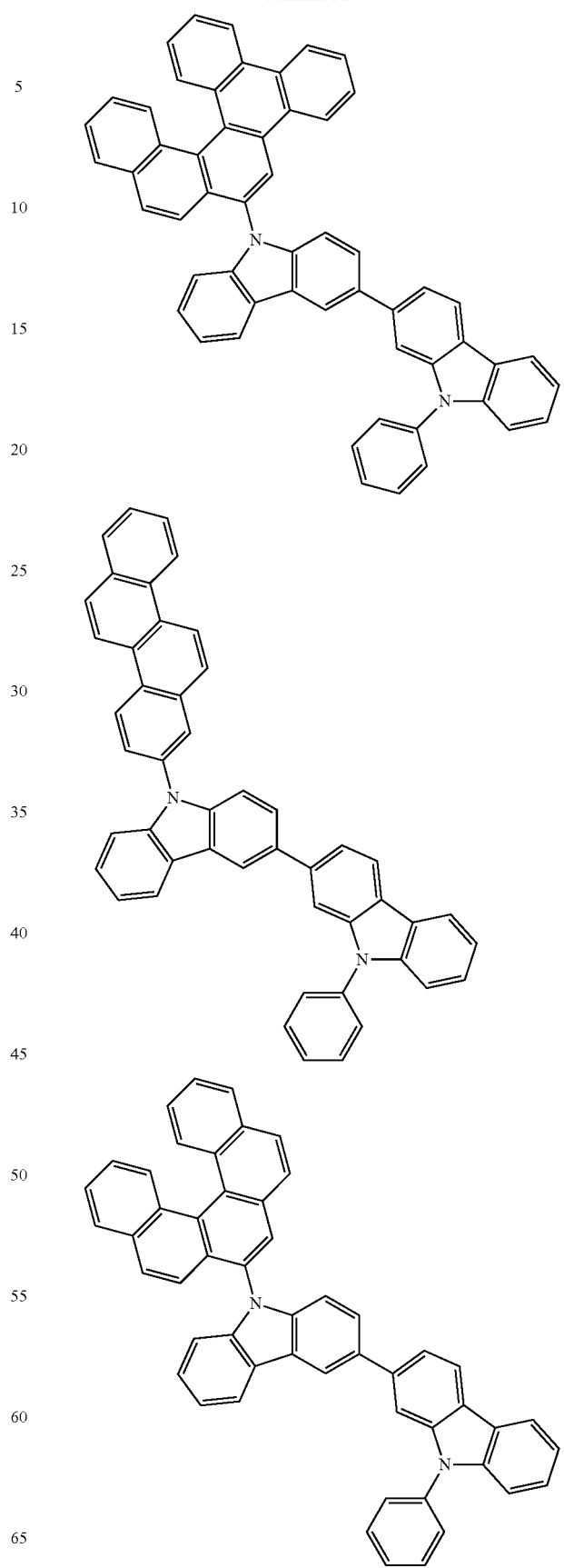

141
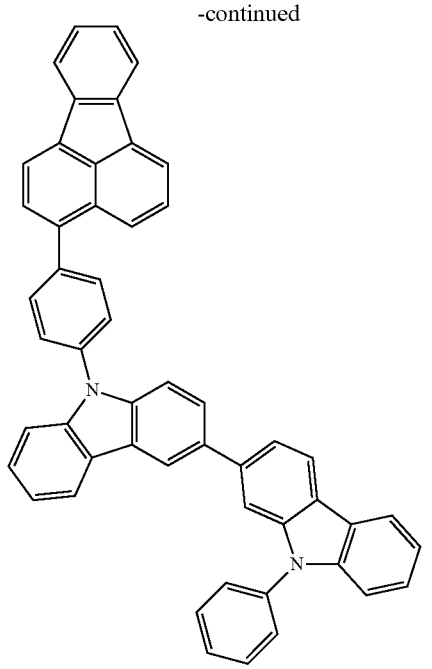
142
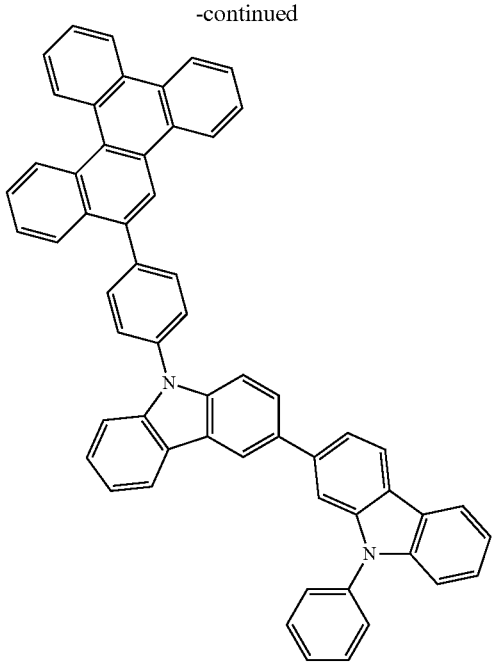
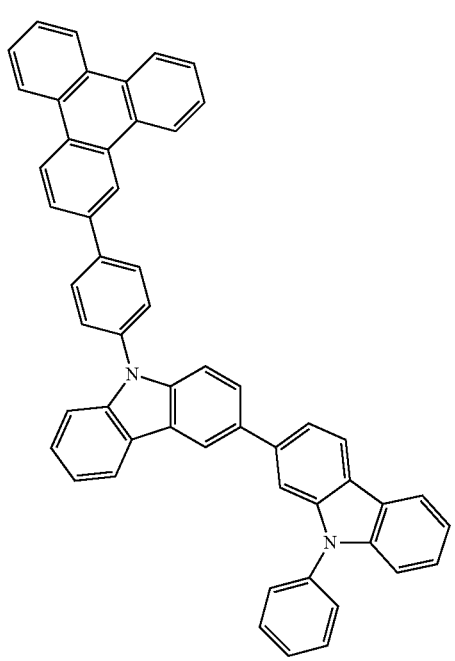
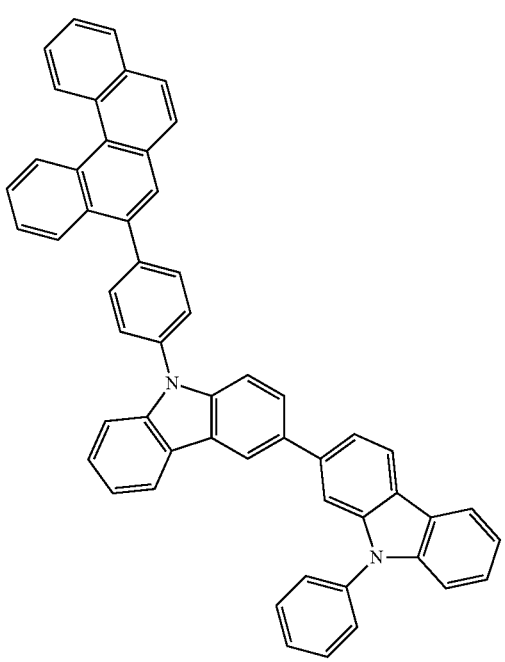

143
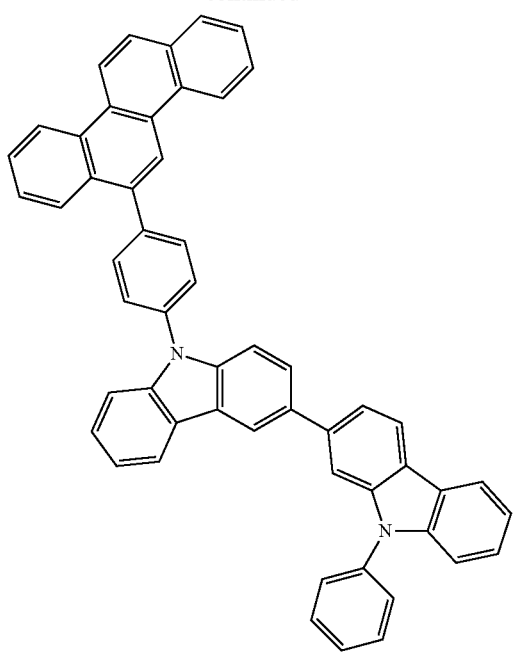
144
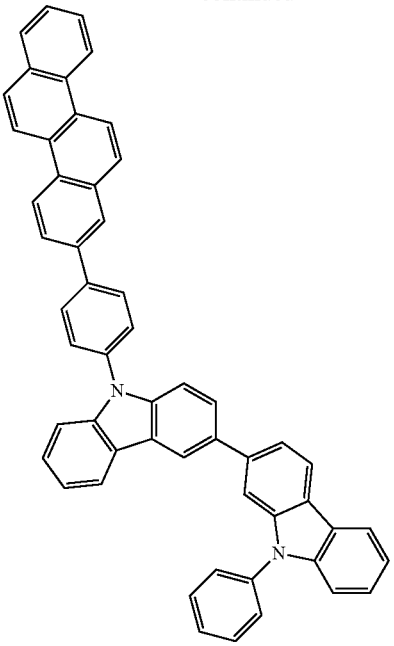
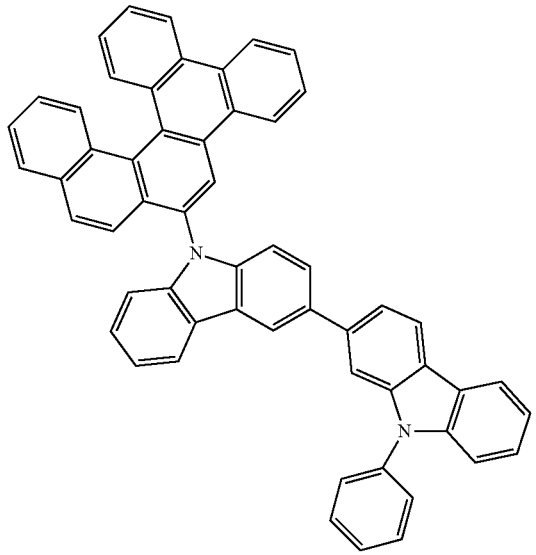
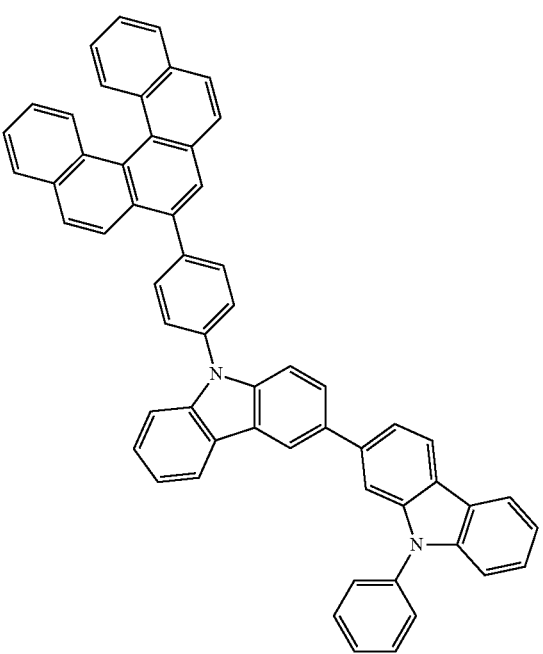

145
-continued
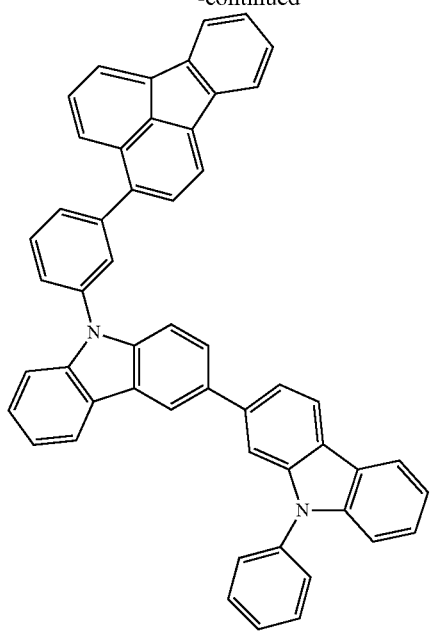
146
-continued
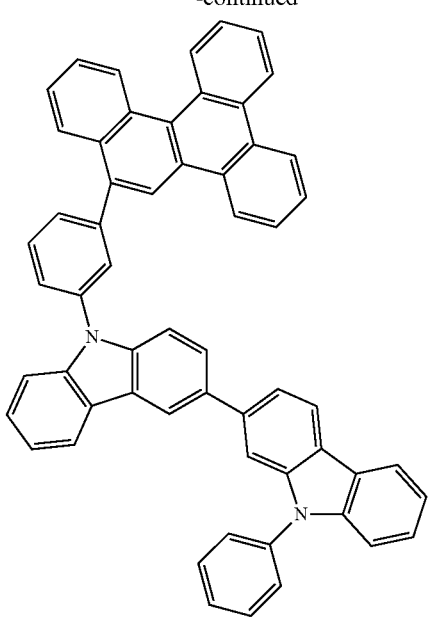
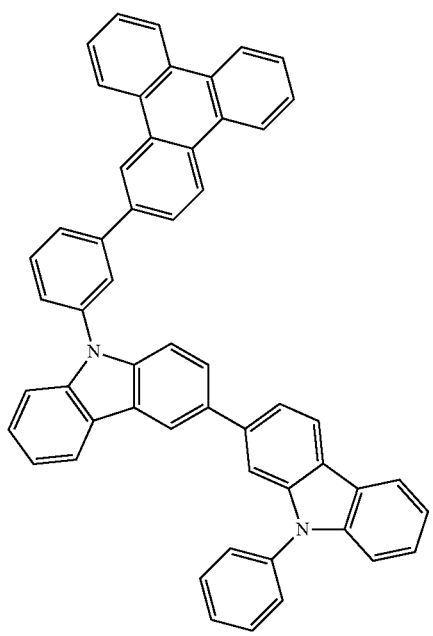
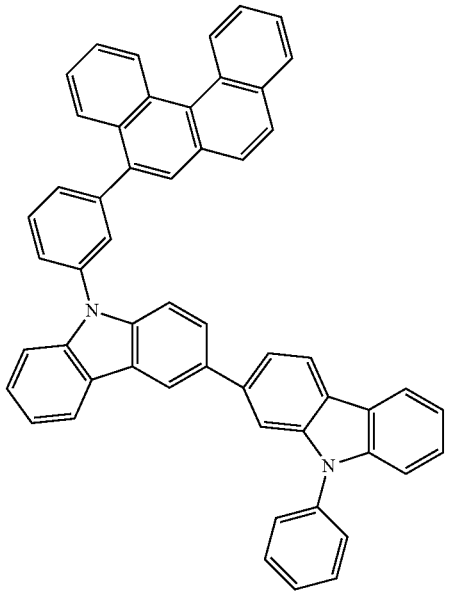

147
-continued
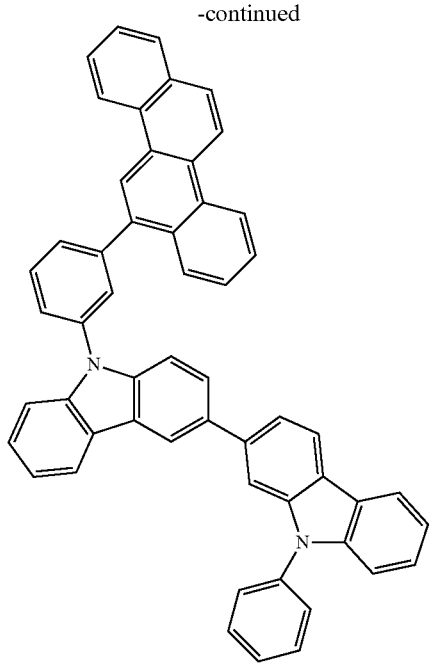
148
-continued
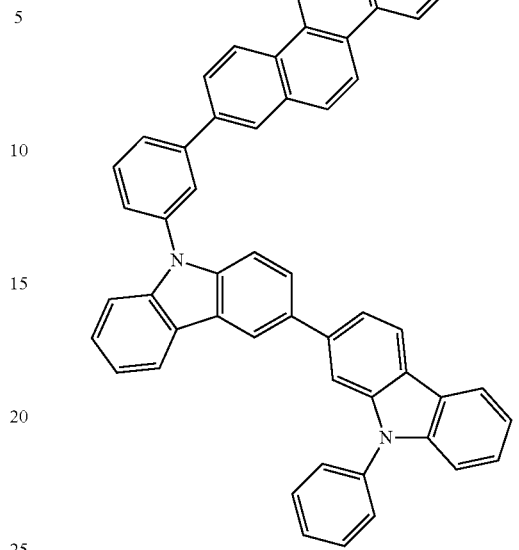
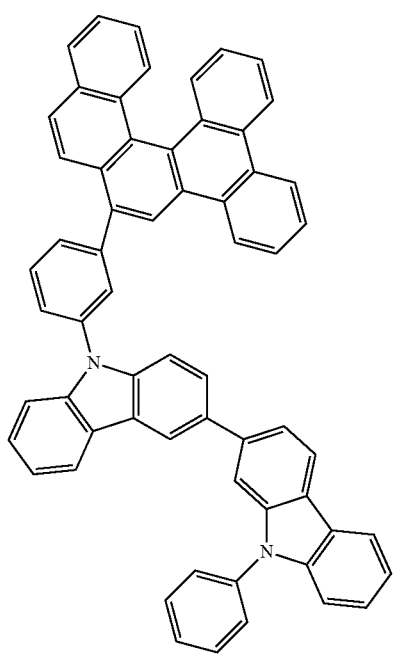
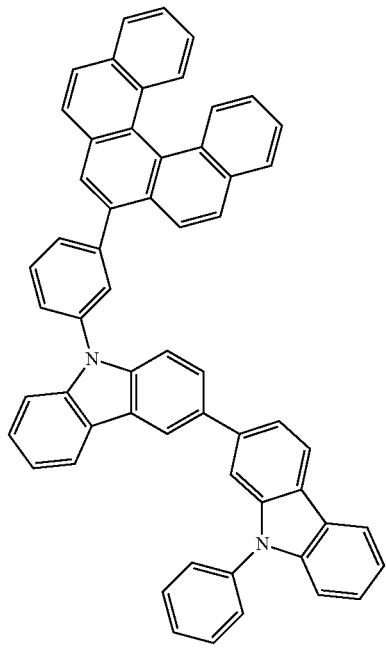

149
-continued
150
-continued
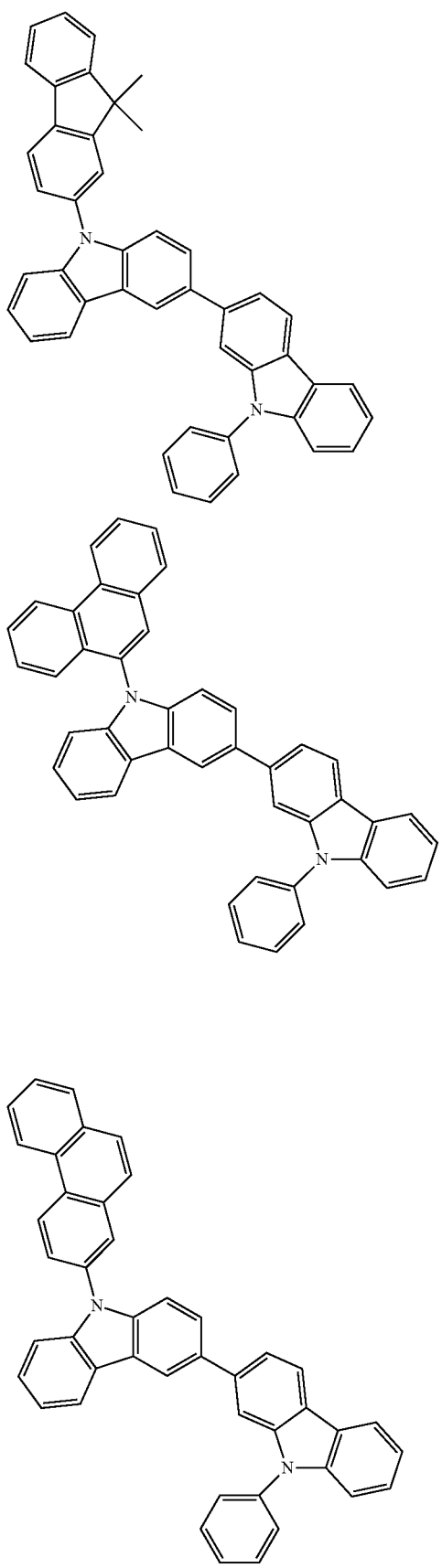
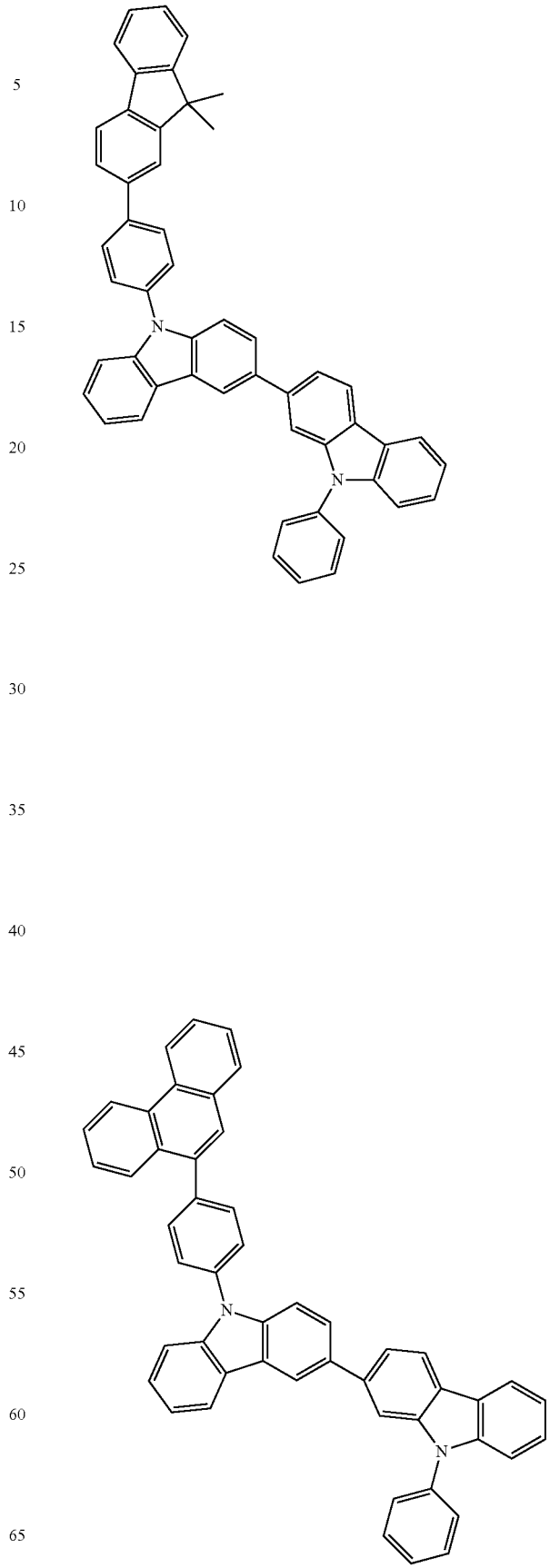

151
-continued
152
-continued
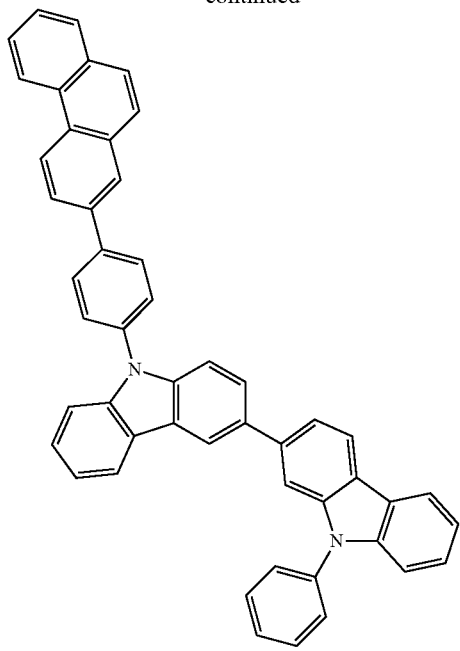
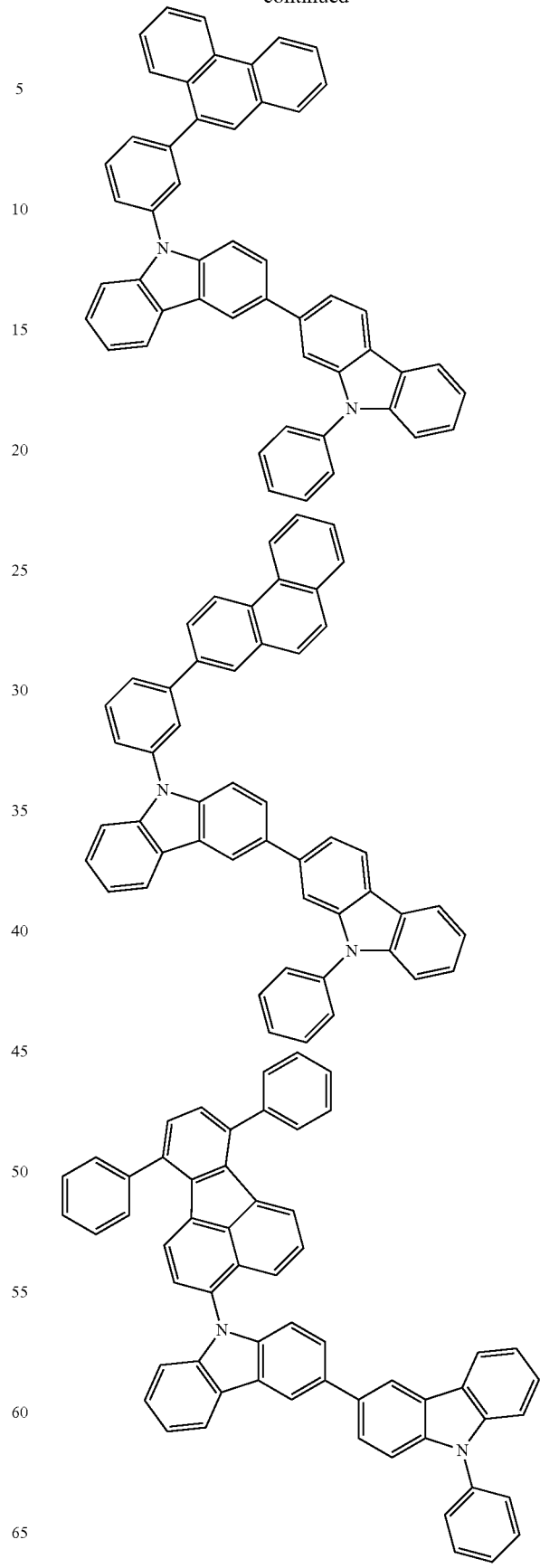

153
-continued
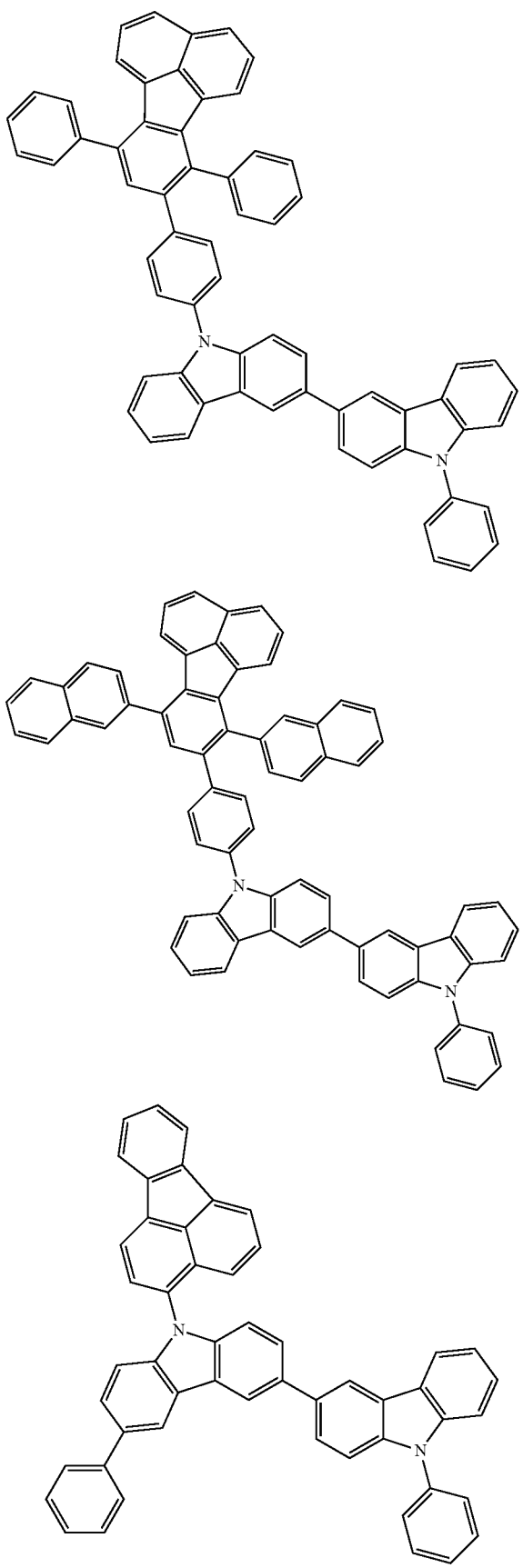
154
-continued
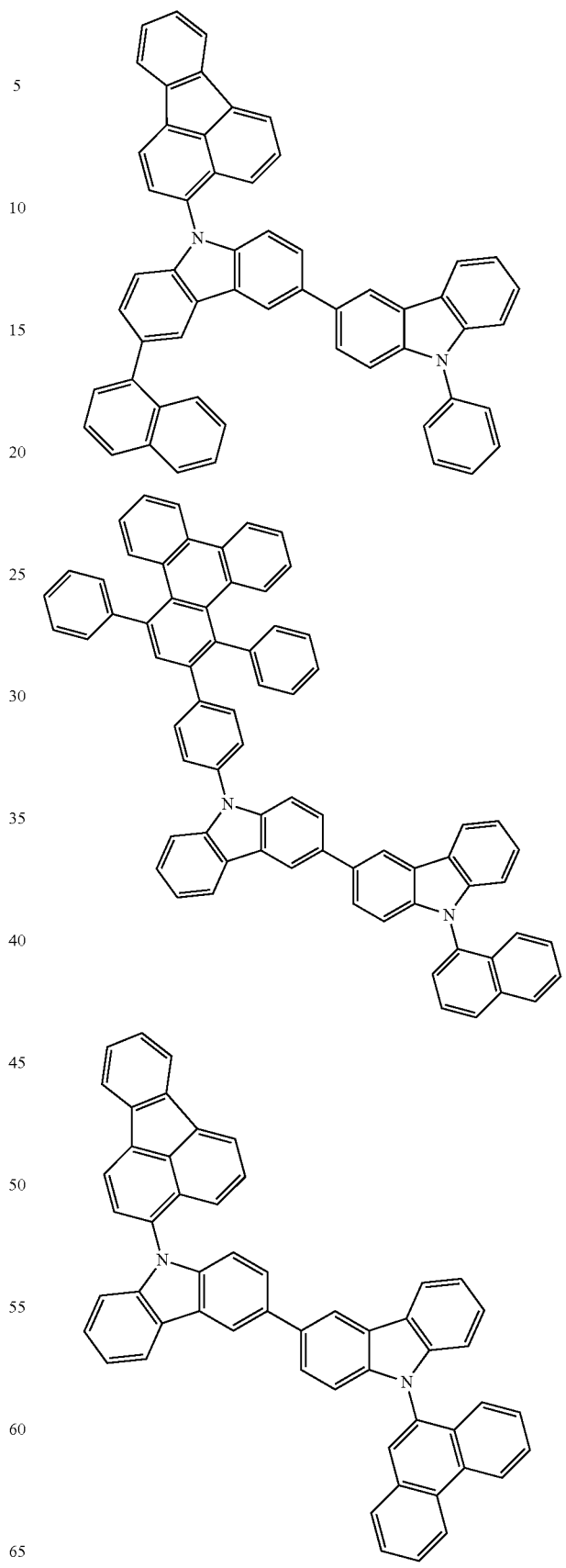

155
-continued
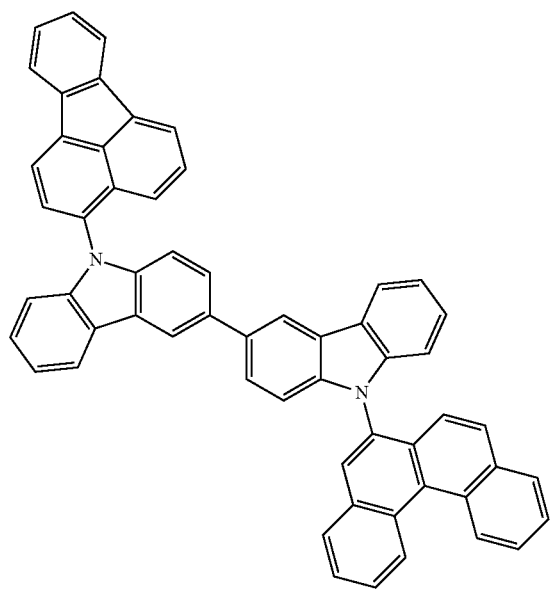
156
-continued
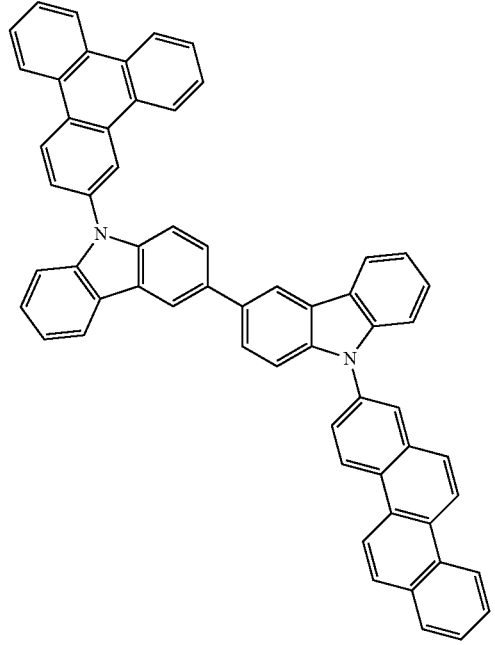
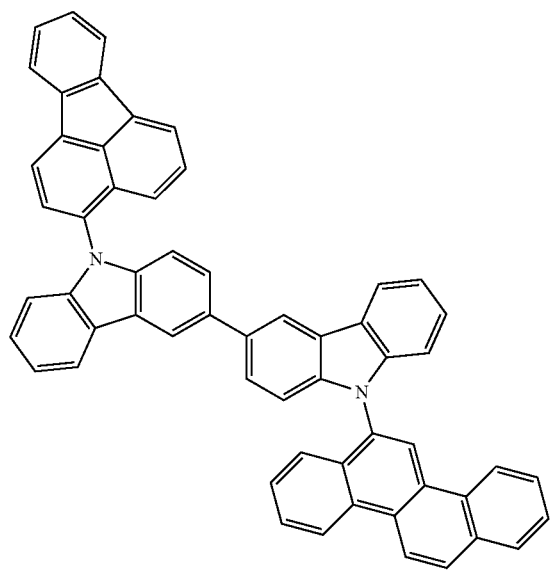
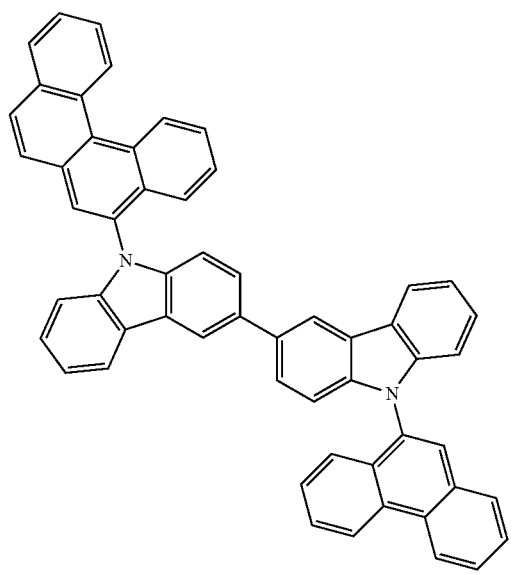

157
-continued
158
-continued
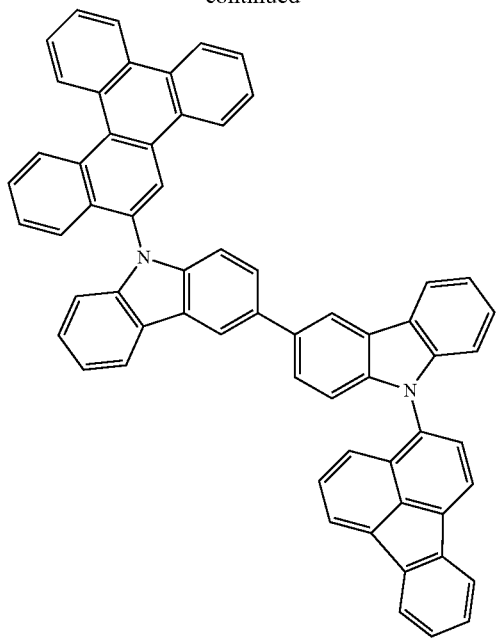
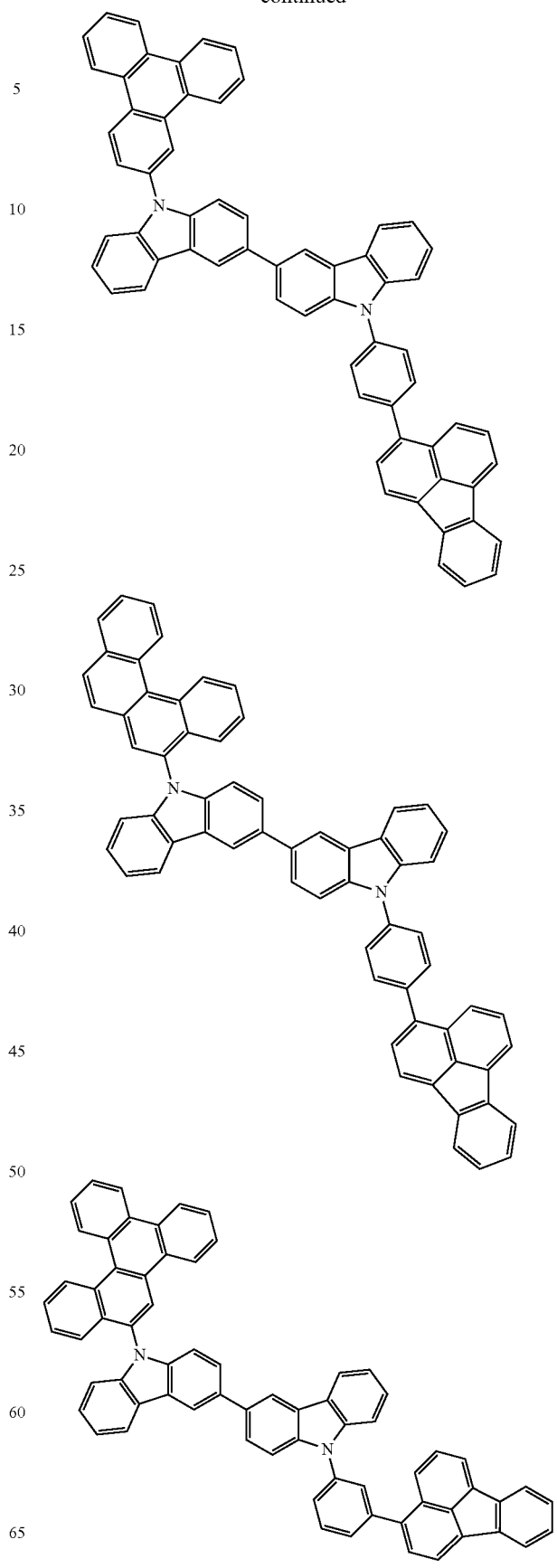

159
-continued
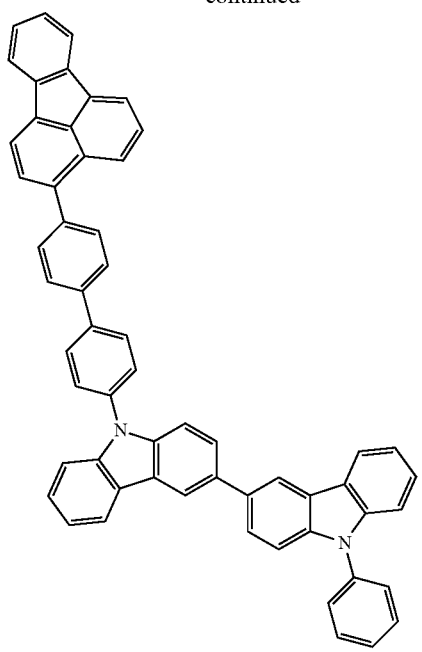
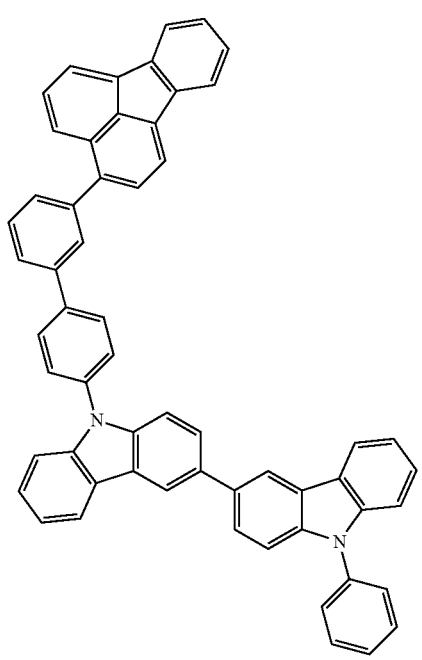
160
-continued
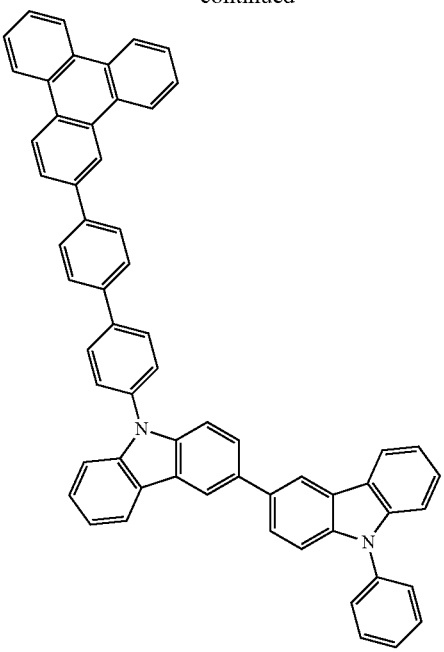
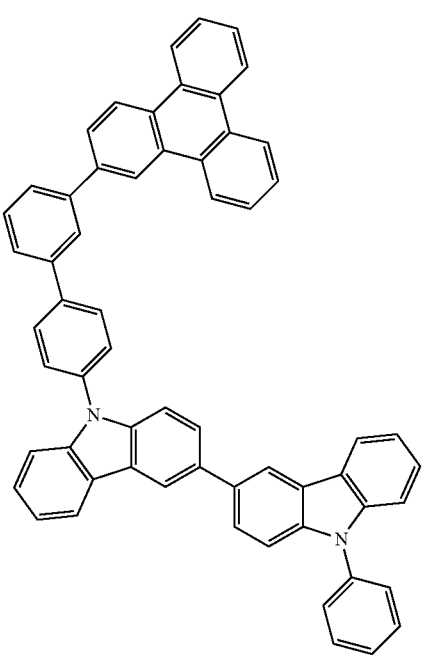

161
-continued
162
-continued
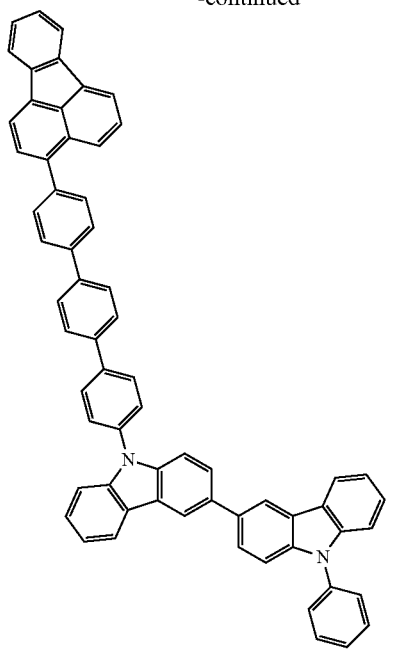
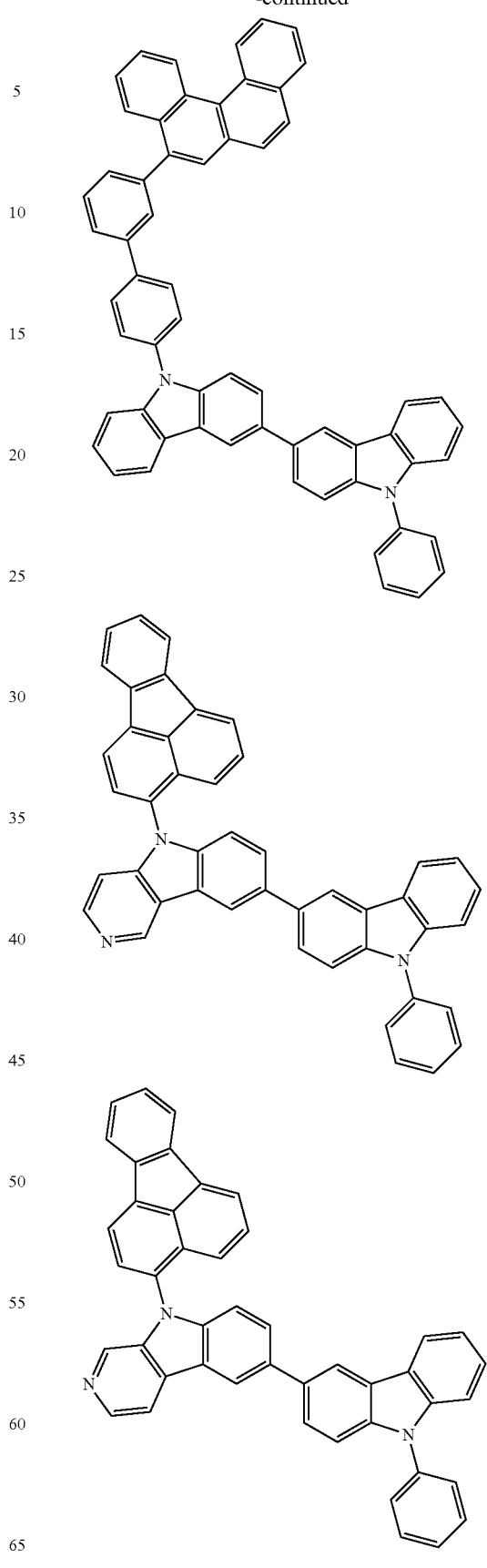

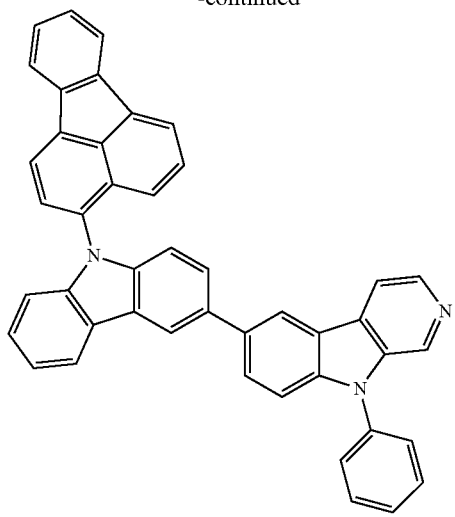
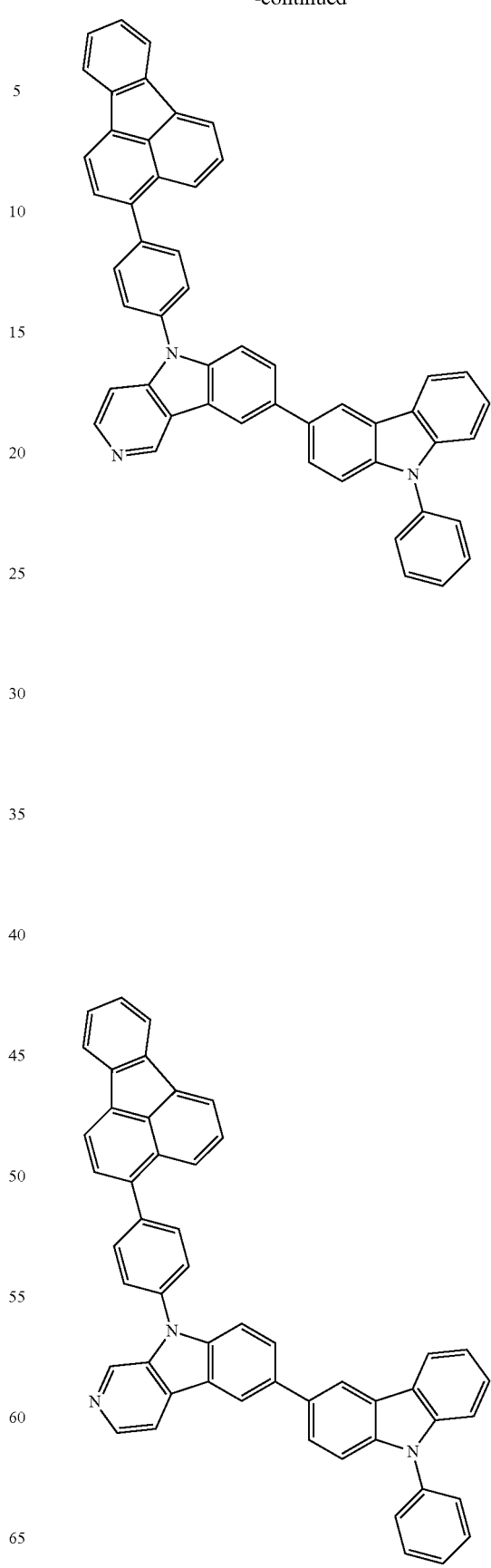

165
-continued
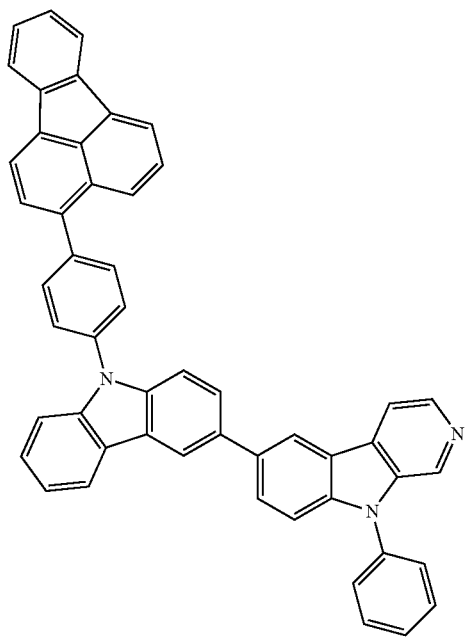
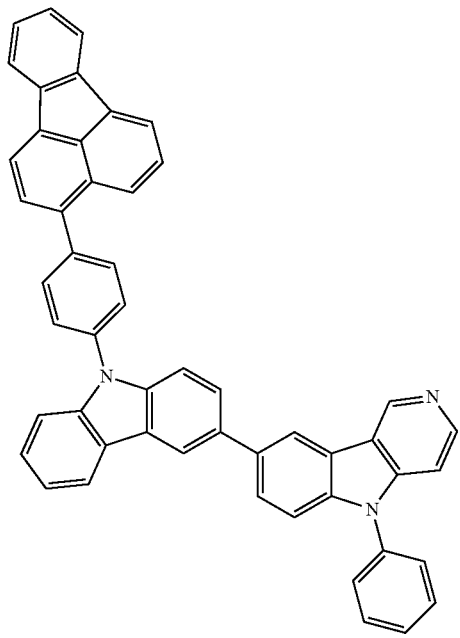
166
-continued
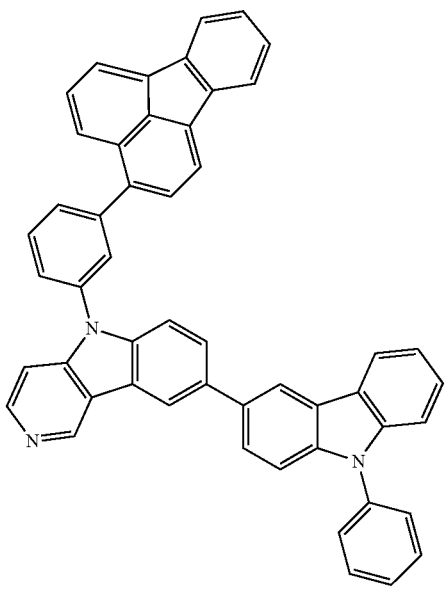
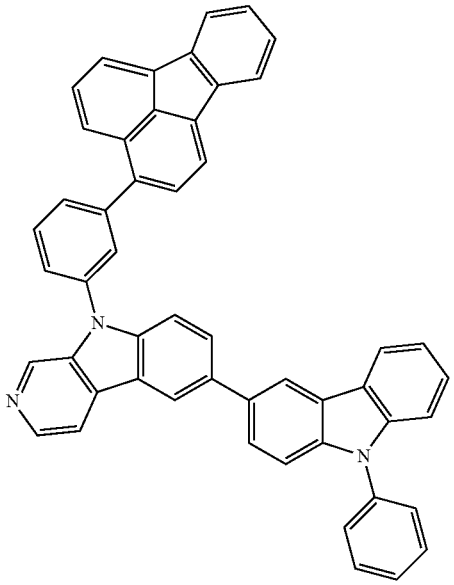

167
-continued
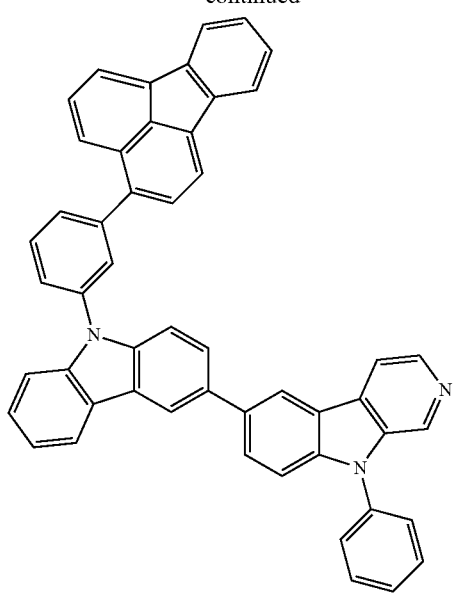
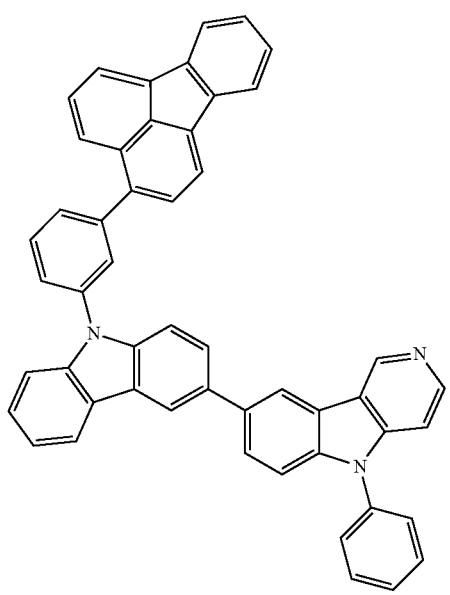
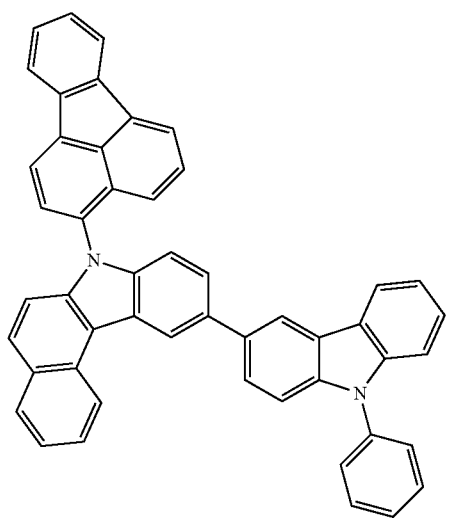
168
-continued
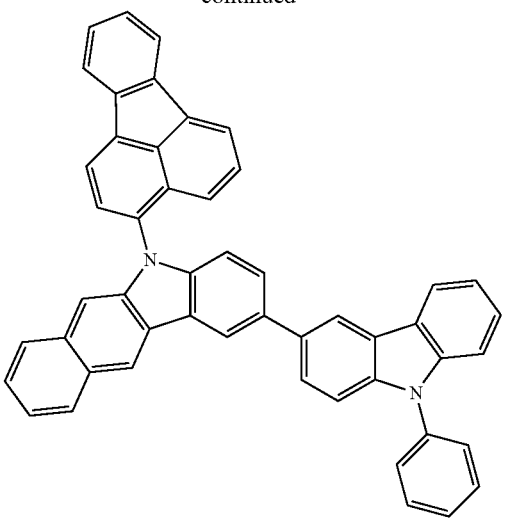

169
-continued
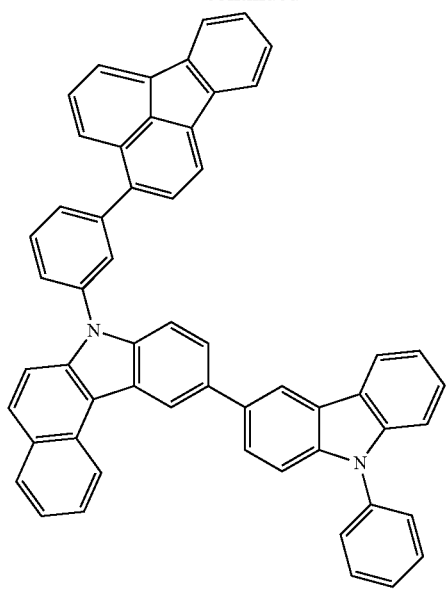
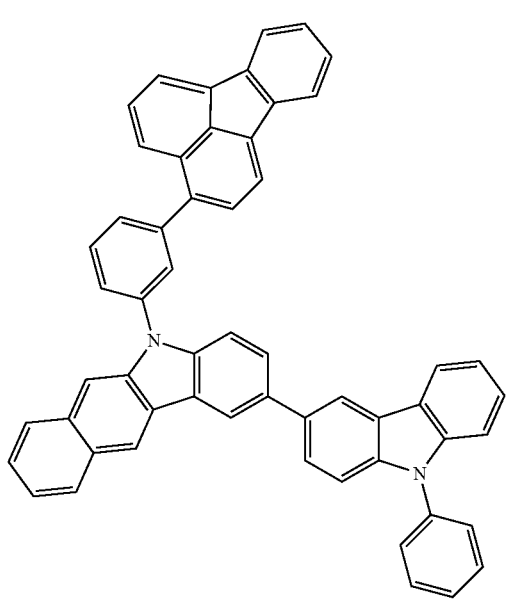
170
-continued
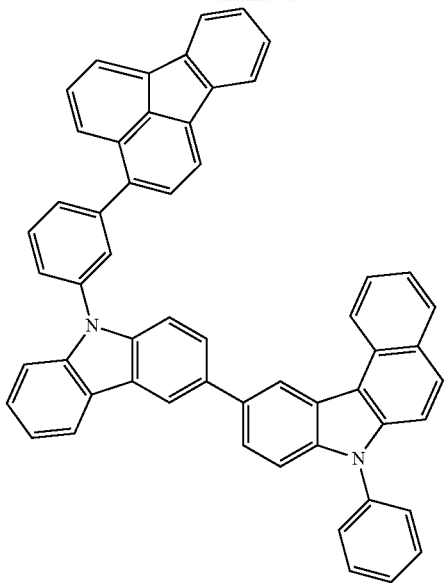
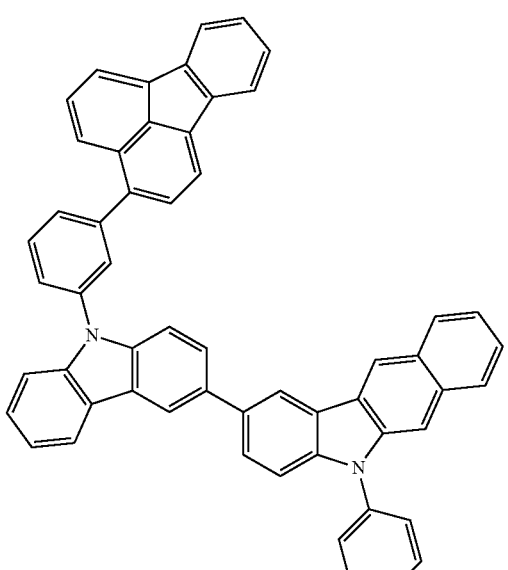
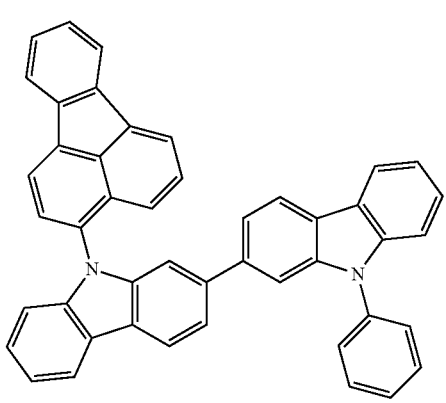

171
-continued
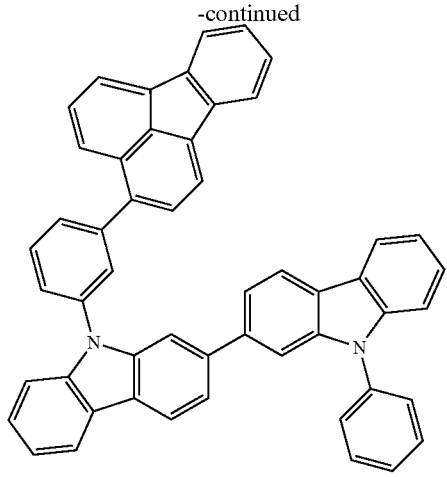
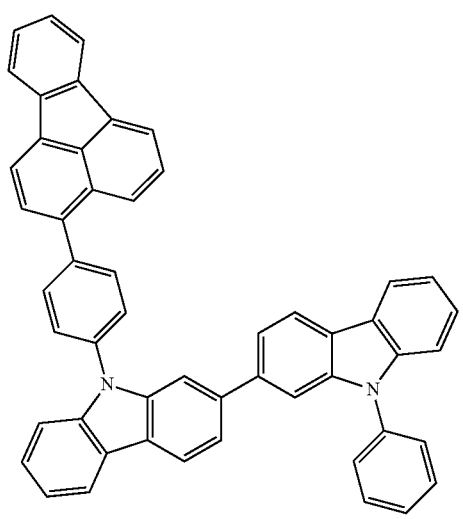
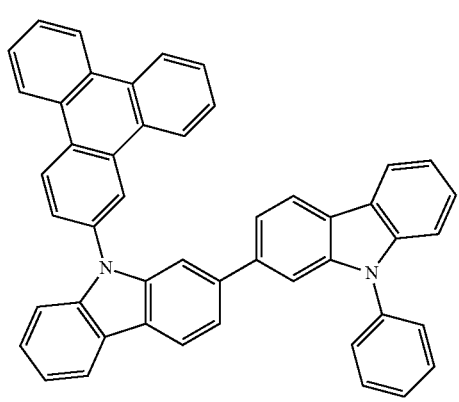
172
-continued
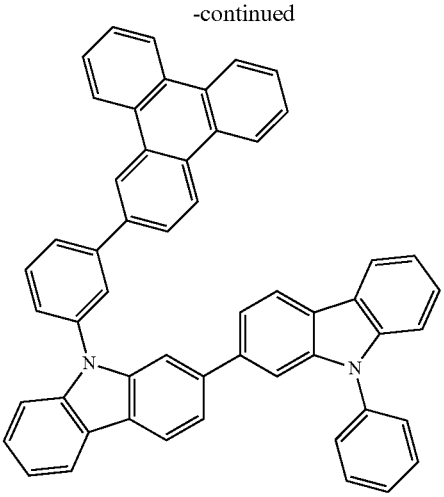
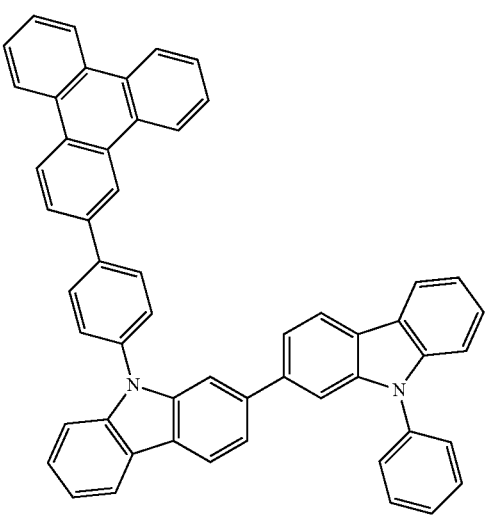
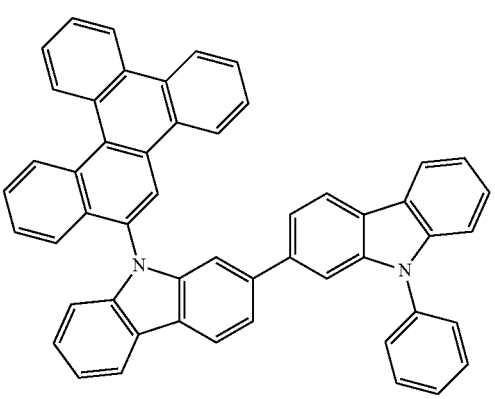

173
-continued
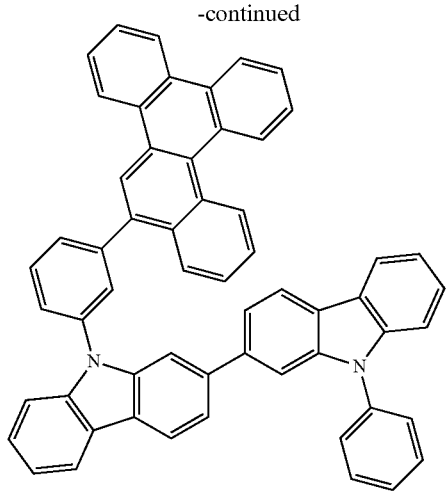
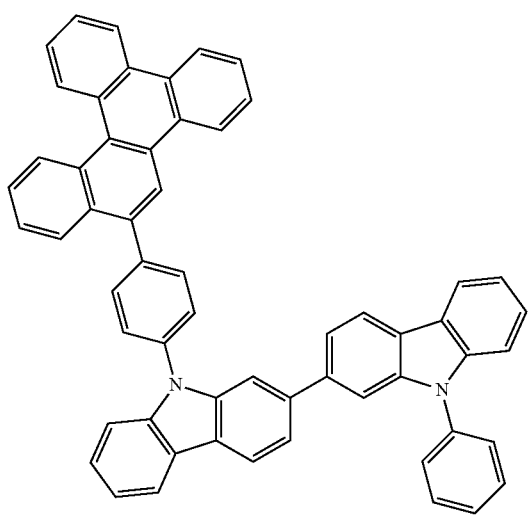
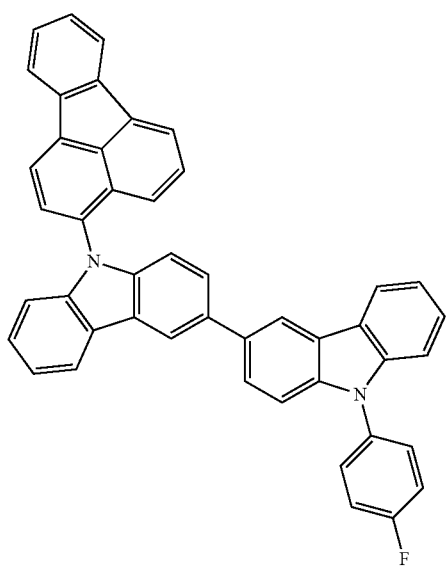
174
-continued
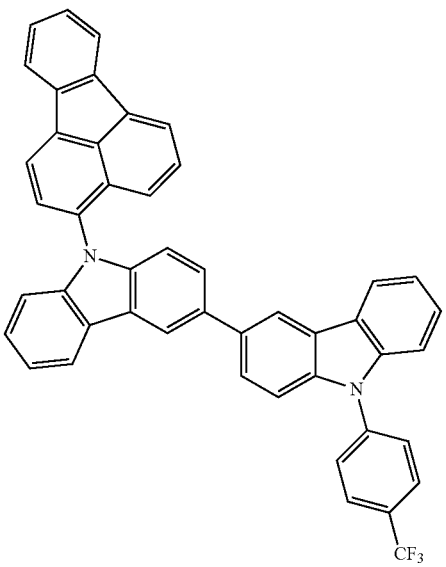
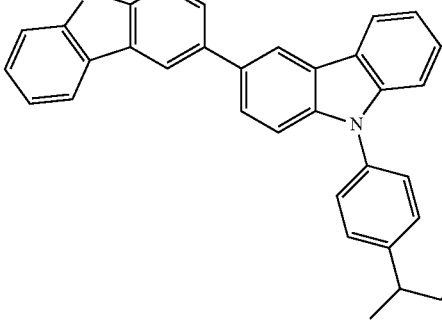

175
-continued
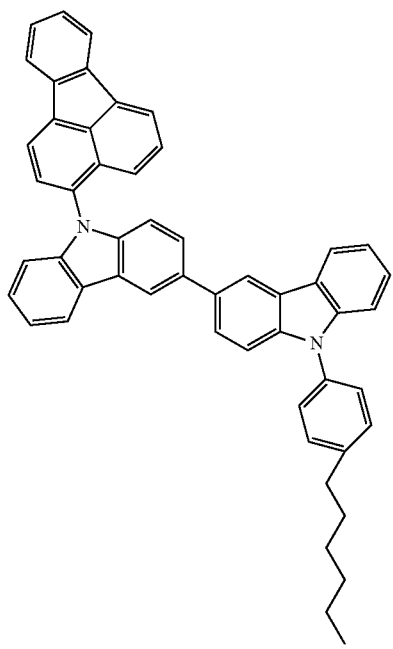
176
-continued
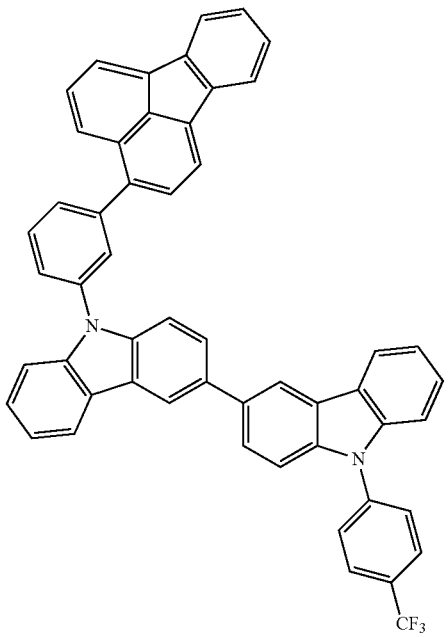
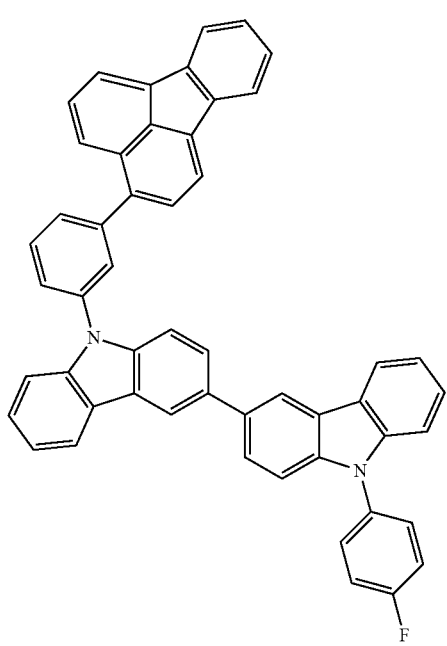
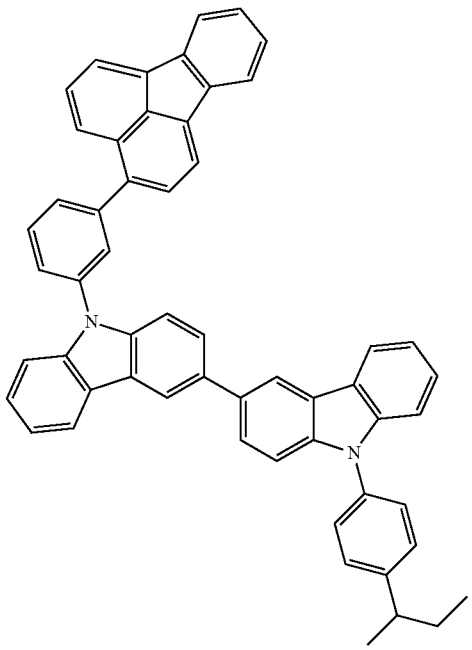

177
-continued
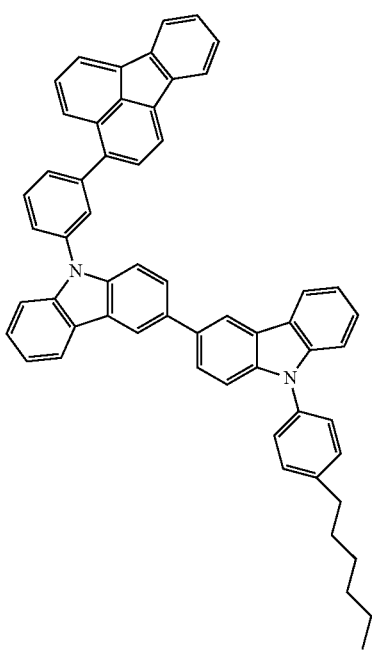
178
-continued
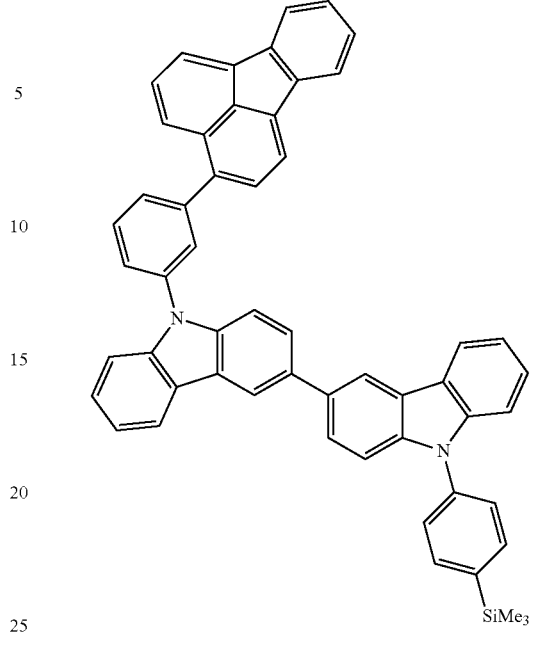
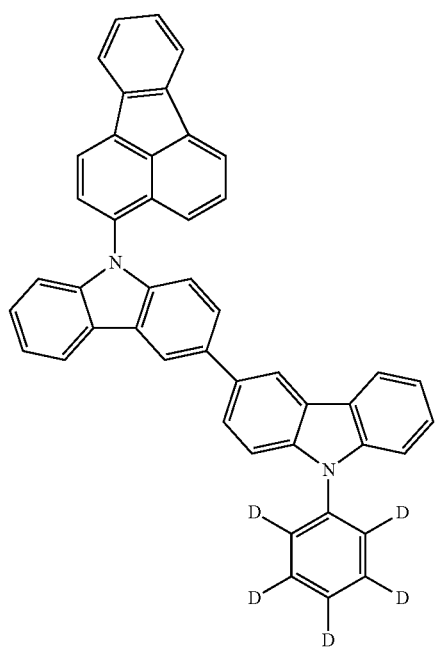

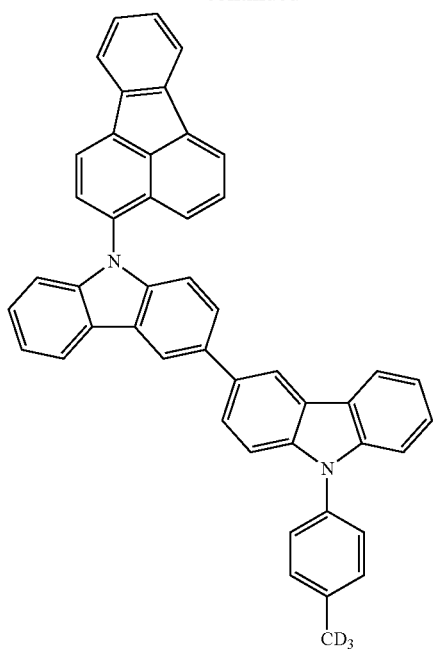
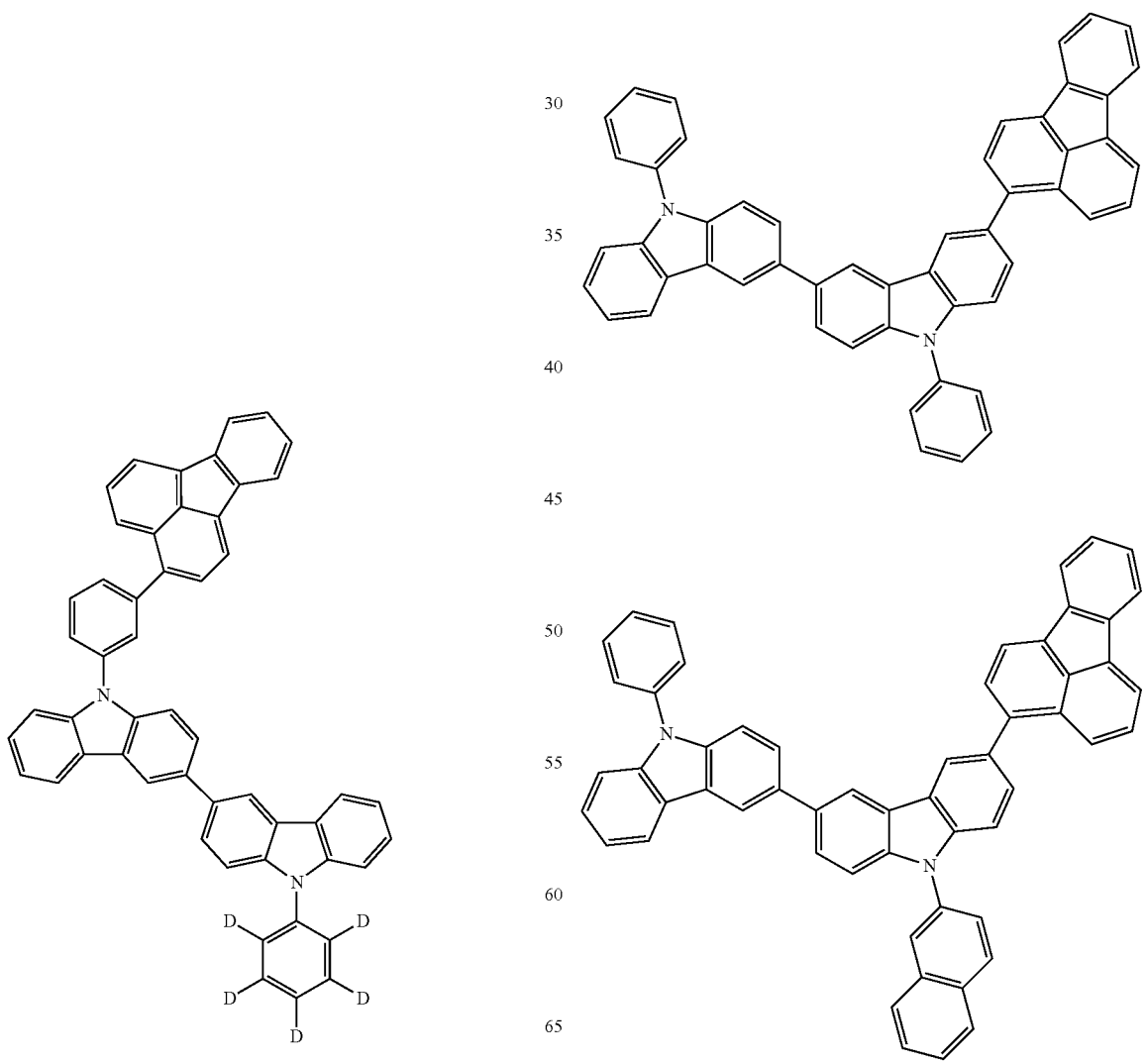

181
-continued
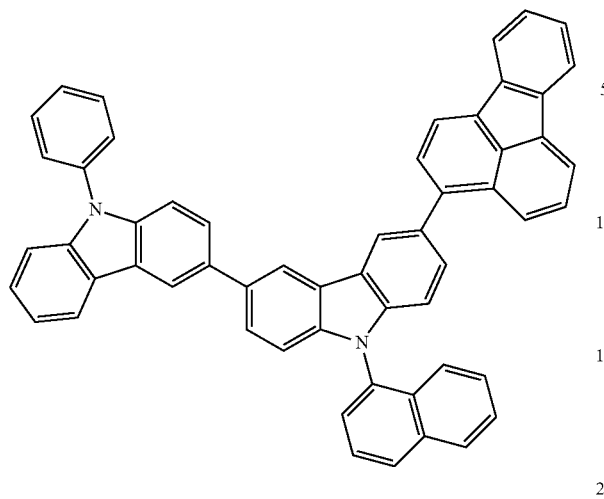
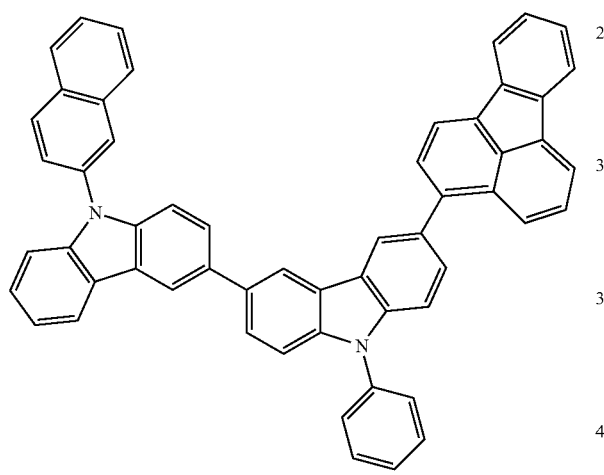
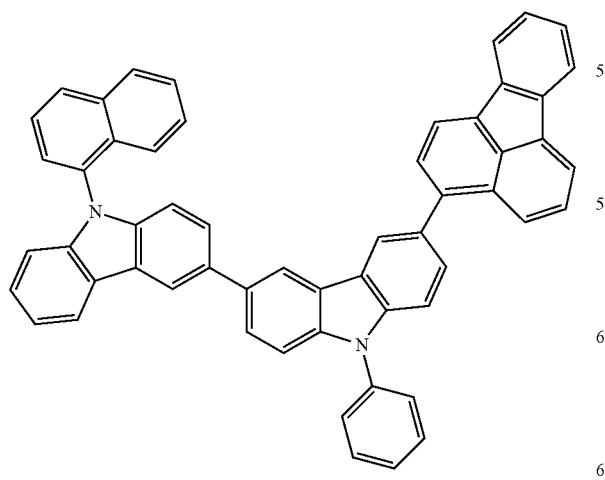
182
-continued
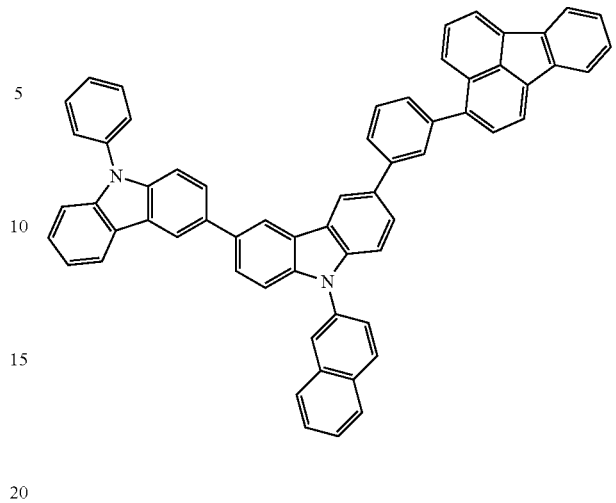
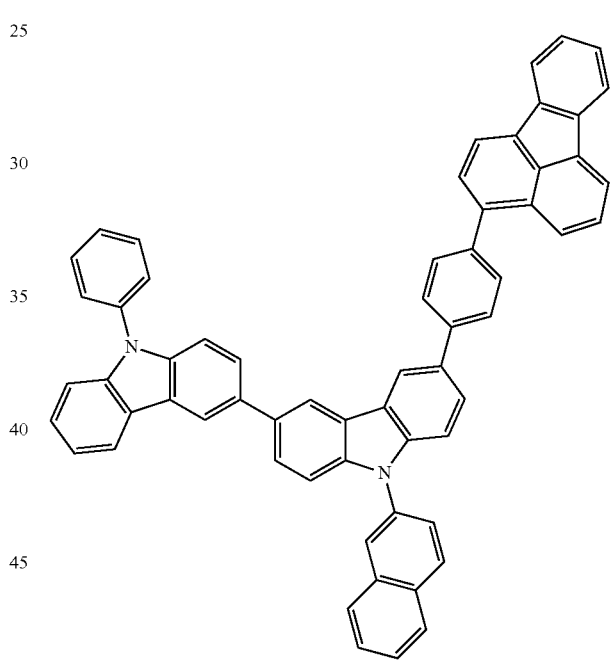
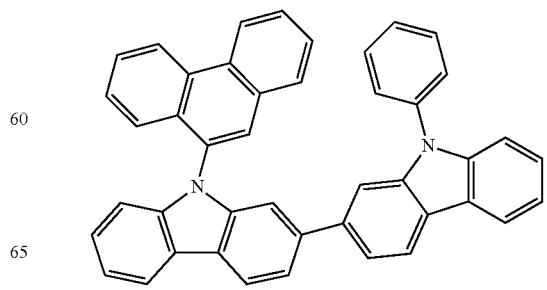

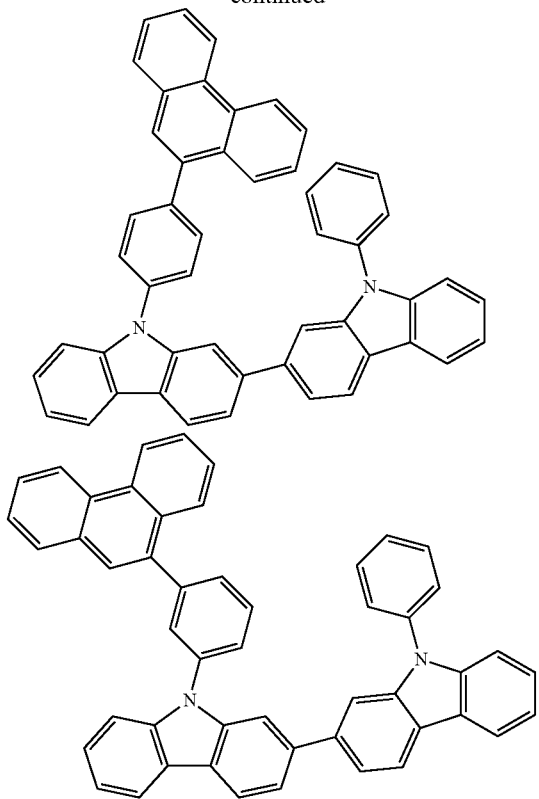
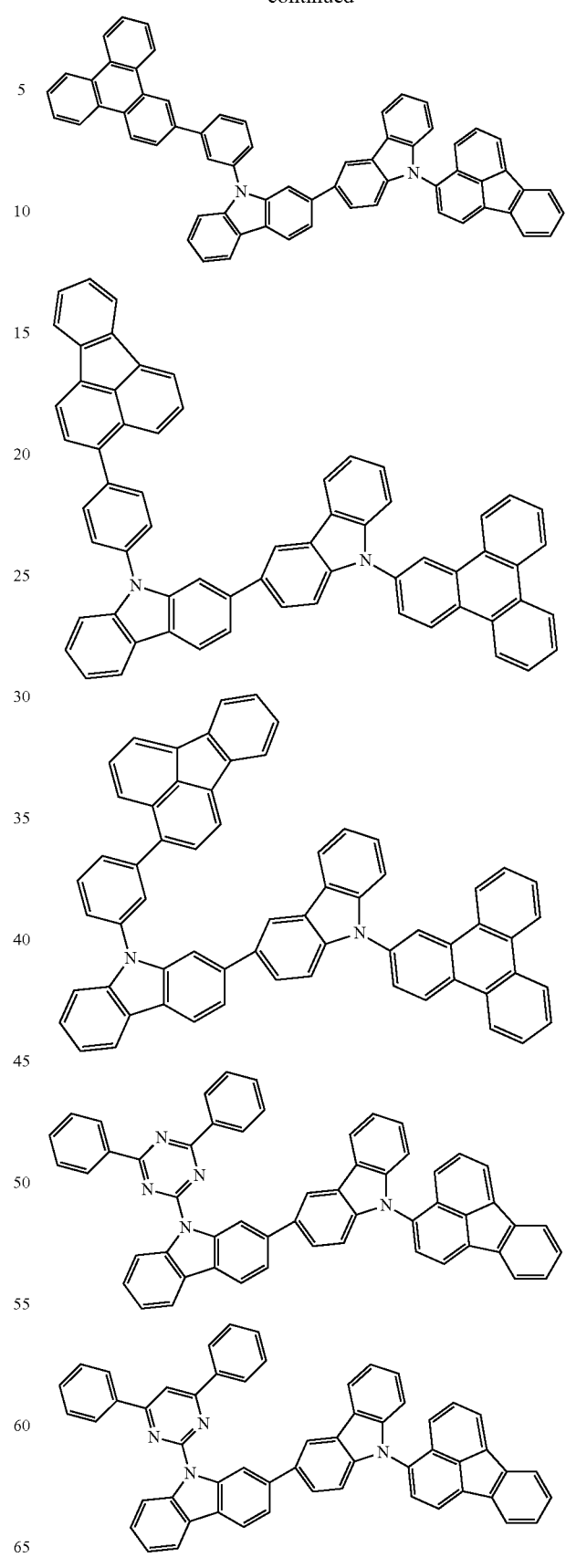

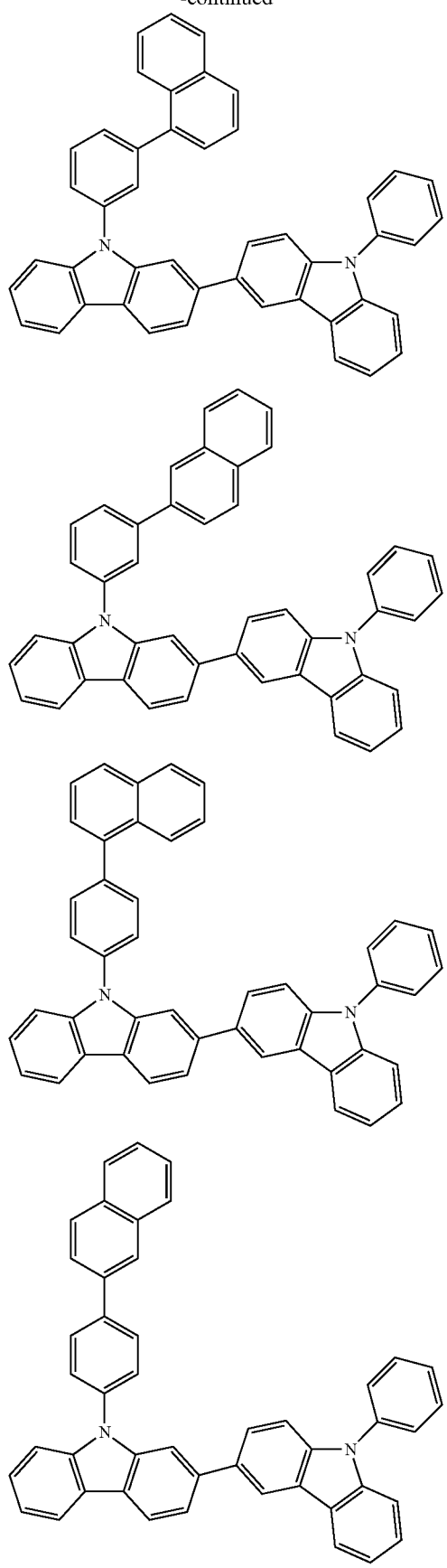
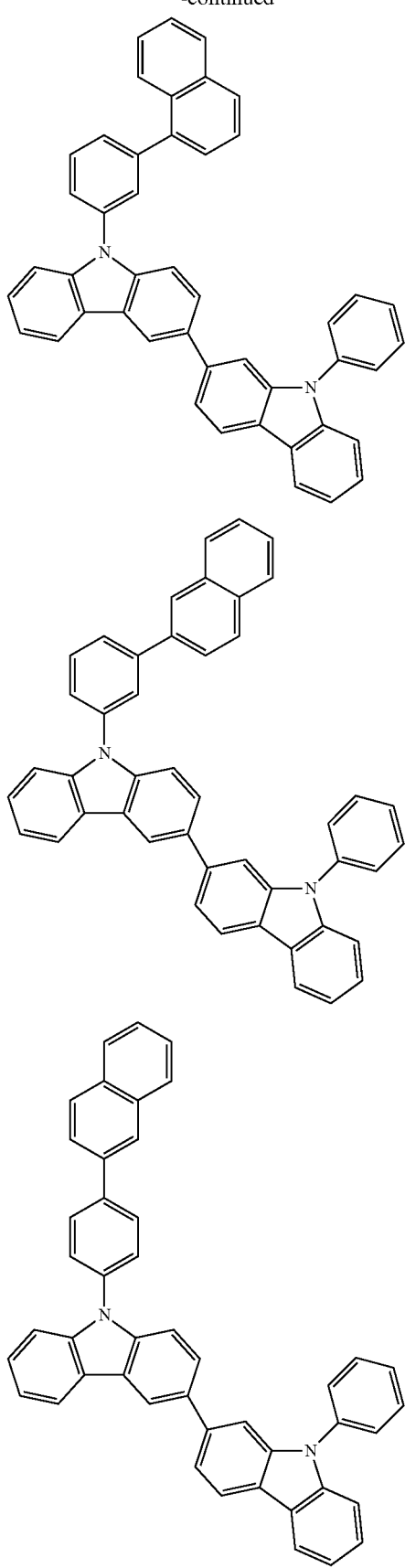

187
-continued
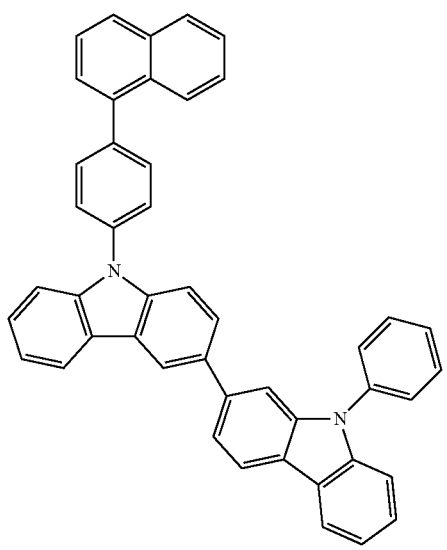
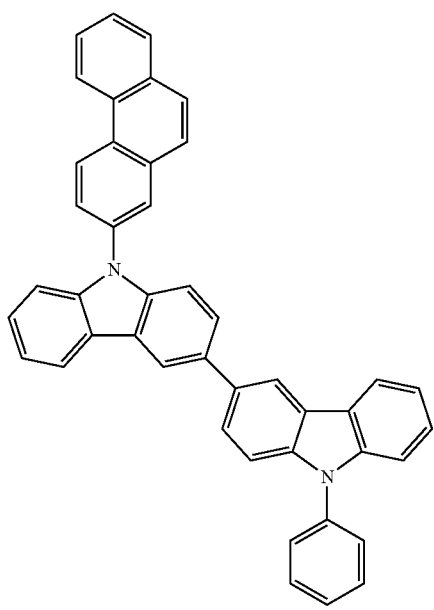
188
-continued
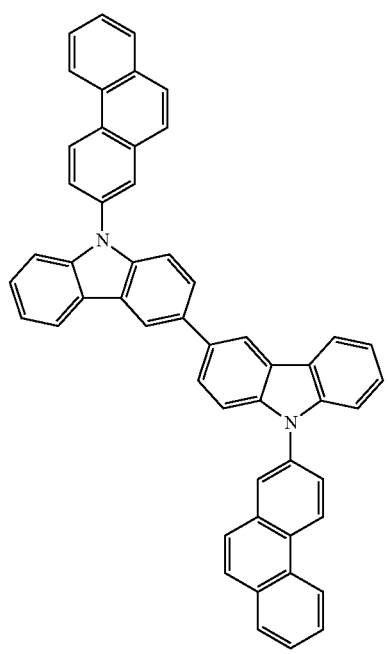
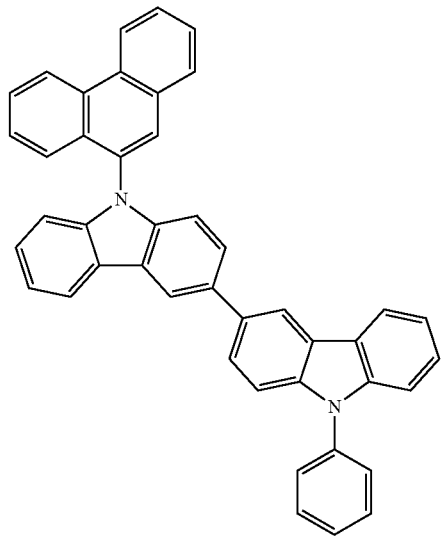

189
-continued
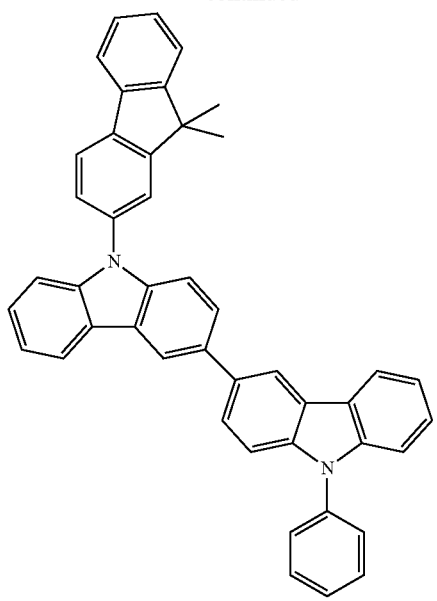
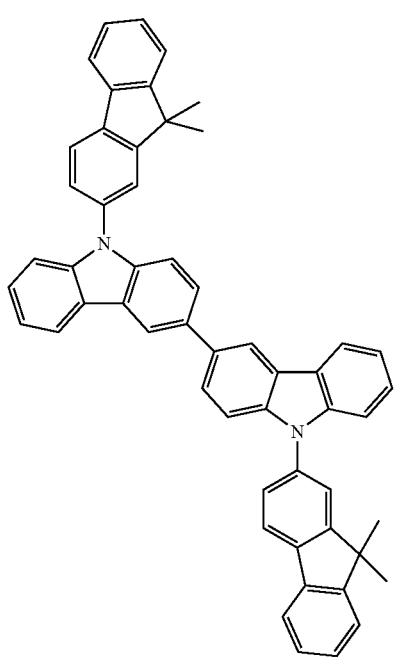
190
-continued
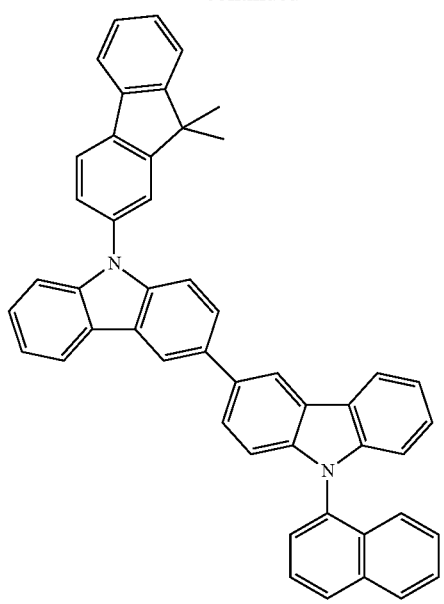
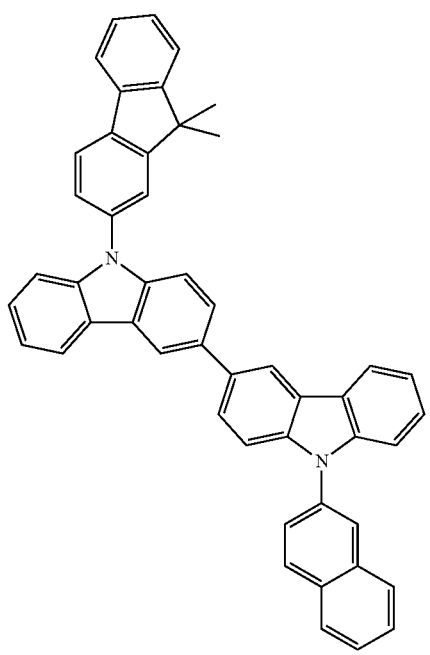

191
-continued
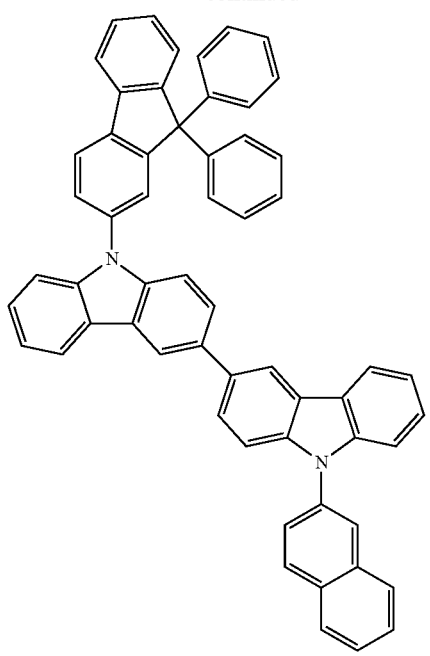
192
-continued
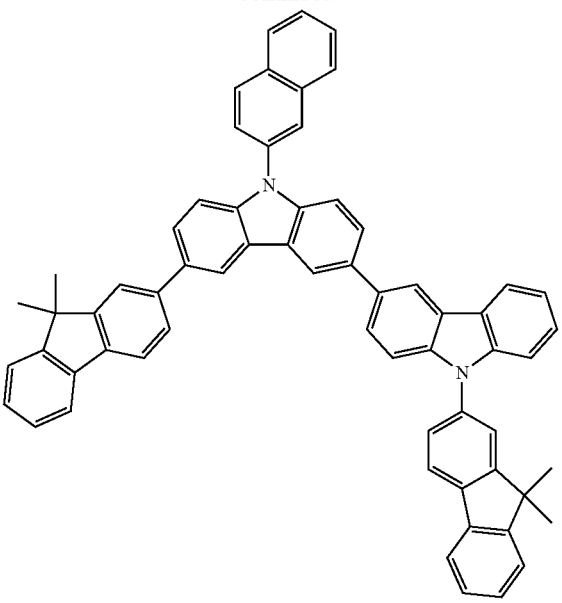
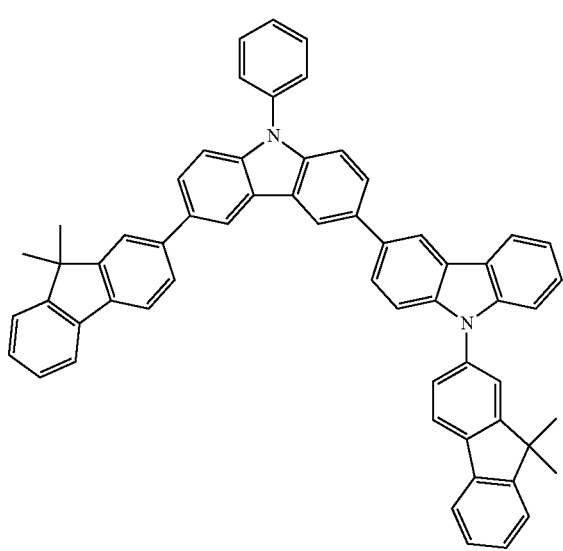
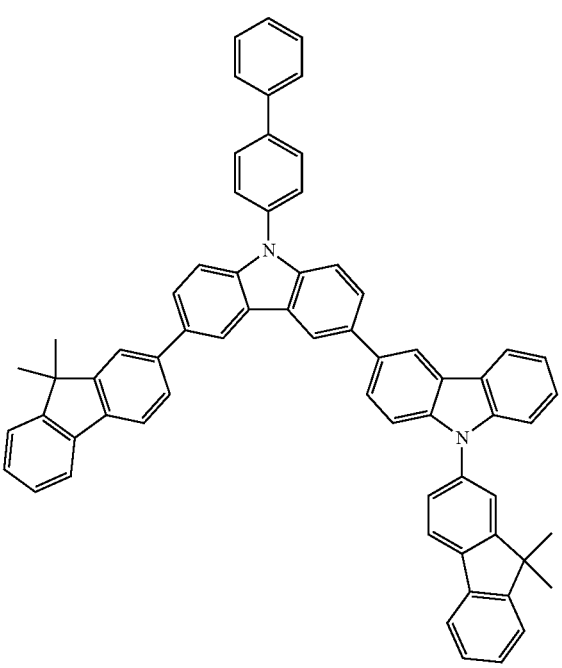

193
-continued
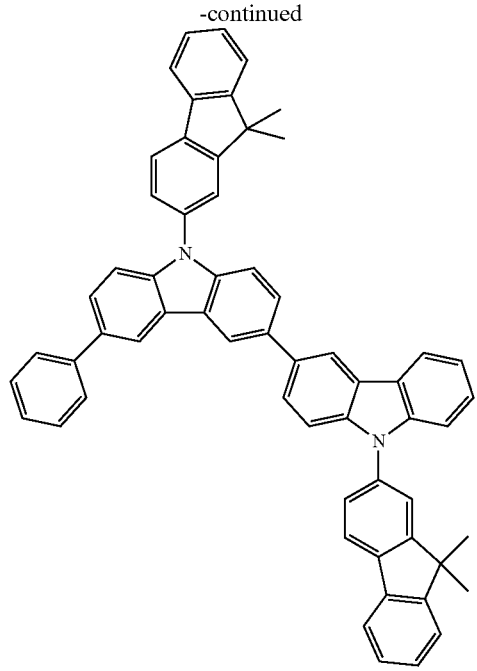
194
-continued
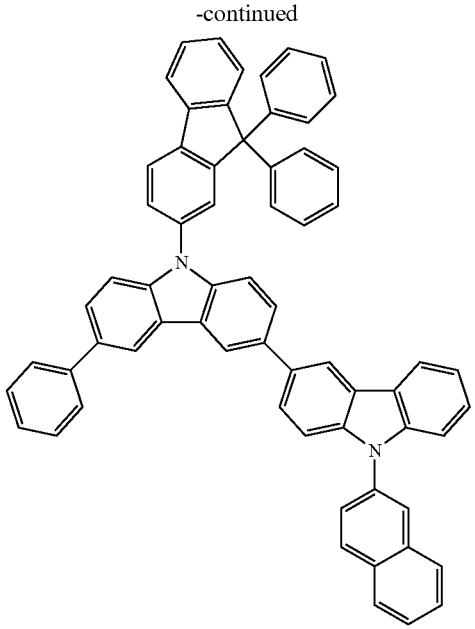
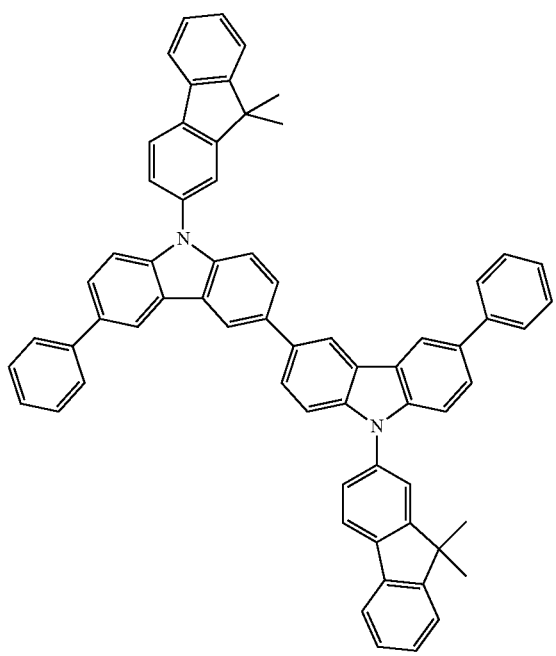
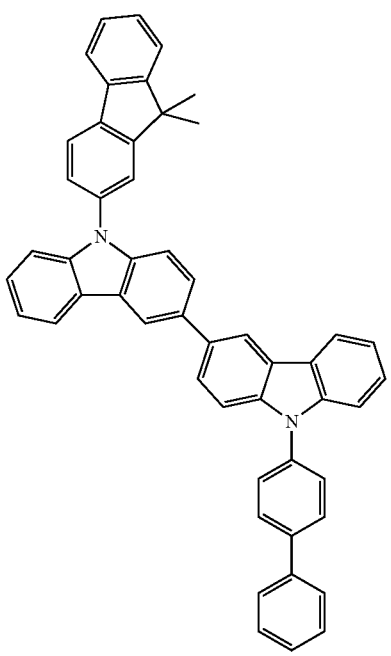

195
-continued
196
-continued
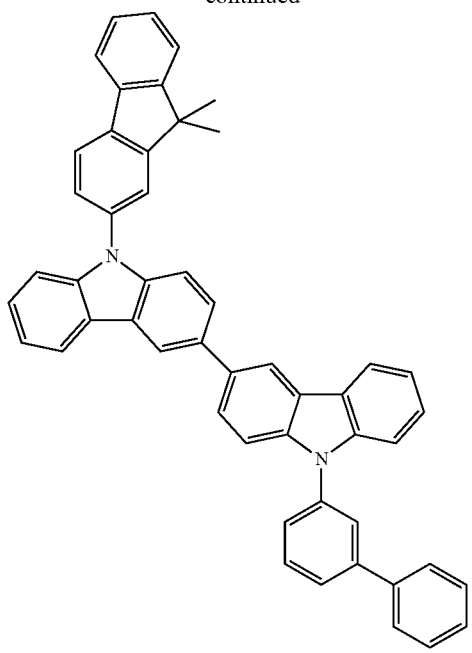
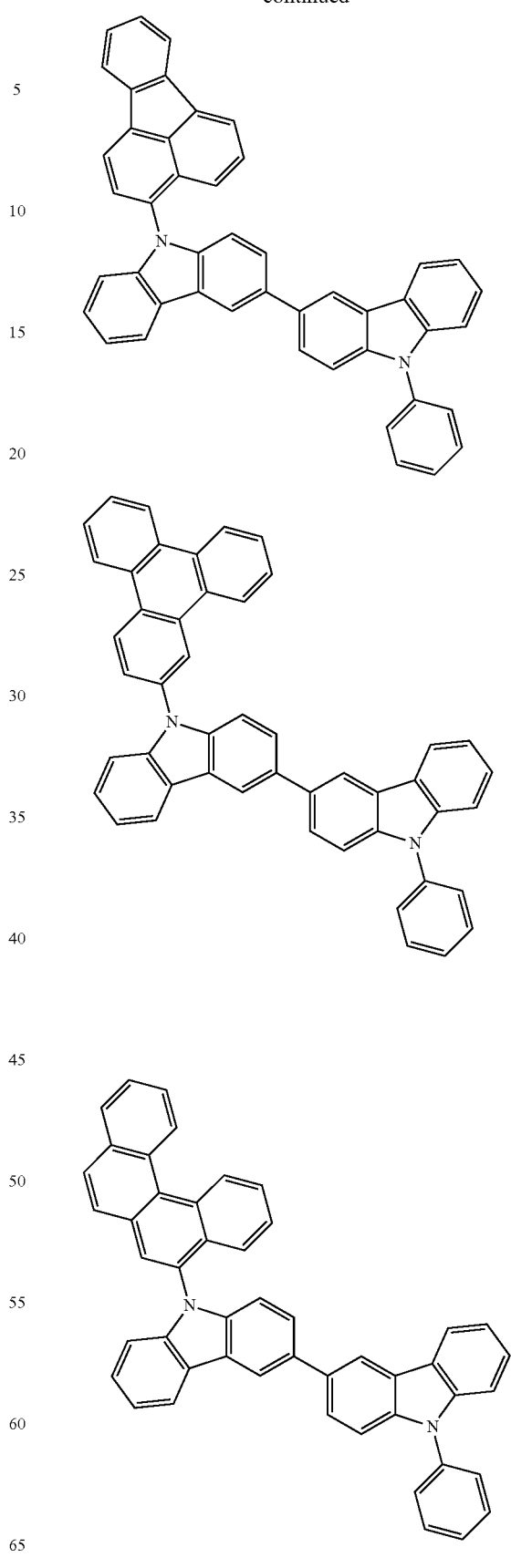

197
-continued
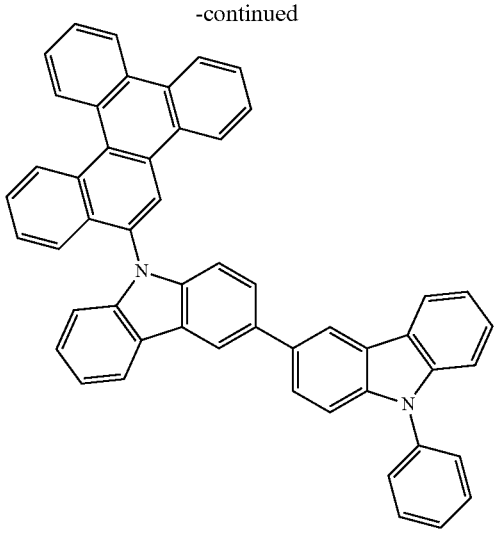
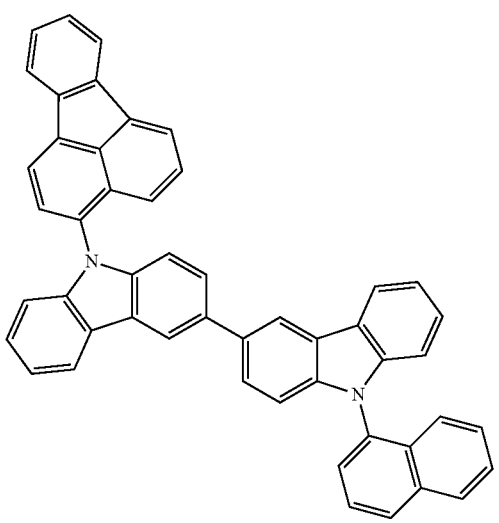
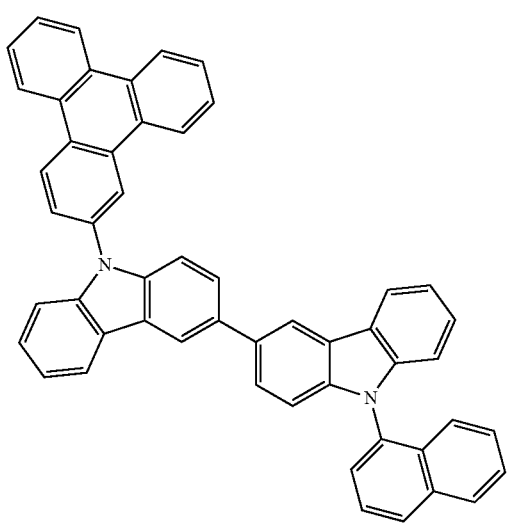
198
-continued
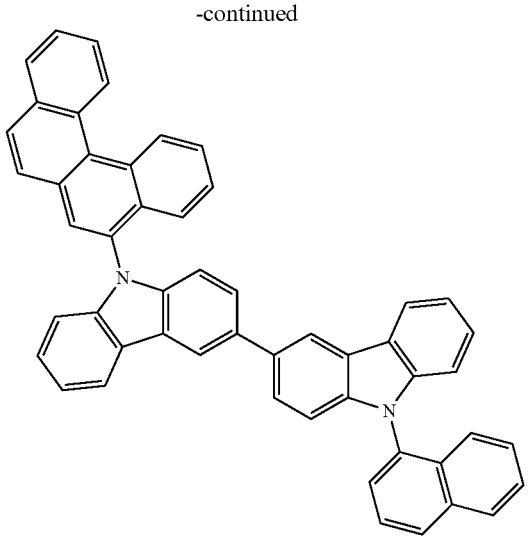
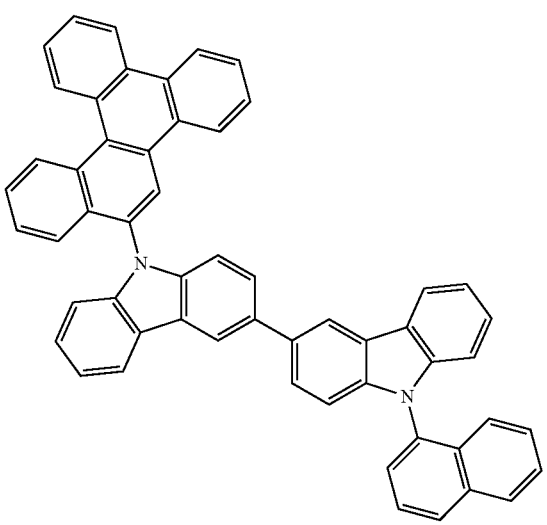
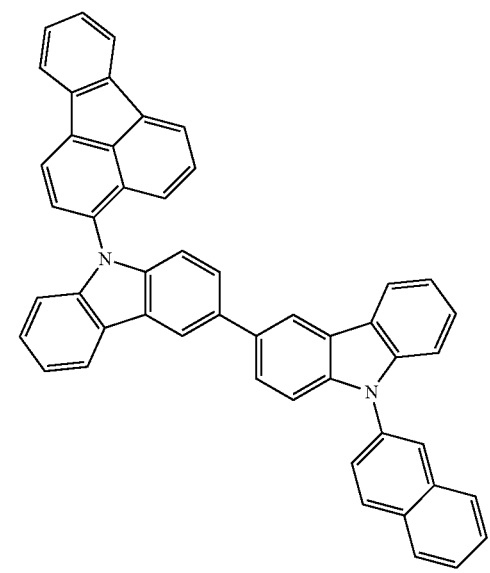

199
-continued
200
-continued
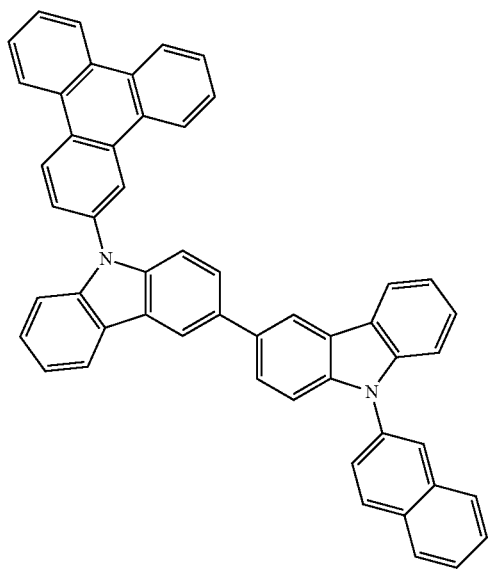
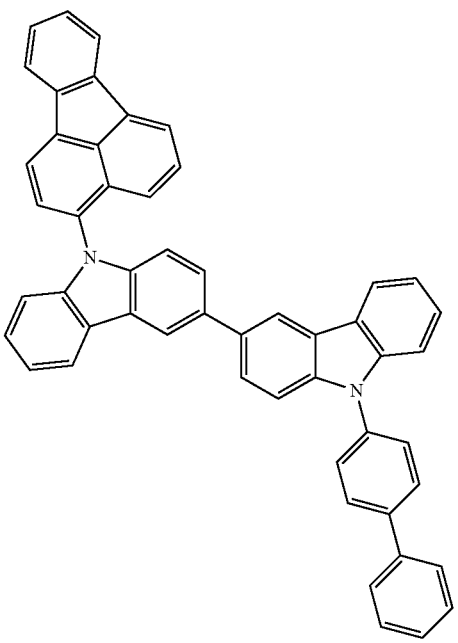
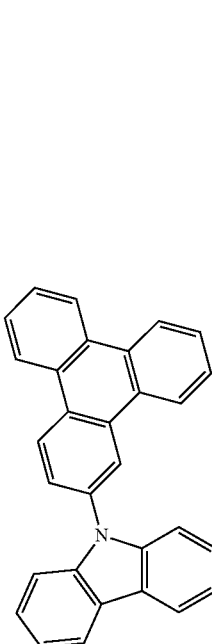
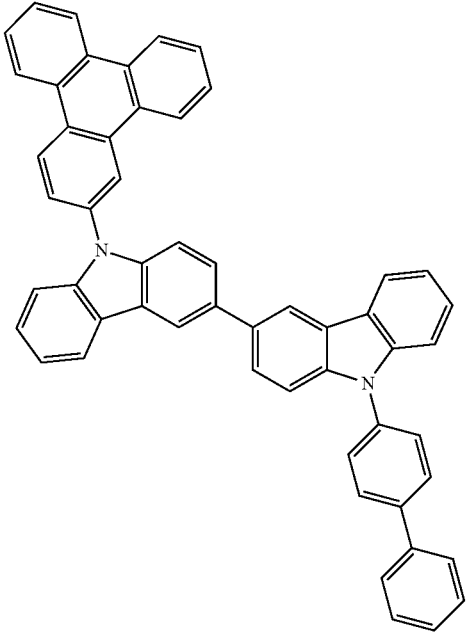

201
-continued
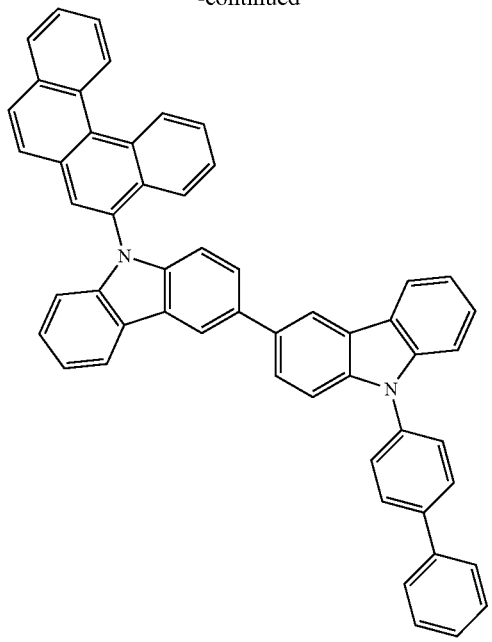
202
-continued
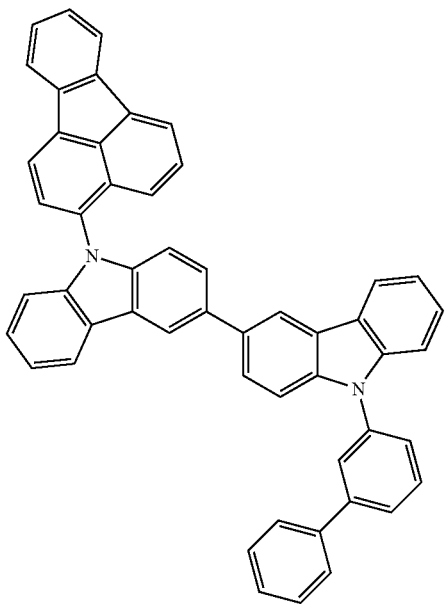
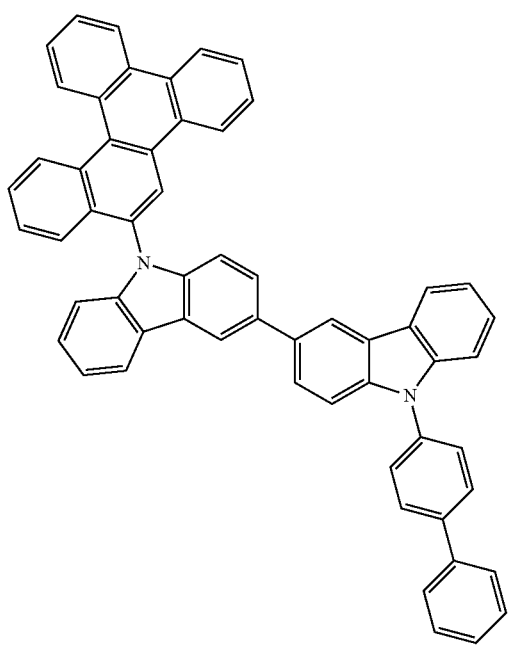
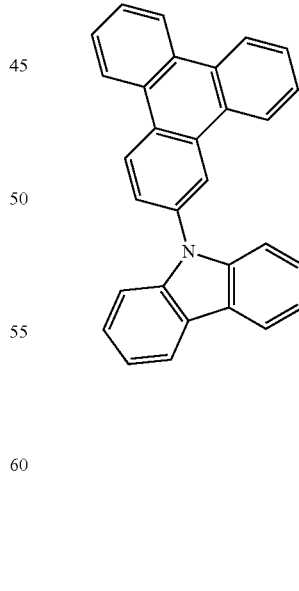

203
-continued
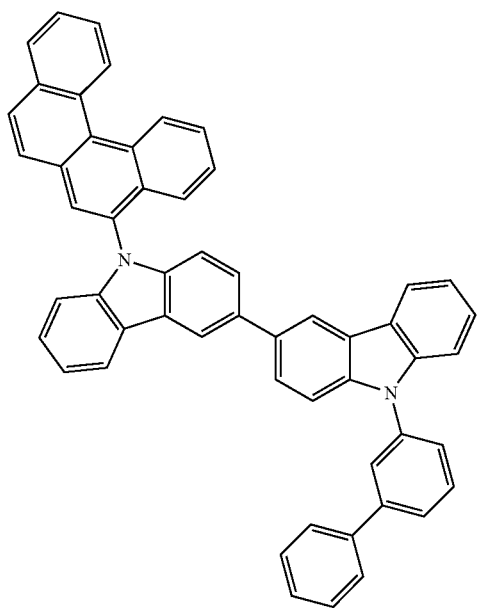
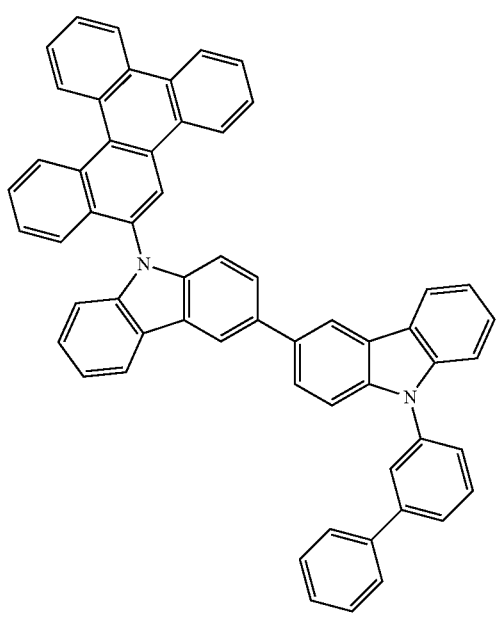
204
-continued
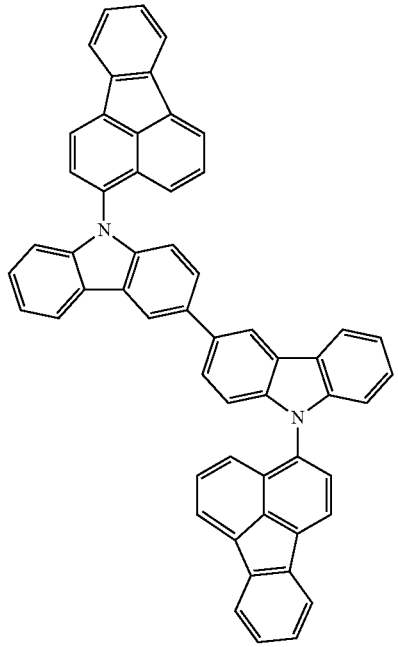
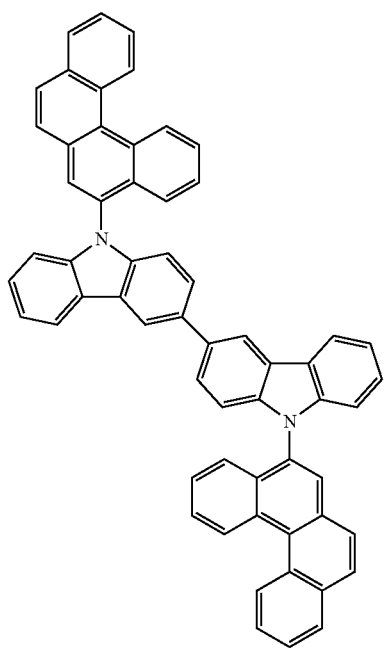

205
-continued
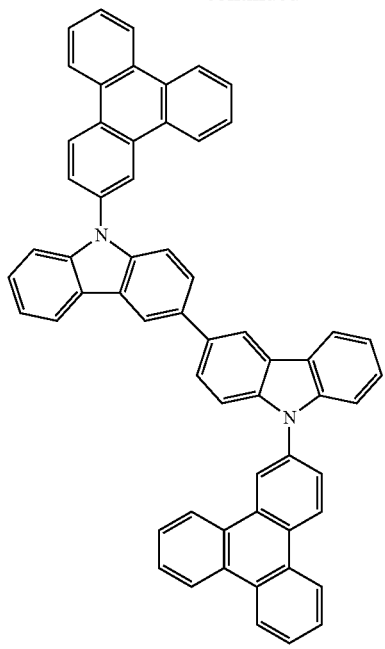
206
-continued
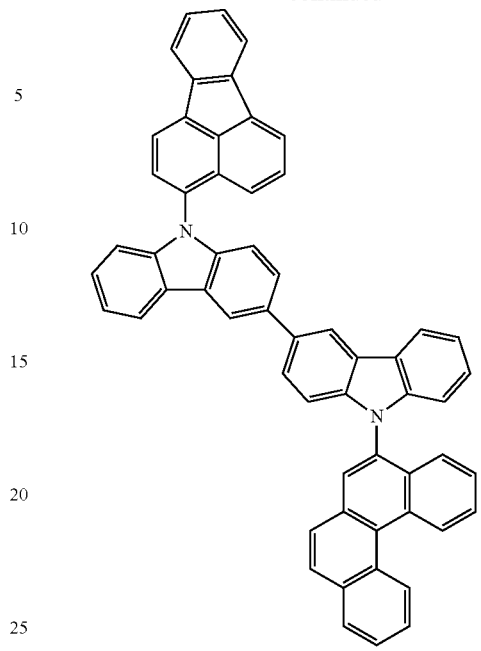
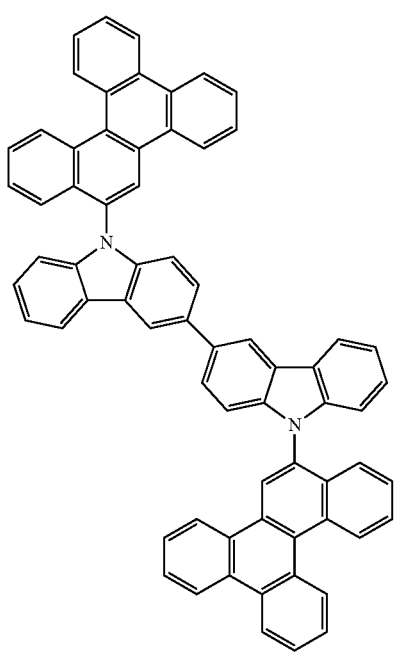
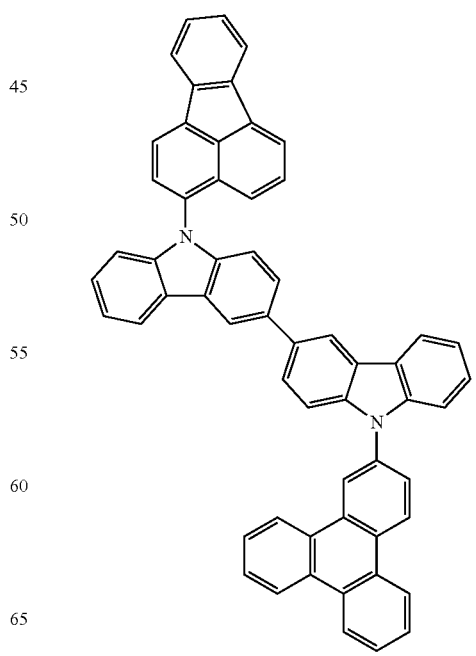

207
-continued
208
-continued
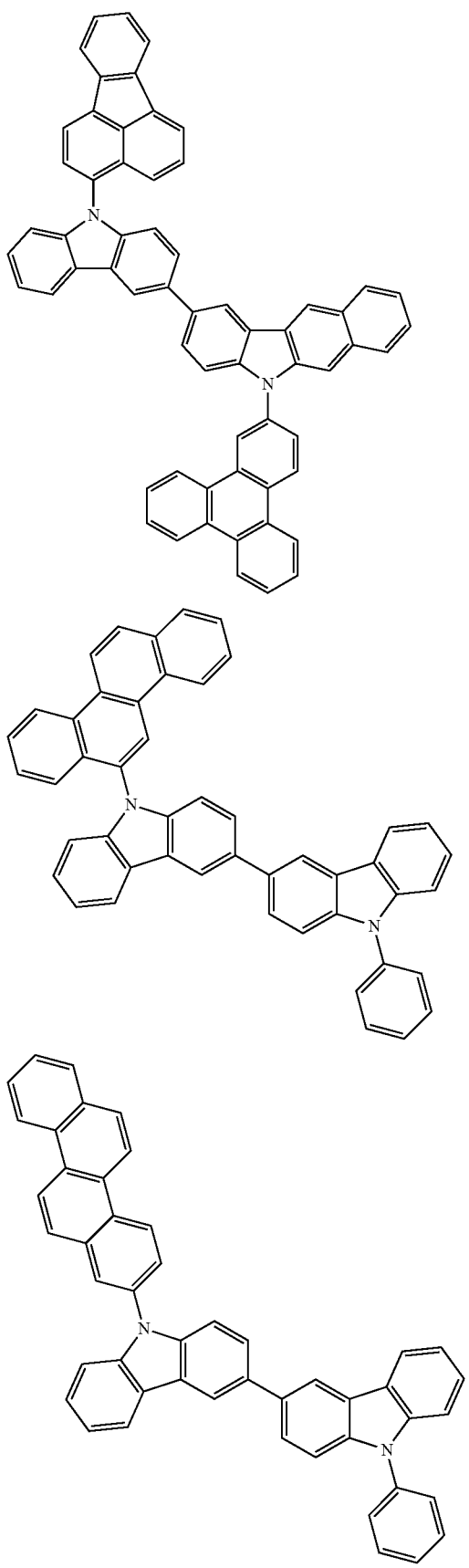
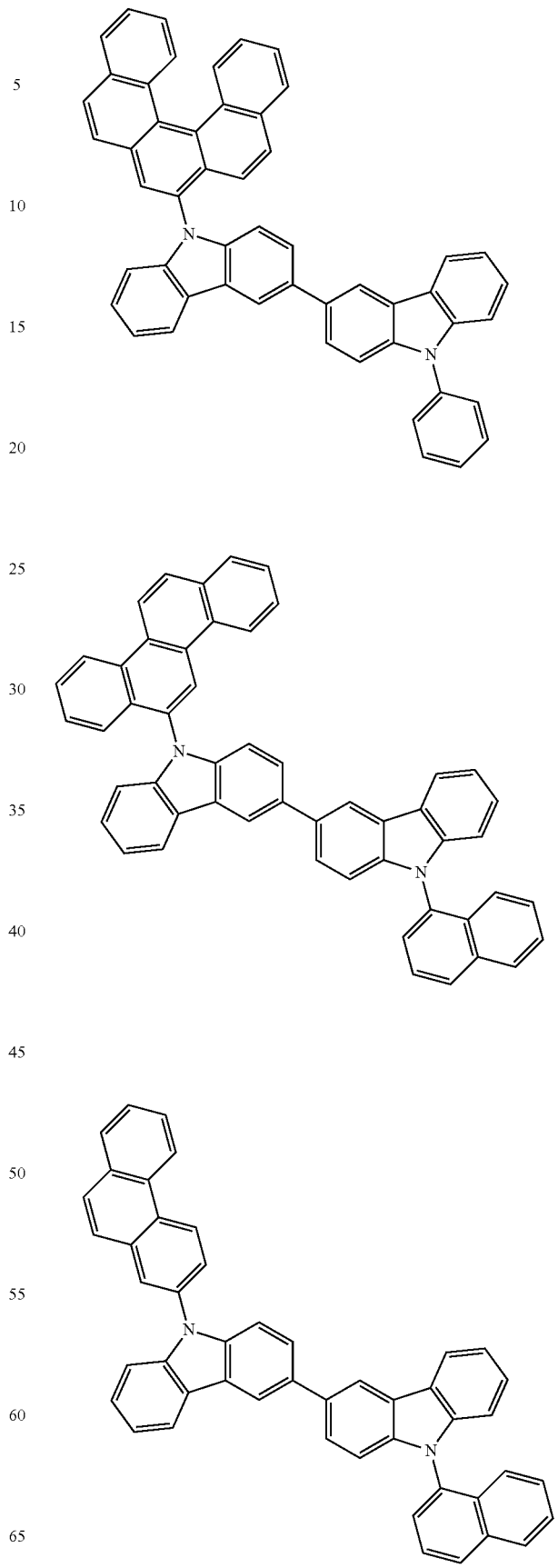

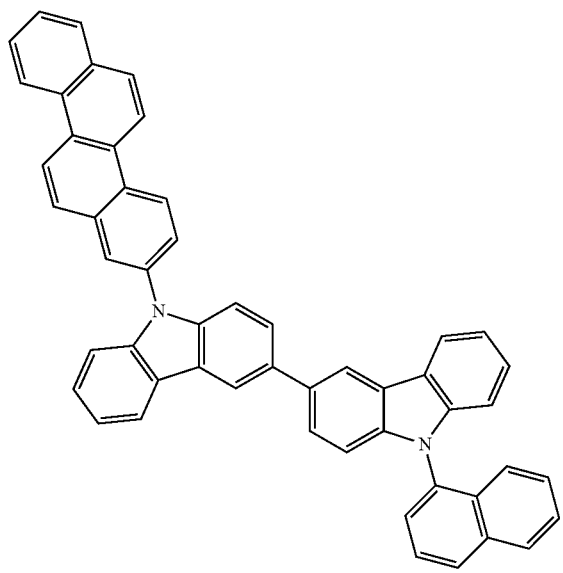
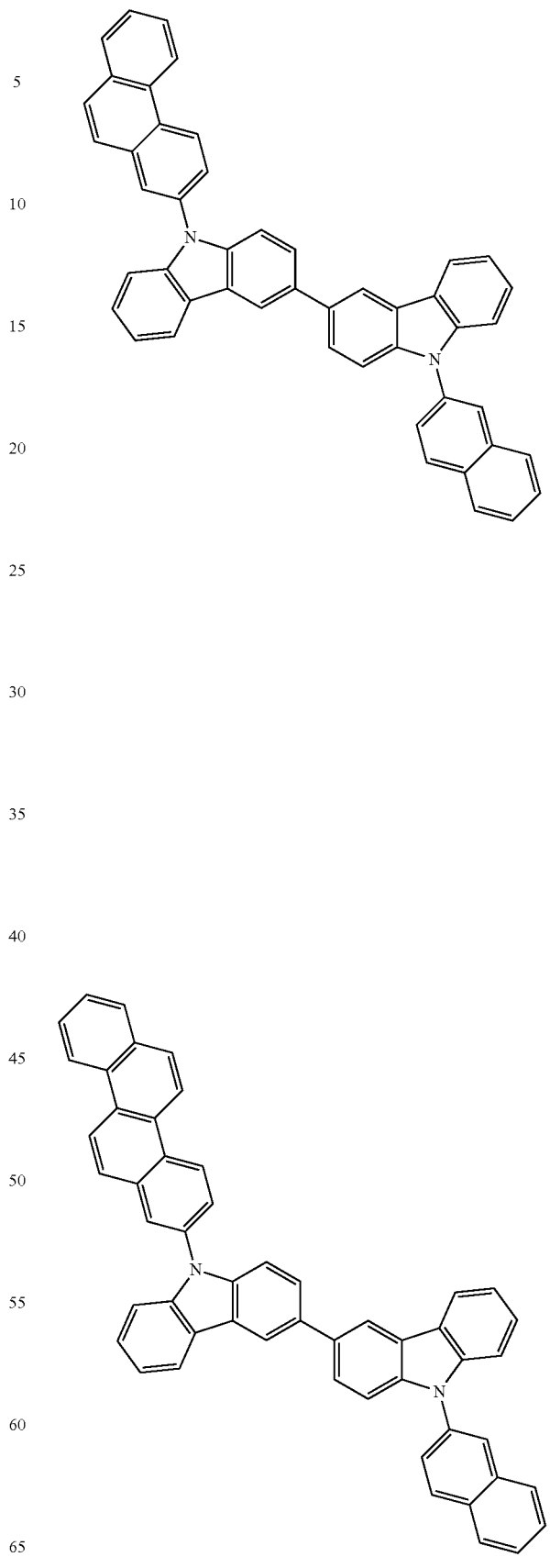

211
-continued
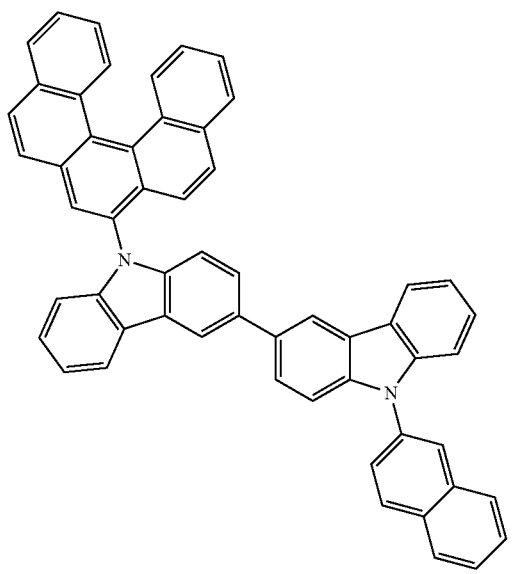
212
-continued
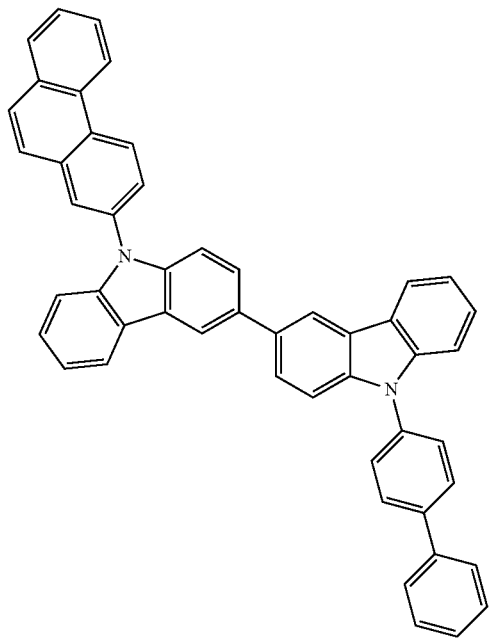
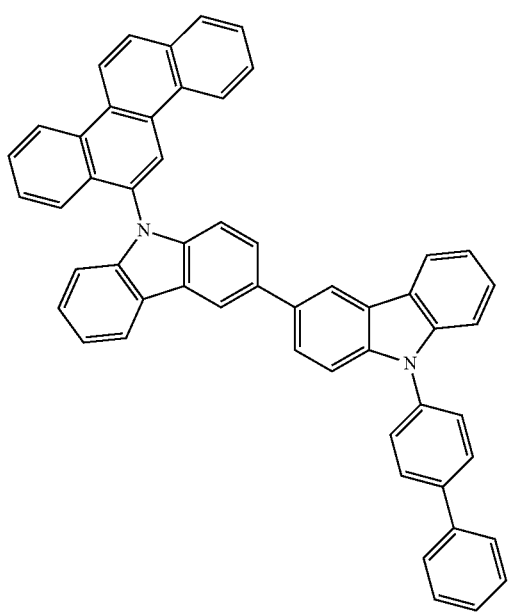
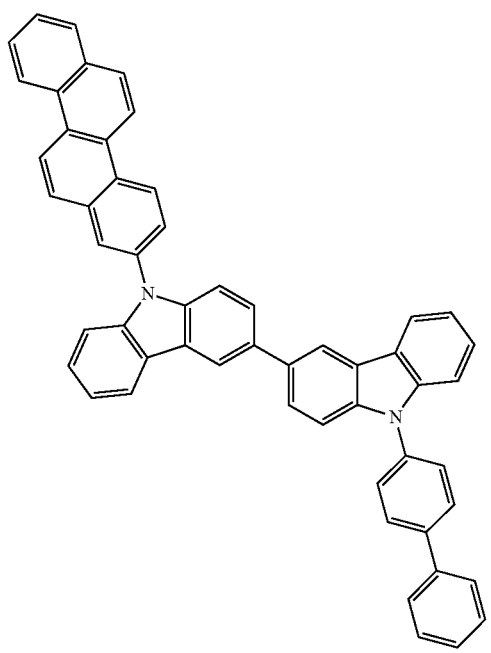

213
-continued
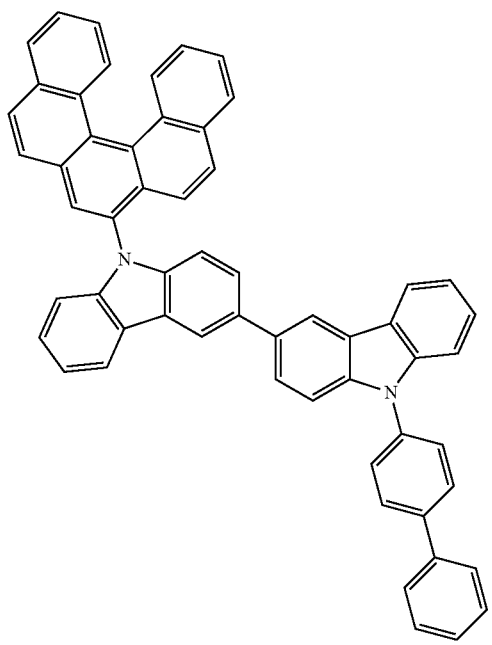
214
-continued
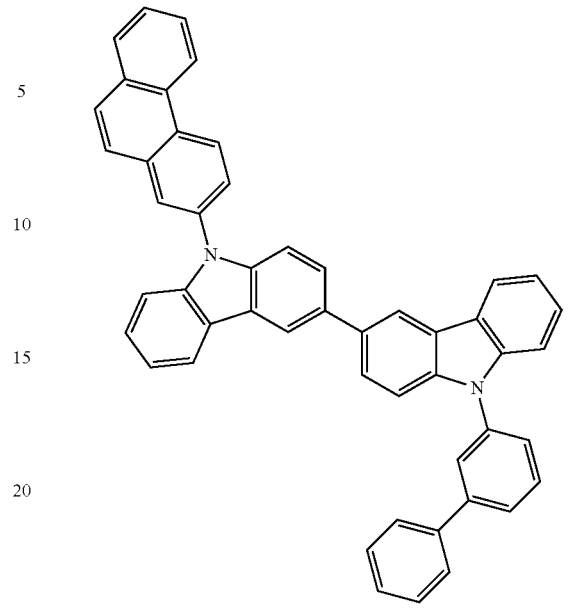
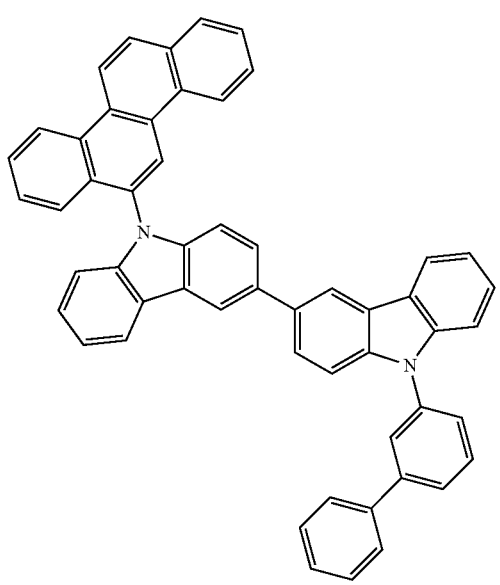
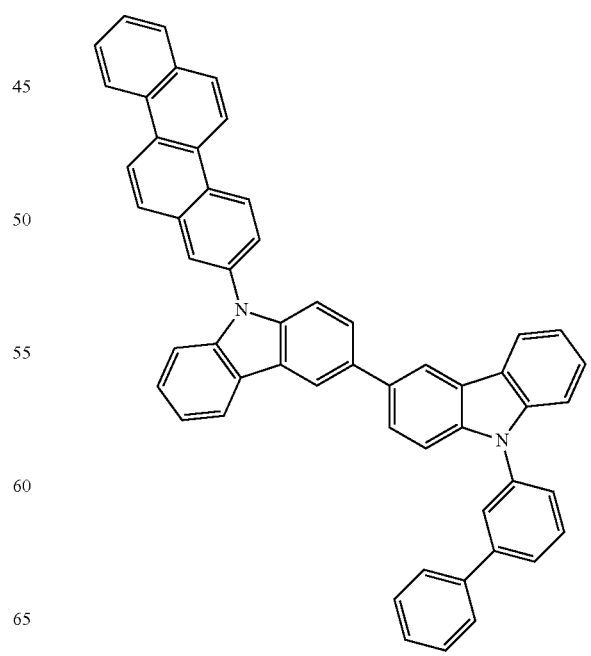

215
-continued
216
-continued
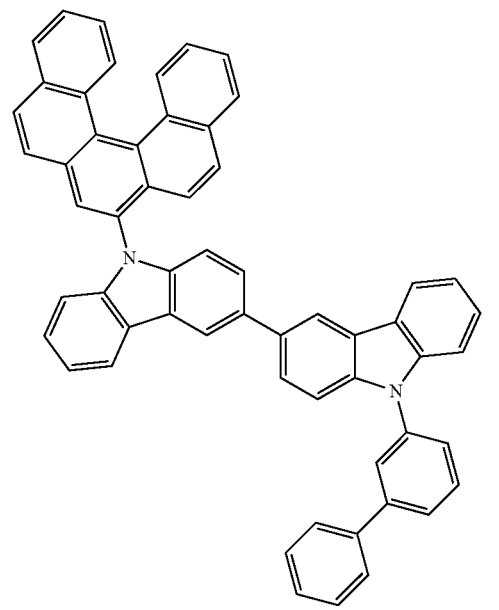
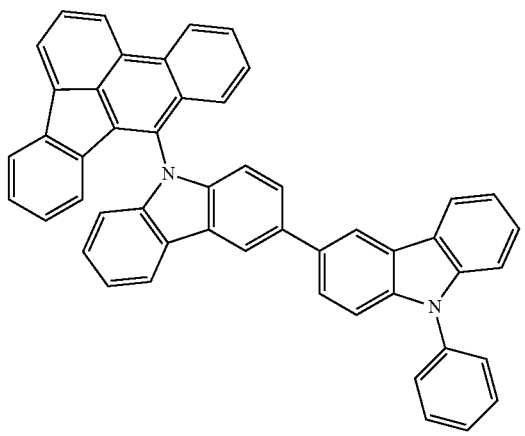
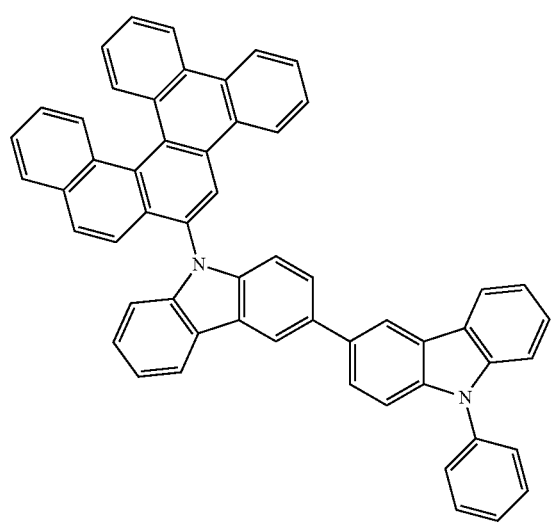
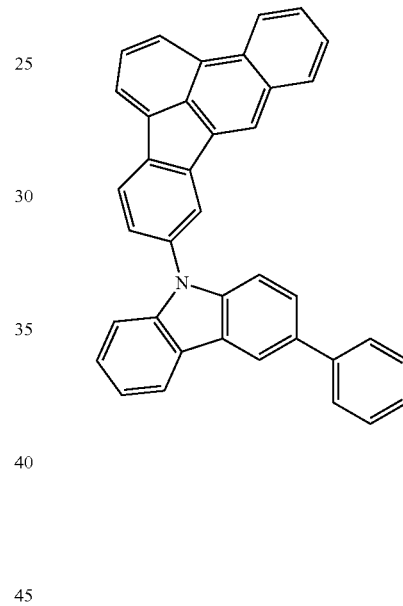
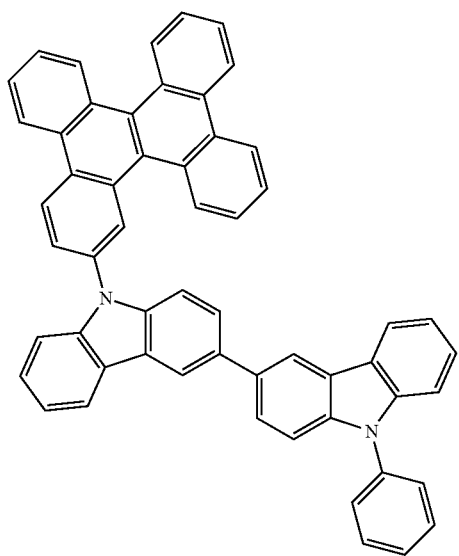
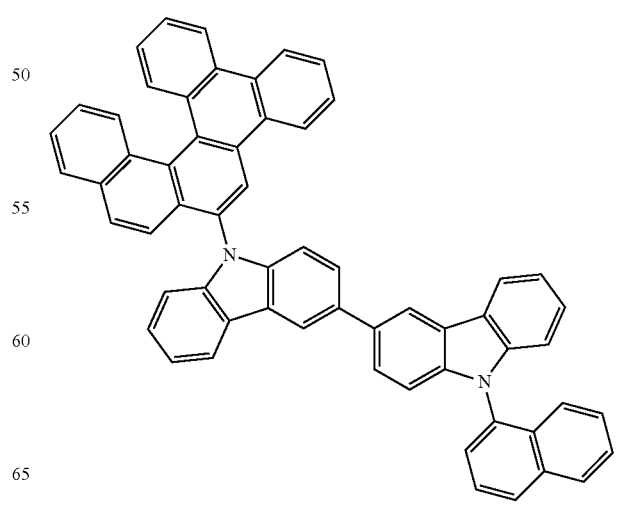

217
-continued
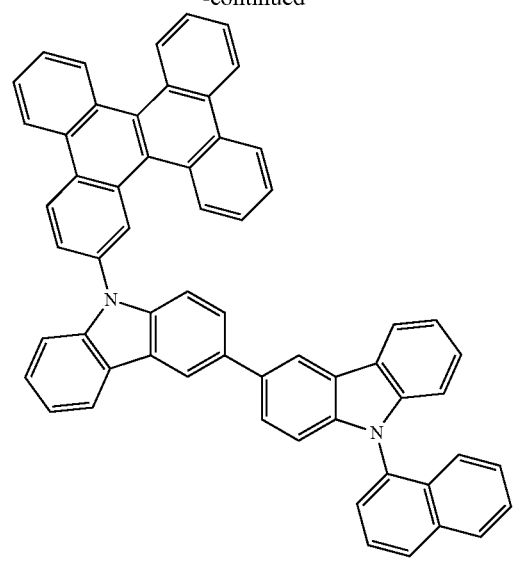
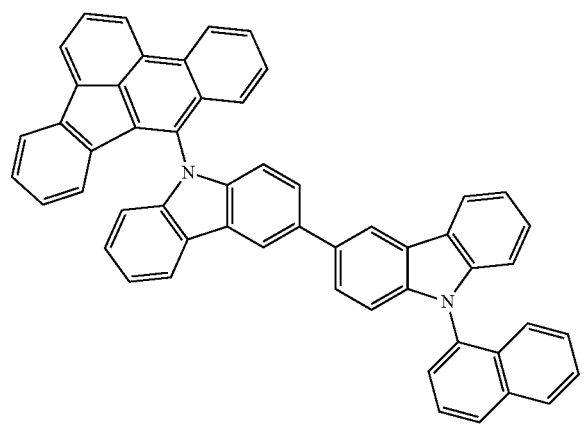
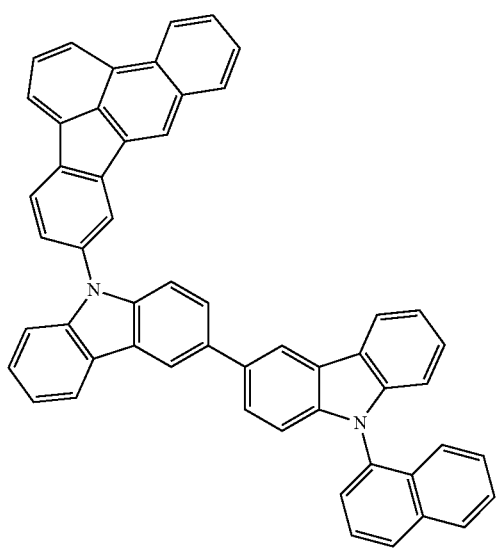
218
-continued
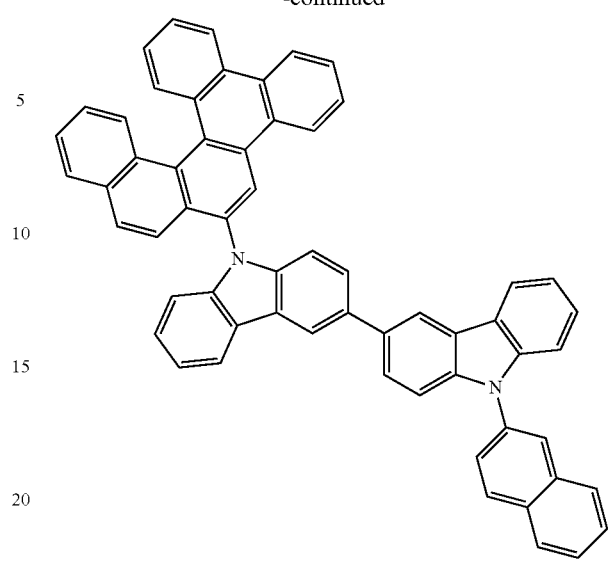
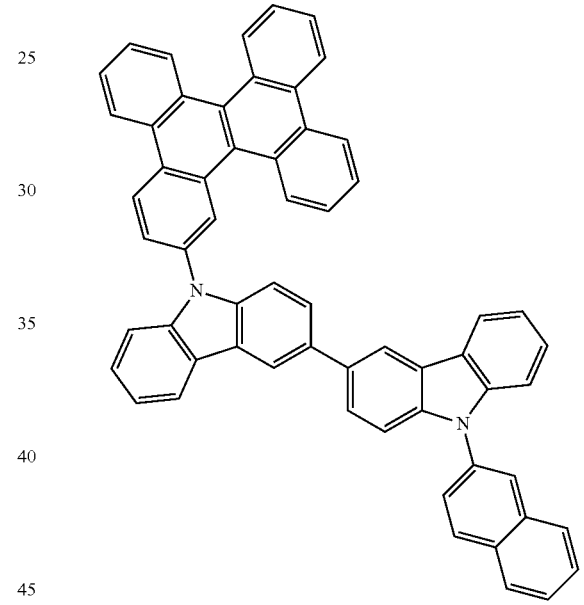
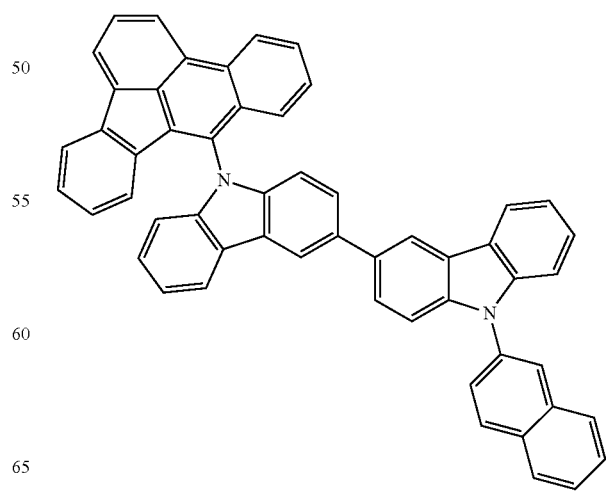

219
-continued
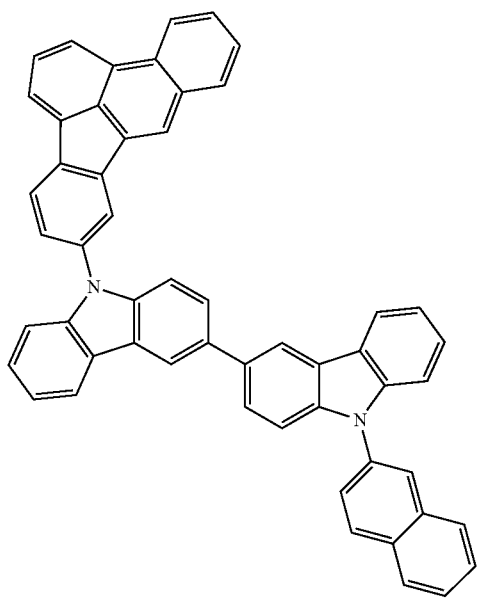
220
-continued
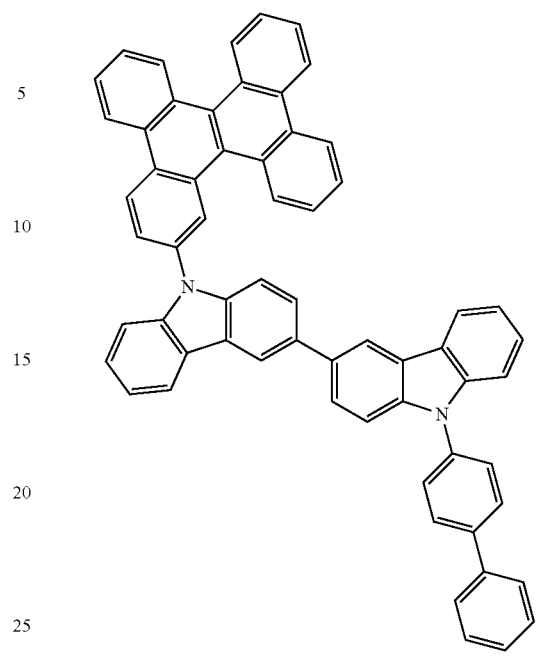
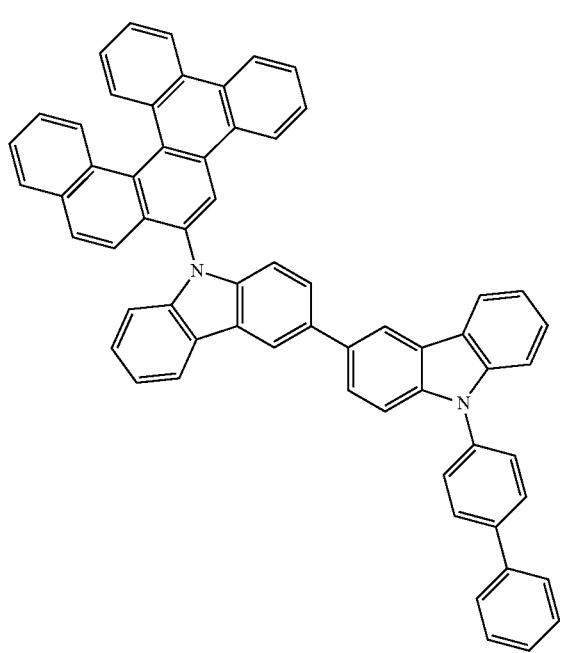
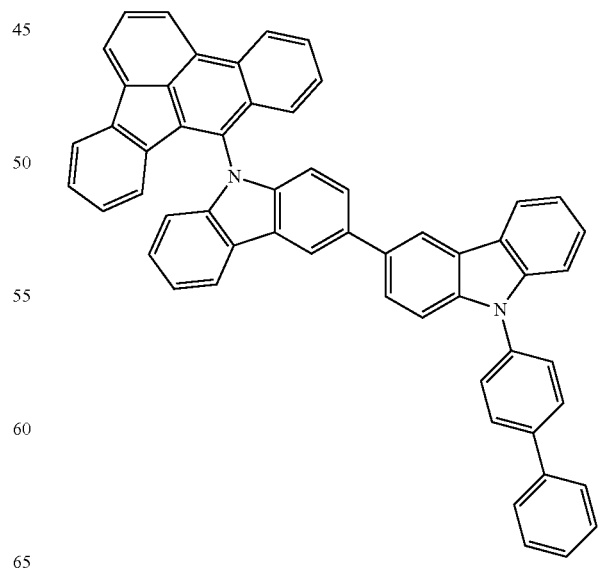

221
-continued
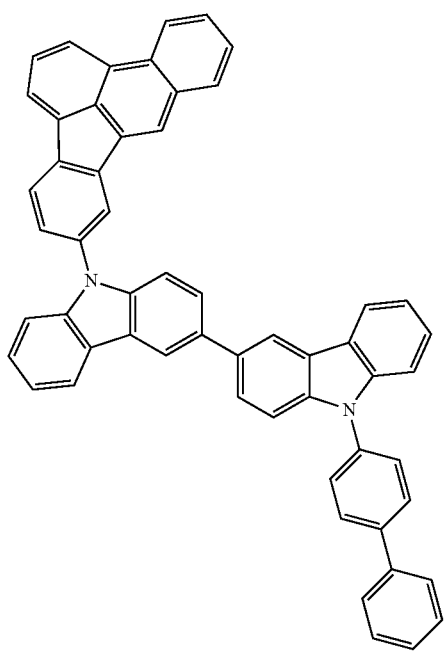
222
-continued
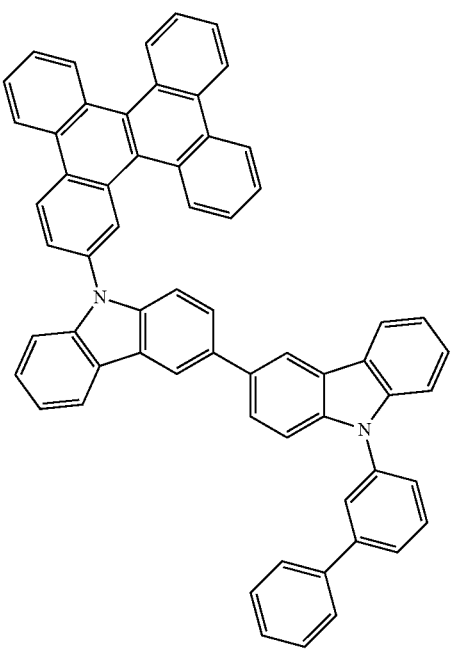
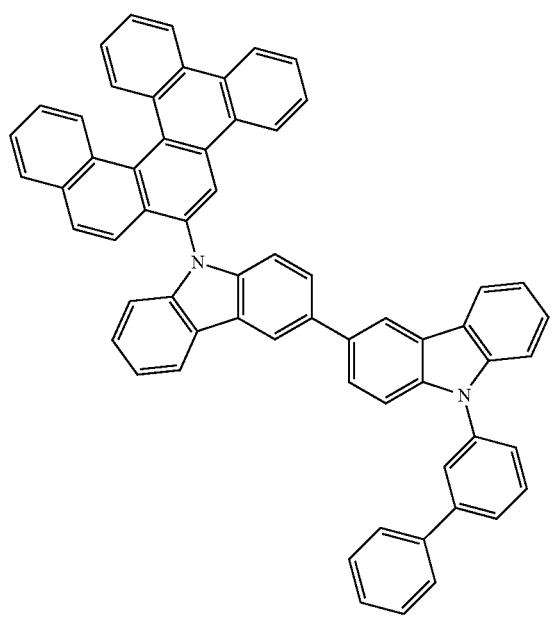
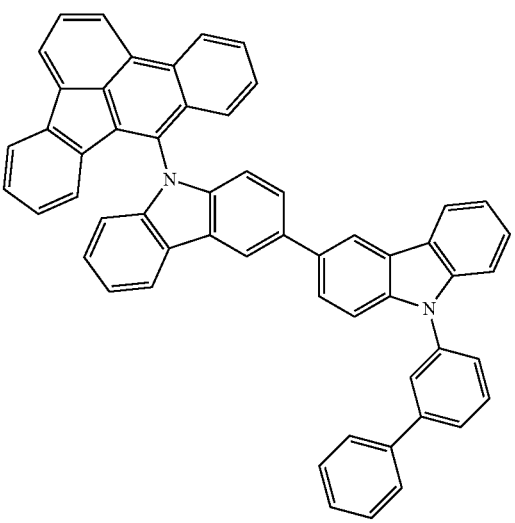

223
-continued
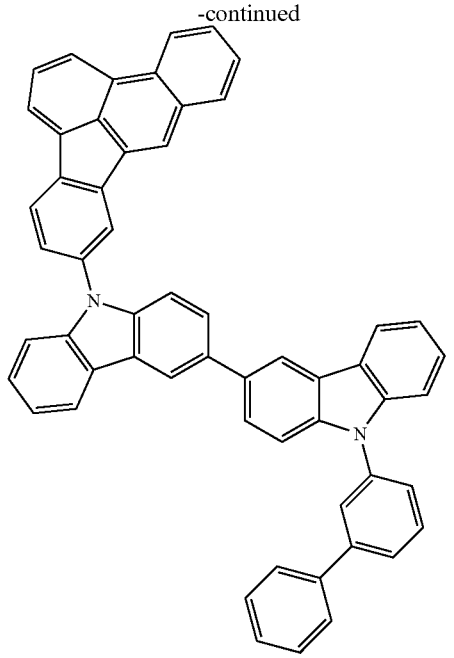
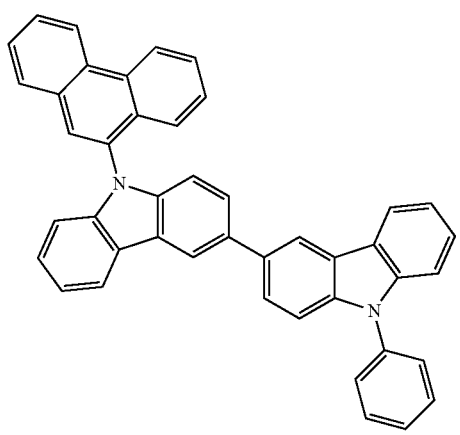
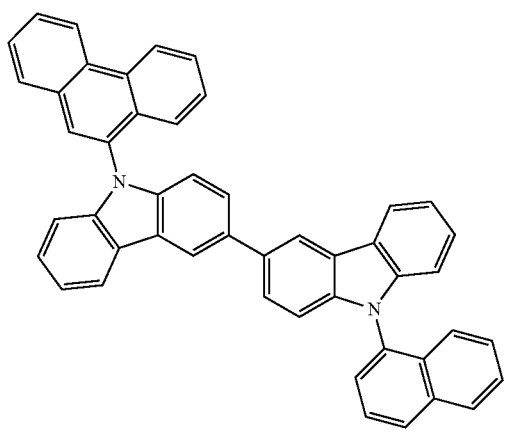
224
-continued
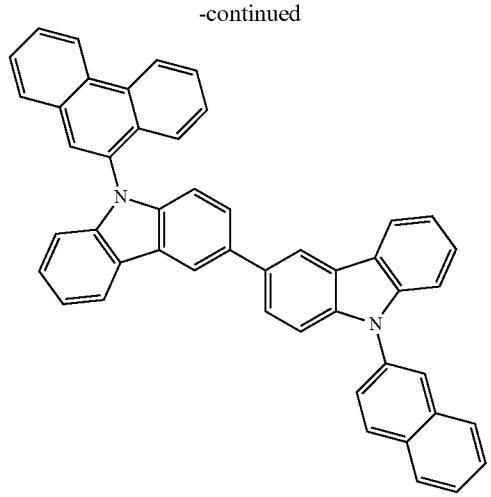

225
-continued
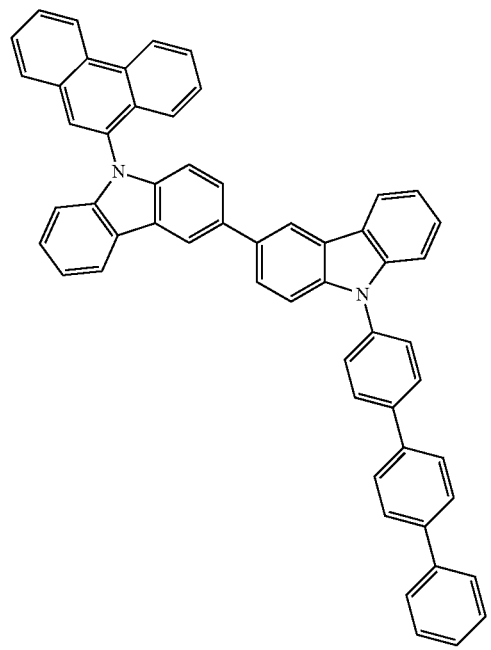
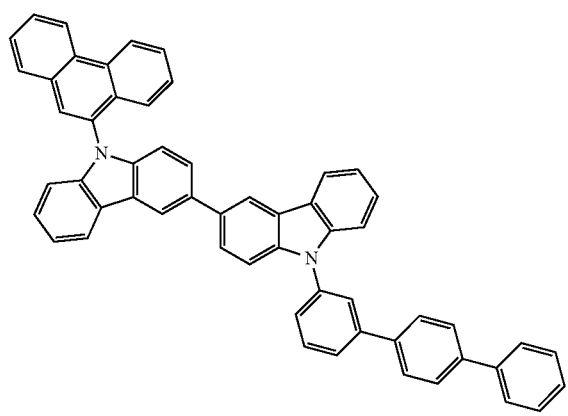
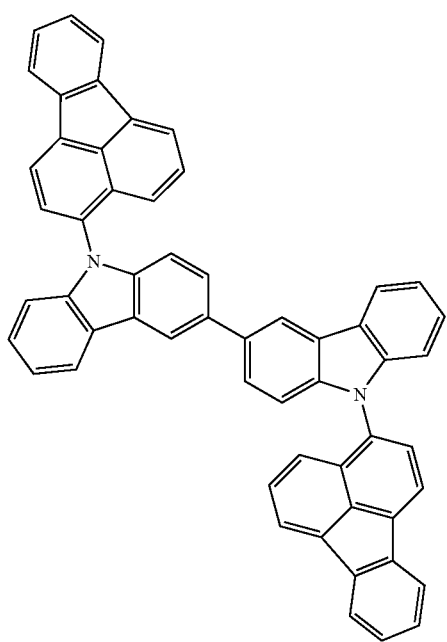
226
-continued
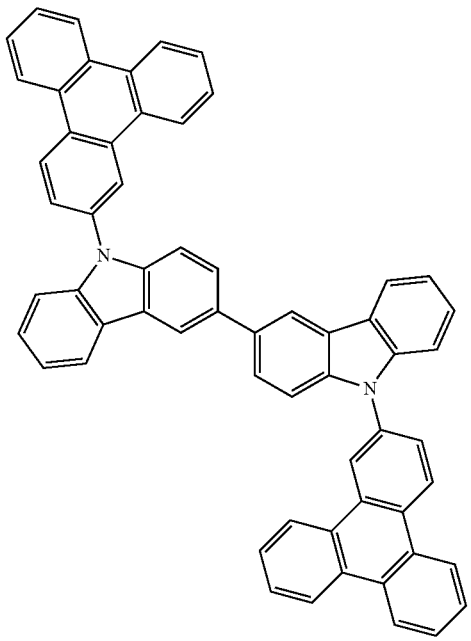
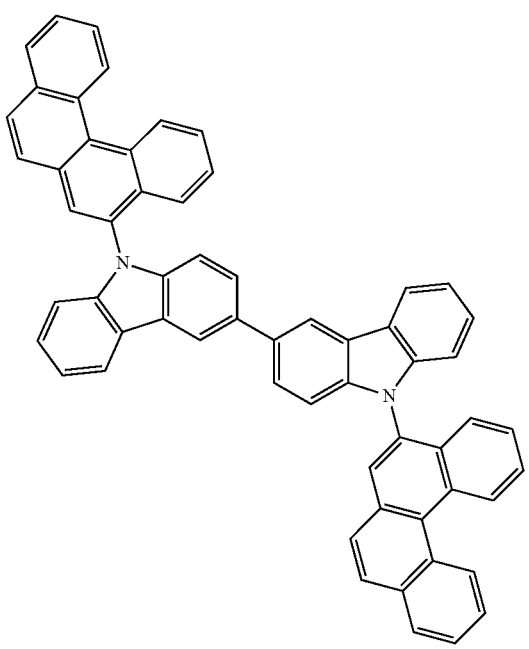

227
-continued
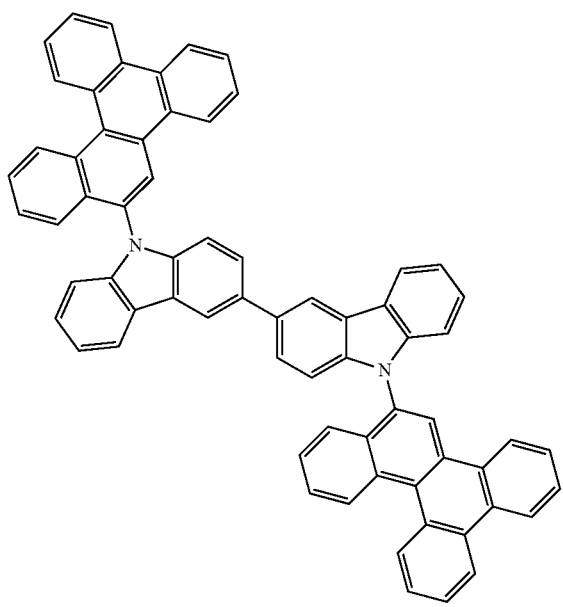
228
-continued
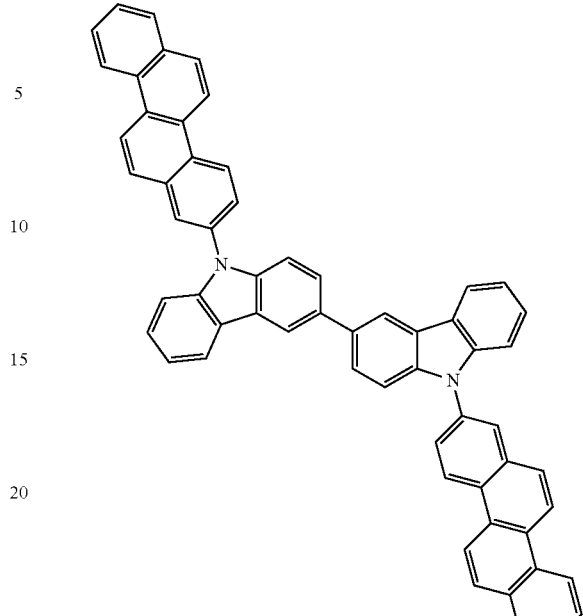
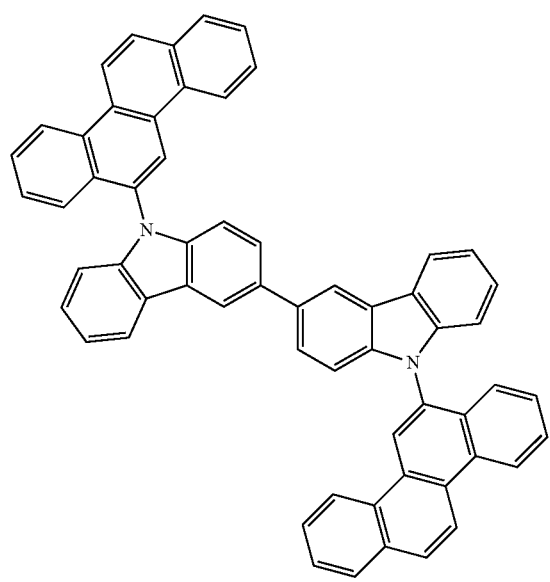
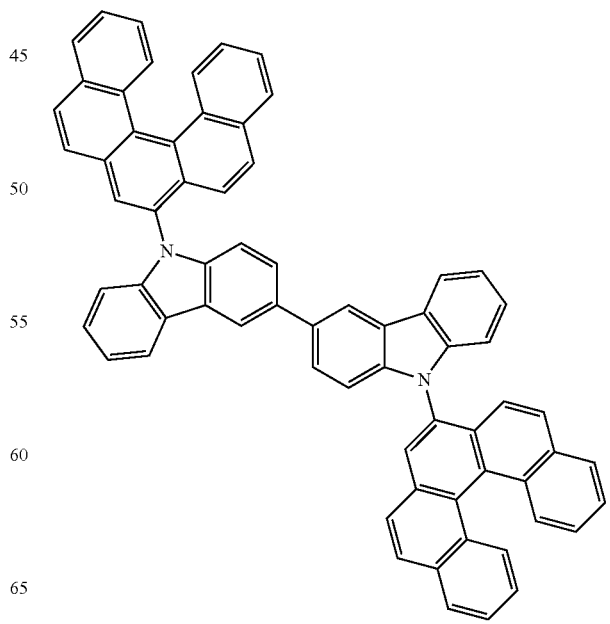

229
-continued
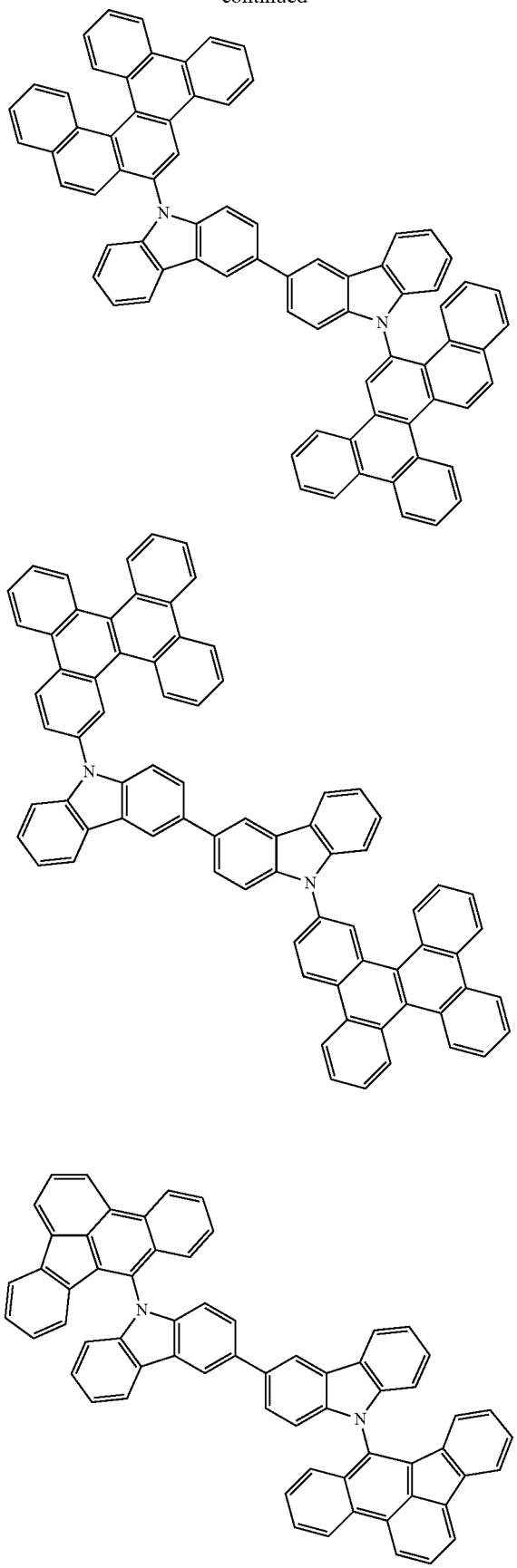
230
-continued
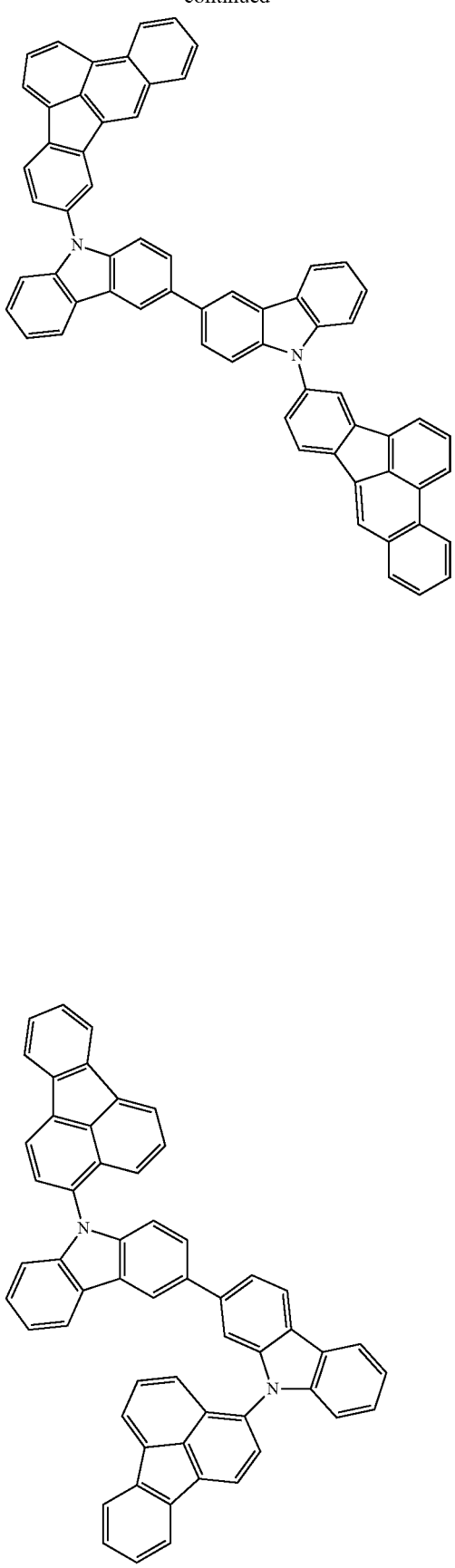

231
-continued
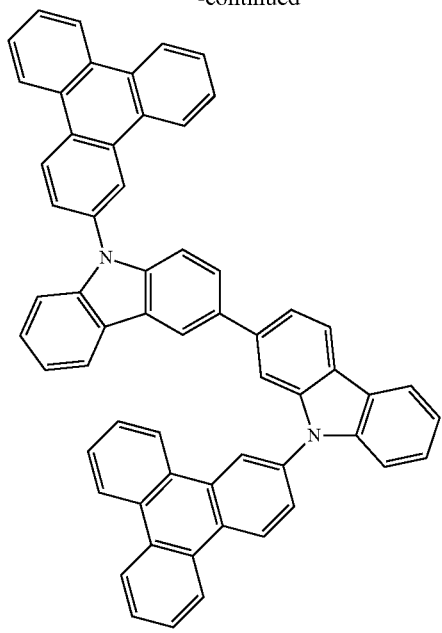
232
-continued
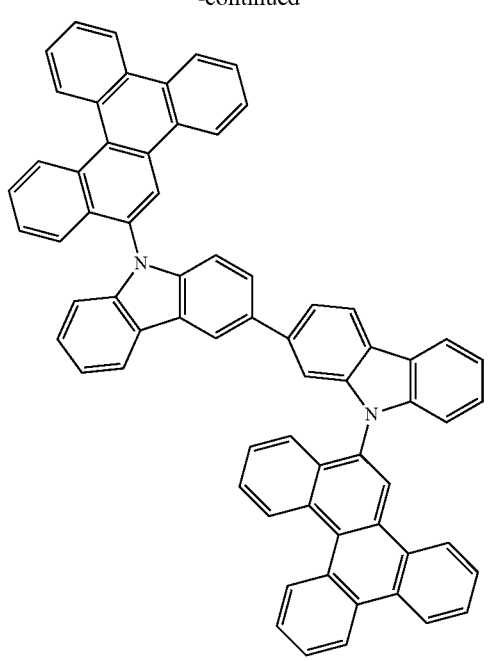
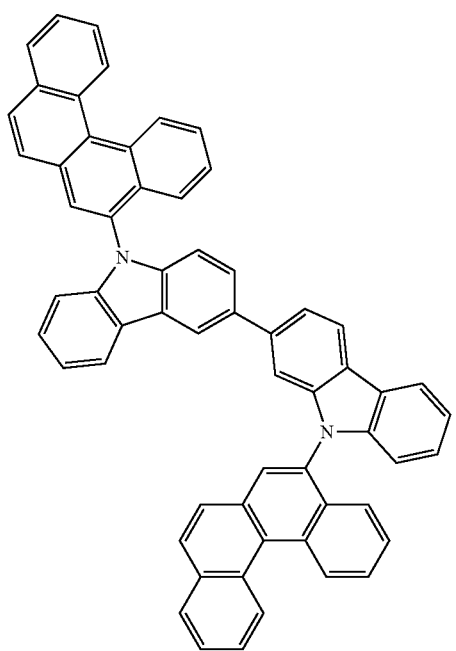
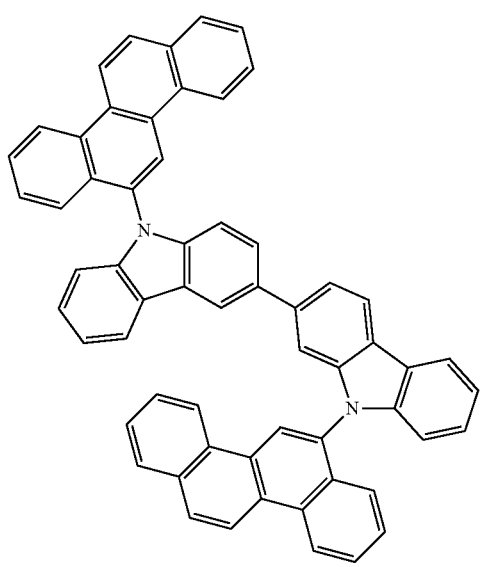

233
-continued
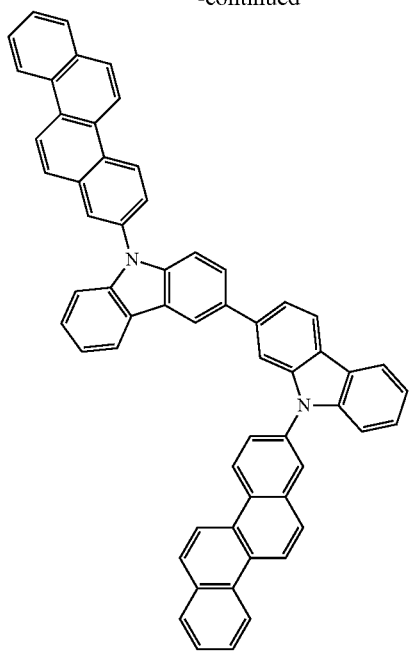
234
-continued
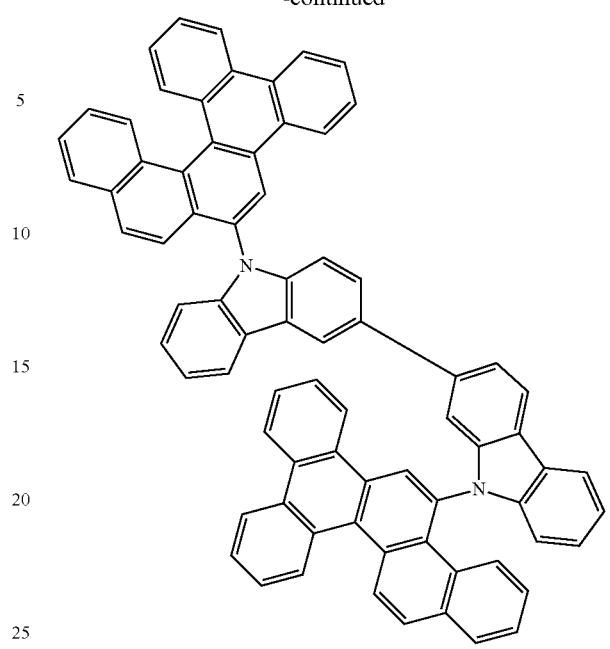
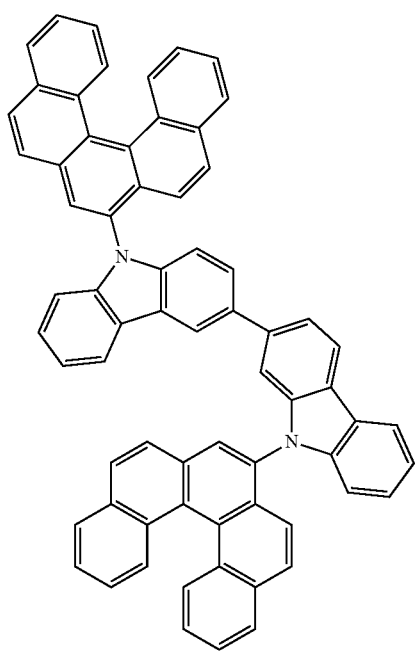
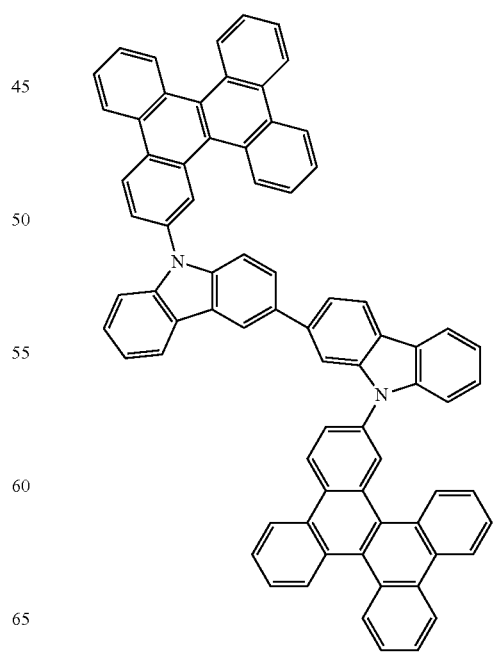

235
-continued
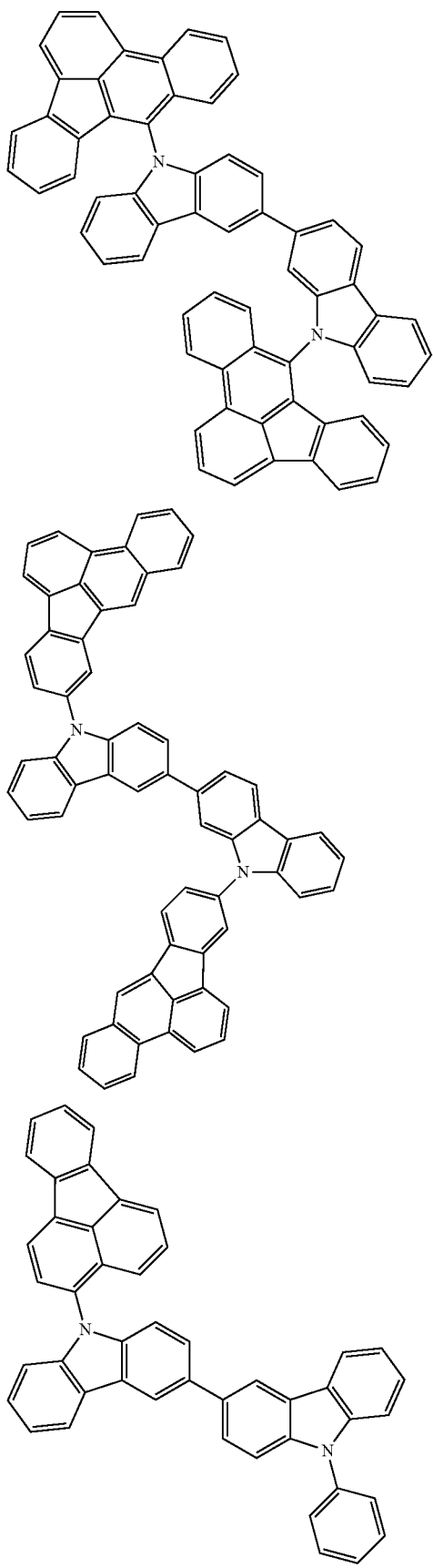
236
-continued
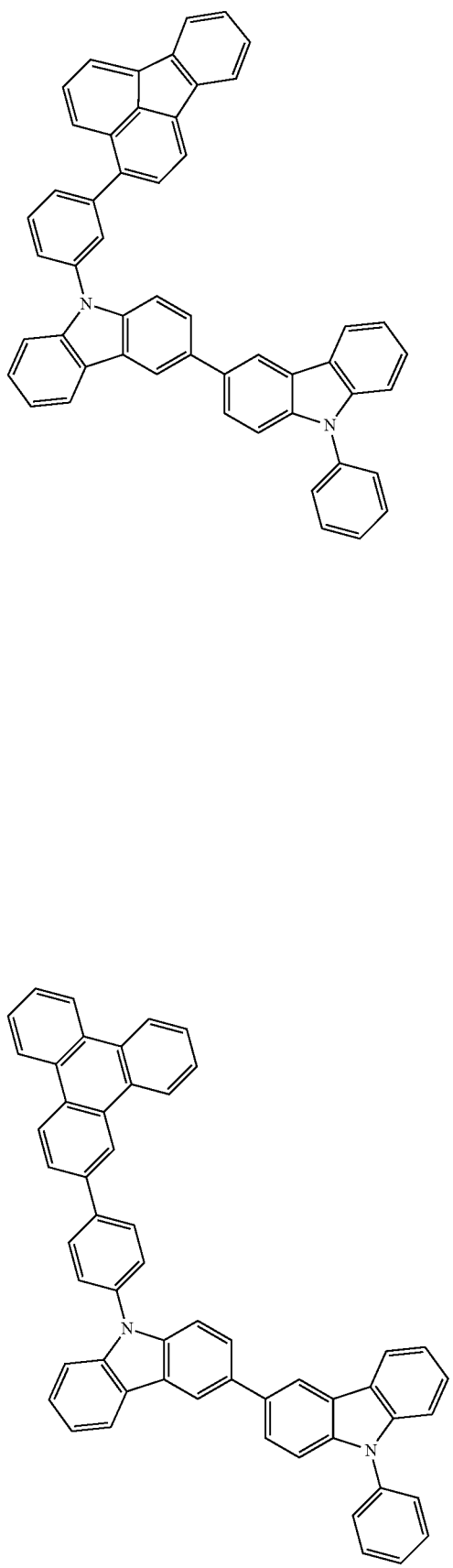

237
-continued
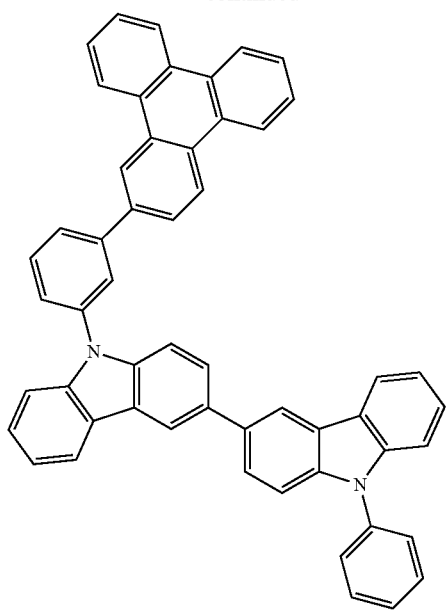
238
-continued
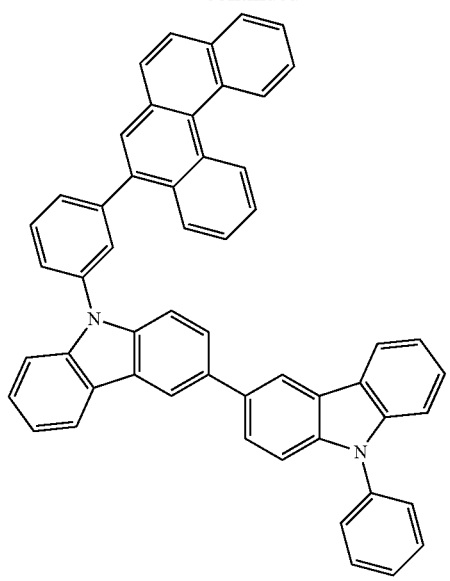
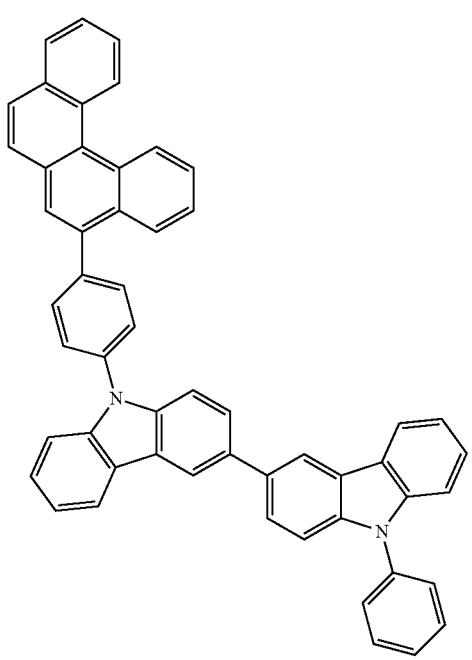
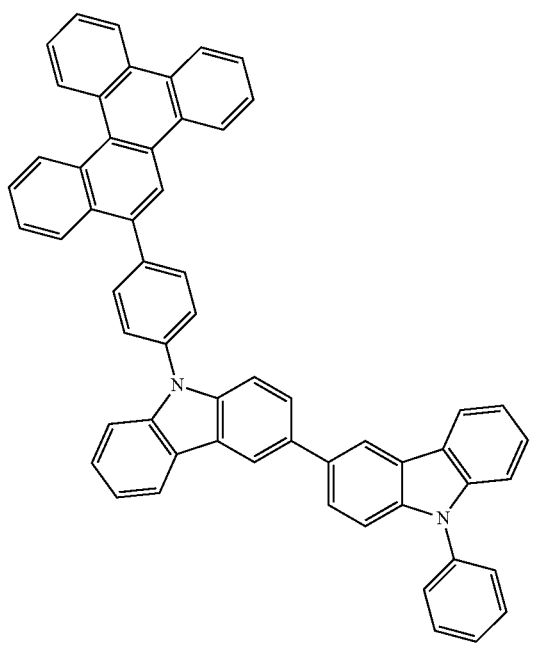

239
-continued
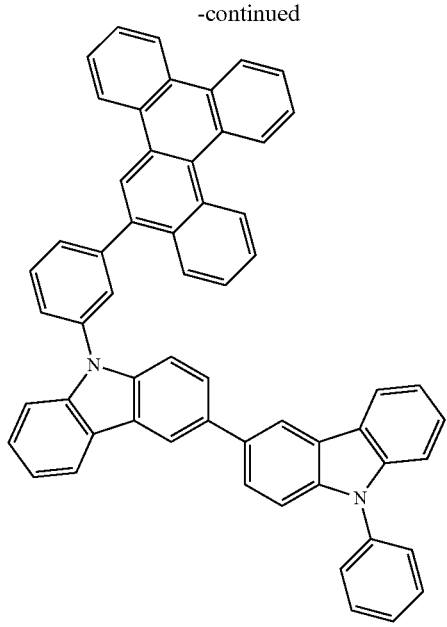
240
-continued
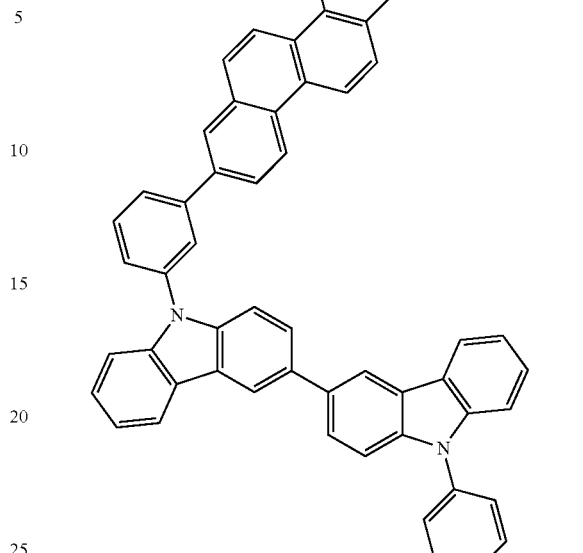
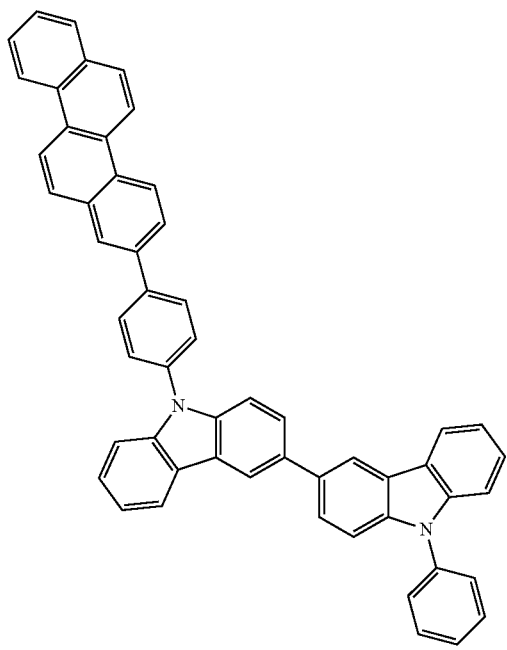
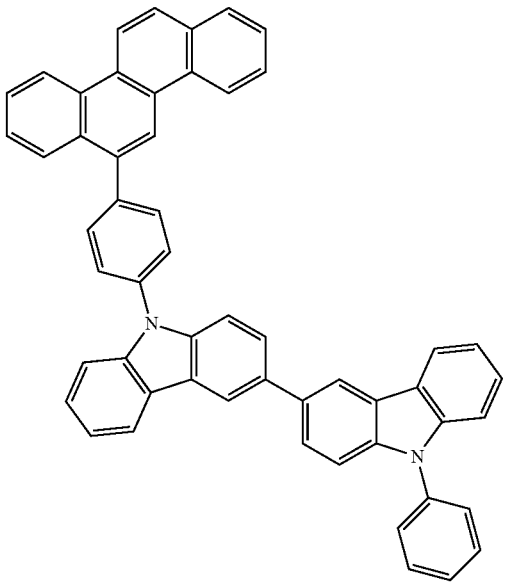

241
-continued
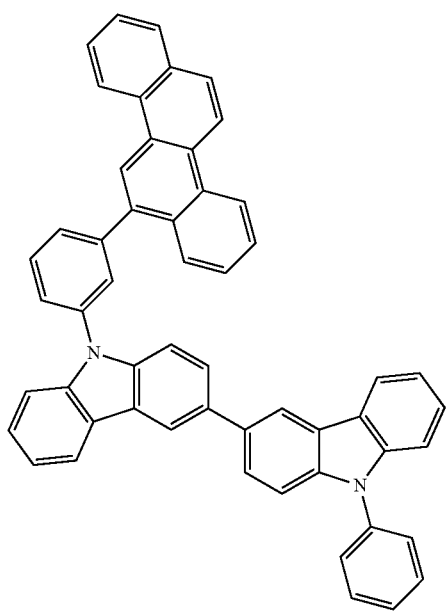
242
-continued
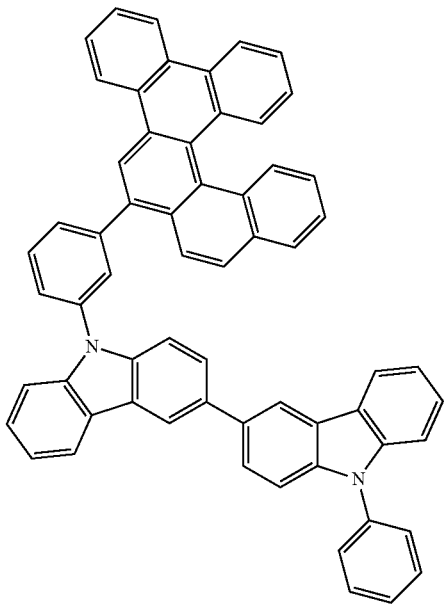
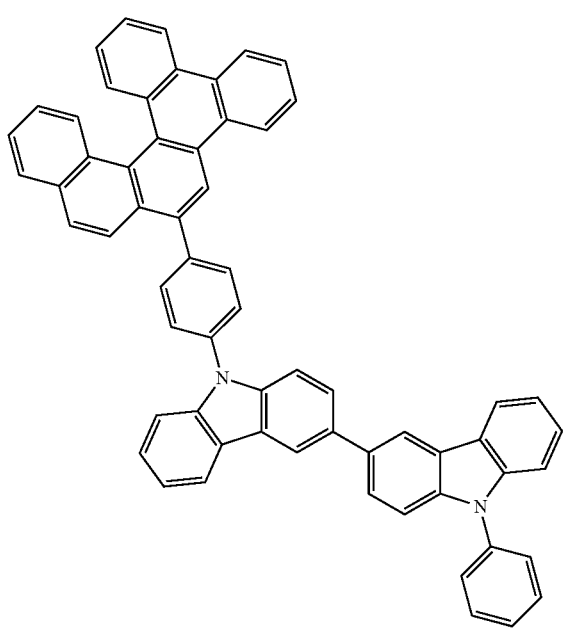
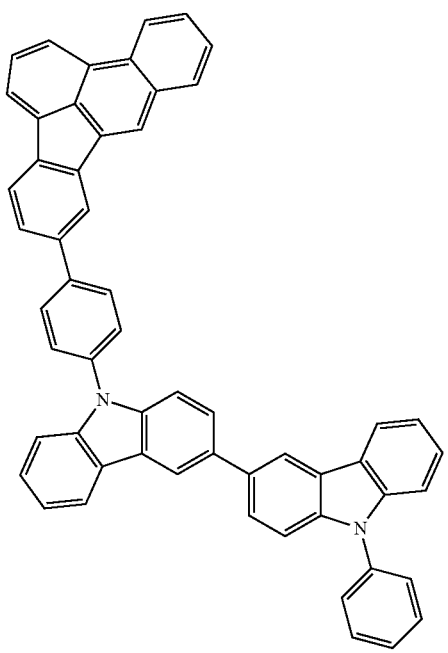

243
-continued
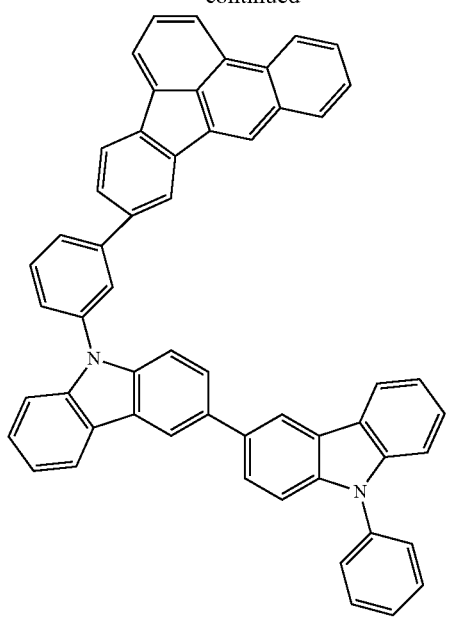
244
-continued
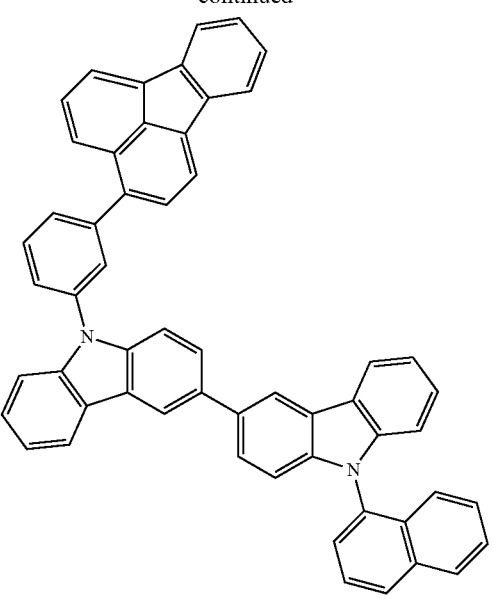
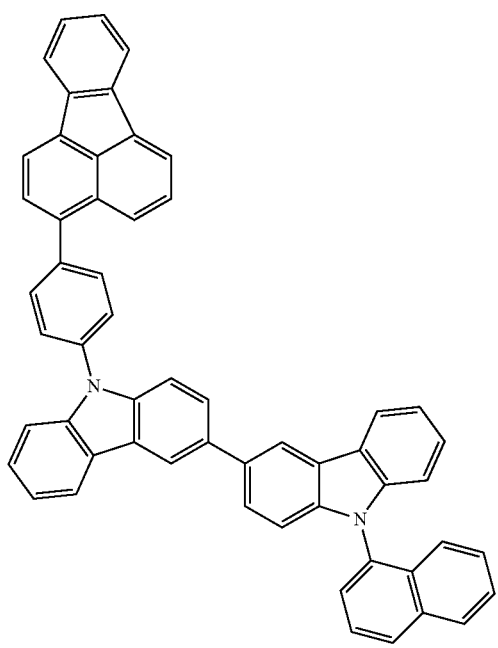
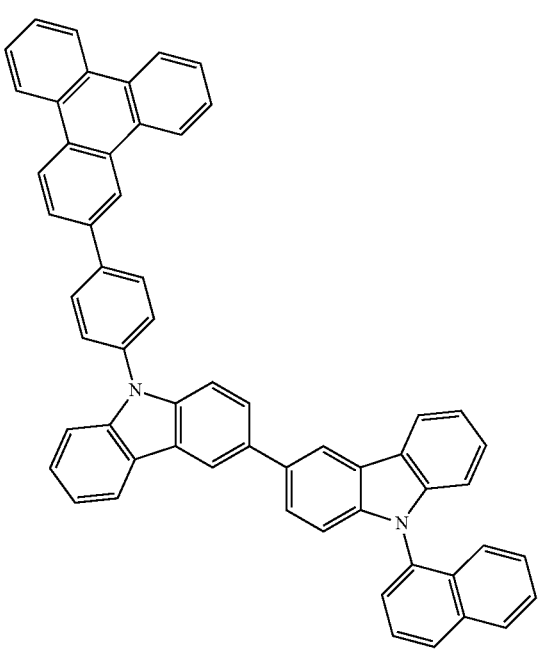

245
-continued
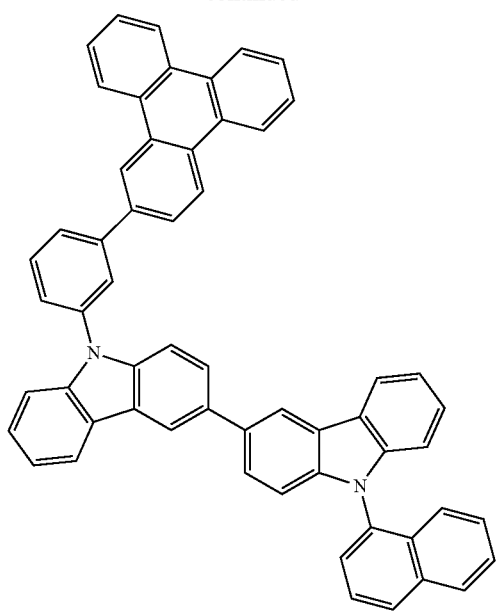
246
-continued
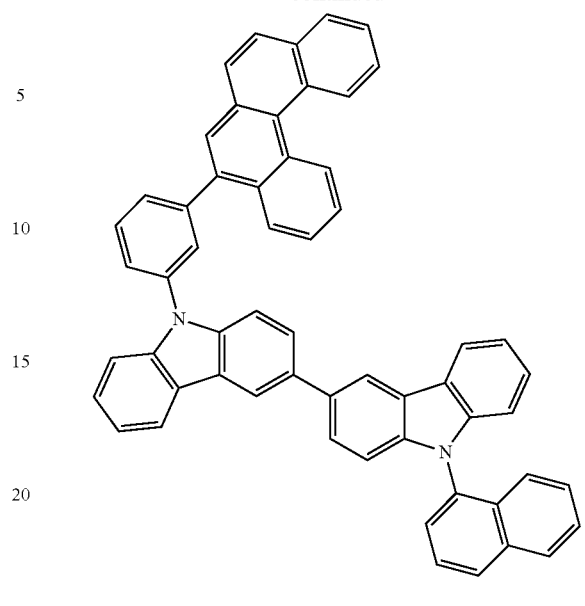
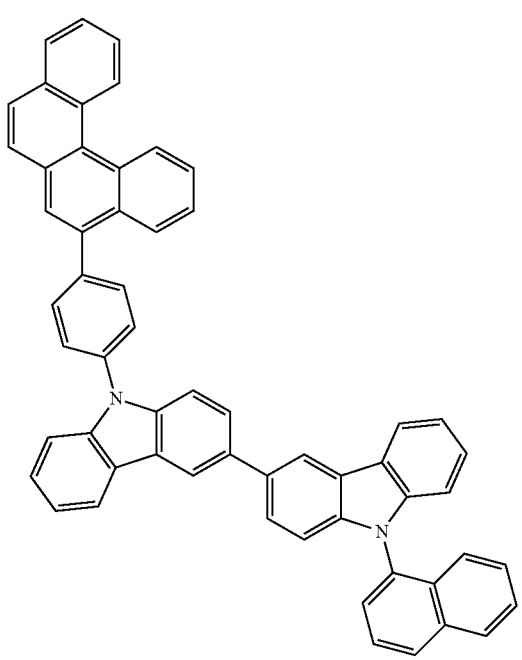
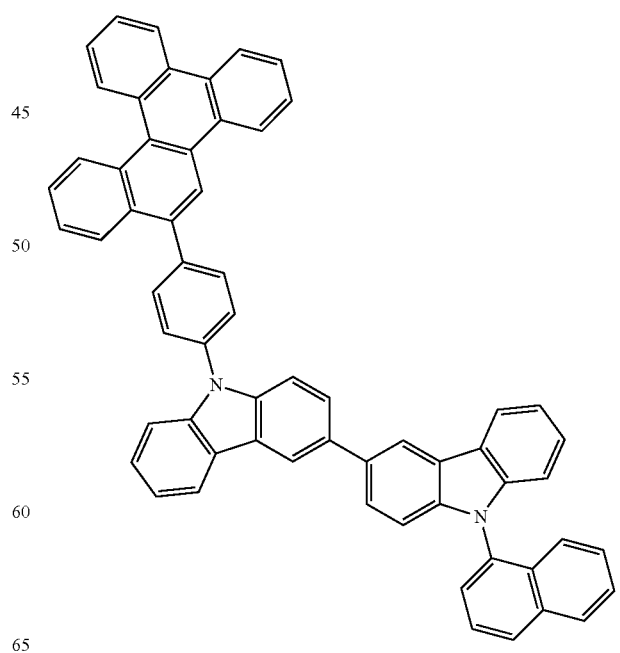

247
-continued
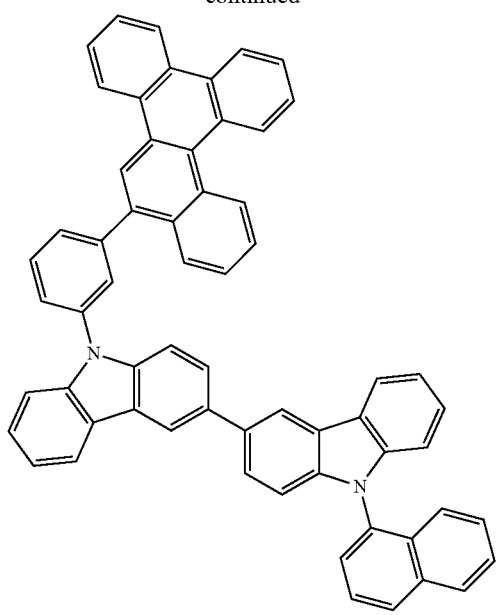
248
-continued
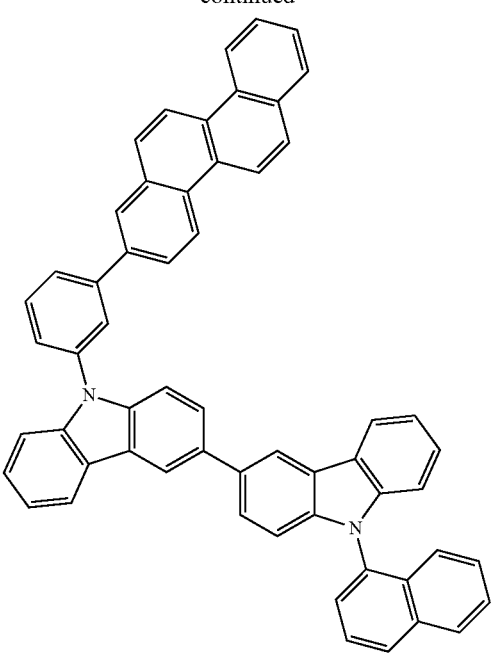
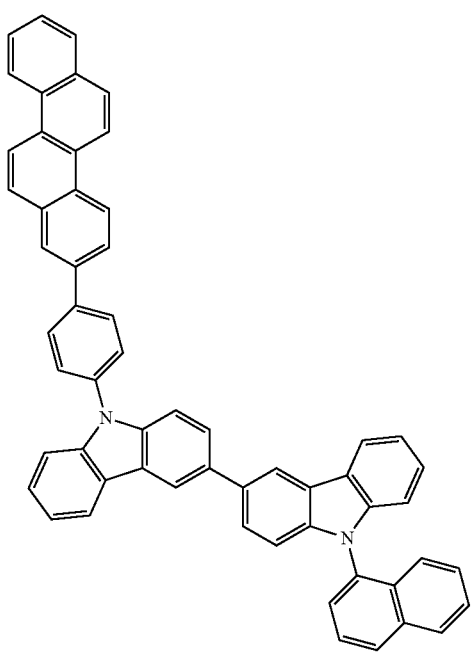
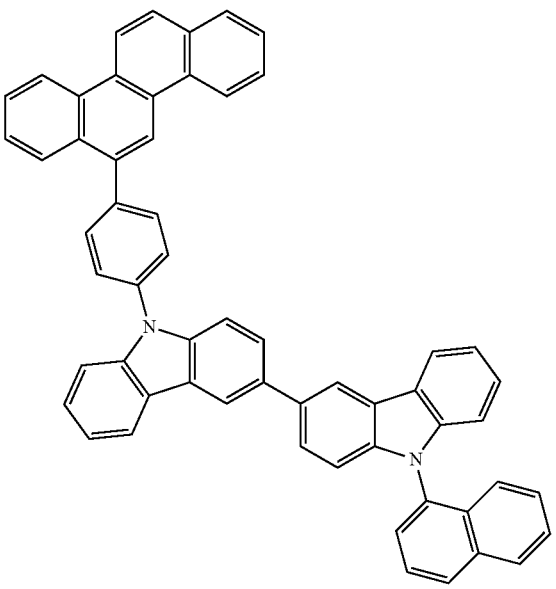

249
-continued
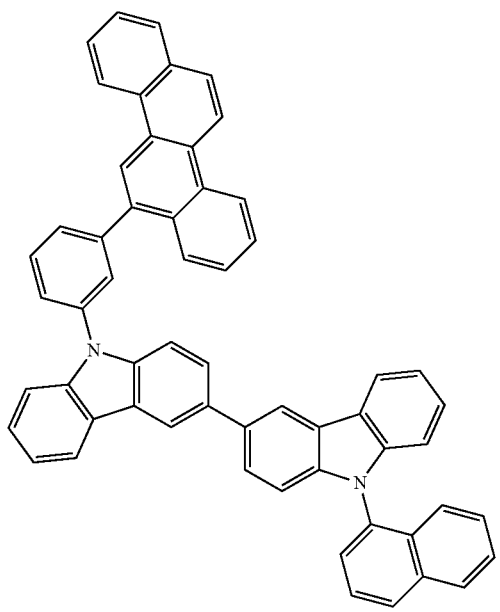
250
-continued
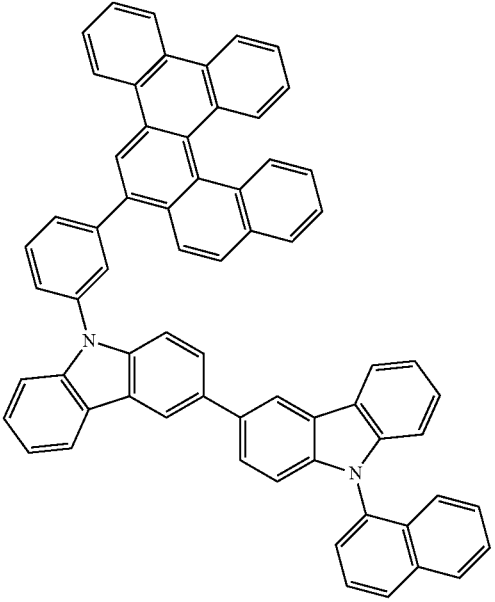
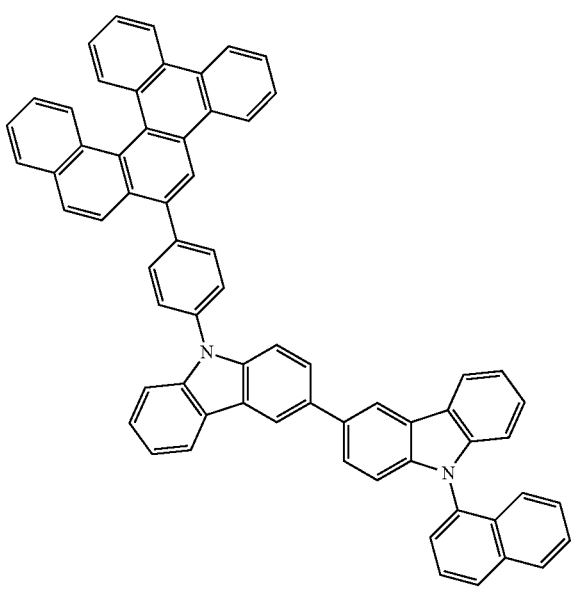
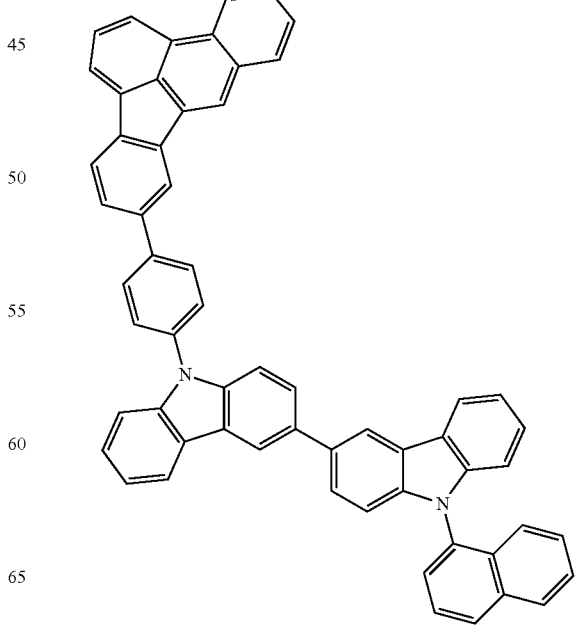

251
-continued
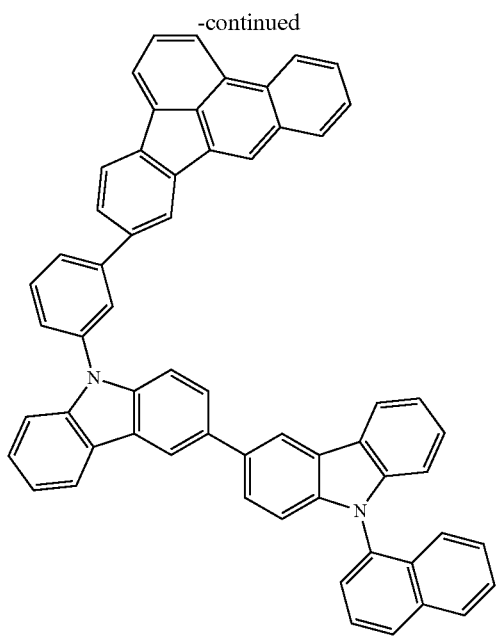
252
-continued
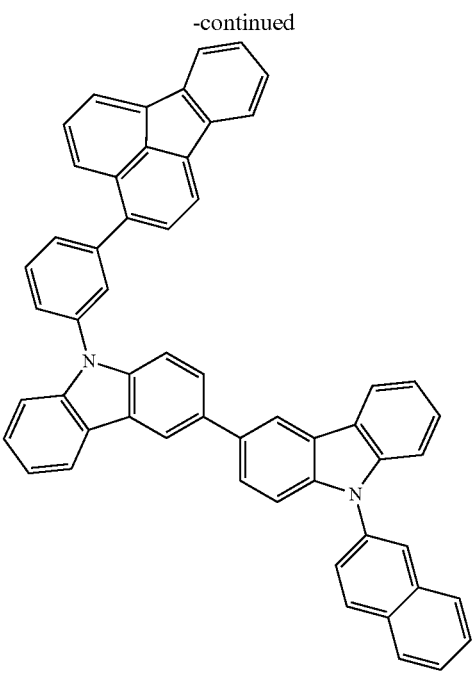
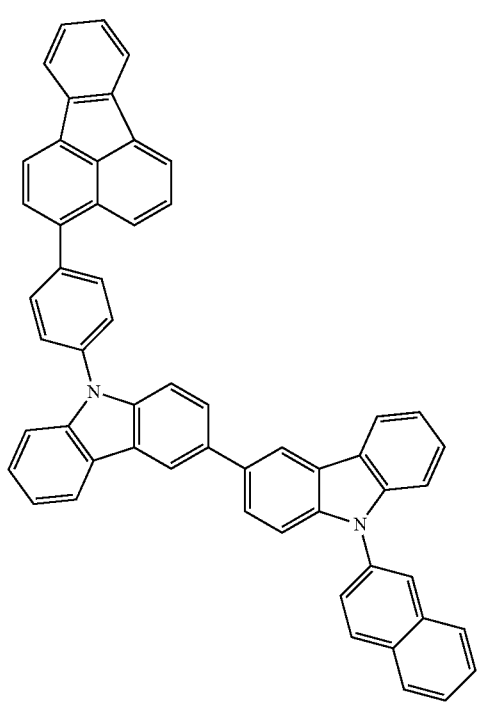
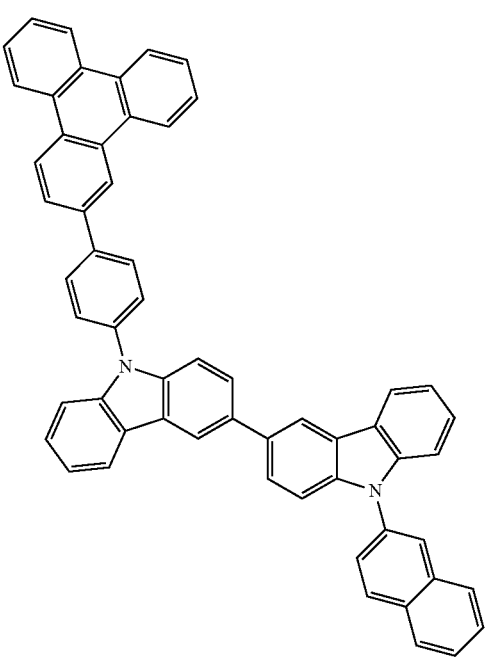

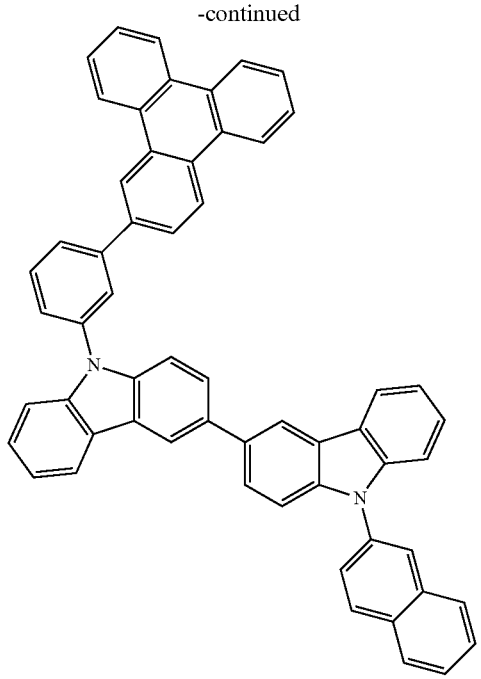
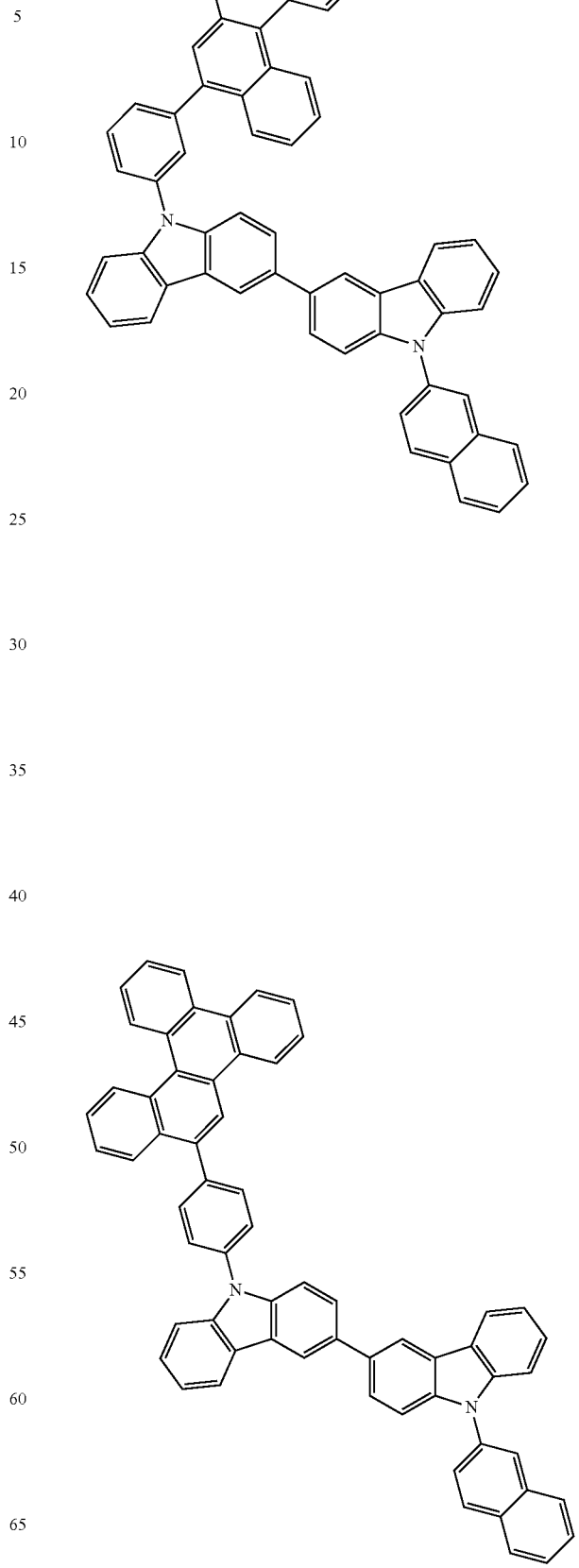

255
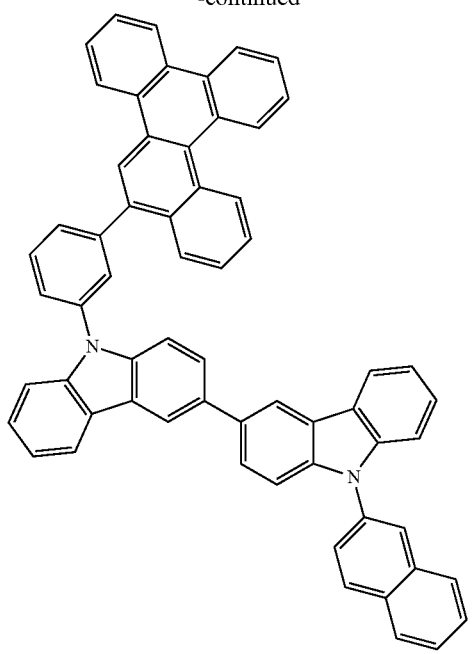
256
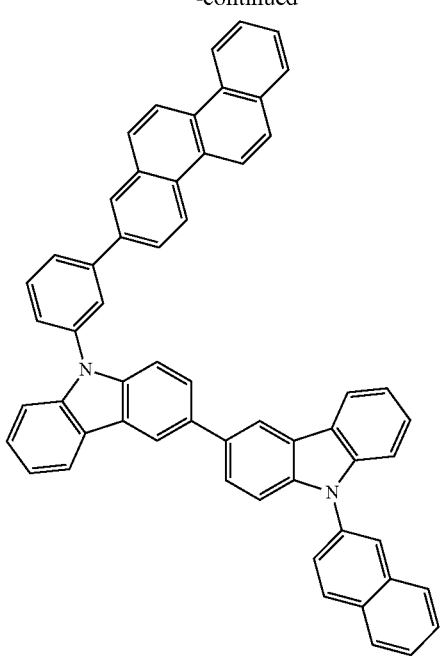
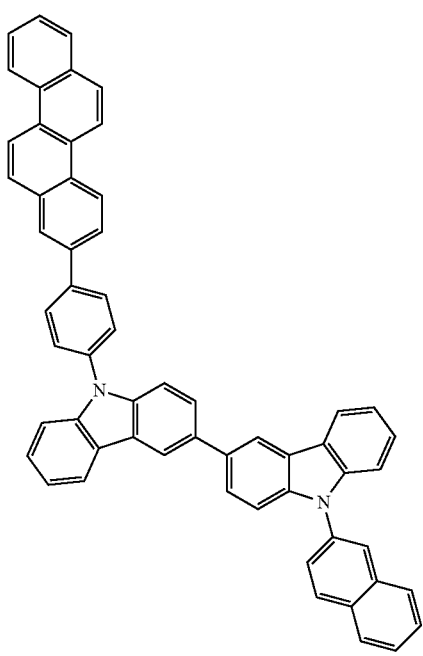
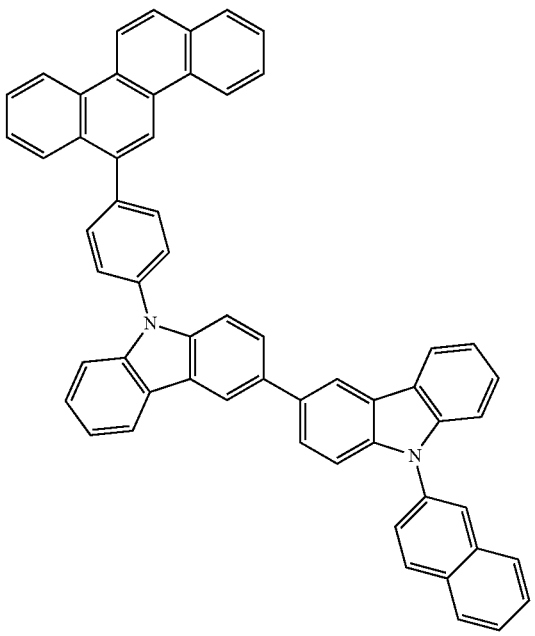

257
-continued
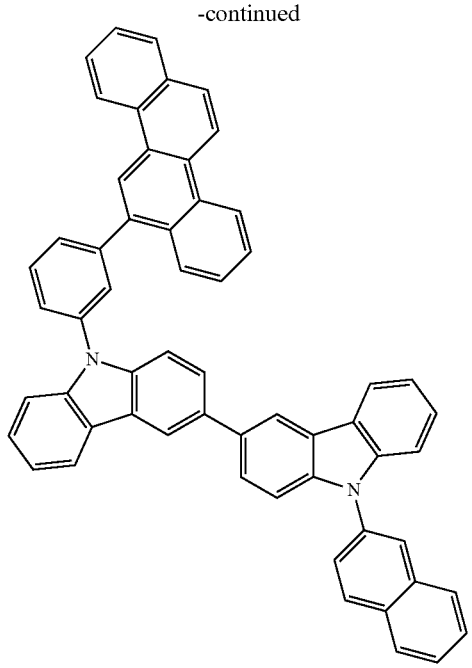
258
-continued
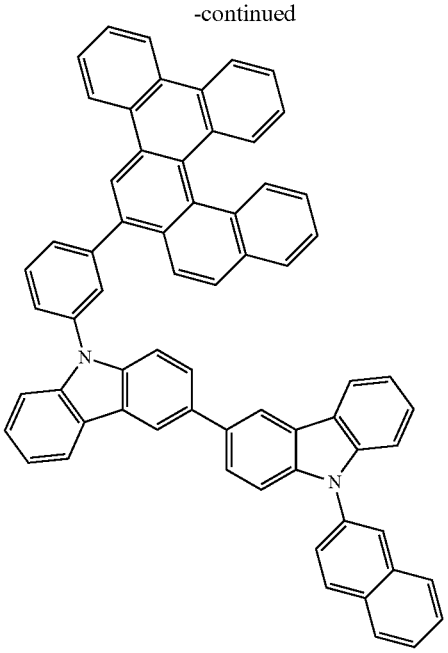
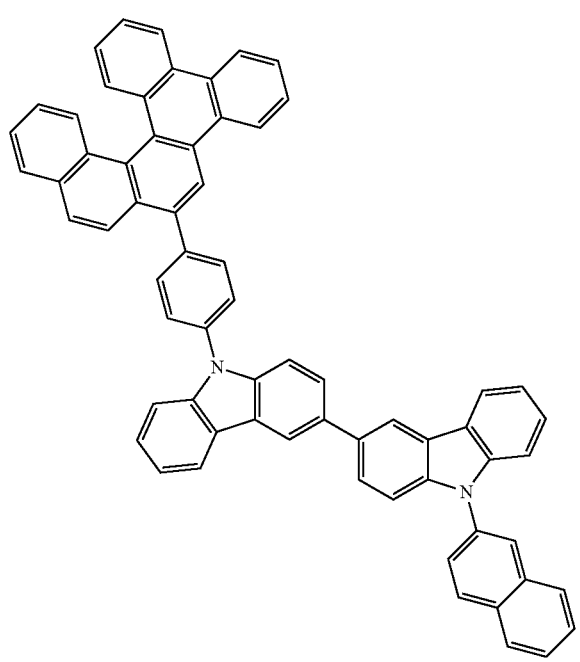
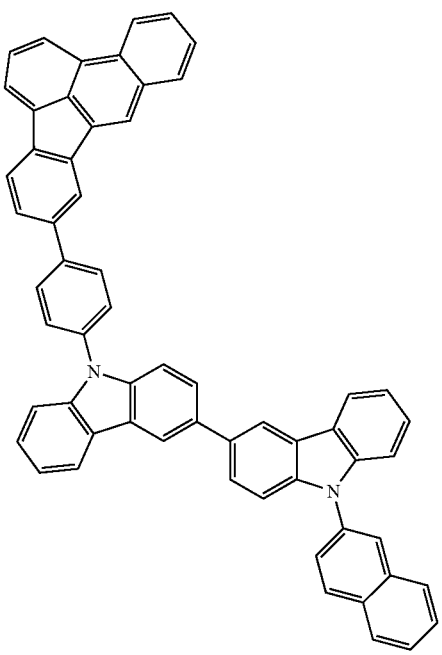

259
-continued
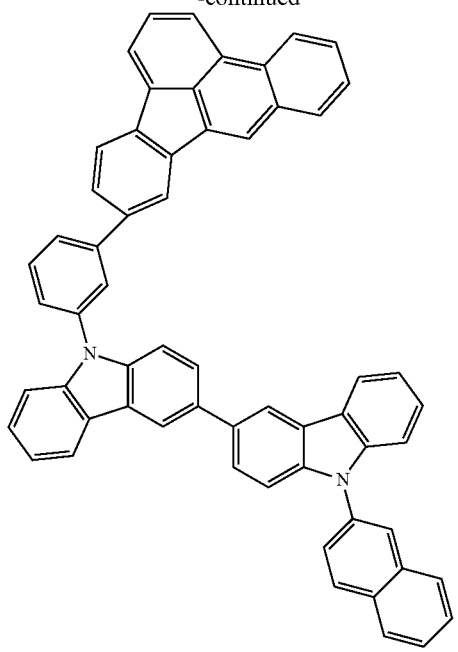
260
-continued
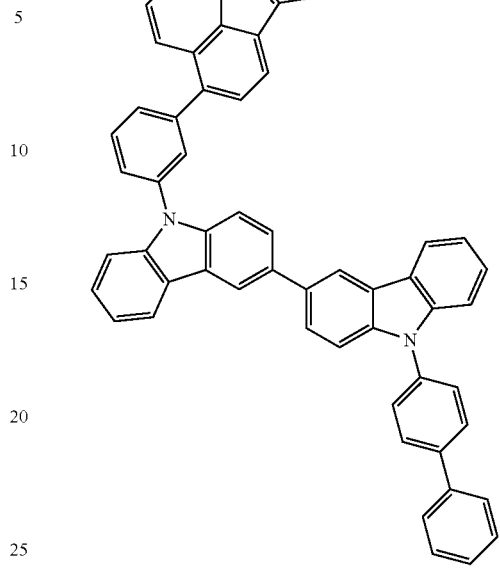
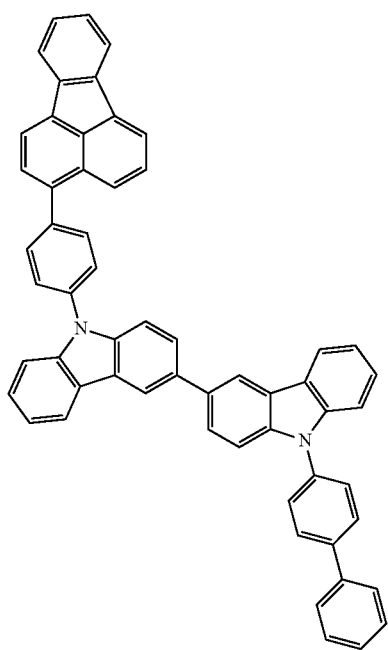
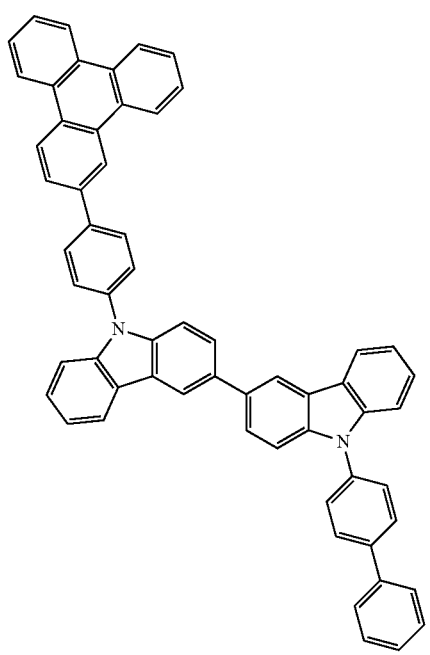

261
-continued
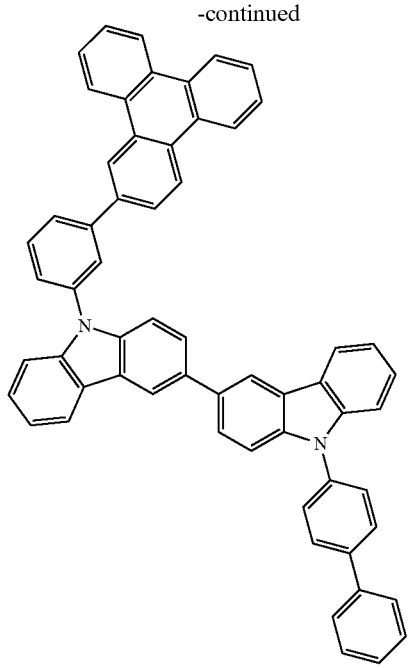
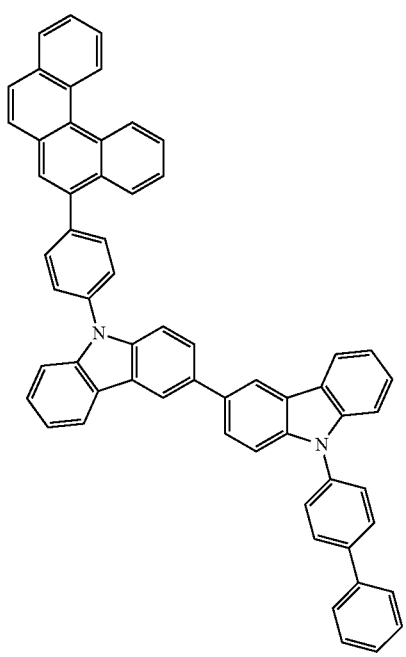
262
-continued
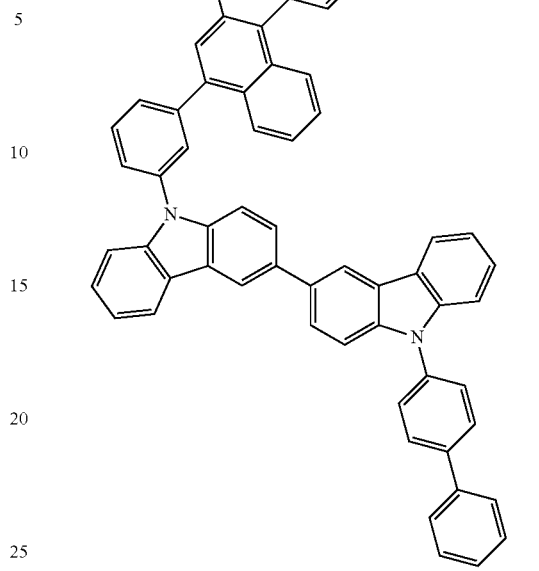
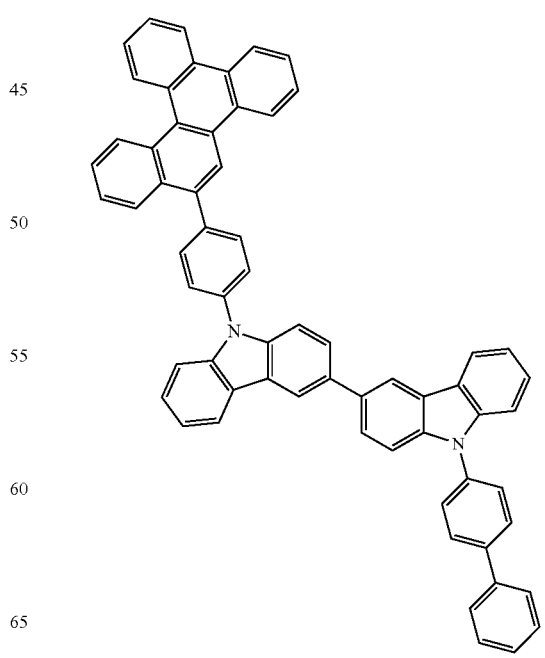

263
-continued
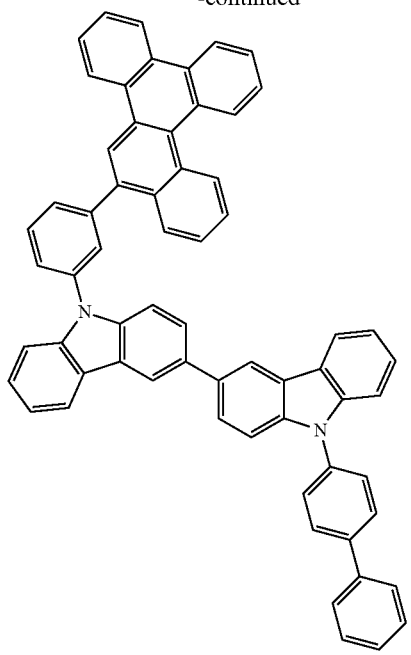
264
-continued
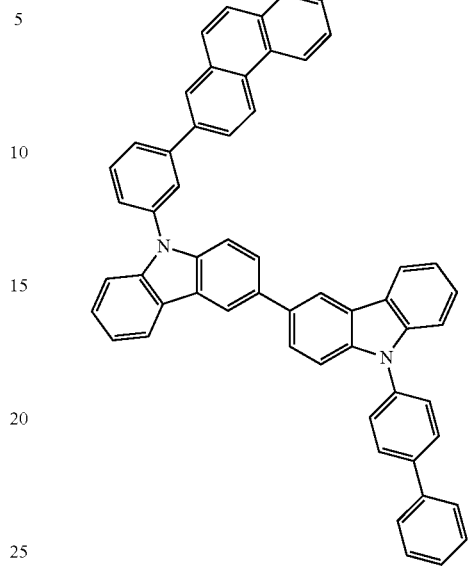
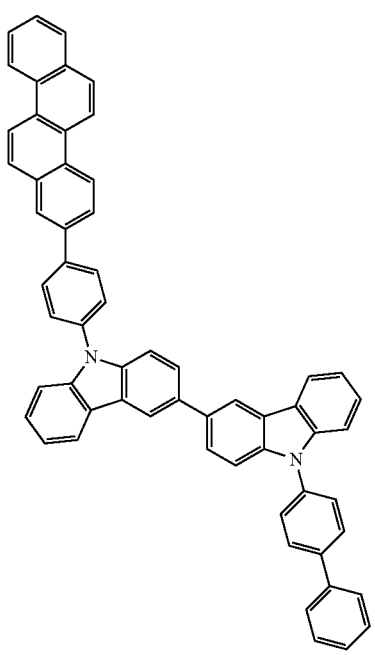
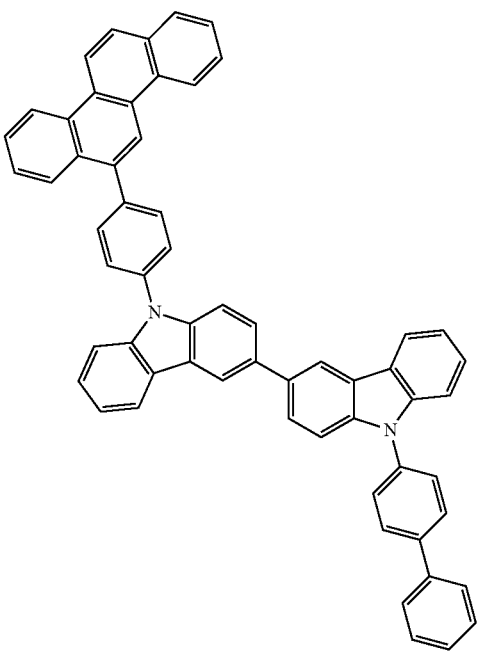

265
-continued
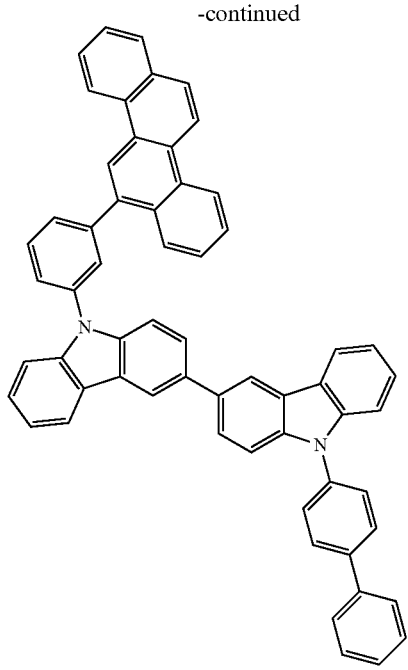
266
-continued
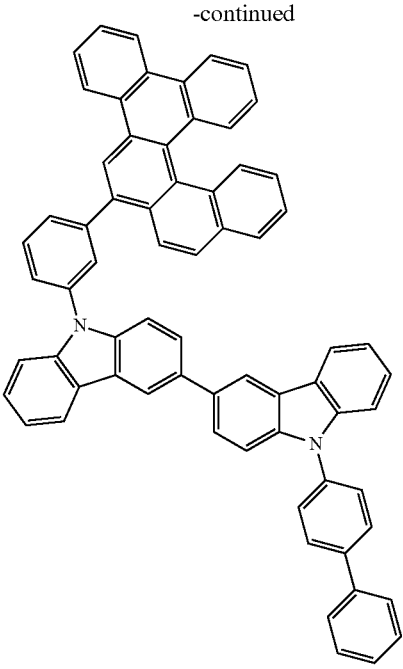
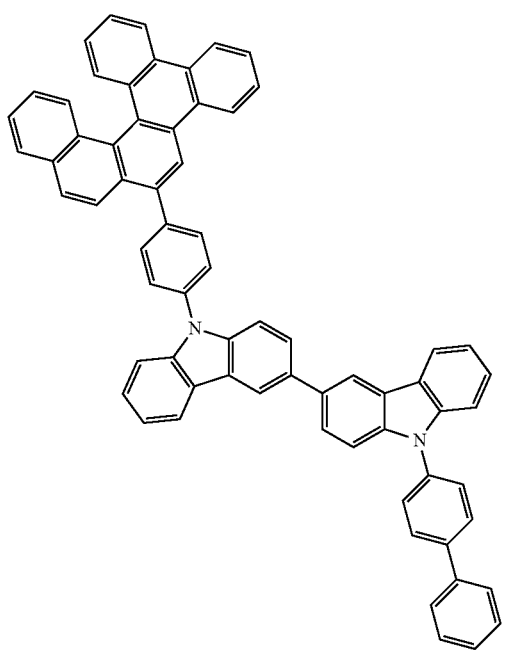
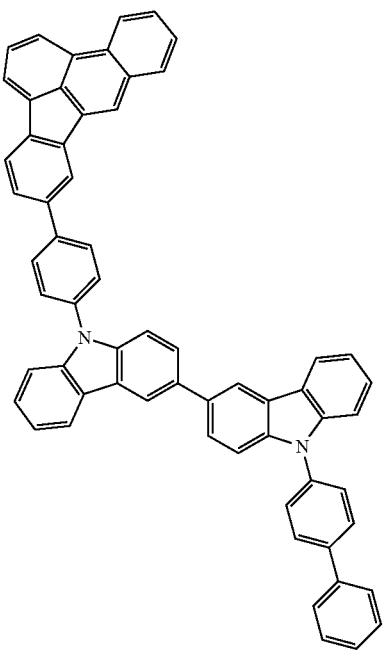

267
-continued
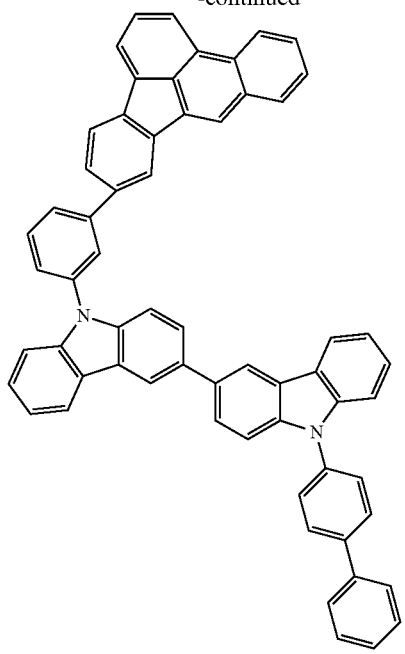
268
-continued
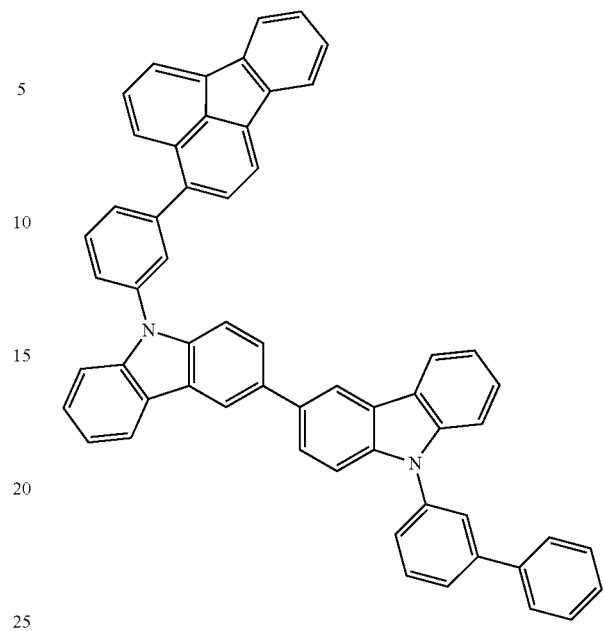
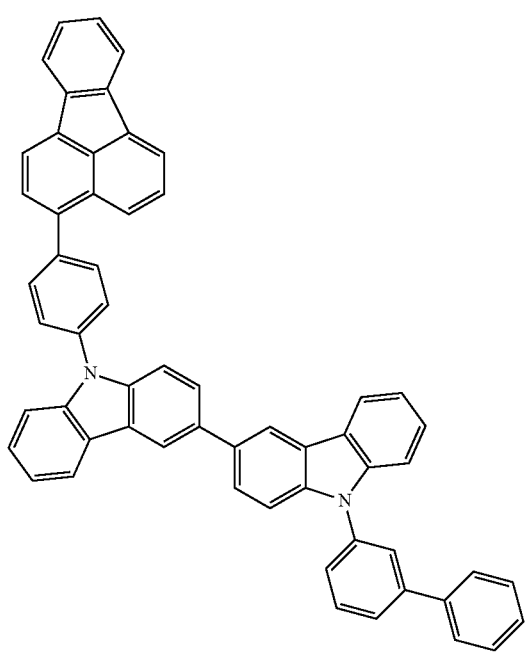

269
-continued
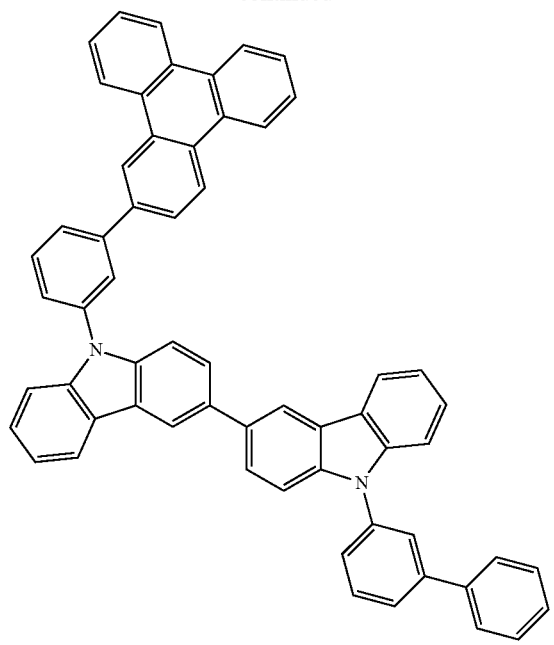
270
-continued
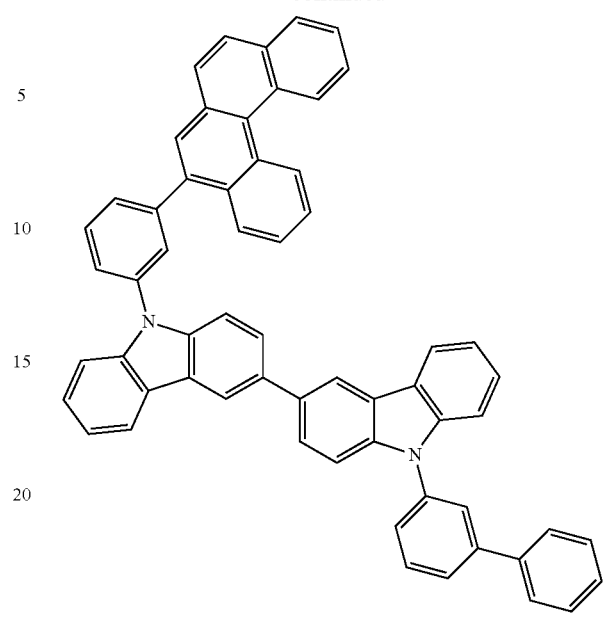
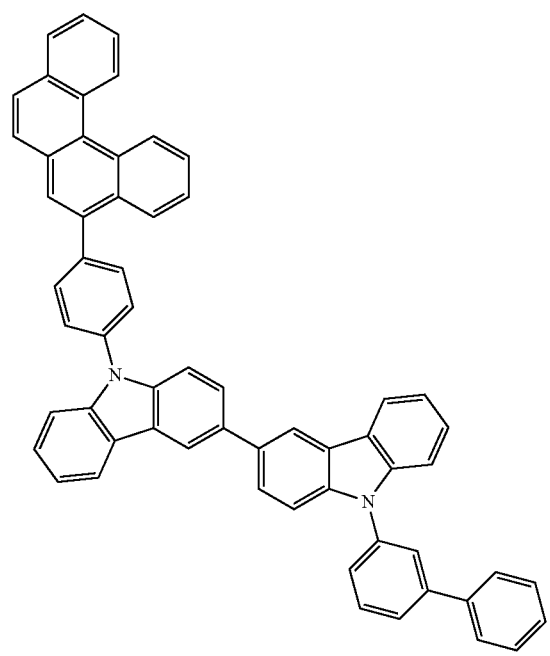
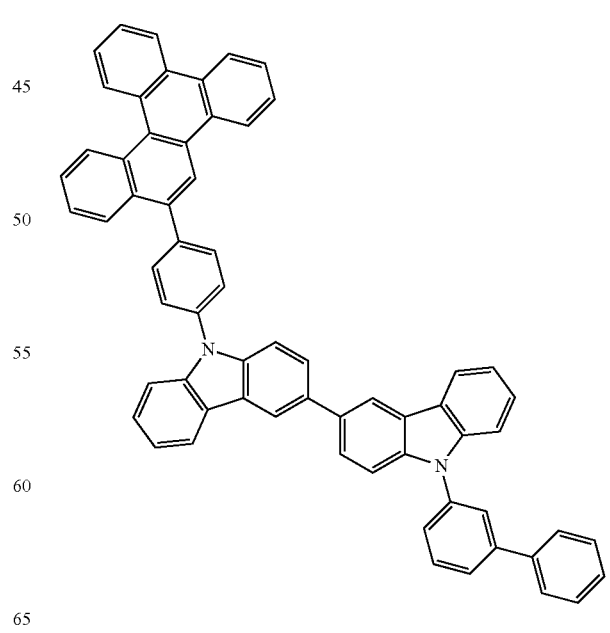

271
-continued
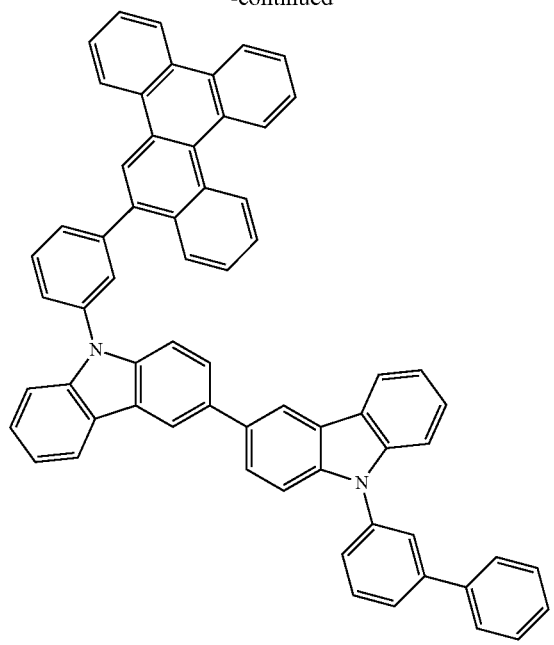
272
-continued
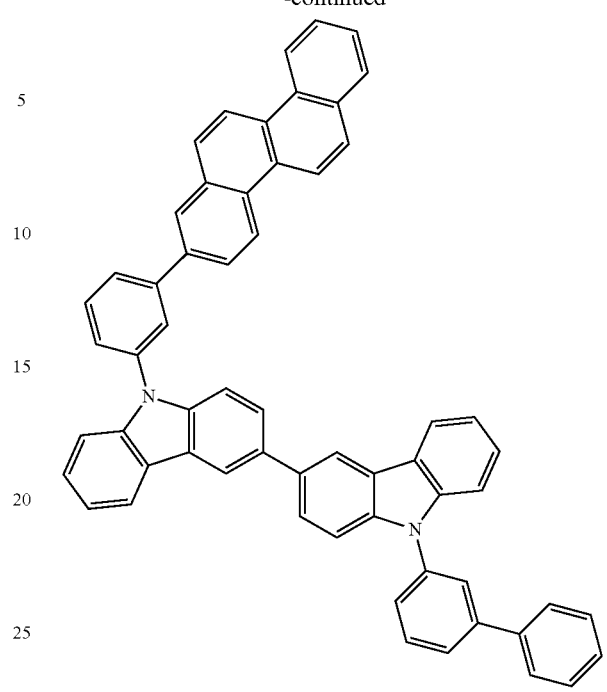
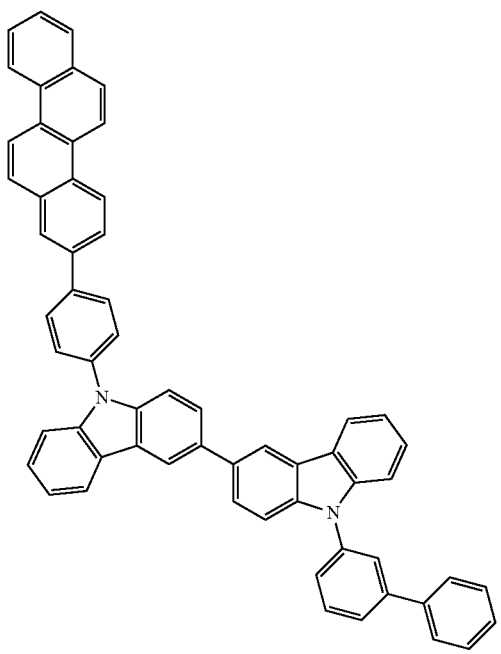
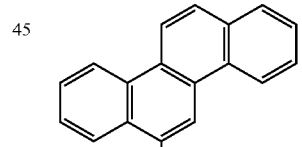
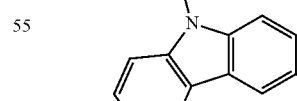

273
-continued
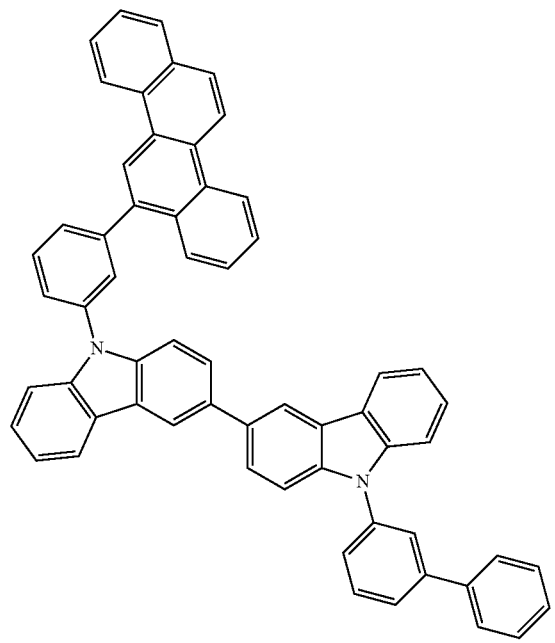
274
-continued
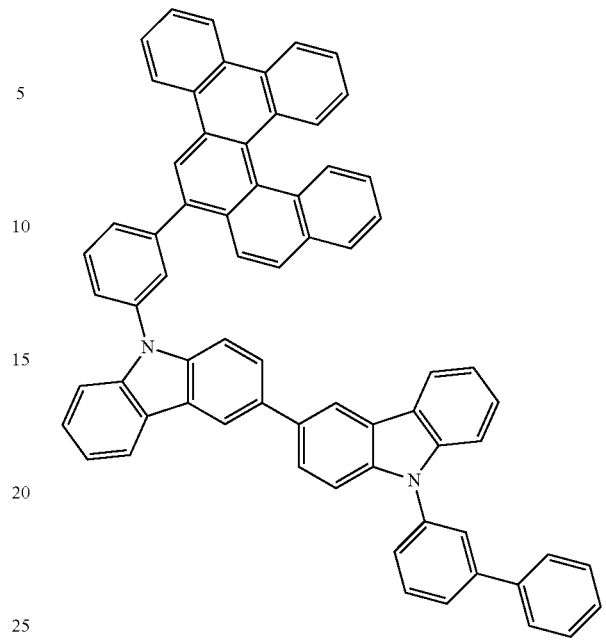
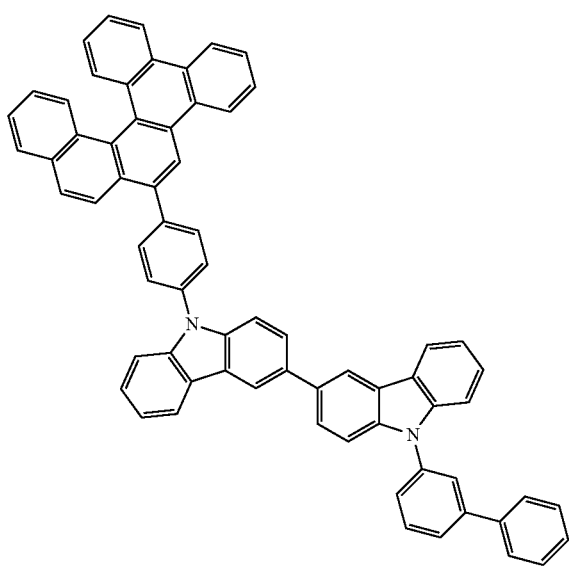
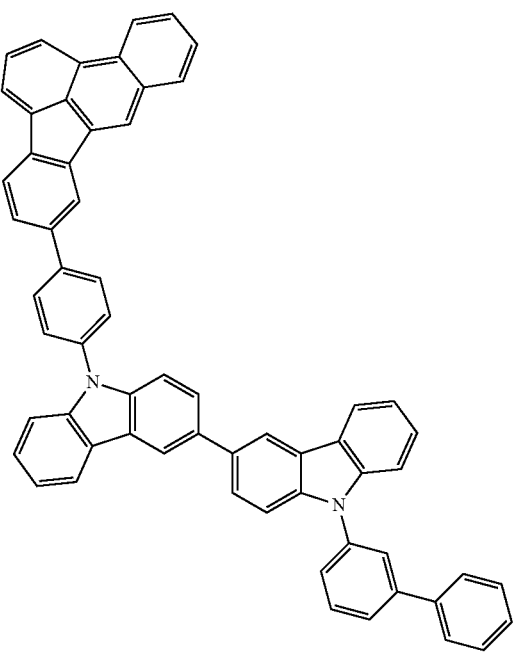

275
-continued
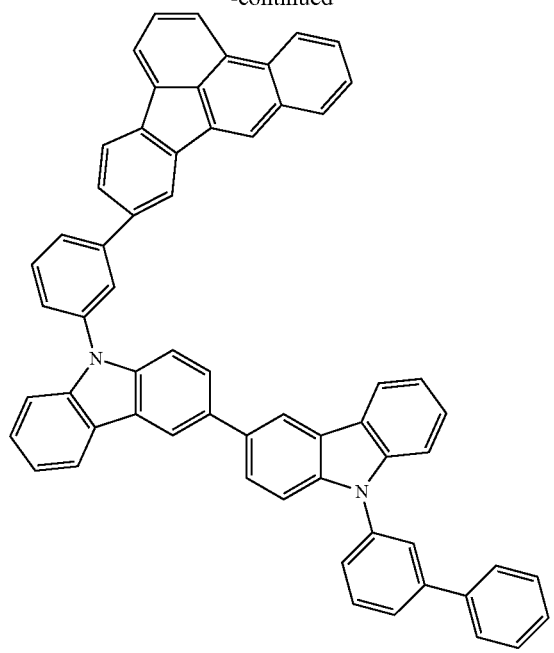
276
-continued
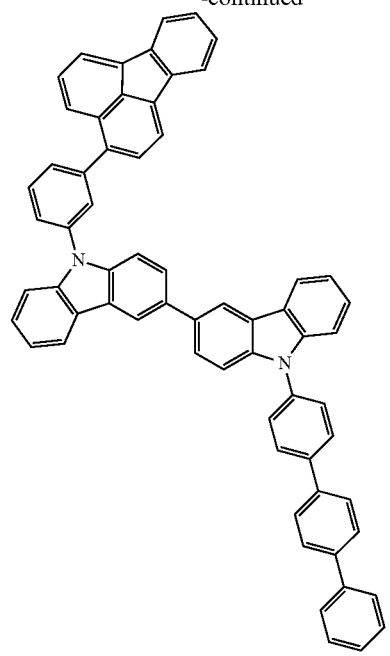
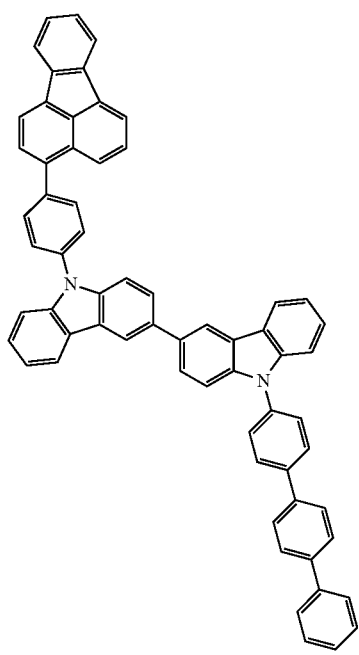
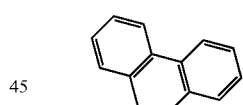

277
-continued
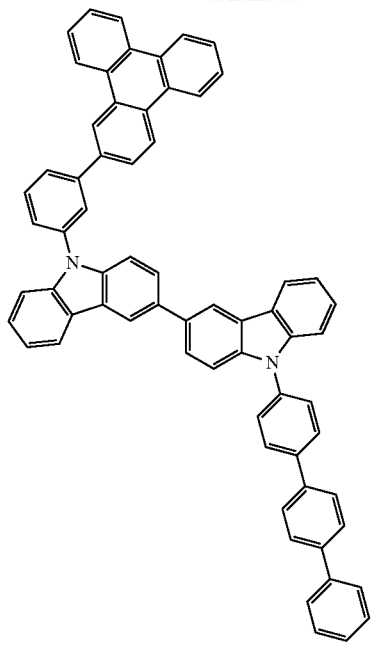
278
-continued
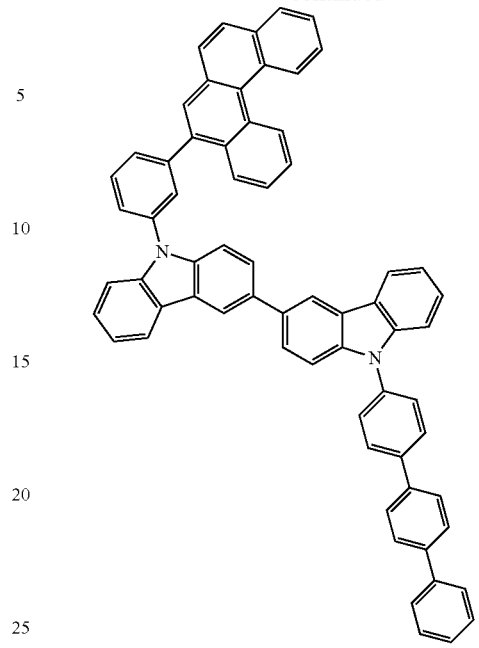
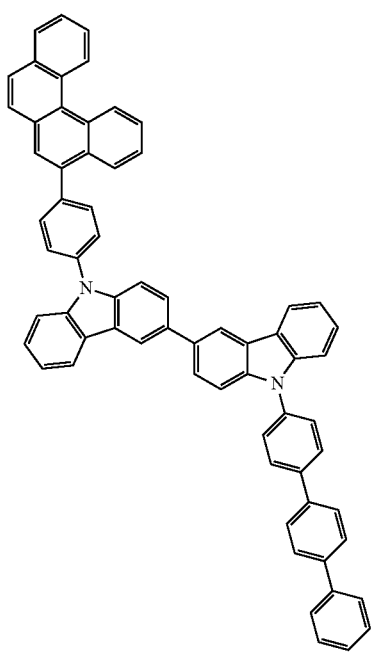
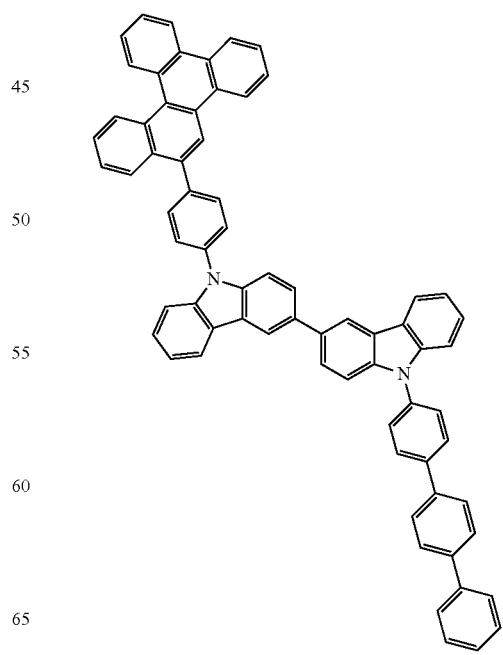

279
-continued
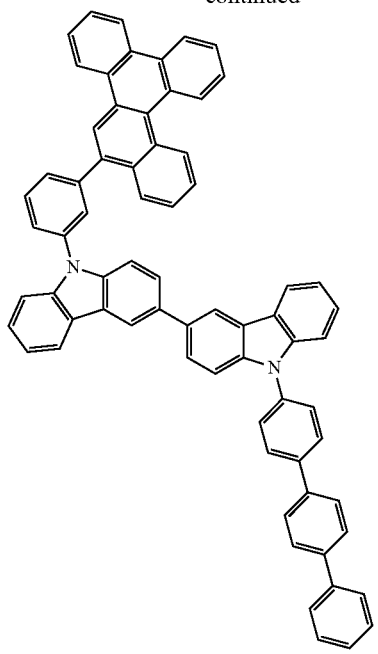
280
-continued
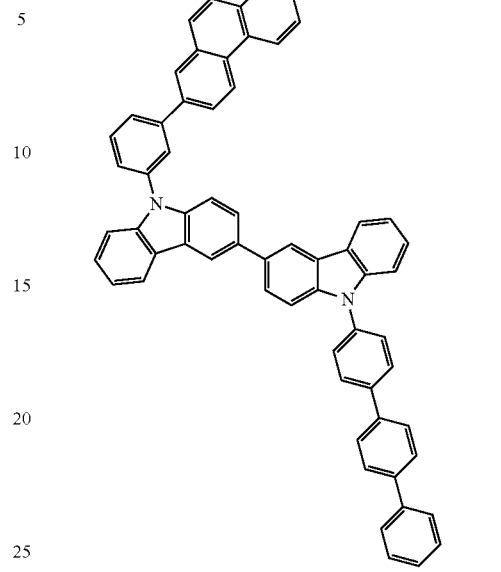
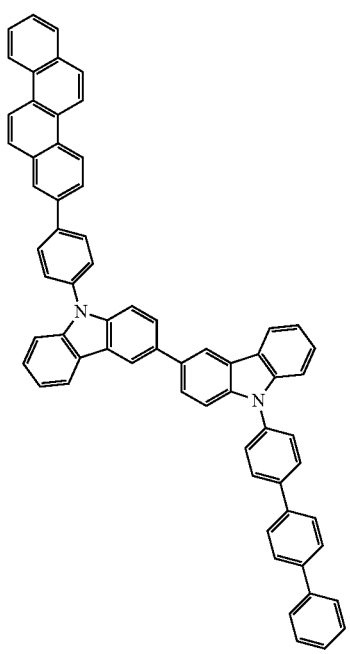
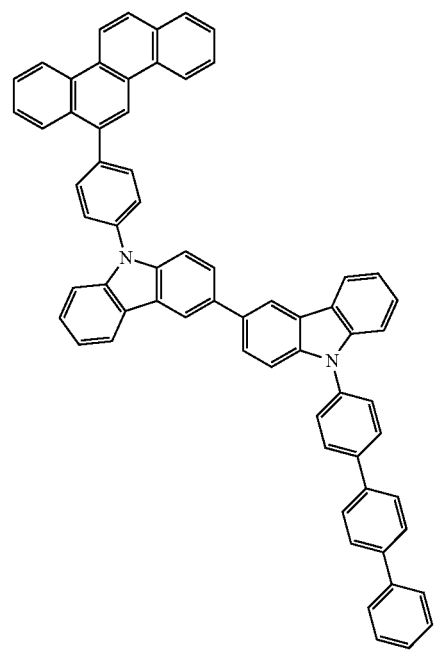

281
-continued
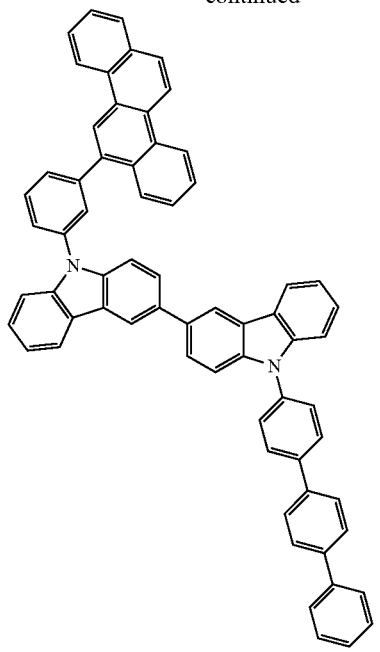
282
-continued
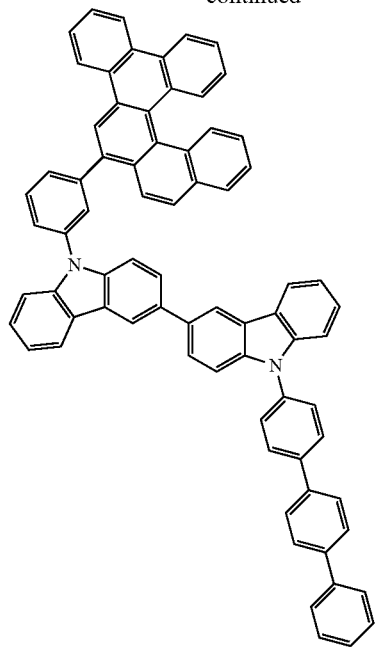
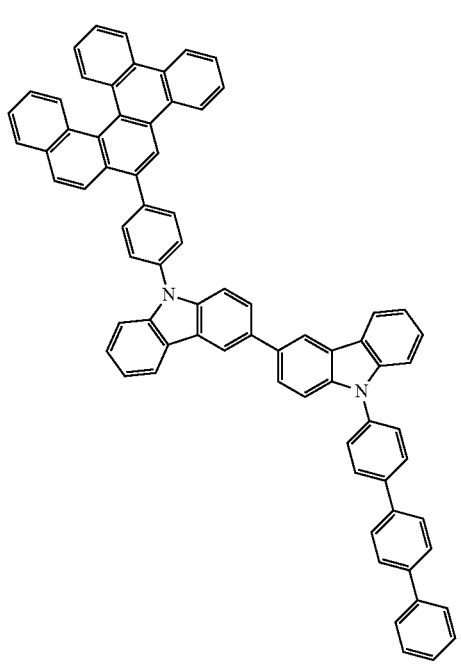
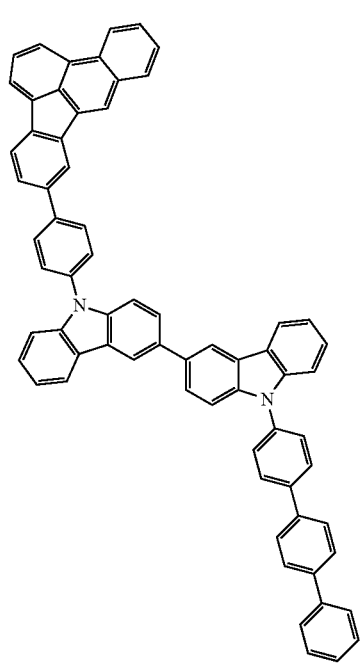

283
-continued
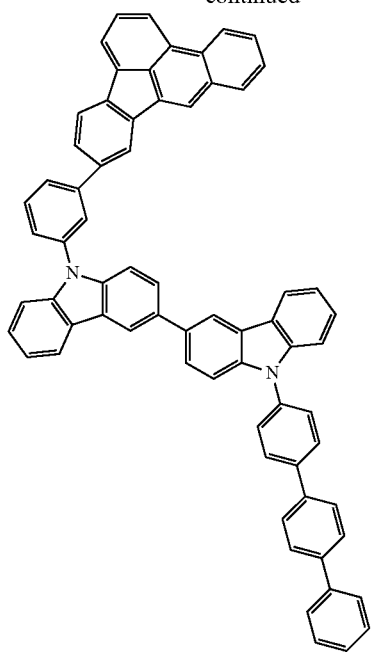
284
-continued
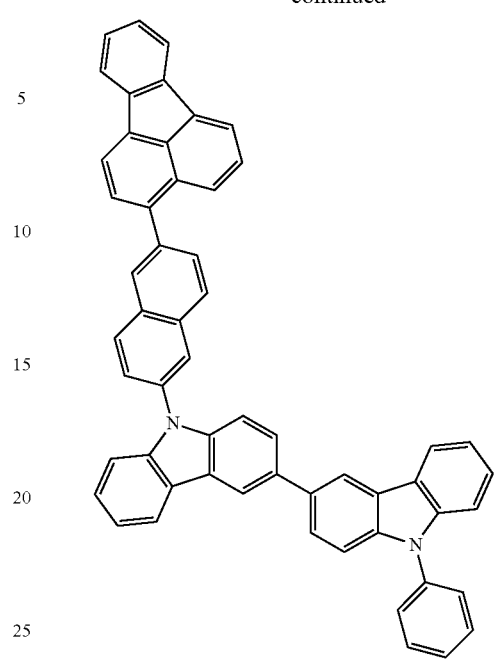
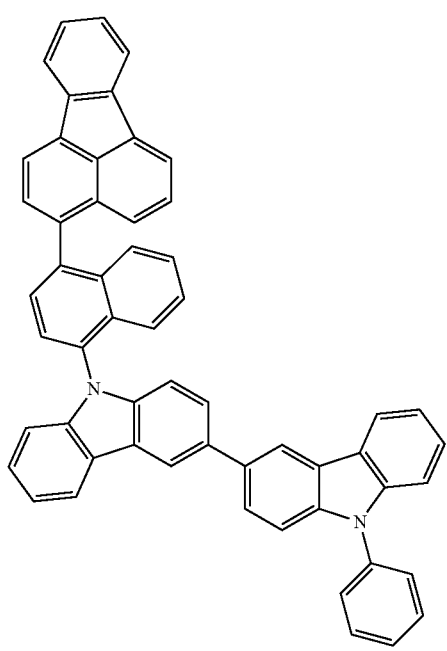
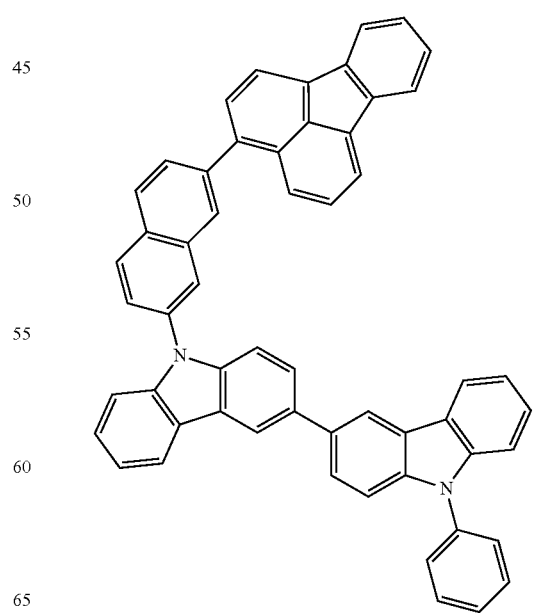

285
-continued
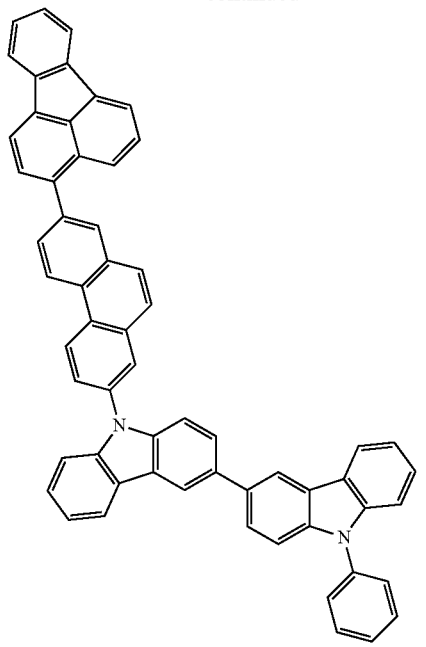
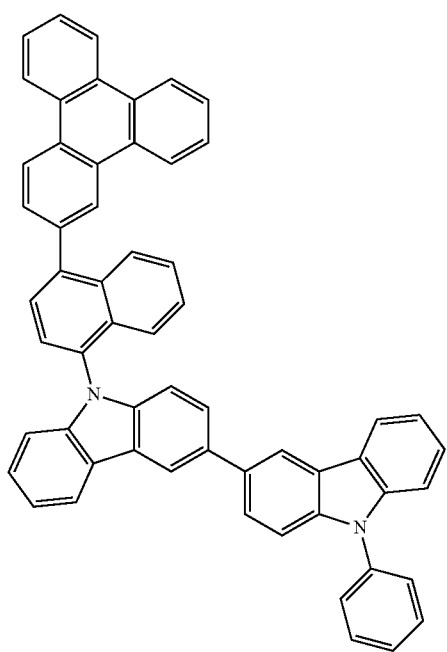
286
-continued
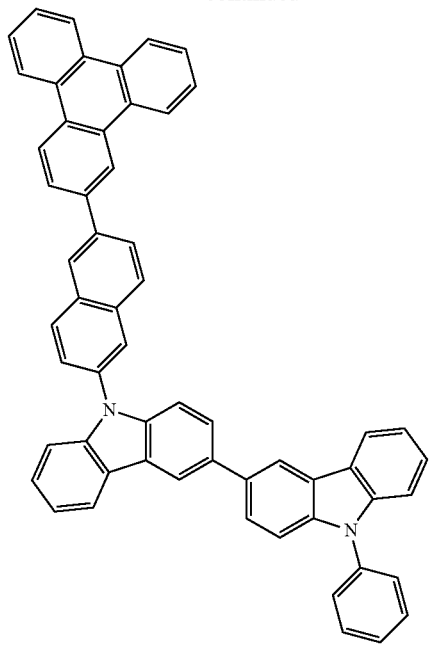
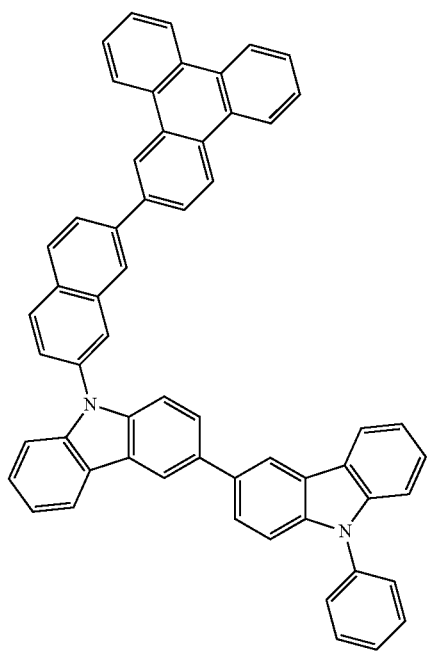

287
-continued
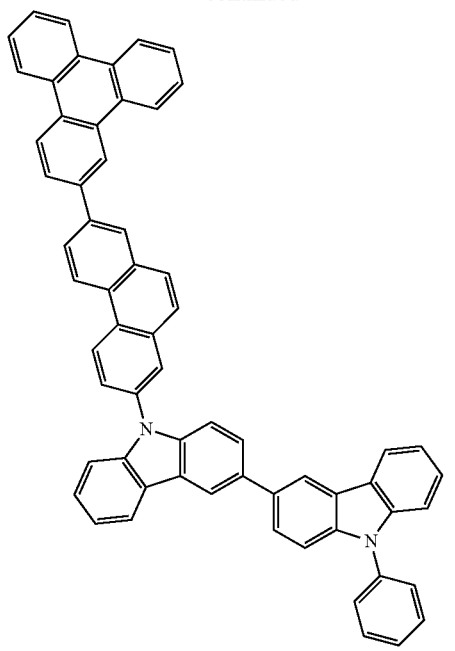
288
-continued
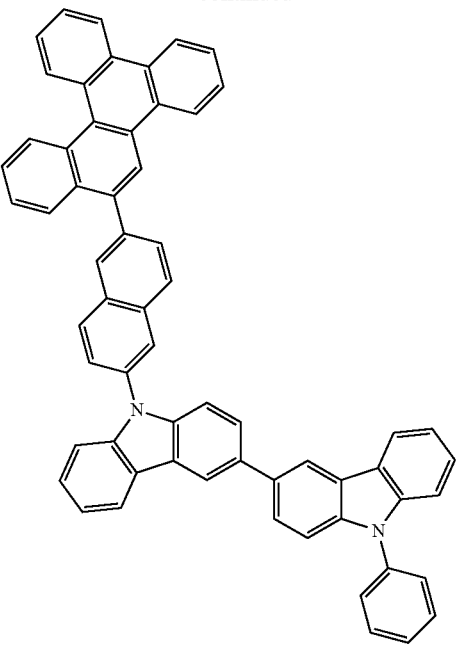
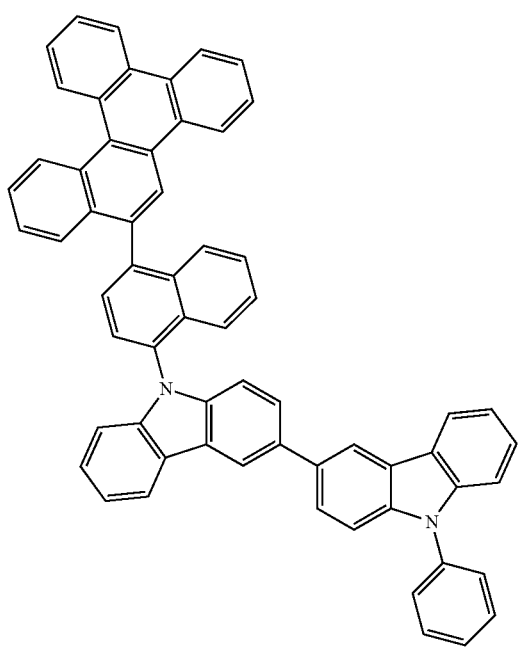
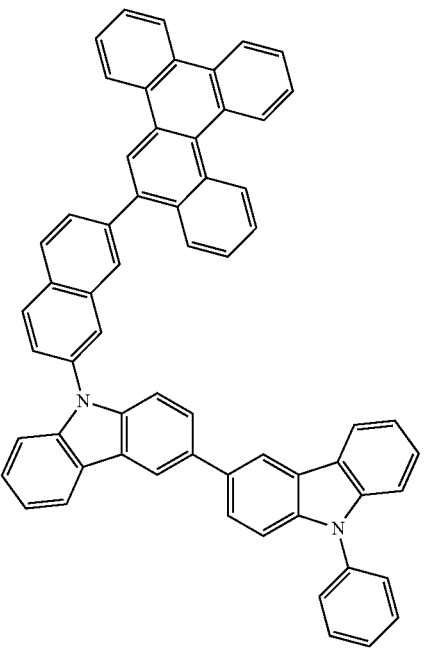

289

290

291
-continued
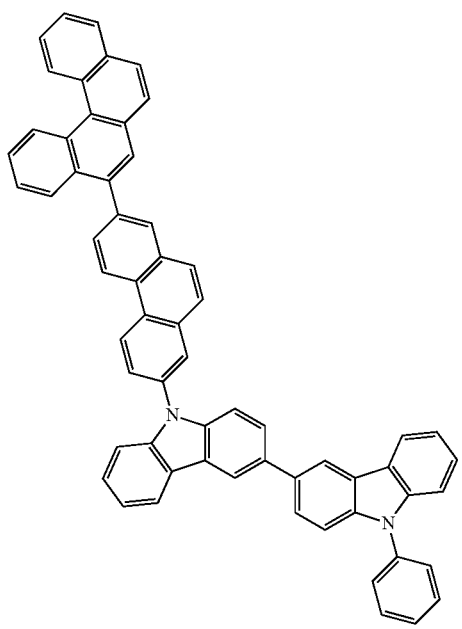
292
-continued
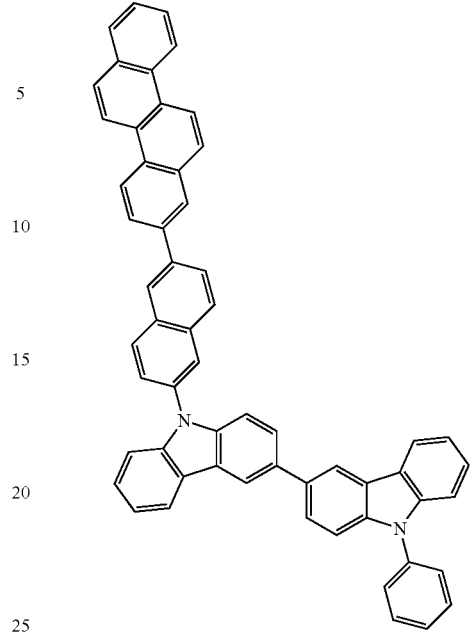
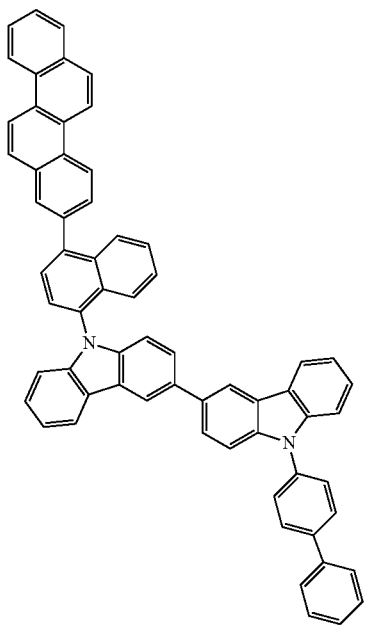
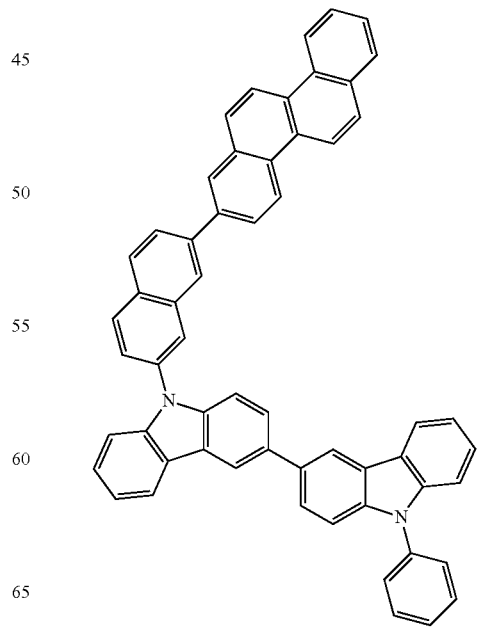

293
-continued
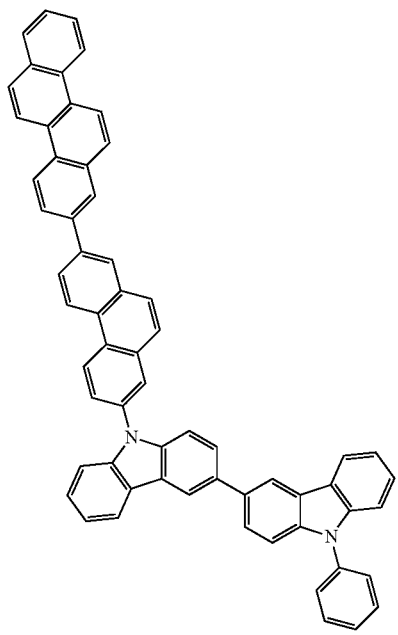
294
-continued
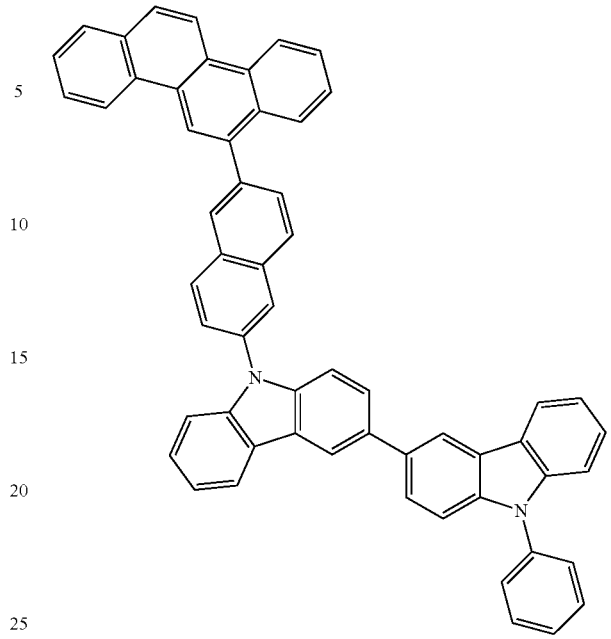
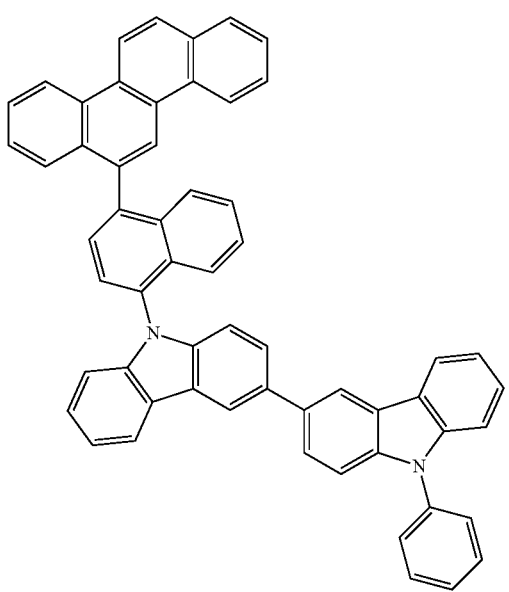
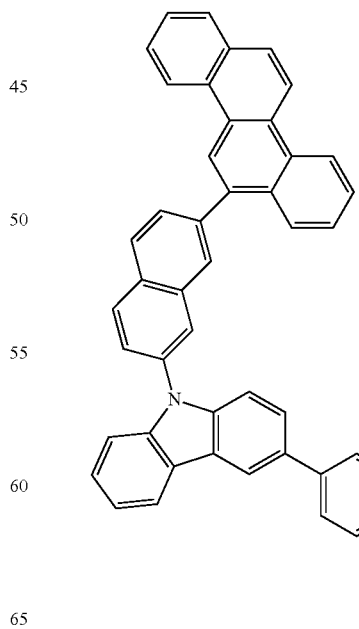

295
-continued
296
-continued
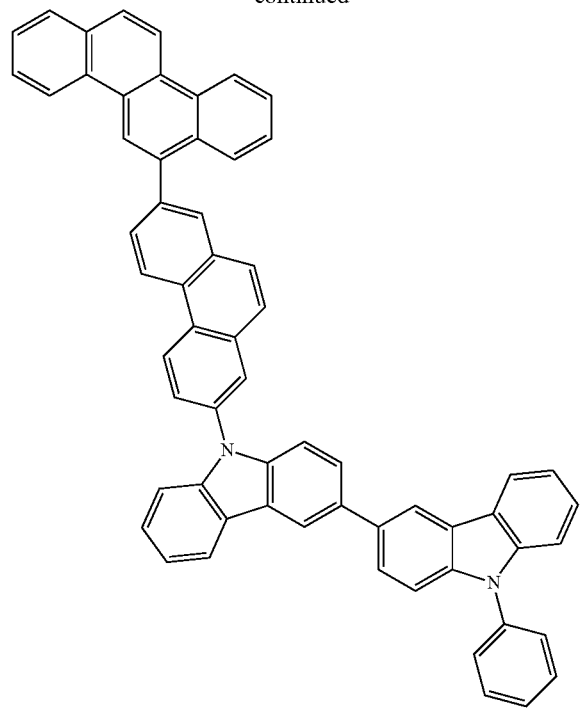
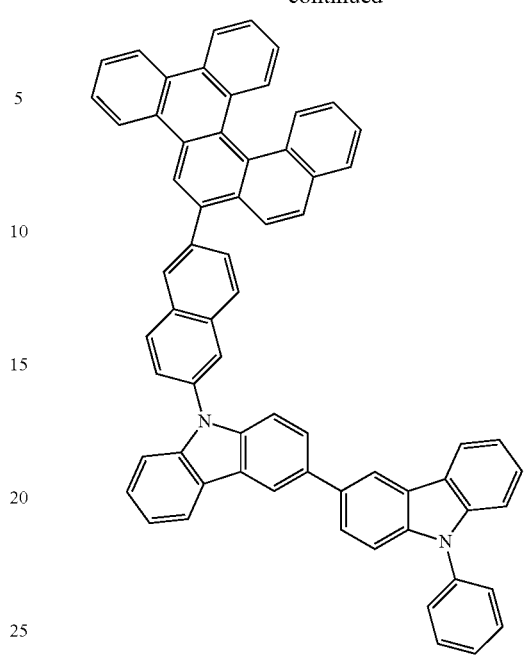
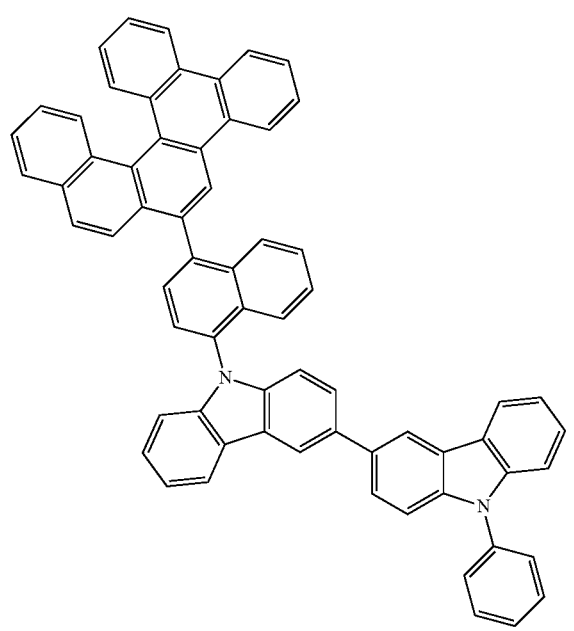
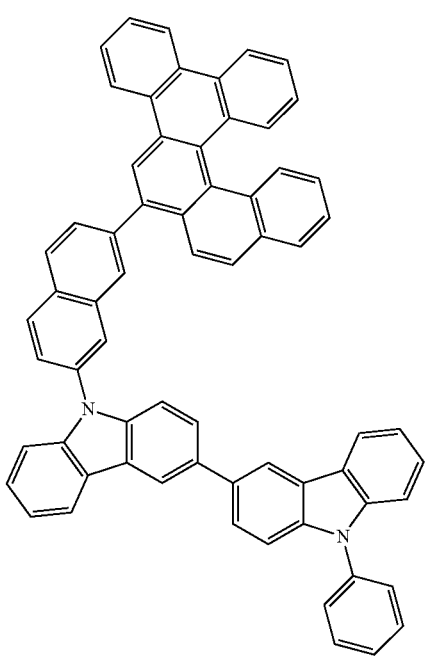

297
-continued
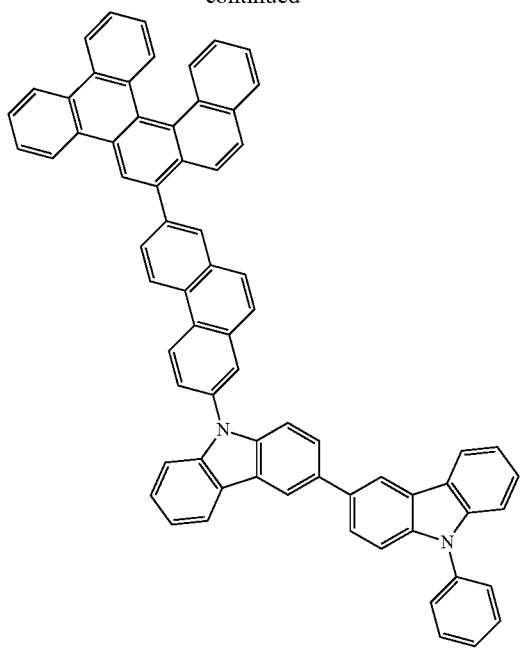
298
-continued
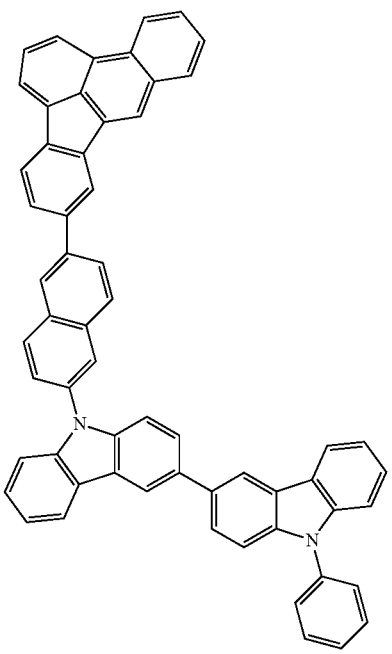
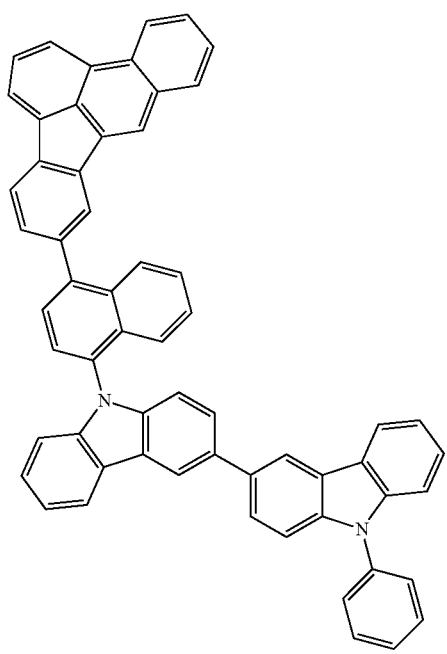
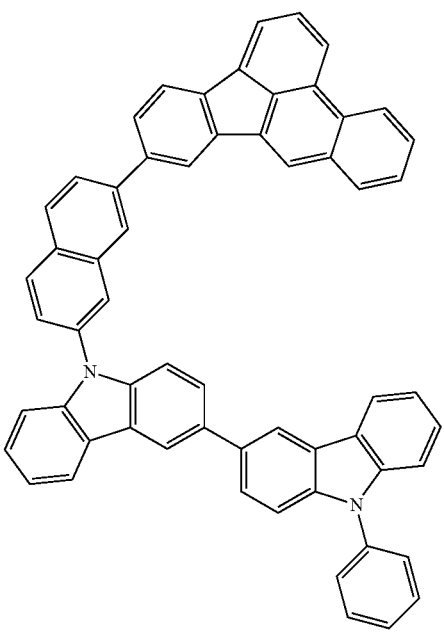

299
-continued
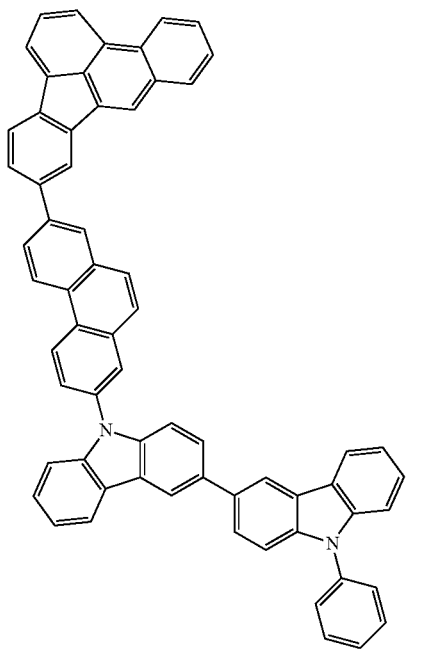
300
-continued
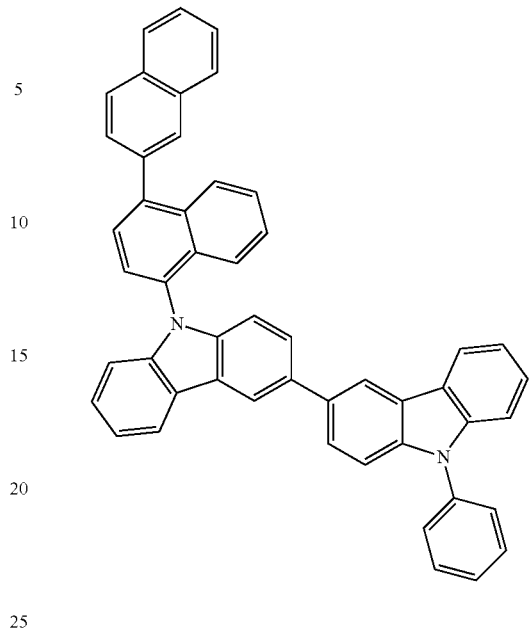
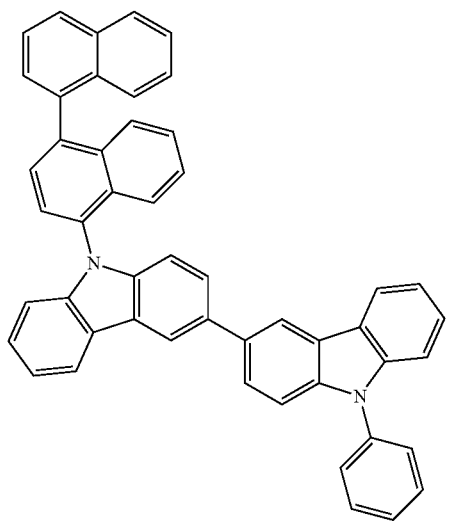
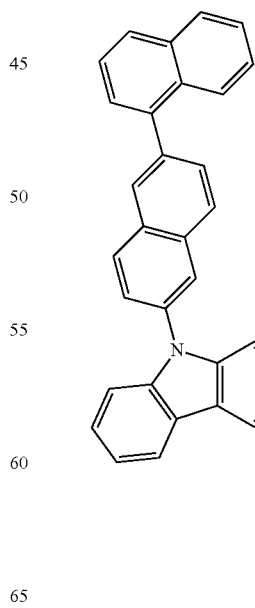

301
-continued
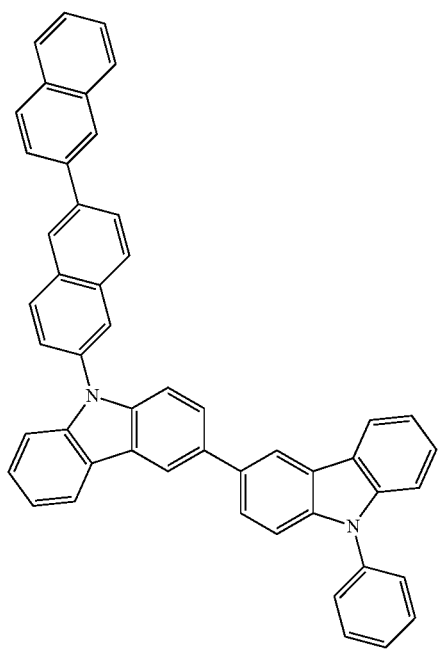
302
-continued
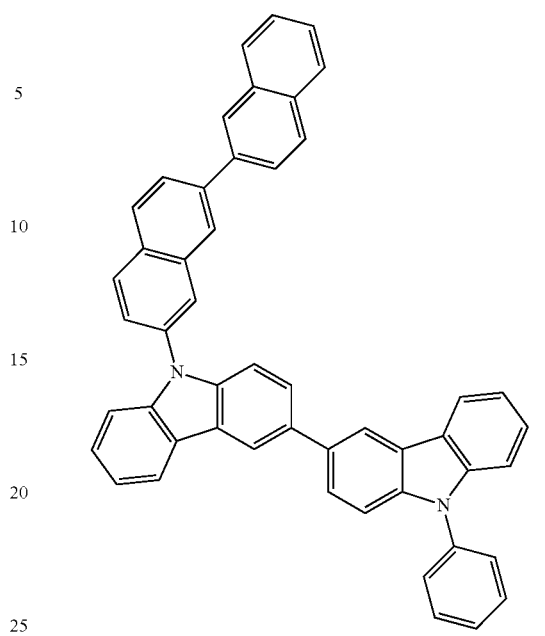
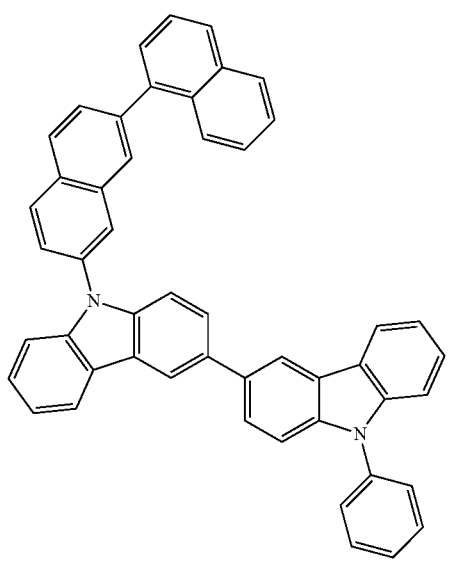

303
-continued
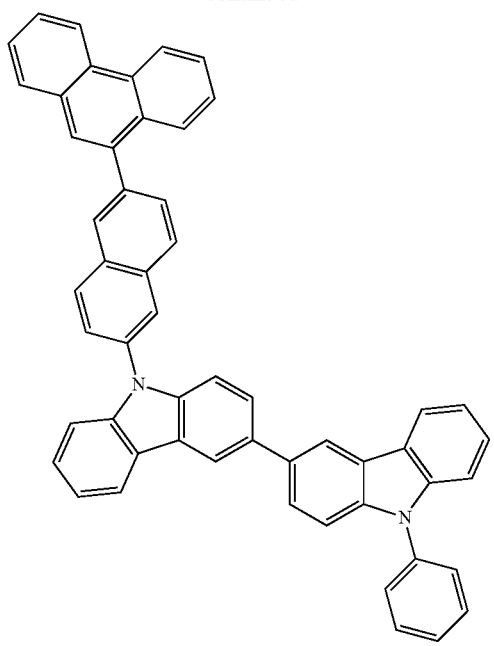
304
-continued
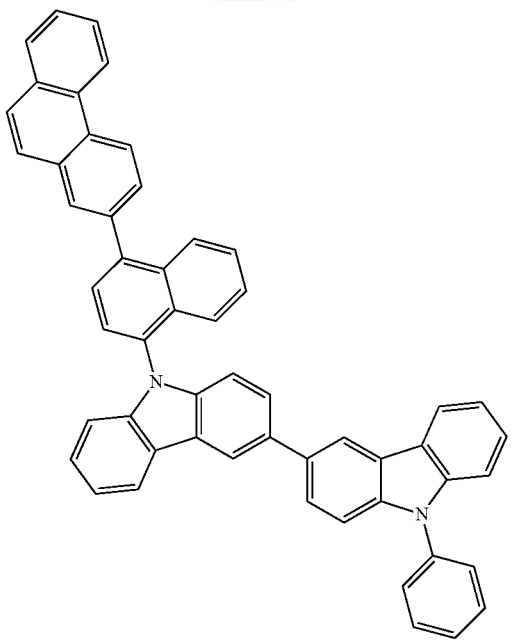
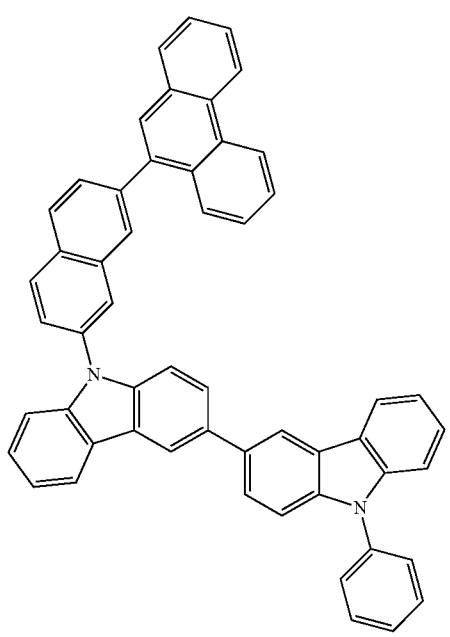
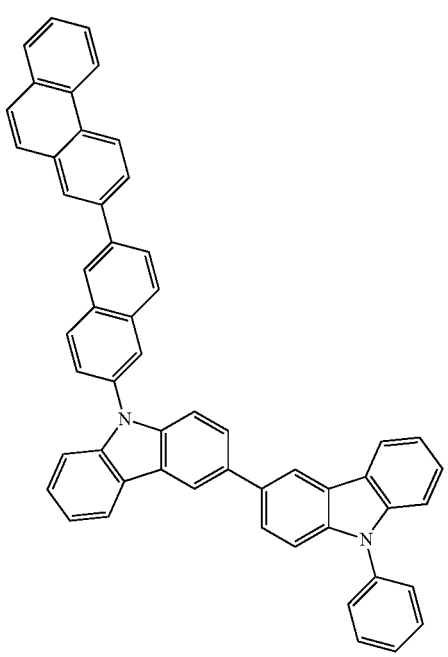

305
-continued
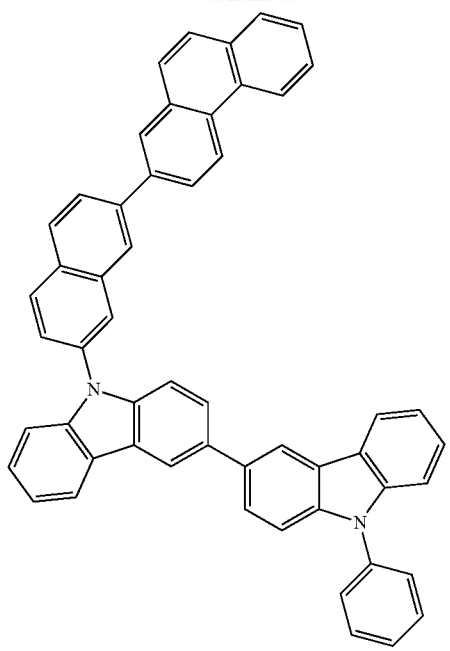
306
-continued
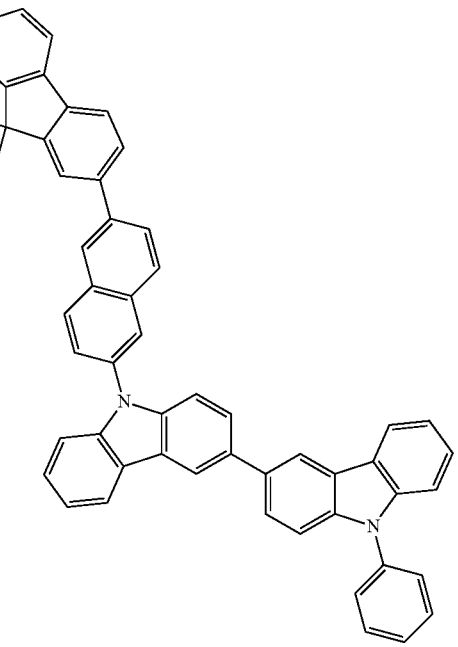
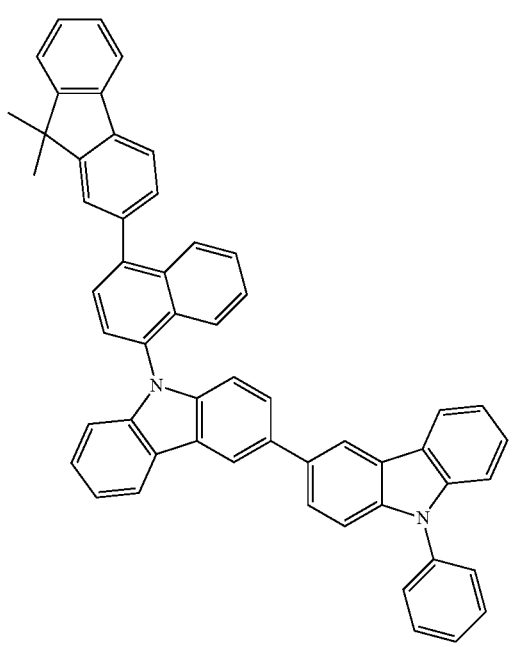
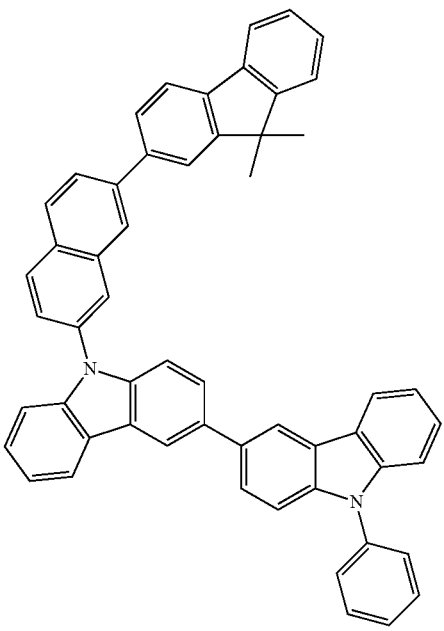

307
-continued
308
-continued
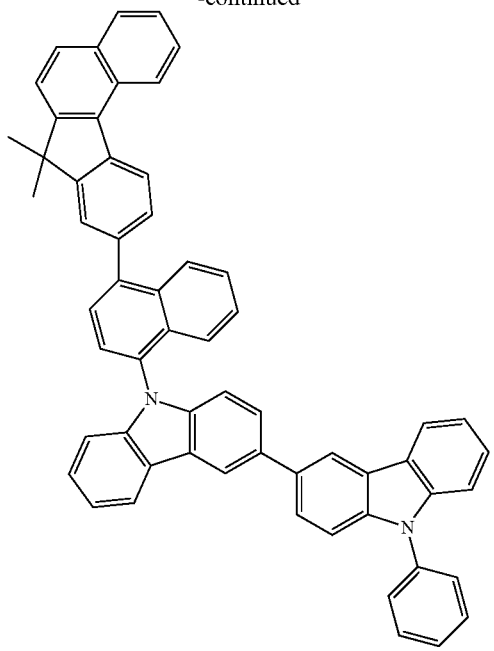
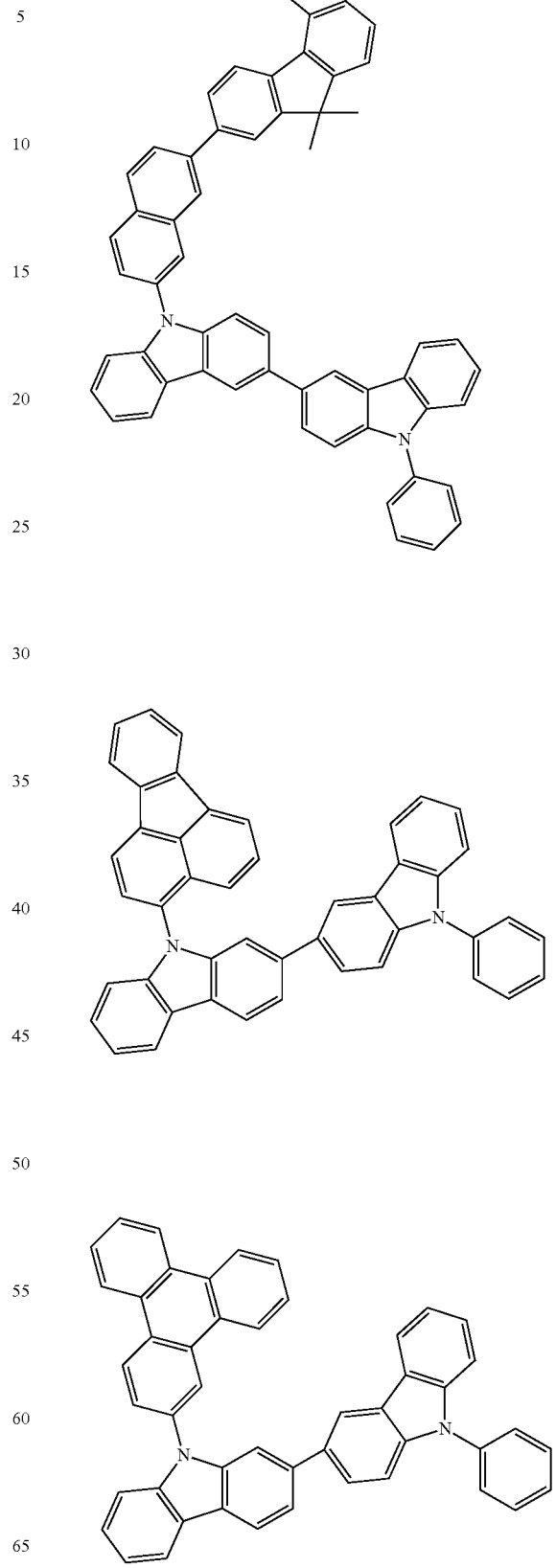

309
-continued
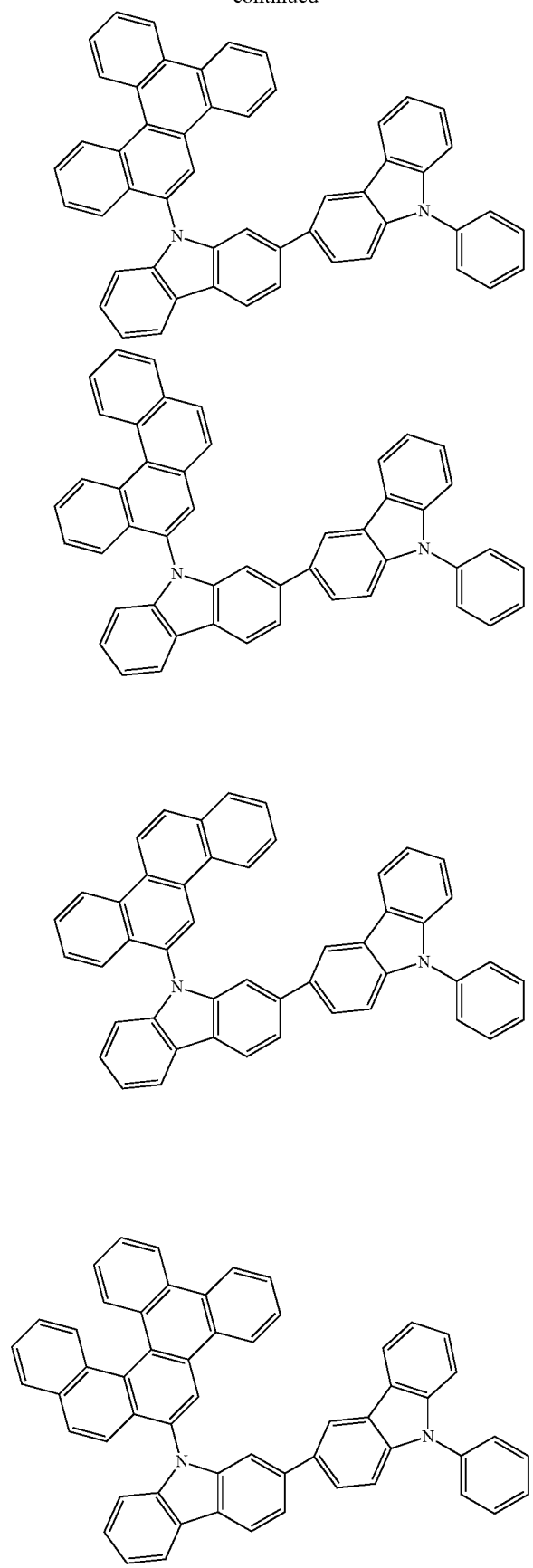
310
-continued
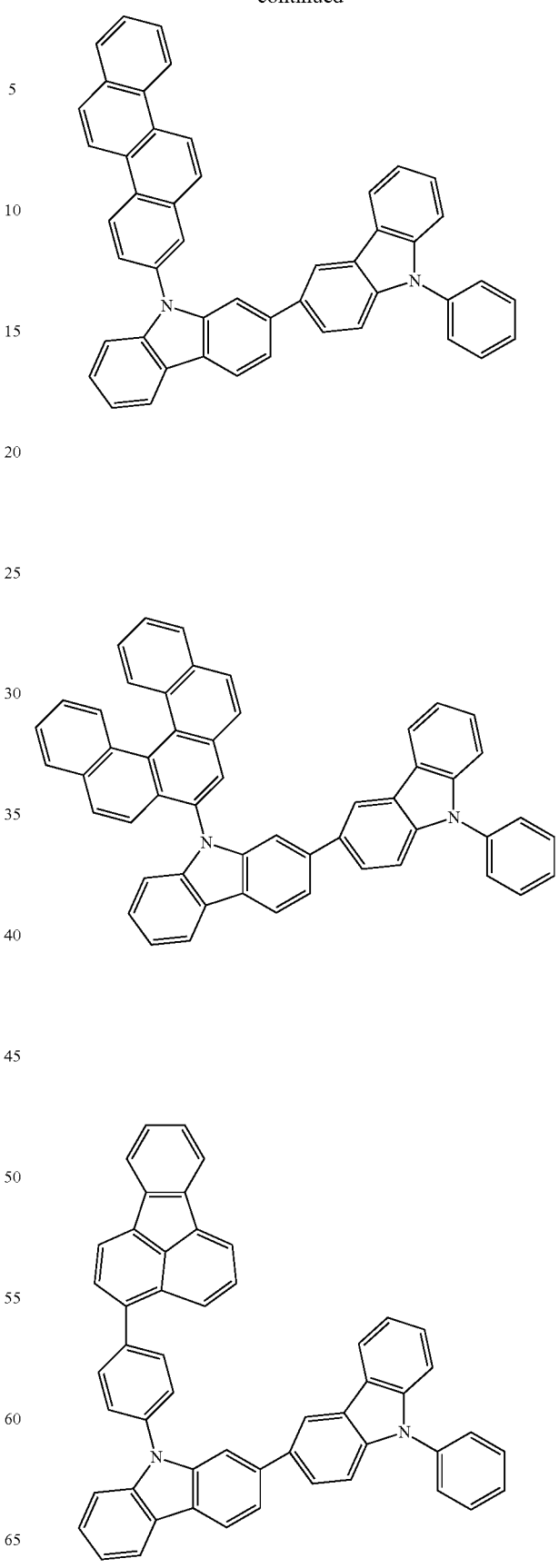

311
-continued
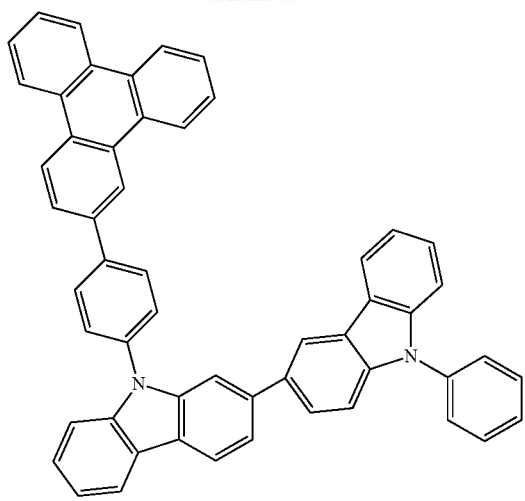
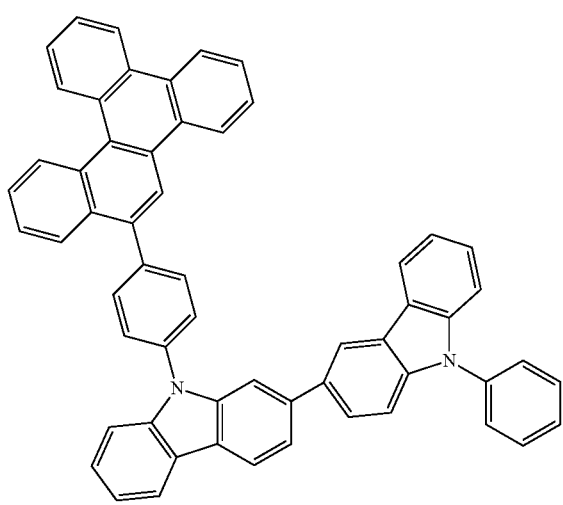
312
-continued
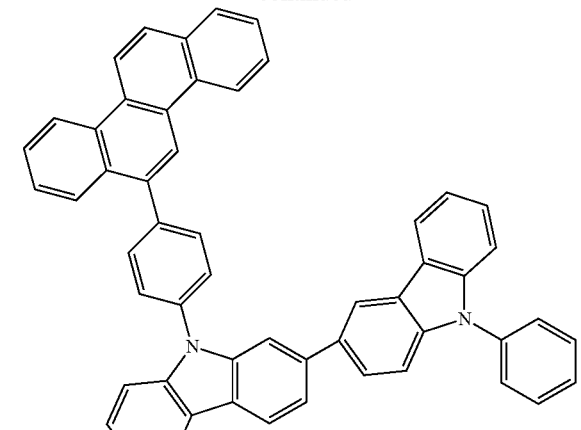
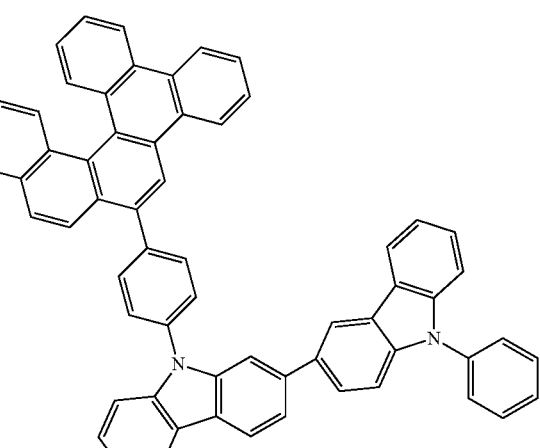
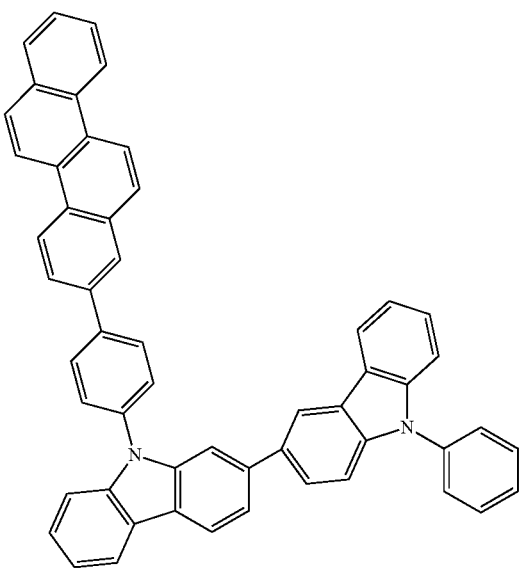

313
-continued
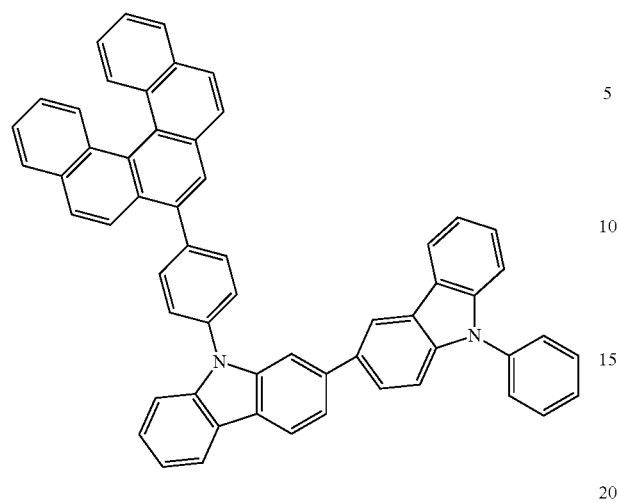
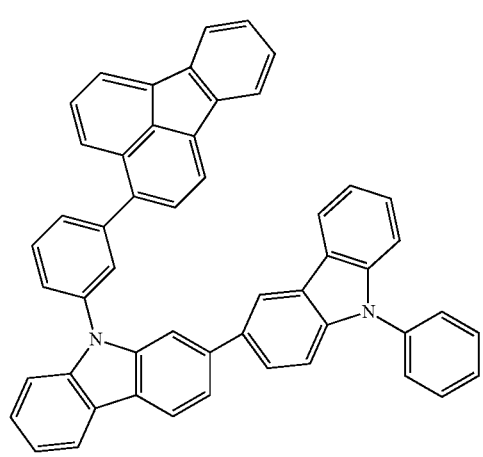
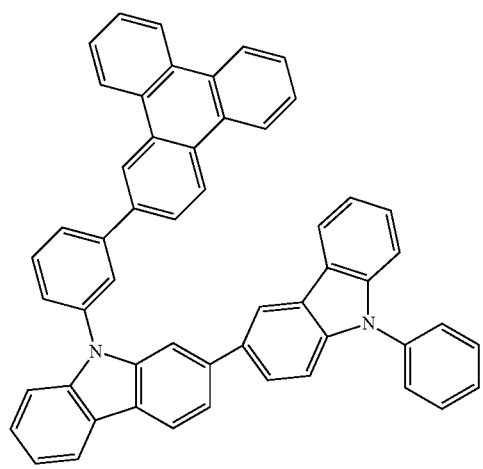
314
-continued
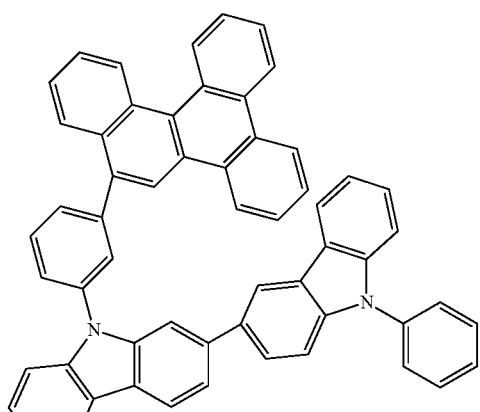
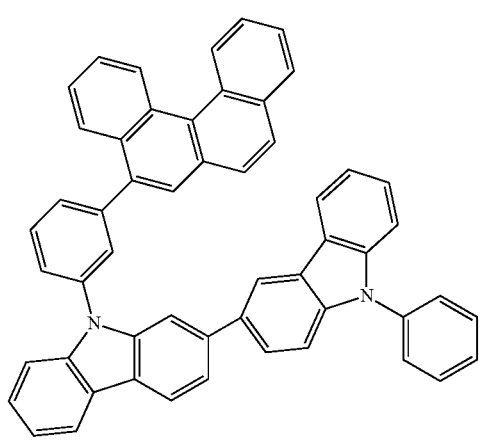

315
-continued
316
-continued
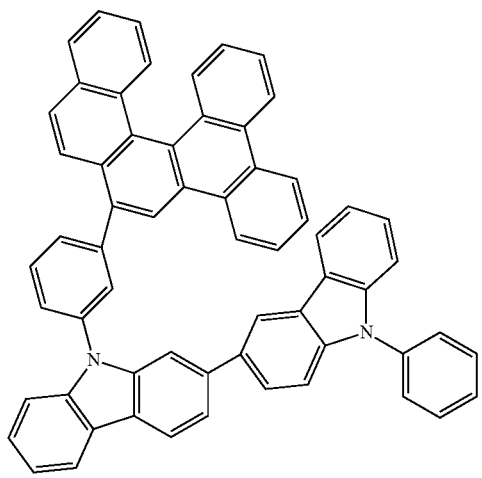
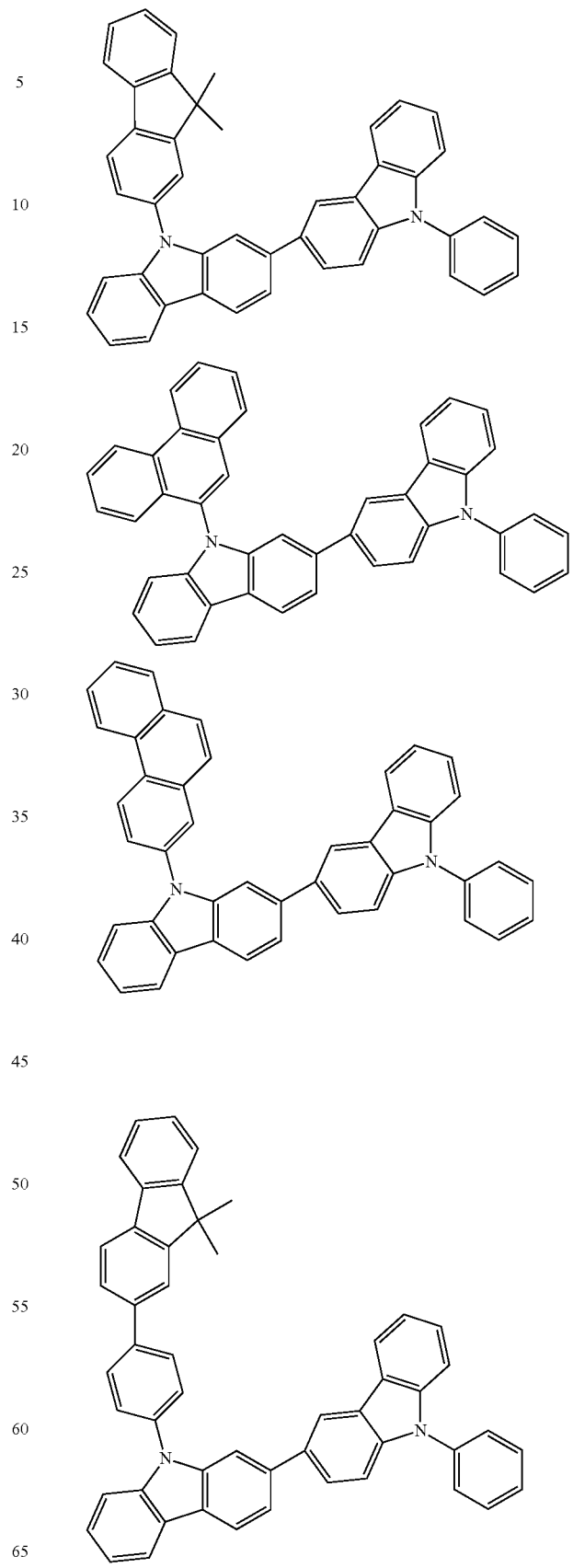

317
-continued
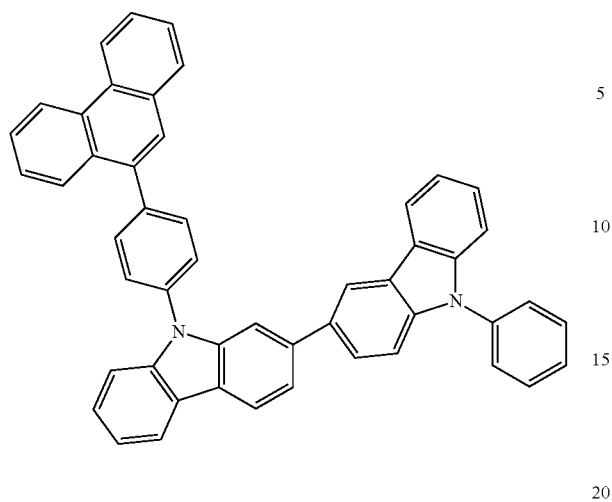
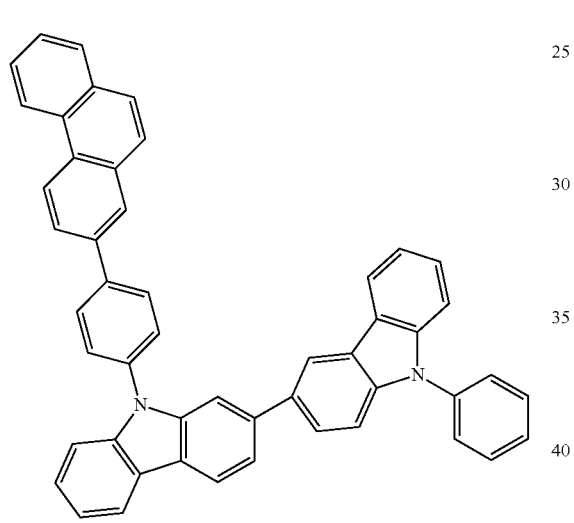
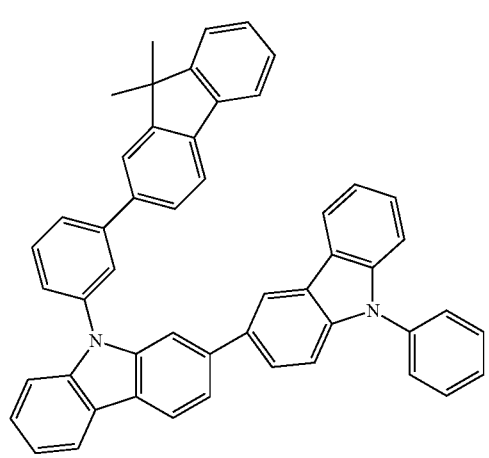
318
-continued
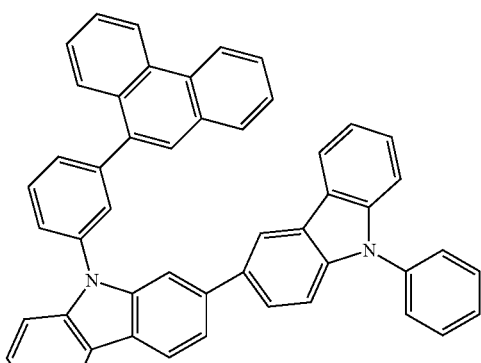
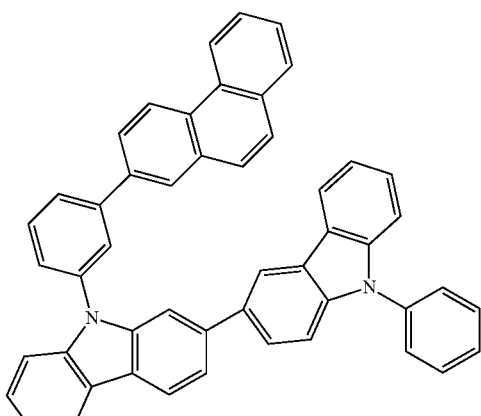
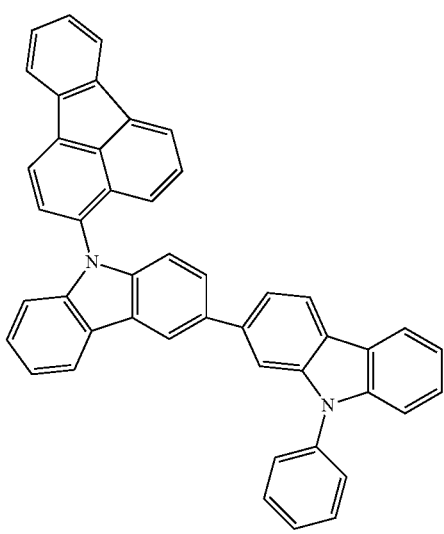

319
-continued
320
-continued
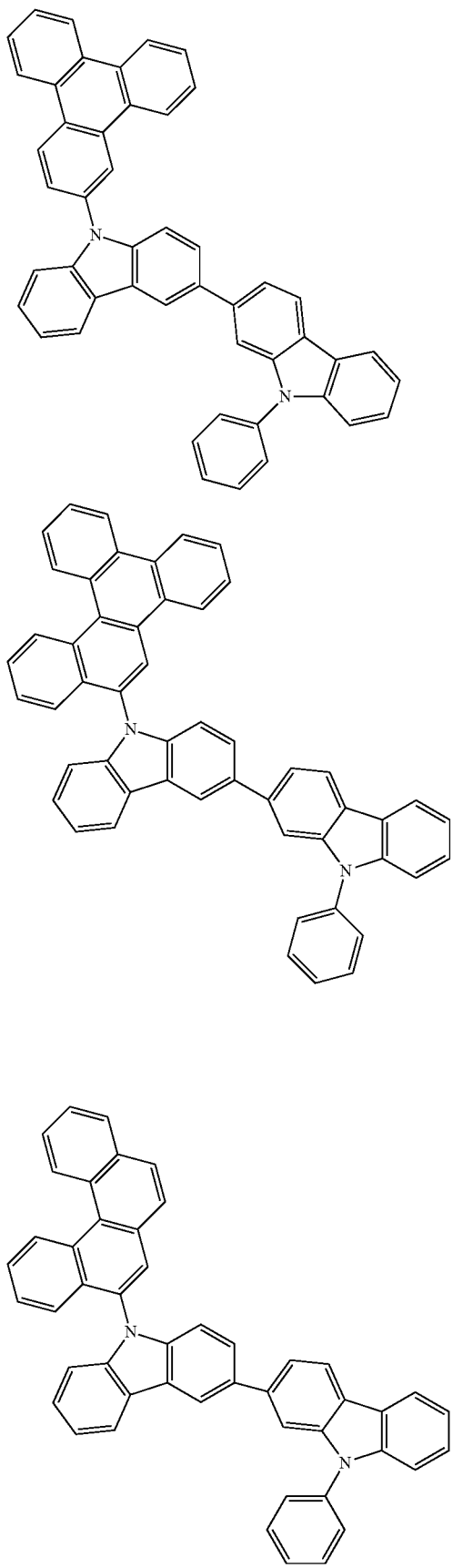
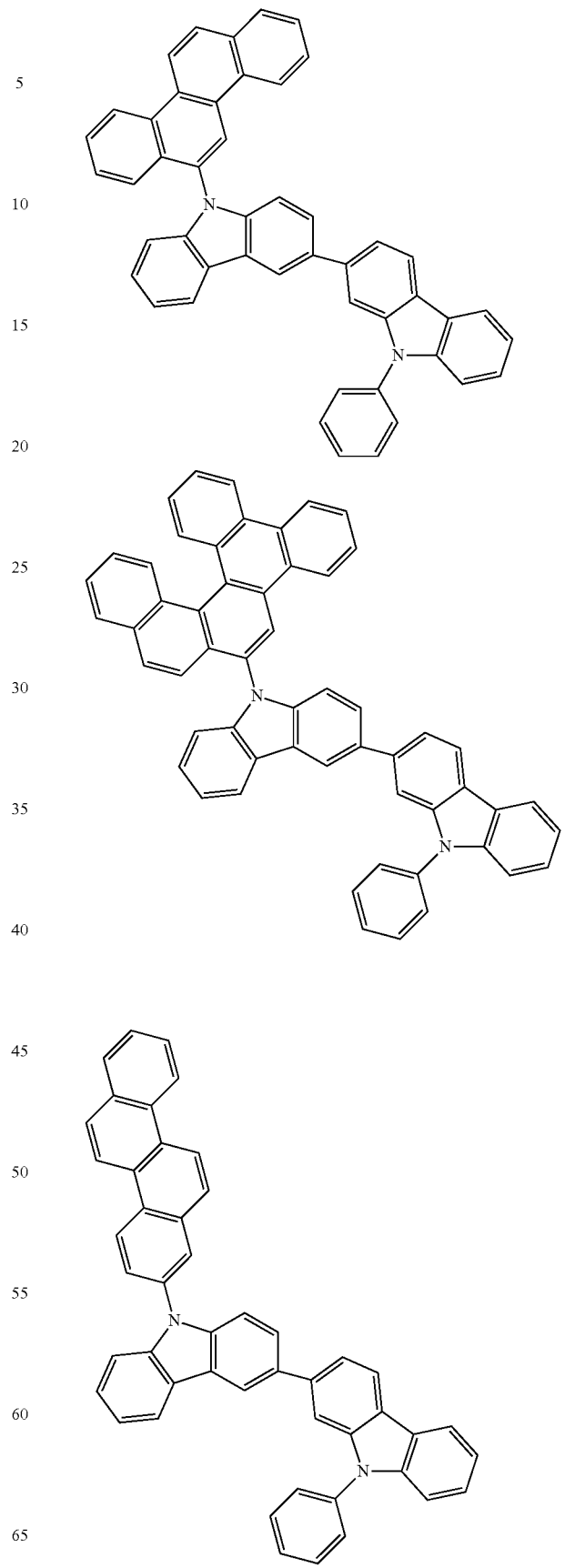

321
-continued
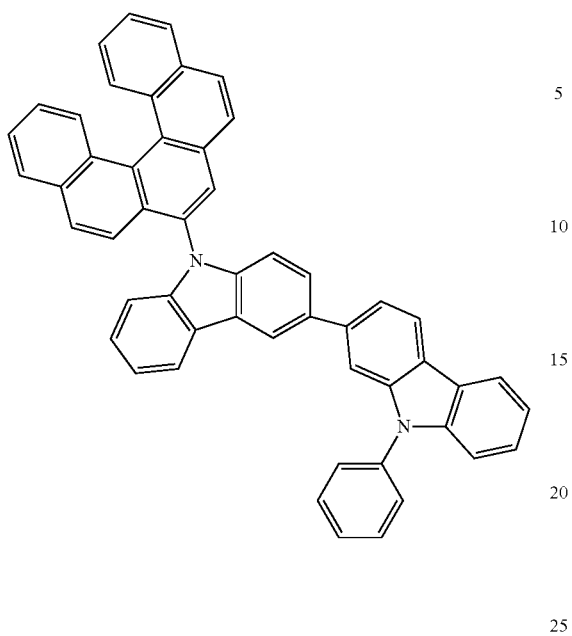
322
-continued
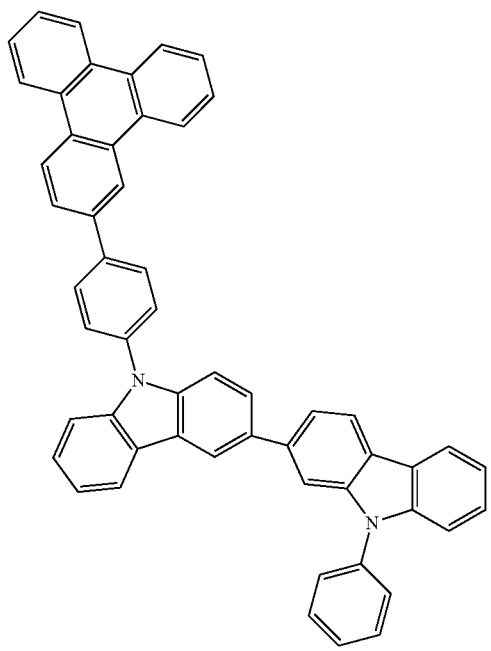
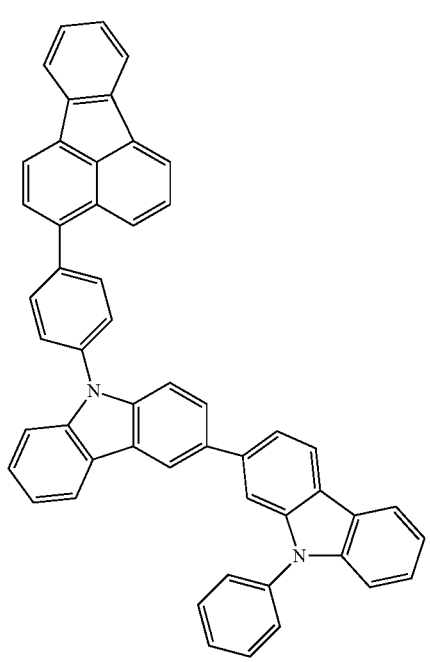
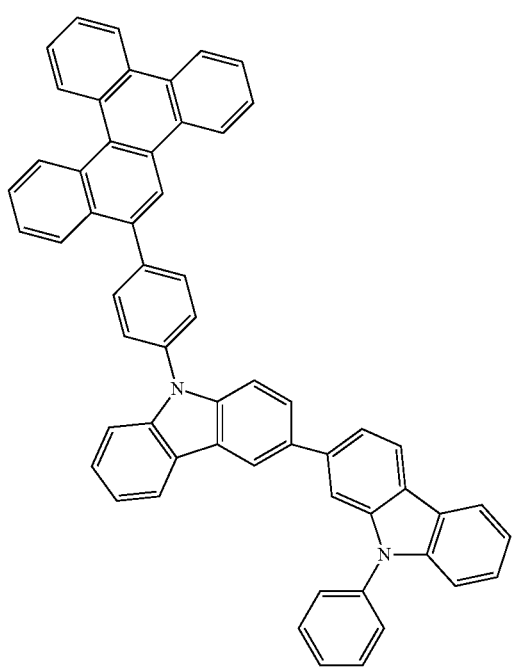

323
-continued
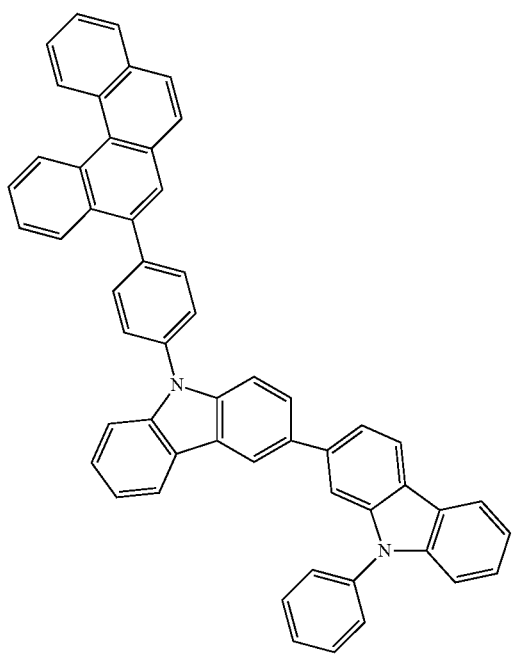
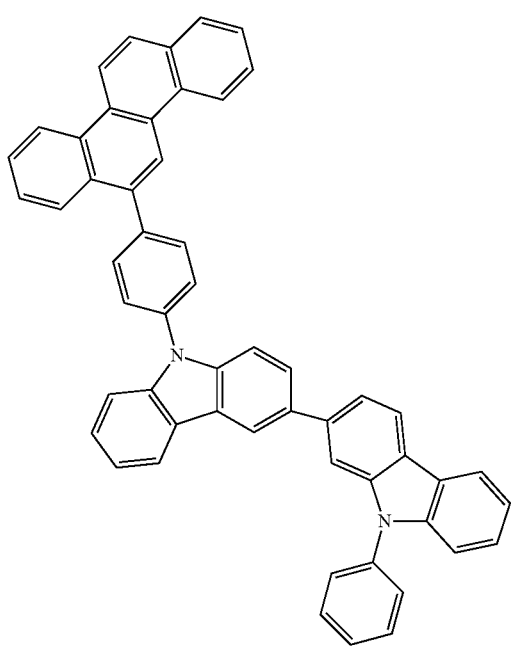
324
-continued
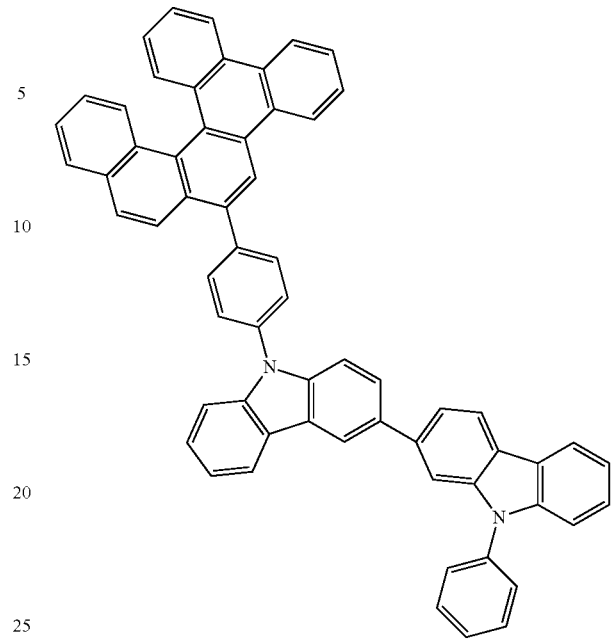
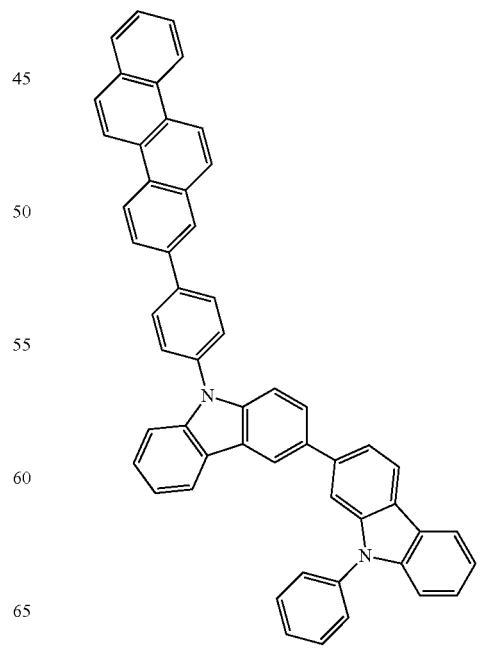

325
-continued
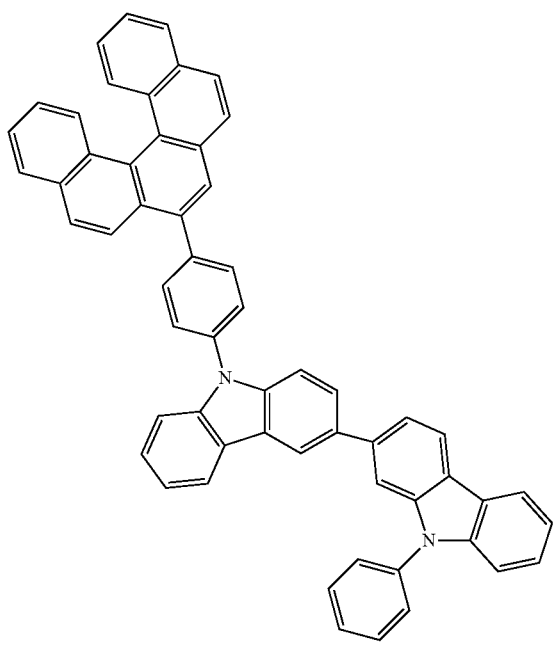
326
-continued
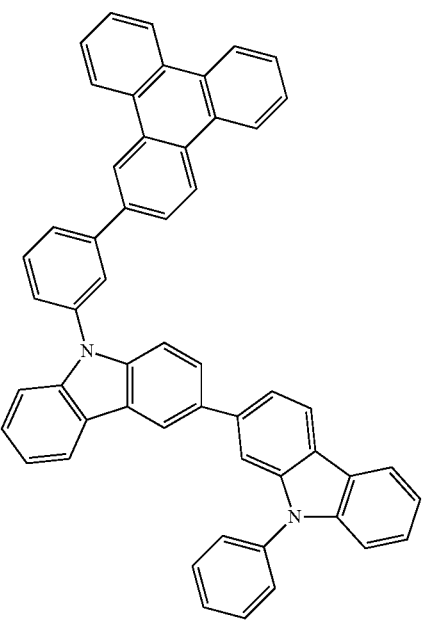
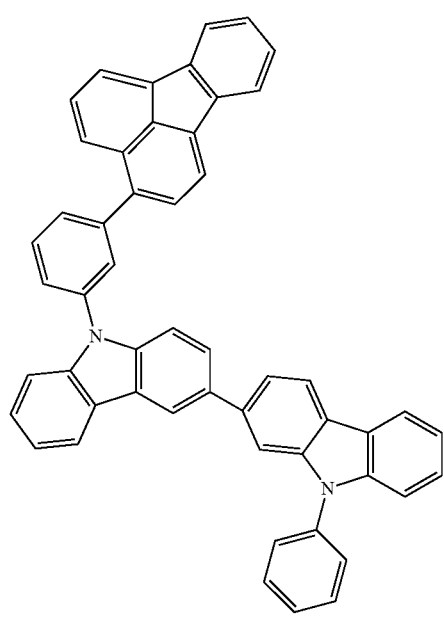
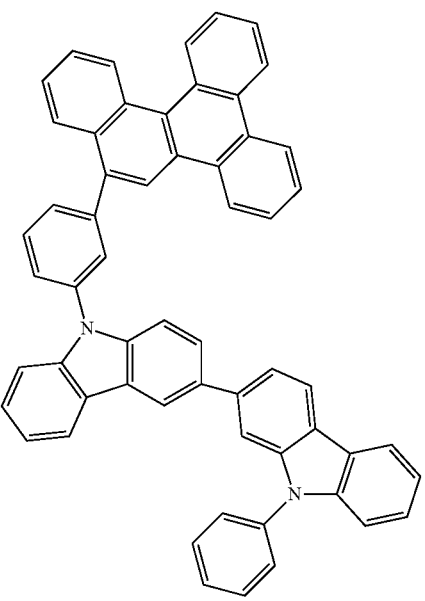

327
-continued
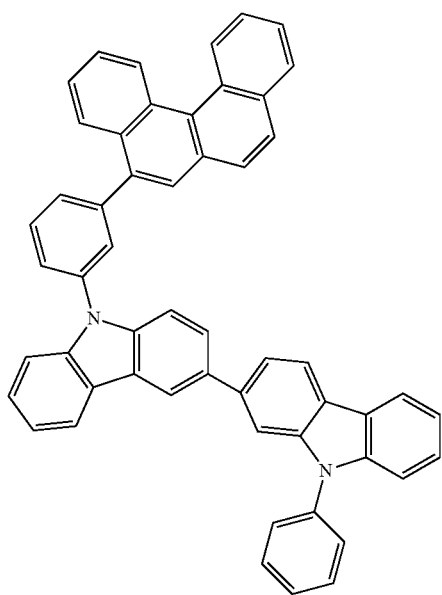
328
-continued
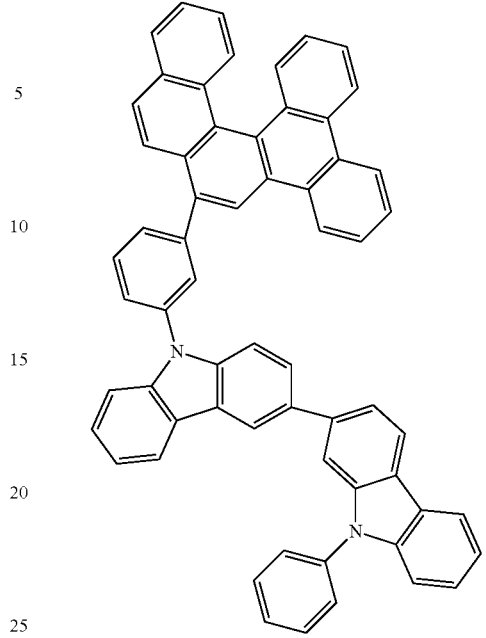
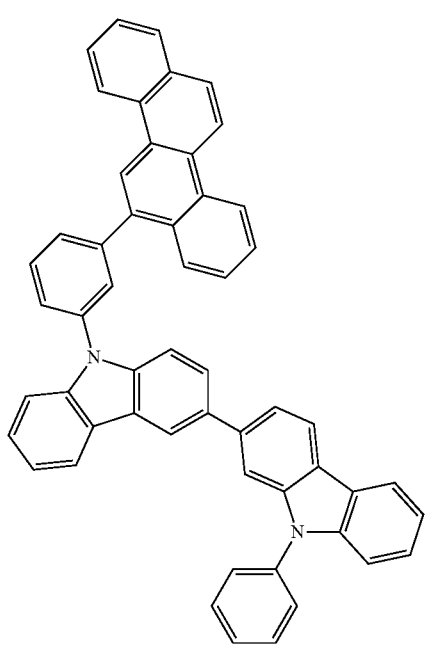
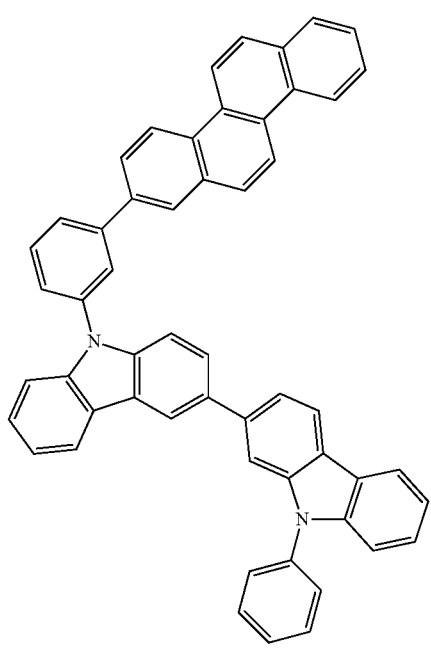

329
-continued
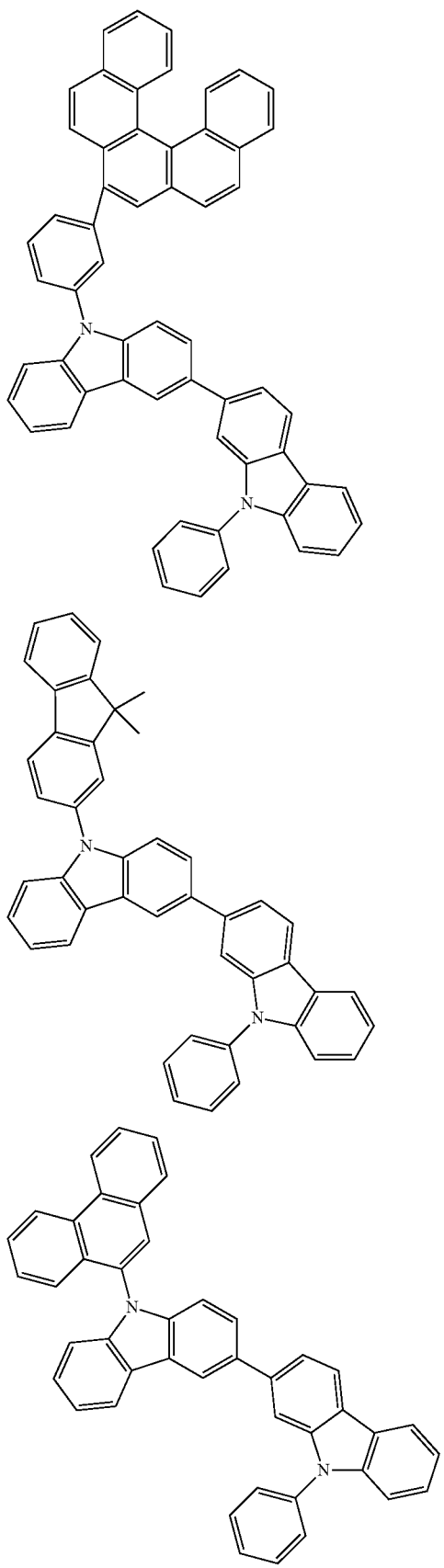
330
-continued
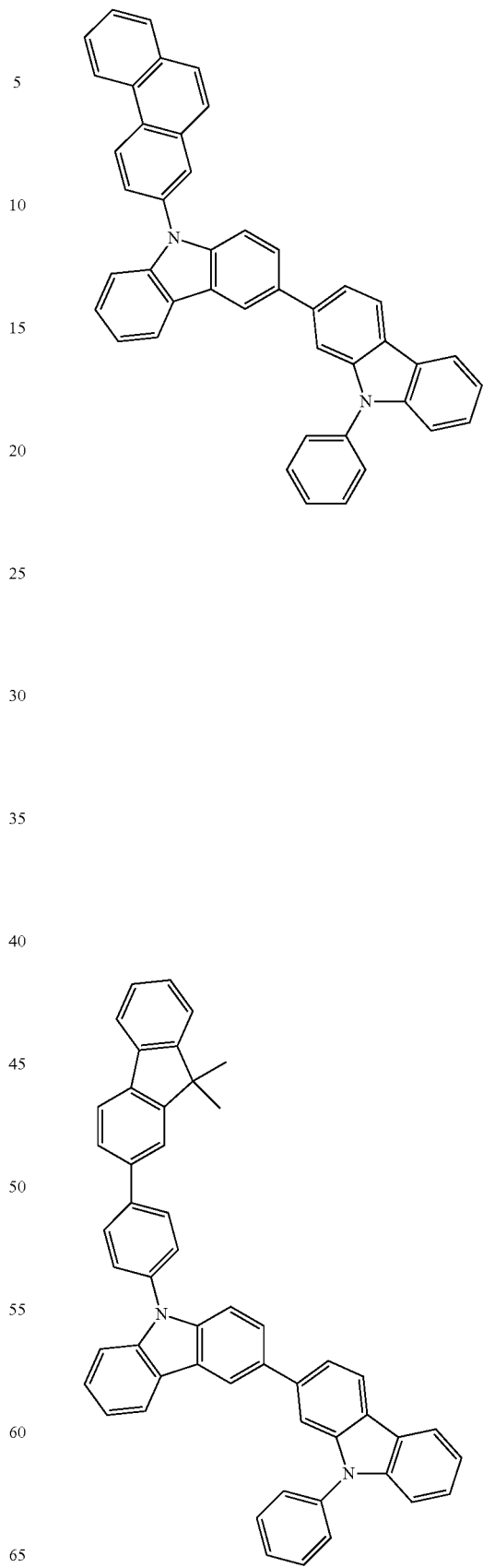

331
-continued
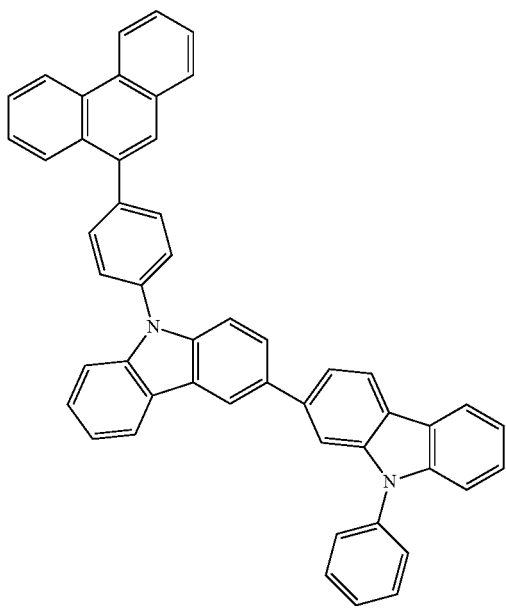
332
-continued
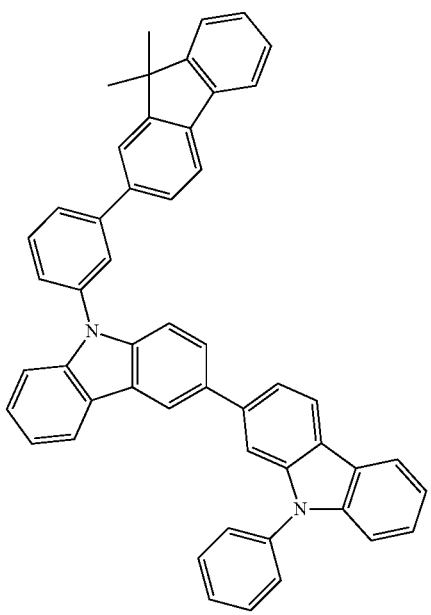
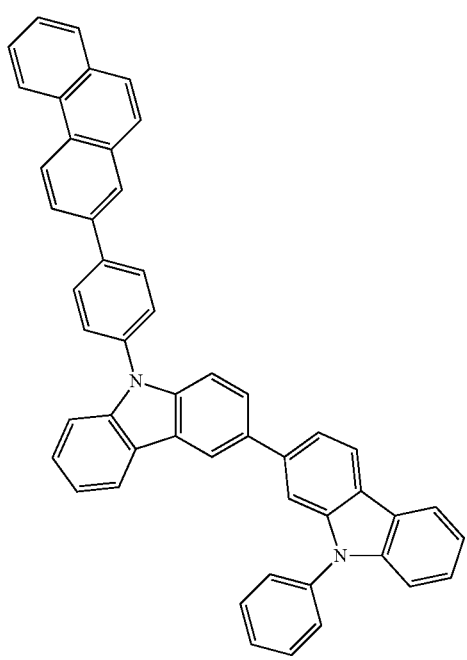
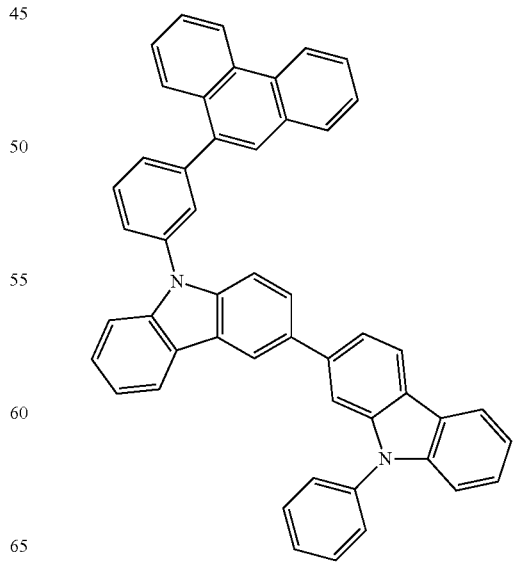

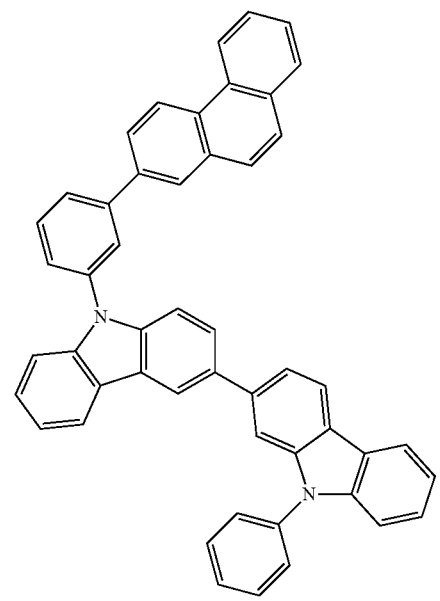
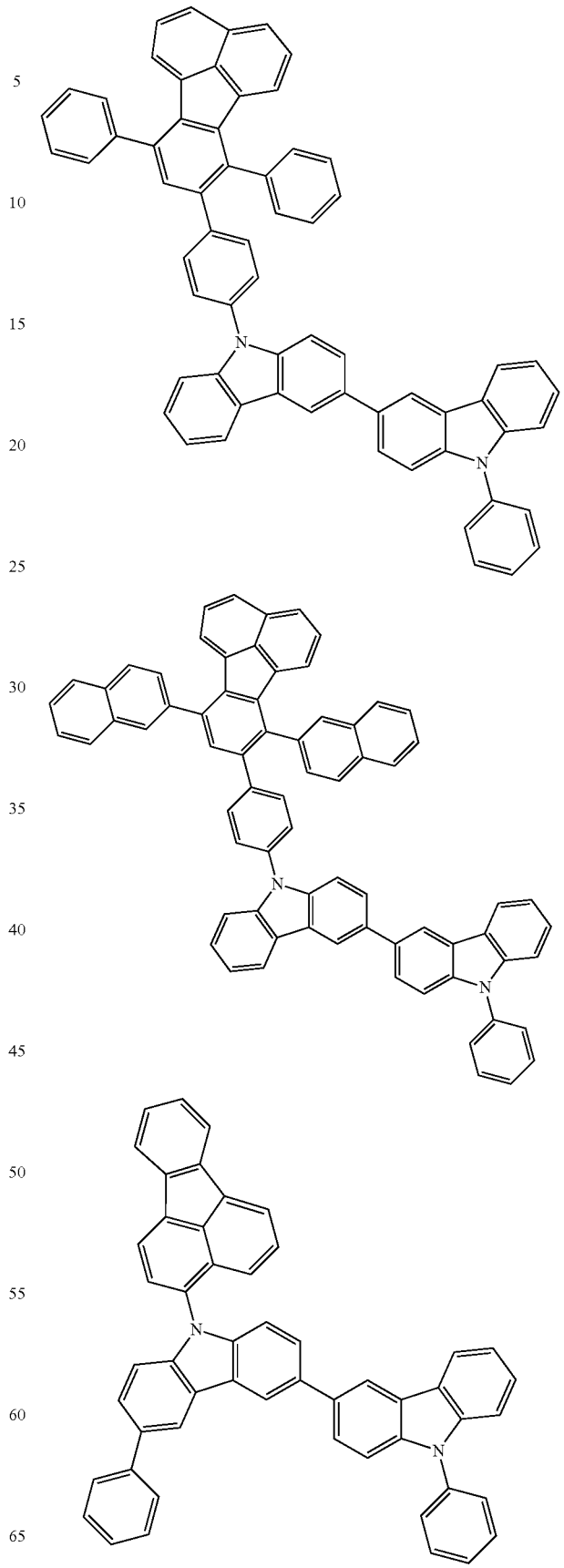

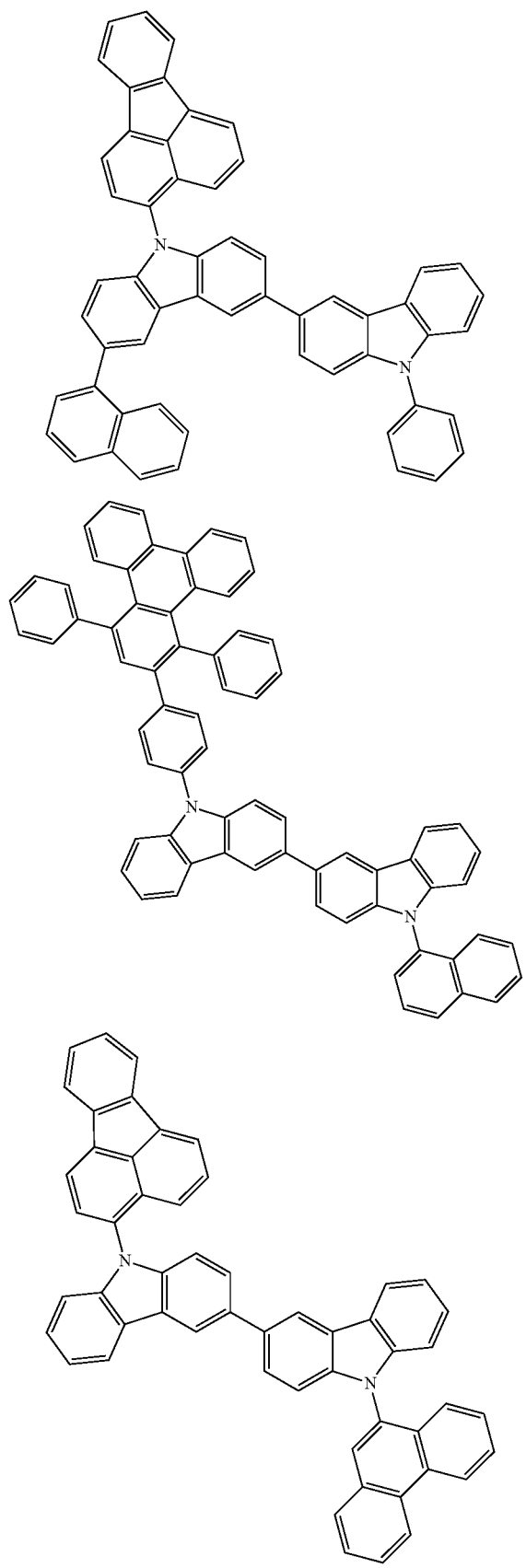
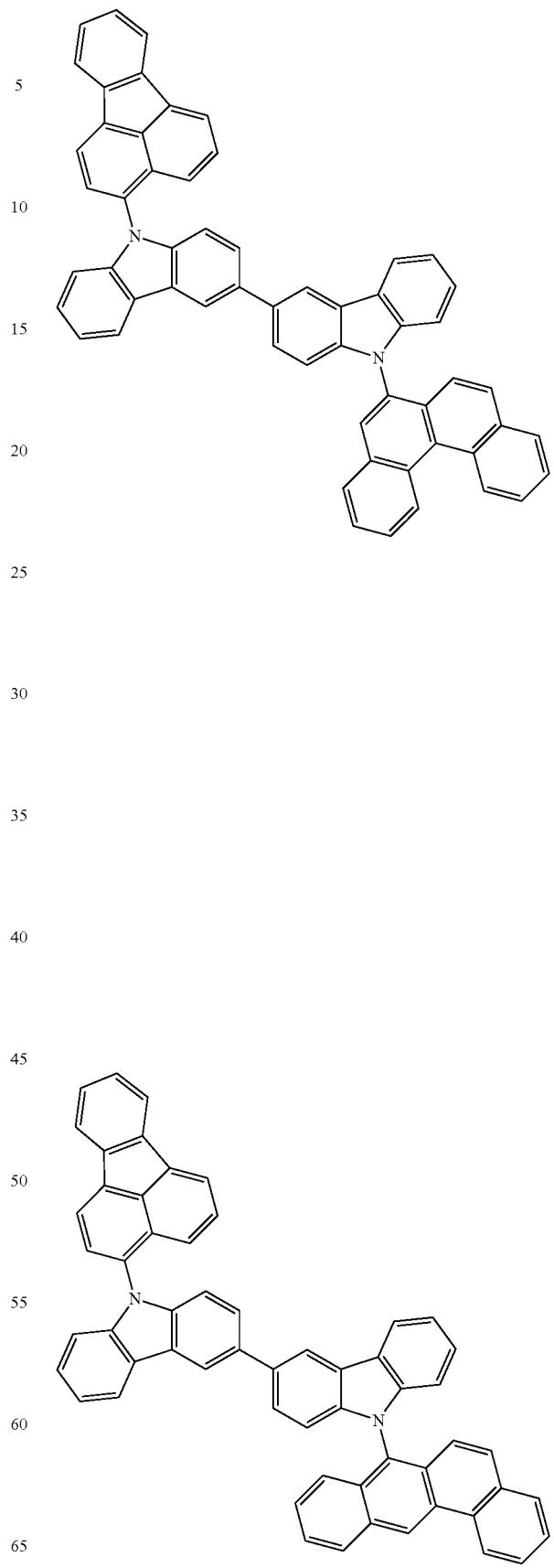

337
-continued
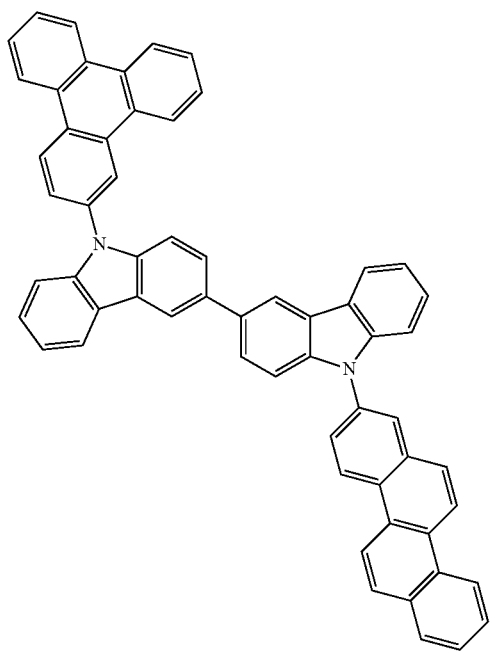
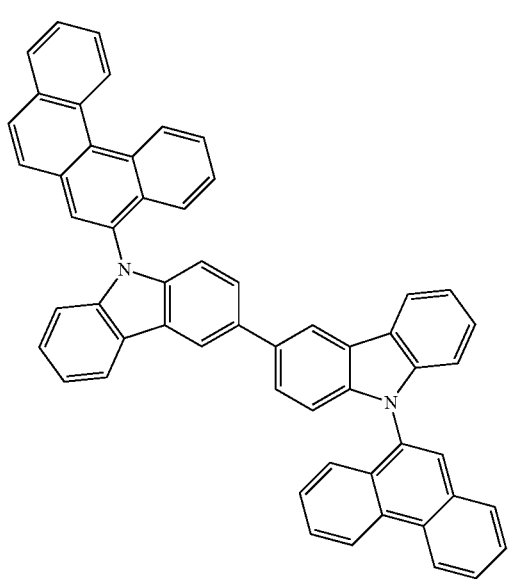
338
-continued
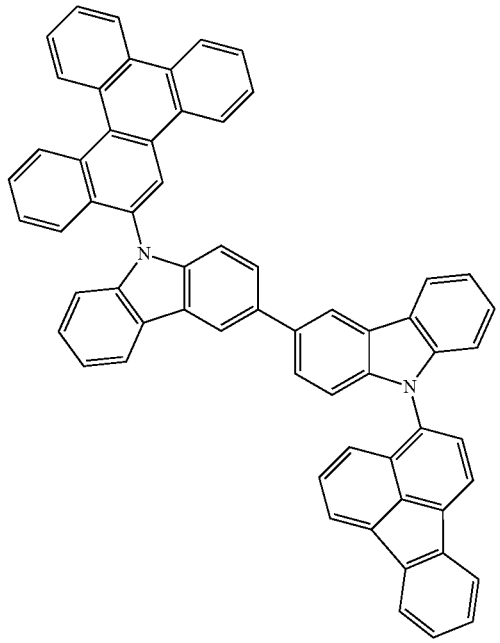
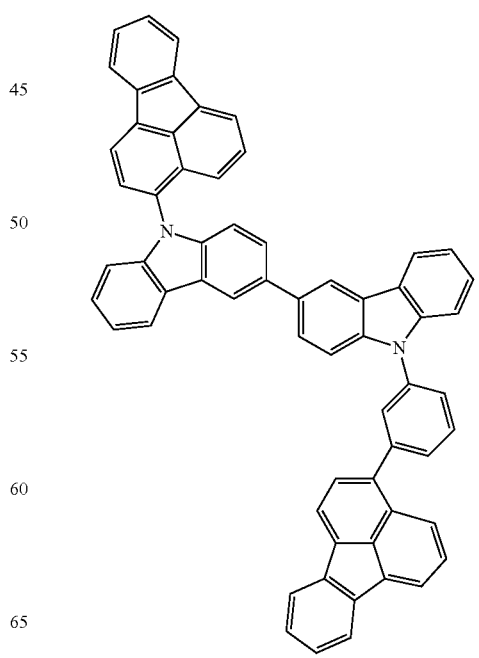

339
-continued
340
-continued
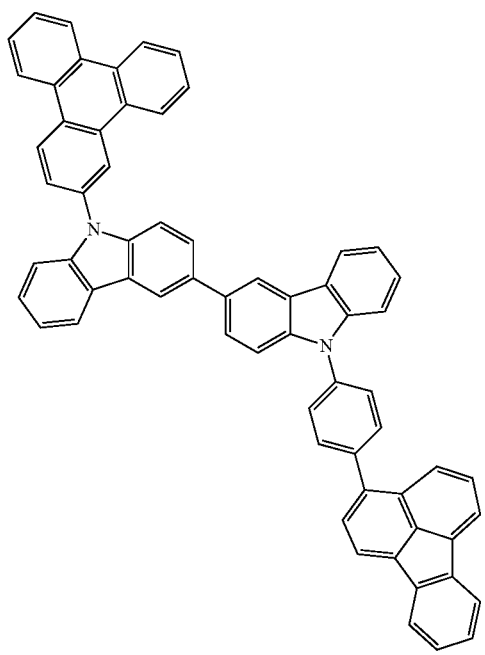
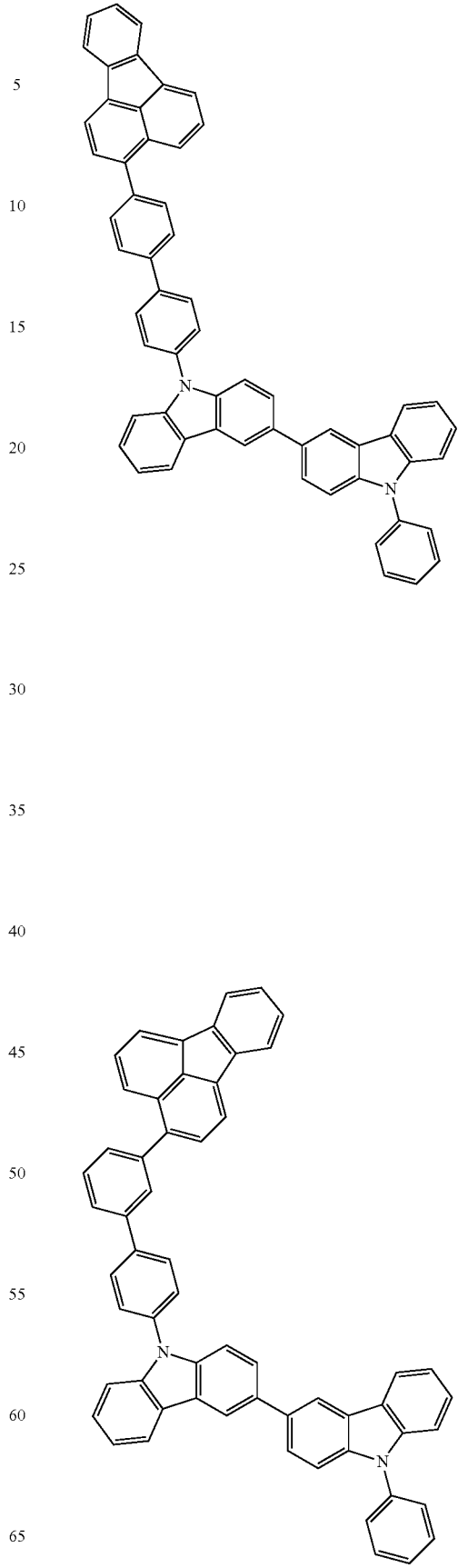

341
-continued
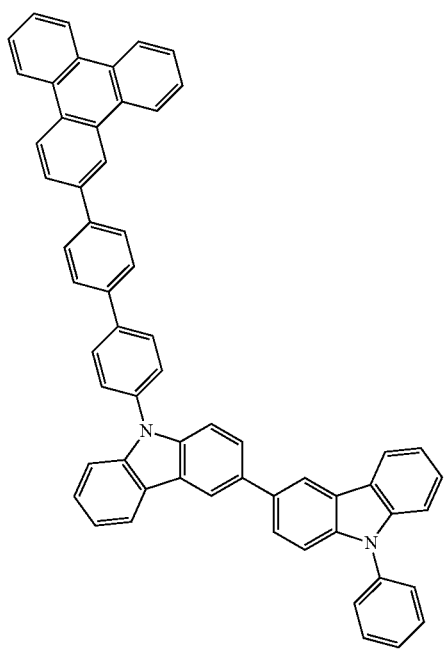
342
-continued
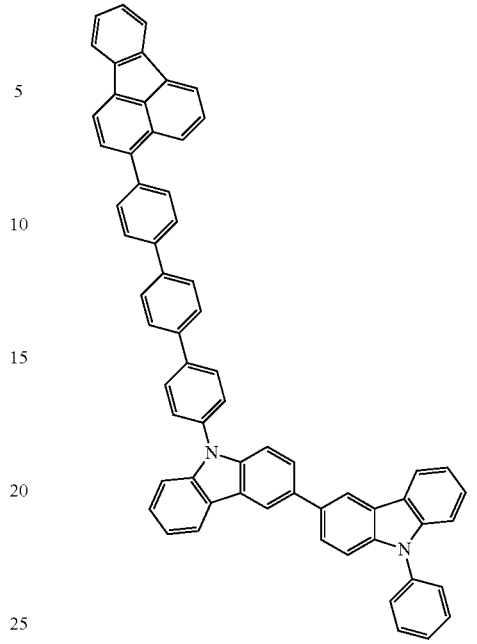
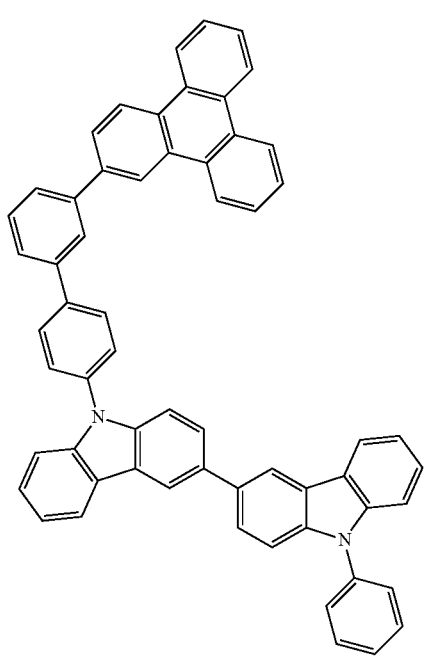
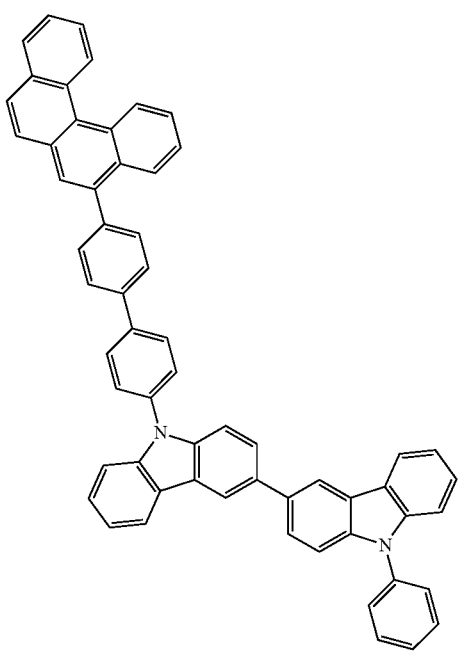

343
-continued
344
-continued
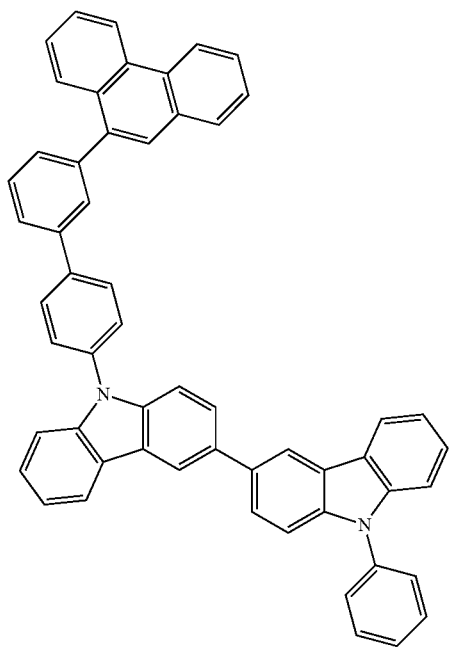
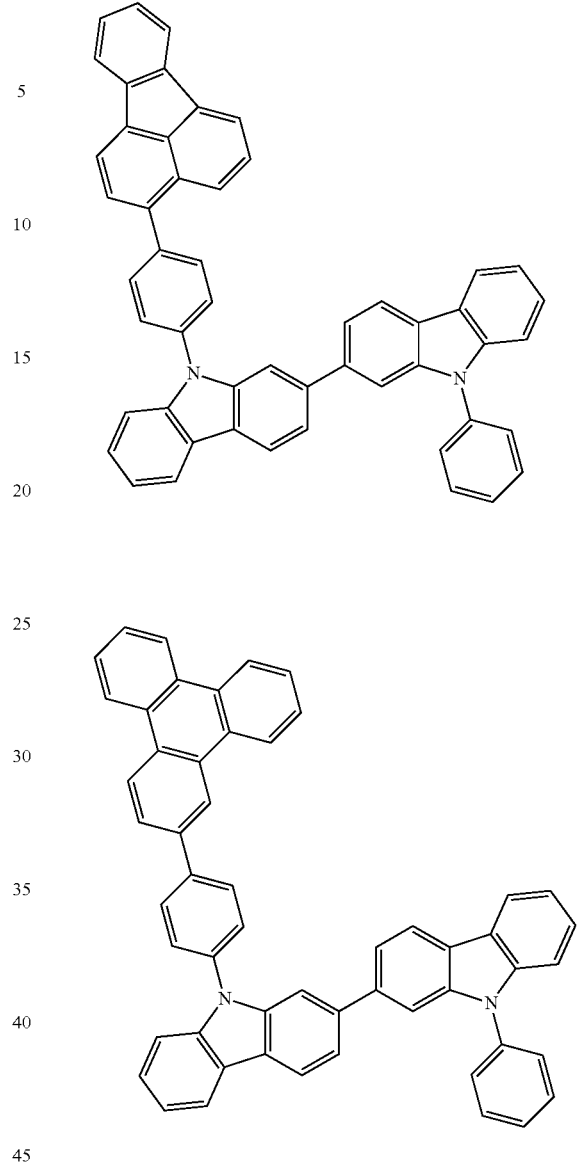
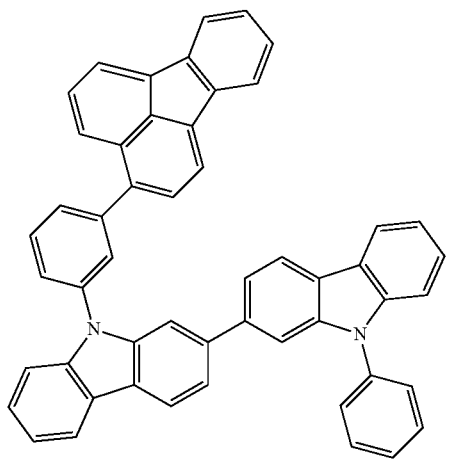
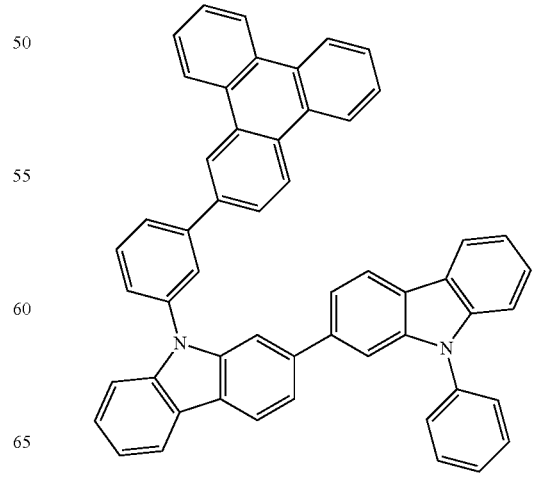

345
-continued
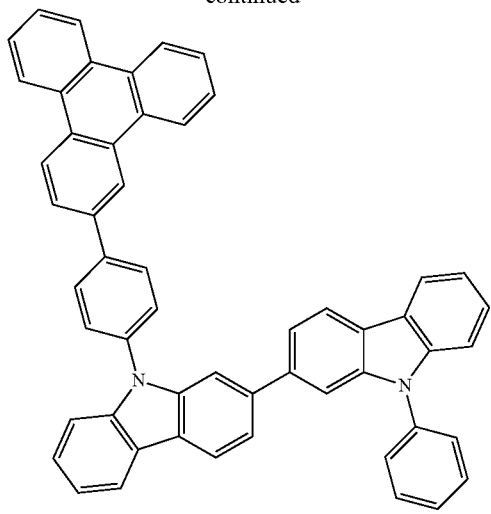
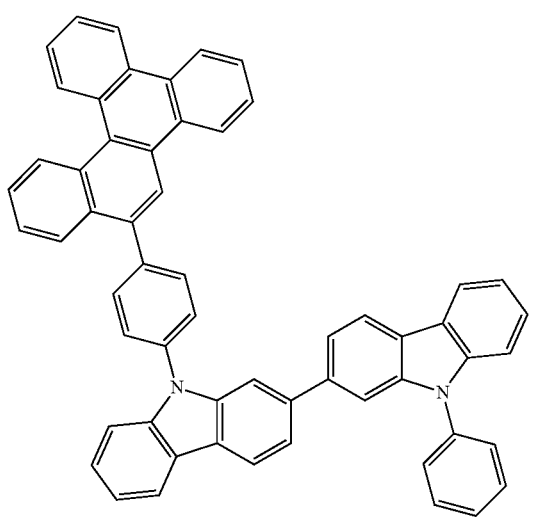
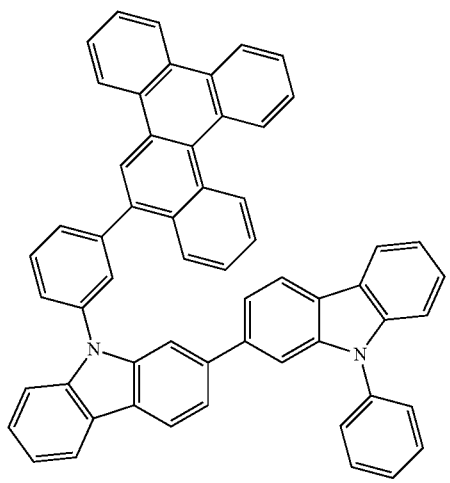
346
-continued
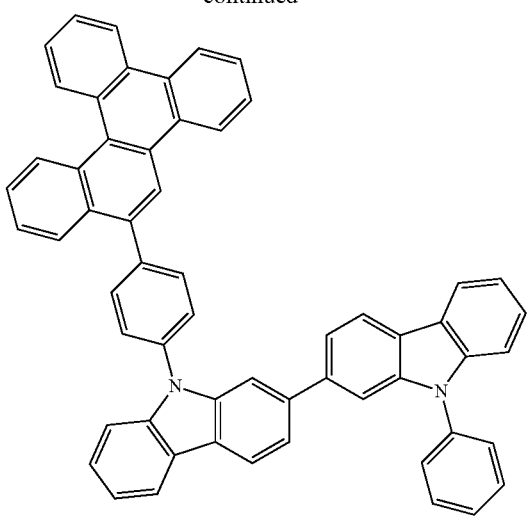
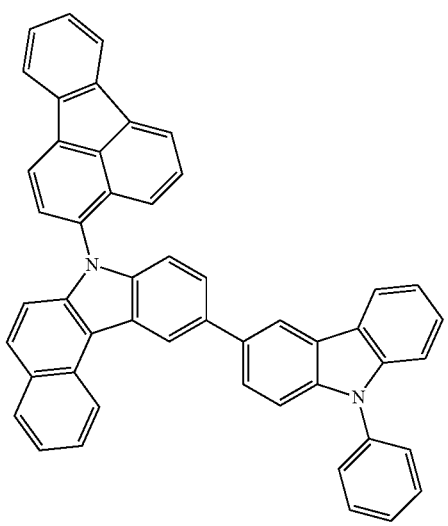
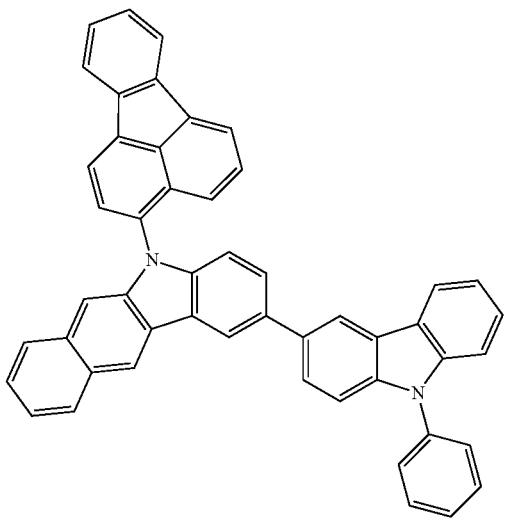

347
-continued
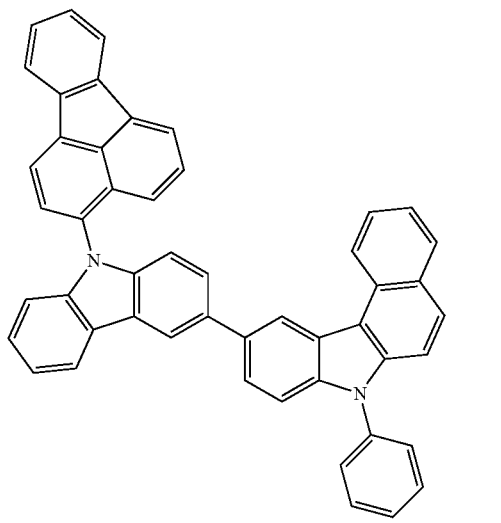
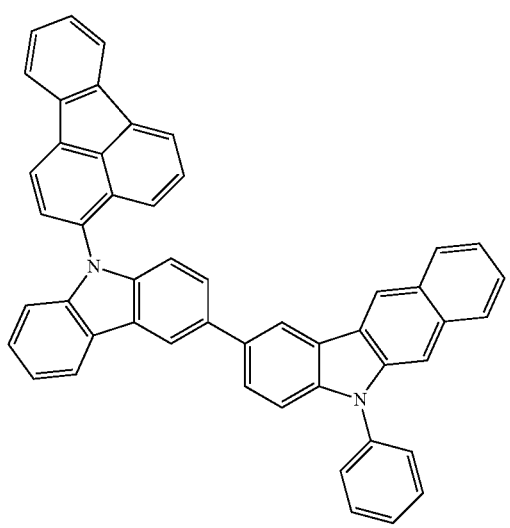
348
-continued
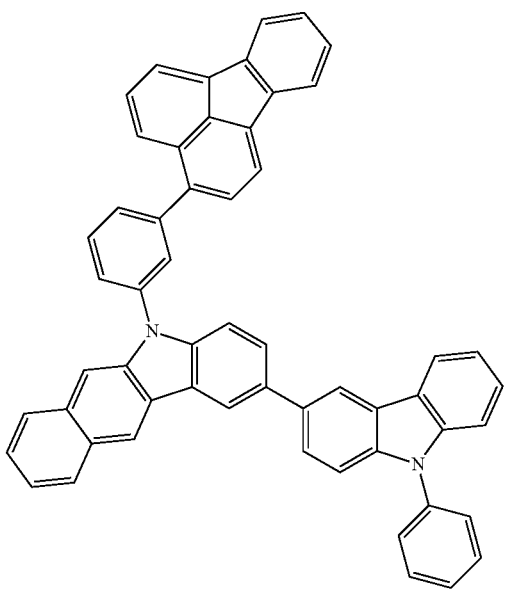
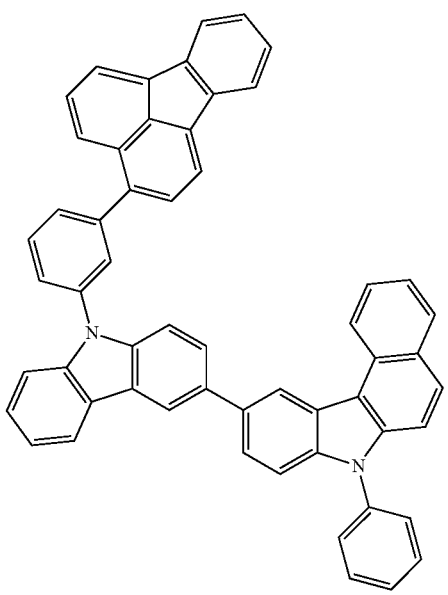

349
-continued
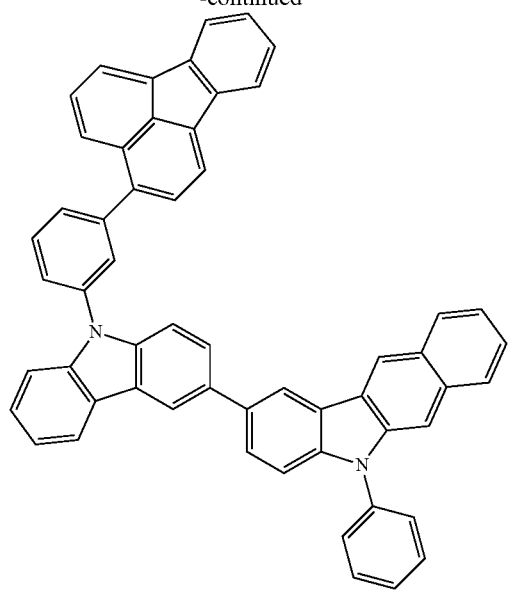
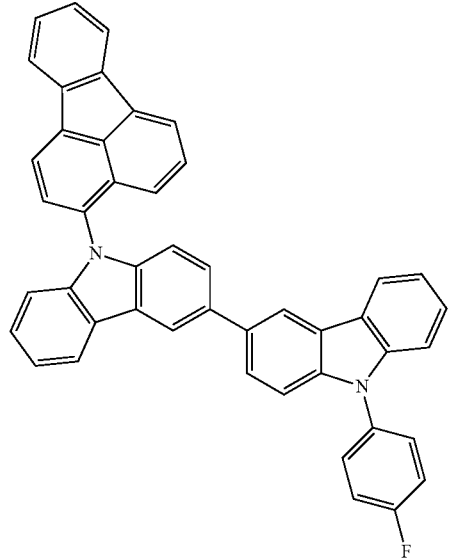
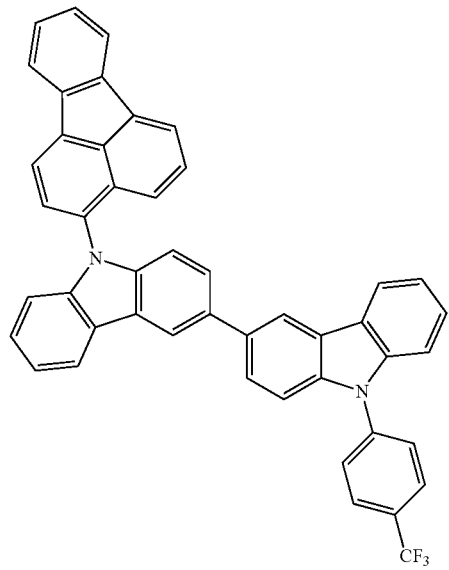
350
-continued
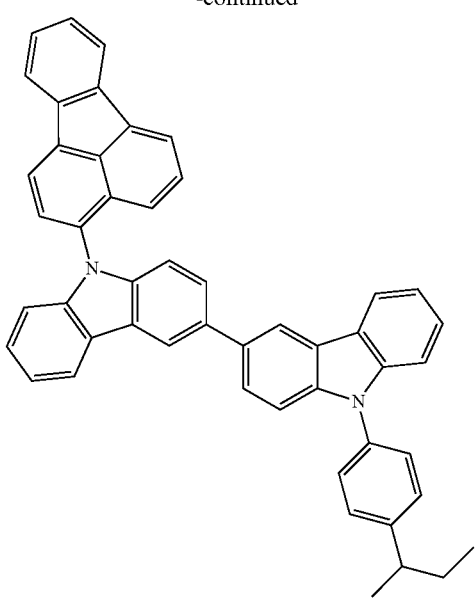
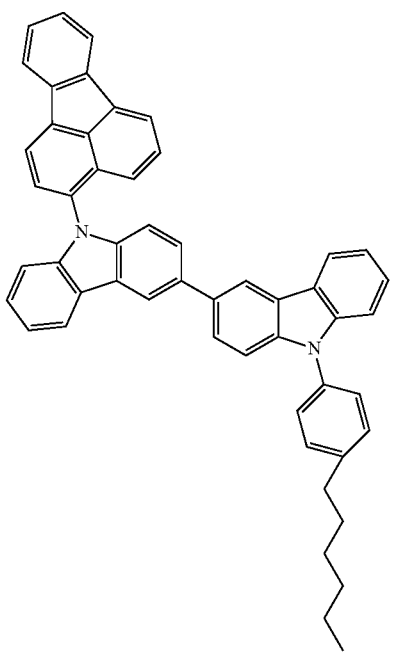

351
-continued
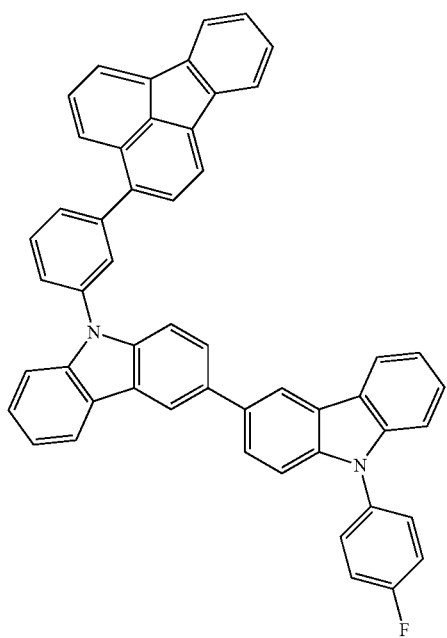
352
-continued
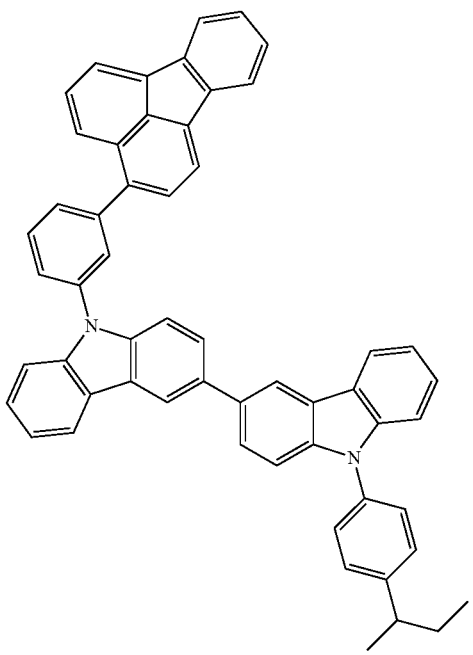
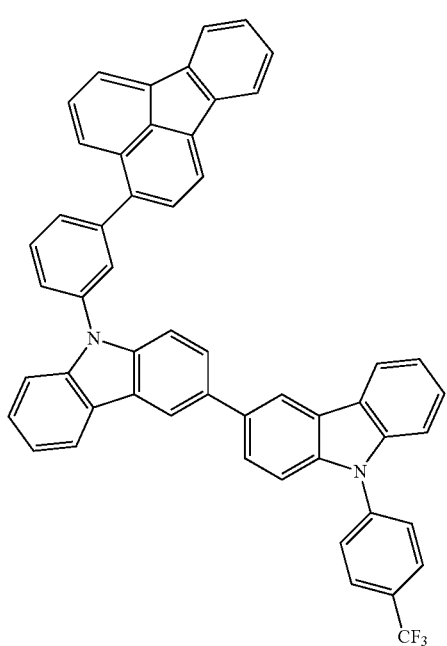
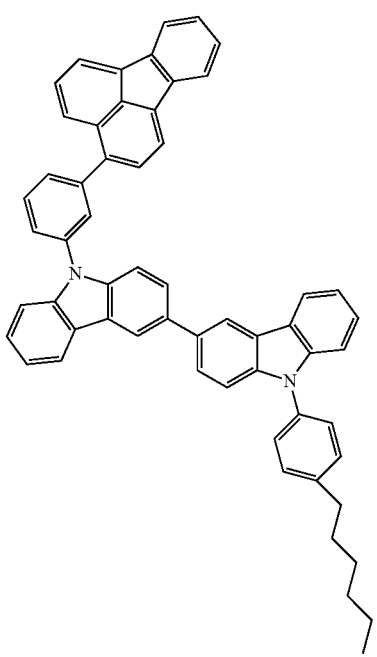

353
-continued
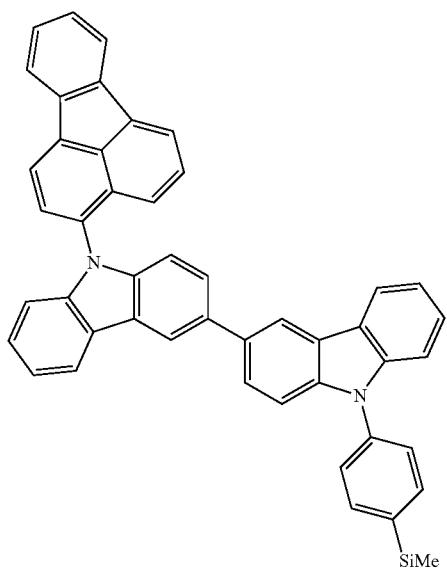
354
-continued
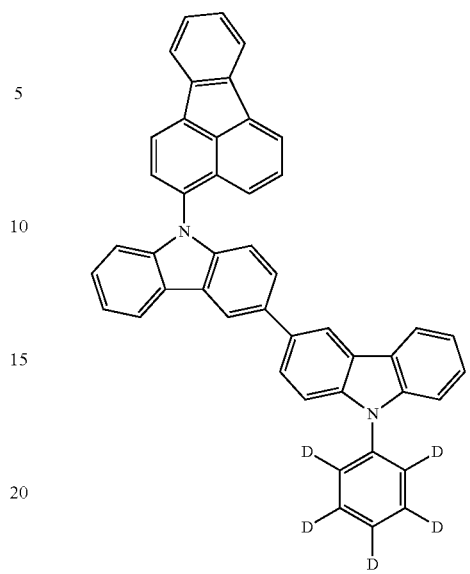
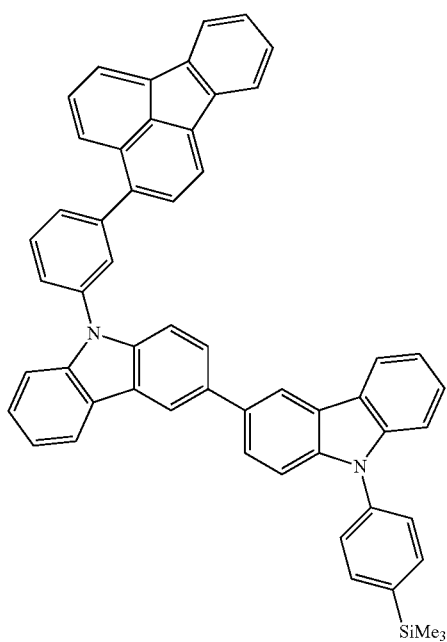
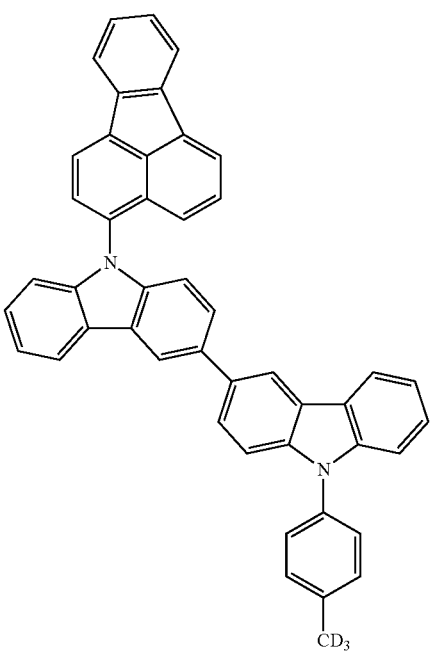

355
-continued
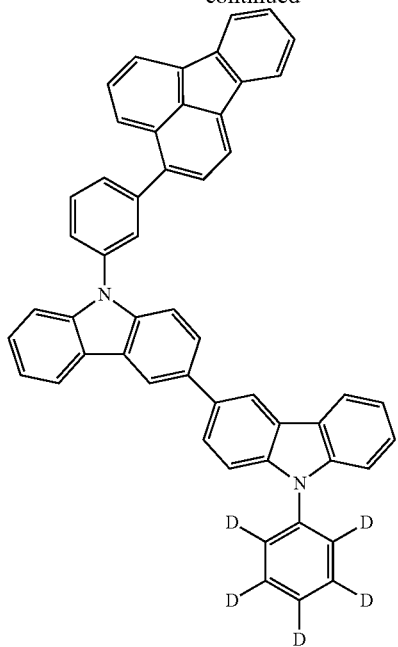
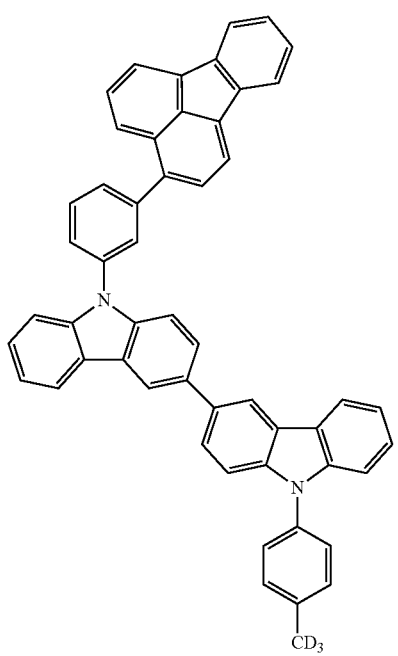
356
-continued
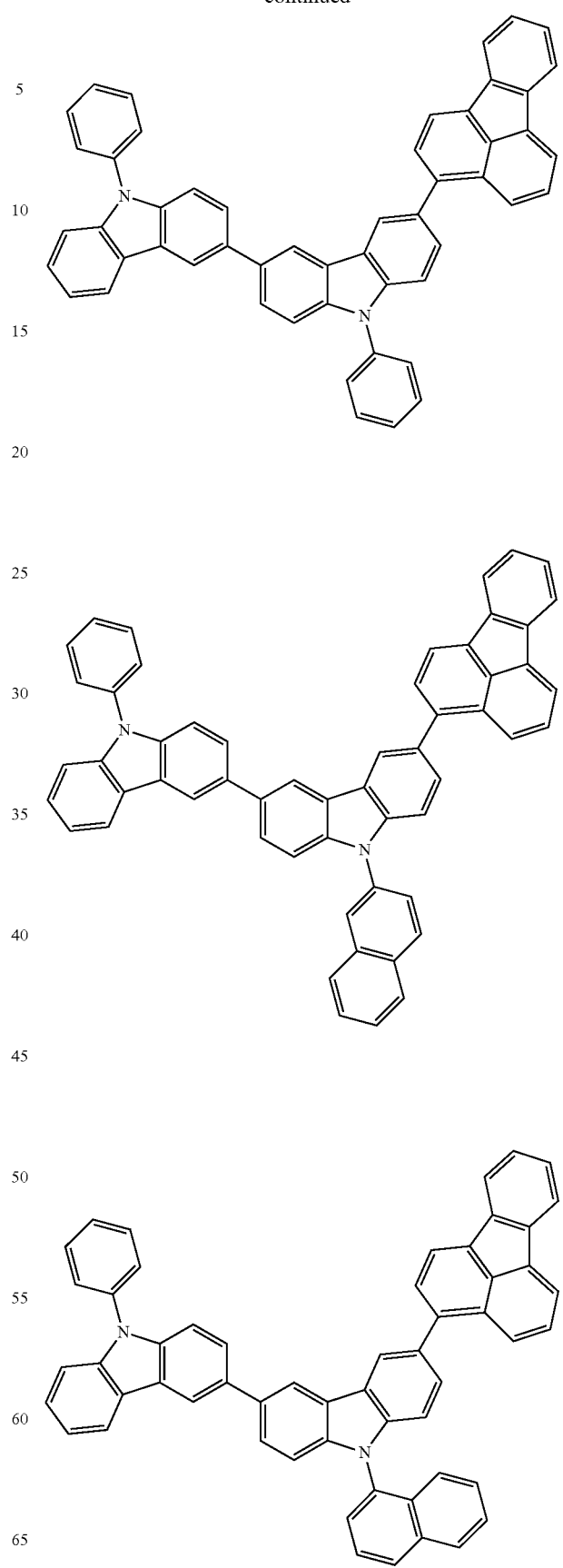

357
-continued

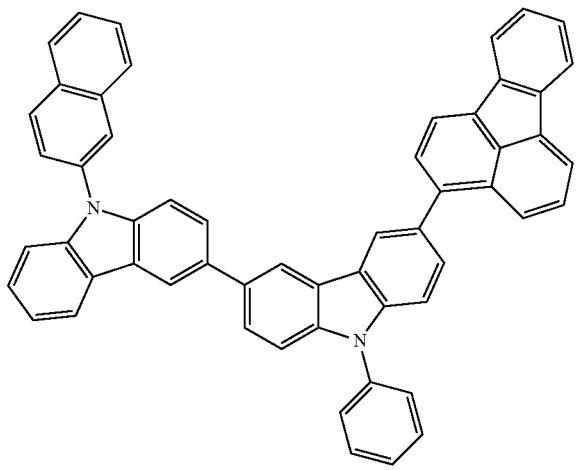

358
-continued

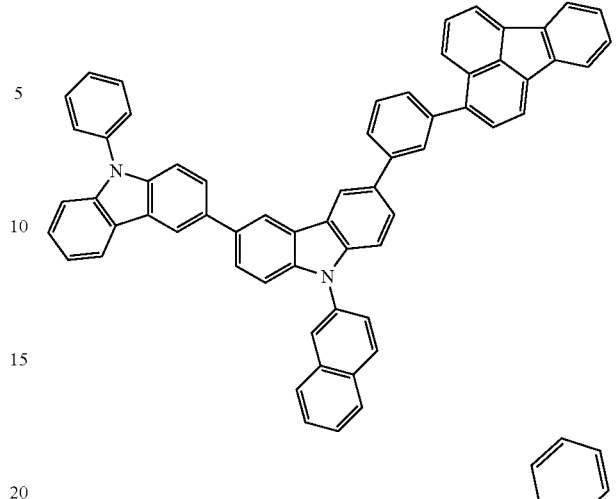

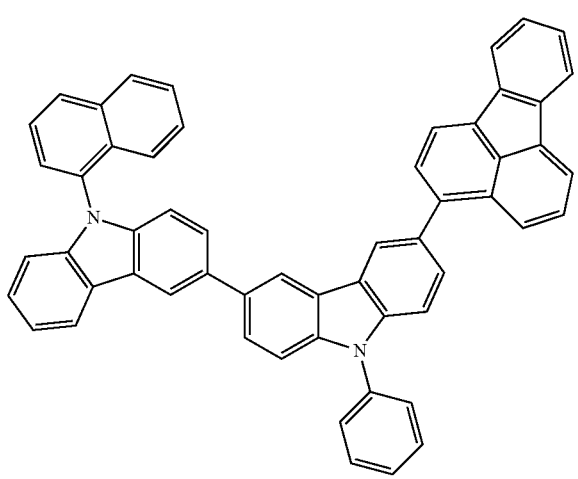

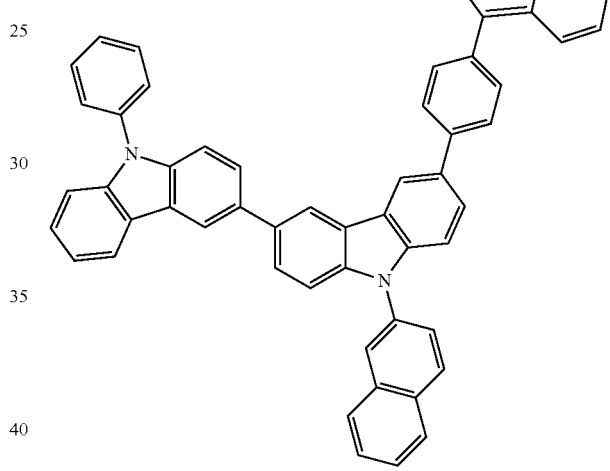

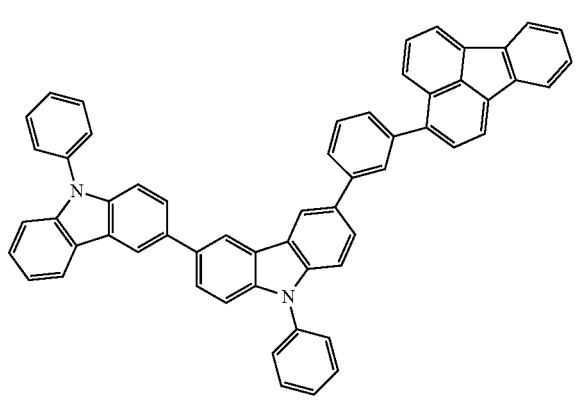

The organic EL device of the invention contains the biscarbazole derivative of the invention preferably in the light emitting layer.

It is also preferred that the organic EL device of the invention comprises a hole transporting layer (hole injecting layer) and the hole transporting layer (hole injecting layer) comprises the biscarbazole derivative of the invention.

Phosphorescent Material

In the present invention, the phosphorescent material comprises a metal complex. The metal complex preferably comprises a metal atom selected from Ir, Pt, Os, Au, Cu, Re, and Ru, and a ligand. In particular, a ligand having an ortho metal bond is preferred.

In view of obtaining a high phosphorescent quantum yield and further improving the external quantum efficiency of electroluminescence device, a metal complex comprising a metal selected from Ir, Os, and Pt is preferred. A metal complex, such as iridium complex, osmium complex, and platinum complex, is more preferred, with iridium complex and platinum complex being still more preferred, and an ortho metallated iridium complex being most preferred.

Specific examples of the preferred metal complex are shown below.

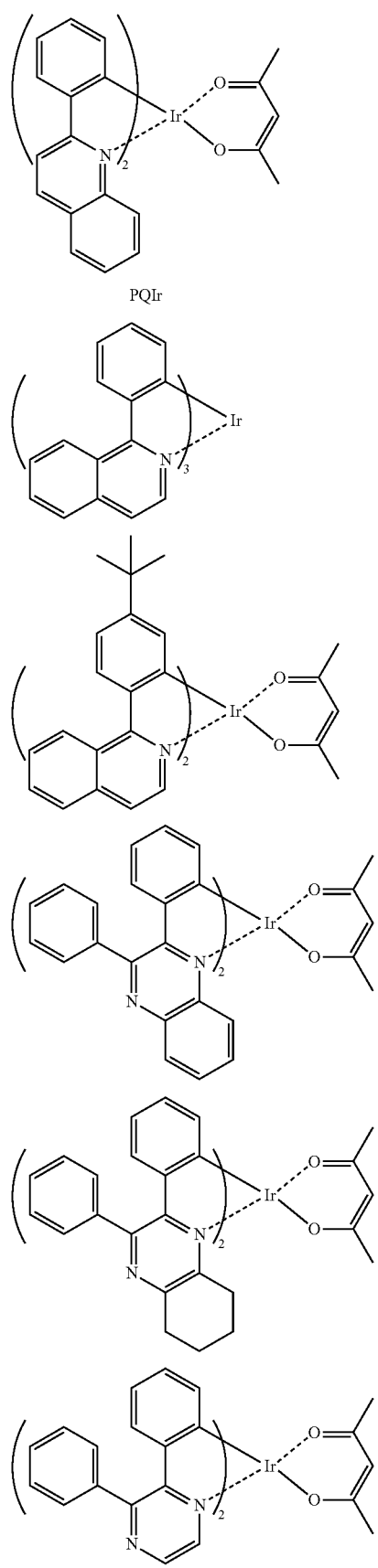
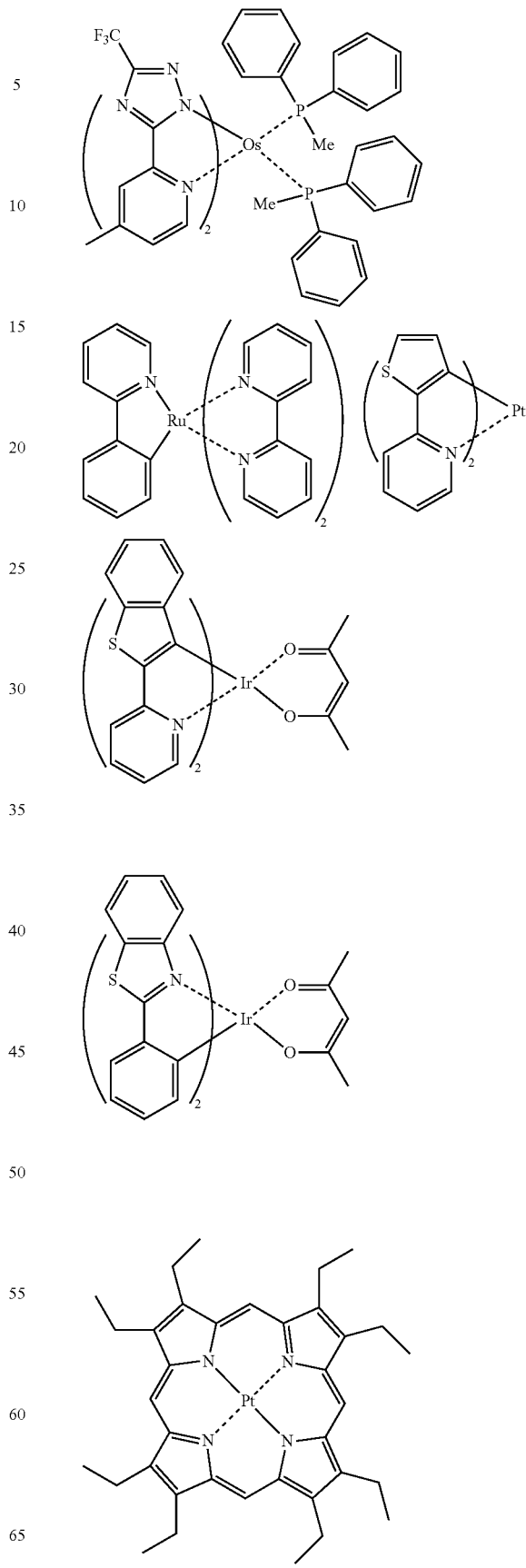

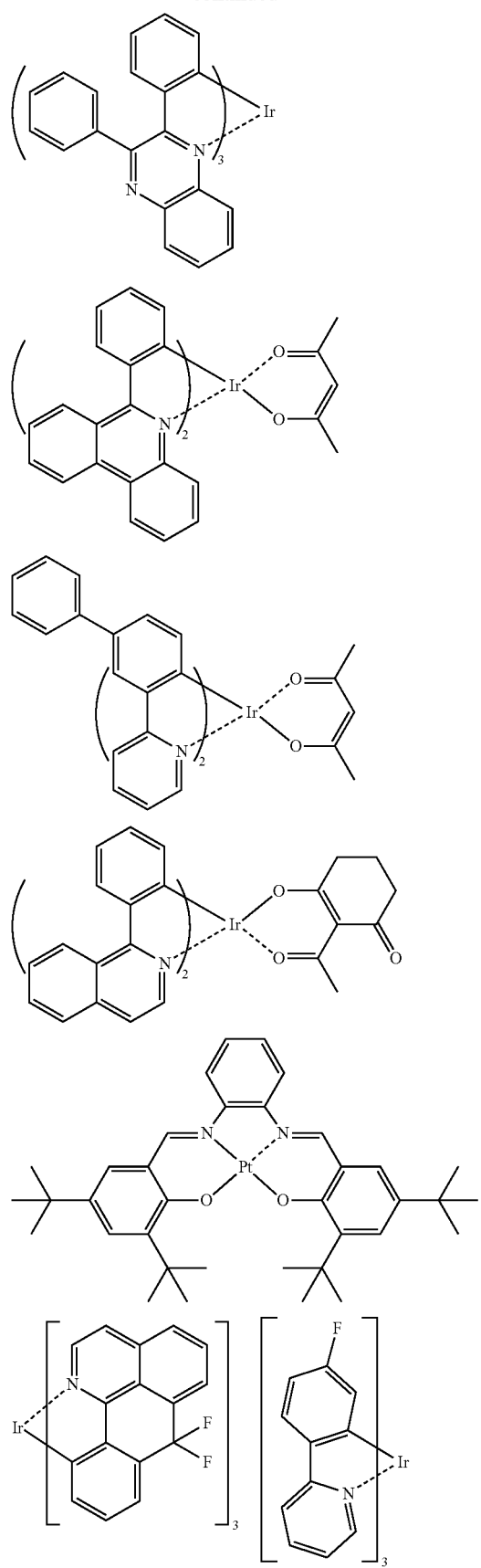
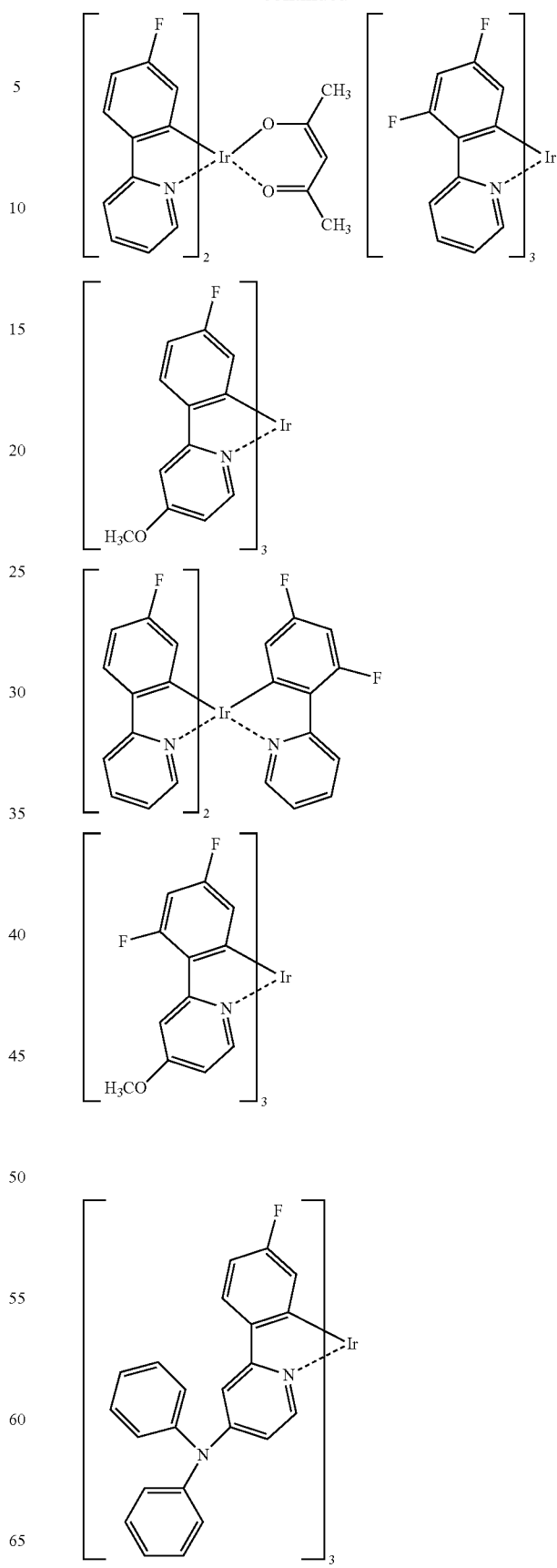

-continued
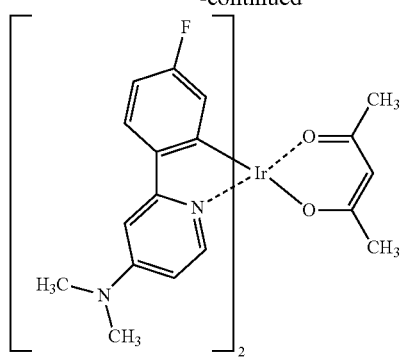
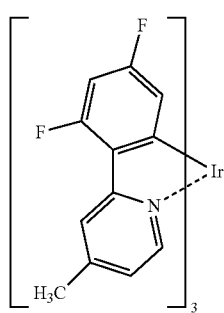
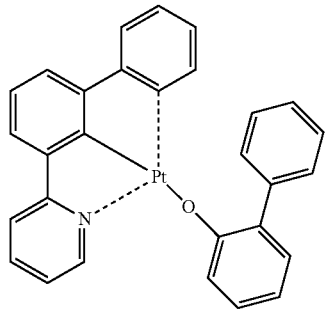
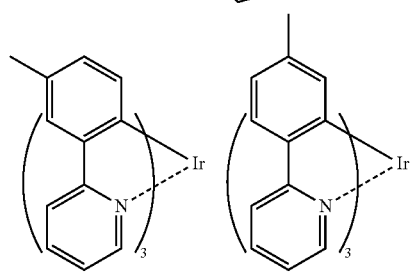
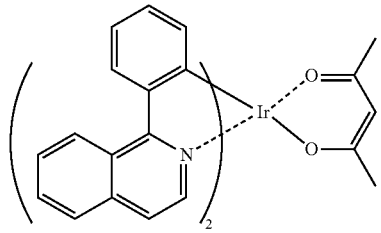
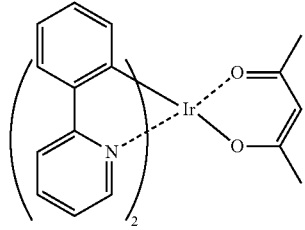
-continued
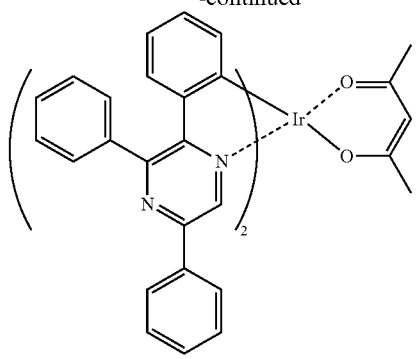
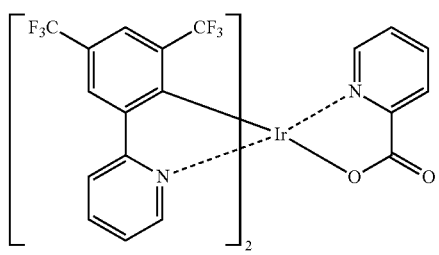
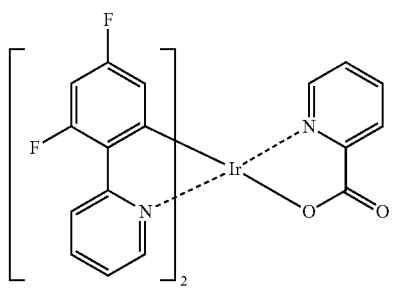
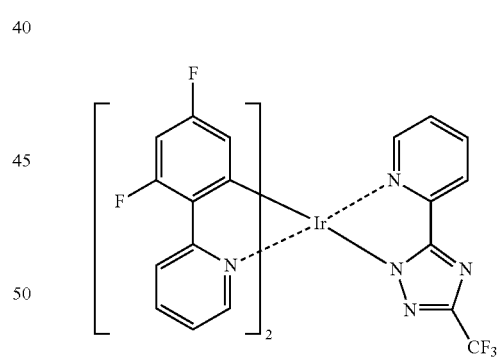
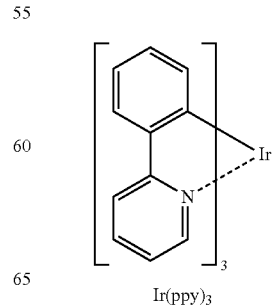
Ir(ppy)₃

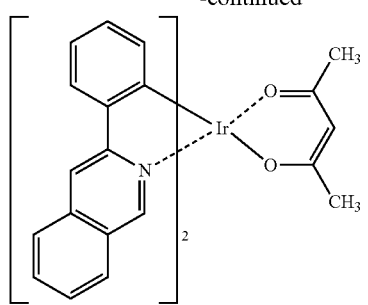
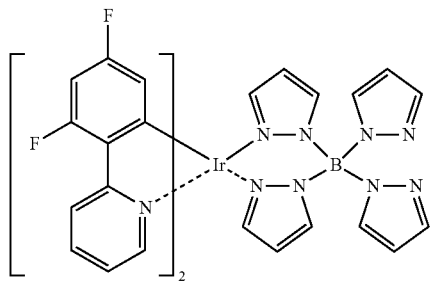
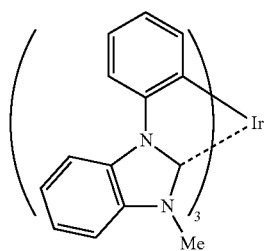
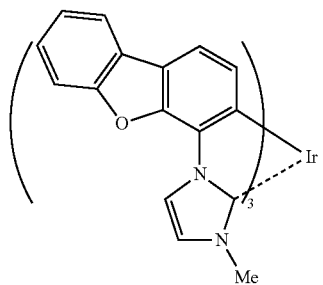
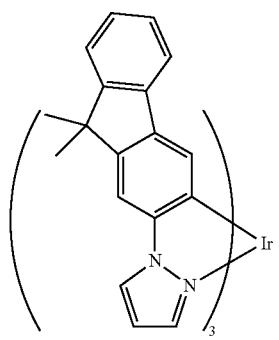
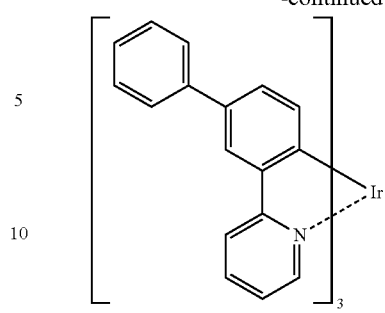
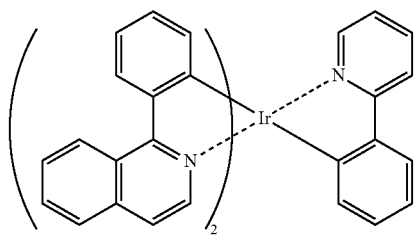
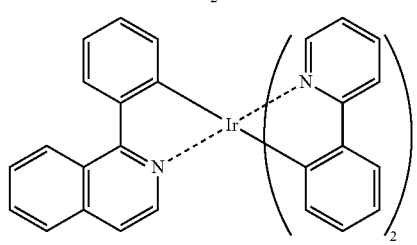
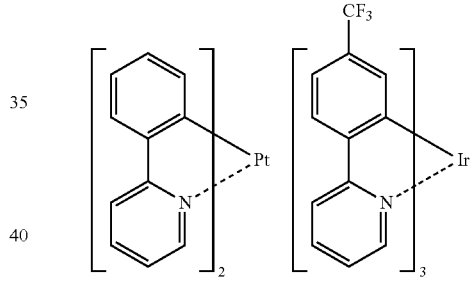
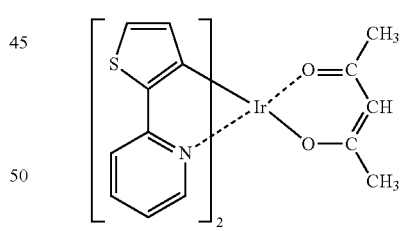
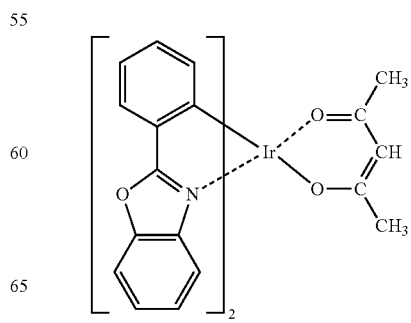

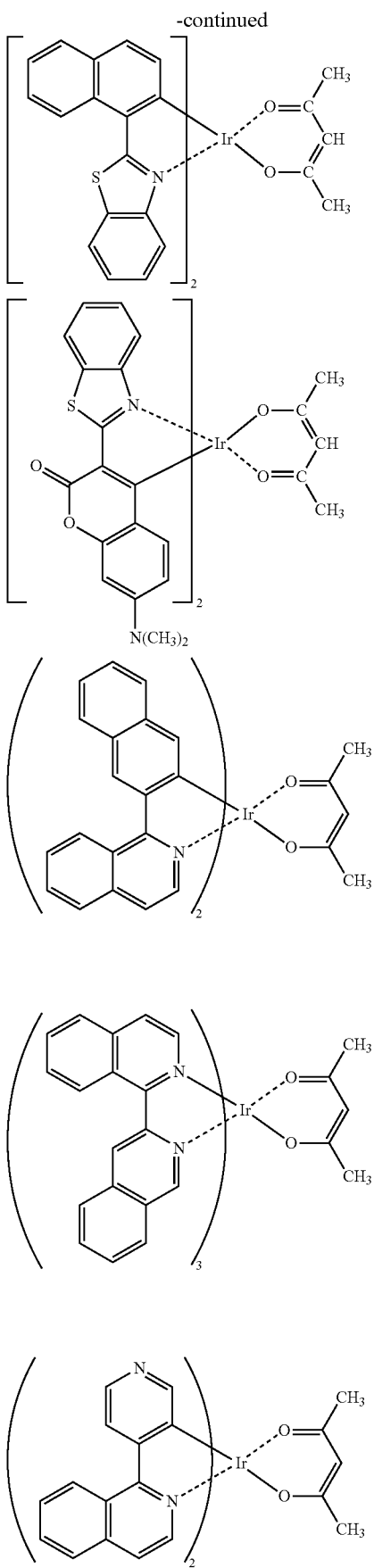
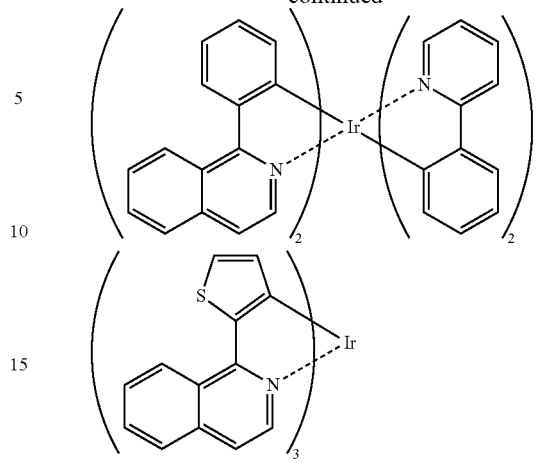

In a preferred embodiment of the invention, at least one of the phosphorescent materials used in the light emitting layer emit light having a maximum emission wavelength of preferably 450 nm or longer and 750 nm or shorter. In another preferred embodiment, the maximum emission wavelength is 450 nm or longer and 495 nm or shorter, 495 nm or longer and 590 nm or shorter, or 590 nm or longer and 750 nm or shorter.

By doping a specific host material used in the invention in the light emitting layer with the phosphorescent material (phosphorescent dopant) having a maximum emission wavelength within the above rages, a high-efficiency organic EL device can be obtained.

Reducing Dopant

The organic EL device of the present invention preferably comprises a reducing dopant at an interfacial region between the cathode and the organic thin film layer.

With such a construction, the organic EL device has an improved luminance and an elongated lifetime.

Examples of the reducing dopant include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

The preferred metals described above have a particularly high reducing ability. Therefore, the emission luminance and life time of an organic EL device can be improved by adding a relatively small amount of the metal to an electron injecting region.

Examples of the alkali metal compound include alkali oxide, such as $Li_2O$, $Cs_2O$, and $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ (0<x<1) and $Ba_xCA^1_{-x}O$ (0<x<1), with BaO, SrO, and CaO being preferred.

Examples of the rare earth metal compound include $YbF_3$, $ScF_3$, $ScO_3$, $Y_2O_3$, $Ce_2O$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The reducing dopant is added to the interfacial region preferably into a form of layer or island. The reducing dopant is added preferably by co-depositing the reducing dopant with the organic compound (light emitting material, electron injecting material) for forming the interfacial region by a resistance heating deposition method, thereby dispersing the reducing dopant into the organic material. The disperse concentration expressed by the molar ratio of the organic material and the reducing dopant is 100:1 to 1:100 and preferably 5:1 to 1:5.

When the reducing dopant is formed into a form of layer, a light emitting material or an electron injecting material is made into a layer which serves as an organic layer in the interface, and then, the reducing dopant alone is deposited by a resistance heating deposition method into a layer having a thickness preferably 0.1 to 15 nm.

When the reducing dopant is formed into a form of island, a light emitting material or an electron injecting material is made into a form of island which serves as an organic layer in the interface, and then, the reducing dopant alone is deposited by a resistance heating deposition method into a form of island having a thickness preferably 0.05 to 1 nm.

The molar ratio of the main component and the reducing dopant in the organic electroluminescence device of the invention is preferably 5:1 to 1:5 and more preferably 2:1 to 1:2.

Electron Injecting Layer and Electron Transporting Layer

The electron injecting layer or the electron transporting layer is a layer that aids the injection of electrons into the light emitting layer, and has a large electron mobility. The electron injecting layer is provided for adjusting an energy level, for example, for reducing an abrupt change in energy level.

It is preferred that the organic EL device of the present invention comprises an electron injecting layer between the light emitting layer and the cathode, and the electron injecting layer comprises a nitrogen-containing ring derivative as a main component. The electron injecting layer may function as the electron transporting layer.

The phrase "as a main component" used herein means that the content of the nitrogen-containing ring derivative in the electron injecting layer is 50 mass % or more.

An aromatic heterocyclic compound having one or more heteroatoms in a molecule thereof is preferably used as an electron transporting material used in the electron injecting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

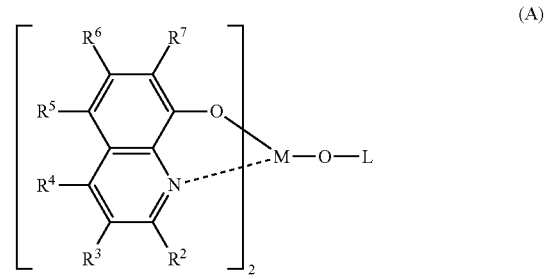

(A)

wherein each of $R^2$ to $R^7$ independently represents a hydrogen atom, a deuterium atom, a halogen atom, a hydroxyl group, an amino group, a hydrocarbon group having 1 to 40 carbon atoms, an alkoxy group, an aryloxy group, an alkoxycarbonyl group, or an aromatic heterocyclic group, each being optionally substituted.

The halogen atom may include fluorine, chlorine, bromine, and iodine. The substituted amino group may include an alkylamino group, an arylamino group, and an aralkylamino group.

The alkoxycarbonyl group is represented by —COOY', wherein Y is selected from the alkyl groups mentioned above. The alkylamino group and the aralkylamino group are represented by —NQ$^1$Q$^2$. Examples and preferred examples of $Q^1$ and $Q^2$ are independently selected from the alkyl groups and aralkyl groups mentioned above. One of Q and $Q^2$ may be a hydrogen atom or a deuterium atom.

The arylamino group is represented by —NAr$^1$Ar$^2$, wherein Ar$^1$ and Ar$^2$ are independently selected from the non-fused aromatic hydrocarbon groups or the fused aromatic hydrocarbon groups mentioned above. One of Ar$^1$ and Ar$^2$ may be a hydrogen atom or a deuterium atom.

M is aluminum (Al), gallium (Ga), or indium (In), with In being preferred.

L in formula (A) is a group represented by formula (A') or (A"):

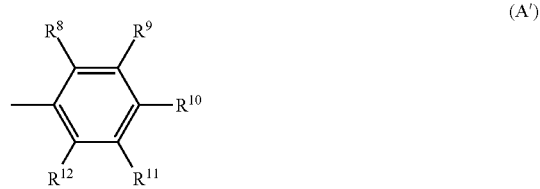

(A')

-continued (A″)

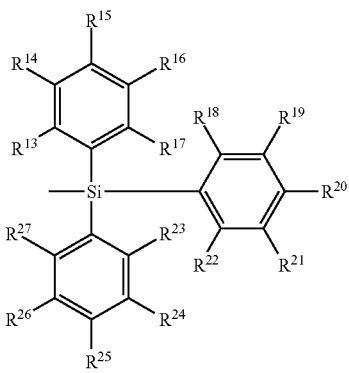

wherein each $R^5$ to $R^{12}$ independently represents a hydrogen atom, a deuterium atom, or a substituted or unsubstituted hydrocarbon group having 1 to 40 carbon atoms. The adjacent two groups may form a ring structure. Each of $R^{13}$ to $R^{27}$ independently represents a hydrogen atom, a deuterium atom, or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A″) are the same as those described above with respect to $R^2$ to $R^7$ of formula (A).

Examples of the divalent group formed by the adjacent two groups of $R^5$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron injecting layer or the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

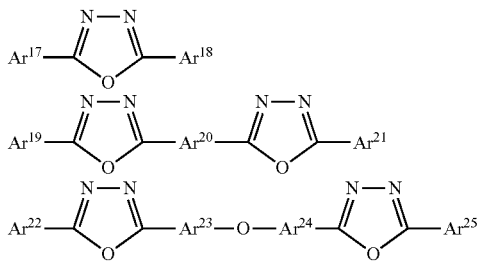

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group, and $Ar^{23}$ and $Ar^{24}$ may be the same or different.

Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

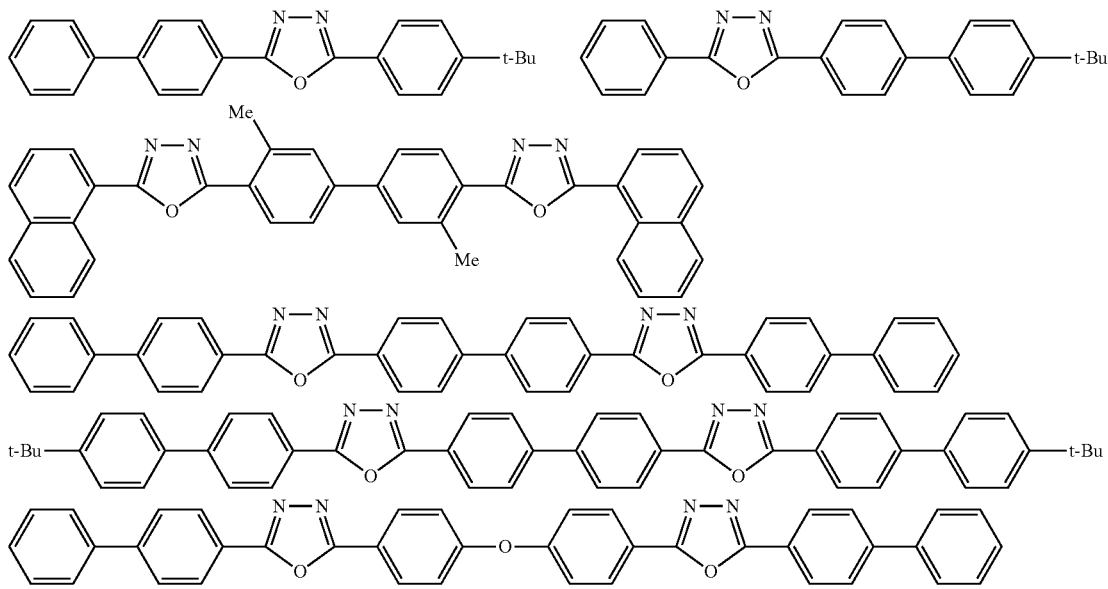

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

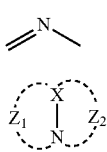

(B)

(C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

(D)

The nitrogen-containing group of the nitrogen-containing aromatic polycyclic compound is selected, for example, from the nitrogen-containing heterocyclic groups shown below:

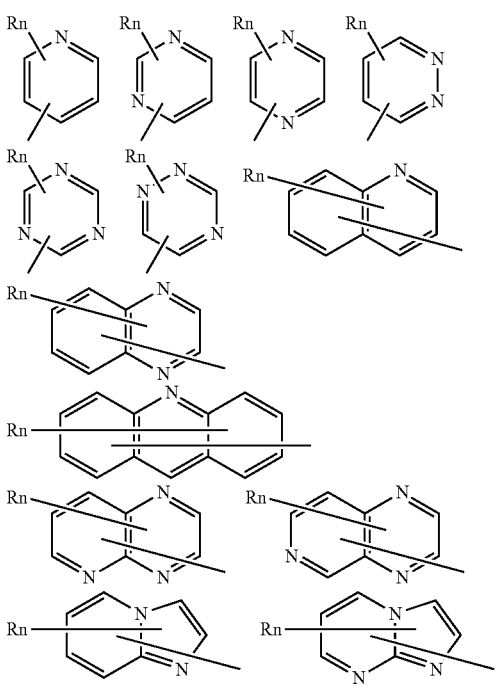

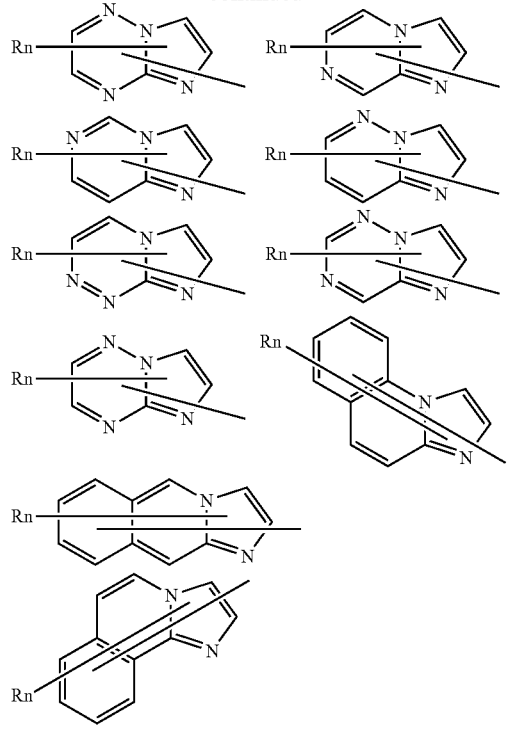

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 3 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

HAr-$L^1$-$Ar^1$—$Ar^2$ wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

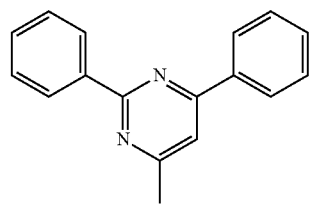

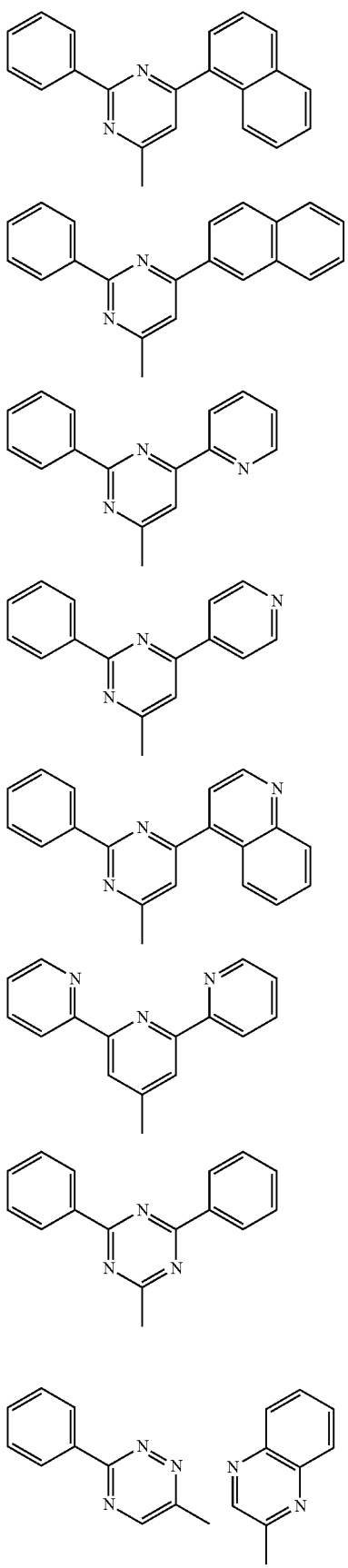
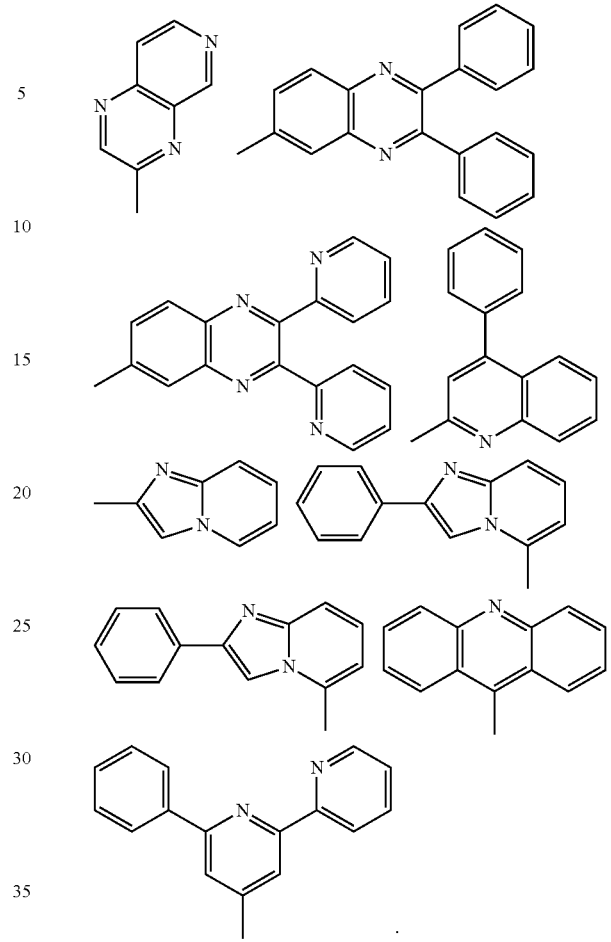
$L^1$ is selected, for example, from the following groups:
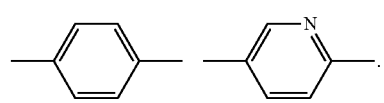
$Ar^1$ is selected, for example, from the following arylanthranyl groups:
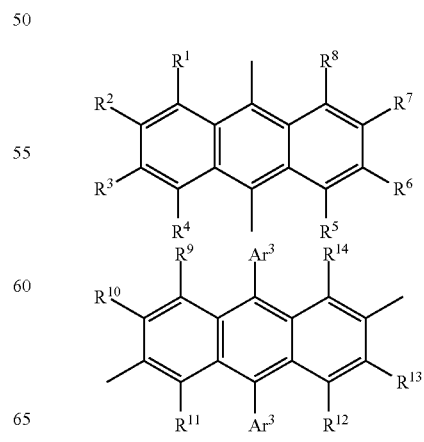

wherein $R^1$ to $R^{14}$ are each independently a hydrogen atom, a deuterium atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

$R^1$ to $R^3$ may be all selected from a hydrogen atom and a deuterium atom.

$Ar^2$ is selected, for example, from the following groups:

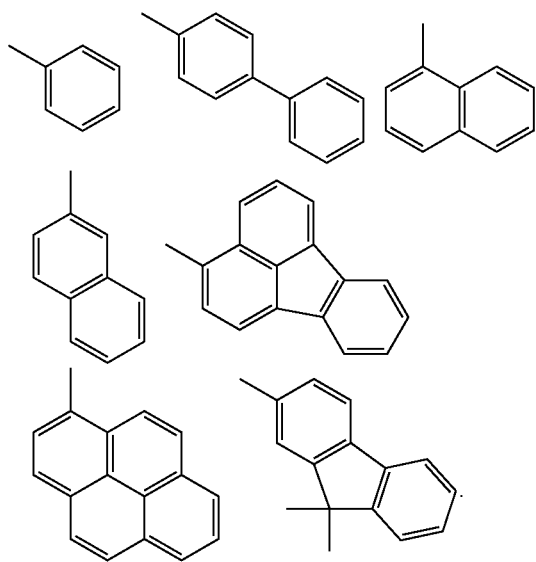

In addition, the following compound (refer to JP 9-3448A) is preferably used as the nitrogen-containing aromatic polycyclic compound for use as the electron transporting compound:

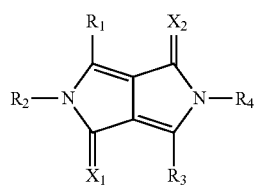

wherein $R_1$ to $R_4$ each independently represent a hydrogen atom, a deuterium atom, a substituted or unsubstituted aliphatic group, a substituted or unsubstituted alicyclic group, a substituted or unsubstituted aromatic hydrocarbon group, or a substituted or unsubstituted heterocyclic group; and $X_1$ and $X_2$ each independently represent an oxygen atom, a sulfur atom, or dicyanomethylene group.

Further, the following compound (refer to JP 2000-173774A) is also suitable as the electron transporting compound:

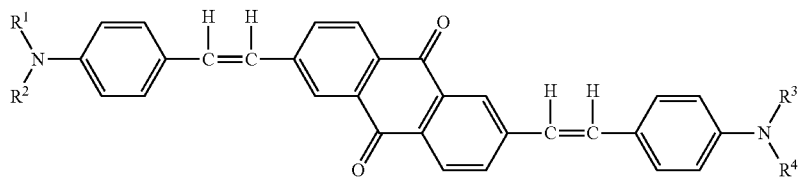

wherein $R^1$, $R^2$, $R^3$, and $R^4$ may be the same or different and each represents an aromatic hydrocarbon group or a fused aromatic hydrocarbon group each represented by the following formula:

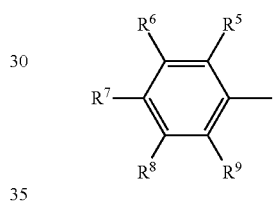

wherein $R^5$, $R^6$, $R^7$, $R^8$, and $R^9$ may be the same or different and each represents a hydrogen atom or a deuterium atom, and at least one of $R^5$, $R^6$, $R^7$, $R^8$, and $R^9$ represents a saturated or unsaturated alkoxyl group, alkyl group, amino group, or alkylamino group.

Further, a polymer having the nitrogen-containing heterocyclic group or the nitrogen-containing heterocyclic derivative is also usable as the electron transporting compound.

The electron transporting layer preferably comprises at least one compound selected from the nitrogen-containing heterocyclic derivatives represented by formulae (201) to (203):

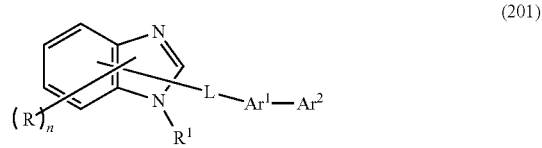

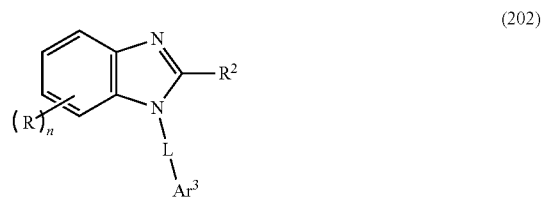

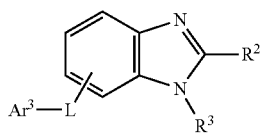
(203)

wherein R is a hydrogen atom, a heavy hydrogen atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms;

n is an integer of 0 to 4;

$R^1$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or an alkoxy group having 1 to 20 carbon atoms;

$R^2$ and $R^3$ are each independently a hydrogen atom, a heavy hydrogen atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms;

L is a substituted or unsubstituted aromatic hydrocarbon group or fused aromatic hydrocarbon group having 6 to 60 carbon atoms, a substituted or unsubstituted pyridnylene group, a substituted or unsubstituted quinolinylene group, or a substituted or unsubstituted fluorenylene group;

$Ar^1$ is a substituted or unsubstituted aromatic hydrocarbon group or fused aromatic hydrocarbon group having 6 to 60 carbon atoms, a substituted or unsubstituted pyridnylene group, or a substituted or unsubstituted quinolinylene group;

$Ar^2$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms; and $Ar^3$ is a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, a substituted or unsubstituted alkoxy group having 1 to 20 carbon atoms, or a group represented by $-Ar^1-Ar^2$ wherein $Ar^1$ and $Ar^2$ are as defined above.

In formulae (201) to (203), R is hydrogen atom, a heavy hydrogen atom, a substituted or unsubstituted aromatic hydrocarbon group or fused aromatic hydrocarbon group having 6 to 60 carbon atoms, a substituted or unsubstituted pyridyl group, a substituted or unsubstituted quinolyl group, a substituted or unsubstituted alkyl group having 1 to 20 carbon atoms, or a substituted or unsubstituted alkoxy group having 1 to 20 carbon atoms.

The thickness of the electron injecting layer and the electron transporting layer is preferably, but not particularly limited to, 1 to 100 nm.

It is preferred that the electron injecting layer comprises an inorganic compound, such as an insulating material and a semiconductor, in addition to the nitrogen-containing ring derivative. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced.

Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the reducing dopant mentioned above.

Hole Injecting Layer and Hole Transporting Layer

The hole injecting layer or the hole transporting layer (inclusive of a hole injecting/transporting layer) preferably comprises an aromatic amine compound, for example, an aromatic amine derivative represented by formula (I):

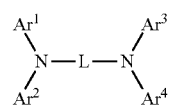

(1)

wherein each of $Ar^1$ to $Ar^4$ is a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group.

Examples of the compound represented by formula (I) are shown below, although not limited thereto.

381
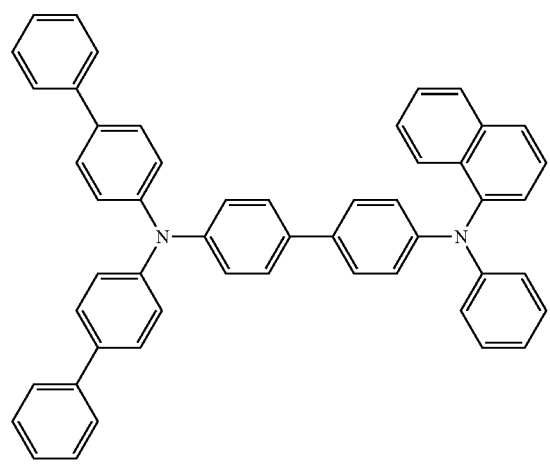
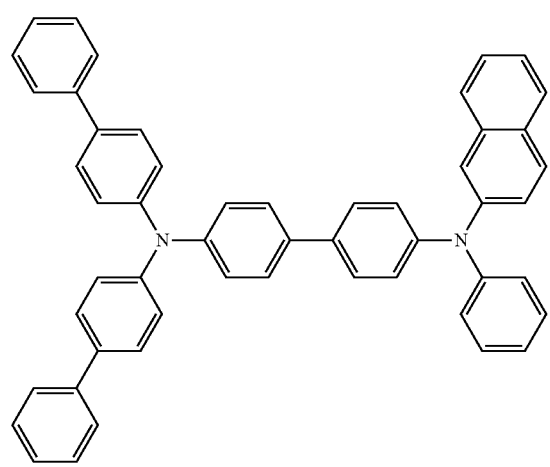
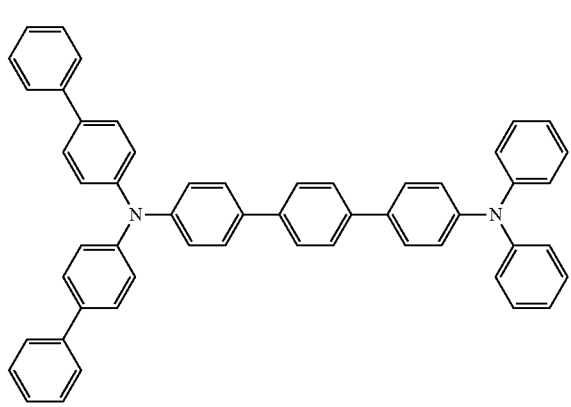
382
-continued
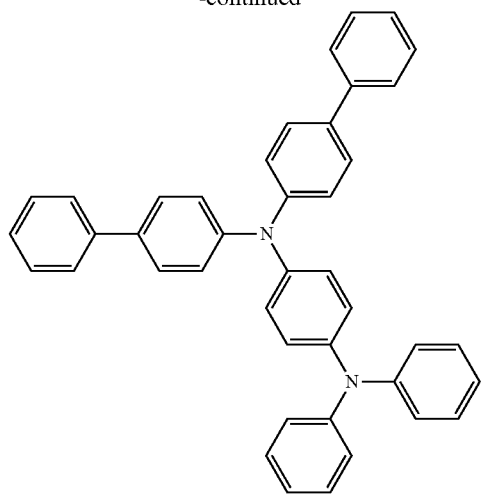
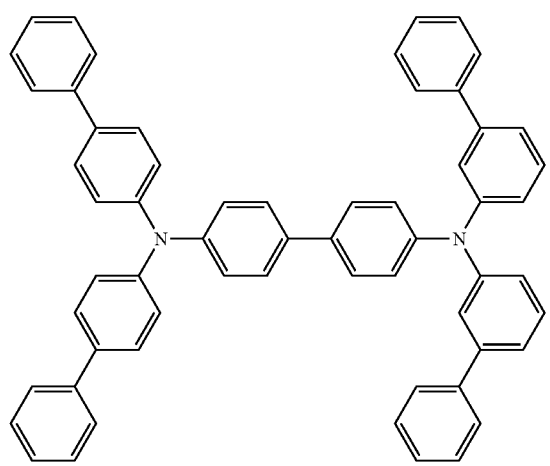
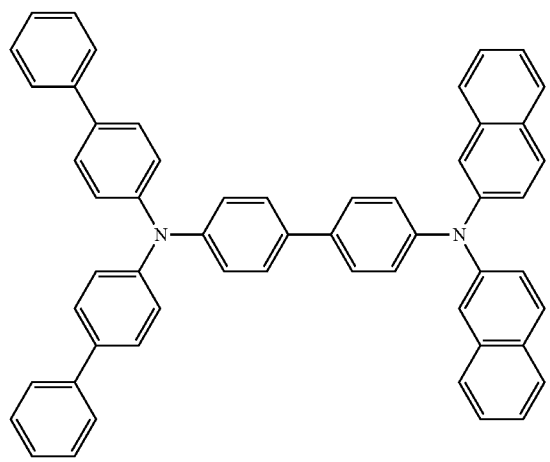

383
-continued
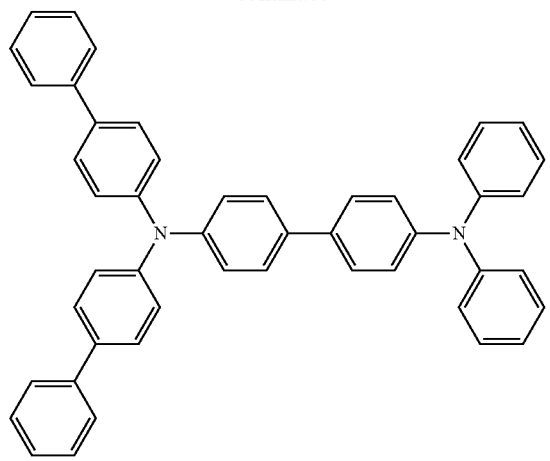
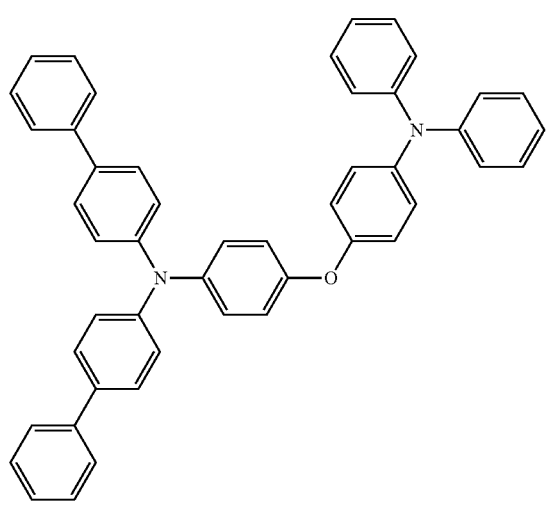
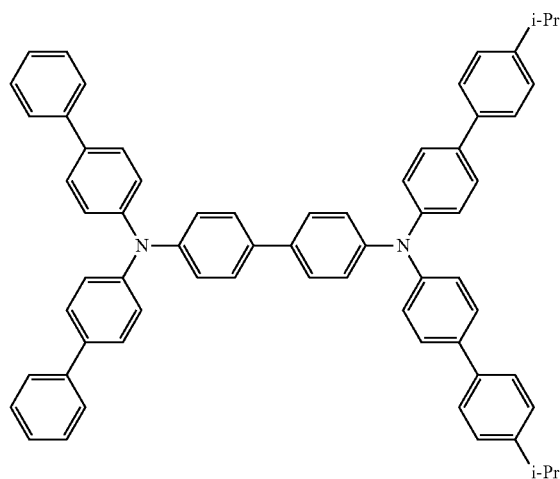
384
-continued
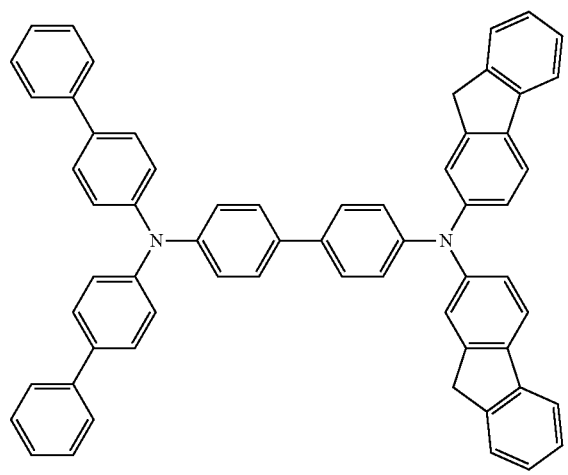
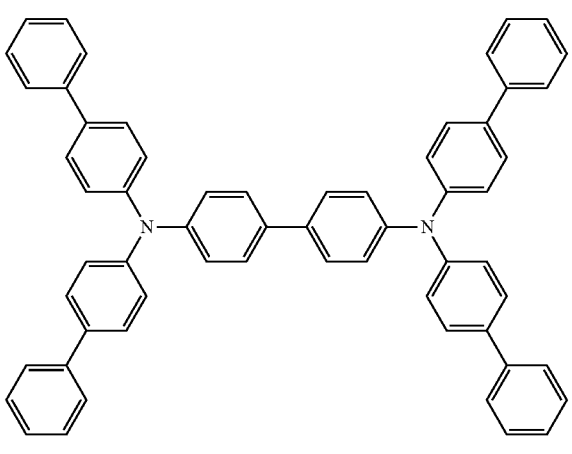

385
-continued
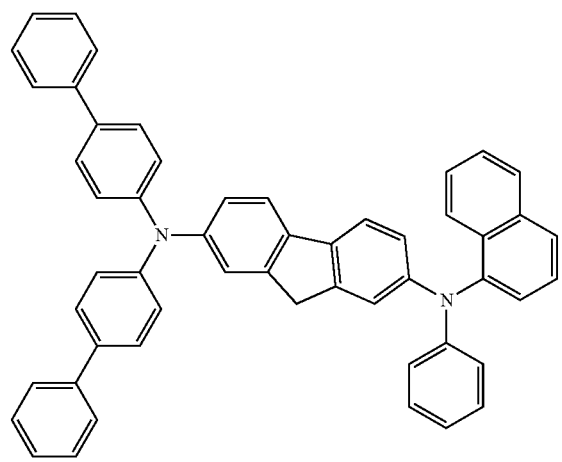
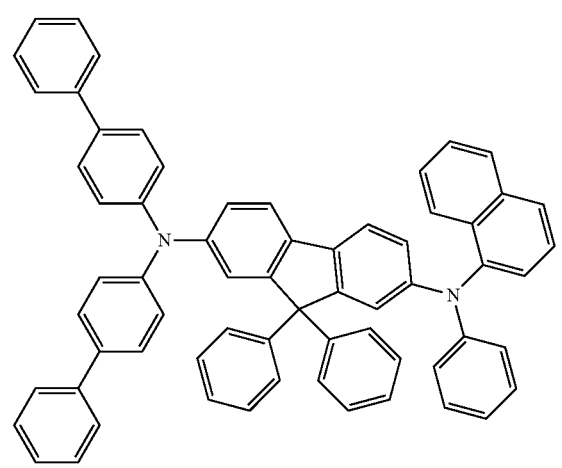
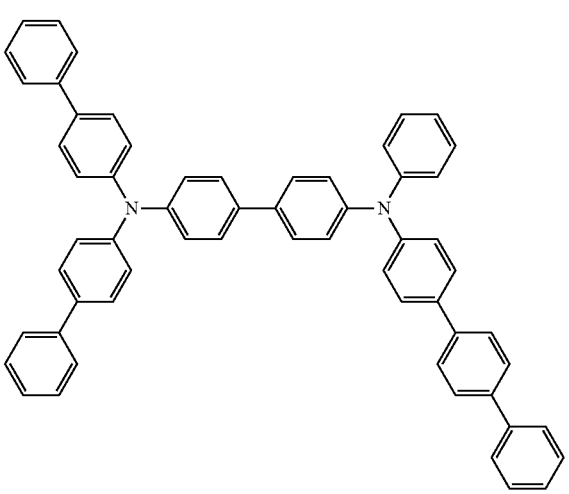
386
-continued
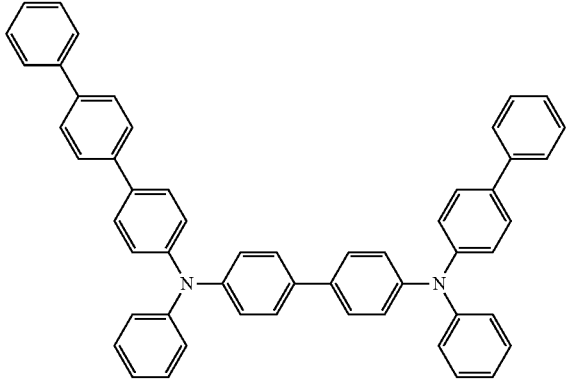
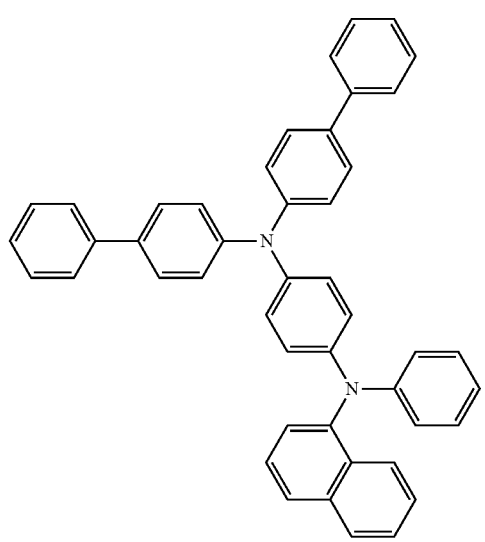
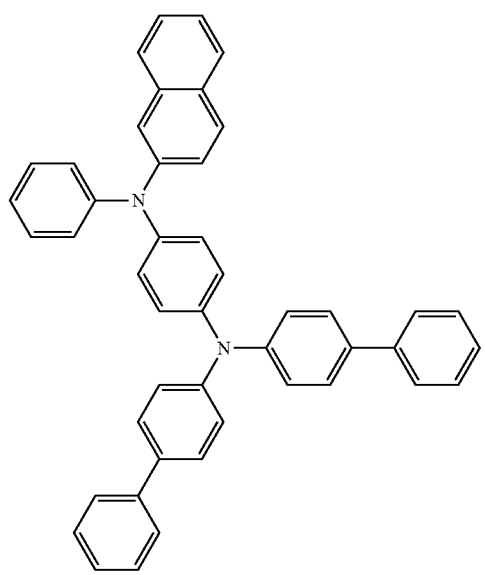

387
-continued
388
-continued
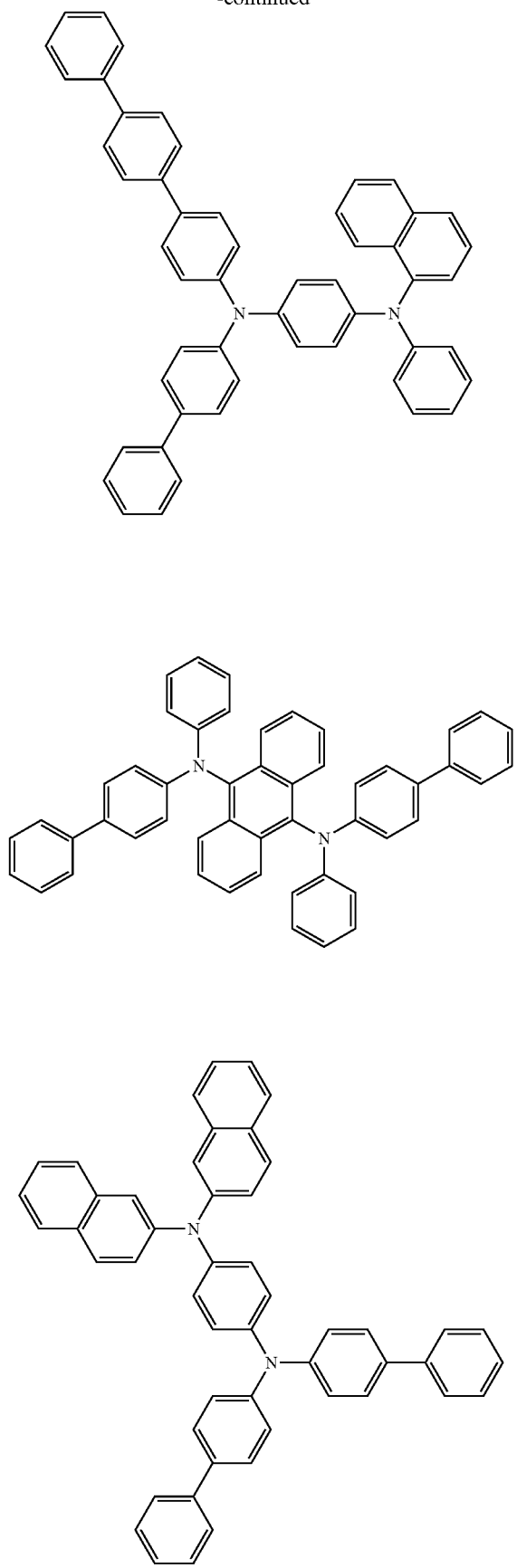
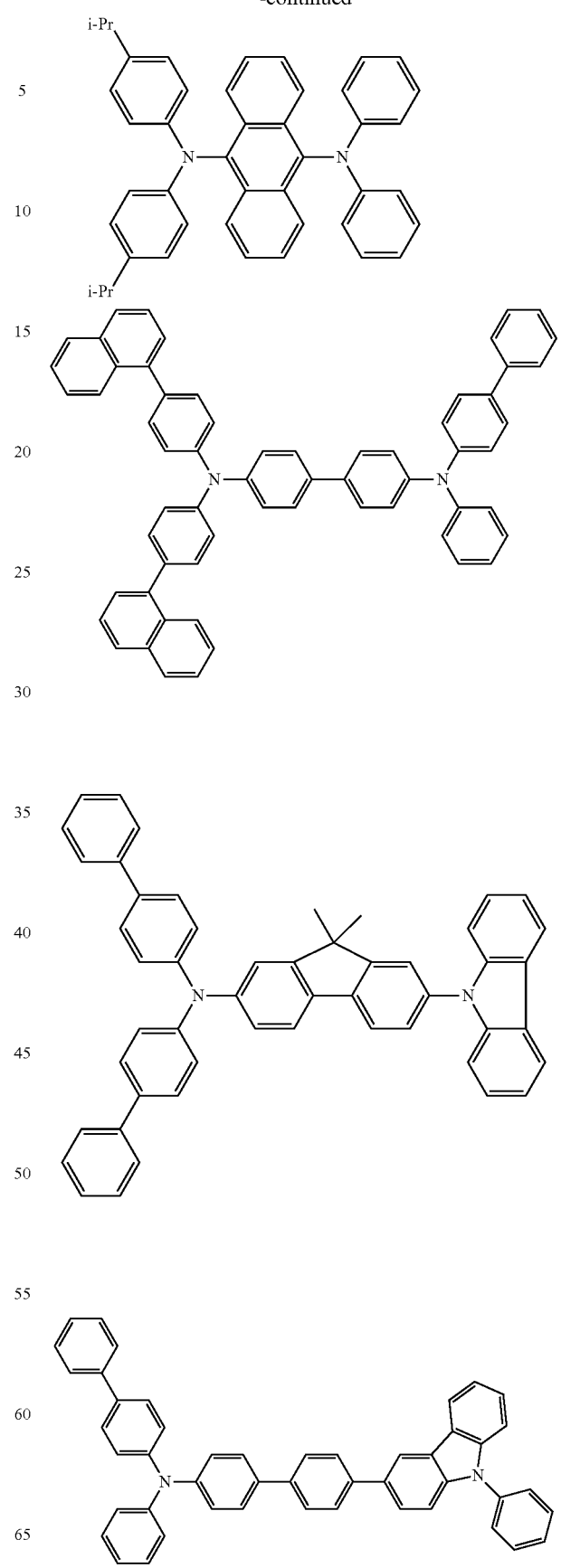

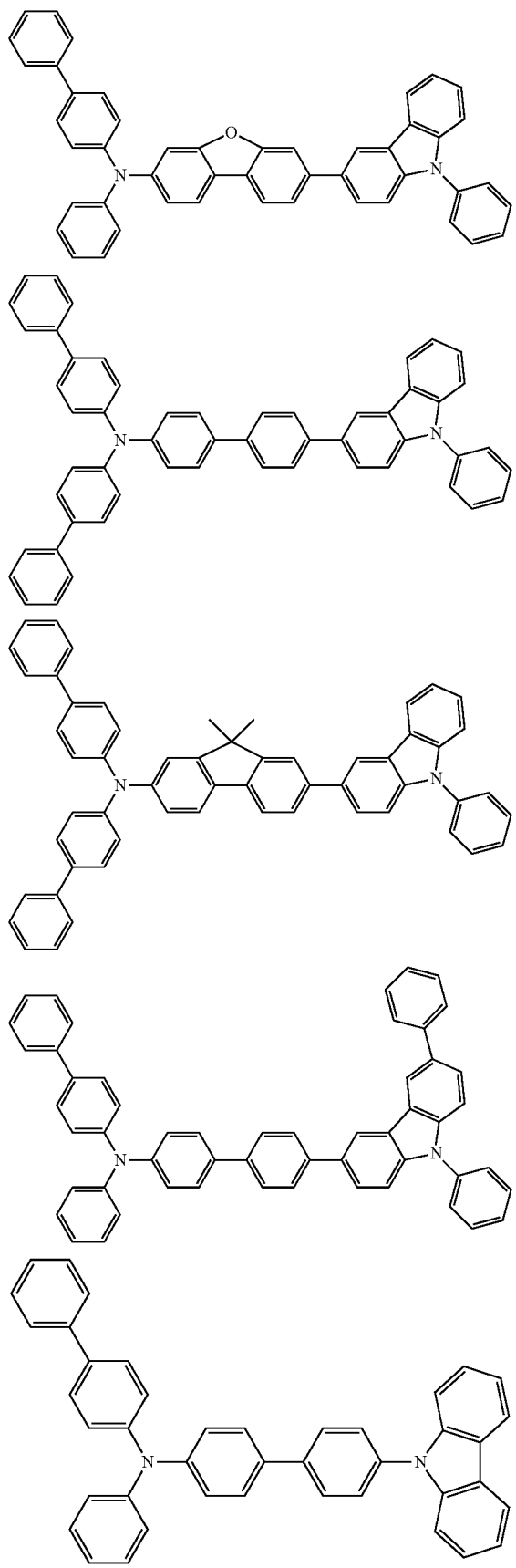
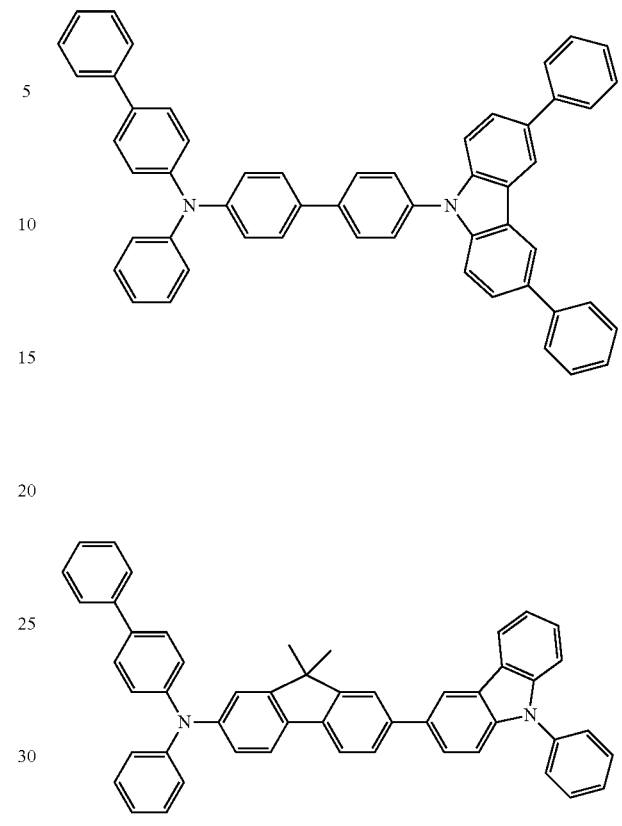
An aromatic amine represented by formula (II) is also preferably used to form the hole injecting layer or the hole transporting layer:
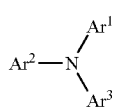
(II)
wherein $Ar^1$ to $Ar^3$ are the same as defined with respect to $Ar^1$ to $Ar^4$ of formula (I). Examples of the compound represented by formula (II) are shown below, although not limited thereto.
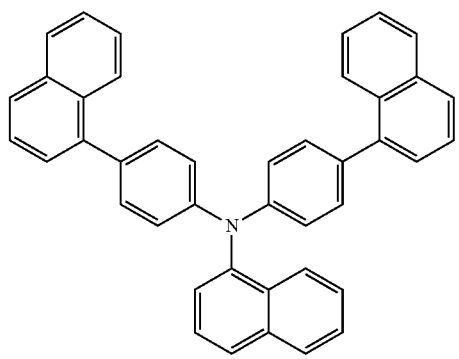

391
-continued
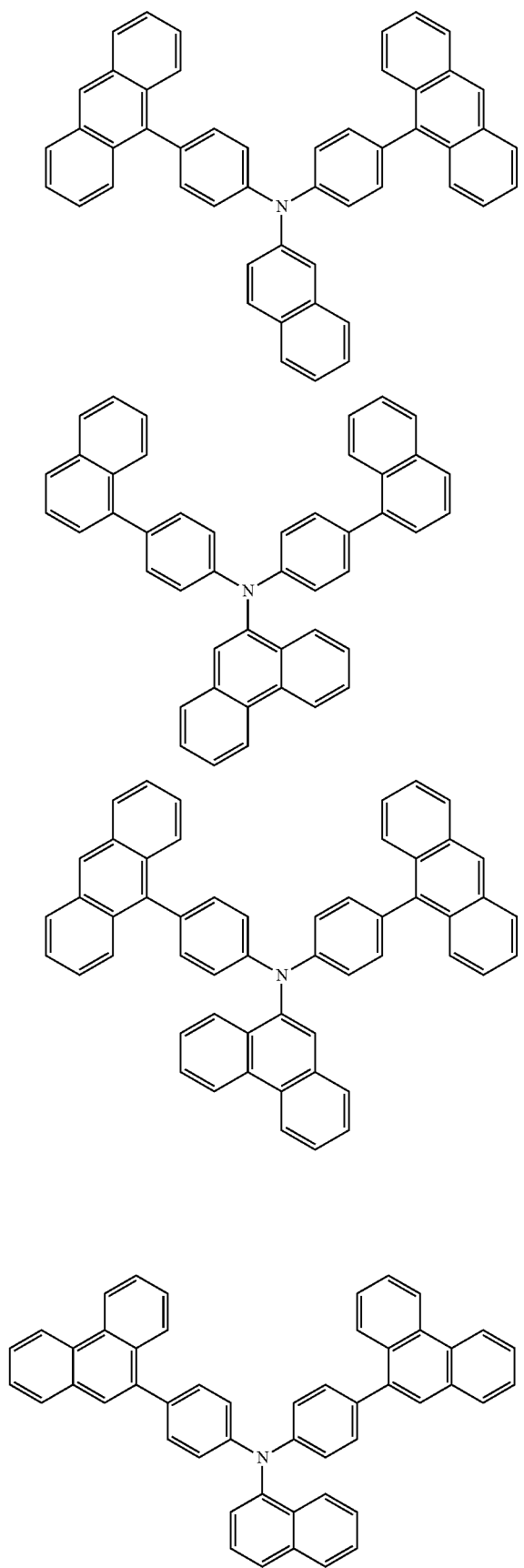
392
-continued
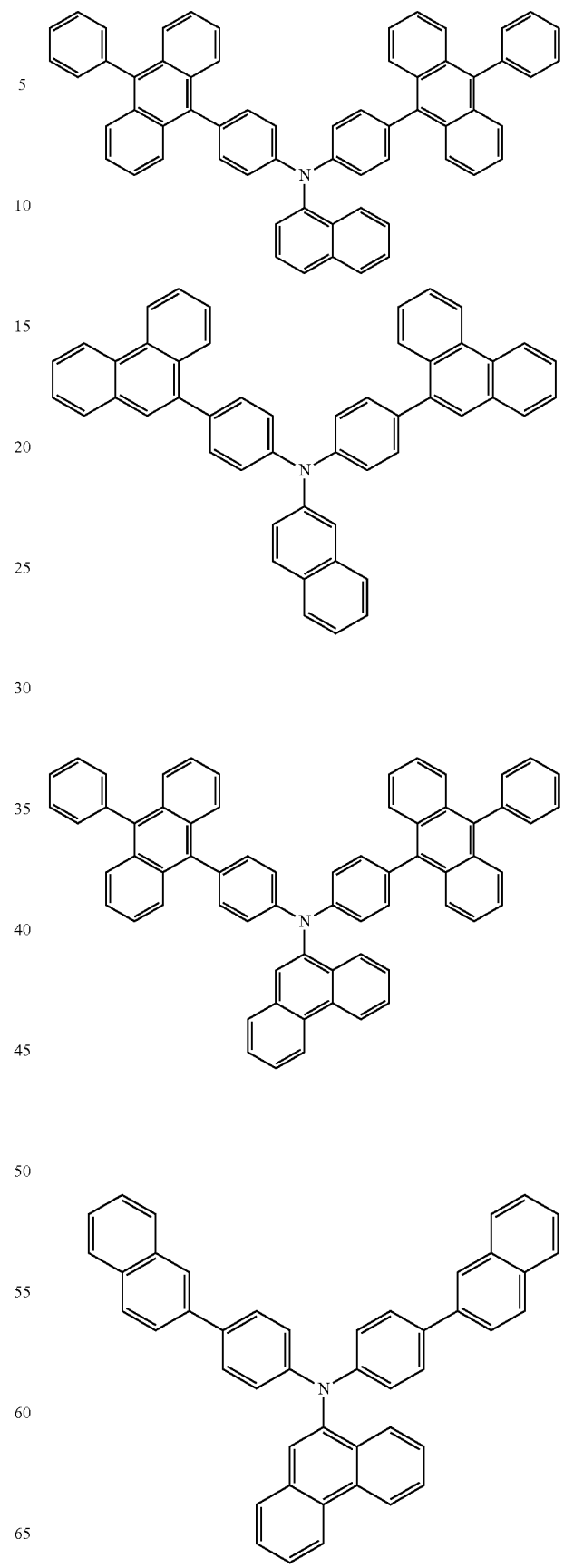

393
-continued
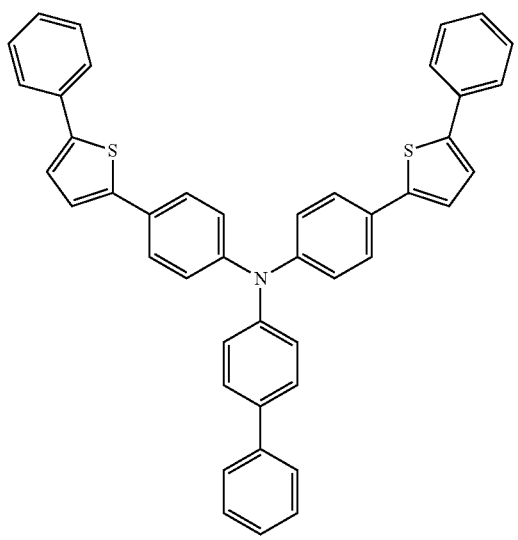
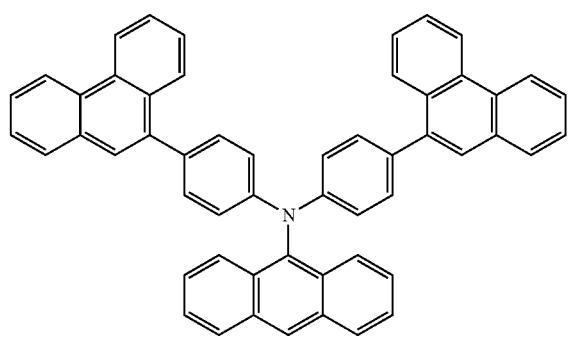
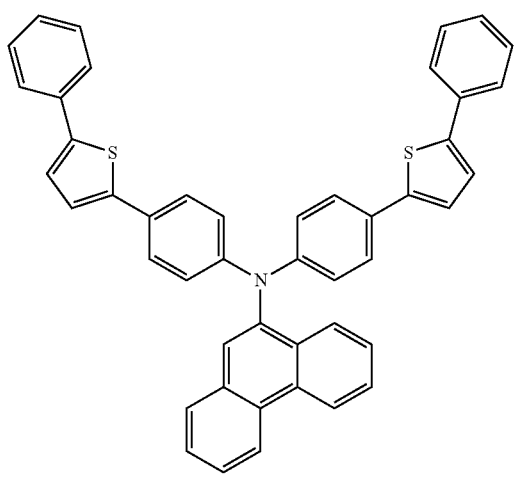
394
-continued
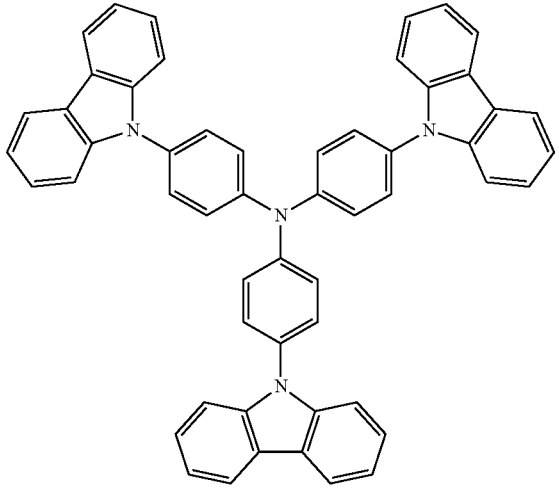
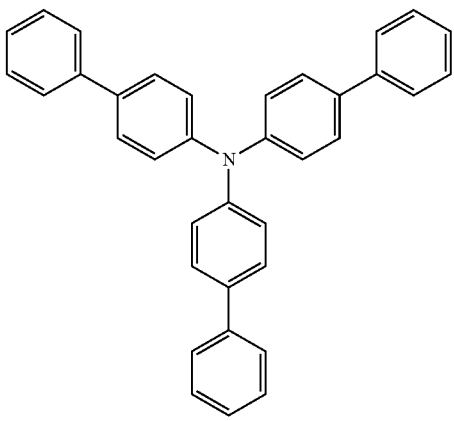
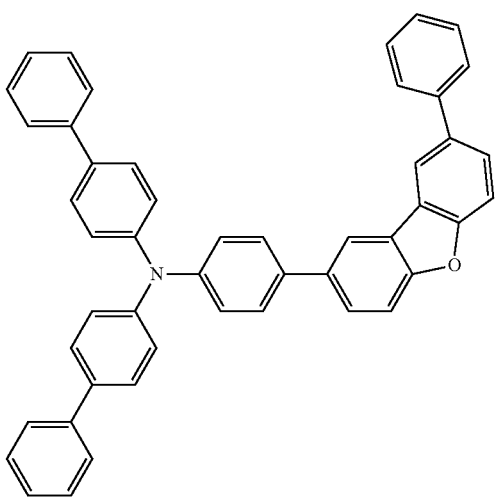

-continued

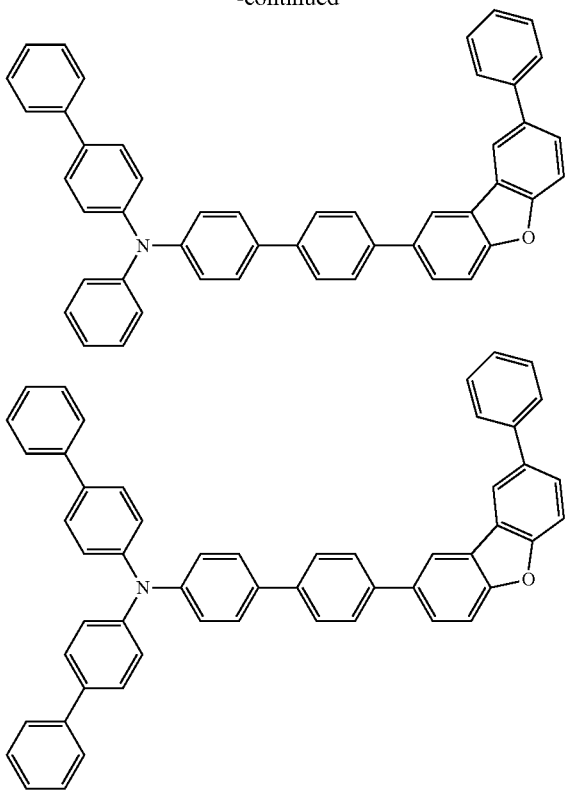

It should be noted that the present invention is not limited to those described above and it will be understood that variations and modifications can be effected within the spirit and scope of the invention.

For example, the following embodiment is one of preferred modifications of the invention.

In the present invention, the light emitting layer preferably comprises a charge injection aid.

When a host material having a wide energy gap is used in the light emitting layer, the difference between the ionization potential (Ip) of the host material and Ip of the hole injecting/transporting layer, etc. becomes large, this making the hole injection into the light emitting layer difficult to likely to increase the driving voltage for obtaining a sufficient luminance.

By adding a hole injecting/transporting charge injection aid into the light emitting layer, the hole injection into the light emitting layer is facilitated and the driving voltage can be reduced.

For example, a hole injecting/transporting material generally known can be use as the charge injection aid.

Examples thereof include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a fluorenone derivative, a hydrazone derivative, a stilbene derivative, a silazane derivative, a polysilane-based copolymer, an aniline-based copolymer, and an electroconductive high-molecular oligomer (particularly, thiophene oligomer).

In addition to the above hole injecting materials, a porphyrin compound, an aromatic tertiary amine compound, and a styryl amine compound are also preferably used, with an aromatic tertiary amine compound being particularly preferred.

Also usable are a compound having two fused aromatic rings in its molecule, for example, 4,4'-bis(N-(1-naphthyl)-N-phenylamino)biphenyl (NPD), and a compound having three triphenylamine units connected in star burst configuration, for example, 4,4',4"-tris (N-(3-methylphenyl)-N-phenylamino)triphenylamine (MTDATA).

Further, a hexaazatriphenylene derivative is preferably used as the hole injecting material.

An inorganic compound, such as p-type Si and p-type SiC, is also usable as the hole injecting material.

Each layer of the organic EL device of the invention may be formed by any one of known methods such as a vacuum vapor deposition method and a spin coating method, although not particularly limited. The organic thin-film layer containing the compound represented by formulae (1) to (4) and (1') in the organic EL device is formed by a known method such as a vacuum vapor deposition method, a molecular beam epitaxy method (MBE method) and a coating method, for example, a dipping method, a spin coating method, a casting method, a bar coating method and a roll coating method each using a solution of the compound in a solvent.

The thickness of each organic thin film layer in the organic EL device of the invention is not particularly limited and preferably several nanometers to 1 μm because an excessively small thickness may cause defects such as pin holes and an excessively large thickness may require a high driving voltage.

EXAMPLES

The present invention will be described in more detail with reference to the examples and comparative examples. However, it should be noted that the scope of the invention is not limited to the following examples.

Synthesis Example 1-1 (Synthesis of Compound 1-1)

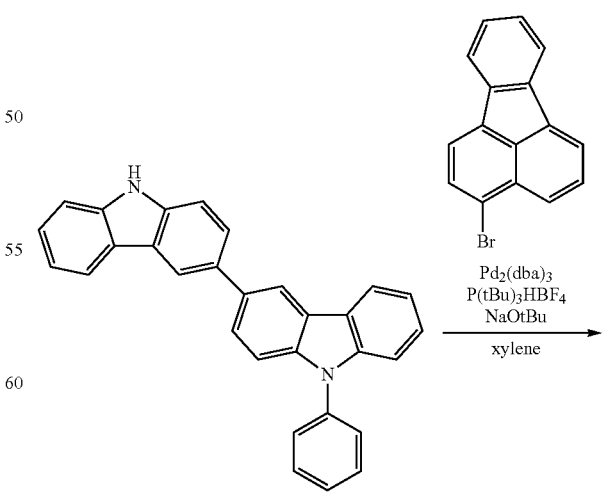

Intermediate 1-1

-continued

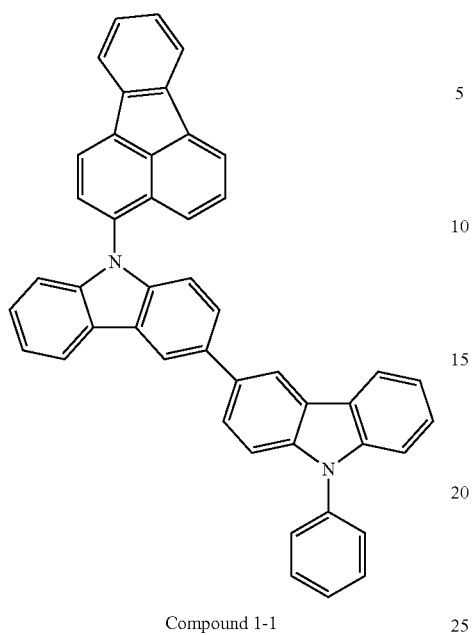

Compound 1-1

-continued

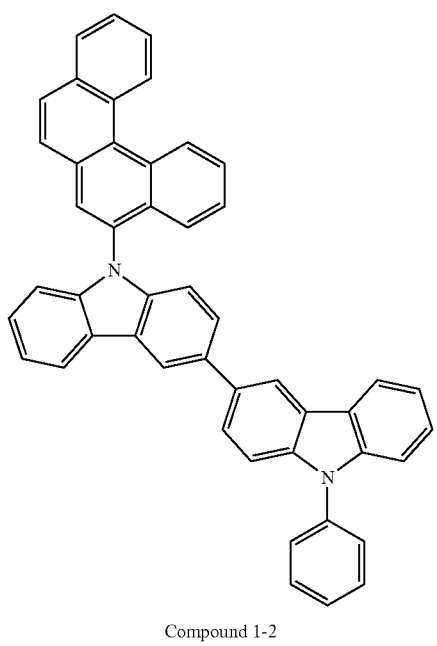

Compound 1-2

In an argon atmosphere, 3-bromofluoranthene (2.3 g, 8.1 mmol), Intermediate 1-1 (3 g, 7.3 mmol), Pd$_2$(dba)$_3$ (0.14 g, 0.15 mmol), P(tBu)$_3$HBF$_4$ (0.17 g, 0.6 mmol), sodium t-butoxide (1.1 g, 11 mmol), and dry xylene (30 mL) were charged in a three-necked flask in this order, and the resultant mixture was refluxed under heating for 8 h.

The solid generated by adding water to the reaction liquid was successively washed with hexane and methanol and then purified by silica gel column chromatography, to obtain Compound 1-1 (2.9 g, yield: 65%).

FD-MS analysis: m/e=608 for molecular weight of 608.

Synthesis Example 1-2 (Synthesis of Compound 1-2)

The procedure of Synthesis Example 1-1 was repeated except for using Intermediate 1-2 (2.5 g, 8.1 mmol) in place of 3-bromofluoranthene and toluene (30 mL) in place of xylene, to obtain Compound 1-2 (3.3 g, yield: 71%).

FD-MS analysis: m/e=634 for molecular weight of 634.

Synthesis Example 1-3 (Synthesis of Compound 1-3)

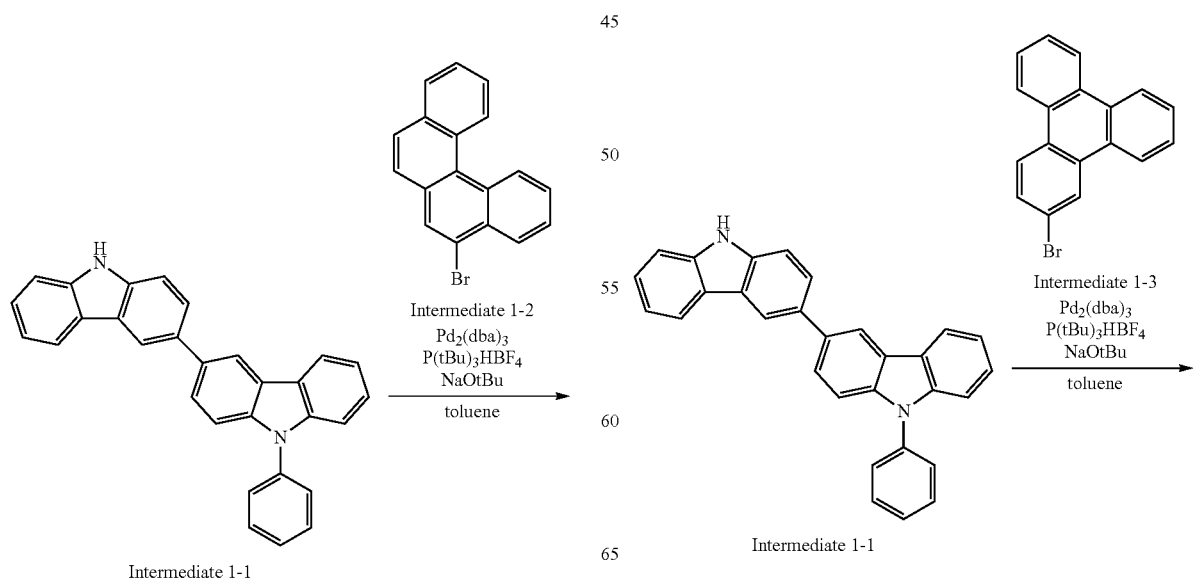

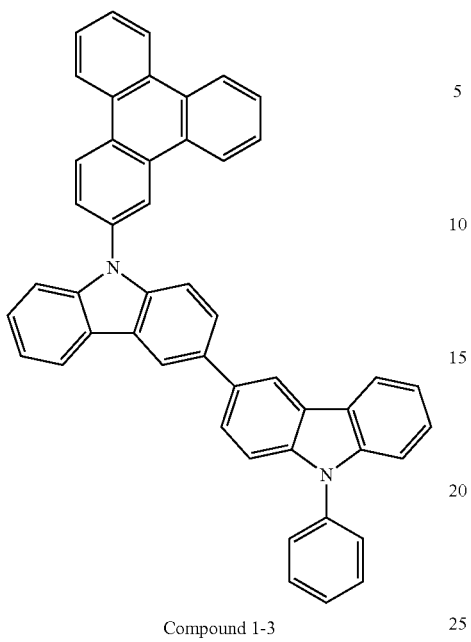

Compound 1-3

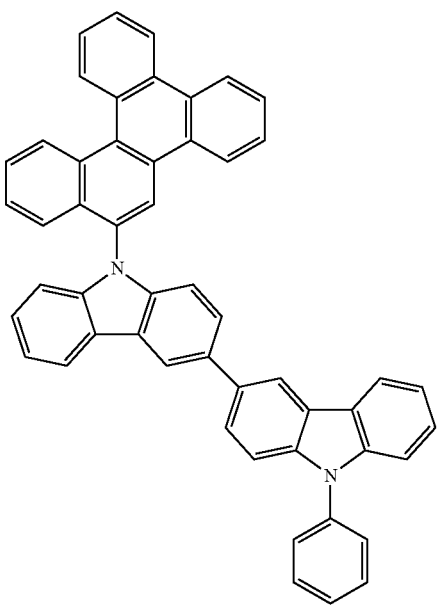

Compound 1-4

The procedure of Synthesis Example 1-2 was repeated except for using Intermediate 1-3 (2.5 g, 8.1 mmol) in place of Intermediate 1-2, to obtain Compound 1-3 (3.7 g, yield: 80%).

FD-MS analysis: m/e=634 for molecular weight of 634.

The procedure of Synthesis Example 1-2 was repeated except for using Intermediate 1-4 (2.89 g, 8.1 mmol) in place of Intermediate 1-2, to obtain Compound 1-4 (3.1 g, yield: 63%).

FD-MS analysis: m/e=684 for molecular weight of 684.

Synthesis Example 1-4 (Synthesis of Compound 1-4)

Synthesis Example 1-5 (Synthesis of Compound 1-5)

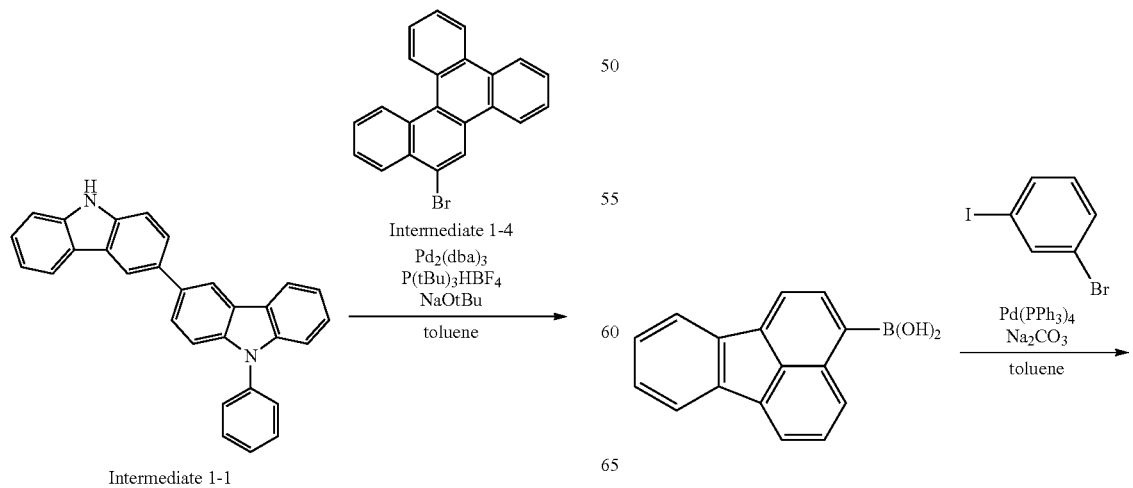

-continued

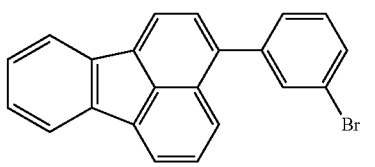
Intermediate 1-5

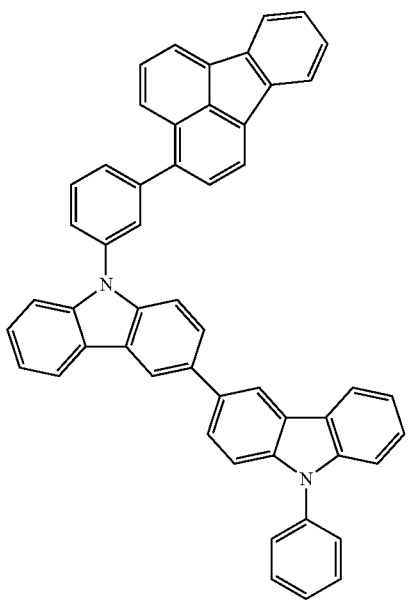
Compound 1-5

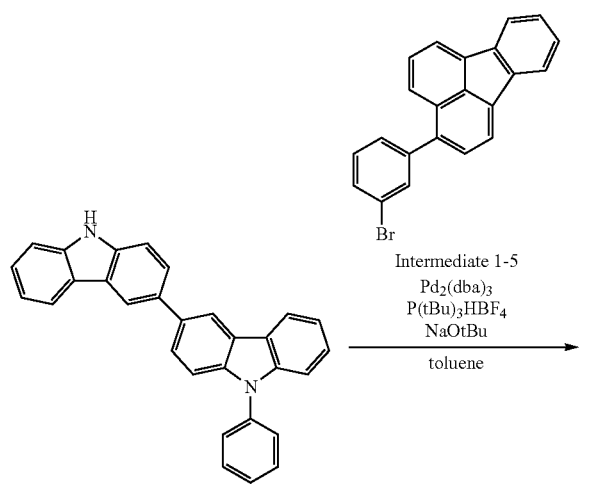

In an argon atmosphere, into a mixture of 3-iodobromobenzene (28.3 g, 100.0 mmol), fluoranthene-3-boronic acid (25.8 g, 105 mmol), and tetrakis(triphenylphosphine)palladium(0) (2.31 g, 2.00 mmol), toluene (300 mL) and a 2 M aqueous sodium carbonate solution (150 mL) were added. The resultant mixture was refluxed under heating for 10 h.

Immediately after the reaction, the reaction liquid was filtered and the water layer was removed from the filtrate. The organic layer was dried over sodium sulfate and then concentrated. The residue was purified by silica gel column chromatography to obtain Intermediate 1-5 (31.8 g, yield: 89%).

FD-MS analysis: m/e=356 for molecular weight of 356.

Then, the procedure of Synthesis Example 1-2 was repeated except for using Intermediate 1-5 (2.9 g, 8.1 mmol) in place of Intermediate 1-2, to obtain Compound 1-5 (2.8 g, yield: 56%).

FD-MS analysis: m/e=684 for molecular weight of 684.

Synthesis Example 1-6 (Compound 1-6)

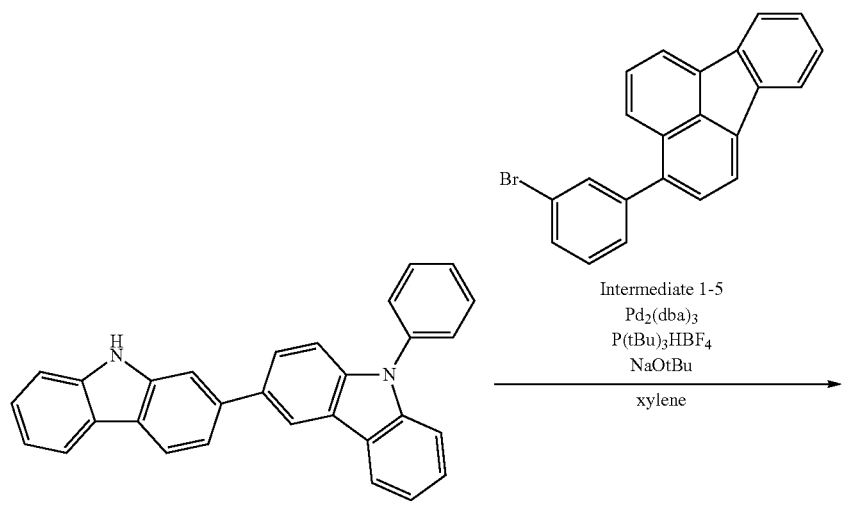

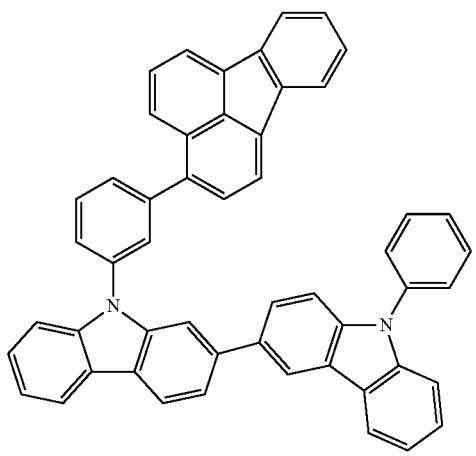

Compound 1-6

In an argon atmosphere, Intermediate 1-5 (2.9 g, 8.1 mmol), Intermediate 1-6 (3 g, 7.3 mmol), $Pd_2(dba)_3$ (0.14 g, 0.15 mmol), $P(tBu)_3HBF_4$ (0.17 g, 0.6 mmol), sodium t-butoxide (1.1 g, 11 mmol), and dry xylene (30 mL) were charged in a three-necked flask in this order, and the resultant mixture was refluxed under heating for 8 h.

The solid generated by adding water to the reaction liquid was successively washed with hexane and methanol and then purified by silica gel column chromatography, to obtain Compound 1-6 (3.6 g, yield: 73%).

FD-MS analysis: m/e=684 for molecular weight of 684.

Synthesis Example 1-7 (Compound 1-7)

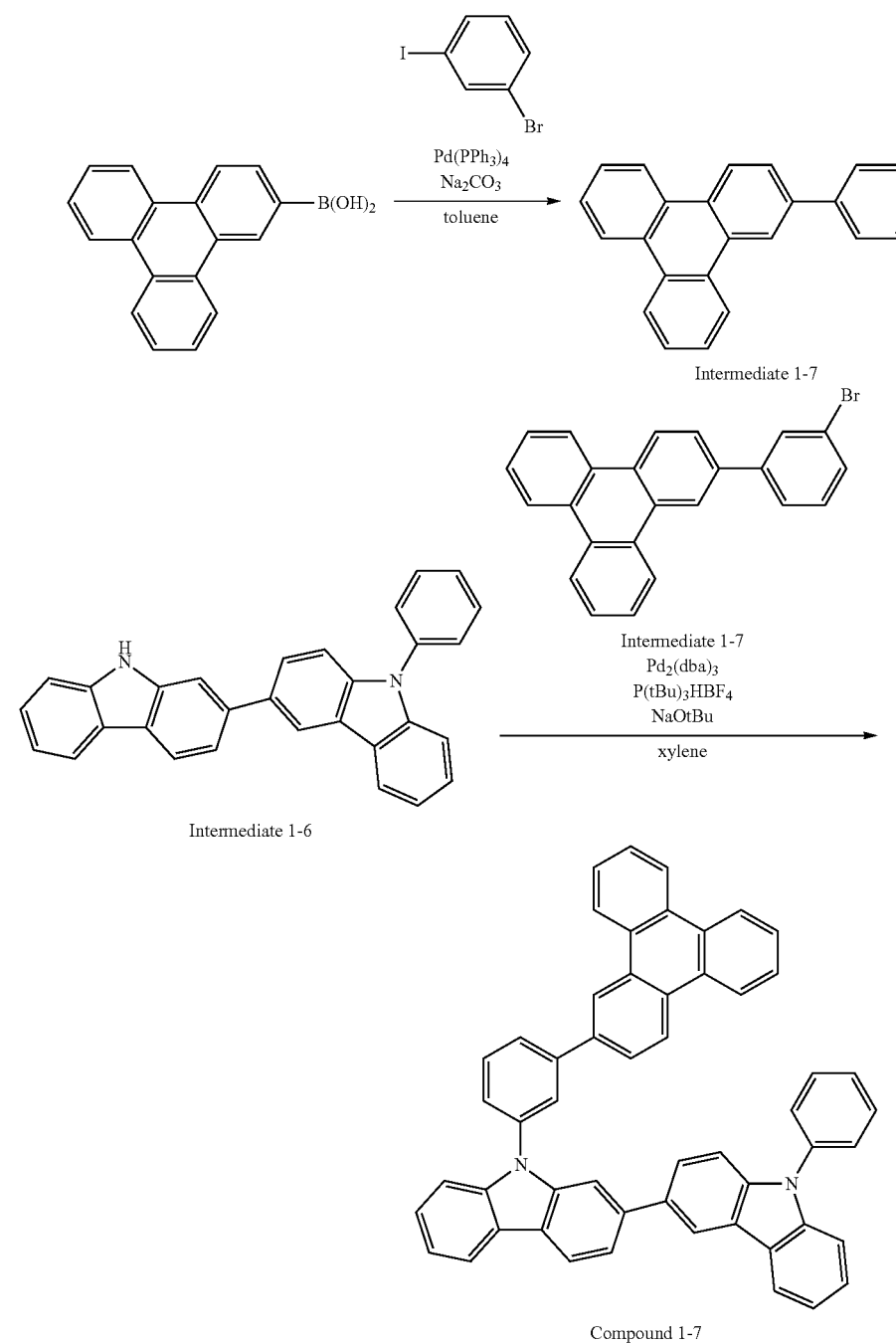

The procedure of synthesizing Intermediate 1-5 was repeated except for using triphenylene-2-boronic acid (28.6 g, 105 mmol) in place of fluoranthene-3-boronic acid, to obtain Intermediate 1-7 (30.6 g, yield: 80%).

Then, the procedure of Synthesis Example 1-6 was repeated except for using Intermediate 1-7 (3.1 g, 8.1 mmol) in place of Intermediate 1-5, to obtain Compound 1-7 (4.4 g, yield: 85%).

FD-MS analysis: m/e=710 for molecular weight of 710.

Synthesis Example 1-8 (Compound 1-8)

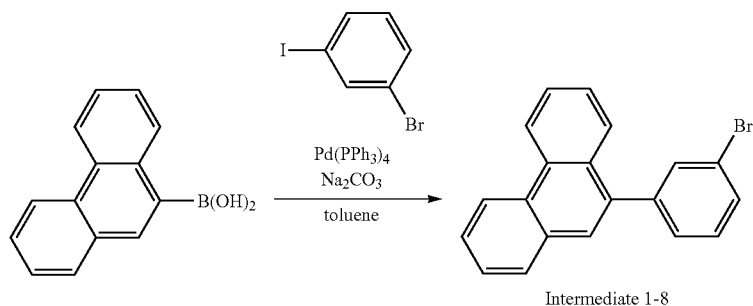

Intermediate 1-8

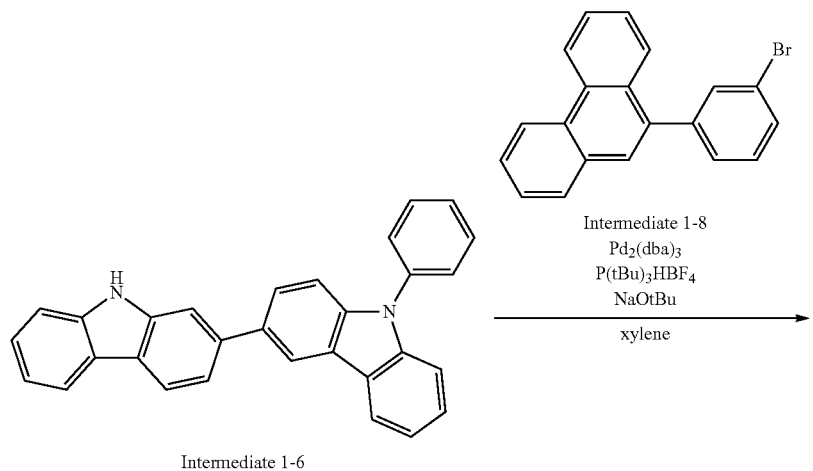

Intermediate 1-6

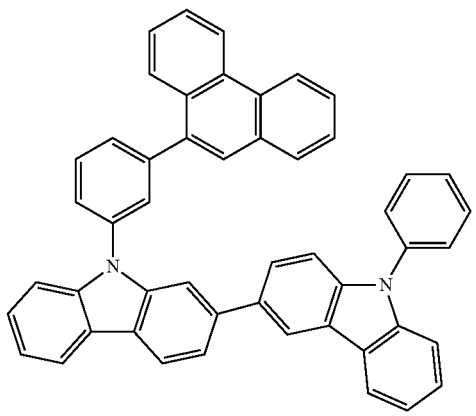

Compound 1-8

The procedure of synthesizing Intermediate 1-5 was repeated except for using phenanthrene-9-boronic acid (23.3 g, 105 mmol) in place of fluoranthene-3-boronic acid, to obtain Intermediate 1-8 (28 g, yield: 84%).

Then, The procedure of Synthesis Example 1-6 was repeated except for using Intermediate 1-8 (2.7 g, 8.1 mmol) in place of Intermediate 1-5, to obtain Compound 1-8 (3.7 g, yield: 77%).

FD-MS analysis: m/e=660 for molecular weight of 660.

Synthesis Example 1-9 (Compound 1-9)

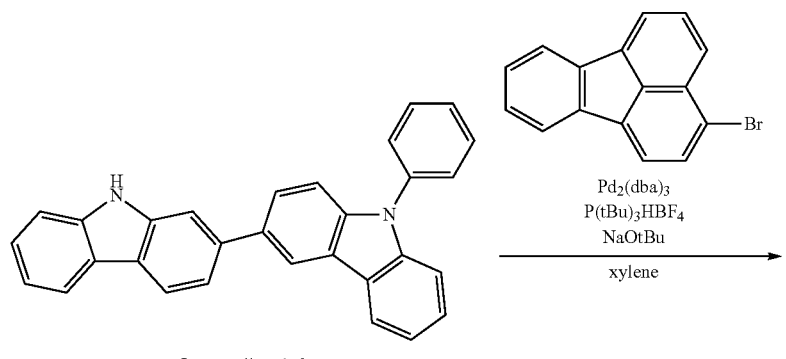

Intermediate 1-6

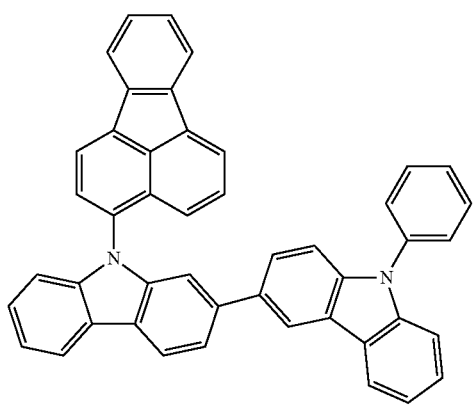

Compound 1-9

The procedure of Synthesis Example 1-1 was repeated except for using Intermediate 1-6 (3 g, 7.3 mmol) in place of Intermediate 1-1, to obtain Compound 1-9 (3.2 g, yield: 72%).

FD-MS analysis: m/e=608 for molecular weight of 608.

Synthesis Example 1-10 (Compound 1-10)

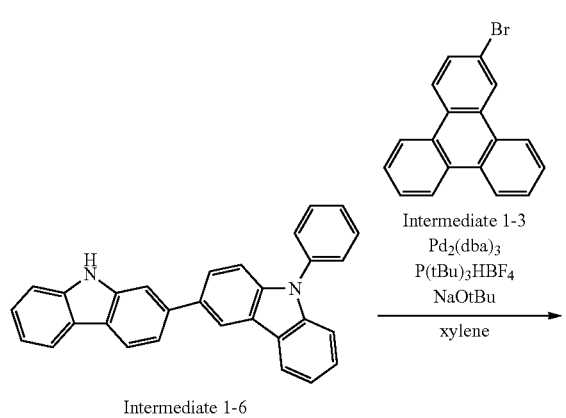

Intermediate 1-6

-continued

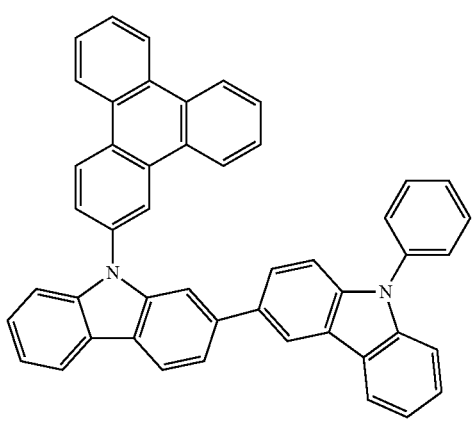

Compound 1-10

Intermediate 1-86 Compound 1-10 The procedure of Synthesis Example 1-3 was repeated except for using Intermediate 1-6 (3 g, 7.3 mmol) in place of Intermediate 1-1, to obtain Compound 1-10 (3.0 g, yield: 65%).

FD-MS analysis: m/e=634 for molecular weight of 634.

Synthesis Example 1-11 (Compound 1-11)
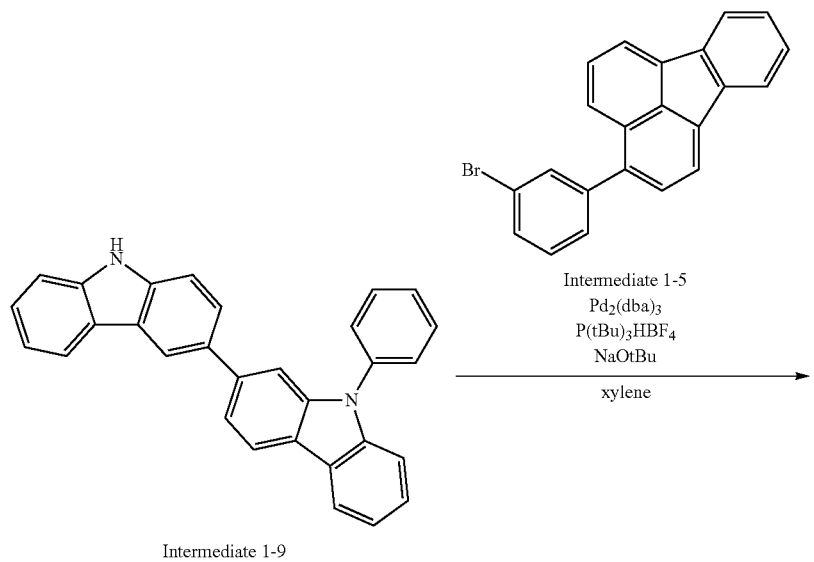
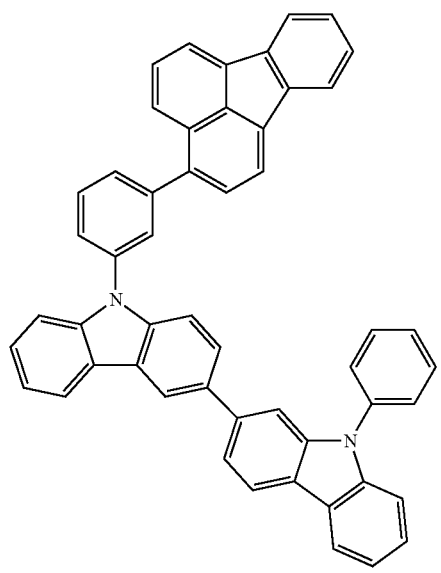
Compound 1-11
The procedure of Synthesis Example 1-6 was repeated except for using Intermediate 1-9 (3 g, 7.3 mmol) in place of Intermediate 1-6, to obtain Compound 1-11 (3.1 g, yield: 62%).
FD-MS analysis: m/e=684 for molecular weight of 684.

Synthesis Example 1-12 (Compound 1-12)
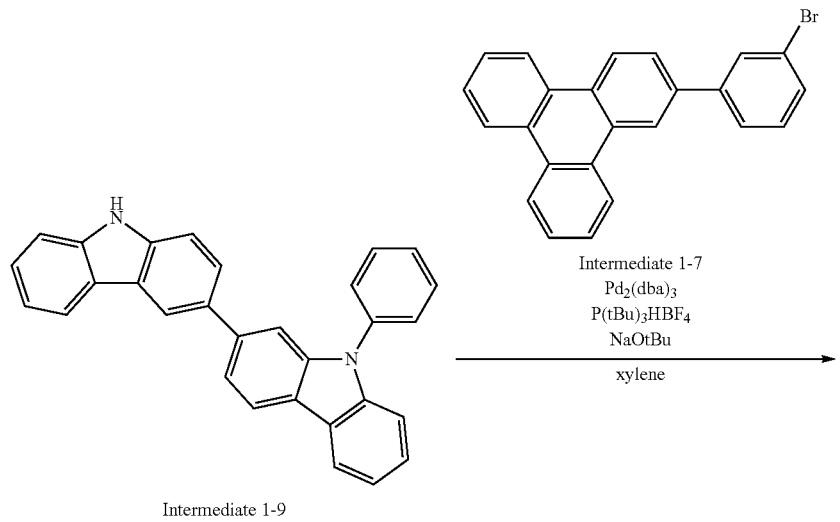
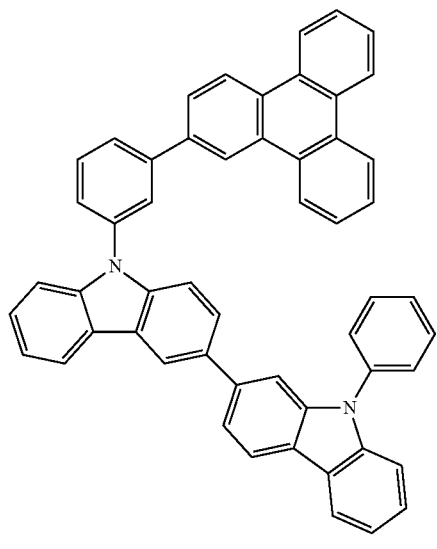
Compound 1-12
The procedure of Synthesis Example 1-7 was repeated except for using Intermediate 1-9 (3 g, 7.3 mmol) in place of Intermediate 1-6, to obtain Compound 1-12 (3.5 g, yield: 68%).
FD-MS analysis: m/e=710 for molecular weight of 710.

Synthesis Example 1-13 (Compound 1-13)

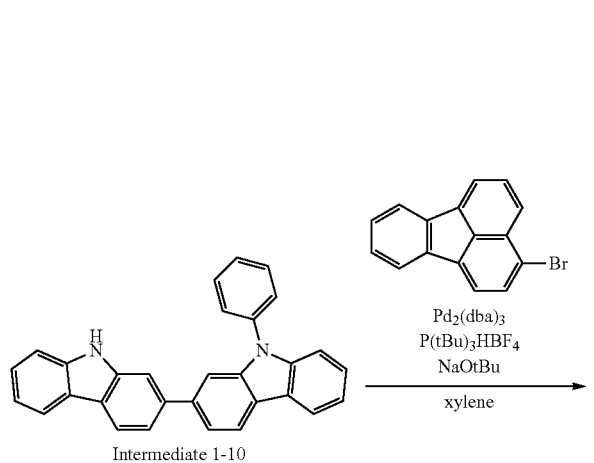

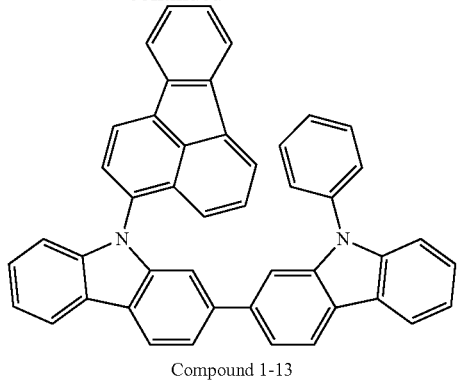

Compound 1-13

The procedure of Synthesis Example 1-1 was repeated except for using Intermediate 1-10 (3 g, 7.3 mmol) in place of Intermediate 1-1, to obtain Compound 1-13 (2.9 g, yield: 65%).

FD-MS analysis: m/e=608 for molecular weight of 608.

Synthesis Example 1-14 (Compound 1-14)

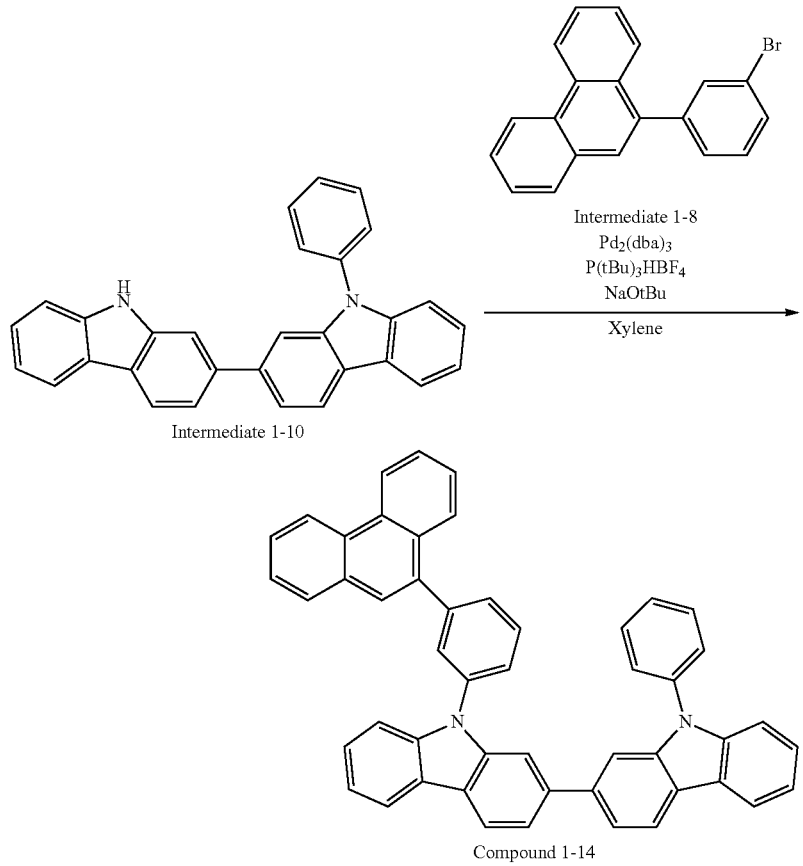

Compound 1-14

The procedure of Synthesis Example 1-13 was repeated except for using Intermediate 1-8 (2.7 g, 8.1 mmol) in place of 3-bromofluoranthene, to obtain Compound 1-14 (3.6 g, yield: 75%)

FD-MS analysis: m/e=660 for molecular weight of 660.

Synthesis Example 1-15 (Compound 1-15)

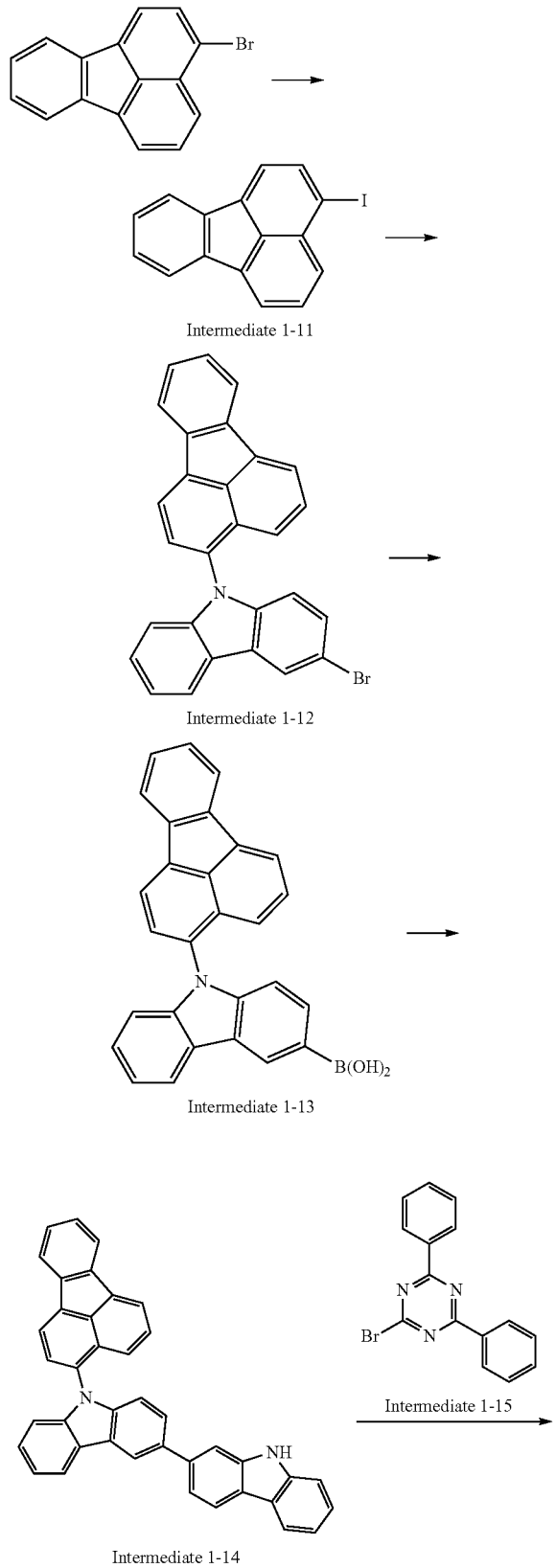

Intermediate 1-11

Intermediate 1-12

Intermediate 1-13

Intermediate 1-14

Intermediate 1-15

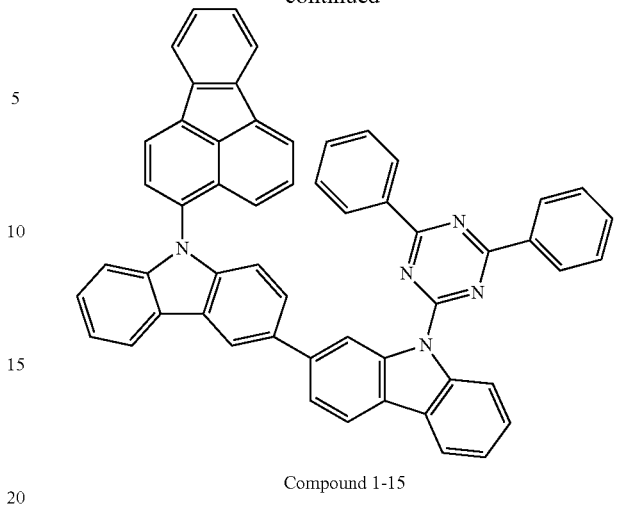

Compound 1-15

In an argon atmosphere, a solution of 3-bromofluoranthene (28.1 g, 100 mmol) in THF (1 L) was cooled to −20° C. and then added with a 1.6 M hexane solution of butyl lithium (69 mL, 110 mmol) dropwise. After 30 min, a solution of iodine (28 g, 110 mmol) in THF (500 mL) was added, the temperature was raised to room temperature, and then the solution was stirred for 3 h. After adding water to the reaction liquid, the organic layer was separated and the solvent was evaporated off. The obtained residue was purified by silica gel column chromatography, to obtain Intermediate 1-11 (23 g, yield: 70%).

Then, into a solution of copper iodide (5.8 g, 30 mmol) in dimethylformamide (300 mL), trans-1,2-cyclohexanediamine (6.9 g, 61 mmol) was added and then 3-bromocarbazole (15 g, 61 mmol), Intermediate 1-11 (20 g, 61 mmol), and tripotassium phosphate (39 g, 183 mmol) were further added. The resultant mixture was stirred at 70° C. for 8 h. The reaction liquid was filtered and the filtrate was concentrated. The obtained residue was purified by silica gel column chromatography, to obtain Intermediate 1-12 (14.9 g, yield: 55%).

Then, a solution of Intermediate 1-12 (14 g, 31 mmol) in THF (500 mL) was cooled to 20° C. and then added with a 1.6 M hexane solution of butyl lithium (23 mL, 37 mmol) dropwise. After stirring for 2 h, a solution of triisopropyl borate (11.7 g, 62 mmol) in THF (50 mL) was added dropwise and the resultant mixture was stirred at room temperature for 6 h. After adding a 2 N hydrochloric acid, the reaction liquid was stirred for 30 min and then the organic layer was separated. The solvent was evaporated off and the obtained residue was purified by silica gel column chromatography, to obtain Intermediate 1-13 (7.9 g, yield: 62%).

Then, Intermediate 1-13 (7 g, 17 mmol), 2-bromocarbazole (4.2 g, 17 mmol), tetrakis(triphenylphosphine)palladium (0.4 g, 0.3 mmol), toluene (25 mL), dimethoxyethane (25 mL), a 2 M aqueous sodium carbonate solution (25 mL) were mixed in this order. The resultant mixture was stirred at 80° C. for 8 h under heating. The organic layer was separated from the reaction liquid and the solvent was evaporated off. The obtained residue was purified by silica gel column chromatography, to obtain Intermediate 1-14 (4.8 g, yield: 53%).

In an argon atmosphere, Intermediate 1-15 (2.5 g, 8.1 mmol), Intermediate 1-16 (3.9 g, 7.3 mmol), $Pd_2(dba)_3$ (0.14 g, 0.15 mmol), $P(tBu)_3HBF_4$ (0.17 g, 0.6 mmol), sodium t-butoxide (1.1 g, 11 mmol), and dry xylene (30 mL) were mixed in this order. The resultant mixture was refluxed for 8 h under heating.

The solid generated by adding water to the reaction liquid was successively washed with hexane and methanol. The obtained solid was purified by silica gel column chromatography, to obtain Compound 1-15 (4.0 g, yield: 72%).

FD-MS analysis: m/e=763 for molecular weight of 763.

Example 1-1 (Production of Organic EL Device)

A glass substrate with an ITO transparent electrode having a size of 25 mm×75 mm long×1.1 mm thick (manufactured by GEOMATEC Co., Ltd.) was ultrasonically cleaned in isopropyl alcohol for 5 min and then UV/ozone cleaned for 30 min.

The cleaned glass substrate with the transparent electrode line was mounted on the substrate holder of a vacuum deposition apparatus. First, the following electron-accepting compound C-1 was vapor-deposited onto the surface on the side where the transparent electrode line was formed so as to cover the transparent electrode, thereby forming a C-1 film having a thickness of 5 nm. On the C-1 film, the following aromatic amine derivative X1 was vapor-deposited to form a first hole transporting layer having a thickness of 50 nm. Successively after the formation of the first hole transporting layer, the following aromatic amine derivative X2 was vapor-deposited to form a second hole transporting layer having a thickness of 60 nm.

Then, Compound 1-1 obtained in Synthesis Example 1-1 was vapor-deposited on the second hole transporting layer to form a light emitting layer having a thickness of 45 nm. At the same time, the following compound D3 as a phosphorescent emitting material was co-deposited. The concentration of the compound D3 was 8.0% by mass. The co-deposited film functions as a light emitting layer.

Successively after the formation of the light emitting layer, the compound ET2 was formed into a film having a thickness of 30 nm. The ET2 film functions as an electron transporting layer.

Next, LiF was formed into a film having a thickness of 1 nm at a film forming rate of 0.1 Å/min to form an electron injecting electrode (cathode). On the LiF film, metal Al was vapor-deposited to form a metal cathode having a thickness of 80 nm. Thus, an organic EL device was produced.

The obtained organic EL device was measured for the emission efficiency while driving the device by constant DC at room temperature at an initial luminance of 2000 cd/m$^2$. The result is shown in Table 1. The half lifetime of the emission was measured while driving the device by constant DC at room temperature at an initial luminance of 5000 cd/m$^2$. The result is also shown in Table 1.

Examples 1-2 to 1-15 and Comparative Examples 1-1 to 1-3

Each organic EL device was produced in the same manner as in Example 1-1 except for forming the light emitting layer from the compound listed in Table 1 in place of Compound 1-1. The measured results of the emission efficiency and the half lifetime are shown in Table 1.

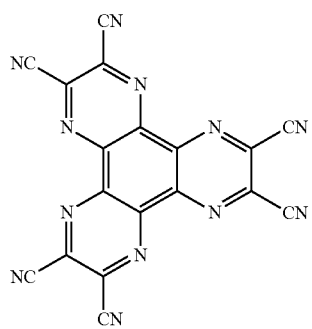

C-1

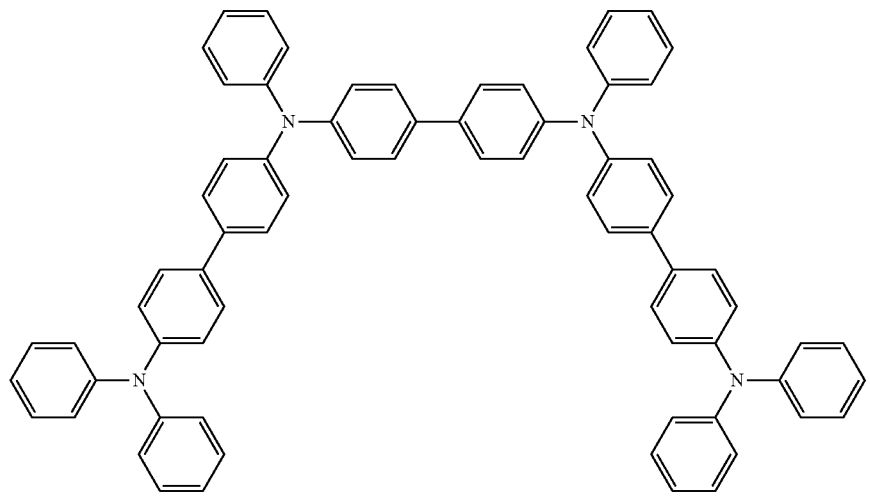

X1

-continued
X2
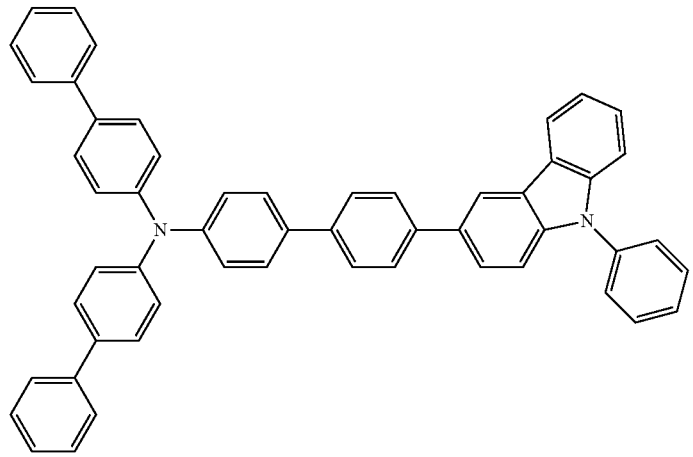
D3
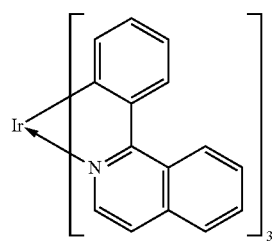
ET2
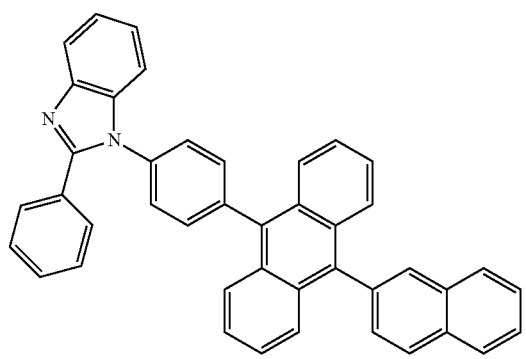
Compound 1-A
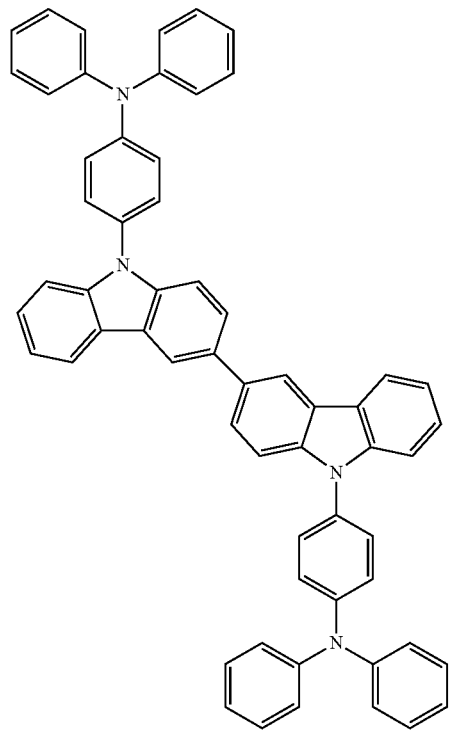
Compound 1-B
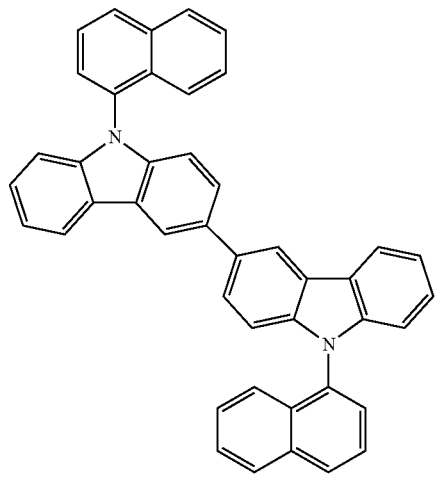

-continued

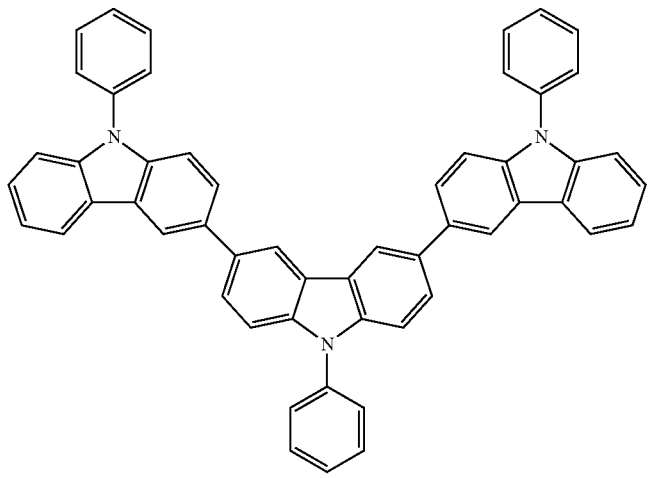

Compound 1-C

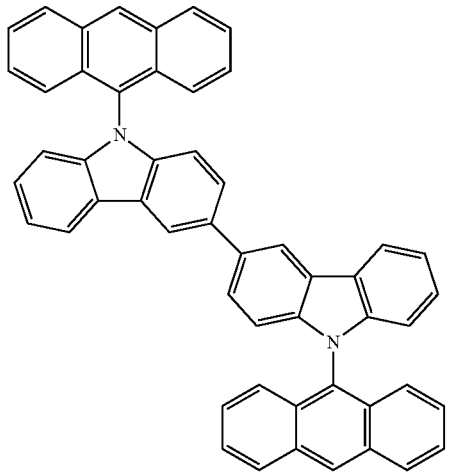

Compound 1-D

TABLE 1

| | Host material | Voltage (V) | Emission efficiency (cd/A) | Half lifetime of luminance (h) |
|---|---|---|---|---|
| Examples | | | | |
| 1-1 | compound 1-1 | 4.1 | 11 | 550 |
| 1-2 | compound 1-2 | 4.3 | 10 | 450 |
| 1-3 | compound 1-3 | 4.2 | 12 | 440 |
| 1-4 | compound 1-4 | 4.4 | 12 | 400 |
| 1-5 | compound 1-5 | 4.3 | 11 | 600 |
| 1-6 | compound 1-6 | 4.2 | 12 | 500 |
| 1-7 | compound 1-7 | 4.4 | 10 | 600 |
| 1-8 | compound 1-8 | 4.3 | 11 | 560 |
| 1-9 | compound 1-9 | 4.1 | 12 | 500 |
| 1-10 | compound 1-10 | 4.3 | 11 | 600 |
| 1-11 | compound 1-11 | 4.0 | 12 | 580 |
| 1-12 | compound 1-12 | 4.3 | 11 | 600 |
| 1-13 | compound 1-13 | 4.2 | 13 | 490 |
| 1-14 | compound 1-14 | 4.3 | 10 | 600 |
| 1-15 | compound 1-15 | 4.0 | 12 | 600 |
| Comparative Examples | | | | |
| 1-1 | compound 1-A | 5.1 | 9 | 100 |
| 1-2 | compound 1-B | 5.6 | 6.5 | 220 |
| 1-3 | compound 1-C | 5.4 | 8.7 | 180 |

Comparative Example 1-4

An organic EL device was produced in the same manner as in Example 1-1 except for forming the light emitting layer from Compound 1-D in place of Compound 1-1. No emission from the phosphorescent emitting material (Compound D3) was observed in the obtained organic EL device.

Compounds 1-A and 1-B are disclosed in Patent Document 9, and Compounds 1-C and 1-D are disclosed in Patent Document 7.

In the devices using Compounds 1-A and 1-C, the light emitting layer contains excess holes, failing to balance electrons and holes. In the device using Compound 1-C, the problem of excess holes cannot be completely solved, because the electron transporting ability of Compound 1-C is poor as compared with that of the biscarbazole derivative of the invention.

From the above results, it would appear that the compounds of the invention are superior to the comparative compounds in the emission efficiency and the lifetime. Namely, the above results show that the specific fused ring bonded to the biscarbazole derivative is important for improving the performance of a host material, and that the aromatic fused ring selected from a fluoranthene, a benzophenanthrene, etc. is suitable as such a fused ring.

Synthesis Example 2-1 (Synthesis of Compound 2-1)

Synthesis Example 2-2 (Synthesis of Compound 2-2)

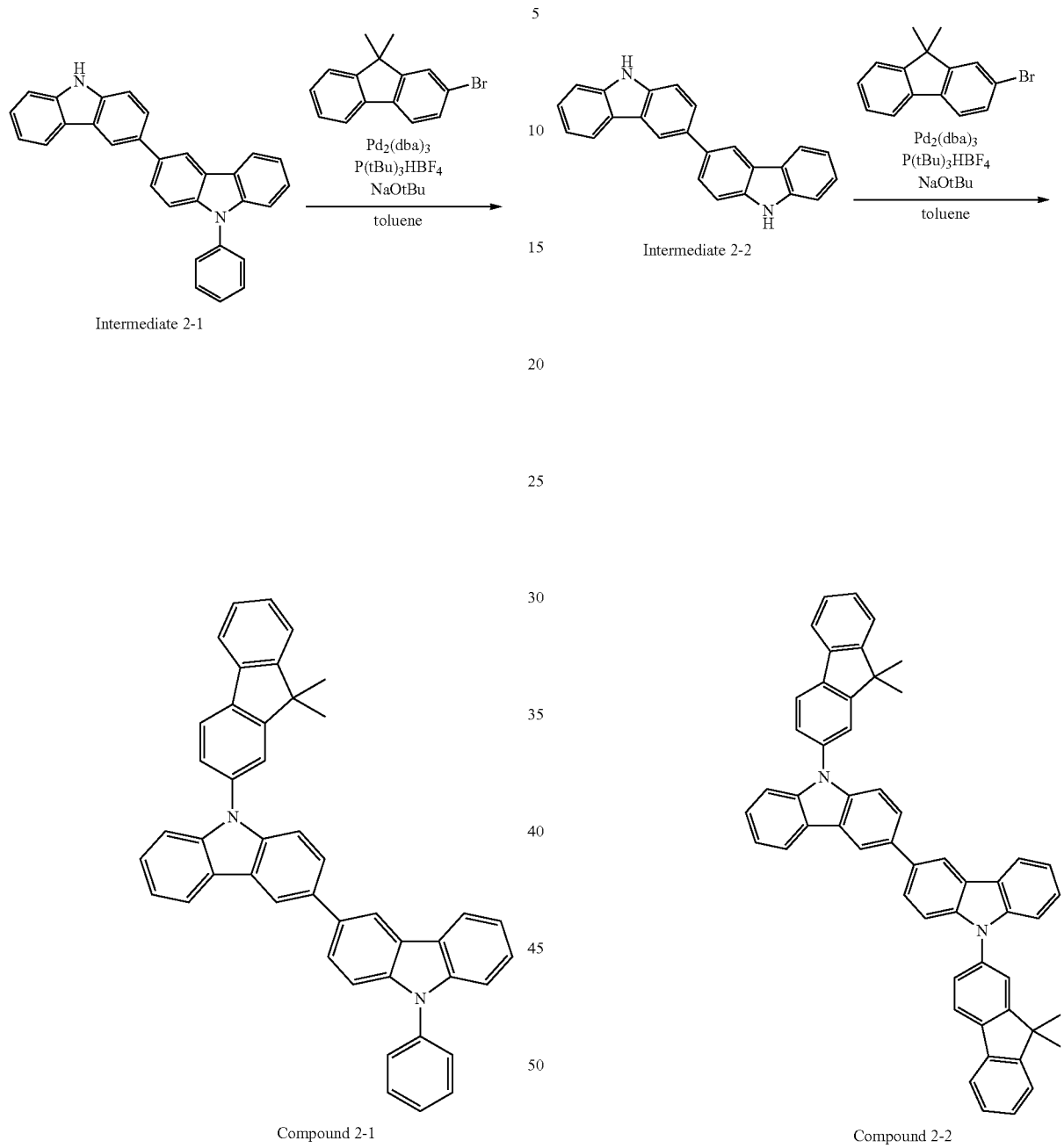

Compound 2-1

Compound 2-2

In an argon atmosphere, 2-bromo-9,9-dimethylfluorene (2.2 g, 8.1 mmol), Intermediate 2-1 (3 g, 7.3 mmol), Pd$_2$(dba)$_3$ (0.14 g, 0.15 mmol), P(tBu)$_3$HBF$_4$ (0.17 g, 0.6 mmol), sodium t-butoxide (1.1 g, 11 mmol), and dry toluene (30 mL) were charged in a three-necked flask in this order. The resultant mixture was refluxed for 8 h under heating.

The solid generated by adding water to the reaction liquid was successively washed with hexane and methanol and then purified by silica gel column chromatography, to obtain Compound 2-1 (2.7 g, yield: 62%).

FD-MS analysis: m/e=600 for molecular weight of 600.

In an argon atmosphere, 2-bromo-9,9-dimethylfluorene (4.4 g, 16.2 mmol), Intermediate 2-2 (3 g, 7.3 mmol), Pd$_2$(dba)$_3$ (0.28 g, 0.3 mmol), P(tBu)$_3$HBF$_4$ (0.34 g, 1.2 mmol), sodium t-butoxide (2.2 g, 22 mmol), and dry toluene (30 mL) were charged in a three-necked flask in this order. The resultant mixture was refluxed for 8 h under heating.

The solid generated by adding water to the reaction liquid was successively washed with hexane and methanol and then purified by silica gel column chromatography, to obtain Compound 2-2 (3.7 g, yield: 70%).

FD-MS analysis: m/e=716 for molecular weight of 716.

Synthesis Example 2-3 (Synthesis of Compound 2-3)

Synthesis Example 2-4 (Synthesis of Compound 2-4)

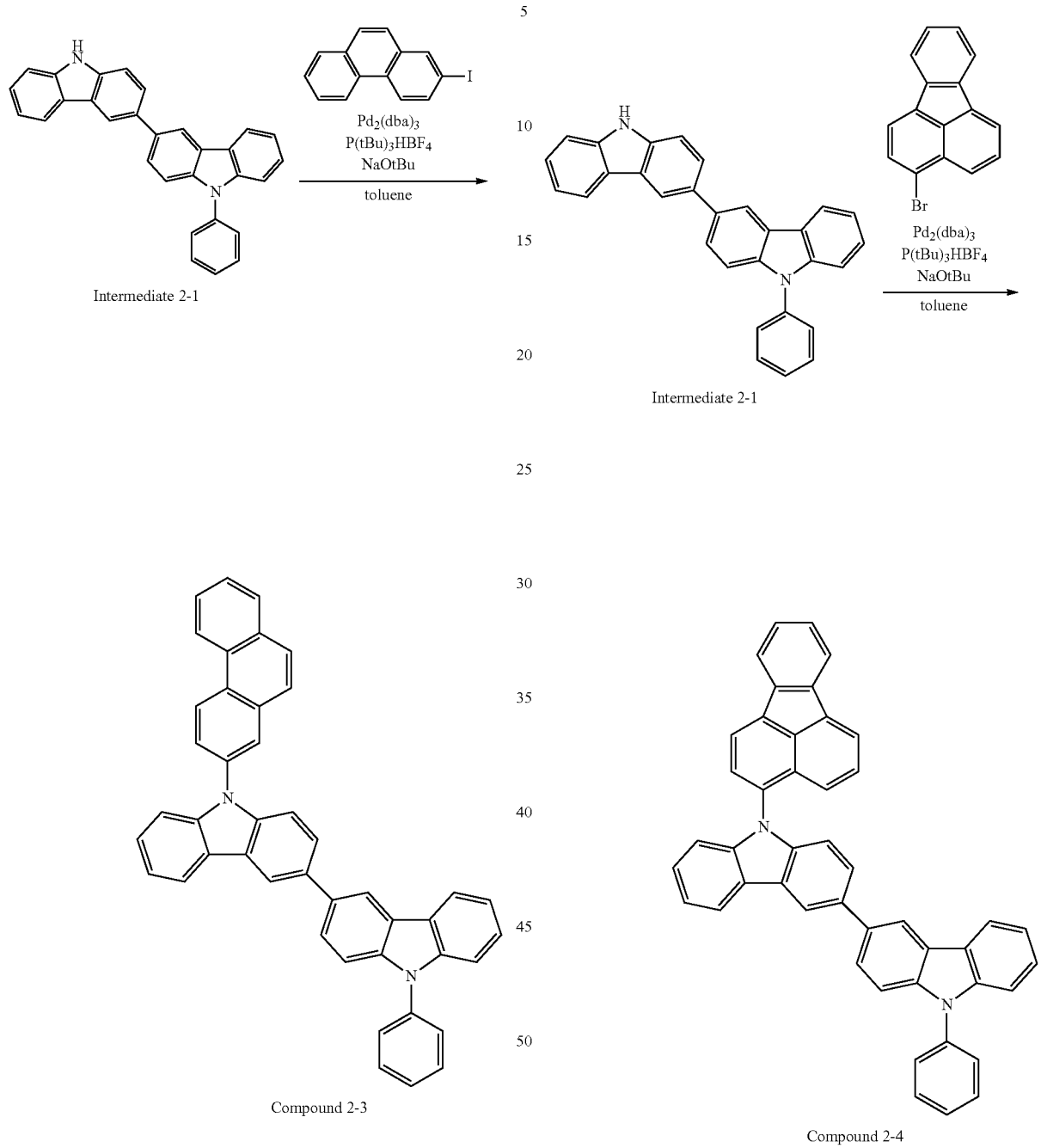

In an argon atmosphere, 2-iodophenanthrene (2.46 g, 8.1 mmol), Intermediate 2-1 (3 g, 7.3 mmol), Pd$_2$(dba)$_3$ (0.14 g, 0.15 mmol), P(tBu)$_3$HBF$_4$ (0.17 g, 0.6 mmol), sodium t-butoxide (1.1 g, 11 mmol), and dry toluene (30 mL) were charged in a three-necked flask in this order. The resultant mixture was refluxed for 8 h under heating.

The solid generated by adding water to the reaction liquid was successively washed with hexane and methanol and then purified by silica gel column chromatography, to obtain Compound 2-3 (3.15 g, yield: 74%).

FD-MS analysis: m/e=584 for molecular weight of 584.

In an argon atmosphere, 3-bromofluoranthene (2.3 g, 8.1 mmol), Intermediate 2-1 (3 g, 7.3 mmol), Pd$_2$(dba)$_3$ (0.14 g, 0.15 mmol), P(tBu)$_3$HBF$_4$ (0.17 g, 0.6 mmol), sodium t-butoxide (1.1 g, 11 mmol), and dry xylene (30 mL) were charged in a three-necked flask in this order. The resultant mixture was refluxed for 8 h under heating.

The solid generated by adding water to the reaction liquid was successively washed with hexane and methanol and then purified by silica gel column chromatography, to obtain Compound 2-4 (2.9 g, yield: 65%).

FD-MS analysis: m/e=608 for molecular weight of 608.

Synthesis Example 2-5 (Synthesis of Compound 2-5)

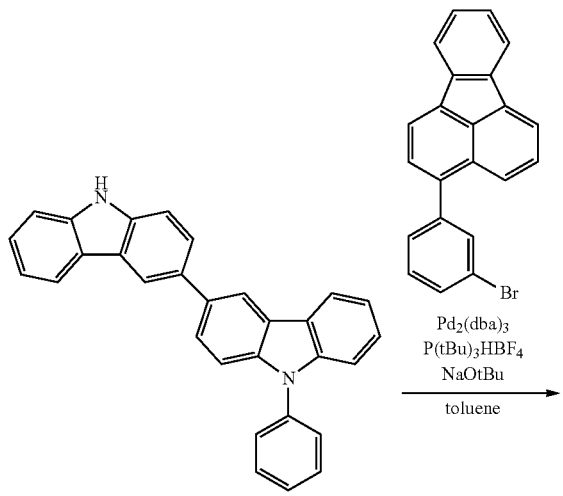

Intermediate 2-1

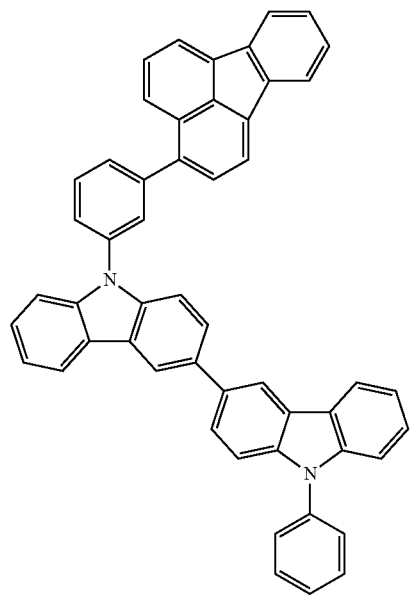

Compound 2-5

The procedure of Synthesis Example 2-1 was repeated except for using 3-(fluoranthene-3'-yl)bromobenzene (2.9 g, 8.1 mmol) in place of 2-bromo-9,9-dimethylfluorene, to obtain Compound 2-5 (2.8 g, yield: 56%).

FD-MS analysis: m/e=684 for molecular weight of 684.

Example 2-1 (Production of Organic EL Device)

A glass substrate with an ITO transparent electrode having a size of 25 mm×75 mm long×1.1 mm thick (manufactured by GEOMATEC Co., Ltd.) was ultrasonically cleaned in isopropyl alcohol for 5 min and then UV/ozone cleaned for 30 min.

The cleaned glass substrate with the transparent electrode line was mounted on the substrate holder of a vacuum deposition apparatus. First, the following electron-accepting compound C-1 was vapor-deposited onto the surface on the side where the transparent electrode line was formed so as to cover the transparent electrode, thereby forming a C-1 film having a thickness of 5 nm. On the C-1 film, the following aromatic amine derivative X1 was vapor-deposited to form a first hole transporting layer having a thickness of 50 nm. Successively after the formation of the first hole transporting layer, the following aromatic amine derivative X2 was vapor-deposited to form a second hole transporting layer having a thickness of 60 nm.

Then, Compound 2-1 obtained in Synthesis Example 2-1 was vapor-deposited on the second hole transporting layer to form a light emitting layer having a thickness of 45 nm. At the same time, the following compound D3 as a phosphorescent emitting material was co-deposited. The concentration of the compound D3 was 8.0% by mass. The co-deposited film functions as a light emitting layer.

Successively after the formation of the light emitting layer, the compound ET2 was formed into a film having a thickness of 30 nm. The ET2 film functions as an electron transporting layer.

Next, LiF was formed into a film having a thickness of 1 nm at a film forming rate of 0.1 Å/min to form an electron injecting electrode (cathode). On the LiF film, metal Al was vapor-deposited to form a metal cathode having a thickness of 80 nm. Thus, an organic EL device was produced.

The obtained organic EL device was measured for the emission efficiency while driving the device by constant DC at room temperature at an initial luminance of 2000 cd/m$^2$. The result is shown in Table 2. The half lifetime of the emission was measured while driving the device by constant DC at room temperature at an initial luminance of 5000 cd/m$^2$. The result is also shown in Table 2.

Examples 2-2 to 2-5 and Comparative Examples 2-1 to 2-3

Each organic EL device was produced in the same manner as in Example 2-1 except for forming the light emitting layer from the compound listed in Table 2 in place of Compound 2-1.

431  432
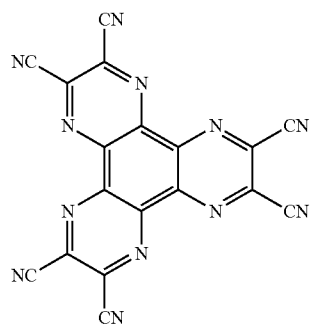
C-1
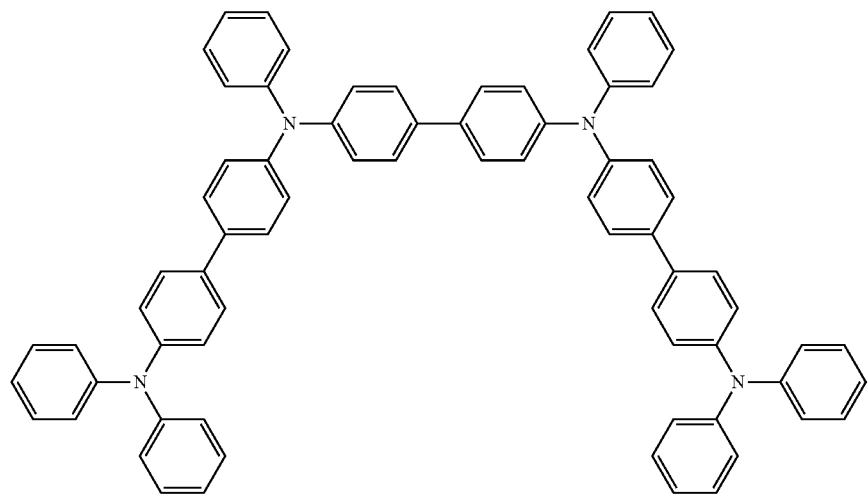
X1
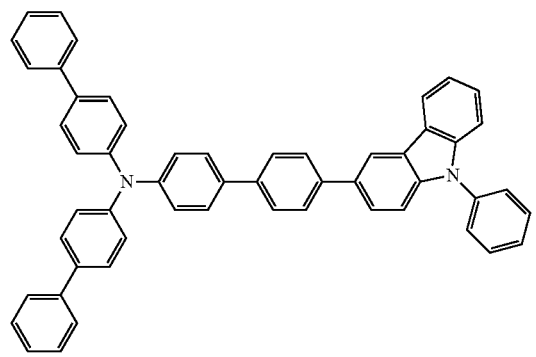
X2
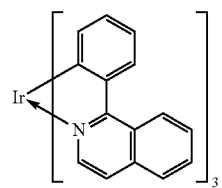
D3
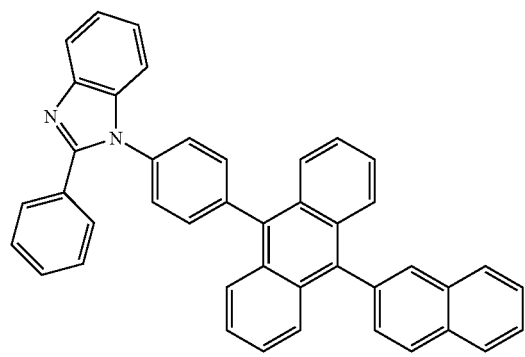
ET2

-continued
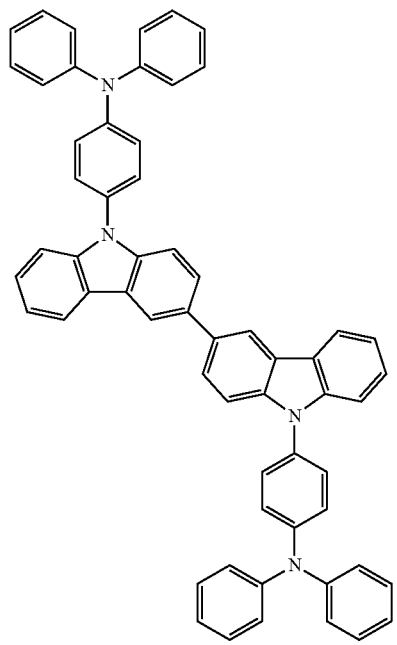
Compound 2-A
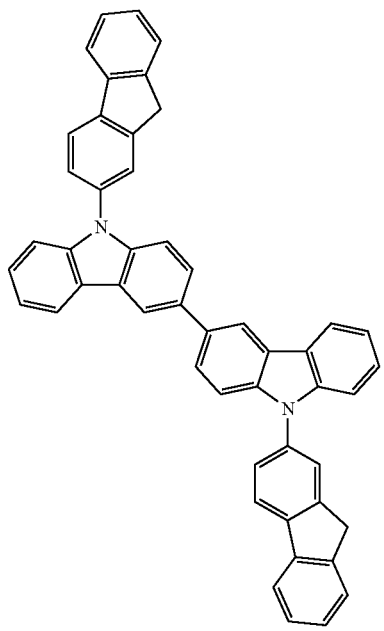
Compound 2-B
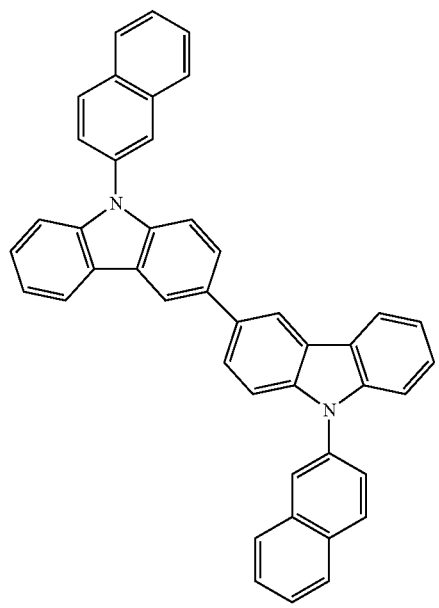
Compound 2-C
| | Host material | Voltage (V) | Emission efficiency (cd/A) | Half lifetime of luminance (h) |
|---|---|---|---|---|
| Examples | | | | |
| 2-1 | compound 2-1 | 4.1 | 11 | 400 |
| 2-2 | compound 2-2 | 4.0 | 10 | 350 |
| 2-3 | compound 2-3 | 4.2 | 12 | 420 |
| 2-4 | compound 2-4 | 4.1 | 11 | 550 |
| 2-5 | compound 2-5 | 4.3 | 11 | 600 |
| Comparative Examples | | | | |
| 2-1 | compound 2-A | 4.1 | 12 | 150 |
| 2-2 | compound 2-B | 4.2 | 12 | 120 |
| 2-3 | compound 2-C | 4.9 | 9 | 280 |

The organic EL devices of the invention employing the compounds 2-1 to 2-5 exhibit good emission efficiencies and good lifetimes. In contrast, the devices employing the compounds 2-A and 2-B which are disclosed in prior art (Patent Document 9) have shorter device lifetimes. This may be attributable to the presence of an amino substituent which is poor in the electron resistance or the presence of a fluorenyl group wherein its active site is not protected. As compared with the devices of the invention, the device employing the compound 2-C requires a higher voltage and has a low efficiency. Namely, the results show that sufficient properties cannot be obtained if the group bonded to 9-position of carbazole is an amino group, a fluorenyl group, or a naphthyl group, and further show that it is important to select an aryl substituent or a fused ring in place such groups.

INDUSTRIAL APPLICABILITY

The material for organic EL devices of the invention is useful for the production of an organic EL device which has a long lifetime and a high emission efficiency and can be driven at low voltage, thereby reducing a power consumption.

REFERENCE NUMERALS

1: Organic electroluminescence device
2: Substrate
3: Anode
4: Cathode
5: Phosphorescent light emitting layer
6: Hole injecting/transporting layer
7: Electron injecting/transporting layer
10: Organic thin film layer

What is claimed is:

1. A biscarbazole derivative represented by formula (1):

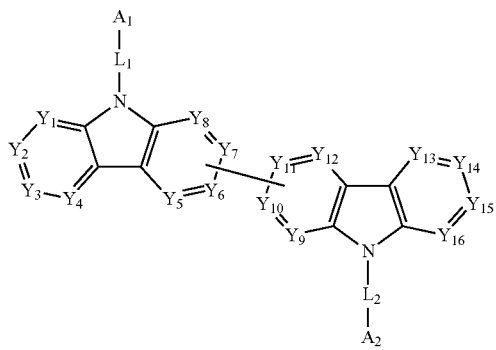

(1)

wherein:
-$L_1$-$A_1$ and -$L_2$-$A_2$ are different from each other;
$A_1$ represents a substituted or unsubstituted triphenylenyl group;
$A_2$ represents a substituted or unsubstituted aromatic hydrocarbon group having 6 to 30 ring carbon atoms;
each of $Y_1$ to $Y_{16}$ independently represents C(R) or a nitrogen atom, and each of R groups independently represents a hydrogen atom, a substituent, or a valence bonded to a carbazole skeleton; and
each of $L_1$ and $L_2$ independently represents a single bond, or a substituted or unsubstituted, divalent aromatic hydrocarbon group having 6 to 30 ring carbon atoms, when $A_2$ has a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, a pyrrolyl group, an indolyl group, an isoindolyl group, a furyl group, a benzofuranyl group, an isobenzofuranyl group, a dibenzofuranyl group, a dibenzothiophenyl group, a carbazolyl group, a thienyl group, a residue of an indole ring, a residue of a carbazole ring, a residue of a furan ring, a residue of a thiophene ring, a residue of an oxazole ring, a residue of an oxadiazole ring, a residue of a benzoxazole ring, a residue of a thiazole ring, a residue of a thiadiazole ring, a residue of a benzothiazole ring, a residue of a triazole ring, a residue of an imidazole ring a residue of a benzimidazole ring, a residue of a pyran ring, a residue of a dibenzofuran ring, or a residue of a benzo[c]dibenzofuran ring.

2. The biscarbazole derivative according to claim 1, wherein said biscarbazole derivative is represented by formula (2), (3) or (4):

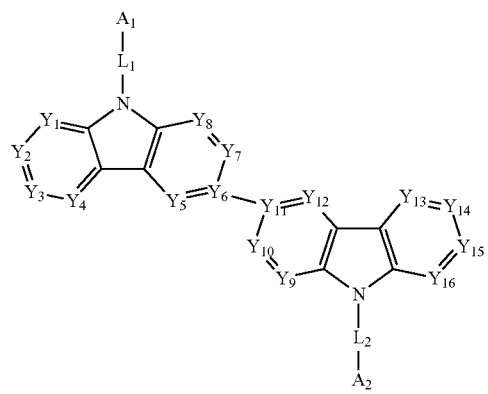

(2)

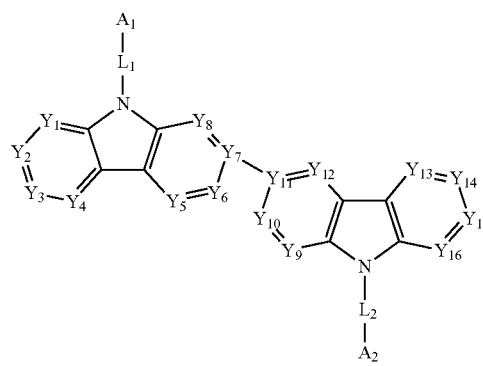

(3)

(4)

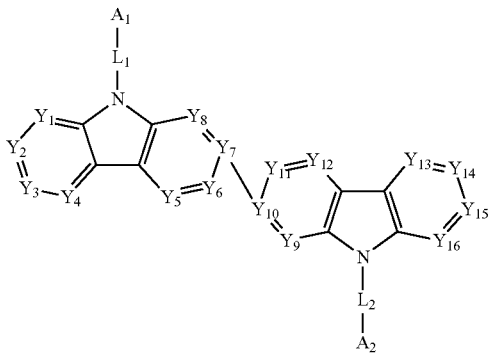

wherein each of $A_1$, $A_2$, $Y_1$ to $Y_{16}$, $L_1$, and $L_2$ is as defined in formula (1).

3. The biscarbazole derivative according to claim 1, wherein when $A_2$ has a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, or a substituted or unsubstituted aromatic hydrocarbon group having 6 to 30 ring carbon atoms.

4. The biscarbazole derivative according to claim 1, wherein $A_2$ represents a substituted or unsubstituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted fluoranthenyl group, a substituted or unsubstituted triphenylenyl group, a substituted or unsubstituted phenanthrenyl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, or a substituted or unsubstituted benzo[b]fluoranthenyl group.

5. The biscarbazole derivative according to claim 1, wherein $A_2$ represents a substituted or unsubstituted phenyl group, a substituted or unsubstituted naphthyl group, a substituted or unsubstituted biphenyl group, or a substituted or unsubstituted terphenyl group.

6. The biscarbazole derivative according to claim 1, wherein at least one of $L_1$ and $L_2$ represents a substituted or unsubstituted, divalent aromatic hydrocarbon group having 6 to 30 ring carbon atoms.

7. The biscarbazole derivative according to claim 1, wherein each of $L_1$ and $L_2$ represents a single bond.

8. The biscarbazole derivative according to claim 1, wherein at least one of $L_1$ and $L_2$ represents a single bond or a substituted or unsubstituted phenylene group.

9. The biscarbazole derivative according to claim 1, wherein when $A_2$ has a substituent, the substituent represents a fluorine atom a cyano group, a substituted or unsubstituted, linear, branched, or cyclic alkyl group having 1 to 20 carbon atoms, a linear, branched, or cyclic alkylene group having 1 to 20 carbon atoms, or a substituted or unsubstituted, linear, branched, or cyclic alkylsilyl group having 1 to 10 carbon atoms.

10. The biscarbazole derivative according to claim 1, wherein when R group represents a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 30 ring carbon atoms.

11. A material for an organic electroluminescence device comprising the biscarbazole derivative according to claim 1.

12. The biscarbazole derivative according to claim 1, wherein each of $L_1$ and $L_2$ represents a single bond; and $A_2$ represents a substituted or unsubstituted phenyl group, a substituted or unsubstituted biphenyl group, or a substituted or unsubstituted terphenyl group,
when $A_2$ has a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, or a substituted or unsubstituted, linear, branched, or cyclic alkylsilyl group having 1 to 10 carbon atoms.

13. An organic electroluminescence device comprising a plurality of organic thin-film layers between a cathode and an anode, wherein the organic thin-film layers comprise a light emitting layer and at least one layer of the organic thin-film layers comprises a biscarbazole derivative represented by formula (1):

(1)

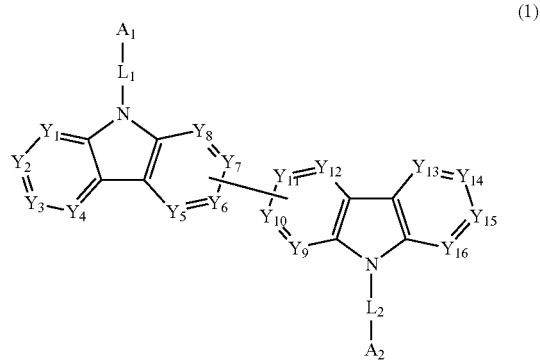

wherein:
L$_1$-A$_1$ and -L$_2$-A$_2$ are different from each other;
A$_1$ represents a substituted or unsubstituted triphenylenyl group;
A$_2$ represents a substituted or unsubstituted aromatic hydrocarbon group having 6 to 30 ring carbon atoms;
each of Y$_1$ to Y$_{16}$ independently represents C(R) or a nitrogen atom, and each of R groups independently represents a hydrogen atom, a substituent, or a valence bonded to a carbazole skeleton; and
each of L$_1$ and L$_2$ independently represents a single bond, or a substituted or unsubstituted, divalent aromatic hydrocarbon group having 6 to 30 ring carbon atoms,
when A$_2$ has a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, a pyrrolyl group, an indolyl group, an isoindolyl group, a furyl group, a benzofuranyl group, an isobenzofuranyl group, a dibenzofuranyl group, a dibenzothiophenyl group, a carbazolyl group, a thienyl group, a residue of an indole ring, a residue of a carbazole ring, a residue of a furan ring, a residue of a thiophene ring, a residue of an oxazole ring, a residue of an oxadiazole ring, a residue of a benzoxazole ring, a residue of a thiazole ring, a residue of a thiadiazole ring, a residue of a benzothiazole ring, a residue of a triazole ring, a residue of an imidazole ring, a residue of a benzimidazole ring, a residue of a pyran ring, a residue of a dibenzofuran ring, or a residue of a benzo[c]dibenzofuran ring.

14. The organic electroluminescence device according to claim 13, wherein said biscarbazole derivative is represented by formula (2), (3) or (4):

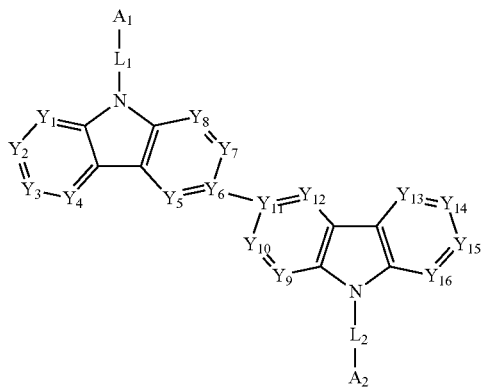

(2)

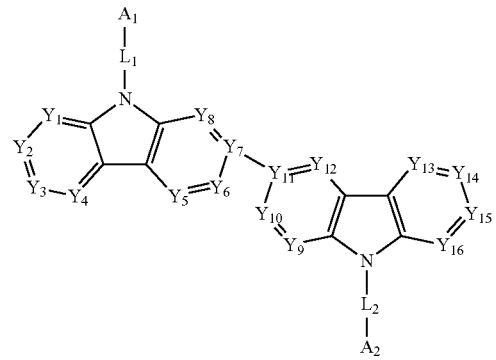

(3)

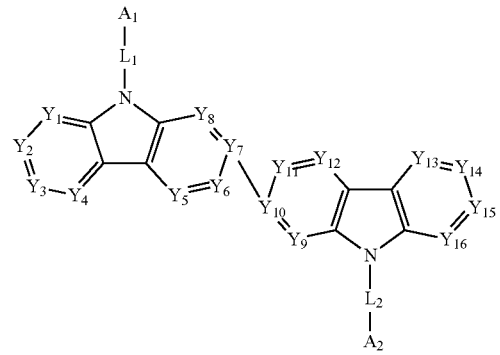

(4)

wherein each of A$_1$, A$_2$, Y$_1$ to Y$_{16}$, L$_1$, and L$_2$ is as defined in formula (1).

15. The organic electroluminescence device according to claim 13, wherein when A$_2$ has a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, or a substituted or unsubstituted aromatic hydrocarbon group having 6 to 30 ring carbon atoms.

16. The organic electroluminescence device according to claim 13, wherein A$_2$ represents a substituted or unsubstituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted quaterphenyl group, a substituted or unsubstituted fluoranthenyl group, a substituted or unsubstituted triphenylenyl group, a substituted or unsubstituted phenanthrenyl group, a substituted or unsubstituted 9,9-dimethylfluorenyl group, a substituted or unsubstituted benzo[c]phenanthrenyl group, a substituted or unsubstituted benzo[a]triphenylenyl group, a substituted or unsubstituted naphtho[1,2-c]phenanthrenyl group, a substituted or unsubstituted naphtho[1,2-a]triphenylenyl group, a substituted or unsubstituted dibenzo[a,c]triphenylenyl group, or a substituted or unsubstituted benzo[b]fluoranthenyl group.

17. The organic electroluminescence device according to claim 13, wherein $A_2$ represents a substituted or unsubstituted phenyl group, a substituted or unsubstituted naphthyl group, a substituted or unsubstituted biphenyl group, or a substituted or unsubstituted terphenyl group.

18. The organic electroluminescence device according to claim 13, wherein at least one of $L_1$ and $L_2$ represents a substituted or unsubstituted, divalent aromatic hydrocarbon group having 6 to 30 ring carbon atoms.

19. The organic electroluminescence device according to claim 13, wherein each of $L_1$ and $L_2$ represents a single bond.

20. The organic electroluminescence device according to claim 13, wherein at least one of $L_1$ and $L_2$ represents a single bond or a substituted or unsubstituted phenylene group.

21. The organic electroluminescence device according to claim 13, wherein when $A_2$ has a substituent, the substituent represents a fluorine atom; a cyano group, a substituted or unsubstituted, linear, branched, or cyclic alkyl group having 1 to 20 carbon atoms, a linear, branched, or cyclic alkylene group having 1 to 20 carbon atoms, or a substituted or unsubstituted, linear, branched, or cyclic alkylsilyl group having 1 to 10 carbon atoms.

22. The organic electroluminescence device according to claim 13, wherein when R group represents a substituent, the substituent represents a fluorine atom, a cyano group, a substituted or unsubstituted, linear, branched, or cyclic alkyl group having 1 to 20 carbon atoms, a linear, branched, or cyclic alkylene group having 1 to 20 carbon atoms, a linear, branched, or cyclic, divalent, unsaturated hydrocarbon group having 1 to 20 carbon atoms, a substituted or unsubstituted, linear, branched, or cyclic alkoxy group having 1 to 20 carbon atoms, a substituted or unsubstituted, linear, branched, or cyclic haloalkyl group having 1 to 20 carbon atoms, a substituted or unsubstituted, linear, branched, or cyclic haloalkoxy group having 1 to 20 carbon atoms, a substituted or unsubstituted, linear, branched, or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, or a substituted or unsubstituted aromatic heterocyclic group having 2 to 30 ring carbon atoms.

23. The organic electroluminescence device according to claim 13, wherein the light emitting layer comprises the biscarbazole derivative as a host material.

24. The organic electroluminescence device according to claim 23, wherein the light emitting layer comprises a phosphorescent material.

25. The organic electroluminescence device according to claim 24, wherein the light emitting layer comprises the host material and the phosphorescent material which is an ortho-metallated complex of a metal atom selected from iridium (Ir), osmium (Os), and platinum (Pt).

26. The organic electroluminescence device according to claim 25, wherein the device further comprises an electron injecting layer between the cathode and the light emitting layer, and the electron injecting layer comprises a nitrogen-containing ring derivative.

27. The organic electroluminescence device according to claim 25, wherein the device further comprises a hole transporting layer between the anode and the light emitting layer.

28. A lighting device comprising the organic electroluminescence device according to claim 13.

29. A display device comprising the organic electroluminescence device according to claim 13.

* * * * *